|||||||||||||||||||||||||||||||||||||||||||||||||||||
US007098015B2

(12) United States Patent
MacBeth et al.

(10) Patent No.: US 7,098,015 B2
(45) Date of Patent: Aug. 29, 2006

(54) 27875, 22025, 27420, 17906, 16319, 55092 AND 10218 MOLECULES AND USES THEREFOR

(75) Inventors: Kyle J. MacBeth, Boston, MA (US); Joseph M. Carroll, Cambridge, MA (US); William James Cook, Hanover, NH (US); Rachel E. Meyers, Newton, MA (US); Miyoung Chun, Belmont, CA (US); Mark J. Williamson, Saugus, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 211 days.

(21) Appl. No.: 10/386,414

(22) Filed: Mar. 11, 2003

(65) Prior Publication Data

US 2004/0006016 A1    Jan. 8, 2004

Related U.S. Application Data

(60) Continuation-in-part of application No. 09/426,282, filed on Oct. 25, 1999, now abandoned, and a continuation-in-part of application No. 10/386,414, which is a continuation-in-part of application No. 09/668,266, filed on Sep. 22, 2000, now abandoned, which is a division of application No. 09/330,970, filed on Jun. 11, 1999, now Pat. No. 6,146,876, application No. 10/386,414, which is a continuation-in-part of application No. 09/724,599, filed on Nov. 28, 2000, now abandoned, application No. 10/386,414, which is a continuation-in-part of application No. 09/860,193, filed on May 16, 2001, now abandoned, which is a division of application No. 09/571,689, filed on May 16, 2000, now abandoned, application No. 10/386,414, which is a continuation-in-part of application No. 10/283,023, filed on Oct. 29, 2002, application No. 10/386,414, which is a continuation-in-part of application No. 10/010,943, filed on Dec. 6, 2001, now abandoned, application No. 10/386,414, which is a continuation-in-part of application No. 09/833,082, filed on Apr. 10, 2001, now abandoned.

(60) Provisional application No. 60/335,044, filed on Oct. 31, 2001, provisional application No. 60/254,037, filed on Dec. 7, 2000.

(51) Int. Cl.
*C12N 9/16*   (2006.01)
*C12N 15/54*  (2006.01)
*C12N 15/62*  (2006.01)
*C12N 15/79*  (2006.01)

(52) U.S. Cl. .................... 435/196; 435/69.1; 435/69.7
(58) Field of Classification Search ................ 435/196, 435/69.1, 69.7; 345/69.7
See application file for complete search history.

(56) References Cited

U.S. PATENT DOCUMENTS

| 5,527,896 A | 6/1996 | Wigler et al. ............... 536/235 |
| 5,702,936 A | 12/1997 | Beavo et al. ............... 435/196 |
| 5,798,246 A | 8/1998 | Au-Young et al. .......... 436/196 |
| 5,851,784 A | 12/1998 | Owens et al. ................. 435/19 |

FOREIGN PATENT DOCUMENTS

| EP | 1 018 559 | 7/2000 |
| WO | WO 91/16457 A1 | 10/1991 |

OTHER PUBLICATIONS

Seffernick, J. L., et al., 2001,"Melamine deaminase and atrazine chlorohydroalsase: 98 Percent identical but functionally different", Journal of Bacteriology, vol. 183, No. 8, pp. 2405-2410.*
Sasaki, T et al., "Identification of Human PDE7B, a cAMP-Specific Phosphodiesterase", Biochemical and Biophysical Research Communications 271(3):575-583 (2000).
Hetman, J. M. et al., "Cloning and Characterization of PDE7B, a cAMP-Specific Phosphodiesterase", PNAS 97(1):472-476 (2000).
Tamar et al., "Isolation and Characterization of a Previously Undetected Human cAMP Phosphodiesterase by Complementation of cAMP Phosphodiesterase-Deficient Saccharomyces Cerevisiae", The Journal of Biological Chemistry 268(17):12925-12932 (1993).
ID CN7A_Human, Jun. 1993.
ID CN7A_Mouse, Nov. 1996.
Beavo, "Cyclic Nucleotide Phospholiesterases: Functional Implications of Multiple Isoforms", Physiological Reviews 75(4) :725-748 (1995).
Bloom et al., "Identification and Tissue-Specific Expression of PDE7 Phosphodiesterase Splice Variants", PNAS USA 93:14188-14192 (1996).

(Continued)

*Primary Examiner*—Ponnathapura Achutamurthy
*Assistant Examiner*—William W. Moore
(74) *Attorney, Agent, or Firm*—Millennium Pharmaceuticals Inc.

(57) ABSTRACT

The invention provides isolated nucleic acids molecules, designated 27875, 22025, 27420, 16319, 55092 and 10218 nucleic acid molecules. The invention also provides antisense nucleic acid molecules, recombinant expression vectors containing 27875, 22025, 27420, 16319, 55092 and 10218 nucleic acid molecules, host cells into which the expression vectors have been introduced, and nonhuman transgenic animals in which a 27875, 22025, 27420, 16319, 55092 and 10218 gene has been introduced or disrupted. The invention still further provides isolated 27875, 22025, 27420, 17906, 16319, 55092 or 10218 proteins, fusion proteins, antigenic peptides and anti-27875, 22025, 27420, 17906, 16319, 55092 or 10218 antibodies. Diagnostic and therapeutic methods utilizing compositions of the invention are also provided.

9 Claims, No Drawings

OTHER PUBLICATIONS

Han et al., "Alternative Splicing of the High Affinity cAMP-Specific Phosphodiesterase (PCE7A) mmA in Human Skeletal Muscle and Heart", The Journal of Biological Chemistry 272(26):16152-16157 (1997).

Houslay et al., "Tailoring cAMP-Signalling Responses Through Isoform Multiplicity", TiBS 22:217-224 (1997).

DNA BLAST Analysis Against NUC, PrevPatent Databases.

Protein BLAST Analysis Against PNU, Patent Databases.

Pitts, William J., et al., "Identification of Purine Inhibitors of Phosphodiesterase 7 (PDE7)", Bioorganic & Medicinal Chemistry Letters 14:2955-2958 (2004).

Gardner, Clare et al., "Cloning and Characterization of the Human and Mouse PDE7B, a Novel cAMP-Specific Cyclic Nucleotide Phosphodiesterase", Biochemical and Biophysical Research Communications 272:186-192 (2000).

\* cited by examiner

SEQUENCE LISTING

<160> NUMBER OF SEQ ID NOS: 19

<210> SEQ ID NO 1
<211> LENGTH: 5353
<212> TYPE: DNA
<213> ORGANISM: Homo Sapien

<400> SEQUENCE: 1

```
aaagggaata agcttgcggc cgcccggttc ctgccatgcc cggcggcccc agtccccgca      60
gccccgcgcc tttgctgcgc cccctcctcc tgctcctctg cgctctggct cccggcgccc     120
ccggacccgc accaggacgt gcaaccgagg gccggcggc actggacatc gtgcacccgg      180
ttcgagtcga cgcgggggc tccttcctgt cctacgagct gtggcccgc gcactgcgca       240 agcgggatgt atctgtgcgc cgagacgcgc ccgccttcta cgagctacaa taccgcgggc     300
gcgagctgcg cttcaacctg accgccaatc agcacctgct ggcgcccggc tttgtgagcg     360
agacgcggcg gcgcggcggc ctgggccgcg cgcacatccg ggcccacacc ccggcctgcc     420
acctgcttgg cgaggtgcag gaccctgagc tcgagggtgg cctggcggcc atcagcgcct    480
gcgacggcct gaaaggtgtg ttccaactct ccaacgagga ctacttcatt gagcccctgg    540
acagtgcccc ggcccggcct ggccacgccc agccccatgt ggtgtacaag cgtcaggccc    600
cggagaggct ggcacagcgg ggtgattcca gtgctccaag cacctgtgga gtgcaagtgt     660
acccagagct ggagtctcga cgggagcgtt gggagcagcg gcagcagtgg cggcggccac    720
ggctgaggcg tctacaccag cggtcggtca gcaaagagaa gtgggtggag accctggtag    780
tagctgatgc caaaatggtg gagtaccacg dacagccgca ggttgagagc tatgtgctga    840
ccatcatgaa catggtggct ggcctgtttc atgacccagc cattgggaac cccatccaca    900
tcaccattgt gcgcctggtc ctgctggaag atgaggagga ggacctaaag atcacgcacc    960
atgcagacaa caccctgaag agcttctgca agtggcagaa aagcatcaac atgaagggg     1020 atgcccatcc cctgcaccat gacactgcca tcctgctcac cagaaaggac ctgtgtgcag    1080
ccatgaaccg gccctgtgag accctgggac tgtcccatgt ggcgggcatg tgccagccgc    1140
accgcagctg cagcatcaac gaggacacgg gcctgccgct ggccttcact gtagcccacg    1200
agctcgggca cagttttggc attcagcatg acggaagcgg caatgactgt gagcccgttg    1260
ggaaacgacc tttcatcatg tctccacagc tcctgtacga cgccgctccc ctcacctggt    1320
cccgctgcag ccgccagtat atcaccaggt tccttgaccg tgggtgggc ctgtgcctgg     1380 acgaccctcc tgccaaggac attatcgact tccccctcgg t gccacctggc gtcctctatg   1440
```

```
atgtaagcca ccagtgccgc ctccagtacg gggcctactc tgccttctgc gaggacatgg    1500
ataatgtctg ccacacactc tggtgctctg tggggaccac ctgtcactcc aagctggatg    1560
cagccgtgga cggcacccgg tgtggggaga ataagtggtg tctcagtggg gagtgcgtac    1620
ccgtgggctt ccggcccgag gccgtggatg gtggctggtc tggctggagc gcctggtcca    1680
tctgctcacg gagctgtggc atgggcgtac agagcgccga gcggcagtgc acgcagccta    1740
cgcccaaata caaaggcaga tactgtgtgg gtgagcgcaa gcgcttccgc ctctgcaacc    1800
tgcaggcctg ccctgctggc crccctcct tccgccacgt ccagtgcagc cactttgacg    1860
ctatgctcta caagggccag ctgcacacat gggtgcccgt ggtcaatgac gtgaacccct    1920
gcgagctgca ctgccggccc gcgaatgagt actttgccga aagctgcgg gacgccgtgg    1980 tcgatggcac cccctgctac caggtccgag ccagccggga cctctgcatc aacggcatct    2040
gtaagaacgt gggctgtgac ttcgagattg actccggtgc tatggaggac cgctgtggtg    2100
tgtgccacgg caacgctcc acctgccaca ccgtgagcgg gaccttcgag gaggccgagg    2160
gcctggggta tgtggatgtg gggctgatcc cagccggcgc acgcgagatc cgcatccaag    2220
aggttgccga ggctgccaac ttcctggcac tgcggagtga ggacccggag aagtacttcc    2280
tcaatggtgg ctggaccatc cagtggaacg gggactacca ggtggcaggg accaccttca    2340
catacgcacg caggggcaac tgggagaacc tcacgtcccc gggtcccacc aaggagcctg    2400
tctggatcca gctgctgttc caggagagca accctggggt gcactacgag tacaccatcc    2460
acagggaggc aggtggccac gacgaggtcc gcccgcccgt gttctcctgg cattatgggc    2520
cctggaccaa gtgcacagtc acctgcggca gaggtgtgca gaggcagaat gtgtactgct    2580
tggagcggca ggcagggccc gtggacgagg agcactgtga cccctgggc cggcctgatg    2640 accaacagag gaagtgcagc gagcagccct gccctgccag gtggtgggca ggtgagtggc    2700
agctgtgctc cagctcctgc gggcctgggg gcctctcccg ccggccgtg ctctgcatcc    2760 gcagcgtggg gctggatgag cagagcgccc tggagccacc cgcctgtgaa caccttcccc    2820
ggccccctac tgaaaccccct tgcaaccgcc atgtaccctg tccggccacc tgggctgtgg    2880
ggaactggtc tcagtgctca gtgacatgtg gggagggcac tcagcgccga aatgtcctct    2940
gcaccaatga caccggtgtc ccctgtgacg aggcccagca gccagccagc gaagtcacct    3000
gctctctgcc actctgtcgg tggccctgg gcacactggg ccctgaaggc tcaggcagcg    3060
gctcctccag ccacgagctc ttcaacgagg ctgacttcat cccgcaccac ctggccccac    3120
gcccttcacc cgcctcatca cccaagccag gcaccatggg caacgccatt gaggaggagg    3180
ctccagagct ggacctgccg gggcccgtgt tgtggacga cttctactac gactacaatt    3240
tcatcaattt ccacgaggat ctgtcctacg ggccctctga ggagcccgat ctagacctgg    3300
cggggacagg ggaccggaca cccccaccac acagccgtcc tgctgcgccc tccacgggta    3360
gccctgtgcc tgccacagag cctcctgcag ccaaggagga gggggtactg ggaccttggt    3420
ccccgagccc ttggcctagc caggccggcc gctccccacc cccacccctca gagcagaccc    3480 ctgggaaccc tttgatcaat ttcctgcctg aggaagacac cccataggg gccccagatc    3540 ttgggctccc cagcctgtcc tggcccaggg tttccactga tggcctgcag acacctgcca    3600
cccctgagag ccaaaatgat ttcccagttg caaggacag ccagagccag ctgccccctc    3660
catggcggga caggaccaat gaggttttca aggatgatga ggaacccaag ggccgcggag    3720 cacccccacct gccccgaga cccagctcca cgctgccccc tttgtcccct gttggcagca    3780
cccactcctc tcctagtcct gacgtggcgg agctgtggac aggaggcaca gtggcctggg    3840
```

```
agccagctct ggagggtggc ctggggcctg tggacagtga actgtggccc actgttgggg    3900
tggcttctct ccttcctcct cccatagccc ctctgccaga gatgaaggtc agggacagtt    3960
ccctggagcc ggggactccc tccttcccag cccaggacc aggctcatgg gacctgcaga    4020
ctgtggcagt gtgggggacc ttcctcccca aaccctgac tggcctcggg cacatgcctg    4080
agcctgccct gaacccagga cccaagggtc agcctgagtc cctcacccct gaggtgcccc    4140
tgagctctag gctgctgtcc acaccagctt gggacagccc cgccaacagc cacagagtcc    4200
ctgagaccca gccgctggct cccagcctgg ctgaagcggg gccccccgcg gacccgttgg    4260
ttgtcaggaa cgccagctgg caagcgggaa actggagcga gtgctctacc acctgtggcc    4320
tgggtgcggt ctggaggccg gtgcgctgta gctccggccg ggatgaggac tgcgcccccg    4380
ctggccggcc ccagcctgcc cgccgctgcc acctacggcc ctgtgccacc tggcactcag    4440
gcaactggag taagtgctcc cgcagctgcg acggaggttc ctcagtgcgg acgtgcagt    4500 gtgtggacac acgggacctc cggccactgc ggcccttcca ttgtcagccc gggcctgcca    4560
agccgcatgc gcaccggccc tgcggggccc agcctgcct cagctggtac acatcttcct    4620
ggagggagtg ctccgaggcc tgtggcggtg gtgagcagca gcgtctagtg acctgcccgg    4680
agccaggcct ctgcgaggag cgctgagacc caacaccac ccggccctgc aacacccacc    4740
cctgcacgca gtgggtggtg gggccctggg gccagtgctc agcccctgt ggtggtggtg    4800 tccagcggcg cctggtcaag tgtgtcaaca cccagacagg gctgcccgag gaagacagtg    4860
accagtgtgg ccacgaggcc tggcctgaga gctcccggcc gtgtggcacc gaggattgtg    4920
agcccgtcga gcctccccgc tgtgagcggg accgcctgtc cttcgggttc tgcgagacgc    4980
tgcgcctact gggccgctgc cagctgcccca ccatccgcac ccagtgctgc cgctcgtgct    5040
ctccgcccag ccacggcgcc ccctcccgag gccatcagcg ggttgcccgc cgctgactgt    5100
gccaggatgc acagaccgac cgacagacct cagtgcccac cacgggctgt ggcggagctc    5160 ccgcccctg cgccctaatg gtgctaaccc cctctcacta cccagcagca ggctggggac    5220
ctcctccccc tcaaaaaagg tatttttta ttctaacagt ttgtgtaaca tttattatga    5280
ttttacataa atgagcatct accaaaaaaa aaaaaaagg gcggccgcta gactagtcta    5340
gagaaaaaac ctc                                                        5353
```

<210> SEQ ID NO 2
<211> LENGTH: 1686
<212> TYPE: PRT
<213> ORGANISM: Homo Sapien

<400> SEQUENCE: 2

Met Pro Gly Gly Pro Ser Pro Arg Ser Pro Ala Pro Leu Leu Arg Pro
1               5                   10                  15

Leu Leu Leu Leu Cys Ala Leu Ala Pro Gly Ala Pro Gly Pro Ala
            20                  25                  30

Pro Gly Arg Ala Thr Glu Gly Arg Ala Ala Leu Asp Ile Val His Pro
        35                  40                  45

Val Arg Val Asp Ala Gly Gly Ser Phe Leu Ser Tyr Glu Leu Trp Pro
    50                  55                  60

Arg Ala Leu Arg Lys Arg Asp Val Ser Val Arg Asp Ala Pro Ala
65                  70                  75                  80

Phe Tyr Glu Leu Gln Tyr Arg Gly Arg Glu Leu Arg Phe Asn Leu Thr
                85                  90                  95

-continued

```
Ala Asn Gln His Leu Ala Pro Gly Phe Val Ser Glu Thr Arg Arg
            100                 105                 110

Arg Gly Gly Leu Gly Arg Ala His Ile Arg Ala His Thr Pro Ala Cys
        115                 120                 125

His Leu Leu Gly Glu Val Gln Asp Pro Glu Leu Glu Gly Gly Leu Ala
        130                 135                 140

Ala Ile Ser Ala Cys Asp Gly Leu Lys Gly Val Phe Gln Leu Ser Asn
145                 150                 155                 160

Glu Asp Tyr Phe Ile Glu Pro Leu Asp Ser Ala Pro Ala Arg Pro Gly
                165                 170                 175

His Ala Gln Pro His Val Val Tyr Lys Arg Gln Ala Pro Glu Arg Leu
        180                 185                 190

Ala Gln Arg Gly Asp Ser Ser Ala Pro Ser Thr Cys Gly Val Gln Val
        195                 200                 205

Tyr Pro Glu Leu Glu Ser Arg Arg Glu Arg Trp Glu Gln Arg Gln Gln
        210                 215                 220

Trp Arg Arg Pro Arg Leu Arg Arg Leu His Gln Arg Ser Val Ser Lys
225                 230                 235                 240

Glu Lys Trp Val Glu Thr Leu Val Val Ala Asp Ala Lys Met Val Glu
                245                 250                 255

Tyr His Gly Gln Pro Gln Val Glu Ser Tyr Val Leu Thr Ile Met Asn
        260                 265                 270

Met Val Ala Gly Leu Phe His Asp Pro Ser Ile Gly Asn Pro Ile His
        275                 280                 285

Ile Thr Ile Val Arg Leu Val Leu Leu Glu Asp Glu Glu Asp Leu
        290                 295                 300

Lys Ile Thr His His Ala Asp Asn Thr Leu Lys Ser Phe Cys Lys Trp
305                 310                 315                 320

Gln Lys Ser Ile Asn Met Lys Gly Asp Ala His Pro Leu His His Asp
                325                 330                 335

Thr Ala Ile Leu Leu Thr Arg Lys Asp Leu Cys Ala Ala Met Asn Arg
        340                 345                 350

Pro Cys Glu Thr Leu Gly Leu Ser His Val Ala Gly Met Cys Gln Pro
        355                 360                 365

His Arg Ser Cys Ser Ile Asn Glu Asp Thr Gly Leu Pro Leu Ala Phe
        370                 375                 380

Thr Val Ala His Glu Leu Gly His Ser Phe Gly Ile Gln His Asp Gly
385                 390                 395                 400

Ser Gly Asn Asp Cys Glu Pro Val Gly Lys Arg Pro Phe Ile Met Ser
                405                 410                 415

Pro Gln Leu Leu Tyr Asp Ala Ala Pro Leu Thr Trp Ser Arg Cys Ser
        420                 425                 430

Arg Gln Tyr Ile Thr Arg Phe Leu Asp Arg Gly Trp Gly Leu Cys Leu
        435                 440                 445

Asp Asp Pro Pro Ala Lys Asp Ile Ile Asp Phe Pro Ser Val Pro Pro
450                 455                 460

Gly Val Leu Tyr Asp Val Ser His Gln Cys Arg Leu Gln Tyr Gly Ala
465                 470                 475                 480

Tyr Ser Ala Phe Cys Glu Asp Met Asp Asn Val Cys His Thr Leu Trp
                485                 490                 495

Cys Ser Val Gly Thr Thr Cys His Ser Lys Leu Asp Ala Ala Val Asp
        500                 505                 510

Gly Thr Arg Cys Gly Glu Asn Lys Trp Cys Leu Ser Gly Glu Cys Val
```

-continued

```
                515                 520                 525
Pro Val Gly Phe Arg Pro Glu Ala Val Asp Gly Gly Trp Ser Gly Trp
    530                 535                 540
Ser Ala Trp Ser Ile Cys Ser Arg Ser Cys Gly Met Gly Val Gln Ser
545                 550                 555                 560
Ala Glu Arg Gln Cys Thr Gln Pro Thr Pro Lys Tyr Lys Gly Arg Tyr
                565                 570                 575
Cys Val Gly Glu Arg Lys Arg Phe Arg Leu Cys Asn Leu Gln Ala Cys
            580                 585                 590
Pro Ala Gly Arg Pro Ser Phe Arg His Val Gln Cys Ser His Phe Asp
        595                 600                 605
Ala Met Leu Tyr Lys Gly Gln Leu His Thr Trp Val Pro Val Val Asn
    610                 615                 620
Asp Val Asn Pro Cys Glu Leu His Cys Arg Pro Ala Asn Glu Tyr Phe
625                 630                 635                 640
Ala Glu Lys Leu Arg Asp Ala Val Asp Gly Thr Pro Cys Tyr Gln
                645                 650                 655
Val Arg Ala Ser Arg Asp Leu Cys Ile Asn Gly Ile Cys Lys Asn Val
            660                 665                 670
Gly Cys Asp Phe Glu Ile Asp Ser Gly Ala Met Glu Asp Arg Cys Gly
        675                 680                 685
Val Cys His Gly Asn Gly Ser Thr Cys His Thr Val Ser Gly Thr Phe
    690                 695                 700
Glu Glu Ala Glu Gly Leu Gly Tyr Val Asp Val Gly Leu Ile Pro Ala
705                 710                 715                 720
Gly Ala Arg Glu Ile Arg Ile Gln Glu Val Ala Glu Ala Ala Asn Phe
                725                 730                 735
Leu Ala Leu Arg Ser Glu Asp Pro Glu Lys Tyr Phe Leu Asn Gly Gly
            740                 745                 750
Trp Thr Ile Gln Trp Asn Gly Asp Tyr Gln Val Ala Gly Thr Thr Phe
        755                 760                 765
Thr Tyr Ala Arg Arg Gly Asn Trp Glu Asn Leu Thr Ser Pro Gly Pro
    770                 775                 780
Thr Lys Glu Pro Val Trp Ile Gln Leu Leu Phe Gln Glu Ser Asn Pro
785                 790                 795                 800
Gly Val His Tyr Glu Tyr Thr Ile His Arg Glu Ala Gly His Asp
                805                 810                 815
Glu Val Pro Pro Val Phe Ser Trp His Tyr Gly Pro Trp Thr Lys
        820                 825                 830
Cys Thr Val Thr Cys Gly Arg Gly Val Gln Arg Gln Asn Val Tyr Cys
    835                 840                 845
Leu Glu Arg Gln Ala Gly Pro Val Asp Glu His Cys Asp Pro Leu
850                 855                 860
Gly Arg Pro Asp Asp Gln Arg Lys Cys Ser Glu Gln Pro Cys Pro
865                 870                 875                 880
Ala Arg Trp Trp Ala Gly Glu Trp Gln Leu Cys Ser Ser Cys Gly
                885                 890                 895
Pro Gly Gly Leu Ser Arg Arg Ala Val Leu Cys Ile Arg Ser Val Gly
            900                 905                 910
Leu Asp Glu Gln Ser Ala Leu Glu Pro Pro Ala Cys Glu His Leu Pro
        915                 920                 925
Arg Pro Pro Thr Glu Thr Pro Cys Asn Arg His Val Pro Cys Pro Ala
    930                 935                 940
```

```
Thr Trp Ala Val Gly Asn Trp Ser Gln Cys Ser Val Thr Cys Gly Glu
945                 950                 955                 960

Gly Thr Gln Arg Arg Asn Val Leu Cys Thr Asn Asp Thr Gly Val Pro
                965                 970                 975

Cys Asp Glu Ala Gln Gln Pro Ala Ser Glu Val Thr Cys Ser Leu Pro
            980                 985                 990

Leu Cys Arg Trp Pro Leu Gly Thr Leu Gly Pro Glu Gly Ser Gly Ser
        995                 1000                1005

Gly Ser Ser His Glu Leu Phe Asn Glu Ala Asp Phe Ile Pro His
    1010                1015                1020

His Leu Ala Pro Arg Pro Ser Pro Ala Ser Ser Pro Lys Pro Gly Thr
1025                1030                1035                1040

Met Gly Asn Ala Ile Glu Glu Glu Ala Pro Glu Leu Asp Leu Pro Gly
                1045                1050                1055

Pro Val Phe Val Asp Asp Phe Tyr Tyr Asp Tyr Asn Phe Ile Asn Phe
                1060                1065                1070

His Glu Asp Leu Ser Tyr Gly Pro Ser Glu Glu Pro Asp Leu Asp Leu
                1075                1080                1085

Ala Gly Thr Gly Asp Arg Thr Pro Pro His Ser Arg Pro Ala Ala
    1090                1095                1100

Pro Ser Thr Gly Ser Pro Val Pro Ala Thr Glu Pro Pro Ala Ala Lys
1105                1110                1115                1120

Glu Glu Gly Val Leu Gly Pro Trp Ser Pro Ser Pro Trp Pro Ser Gln
                1125                1130                1135

Ala Gly Arg Ser Pro Pro Pro Ser Glu Gln Thr Pro Gly Asn Pro
    1140                1145                1150

Leu Ile Asn Phe Leu Pro Glu Glu Asp Thr Pro Ile Gly Ala Pro Asp
                1155                1160                1165

Leu Gly Leu Pro Ser Leu Ser Trp Pro Arg Val Ser Thr Asp Gly Leu
                1170                1175                1180

Gln Thr Pro Ala Thr Pro Glu Ser Gln Asn Asp Phe Pro Val Gly Lys
1185                1190                1195                1200

Asp Ser Gln Ser Gln Leu Pro Pro Pro Trp Arg Asp Arg Thr Asn Glu
                1205                1210                1215

Val Phe Lys Asp Asp Glu Glu Pro Lys Gly Arg Gly Ala Pro His Leu
                1220                1225                1230

Pro Pro Arg Pro Ser Ser Thr Leu Pro Pro Leu Ser Pro Val Gly Ser
            1235                1240                1245

Thr His Ser Ser Pro Ser Pro Asp Val Ala Glu Leu Trp Thr Gly Gly
    1250                1255                1260

Thr Val Ala Trp Glu Pro Ala Leu Glu Gly Leu Gly Pro Val Asp
1265                1270                1275                1280

Ser Glu Leu Trp Pro Thr Val Gly Val Ala Ser Leu Pro Pro
                1285                1290                1295

Ile Ala Pro Leu Pro Glu Met Lys Val Arg Asp Ser Ser Leu Glu Pro
            1300                1305                1310

Gly Thr Pro Ser Phe Pro Ala Pro Gly Pro Gly Ser Trp Asp Leu Gln
        1315                1320                1325

Thr Val Ala Val Trp Gly Thr Phe Leu Pro Thr Thr Leu Thr Gly Leu
    1330                1335                1340

Gly His Met Pro Glu Pro Ala Leu Asn Pro Gly Pro Lys Gly Gln Pro
1345                1350                1355                1360
```

-continued

Glu Ser Leu Thr Pro Glu Val Pro Leu Ser Ser Arg Leu Leu Ser Thr
            1365                1370                1375

Pro Ala Trp Asp Ser Pro Ala Asn Ser His Arg Val Pro Glu Thr Gln
        1380                1385                1390

Pro Leu Ala Pro Ser Leu Ala Glu Ala Gly Pro Ala Asp Pro Leu
    1395                1400                1405

Val Val Arg Asn Ala Ser Trp Gln Ala Gly Asn Trp Ser Glu Cys Ser
1410                1415                1420

Thr Thr Cys Gly Leu Gly Ala Val Trp Arg Pro Val Arg Cys Ser Ser
1425                1430                1435                1440

Gly Arg Asp Glu Asp Cys Ala Pro Ala Gly Arg Pro Gln Pro Ala Arg
            1445                1450                1455

Arg Cys His Leu Arg Pro Cys Ala Thr Trp His Ser Gly Asn Trp Ser
            1460                1465                1470

Lys Cys Ser Arg Ser Cys Gly Gly Gly Ser Ser Val Arg Asp Val Gln
            1475                1480                1485

Cys Val Asp Thr Arg Asp Leu Arg Pro Leu Arg Pro Phe His Cys Gln
1490                1495                1500

Pro Gly Pro Ala Lys Pro Pro Ala His Arg Pro Cys Gly Ala Gln Pro
1505                1510                1515                1520

Cys Leu Ser Trp Tyr Thr Ser Ser Trp Arg Glu Cys Ser Glu Ala Cys
            1525                1530                1535

Gly Gly Gly Glu Gln Gln Arg Leu Val Thr Cys Pro Glu Pro Gly Leu
            1540                1545                1550

Cys Glu Glu Ala Leu Arg Pro Asn Thr Thr Arg Pro Cys Asn Thr His
        1555                1560                1565

Pro Cys Thr Gln Trp Val Val Gly Pro Trp Gly Gln Cys Ser Ala Pro
    1570                1575                1580

Cys Gly Gly Gly Val Gln Arg Arg Leu Val Lys Cys Val Asn Thr Gln
1585                1590                1595                1600

Thr Gly Leu Pro Glu Glu Asp Ser Asp Gln Cys Gly His Glu Ala Trp
            1605                1610                1615

Pro Glu Ser Ser Arg Pro Cys Gly Thr Glu Asp Cys Glu Pro Val Glu
            1620                1625                1630

Pro Pro Arg Cys Glu Arg Asp Arg Leu Ser Phe Gly Phe Cys Glu Thr
            1635                1640                1645

Leu Arg Leu Leu Gly Arg Cys Gln Leu Pro Thr Ile Arg Thr Gln Cys
    1650                1655                1660

Cys Arg Ser Cys Ser Pro Pro Ser His Gly Ala Pro Ser Arg Gly His
1665                1670                1675                1680

Gln Arg Val Ala Arg Arg
            1685

<210> SEQ ID NO 3
<211> LENGTH: 2662
<212> TYPE: DNA
<213> ORGANISM: Homo Sapien
<220> FEATURE:
<221> NAME/KEY: misc_feature
<222> LOCATION: (1)...(2662)
<223> OTHER INFORMATION: n = A,T,C or G

<400> SEQUENCE: 3
ggagggcctg aagagacagg gaggttgtgc caggctggag gaggcttgtc tttccgaagc      60
tggagaggat cttacggggg ttcgcttttc cctgcctggg aagaatttcc cctgtggtag     120

-continued

```
cagcagcagc agcagcagaa gcagaaacag cagcagcagc aacagcagca gcagcagcag      180
caccaccacc accactacct cctcttctgg ggcacaagac agaatgcctg tgctagagcg      240
atatttccac ccagcagagc taggcaggag gtggacaggc ccagaaggtg tgctgccctc      300
ctccccggga agccggccgg ggtgccagca ggggccgctg ccctgggact tgccagagat      360
gatcaggatg gtaaagctgg tttggaaatc caaaagtgag ctgcaggcga ccaaacagag      420
aggcattctg gacaatgaag atgctctccg cagctttcca ggagatatac gactaagggg      480
tcagacgggg gttcgtgctg aacgccgtgg ctcctaccca ttcattgact tccgcctact      540
taacagtaca acatactcag gggagattgg caccaagaaa aaggtgaaaa gactattaag      600
ctttcaaaga tacttccatg catcaaggct gcttcgtgga attataccac aagcccctct      660
gcacctgctg gatgaagact accttggaca agcaaggcat atgctctcca agtgggaat       720 gtgggatttt gacatttct tgtttgatcg cttgacaaat ggaaacagcc tggtaacact        780
gttgtgccac ctcttcaata cccatggact cattcaccat ttcaagttag atatggtgac      840
cttacaccga ttttagtca tggttcaaga agattaccac agccaaaacc cgtatcacaa       900
tgctgttcac gcagccgacg tcacccaggc catgcactgc tacctgaaag agccaaagct      960
tgccagcttc ctcacgcctc tggacatcat gcttggactg ctggctgcag cagcacacga     1020
tgtgaccacc ccaggggtga accagccatt tttgataaaa actaaccacc atcttgcaaa     1080
cctatatcag aatatgtctg tgctggagaa tcatcactgg cgatctacaa ttggcatgct     1140
tcgagaatca aggcttcttg ctcatttgcc aaaggaaatg acacaggata ttgaacagca     1200
gctgggctcc ttgatcttgg caacagacat caacaggcag aatgaatttt tgaccagatt     1260
gaaagctcac ctcccacaata aagacttaag actggaggat gcacaggaca ggcactttat    1320
gcttcagatc gcccttgaagt gtgctgacat ttgcaatcct tgtagaatct gggagatgag     1380
caagcagtgg agtgaaaggg tctgtgaaga attctacagg caaggtgaac ttgaacagaa     1440
atttgaactg gaaatcagtc ctctttgtaa tcaacagaaa gattccatcc ctagtataca     1500
aattggtttc atgagctaca tcgtggagcc gctcttccgg aatgggccc atttcacggg       1560 taacagcacc ctgtcggaga acatgctggg ccacctcgca cacaacaagg cccagtggaa     1620
gagcctgttg cccaggcagc acagaagcag gggcagcagt ggcagcgggc ctgaccacga     1680
ccacgcaggc caagggactg agagcgagga gcaggaaggc gacagcccct aggggccggc     1740
ccaacttaga cgcggctctc ctccggcagg gcccccagag ggcagaagca gcgtggaggg    1800
gccctcacgc agcagcccag ccactttctg agtgttgtcc tggggctctt tggaacgcca     1860
tcttcctccc acttacctgc ctcccctcct tttcgcaaat gtacagaagc catttgtcac     1920
ctcagcattc gctgccgaaa tgagcaactc cattcagtaa cgtgggagct gatcccacgg     1980
gcaggctctc cctgctccag gagaagacta ggaggaagaa tgaggtgctc ctgccgtgtc     2040
cgccttgttc cgggtcgcac tggaacaggc agcaattcct aagtccggag cgtttgagcg     2100
tttgctatct gactgctgat ctgcgtgaca gaaacaccag catatttgca acgccaagga    2160
tattggtctt aagtgcaaga gcacaaatga gagtgtgaga gaaagkacct tctattttaa     2220
taataatatt attataaaaa taataaatct ttttaacttt tatattttat gcactagnca     2280
atggatctgc aactttggac taaggtcatt caatgtaccc aaacttgaac aggggttca     2340 ttgttttgct attgacttta ttatgccact ttggggcaga gacttggcat cttcgcagtt    2400
taagaaacca cgtttcctat ccaatccgaa gggaaggtgc tgtacagttc attcctttgc     2460
accattagcc aatctgtctt ttatggattc tgtgacatgt ttatattcac ccatgtacat     2520
```

-continued

```
tttctgtaaa taccaaacgg ctactgattc ccatgccaaa atacatgagt attatgggat   2580
tgctacctgt ataaacaatg gcactgtgaa atactgtta gttttaatac aanagaatgc    2640
atttgtaaaa aaaaaaaaaa aa                                            2662
```

<210> SEQ ID NO 4
<211> LENGTH: 502
<212> TYPE: PRT
<213> ORGANISM: Homo Sapien

<400> SEQUENCE: 4

```
Met Pro Val Leu Glu Arg Tyr Phe His Pro Ala Glu Leu Gly Arg Arg
 1               5                  10                  15

Trp Thr Gly Pro Glu Gly Val Leu Pro Ser Ser Pro Gly Ser Arg Pro
            20                  25                  30

Gly Cys Gln Gln Gly Pro Leu Pro Trp Asp Leu Pro Glu Met Ile Arg
        35                  40                  45

Met Val Lys Leu Val Trp Lys Ser Lys Ser Glu Leu Gln Ala Thr Lys
    50                  55                  60

Gln Arg Gly Ile Leu Asp Asn Glu Asp Ala Leu Arg Ser Phe Pro Gly
65                  70                  75                  80

Asp Ile Arg Leu Arg Gly Gln Thr Gly Val Arg Ala Glu Arg Arg Gly
                85                  90                  95

Ser Tyr Pro Phe Ile Asp Phe Arg Leu Leu Asn Ser Thr Thr Tyr Ser
            100                 105                 110

Gly Glu Ile Gly Thr Lys Lys Val Lys Arg Leu Leu Ser Phe Gln
        115                 120                 125

Arg Tyr Phe His Ala Ser Arg Leu Leu Arg Gly Ile Ile Pro Gln Ala
    130                 135                 140

Pro Leu His Leu Leu Asp Glu Asp Tyr Leu Gly Gln Ala Arg His Met
145                 150                 155                 160

Leu Ser Lys Val Gly Met Trp Asp Phe Asp Ile Phe Leu Phe Asp Arg
                165                 170                 175

Leu Thr Asn Gly Asn Ser Leu Val Thr Leu Leu Cys His Leu Phe Asn
            180                 185                 190

Thr His Gly Leu Ile His His Phe Lys Leu Asp Met Val Thr Leu His
        195                 200                 205

Arg Phe Leu Val Met Val Gln Glu Asp Tyr His Ser Gln Asn Pro Tyr
    210                 215                 220

His Asn Ala Val His Ala Ala Asp Val Thr Gln Ala Met His Cys Tyr
225                 230                 235                 240

Leu Lys Glu Pro Lys Leu Ala Ser Phe Leu Thr Pro Leu Asp Ile Met
                245                 250                 255

Leu Gly Leu Leu Ala Ala Ala His Asp Val Asp His Pro Gly Val
            260                 265                 270

Asn Gln Pro Phe Leu Ile Lys Thr Asn His His Leu Ala Asn Leu Tyr
        275                 280                 285

Gln Asn Met Ser Val Leu Glu Asn His His Trp Arg Ser Thr Ile Gly
    290                 295                 300

Met Leu Arg Glu Ser Arg Leu Leu Ala His Leu Pro Lys Glu Met Thr
305                 310                 315                 320

Gln Asp Ile Glu Gln Gln Leu Gly Ser Leu Ile Leu Ala Thr Asp Ile
                325                 330                 335

Asn Arg Gln Asn Glu Phe Leu Thr Arg Leu Lys Ala His Leu His Asn
```

-continued

```
              340                 345                 350
Lys Asp Leu Arg Leu Glu Asp Ala Gln Asp Arg His Phe Met Leu Gln
            355                 360                 365
Ile Ala Leu Lys Cys Ala Asp Ile Cys Asn Pro Cys Arg Ile Trp Glu
    370                 375                 380
Met Ser Lys Gln Trp Ser Glu Arg Val Cys Glu Phe Tyr Arg Gln
385                 390                 395                 400
Gly Glu Leu Glu Gln Lys Phe Glu Leu Glu Ile Ser Pro Leu Cys Asn
                405                 410                 415
Gln Gln Lys Asp Ser Ile Pro Ser Ile Gln Ile Gly Phe Met Ser Tyr
            420                 425                 430
Ile Val Glu Pro Leu Phe Arg Glu Trp Ala His Phe Thr Gly Asn Ser
            435                 440                 445
Thr Leu Ser Glu Asn Met Leu Gly His Leu Ala His Asn Lys Ala Gln
    450                 455                 460
Trp Lys Ser Leu Leu Pro Arg Gln His Arg Ser Arg Gly Ser Ser Gly
465                 470                 475                 480
Ser Gly Pro Asp His Asp His Ala Gly Gln Gly Thr Glu Ser Glu Glu
                485                 490                 495
Gln Glu Gly Asp Ser Pro
            500
```

<210> SEQ ID NO 5
<211> LENGTH: 3336
<212> TYPE: DNA
<213> ORGANISM: Homo Sapien
<220> FEATURE:
<221> NAME/KEY: misc_feature
<222> LOCATION: (1)...(3336)
<223> OTHER INFORMATION: n = A,T,C or G

<400> SEQUENCE: 5

```
gagggcctga agagacaggg aggttgtgcc aggctggagg aggcttgtct ttccgaagct      60
ggagaggatc ttacgggggt tcgcttttcc ctgcctggga agaatttccc ctgtggtagc     120
agcagcagca gcagcagaag cagaaacagc agcagcagca acagcagcag cagcagcagc     180
accaccacca ccactacctc ctcttctggg gcacaagaca gaatgcctgt gctagagcgc     240
tatttccacc cagcagagct aggcaggagg tggacaggcc cagaaggtgt gctgccctcc     300
tccccgggaa gccggccggg gtgccagcag gggccgctgc cctgggactt gccagagatg     360
atcaggatgg taaagctggt ttggaaatcc aaaagtgagc tgcaggcgac caaacagaga     420
ggcattctgg acaatgaaga tgctctccgc agctttccag gagatatacg actaaggggt     480
cagacggggg ttcgtgctga acgccgtggc tcctacccat tcattgactt ccgcctactt     540
aacagtacaa catactcagg ggagattggc accaagaaaa aggtgaaaag actattaagc     600
tttcaaagat acttccatgc atcaaggctg cttcgtggaa ttataccaca gcccctctg     660
cacctgctgg atgaagacta ccttggacaa gcaaggcata tgctctccaa agtgggaatg     720
tgggatttttg acatttttctt gtttgatcgc ttgacaaatg gaaacagcct ggtaacactg     780
ttgtgccacc tcttcaatac ccatggactc attcaccatt tcaagttaga tatggtgacc     840
ttacaccgat ttttagtcat ggttcaagaa gattaccaca gccaaaaccc gtatcacaat     900
gctgttcacg cagccgacgt cacccaggcc atgcactgct acctgaaaga gccaaagctt     960
gccagcttcc tcacgcctct ggacatcatg cttggactgc tggctgcagc agcacacgat    1020
gtggaccacc caggggtgaa ccagccattt ttgataaaaa ctaaccacca tcttgcaaac    1080
```

```
ctatatcaga atatgtctgt gctggagaat catcactggc gatctacaat tggcatgctt    1140
cgagaatcaa ggcttcttgc tcatttgcca aggaaatga cgtaagtgct gccgagatga    1200
aacatactga tgtgcatgca gtaaagataa gccactttct ctagggcagg cttgggacct    1260
tttgcgtgaa tggcagagag ccccccggct gtacttcctg cctgcactga gctgtctatc    1320
agaggagatt tggtgtcagt tacagcaacc cagaaaccaa aatctctctg tgtgctttga    1380
aagggccttg cagagtcaat gacctacagt caggaaaagg gataataaac agctctcagt    1440
tttcacacgc ttcagtatca gtgctcgact ttgccaaatt cccgaccttt agtttagcaa    1500
aattgtcctt ccatgtagct ccaaatagta aatatttatc aagaaggaac ccaggcattc    1560
taaagctaga gttcaaaaaa gtatattttg taattgctag tctcagcaaa aatagaagtc    1620
agaaattctt ttctaaaatg tcttttgcta agtaattgaa atggccctag cattttttc     1680 accaattaat ttaccttacg tctcttgcac tttaaacaga aggggagaca ctcattttct    1740
ggttcactat ttgatagcca tggtatgtag gctgagtccc actaaatctg aggccattgt    1800
ttcattttcc tggtggcccc aagttagctg ctaaatactgt cttccaaggc caccattaat    1860
tctgatctgt ttaatgaaca cgtgcagaac ccaagaaacc taggtgaaaa gagtacatag    1920
attgctgtac ccttcttcaa gacaagcaca taacttgagg tcaaggacca agtgctgtct    1980
cccaactgaa caagcagtat actctgggtt gtggattgat tcctggccct ctgatttgat    2040
ctcatgctgt ttcctagcac ccagaggaat gtgaaatttg caggaggaat ttcagttctg    2100
ataaattttt actccctgga actaaataaa accagttctc gtgcatggaa taaaaactta    2160
tgcctcttac tagaataata aattgcaaag attgaaagaa ttaaatgcaa aaagaactaa    2220
aaactagagc aaaagatcaa gtgagaagaa gaaaagagga ggtaaggaga gagacaagga    2280
agaaagaagg agaaggaaag gaagaatagt gaggacagga agaagaaaa tgcaagggaa     2340 atgggaaagg actctggggt gaccagactt ctcctggtca gtacctgcat tcatcctgtt    2400
tgttactcaa tatttctttc ctaaaatatt catttcacat ctatggattc caatgaaaaa    2460 tatatttta tgtgtctttg tggaacacag tgttataaat tgttttgcc agaagaataa       2520 ttgttataca ataatatatg tgaaaacttt attacaaaag ccattatcat aatcattatt    2580
attccttcta tcacaggtaa atgctttaat gtcatttttc tgattttaaa agtagggcag    2640
gttaattgta gaaagtaagg aaaattcagg aaagtgttag tttgaactat gtgaagttgc    2700
tctttttaag ggccaaaaac aggagacttt tagcactttc atatgtttca gcttgatatg    2760
aaagagaaaa ctgaaactgc tagtaatcct gccatccagg tatagttcat gttaacctgg    2820
ctagtttatt ttcttttagt cttttttcaa tacaaactta ttttaacaaa atatgattan    2880
atttggggaa cttatttac agtttacgtc ctgaaattt ttatttacaa taaagacttt       2940
tttccaaatc attaaacctg ttaaattaaa atgattttgt cagccgtatg gcattattgt    3000
ataccactac tgcctttcat ttggaattca aatggtttcc aatatcccaa actttgatac    3060
tctgttttct caggaagtat ttgtagataa aaattattgg tcagaaaggt ctgaactttt    3120
aagtttcttg tatattatcc agttgttctt ctaaaaggct gtatctacct gtattccaac    3180
tgatggattg taagaaaatg taccaatgta ccatcaccaa aattgagttt attttatct    3240 ttttaaaata tttgcaaatt tgacatatat gtatgtatat acacaaatat atatgtaaag    3300
tggttttcat taaattagta tgcatccttt acttac                              3336
```

<210> SEQ ID NO 6

<211> LENGTH: 320
<212> TYPE: PRT
<213> ORGANISM: Homo Sapien

<400> SEQUENCE: 6

```
Met Pro Val Leu Glu Arg Tyr Phe His Pro Ala Glu Leu Gly Arg Arg
 1               5                  10                  15

Trp Thr Gly Pro Glu Gly Val Leu Pro Ser Ser Pro Gly Ser Arg Pro
            20                  25                  30

Gly Cys Gln Gln Gly Pro Leu Pro Trp Asp Leu Pro Glu Met Ile Arg
        35                  40                  45

Met Val Lys Leu Val Trp Lys Ser Lys Ser Glu Leu Gln Ala Thr Lys
 50                  55                  60

Gln Arg Gly Ile Leu Asp Asn Glu Asp Ala Leu Arg Ser Phe Pro Gly
 65                  70                  75                  80

Asp Ile Arg Leu Arg Gly Gln Thr Gly Val Arg Ala Glu Arg Arg Gly
                85                  90                  95

Ser Tyr Pro Phe Ile Asp Phe Arg Leu Leu Asn Ser Thr Thr Tyr Ser
            100                 105                 110

Gly Glu Ile Gly Thr Lys Lys Val Lys Arg Leu Leu Ser Phe Gln
        115                 120                 125

Arg Tyr Phe His Ala Ser Arg Leu Leu Arg Gly Ile Ile Pro Gln Ala
130                 135                 140

Pro Leu His Leu Leu Asp Glu Asp Tyr Leu Gly Gln Ala Arg His Met
145                 150                 155                 160

Leu Ser Lys Val Gly Met Trp Asp Phe Asp Ile Phe Leu Phe Asp Arg
                165                 170                 175

Leu Thr Asn Gly Asn Ser Leu Val Thr Leu Leu Cys His Leu Phe Asn
            180                 185                 190

Thr His Gly Leu Ile His His Phe Lys Leu Asp Met Val Thr Leu His
        195                 200                 205

Arg Phe Leu Val Met Val Gln Glu Asp Tyr His Ser Gln Asn Pro Tyr
    210                 215                 220

His Asn Ala Val His Ala Ala Asp Val Thr Gln Ala Met His Cys Tyr
225                 230                 235                 240

Leu Lys Glu Pro Lys Leu Ala Ser Phe Leu Thr Pro Leu Asp Ile Met
                245                 250                 255

Leu Gly Leu Leu Ala Ala Ala His Asp Val Asp His Pro Gly Val
            260                 265                 270

Asn Gln Pro Phe Leu Ile Lys Thr Asn His His Leu Ala Asn Leu Tyr
        275                 280                 285

Gln Asn Met Ser Val Leu Glu Asn His His Trp Arg Ser Thr Ile Gly
    290                 295                 300

Met Leu Arg Glu Ser Arg Leu Leu Ala His Leu Pro Lys Glu Met Thr
305                 310                 315                 320
```

<210> SEQ ID NO 7
<211> LENGTH: 2898
<212> TYPE: DNA
<213> ORGANISM: Homo Sapien

<400> SEQUENCE: 7

```
gcagcggcgg cggcggcggg gcctggagcc ggatctaaga tggcagcggc ggcagcggcg    60
gtggggccgg gcgcgggggg cgcggggtcg gcggtcccgg gcggcgcggg gccctgcgct   120
accgtgtcgg tgttccccgg cgcccgcctc ctcaccatcg gcgacgcgaa cggcgagatc   180
```

-continued

```
cagcggcacg cggagcagca ggcgctgcgc ctcgaggtgc gcgccggccc ggactcggcg    240
ggcatcgccc tctacagcca tgaagatgtg tgtgtcttta agtgctcagt gtcccgagag    300
acagagtgca gccgtgtggg caagcagtcc ttcatcatca ccctgggctg caacagcgtc    360
ctcatccagt tcgccacacc caacgatttc tgttccttct acaacatcct gaaaacctgc    420
cggggccaca ccctggagcg gtctgtgttc agcgagcgga cggaggagtc ttctgccgtg    480
cagtacttcc agttttatgg ctacctgtcc cagcagcaga acatgatgca ggactacgtg    540
cggacaggca cctaccagcg cgccatcctg caaaaccaca ccgacttcaa ggacaagatc    600
gttcttgatg ttggctgtgg ctctgggatc ctgtcgtttt ttgccgccca agctggagca    660
cggaaaatct acgcggtgga ggccagcacc atggcccagc acgctgaggt cttggtgaag    720
agtaacaacc tgacggaccg catcgtggtc atcccgggca aggtggagga ggtgtcactc    780
cccgagcagg tggacatcat catctcggag cccatgggct acatgctctt caacgagcgc    840
atgctggaga gctacctcca cgccaagaag tacctgaagc ccagcggaaa catgtttcct    900
accattggtg acgtccacct tgcacccttc acggatgaac agctctacat ggagcagttc    960
accaaggcca acttctggta ccagccatct ttccatggag tggacctgtc ggccctccga   1020
ggtgccgcgg tggatgagta tttccggcag cctgtggtgg acacatttga catccggatc   1080
ctgatggcca agtctgtcaa gtacacggtg aacttcttag aagccaaaga aggagatttg   1140
cacaggatag aaatcccatt caaattccac atgctgcatt cagggctggt ccacggcctg   1200
gctttctggt ttgacgttgc tttcatcggc tccataatga ccgtgtggct gtccacagcc   1260
ccgacagagc ccctgaccca ctggtaccag gtgcggtgcc tgttccagtc accactgttc   1320
gccaaggcag gggacacgct ctcagggaca tgtctgctta ttgccaacaa agacagagc   1380 tacgacatca gtattgtggc ccaggtggac cagaccggct ccaagtccag taacctcctg   1440
gatctgaaaa ccccttctt tagatacacg ggcacaacgc cctcacccccc acccggctcc   1500 cactacacat ctcccctcgga aaacatgtgg aacacgggca gcacctacaa cctcagcagc   1560
gggatggccg tggcagggat gccgaccgcc tatgacttga gcagtgttat tgccagtggc   1620
tccagcgtgg gccacaacaa cctgattcct ttagccaaca cggggattgt caatcacacc   1680
cactcccgga tgggctccat aatgagcacg gggattgtcc aagggtcctc cggcgcccag   1740
ggcagtggtg gtggcagcac gagtgcccac tatgcagtca acagccagtt caccatgggc   1800 ggcccccgcca tctccwtggc gtcgcccatg tccatcccga ccaacaccat gcactacggg   1860 agctagggc ccgccccgcg gactgacagc accaggaaac caaatgatgt ccctgcccgc   1920 cgccccgcc gggcggcttt ccccccttgta ctggagaagc tcgaacaccc ggtcacagct   1980
ctctttgcta tgggaactgg gacactttt tacacgatgt tgccgccgtc cccacccttaa   2040 cccccacctc ccgccctga gcgtgtgtcg ctgccatatt ttacacaaaa tcatgttgtg   2100
ggagccctcg tcccccctcc tgcccgctct accctgacct gggcttgtca tctgctggaa   2160
caggcgccat ggggcctgcc agccctgcct gccaggtccc ttagcacctg tcccctgcc   2220 tgtctccagt gggaaggtag cctggccagg cggggcctcc ccttcgacga ccaggcctcg   2280
gtcacaacgg acgtgacatg ctgctttttt taatttattt tttttatgaa agaaccagt   2340 gtcaatccgc agaccctctg tgaagccagg ccggccgggc cgagccagca gccctctcc   2400 ctagactcag aggcgccgcg gggagggtg gcccgccga ggcttcaggg gcccctccc   2460 caccaaaggg ttcacctcac acttgaatgt acaacccacc ccactgtcgg gaaggcctcc   2520
```

-continued

```
gtcctcggcc cctgcctctt gctgctgtcc tgtccccgag cccctgcagg tccccccccg    2580
cccccccact caagagttag agcaggtggc tgcaggcctt gggcccggag ggaaggccac    2640
tgccggccac ttgggcagaa cacagacacc tcaaggatct gtcacggaag gcgtcctttt    2700
tccttgtagc taacgttagg cctgagtagc tcccctccat ccttgtagac gctccagtcc    2760
ctactactgt gacggcattt ccatccctcc cctgcccggg aagggaccct gcagggacct    2820
ctccctccaa aaaaaaaaaa aaaaaaaaaa aaaaaaaaaa aaaagggsr aacgtgttgc     2880 aaaaaaaaaa aaaaaaaa                                                  2898
```

<210> SEQ ID NO 8
<211> LENGTH: 608
<212> TYPE: PRT
<213> ORGANISM: Homo Sapien
<220> FEATURE:
<221> NAME/KEY: VARIANT
<222> LOCATION: (1)...(608)
<223> OTHER INFORMATION: Xaa = Any Amino Acid

<400> SEQUENCE: 8

```
Met Ala Ala Ala Ala Ala Val Gly Pro Gly Ala Gly Gly Ala Gly
 1               5                  10                  15

Ser Ala Val Pro Gly Gly Ala Gly Pro Cys Ala Thr Val Ser Val Phe
                20                  25                  30

Pro Gly Ala Arg Leu Leu Thr Ile Gly Asp Ala Asn Gly Glu Ile Gln
                35                  40                  45

Arg His Ala Glu Gln Gln Ala Leu Arg Leu Glu Val Arg Ala Gly Pro
            50                  55                  60

Asp Ser Ala Gly Ile Ala Leu Tyr Ser His Glu Asp Val Cys Val Phe
 65                 70                  75                      80

Lys Cys Ser Val Ser Arg Glu Thr Glu Cys Ser Arg Val Gly Lys Gln
                    85                  90                  95

Ser Phe Ile Ile Thr Leu Gly Cys Asn Ser Val Leu Ile Gln Phe Ala
                100                 105                 110

Thr Pro Asn Asp Phe Cys Ser Phe Tyr Asn Ile Leu Lys Thr Cys Arg
                115                 120                 125

Gly His Thr Leu Glu Arg Ser Val Phe Ser Glu Arg Thr Glu Glu Ser
            130                 135                 140

Ser Ala Val Gln Tyr Phe Gln Phe Tyr Gly Tyr Leu Ser Gln Gln Gln
145                 150                 155                 160

Asn Met Met Gln Asp Tyr Val Arg Thr Gly Thr Tyr Gln Arg Ala Ile
                    165                 170                 175

Leu Gln Asn His Thr Asp Phe Lys Asp Lys Ile Val Leu Asp Val Gly
                180                 185                 190

Cys Gly Ser Gly Ile Leu Ser Phe Phe Ala Ala Gln Ala Gly Ala Arg
                195                 200                 205

Lys Ile Tyr Ala Val Glu Ala Ser Thr Met Ala Gln His Ala Glu Val
            210                 215                 220

Leu Val Lys Ser Asn Asn Leu Thr Asp Arg Ile Val Val Ile Pro Gly
225                 230                 235                 240

Lys Val Glu Glu Val Ser Leu Pro Glu Gln Val Asp Ile Ile Ile Ser
                    245                 250                 255

Glu Pro Met Gly Tyr Met Leu Phe Asn Glu Arg Met Leu Glu Ser Tyr
                260                 265                 270

Leu His Ala Lys Lys Tyr Leu Lys Pro Ser Gly Asn Met Phe Pro Thr
            275                 280                 285
```

-continued

Ile Gly Asp Val His Leu Ala Pro Phe Thr Asp Glu Gln Leu Tyr Met
     290                 295                 300
Glu Gln Phe Thr Lys Ala Asn Phe Trp Tyr Gln Pro Ser Phe His Gly
305                 310                 315                 320
Val Asp Leu Ser Ala Leu Arg Gly Ala Ala Val Asp Glu Tyr Phe Arg
                325                 330                 335
Gln Pro Val Val Asp Thr Phe Asp Ile Arg Ile Leu Met Ala Lys Ser
            340                 345                 350
Val Lys Tyr Thr Val Asn Phe Leu Glu Ala Lys Glu Gly Asp Leu His
        355                 360                 365
Arg Ile Glu Ile Pro Phe Lys Phe His Met Leu His Ser Gly Leu Val
    370                 375                 380
His Gly Leu Ala Phe Trp Phe Asp Val Ala Phe Ile Gly Ser Ile Met
385                 390                 395                 400
Thr Val Trp Leu Ser Thr Ala Pro Thr Glu Pro Leu Thr His Trp Tyr
                405                 410                 415
Gln Val Arg Cys Leu Phe Gln Ser Pro Leu Phe Ala Lys Ala Gly Asp
            420                 425                 430
Thr Leu Ser Gly Thr Cys Leu Leu Ile Ala Asn Lys Arg Gln Ser Tyr
        435                 440                 445
Asp Ile Ser Ile Val Ala Gln Val Asp Gln Thr Gly Ser Lys Ser Ser
    450                 455                 460
Asn Leu Leu Asp Leu Lys Asn Pro Phe Phe Arg Tyr Thr Gly Thr Thr
465                 470                 475                 480
Pro Ser Pro Pro Pro Gly Ser His Tyr Thr Ser Pro Ser Glu Asn Met
                485                 490                 495
Trp Asn Thr Gly Ser Thr Tyr Asn Leu Ser Ser Gly Met Ala Val Ala
            500                 505                 510
Gly Met Pro Thr Ala Tyr Asp Leu Ser Ser Val Ile Ala Ser Gly Ser
        515                 520                 525
Ser Val Gly His Asn Asn Leu Ile Pro Leu Ala Asn Thr Gly Ile Val
    530                 535                 540
Asn His Thr His Ser Arg Met Gly Ser Ile Met Ser Thr Gly Ile Val
545                 550                 555                 560
Gln Gly Ser Ser Gly Ala Gln Gly Ser Gly Gly Ser Thr Ser Ala
                565                 570                 575
His Tyr Ala Val Asn Ser Gln Phe Thr Met Gly Gly Pro Ala Ile Ser
            580                 585                 590
Xaa Ala Ser Pro Met Ser Ile Pro Thr Asn Thr Met His Tyr Gly Ser
        595                 600                 605

<210> SEQ ID NO 9
<211> LENGTH: 1824
<212> TYPE: DNA
<213> ORGANISM: Homo Sapien

<400> SEQUENCE: 9
atggcagcgg cggcagcggc ggtggggccg ggcgcggggg gcgcggggtc ggcggtcccg      60
ggcggcgcgg ggccctgcgc taccgtgtcg gtgttccccg cgcccgcct cctcaccatc     120 ggcgacgcga acggcgagat ccagcggcac gcggagcagc aggcgctgcg cctcgaggtg     180
cgcgccggcc cggactcggc gggcatcgcc ctctacagcc atgaagatgt gtgtgtcttt     240
aagtgctcag tgtcccgaga gacagagtgc agccgtgtgg gcaagcagtc cttcatcatc     300

|  |  |  |  |  |
|---|---|---|---|---|
| accctgggct | gcaacagcgt | cctcatccag | ttcgccacac | ccaacgattt ctgttccttc | 360 |
| tacaacatcc | tgaaaacctg | ccggggccac | acctggagcc | ggtctgtgtt cagcgagcgg | 420 |
| acggaggagt | cttctgccgt | gcagtacttc | cagtttttatg | gctacctgtc ccagcagcag | 480 |
| aacatgatgc | aggactacgt | gcggacaggc | acctaccagc | gcgccatcct gcaaaaccac | 540 |
| accgacttca | aggacaagat | cgttcttgat | gttggctgtg | gctctgggat cctgtcgttt | 600 |
| tttgccgccc | aagctggagc | acggaaaatc | tacgcggtgg | aggccagcac catggcccag | 660 |
| cacgctgagg | tcttggtgaa | gagtaacaac | ctgacggacc | gcatcgtggt catcccgggc | 720 |
| aaggtggagg | aggtgtcact | ccccgagcag | gtggacatca | tcatctcgga gcccatgggc | 780 |
| tacatgctct | caacgagcg | catgctggag | agctacctcc | acgccaagaa gtacctgaag | 840 |
| cccagcggaa | acatgtttcc | taccattggt | gacgtccacc | ttgcacccct cacggatgaa | 900 |
| cagctctaca | tggagcagtt | caccaaggcc | aacttctggt | accagccatc tttccatgga | 960 |
| gtggacctgt | cggccctccg | aggtgccgcg | gtggatgagt | atttccggca gcctgtggtg | 1020 |
| gacacatttg | acatccggat | cctgatggcc | aagtctgtca | gtacacggt gaacttctta | 1080 |
| gaagccaaag | aaggagattt | gcacaggata | gaaatcccat | tcaaattcca catgctgcat | 1140 |
| tcagggctgg | tccacggcct | ggctttctgg | tttgacgttg | ctttcatcgg ctccataatg | 1200 |
| accgtgtggc | tgtccacagc | cccgacagag | cccctgaccc | actggtacca ggtgcggtgc | 1260 |
| ctgttccagt | caccactgtt | cgccaaggca | ggggacacgc | tctcagggac atgtctgctt | 1320 |
| attgccaaca | aaagacagag | ctacgacatc | agtattgtgg | cccaggtgga ccagaccggc | 1380 |
| tccaagtcca | gtaacctcct | ggatctgaaa | acccccttct | ttagatacac gggcacaacg | 1440 |
| ccctcacccc | cacccggctc | ccactacaca | tctcccctcgg | aaaacatgtg aacacgggc | 1500 |
| agcacctaca | acctcagcag | cgggatggcc | gtggcaggga | tgccgaccgc ctatgacttg | 1560 |
| agcagtgtta | ttgccagtgg | ctccagcgtg | gccacaaca | acctgattcc tttagccaac | 1620 |
| acggggattg | tcaatcacac | ccactcccgg | atgggctcca | taatgagcac ggggattgtc | 1680 |
| caagggtcct | ccggcgccca | gggcagtggt | ggtggcagca | cgagtgccca ctatgcagtc | 1740 |
| aacagccagt | tcaccatggg | cggccccgcc | atctccwtgg | cgtcgcccat gtccatcccg | 1800 |
| accaacacca | tgcactacgg | gagc |  |  | 1824 |

<210> SEQ ID NO 10  
<211> LENGTH: 2795  
<212> TYPE: DNA  
<213> ORGANISM: Homo Sapien

<400> SEQUENCE: 10

|  |  |  |  |  |
|---|---|---|---|---|
| cggggacatg | aggtggatac | tgttcattgg | ggcccttatt | gggtccagca tctgtggccg | 60 |
| agaaaaattt | tttgggggacc | aagttttgag | gattaatgtc | agaaatggag acgagatcag | 120 |
| caaattgagt | caactagtga | attcaaacaa | cttgaagctc | aatttctgga atctcccctc | 180 |
| ctccttcaat | cggcctgtgg | atgtcctggt | cccatctgtc | agtctgcagg catttaaatc | 240 |
| cttcctgaga | tccagggct | tagagtacgc | agtgacaatt | gaggacctgc aggcccttt | 300 |
| agacaatgaa | gatgatgaaa | tgcaacacaa | tgaagggcaa | gaacggagca gtaataactt | 360 |
| caactacggg | gcttaccatt | ccctggaagc | tatttaccac | gagatggaca cattgccgc | 420 |
| agactttcct | gacctggcga | ggagggtgaa | gattggacat | tcgtttgaaa accggccgat | 480 |
| gtatgtactg | aagttcagca | ctgggaaagg | cgtgaggcgg | ccggccgttt ggctgaatgc | 540 |
| aggcatccat | tcccgagagt | ggatctccca | ggccactgca | atctggacgg caaggaagat | 600 |

-continued

```
tgtatctgat taccagaggg atccagctat cacctccatc ttggagaaaa tggatatttt      660
cttgttgcct gtggccaatc ctgatggata tgtgtatact caaactcaaa accgattatg      720
gaggaagacg cggtcccgaa atcctggaag ctcctgcatt ggtgctgacc caaatagaaa      780
ctggaacgct agttttgcag gaaagggagc cagcgacaac ccttgctccg aagtgtacca      840
tggaccccac gccaattcgg aagtggaggt gaaatcagtg gtagatttca tccaaaaaca      900
tgggaatttc aagggcttca tcgacctgca cagctactcg cagctgctga tgtatccata      960
tgggtactca gtcaaaaagg ccccagatgc cgaggaactc gacaaggtgg cgaggcttgc     1020
ggccaaagct ctggcttctg tgtcgggcac tgagtaccaa gtgggtccca cctgcaccac     1080
tgtctatcca gctagcggga gcagcatcga ctgggcgtat gacaacggca tcaaatttgc     1140
attcacattt gagttgagag ataccgggac ctatggcttc ctcctgccag ctaaccagat     1200
catcccccact gcagaggaga cgtggctggg gctgaagacc atcatggagc atgtgcggga    1260
caacctctac taggcgatgg ctctgctctg tctacattta tttgtaccca cacgtgcacg     1320
cactgaggcc attgttaaag gagctctttc ctacctgtgt gagtcagagc cctctgggtt     1380
tgtggagcac acaggcctgc ccctctccag ccagctccct ggagtcgtgt gtcctggcgg     1440
tgtccctgca agaactggtt ctgccagcct gctcaatttt ggtcctgctg tttttgatga     1500
gccttttgtc tgtttctcct tccaccctgc tggctgggcg gctgcactca gcatcacccc     1560
ttcctgggtg gcatgtctct ctctacctca ttttagaaac caaagaacat ctgagatgat     1620
tctctaccct cattcacatc tagccaagcc agtgaccttt gctctggtgg cactgtggga     1680
gacaccactt gtctttaggt gggtctcaaa gatgatgtag aatttccttt aatttctcgc     1740
agtcttcctg gaaatatttt cctttgagc agcaaatctt gtaggatat cagtgaaggt      1800
ctctccctcc ctcctctcct gttttttttt tttgaggcag agttttgctc ttgttgccca     1860
ggctggagtg tgatgggctc gatcttggct caccacaacc tctgcctcct gggttcaagc     1920
aattctcctg cctcagcctc ttgagtagct tggtttatag gcgcatgcca ccatgcctgg     1980
ctaattttgt gttttagta gagacagggt ttctccatgt tggtcaggct ggtctcaaac      2040
tcccaacctc aggtgatctg ccctccttgg cctcccagag tgctgggatt acaggggag      2100
ccactgtgcc ggtcccgtcc cctccttttt taggcctgaa tacaaagtag aagatcactt     2160
tccttcactg tgctgagaat ttctagatac tacagttctt actcctctct tcccttttgtt   2220
attcagtgtg accaggatgg gcgggagggg atctgtgtca ctgtaggtac tgtgcccagg     2280
aaggctgggt gaagtcccca tctaaattgc aggatggcga aattatcccc atctgtccta    2340
atgggcttcc ctcctcttg cctttgaac tcacttcaaa gatgtaggcc tcatcttaca       2400
ggtcctaaat cactcatctg gcctggataa tctcactgcc ctggcacatt cccatttgtg     2460
ctggggtatc ctgtgtttcc ttgtcctggt tgtgtgtgt gtgtgtgtgt gtgtgtgtgt     2520
gtgtgtgtgt ttgtgtgtgt gtgtctgtct attttgatcc ggcccaagtt cctaagtaga     2580
gcaagaattc atcaaccagc tgcctttgtt tcatttcacc tcagcacgta ccatcgtcct     2640
ttgggggggtt gtttgttttt gttttttgct ttaaccaaaa tgtttgtaaa tcttaacctc   2700
ctgcctagga tttgtacagc atttggtgtg tgcttataag ccaataaata ttcaatgtga     2760
gttccaaaaa aaaaaaaaaa aaaaaaaaaa aaaaa                                2795
```

<210> SEQ ID NO 11
<211> LENGTH: 421
<212> TYPE: PRT

<213> ORGANISM: Homo Sapien

<400> SEQUENCE: 11

```
Met Arg Trp Ile Leu Phe Ile Gly Ala Leu Ile Gly Ser Ser Ile Cys
 1               5                  10                  15
Gly Arg Glu Lys Phe Phe Gly Asp Gln Val Leu Arg Ile Asn Val Arg
            20                  25                  30
Asn Gly Asp Glu Ile Ser Lys Leu Ser Gln Leu Val Asn Ser Asn Asn
        35                  40                  45
Leu Lys Leu Asn Phe Trp Lys Ser Pro Ser Ser Phe Asn Arg Pro Val
 50                  55                  60
Asp Val Leu Val Pro Ser Val Ser Leu Gln Ala Phe Lys Ser Phe Leu
 65                  70                  75                  80
Arg Ser Gln Gly Leu Glu Tyr Ala Val Thr Ile Glu Asp Leu Gln Ala
                85                  90                  95
Leu Leu Asp Asn Glu Asp Asp Glu Met Gln His Asn Glu Gly Gln Glu
            100                 105                 110
Arg Ser Ser Asn Asn Phe Asn Tyr Gly Ala Tyr His Ser Leu Glu Ala
        115                 120                 125
Ile Tyr His Glu Met Asp Asn Ile Ala Ala Asp Phe Pro Asp Leu Ala
130                 135                 140
Arg Arg Val Lys Ile Gly His Ser Phe Glu Asn Arg Pro Met Tyr Val
145                 150                 155                 160
Leu Lys Phe Ser Thr Gly Lys Gly Val Arg Arg Pro Ala Val Trp Leu
                165                 170                 175
Asn Ala Gly Ile His Ser Arg Glu Trp Ile Ser Gln Ala Thr Ala Ile
            180                 185                 190
Trp Thr Ala Arg Lys Ile Val Ser Asp Tyr Gln Arg Asp Pro Ala Ile
        195                 200                 205
Thr Ser Ile Leu Glu Lys Met Asp Ile Phe Leu Leu Pro Val Ala Asn
210                 215                 220
Pro Asp Gly Tyr Val Tyr Thr Gln Thr Gln Asn Arg Leu Trp Arg Lys
225                 230                 235                 240
Thr Arg Ser Arg Asn Pro Gly Ser Ser Cys Ile Gly Ala Asp Pro Asn
                245                 250                 255
Arg Asn Trp Asn Ala Ser Phe Ala Gly Lys Gly Ala Ser Asp Asn Pro
            260                 265                 270
Cys Ser Glu Val Tyr His Gly Pro His Ala Asn Ser Glu Val Glu Val
        275                 280                 285
Lys Ser Val Val Asp Phe Ile Gln Lys His Gly Asn Phe Lys Gly Phe
290                 295                 300
Ile Asp Leu His Ser Tyr Ser Gln Leu Leu Met Tyr Pro Tyr Gly Tyr
305                 310                 315                 320
Ser Val Lys Lys Ala Pro Asp Ala Glu Leu Asp Lys Val Ala Arg
                325                 330                 335
Leu Ala Ala Lys Ala Leu Ala Ser Val Ser Gly Thr Glu Tyr Gln Val
            340                 345                 350
Gly Pro Thr Cys Thr Thr Val Tyr Pro Ala Ser Gly Ser Ser Ile Asp
        355                 360                 365
Trp Ala Tyr Asp Asn Gly Ile Lys Phe Ala Phe Thr Phe Glu Leu Arg
        370                 375                 380
Asp Thr Gly Thr Tyr Gly Phe Leu Leu Pro Ala Asn Gln Ile Ile Pro
385                 390                 395                 400
```

Thr Ala Glu Glu Thr Trp Leu Gly Leu Lys Thr Ile Met Glu His Val
            405                 410                 415
Arg Asp Asn Leu Tyr
            420

<210> SEQ ID NO 12
<211> LENGTH: 1705
<212> TYPE: DNA
<213> ORGANISM: Homo Sapien

<400> SEQUENCE: 12

| | | | | | |
|---|---|---|---|---|---|
| atgtctacag | cctctgccgc | ctcctcctcc | tcctcgtctt | cggccggtga | gatgatcgaa | 60 |
| gccccttccc | aggtcctcaa | ctttgaagag | atcgactaca | aggagatcga | ggtggaagag | 120 |
| gttgttggaa | gaggagcctt | ggagttgtt | tgcaaagcta | agtggagagc | aaaagatgtt | 180 |
| gctattaaac | aaatagaaag | tgaatctgag | aggaaagcgt | ttattgtaga | gcttcggcag | 240 |
| ttatcccgtg | tgaaccatcc | taatattgta | aagcttatg | gagcctgctt | gaatccagtg | 300 |
| tgtcttgtga | tggaatatgc | tgaagggggc | tctttatata | atgtgctgca | tggtgctgaa | 360 |
| ccattgccat | attatactgc | tgcccacgca | atgagttggt | gtttacagtg | ttcccaagga | 420 |
| gtggcttatc | ttcacagcat | gcaacccaaa | gcgctaattc | acagggacct | gaaaccacca | 480 |
| aacttactgc | tggttgcagg | ggggacagtt | ctaaaaattt | gtgattttgg | tacagcctgt | 540 |
| gacattcaga | cacacatgac | caataacaag | gggagtgctg | cttggatggc | acctgaagtt | 600 |
| tttgaaggta | gtaattacag | tgaaaaatgt | gacgtcttca | gctggggtat | tattctttgg | 660 |
| gaagtgataa | cgcgtcggaa | acccttgat | gagattggtg | gcccagcttt | ccgaatcatg | 720 |
| tgggctgttc | ataatggtac | tcgaccacca | ctgataaaaa | atttacctaa | gcccattgag | 780 |
| agcctgatga | ctcgttgttg | gtctaaagat | ccttcccagc | gcccttcaat | ggaggaaatt | 840 |
| gtgaaaataa | tgactcactt | gatgcggtac | tttccaggag | cagatgagcc | attacagtat | 900 |
| ccttgtcagt | attcagatga | aggacagagc | aactctgcca | ccagtacagg | ctcattcatg | 960 |
| gacattgctt | ctacaaatac | gagtaacaaa | agtgacacta | tatggagca | agttcctgcc | 1020 |
| acaaatgata | ctattaagcg | cttagaatca | aaattgttga | aaaatcaggc | aaagcaacag | 1080 |
| agtgaatctg | gacgtttaag | cttgggagcc | tcccgtgga | gcagtgtgga | gagcttgccc | 1140 |
| ccaacctctg | agggcaagag | gatgagtgct | gacatgtctg | aaatagaagc | taggatcgcc | 1200 |
| gcaaccacag | cctattccaa | gcctaaacgg | ggccaccgta | aaactgcttc | atttggcaac | 1260 |
| attctggatg | tccctgagat | cgtcatatca | ggcaacggac | agccaagacg | tagatccatc | 1320 |
| caagacttga | ctgtaactgg | aacagaacct | ggtcaggtga | gcagtaggtc | atccagtccc | 1380 |
| agtgtcagaa | tgattactac | ctcaggacca | acctcagaaa | agccaactcg | aagtcatcca | 1440 |
| tggaccctg | atgattccac | agataccaat | ggatcagata | actccatccc | aatggcttat | 1500 |
| cttacactgg | atcaccaact | acaggcaaga | actagttgca | gaactggacc | aggatgaaaa | 1560 |
| ggaccagcaa | aatacatctc | gcctggtaca | ggaacataaa | aagcttttag | atgaaaacaa | 1620 |
| aggcctttct | acttactacc | agcaatgcaa | aaaacaacta | gaggtcatca | gaagtcagca | 1680 |
| gcagaaacga | caaggcactt | catga | | | | 1705 |

<210> SEQ ID NO 13
<211> LENGTH: 518
<212> TYPE: PRT
<213> ORGANISM: Homo Sapien

<400> SEQUENCE: 13

-continued

```
Met Ser Thr Ala Ser Ala Ala Ser Ser Ser Ser Ser Ser Ala Gly
 1               5                  10                  15

Glu Met Ile Glu Ala Pro Ser Gln Val Leu Asn Phe Glu Glu Ile Asp
                20                  25                  30

Tyr Lys Glu Ile Glu Val Glu Val Val Gly Arg Gly Ala Phe Gly
                35                  40                  45

Val Val Cys Lys Ala Lys Trp Arg Ala Lys Asp Val Ala Ile Lys Gln
     50                  55                  60

Ile Glu Ser Glu Ser Glu Arg Lys Ala Phe Ile Val Glu Leu Arg Gln
 65                  70                  75                  80

Leu Ser Arg Val Asn His Pro Asn Ile Val Lys Leu Tyr Gly Ala Cys
                 85                  90                  95

Leu Asn Pro Val Cys Leu Val Met Glu Tyr Ala Glu Gly Gly Ser Leu
                100                 105                 110

Tyr Asn Val Leu His Gly Ala Glu Pro Leu Pro Tyr Tyr Thr Ala Ala
                115                 120                 125

His Ala Met Ser Trp Cys Leu Gln Cys Ser Gln Gly Val Ala Tyr Leu
    130                 135                 140

His Ser Met Gln Pro Lys Ala Leu Ile His Arg Asp Leu Lys Pro Pro
145                 150                 155                 160

Asn Leu Leu Leu Val Ala Gly Gly Thr Val Leu Lys Ile Cys Asp Phe
                165                 170                 175

Gly Thr Ala Cys Asp Ile Gln Thr His Met Thr Asn Asn Lys Gly Ser
                180                 185                 190

Ala Ala Trp Met Ala Pro Glu Val Phe Glu Gly Ser Asn Tyr Ser Glu
            195                 200                 205

Lys Cys Asp Val Phe Ser Trp Gly Ile Ile Leu Trp Glu Val Ile Thr
    210                 215                 220

Arg Arg Lys Pro Phe Asp Glu Ile Gly Gly Pro Ala Phe Arg Ile Met
225                 230                 235                 240

Trp Ala Val His Asn Gly Thr Arg Pro Pro Leu Ile Lys Asn Leu Pro
                245                 250                 255

Lys Pro Ile Glu Ser Leu Met Thr Arg Cys Trp Ser Lys Asp Pro Ser
                260                 265                 270

Gln Arg Pro Ser Met Glu Glu Ile Val Lys Ile Met Thr His Leu Met
            275                 280                 285

Arg Tyr Phe Pro Gly Ala Asp Glu Pro Leu Gln Tyr Pro Cys Gln Tyr
            290                 295                 300

Ser Asp Glu Gly Gln Ser Asn Ser Ala Thr Ser Thr Gly Ser Phe Met
305                 310                 315                 320

Asp Ile Ala Ser Thr Asn Ser Asn Lys Ser Asp Thr Asn Met Glu
                325                 330                 335

Gln Val Pro Ala Thr Asn Asp Thr Ile Lys Arg Leu Glu Ser Lys Leu
                340                 345                 350

Leu Lys Asn Gln Ala Lys Gln Gln Ser Glu Ser Gly Arg Leu Ser Leu
            355                 360                 365

Gly Ala Ser Arg Gly Ser Ser Val Glu Ser Leu Pro Pro Thr Ser Glu
    370                 375                 380

Gly Lys Arg Met Ser Ala Asp Met Ser Glu Ile Glu Ala Arg Ile Ala
385                 390                 395                 400

Ala Thr Thr Ala Tyr Ser Lys Pro Lys Arg Gly His Arg Lys Thr Ala
                405                 410                 415
```

-continued

| | | | | | | | | | | |
|---|---|---|---|---|---|---|---|---|---|---|
|Ser|Phe|Gly|Asn|Ile|Leu|Asp|Val|Pro|Glu|Ile|Val|Ile|Ser|Gly|Asn|
| | | |420| | |425| | | |430| | | | | |

Gly Gln Pro Arg Arg Ser Ile Gln Asp Leu Thr Val Thr Gly Thr
              435                 440                 445

Glu Pro Gly Gln Val Ser Ser Arg Ser Ser Pro Ser Val Arg Met
        450                 455                 460

Ile Thr Thr Ser Gly Pro Thr Ser Glu Lys Pro Thr Arg Ser His Pro
465                 470                 475                 480

Trp Thr Pro Asp Asp Ser Thr Asp Thr Asn Gly Ser Asp Asn Ser Ile
                485                 490                 495

Pro Met Ala Tyr Leu Thr Leu Asp His Gln Leu Gln Ala Arg Thr Ser
            500                 505                 510

Cys Arg Thr Gly Pro Gly
        515

<210> SEQ ID NO 14
<211> LENGTH: 1917
<212> TYPE: DNA
<213> ORGANISM: Homo Sapien

<400> SEQUENCE: 14

```
gtgagctgca gagaagagga ggttggtgtg gagcacaggc agcaccgagc ctgccccgtg      60
agctgagggc ctgcagtctg cggctggaat caggatagac accaaggcag gaccccagga    120
gatgctgaag cctctttgga aagcagcagt ggcccccaca tggccatgct ccatgccgcc    180
ccgccgcccg tgggacagag aggctggcac gttgcaggtc ctgggagcgc tggctgtgct    240
gtggctgggc tccgtggctc ttatctgcct cctgtggcaa gtccccgtc ctcccacctg      300
gggccaggtg cagcccaagg acgtgcccag gtcctgggag catggctcca gcccagcttg    360
ggagcccctg gaagcagagg ccaggcagca gagggactcc tgccagcttg tccttgtgga    420
aagcatcccc caggacctgc catctgcagc cggcagcccc tctgcccagc tctgggcca     480
ggcctggctg cagctgctgg acactgccca ggagagcgtc cacgtggctt catactactg    540
gtccctcaca gggcctgaca tcggggtcaa cgactcgtct tcccagctgg agaggctct     600
tctgcagaag ctgcagcagc tgctgggcag gaacatttcc ctggctgtgg ccaccagcag    660
cccgacactg gccaggacat ccaccgacct gcaggttctg gctgcccgag gtgcccatgt    720
acgacaggtg cccatggggc ggctcaccag gggtgttttg cactccaaat ctgggttgt     780
ggatggacgg cacatataca tgggcagtgc caacatggac tggcggtctc tgacgcaggt    840
gaaggagctt ggcgctgtca tctataactg cagccacctg gcccaagacc tggagaagac    900
cttccagacc tactgggtac tggggggtgcc caaggctgtc ctccccaaaa cctggcctca    960
gaacttctca tctcacttca accgtttcca gcccttccac ggcctctttg atgggggtgcc  1020
caccactgcc tacttctcag cgtcgccacc agcactctgt cccagggcc gcacccggga   1080
cctggaggcg ctgctggcgg tgatggggag cgcccaggag ttcatctatg cctccgtgat  1140
ggagtatttc cccaccacgc gcttcagcca cccccgagg tactggccgg tgctggacaa   1200
cgcgctgcgg gcggcagcct tcggcaaggg cgtgcgcgtg cgcctgctgg tcggctgcgg  1260
actcaacacg gaccccacca tgttccccta cctgcggtcc ctgcaggcgc tcagcaaccc  1320
cgcggccaac gtctctgtgg acgtgaaagt cttcatcgtg ccggtgggga accattccaa  1380
catcccattc agcagggtga accacagcaa gttcatggtc acggagaagg cagcctacat  1440
aggcacctcc aactggtcgg aggattactt cagcagcacg gcgggggtgg gcttggtggt  1500
```

-continued

```
cacccagagc cctggcgcgc agcccgcggg ggccacggtg caggagcagc tgcggcagct    1560
ctttgagcgg gactggagtt cgcgctacgc cgtcggcctg gacggacagg ctccgggcca    1620
ggactgcgtt tggcagggct gagggggggcc tcttttctc tcggcgaccc cgccccgcac    1680
gcgccctccc ctctgacccc ggcctgggct tcagccgctt cctcccgcaa gcagcccggg    1740
tccgcactgc gccaggagcc gcctgcgacc gcccgggcgt cgcaaaccgc ccgcctgctc    1800
tctgatttcc gagtccagcc ccccctgagc cccacctcc ccaggagcc ctccaggaag    1860 ccccttccct gactcctggc ccacaggcca ggcctaaaaa aaactcgtgg cttcaaa      1917
```

<210> SEQ ID NO 15
<211> LENGTH: 506
<212> TYPE: PRT
<213> ORGANISM: Homo Sapien

<400> SEQUENCE: 15

```
Met Leu Lys Pro Leu Trp Lys Ala Ala Val Ala Pro Thr Trp Pro Cys
 1               5                   10                  15

Ser Met Pro Pro Arg Arg Pro Trp Asp Arg Glu Ala Gly Thr Leu Gln
             20                  25                  30

Val Leu Gly Ala Leu Ala Val Leu Trp Leu Gly Ser Val Ala Leu Ile
         35                  40                  45

Cys Leu Leu Trp Gln Val Pro Arg Pro Thr Trp Gly Gln Val Gln
     50                  55                  60

Pro Lys Asp Val Pro Arg Ser Trp Glu His Gly Ser Pro Ala Trp
 65                  70                  75                  80

Glu Pro Leu Glu Ala Glu Ala Arg Gln Gln Arg Asp Ser Cys Gln Leu
                 85                  90                  95

Val Leu Val Glu Ser Ile Pro Gln Asp Leu Pro Ser Ala Ala Gly Ser
            100                 105                 110

Pro Ser Ala Gln Pro Leu Gly Gln Ala Trp Leu Gln Leu Leu Asp Thr
        115                 120                 125

Ala Gln Glu Ser Val His Val Ala Ser Tyr Tyr Trp Ser Leu Thr Gly
    130                 135                 140

Pro Asp Ile Gly Val Asn Asp Ser Ser Ser Gln Leu Gly Glu Ala Leu
145                 150                 155                 160

Leu Gln Lys Leu Gln Gln Leu Leu Gly Arg Asn Ile Ser Leu Ala Val
                165                 170                 175

Ala Thr Ser Ser Pro Thr Leu Ala Arg Thr Ser Thr Asp Leu Gln Val
            180                 185                 190

Leu Ala Ala Arg Gly Ala His Val Arg Gln Val Pro Met Gly Arg Leu
        195                 200                 205

Thr Arg Gly Val Leu His Ser Lys Phe Trp Val Val Asp Gly Arg His
    210                 215                 220

Ile Tyr Met Gly Ser Ala Asn Met Asp Trp Arg Ser Leu Thr Gln Val
225                 230                 235                 240

Lys Glu Leu Gly Ala Val Ile Tyr Asn Cys Ser His Leu Ala Gln Asp
                245                 250                 255

Leu Glu Lys Thr Phe Gln Thr Tyr Trp Val Leu Gly Val Pro Lys Ala
            260                 265                 270

Val Leu Pro Lys Thr Trp Pro Gln Asn Phe Ser Ser His Phe Asn Arg
        275                 280                 285

Phe Gln Pro Phe His Gly Leu Phe Asp Gly Val Pro Thr Thr Ala Tyr
    290                 295                 300
```

```
Phe Ser Ala Ser Pro Ala Leu Cys Pro Gln Gly Arg Thr Arg Asp
305                 310                 315                 320

Leu Glu Ala Leu Leu Ala Val Met Gly Ser Ala Gln Glu Phe Ile Tyr
            325                 330                 335

Ala Ser Val Met Glu Tyr Phe Pro Thr Thr Arg Phe Ser His Pro Pro
            340                 345                 350

Arg Tyr Trp Pro Val Leu Asp Asn Ala Leu Arg Ala Ala Phe Gly
        355                 360                 365

Lys Gly Val Arg Val Arg Leu Leu Val Gly Cys Gly Leu Asn Thr Asp
        370                 375                 380

Pro Thr Met Phe Pro Tyr Leu Arg Ser Leu Gln Ala Leu Ser Asn Pro
385                 390                 395                 400

Ala Ala Asn Val Ser Val Asp Val Lys Val Phe Ile Val Pro Val Gly
            405                 410                 415

Asn His Ser Asn Ile Pro Phe Ser Arg Val Asn His Ser Lys Phe Met
            420                 425                 430

Val Thr Glu Lys Ala Ala Tyr Ile Gly Thr Ser Asn Trp Ser Glu Asp
        435                 440                 445

Tyr Phe Ser Ser Thr Ala Gly Val Gly Leu Val Val Thr Gln Ser Pro
        450                 455                 460

Gly Ala Gln Pro Ala Gly Ala Thr Val Gln Glu Gln Leu Arg Gln Leu
465                 470                 475                 480

Phe Glu Arg Asp Trp Ser Ser Arg Tyr Ala Val Gly Leu Asp Gly Gln
                485                 490                 495

Ala Pro Gly Gln Asp Cys Val Trp Gln Gly
            500                 505

<210> SEQ ID NO 16
<211> LENGTH: 2048
<212> TYPE: DNA
<213> ORGANISM: Homo Sapien

<400> SEQUENCE: 16
ccgcaaagtg ctgggatgac aggtgtgagc caccgccccc ggcccctcgc ccgccttttg      60
aaggagcctt tcgtcctcaa gggagaggcc actcccccccc gcgagttcc atgccccta     120
gagggtcatc gttcccgacg gggaggtggc gccctcccc gggccccggg ccccgaccgc     180
ccgtgctgcc tccttccggg ccatcatccg cgatgacggc gccgccagca ggccaggcgg     240
actgggcggg gctccgagcg gggactggga cccagaccga ctaggggact gggagcgggc     300
ggcgcggcca tggcgggctg ctgcgccgcg ctggcggcct tcctgttcga gtacgacacg     360
ccgcgcatcg tgctcatccg cagccgcaaa gtgggggctca tgaaccgcgc cgtgcaactg     420
ctcatcctgg cctacgtcat cgggtgggtg tttgtgtggg aaaagggcta ccaggaaact     480
gactccgtgg tcagctccgt tacgaccaag gtcaagggcg tggctgtgac caacacttct     540
aaacttggat tccggatctg ggatgtggcg gattatgtga taccagctca ggaggaaaac     600
tccctcttcg tcatgaccaa cgtgatcctc accatgaacc agacacaggg cctgtgcccc     660
gagattccag atgcgaccac tgtgtgtaaa tcagatgcca gctgtactgc cggctctgcc     720
ggcacccaca gcaacggagt ctcaacaggc aggtgcgtag cttttcaacgg gtctgtcaag     780
acgtgtgarg tggcggcctg gtgcccggtg gaggatgaca cacacgtgcc acaacctgct     840
tttttaaagg ctgcagaaaa cttcactctt ttggttaaga acaacatctg gtatcccaaa     900
tttaatttca gcaagaggaa tatccttccc aacatcacca ctacttacct caagtcgtgc     960
```

```
atttatgatg ctaaaacaga tcccttctgc cccatattcc gtcttggcaa aatagtggag    1020
aacgcaggac acagtttcca ggacatggcc gtggagggag gcatcatggg catccaggtc    1080
aactgggact gcaacctgga cagagccgcc tccctctgct tgcccaggta ctccttccgc    1140
cgcctcgata cacgggacgt tgagcacaac gtatctcctg ctacaatttt caggtttgcc    1200
aagtactaca gagacctggc tggcaacgag cagcgcacgc tcatcaaggc ctatggcatc    1260
cgcttcgaca tcattgtgtt tgggaaggca gggaaatttg acatcatccc cactatgatc    1320
aacatcggct ctggcctggc actgctaggc atggcgaccg tgctgtgtga catcatagtc    1380
ctctactgca tgaagaaaag actctactat cgggagaaga aatataaata tgtggaagat    1440
tacgagcagg gtcttgctag tgagctggac cagtgaggcc tacccacac ctgggctctc     1500 cacagcccca tcaaagaaca gagaggagga ggagggagaa atggccacca catcacccca    1560
gagaaatttc tggaatctga ttgagtctcc actccacaag cactcagggt tccccagcag    1620
ctcctgtgtg ttgtgtgcag gatctgtttg cccactcggc ccaggaggtc agcagtctgt    1680
tcttggctgg gtcaactctg cttttcccgc aacctggggt tgtcggggga gcgctggccc    1740
gacgcagtgg cactgctgtg gctttcaggg ctggagctgg cttgctcag aagcctcctg     1800 tctccagctc tctccaggac aggcccagtc tctgaggca cggcggctct gttcaagcac     1860
tttatgcggc aggggaggcc gcctggctgc agtcactaga cttgtagcag gcctgggctg    1920
caggcttccc cccgaccatt ccctgcagcc atgcggcaga gctggcattt ctcctcagag    1980
aagcgctgtg ctaaggtgat cgaggaccag acattaaagc gtgattttct taaaaaaaaa    2040
aaaaaaaa                                                             2048
```

<210> SEQ ID NO 17
<211> LENGTH: 388
<212> TYPE: PRT
<213> ORGANISM: Homo Sapien
<220> FEATURE:
<221> NAME/KEY: VARIANT
<222> LOCATION: (1)...(388)
<223> OTHER INFORMATION: Xaa = Any Amino Acid

<400> SEQUENCE: 17

```
Met Ala Gly Cys Cys Ala Ala Leu Ala Ala Phe Leu Phe Glu Tyr Asp
1               5                   10                  15

Thr Pro Arg Ile Val Leu Ile Arg Ser Arg Lys Val Gly Leu Met Asn
            20                  25                  30

Arg Ala Val Gln Leu Leu Ile Leu Ala Tyr Val Ile Gly Trp Val Phe
        35                  40                  45

Val Trp Glu Lys Gly Tyr Gln Glu Thr Asp Ser Val Val Ser Ser Val
    50                  55                  60

Thr Thr Lys Val Lys Gly Val Ala Val Thr Asn Thr Ser Lys Leu Gly
65                  70                  75                  80

Phe Arg Ile Trp Asp Val Ala Asp Tyr Val Ile Pro Ala Gln Glu Glu
                85                  90                  95

Asn Ser Leu Phe Val Met Thr Asn Val Ile Leu Thr Met Asn Gln Thr
            100                 105                 110

Gln Gly Leu Cys Pro Glu Ile Pro Asp Ala Thr Thr Val Cys Lys Ser
        115                 120                 125

Asp Ala Ser Cys Thr Ala Gly Ser Ala Gly Thr His Ser Asn Gly Val
    130                 135                 140

Ser Thr Gly Arg Cys Val Ala Phe Asn Gly Ser Val Lys Thr Cys Xaa
145                 150                 155                 160
```

```
Val Ala Ala Trp Cys Pro Val Glu Asp Asp Thr His Val Pro Gln Pro
            165                 170                 175

Ala Phe Leu Lys Ala Ala Glu Asn Phe Thr Leu Leu Val Lys Asn Asn
        180                 185                 190

Ile Trp Tyr Pro Lys Phe Asn Phe Ser Lys Arg Asn Ile Leu Pro Asn
        195                 200                 205

Ile Thr Thr Thr Tyr Leu Lys Ser Cys Ile Tyr Asp Ala Lys Thr Asp
    210                 215                 220

Pro Phe Cys Pro Ile Phe Arg Leu Gly Lys Ile Val Glu Asn Ala Gly
225                 230                 235                 240

His Ser Phe Gln Asp Met Ala Val Glu Gly Ile Met Gly Ile Gln
                245                 250                 255

Val Asn Trp Asp Cys Asn Leu Asp Arg Ala Ala Ser Leu Cys Leu Pro
            260                 265                 270

Arg Tyr Ser Phe Arg Arg Leu Asp Thr Arg Asp Val Glu His Asn Val
        275                 280                 285

Ser Pro Gly Tyr Asn Phe Arg Phe Ala Lys Tyr Tyr Arg Asp Leu Ala
    290                 295                 300

Gly Asn Glu Gln Arg Thr Leu Ile Lys Ala Tyr Gly Ile Arg Phe Asp
305                 310                 315                 320

Ile Ile Val Phe Gly Lys Ala Gly Lys Phe Asp Ile Ile Pro Thr Met
                325                 330                 335

Ile Asn Ile Gly Ser Gly Leu Ala Leu Leu Gly Met Ala Thr Val Leu
            340                 345                 350

Cys Asp Ile Ile Val Leu Tyr Cys Met Lys Lys Arg Leu Tyr Tyr Arg
        355                 360                 365

Glu Lys Lys Tyr Lys Tyr Val Glu Asp Tyr Glu Gln Gly Leu Ala Ser
    370                 375                 380

Glu Leu Asp Gln
385

<210> SEQ ID NO 18
<211> LENGTH: 1167
<212> TYPE: DNA
<213> ORGANISM: Homo Sapien

<400> SEQUENCE: 18
atggcgggct gctgcgccgc gctggcggcc ttcctgttcg agtacgacac gccgcgcatc      60
gtgctcatcc gcagccgcaa agtggggctc atgaaccgcg ccgtgcaact gctcatcctg     120
gcctacgtca tcgggtgggt gtttgtgtgg gaaaagggct accaggaaac tgactccgtg     180
gtcagctccg ttacgaccaa ggtcaagggc gtggctgtga ccaacacttc taaacttgga     240
ttccggatct gggatgtggc ggattatgtg ataccagctc aggaggaaaa ctccctcttc     300
gtcatgacca acgtgatcct caccatgaac agacacagg gcctgtgccc cgagattcca     360
gatgcgacca ctgtgtgtaa atcagatgcc agctgtactg ccggctctgc cggcacccac     420
agcaacggag tctcaacagg caggtgcgta gctttcaacg ggtctgtcaa gacgtgtgar     480
gtggcggcct ggtgcccggt ggaggatgac acacacgtgc cacaacctgc tttttttaaag   540 gctgcagaaa acttcactct tttggttaag aacaacatct ggtatcccaa atttaatttc    600
agcaagagga atatccttcc caacatcacc actacttacc tcaagtcgtg catttatgat    660
gctaaaacag atccccttctg ccccatattc cgtcttggca aaatagtgga gaacgcagga    720
cacagtttcc aggacatggc cgtggaggga ggcatcatgg gcatccaggt caactgggac   780
```

```
tgcaacctgg acagagccgc ctccctctgc ttgcccaggt actccttccg ccgcctcgat    840
acacgggacg ttgagcacaa cgtatctcct ggctacaatt tcaggtttgc caagtactac    900
agagacctgc ctggcaacga gcagcgcacg ctcatcaagg cctatggcat ccgcttcgac    960
atcattgtgt ttgggaaggc agggaaattt gacatcatcc ccactatgat caacatcggc   1020
tctggcctgg cactgctagg catggcgacc gtgctgtgtg acatcatagt cctctactgc   1080
atgaagaaaa gactctacta tcgggagaag aaatataaat atgtggaaga ttacgagcag   1140
ggtcttgcta gtgagctgga ccagtga                                       1167

<210> SEQ ID NO 19
<211> LENGTH: 8
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: (2)...(2)
<223> OTHER INFORMATION: Xaa = any amino acid
<220> FEATURE:
<221> NAME/KEY: VARIANT
<222> LOCATION: (4)...(7)
<223> OTHER INFORMATION: Xaa = any amino acid
<220> FEATURE:
<221> NAME/KEY: VARIANT
<222> LOCATION: (1)...(8)
<223> OTHER INFORMATION: Xaa = Any Amino Acid

<400> SEQUENCE: 19

His Xaa Lys Xaa Xaa Xaa Xaa Asp
 1               5
```

27875, 22025, 27420, 17906, 16319, 55092 AND 10218 MOLECULES AND USES THEREFOR

RELATED APPLICATIONS

The new application being transmitted is a continuation-in-part of U.S. patent application Ser. No. 09/426,282, filed Oct. 25, 1999 now abandoned. The present application is also a continuation-in-part of U.S. patent application Ser. No. 09/668,266, filed Sep. 22, 2000 now abandoned, which is a divisional of U.S. application Ser. No. 09/330,970, filed Jun. 11, 1999, now U.S. Pat. Ser. No. 6,146,876. The present application is also a continuation-in-part of U.S. patent application Ser. No. 09/724,599, filed Nov. 28, 2000 now abandoned. The present application is also a continuation-in-part of U.S. patent application Ser. No. 09/860,193, filed May 16, 2001 now abandoned, which is a divisional of U.S. application Ser. No. 09/571,689, filed May 16, 2000 now abandoned. The present application is also a continuation-in-part of U.S. patent application Ser. No. 10/283,023, filed Oct. 29, 2002 (pending), which claims the benefit of U.S. Provisional Application Ser. No. 60/335,044, filed Oct. 31, 2001. The present application is also a continuation-in-part of U.S. patent application Ser. No. 10/010,943, filed Dec. 6, 2001 now abandoned, which claims the benefit of U.S. Provisional Application Ser. No. 60/254,037, filed Dec. 7, 2000. The present application is also a continuation-in-part of U.S. patent application Ser. No. 09/833,082, filed Apr. 10, 2001 now abandoned.

INDEX

| Chapter | Page | Title |
|---|---|---|
| I. | 2 | 27875, A NOVEL HUMAN ADAMS-TS HOMOLOG |
| II. | 78 | 22025, A NOVEL HUMAN CYCLIC NUCLEOTIDE PHOSPHODIESTERASE |
| III. | 143 | METHODS AND COMPOSITIONS FOR DIAGNOSIS AND TREATMENT OF CANCER USING 27420 |
| IV. | 228 | METHOD OF TREATING BONE DISEASE USING 17906 |
| V. | 318 | METHODS AND COMPOSITIONS FOR THE DIAGNOSIS AND TREATMENT OF HEMATOLOGICAL DISORDERS USING 16319 |
| VI. | 375 | METHODS AND COMPOSITIONS FOR THE DIAGNOSIS AND TREATMENT OF VIRAL DISEASE USING 55092 |
| VII. | 451 | METHODS AND COMPOSITIONS FOR TREATING CARDIOVASCULAR DISEASE USING 10218 |

I. 27875, A NOVEL HUMAN ADAMS-TS HOMOLOG

BACKGROUND OF THE INVENTION

Metalloproteinases are a group of widely distributed proteolytic enzymes that depend on bound $Ca^{2+}$ or $Zn^{2+}$ for activity; however, certain metalloproteinases can readily utilize $Mn^{2+}$ and $Mg^{2+}$. Biological functions of metalloproteinases include protein maturation, degradation of proteins, such as extracellular matrix proteins, tumor growth, metastasis and angiogenesis.

Disintegrins are integrin ligands that disrupt cell/cell (aggregation) and cell-matrix (adhesion) interactions by inhibiting the binding of other physiological ligands to integrins. Disintegrins have a conserved spacing of cysteine residues that is required for their direct binding to integrin metalloproteinases (Niewiarowski et al. (1994) *Semin Hematol* 31:289).

TSP I motifs are conserved domains in Thrombospondin 1 and 2, multifunctional secretory glycoproteins involved in blood clotting, inhibiting angiogenesis and regulating the proliferation, adhesion and migration of normal and tumor cells. The biological activities of thrombospondin 1 and 2 are mediated by the binding of the TSP type I motifs to extracellular matrix molecules, such as heparan sulfate, proteoglycans, fibronectin, laminin and collagen. Thrombospondin-1 is a platelet-derived glycoprotein that is released from platelet alpha granules in response to thrombin stimulation. It is involved in cell adhesion and modulates cell movement, cell proliferation, neurite outgrowth and angiogenesis.

ADAMs comprise a broad family of multifunctional proteins, characterized as having a disintegrin and metalloproteinase domain (Wolfsberg et al. (1995) *Developmental Biol* 169:378–383; Wolfsberg et al. (1995) *J Cell Biol* 131:275–278). Approximately 20 ADAMs have been identified to date. The prototypical ADAM is a membrane-anchored glycoprotein with pro-, metalloproteinase, disintegrin, cystine-rich, epidermal growth factor-like, transmembrane and cytoplasmic domains. Members of the ADAM family of proteins include MDC (ADAM1), fertilin β (ADAM2), cryitestin (ADAM3), epididymal apical protein I, meltrin, MS2, TNF-α converting enzyme, Kuzbanian and metargidin.

ADAMs participate in a variety of roles, including cell-cell and cell-matrix interactions and polypeptide processing. Examples of ADAM functions include tumor cell adhesion (Iba et al. (1999) *Am J Pathol* 154:1489–1501), tumor suppression (Emi et al. (1993) *Nature Genet* 5:151–157), spermatogenesis and mediation of fusion of gamete membranes (Evans et al. (1999) *Biol Reprod* 59:145–152), blastocyst implantation (Olson et al. (1998) *Cell Tissue Res* 293:489–498), myotube formation and myoblast fusion (Gilpin et al. (1998) *J Biol Chem* 273:157–166), immunity (Higuchi et al. (1999) *Immunol Today* 20:278–284), proteolytic processing of ligands that activate epidermal growth factor metalloproteinase (Dong et al. (1999) *Proc Natl Acad Sci USA* 96:6235–6240), proteolytic cleavage of Alzheimer's amyloid precursor protein (Lammich et al (1999) *Proc Natl Acad Sci USA* 96:3922–3927; Buxbaum et al. (1998) *J Biol Chem* 273:27765–27767), processing of Notch ligands (Qi et al. (1999) *Science* 283:91–94), neurogenesis (Rooke et al. (1996) *Science* 273:1227–1231), cleavage of murine mannose metalloproteinase to produce a soluble mannose metalloproteinase (Martinez-Pomares et al. (1998) *J Biol Chem* 273:23376–23380), and maturation of TNF-α (Lunn et al. (1997) *FEBS Lett* 400:333–335). The cell-cell interactions are thought to be mediated by the disintegrin domain.

The cloning of ADAM-TS-1, a novel murine ADAM, was reported (Kuno et al. (1997) *J Biol Chem* 272:556–562). ADAM-TS-1 is selectively expressed in the cachexigenic colon 26 adenocarcinoma cell line and is believed to be associated with acute inflammation and cancer cachexia. ADAM-TS-1 is a 951 amino acid polypeptide comprising a signal peptide, a prodomain, a catalytically active zinc-dependent metalloproteinase domain, a disintegrin domain, and three thrombospondin (TSP) type 1 domains, which are responsible for anchoring ADAM-TS-1 to the extracellular matrix. In contrast to other ADAMs, ADAM-TS-1 does not possess a transmembrane domain or an epidermal growth factor-like domain. Rather, ADAM-TS-1 is secreted and is associated with the extracellular matrix.

More recent reports from this group (Kuno et al. (1999) *J. Biol. Chem.* 274:18821–18826; Kuno et al. (1998) *J. Biol. Chem.* 273:13912–13917) also showed ADAM-TS-1 to be a unique ADAM family protein with respect to the presence of thrombospondin type 1 motifs and the capacity to bind to the extracellular matrix. Like the other members of the ADAM family, the amino terminal half region of ADAM-TS-1 consists of a proprotein and a metalloproteinase domain and a disintegrin-like domain that share sequence similarity to snake venom metalloproteinases. In contrast, the domain organization of the carboxy terminal half is completely different from other ADAMs. Instead of the transmembrane region, ADAM-TS-1 has three thrombospondin-type 1 motifs found in thrombospondins 1 and 2. These motifs are functional for binding two molecules of heparin. The ADAM-TS-1 is secreted and incorporated into the extracellular matrix. The three thrombospondin-type 1 motifs are responsible for anchoring to the extracellular matrix. The ADAM-TS-1 was shown to have a zinc-binding motif in the metalloproteinase domain providing the capacity to bind to $\alpha_2$-macroglobulin. Accordingly, soluble ADAM-TS-1 was shown to be able to form a covalent binding complex with $\alpha_2$-macroglobulin. A point mutation in this motif was shown to eliminate the capacity to bind to the $\alpha_2$-macroglobulin. In addition, the studies reported that the removal of the pro-domain from the ADAM-TS-1 precursor was impaired in a furin-deficient cell line and that the processing ability of the cells was restored by coexpression of the furin cDNA. These results provided evidence that the ADAM-TS-1 precursor is processed in vivo by furin endopeptidase in the secretory pathway. It was accordingly proposed that ADAM-TS-1 plays a role in the inflammatory process through its protease activity.

Expression of the gene was shown to be induced in kidney and in heart by in vivo administration of lipopolysaccharide, suggesting a possible role in the inflammatory reaction. (Kuno et al. (1998)).

Using a transient expression system, it was shown that both precursor and processed forms of ADAM-TS-1 are secreted from cells. The majority was associated with the extracellular matrix. When cells were cultured in the presence of heparin, the mature form of ADAM-TS-1 was detected in cell culture medium, suggesting that the binding of the protein to the extracellular matrix is mediated through a sulfated glycosaminoglycan. Deletion mutation analysis showed that the spacer region and the three thrombospondin-type 1 motifs in the carboxy terminal region are important for interaction with the extracellular matrix (Kuno et al. (1998)).

The thrombospondin-type 1 motif is conserved in thrombospondins 1 and 2 which are multifunctional extracellular matrix proteins that influence cell adhesion, motility, and growth (Kuno et al. (1998)). Thrombospondin-type 1 motifs and thrombospondins have two conserved heparin-binding segments: W(S/G)XWSXW (SEQ ID NO:20) and CSVTCG (SEQ ID NO:21)). ADAM-TS-1 contains a middle thrombospondin 1 motif with sequences similar to the following heparin-binding segments in thrombospondins: WGPWGPW (SEQ ID NO:22) and CS(R/K)TCG (SEQ ID NO:23). The carboxy terminal submotifs have only the latter sequence. Kuno et al. (1998) show that the middle and carboxy terminal TSP submotifs of the ADAM-TS-1 protein are able to bind heparin. The report concluded that the data demonstrate that the interaction between the three motifs and sulfated glycosaminoglycans in the extracellular matrix, such as heparan sulfate, plays a role in the extracellular matrix binding of the ADAM-TS protein. However, the report also showed that truncation of the spacer region intervening between the middle and carboxyl terminal TSP-type 1 motifs significantly reduced the extracellular matrix binding of the protein. Accordingly, it was concluded that, in addition to the three TSP Type 1 motifs, the carboxy terminal spacer domain is important for tight binding to the extracellular matrix. Finally, the report showed that the protein is associated with the extracellular matrix through multiple independent extracellular matrix attachment sites in the carboxy terminal region.

Within the proprotein domain, there are two cleavage sites (RRRR, 178–182 (SEQ ID NO:24)) (RKKR, 233–236 (SEQ ID NO:25)) for the furin-like protease. Furin cleaves a wide variety of precursor proteins at the concensus sequence RX(K/R)R (SEQ ID NO:26). Furin cleavage sites are found in a number of precursor proteins that are transported to the cell surface. (Kuno et al. (1998)). The ADAM-TS-1 protein has a zinc-binding motif (HEXXH (SEQ ID NO:27)) in its metalloproteinase domain. Accordingly, it was suggested that this protein is secreted from cells as a proteolytically active form by cleavage with a furin-like enzyme.

Tortorella et al. ((1999) *Science* 284:1664–1666) purified the metalloproteinase aggrecanase-1 (ADAM-TS-4) from IL-1-stimulated bovine nasal cartilage conditioned medium and then cloned and expressed the human ortholog. This protease represents a cartilage aggrecanase that cleaves aggrecan at the $\text{Glu}^{373}$-$\text{Ala}^{374}$ bond to produce fragments similar to those found in the synovial fluid of patients with various types of arthritis. This recombinant molecule provides a target for development of therapeutics to prevent the loss of articular cartilage in arthritis. Aggrecan degradation is an important factor in the erosion of articular cartilage in arthritic diseases. The degradation involves proteolysis in the core protein near the amino terminus where two major cleavage sites have been identified. One of these is the $\text{Glu}^{373}$-$\text{Ala}^{374}$ cleavage site. Aggrecan fragments cleaved from this site have been identified in cultures undergoing cartilage matrix degradation and in arthritic synovial fluids. Incubation of purified aggrecanase-1 with bovine aggrecan produced fragments generated by cleavage at this site. The fragments were identified by an assay using the neoepitope antibody, BC-3, to detect products formed by specific cleavage at this bond. Further, including SF775, a potent aggrecanase inhibitor, blocked binding of the aggrecanase to a specific inhibitor resin.

The amino terminal and two internal sequences of bovine aggrecanase 1 were found to be 50 to 60% identical to the inflammation-associated murine protein ADAM-TS-1. The aggrecanase 1 contains a signal sequence followed by a propeptide domain with a potential cysteine switch at $\text{Cys}^{194}$ and a potential furin cleavage site that precedes the catalytic domain. The catalytic domain has a zinc-binding motif similar to the HEXXHXXGXXH motif found in matrix metalloproteinases and ADAMs. The enzyme also contains a disintegrin-like domain and lacks the transmembrane domain and cytoplasmic tail present in many ADAMs. It ends with a carboxy terminal domain that contains a thrombospondin-type 1 motif similar to those present in ADAM-TS-1. It is likely synthesized as a zymogen that is cleaved to remove the propeptide domain to generate the mature active enzyme. A compound that interferes with the normal pro-MMP activation through a cysteine switch mechanism inhibits cleavage of aggrecan in cartilage organ cultures. The enzyme was shown to be ineffective in cleaving several substrates that are cleaved by matrix metalloproteinases including the extracellular matrix molecules type II collagen, thrombospondin, and fibronectin, as well as more general protease substrates, casein and gelatin. The activity was inhibited by several hydroxamates that are effective in blocking the cleavage of aggrecan at the Glu-Ala bond by native bovine aggrecanase. These researchers also identified a second aggrecanase designated aggrecanase-2 with a similar specificity for the cleavage of aggrecan at the Glu-Ala bond. Preliminary data from this group indicated that ADAM-TS-1 does not cleave aggrecan at the Glu-Ala bond.

Vazquez et al. ((1999) *J. Biol. Chem.* 274:R23349–23357) reported studies of two ADAM proteins that were designated METH-1 AND METH-2. Both proteins suppressed fibroblast growth factor 2-induced vascularization in the cornea pocket assay and inhibited vascular endothelial growth factor-induced angiogenesis in the chorioallantoic membrane assay. The suppression was reported to be considerably greater than that mediated by either thrombospondin 1 or endostatin on a molar basis. Both proteins were also shown to inhibit endothelial cell proliferation but not fibroblast or smooth muscle growth. Accordingly, the proteins show an endothelial-specific response. Although not designated as ADAM-TS proteins, the proteins are clearly members of the ADAM-TS family, containing metalloproteinase, disintegrin, and thrombospondin domains. In fact, the reference indicates that the mouse homolog of one of the cloned genes is the ADAM-TS-1. The report also refers to pNP-1 (procollagenase 1 N-proteinase) having a structural resemblance and high sequence similarity to both of the cloned METH proteins. The reference cites Colige et al. (*Proc. Natl. Acad. Sci. USA* 94:2374–2379 (1997)) for the identification of this new protein. The authors discussed the two proteins as novel inhibitors of angiogenesis. They cited four additional members of the family represented as partial ESTs. The authors also pointed out that despite the identical structure and the high levels of amino acid similarities in the two proteins, the pattern of expression differs significantly. It was suggested that the differences are most likely the result of specific cis-acting elements in the non-coding regulatory sequences. It was proposed that proteins with similar or identical function, but different tissue specificity, may participate as specific angiogenic inhibitors regulating vascular networks in different organs or in specific physiological responses. Alternatively, it was proposed that small differences in sequence might confer significant differences in tissue specificity. Further, whereas ADAM-TS-1 was identified in a screen of genes associated with the induction of cachexia and appears to be regulated by inflammatory cytokines, the METH-2 is not reported to have these features. Finally, the authors discussed the disintegrin motif present in both proteins. The disintegrin motif can contain an RGD (or RGX) motif with a negatively charged residue at the X-position. This sequence binds two integrins and serves as ligand or an antagonist of ligand binding. The authors pointed out that inactivation of integrins with antibodies has been shown to inhibit neovascularization during development and in tumorigenesis.

Abbaszade et al. ((1999) *J. Biol. Chem.* 274:23443–23450)) report the cloning and characterization of a second aggrecanase, designated ADAM-TS-11. It was shown to have extensive homology to ADAM-TS-4 (aggrecanase-1) and to ADAM-TS-1. The recombinant human ADAM-TS-11 was expressed in insect cells and shown to cleave aggrecan at the Glu-Ala site. Aggrecan is the major proteoglycan of cartilage and is responsible for its compressibility and stiffness. Results from several studies cited by the authors suggest that the cleavage at the Glu-Ala site is responsible for increased aggrecan degradation observed in inflammatory joint disease. Gene expression of both the ADAM-TS-4 and ADAM-TS-1 were examined in a variety of normal and arthritic human tissues. ADAM-TS-1 was shown to be highly expressed in arthritic fibrous tissues and arthritic joint capsule. The ADAM-TS-4 and ADAM-TS-11 both showed moderate expression in arthritic fibrous tissue and arthritic joint capsule. However, expression was not limited to these tissues alone. The ADAM-TS-11 appears to be synthesized in an inactive pro form. The N-terminal peptide sequence of the enzyme purified from bovine-cartilage-conditioned medium starts immediately C terminal of the consensus furin cleavage site. Accordingly, the inhibition of furin can block aggrecan cleavage.

Accordingly, ADAMs and ADAM-TSs are a major target for drug action and development. Therefore, it is valuable to the field of pharmaceutical development to identify and characterize previously unknown ADAMs and ADAM-TSs. The present invention advances the state of the art by providing a previously unidentified human ADAM-TS having 39% sequence identity and 67% sequence similarity with murine ADAM-TS-1 and a second human metalloproteinase with homology to the ADAM-TS family, and especially high homology to the above novel ADAM-TS.

SUMMARY OF THE INVENTION

A novel ADAM-TS cDNA, 27875 metalloproteinase, and the deduced 27875 metalloproteinase polypeptide are described herein. The human 27875 sequence (SEQ ID NO:1), is approximately 5366 nucleotides long including untranslated regions. The coding sequence, located at about nucleic acid 46 to 5106 of SEQ ID NO:1, encodes a 1687 amino acid protein (SEQ ID NO:2).

It is also an object of the invention to provide nucleic acid molecules encoding the 27875 metalloproteinase polypeptide, and variants and fragments thereof. Such nucleic acid molecules are useful as targets and reagents in 27875 metalloproteinase expression assays, are applicable to treatment and diagnosis of 27875 metalloproteinase-related disorders and are useful for producing novel 27875 metalloproteinase polypeptides by recombinant methods.

The invention also provides a partial cDNA and deduced amino acid sequence for a second human metalloproteinase with homology to the ADAM-TS family, and particularly high homology to the 27875 metalloproteinase. This protein has been designated 42812. Further, where appropriate, although the disclosure herein and all embodiments are explicitly directed to the 27875 metalloproteinase, these embodiments apply as well to the 42812 metalloproteinase protein. An alignment between these two proteins is shown herein.

The invention thus further provides nucleic acid constructs comprising the nucleic acid molecules described herein. In a preferred embodiment, the nucleic acid molecules of the invention are operatively linked to a regulatory sequence. The invention also provides vectors and host cells for expressing the 27875 metalloproteinase nucleic acid molecules and polypeptides, and particularly recombinant vectors and host cells.

In another aspect, it is an object of the invention to provide isolated 27875 metalloproteinase polypeptides and fragments and variants thereof, including a polypeptide having the amino acid sequence shown in SEQ ID NO:2 or the amino acid sequence encoded by the deposited cDNA. The disclosed 27875 metalloproteinase polypeptides are useful as reagents or targets in 27875 metalloproteinase assays and are applicable to treatment and diagnosis of 27875 metalloproteinase-related disorders.

The invention also provides assays for determining the activity of or the presence or absence of the 27875 metalloproteinase polypeptides or nucleic acid molecules in a biological sample, including for disease diagnosis. In addition, the invention provides assays for determining the presence of a mutation in the polypeptides or nucleic acid molecules, including for disease diagnosis.

A further object of the invention is to provide compounds that modulate expression of the 27875 metalloproteinase for treatment and diagnosis of 27875 metalloproteinase-related disorders. Such compounds may be used to treat conditions related to aberrant activity or expression of the 27875 metalloproteinase polypeptides or nucleic acids.

The disclosed invention further relates to methods and compositions for the study, modulation, diagnosis and treatment of 27875 metalloproteinase related disorders. The compositions include 27875 metalloproteinase polypeptides, nucleic acids, vectors, transformed cells and related variants thereof. In particular, the invention relates to the diagnosis and treatment of 27875 metalloproteinase-related disorders of bone, lung, heart, skeletal muscle, aorta, testis, and kidney, and more specifically of bone. Since the gene is highly expressed in undifferentiated osteoblasts, the invention even more specifically relates to disorders involving osteoblast function, growth, and differentiation, and to modulation of gene expression in osteoblasts. Accordingly, specific disorders include, but are not limited to, osteoporosis and osteopetrosis.

In yet another aspect, the invention provides antibodies or antigen-binding fragments thereof that selectively bind the 27875 metalloproteinase polypeptides and fragments. Such antibodies and antigen binding fragments have use in the detection of the 27875 metalloproteinase polypeptide, and in the prevention, diagnosis and treatment of 27875 metalloproteinase related disorders.

DETAILED DESCRIPTION OF THE INVENTION

The growth, development and maintenance of bone is a highly regulated process. Bone mass reflects the balance of bone formation and resorption which at the cellular level involves the coordinate regulation of bone forming (osteoblast) and bone resorbing (osteoclast) cells. Each of these cell types is influenced by a wide variety of hormones, inflammatory mediators and growth factors. Importantly, osteoblast-derived secreted factors are known regulators of osteoclast formation and/or activity in vivo. Accordingly, it would be beneficial to identify these osteoblast-secreted factors. Such factors may function to regulate osteoblast activity including both cytokine and hormone processing as well as extracellular matrix homeostasis. Modulation of the activity of such factors (for example, via the use of small molecule inhibitors) may prove beneficial for blocking activities of osteoblasts that are associated with accelerated osteoclast formation/activities and subsequent bone resorptive function.

The invention is based on the identification of the novel human ADAM-TS 27875 metalloproteinase, which is expressed at high levels in undifferentiated osteoblast, fetal heart and fetal kidney. The 27875 metalloproteinase cDNA was identified based on consensus motifs or protein domains characteristic of the ADAM-TS family of metalloproteases. Specifically, a novel human gene, termed the 27875 metalloproteinase, is provided. This sequence, and other nucleotide sequences encoding the 27875 metalloproteinase protein or fragments and variants thereof, are referred to as "27875 metalloproteinase sequences".

The 27875 metalloproteinase cDNA was identified in a human bone cell cDNA library. Specifically, an expressed sequence tag (EST) found in a human bone library was selected based on homology to known ADAM-TS sequences. Based on this EST sequence, primers were designed to identify a full length clone from a human bone cDNA library. Positive clones were sequenced and the overlapping fragments were assembled.

Analysis of the assembled sequence revealed that the cloned cDNA molecule encodes an ADAM-TS-like polypeptide. BLAST analysis indicated that the 27875 metalloproteinase protein displays closest similarity to the murine ADAM-TS-1 protein, with approximately 39% identity and 67% overall similarity, indicating that the 27875 metalloproteinase is the human ortholog of this murine protein.

The 27875 metalloproteinase sequence of the invention belongs to the ADAM-TS family of molecules having conserved functional features. The term "family" when referring to the proteins and nucleic acid molecules of the invention is intended to mean two or more proteins or nucleic acid molecules having sufficient amino acid or nucleotide sequence identity as defined herein to provide a specific function. Such family members can be naturally occurring and can be from either the same or different species. For example, a family can contain a first protein of murine origin and an ortholog of that protein of human origin, as well as a second, distinct protein of human origin and a murine ortholog homolog of that protein.

The 27875 metalloproteinase nucleotide sequence (SEQ ID NO:1), is approximately 5366 nucleotides long including untranslated regions. The coding sequence, located at about nucleic acid 46 to 5106 of SEQ ID NO:1, encodes a 1687 amino acid protein (SEQ ID NO:2). The 27875 metalloproteinase contains a metalloproteinase domain at residues 244–259 of SEQ ID NO:2 and a disintegrin domain at residues 541–592 of SEQ ID NO:2. A zinc-binding domain (active site) is found at approximately amino acids 385–394 of SEQ ID NO:2. The protein also contains S thrombospondin domains located from about amino acid 542–592, 825–868, 949–988, 1415–1463, and 1466–1521 of SEQ ID NO:2. SignalP (eukaryote) analysis of the amino terminal 70 amino acids of the polypeptide predicts a 30 amino acid signal peptide, which is cleaved to produce the mature 27875 metalloproteinase polypeptide (residues 31–1687 of SEQ ID NO:2).

Prosite program analysis was used to predict various sites within the 27875 metalloproteinase protein. N-glycosylation sites were predicted at about amino acid residues 94–97, 693–696, 778–781, 950–953, 971–974, 1412–1415, 1419–1422 and 1470 to 1473 of SEQ ID NO:2. A glycosaminoglycan attachment site was predicted at about amino acid residues 1006–1009 of SEQ ID NO:2. cAMP- and cGMP-dependent protein kinase phosphorylation sites were predicted at amino acid residues 872–875 and 1606–1609 of SEQ ID NO:2. Protein kinase C phosphorylation sites were predicted at amino acid residues 6–8, 73–75, 110–112, 214–216, 313–315, 342–344, 569–571, 598–600, 901–903, 962–964, 1035–1037, 1370–1372, 1385–1387, 1440–1442, 1483–1485, 1528–1530, 1599–1601, 1620–1622, 1649–1651 and 1660–1662 of SEQ ID NO:2. Casein kinase II phosphorylation sites were predicted at amino acid residues 147–150, 159–162, 214–217, 342–345, 373–376, 401–404, 505–508, 605–608, 703–706, 917–920, 957–960, 1011–1014, 1192–1195, 1308–1311, 1397–1400, 1440–1443, 1483–1486, 1528–1531 and 1546–1549 of SEQ ID NO:2. A tyrosine kinase phosphorylation site was predicted at amino acid residues 740–747 of SEQ ID NO:2. N-myristoylation sites were predicted at amino acid residues 55–60, 115–120, 141–146, 379–384, 479–484, 513–518, 539–544, 557–562, 614–619, 667–672, 688–693, 716–721, 765–770, 774–779, 1005–1010, 1039–1044, 1263–1252, 1263–1268, 1358–1363, 1517–1522, 1592–1597 and 1625–1630 of SEQ ID NO:2. An amidation site was predicted at amino acid residues 408–411 of SEQ ID NO:2. A cell attachment sequence was predicted at amino acid residues 195–197 of SEQ ID NO:2. A zinc binding domain is predicted at residues 385 to 394 of SEQ ID NO:2. A Cytochrome C family heme-binding site was predicted at amino acid residues 687–692 of SEQ ID NO:2. A crystallins beta and gamma Greek key motif is predicted at amino acid residues 78–93 of SEQ ID NO:2. A growth factor and cytokine metalloproteinase family signature 2 domain was predicted at amino acid residues 539–545 of SEQ ID NO:2. Thrombospondin domains were predicted by HMMer, Version 2, at amino acid residues 488–567, 542–592, 825–879, 949–994, 1415–1463 and 1466–1521 of SEQ ID NO:2.

Northern blot analysis of 27875 metalloproteinase expression in human tissues shows high level expression in cells of osteoblast lineage. A transcript of approximately 4 kb was detected in osteoblast-derived polyA+ RNA (not shown). In situ hybridization with human fetal bone also showed significant levels of expression in mature and stromal osteoblast progenitors. High 27875 metalloproteinase expression was also detected in human fetal kidney and fetal heart. The gene is also significantly expressed in human adult skeletal muscle, heart, lung, aorta, testes, and lymph node as well as in thymus and normal foreskin melanocytes (not shown).

Expression of 27875 metalloproteinase mRNA in the above cells and tissues indicates that the 27875 metalloproteinase is likely to be involved in the proper function and in disorders of these tissues, especially the bone, where the gene is expressed in osteoblasts. Accordingly, the disclosed invention further relates to methods and compositions for the study, modulation, diagnosis and treatment of 27875 metalloproteinase related disorders, especially disorders of the bone that include, but are not limited to, osteoporosis and osteopetrosis. Since the gene is expressed in undifferentiated osteoblasts, disorders related to osteoblast production, function, and differentiation are particularly relevant to the invention. The compositions include 27875 metalloproteinase polypeptides, nucleic acids, vectors, transformed cells and related variants and fragments thereof, as well as agents that modulate expression of the polypeptides and polynucleotides. In particular, the invention relates to the modulation, diagnosis and treatment of 27875 metalloproteinase related disorders as described herein.

Disorders involving the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffuse interstitial (infiltrative, restrictive) diseases, such as pneumoconioses, sarcoidosis, idiopathic pulmonary fibrosis, desquamative interstitial pneumonitis, hypersensitivity pneumonitis, pulmonary eosinophilia (pulmonary infiltration with eosinophilia), *Bronchiolitis obliterans*-organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Disorders involving the heart, include but are not limited to, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

Disorders involving the skeletal muscle include tumors such as rhabdomyosarcoma.

Disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

Disorders involving the testis and epididymis include, but are not limited to, congenital anomalies such as cryptorchidism, regressive changes such as atrophy, inflammations such as nonspecific epididymitis and orchitis, granulomatous (autoimmune) orchitis, and specific inflammations including, but not limited to, gonorrhea, mumps, tuberculosis, and syphilis, vascular disturbances including torsion, testicular tumors including germ cell tumors that include, but are not limited to, seminoma, spermatocytic seminoma, embryonal carcinoma, yolk sac tumor choriocarcinoma, teratoma, and mixed tumors, tumore of sex cord-gonadal stroma including, but not limited to, leydig (interstitial) cell tumors and sertoli cell tumors (androblastoma), and testicular lymphoma, and miscellaneous lesions of tunica vaginalis.

Disorders involving the kidney include, but are not limited to, congenital anomalies including, but not limited to, cystic diseases of the kidney, that include but are not limited to, cystic renal dysplasia, autosomal dominant (adult) polycystic kidney disease, autosomal recessive (childhood) polycystic kidney disease, and cystic diseases of renal medulla, which include, but are not limited to, medullary sponge kidney, and nephronophthisis-uremic medullary cystic disease complex, acquired (dialysis-associated) cystic disease, such as simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive (crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus erythematosus, Henoch-Schönlein purpura, bacterial endocarditis, diabetic glomerulosclerosis, amyloidosis, fibtillary and immunotactoid glomerulonephritis, and other systemic disorders; diseases affecting tubules and interstitium, including acute tubular necrosis and tubulointerstitial nephritis, including but not limited to, pyelonephritis and urinary tract infection, acute pyelonephritis, chronic pyelonephritis and reflux nephropathy, and tubulointerstitial nephritis induced by drugs and toxins, including but not limited to, acute drug-induced interstitial nephritis, analgesic abuse nephropathy, nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including benign nephrosclerosis, malignant hypertension and accelerated nephrosclerosis, renal artery stenosis, and thrombotic microangiopathies including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypernephroma, adenocarcinoma of kidney), which includes urothelial carcinomas of renal pelvis.

Bone-forming cells include the osteoprogenitor cells, osteoblasts, and osteocytes. The disorders of the bone are complex because they may have an impact on the skeleton during any of its stages of development. Hence, the disorders may have variable manifestations and may involve one, multiple or all bones of the body. Such disorders include, congenital malformations, achondroplasia and thanatophoric dwarfism, diseases associated with abnormal matix such as type 1 collagen disease, osteoporosis, Paget disease, rickets, osteomalacia, high-turnover osteodystrophy, low-turnover aplastic disease, osteonecrosis, pyogenic osteomyelitis, tuberculous osteomyelitism, osteoma, osteoid osteoma, osteoblastoma, osteosarcoma, osteochondroma, chondromas, chondroblastoma, chondromyxoid fibroma, chondrosarcoma, fibrous cortical defects, fibrous dysplasia, fibrosarcoma, malignant fibrous histiocytoma, Ewing sarcoma, primitive neuroectodermal tumor, giant cell tumor, and metastatic tumors.

Disorders involving the thymus include developmental disorders, such as DiGeorge syndrome with thymic hypoplasia or aplasia; thymic cysts; thymic hypoplasia, which involves the appearance of lymphoid follicles within the thymus, creating thymic follicular hyperplasia; and thymomas, including germ cell tumors, lynphomas, Hodgkin disease, and carcinoids. Thymomas can include benign or encapsulated thymoma, and malignant thymoma Type I (invasive thymoma) or Type II, designated thymic carcinoma.

The sequences of the invention find use in diagnosis of disorders involving an increase or decrease in 27875 metalloproteinase expression relative to normal expression, such as a proliferative disorder, a differentiative disorder, or a developmental disorder. The sequences also find use in modulating 27875 metalloproteinase-related responses. By "modulating" is intended the upregulating or downregulating of a response. That is, the compositions of the invention affect the targeted activity in either a positive or negative fashion.

27875 Metalloproteinase Polypeptides

The invention relates to the novel 27875 metalloproteinase, having the deduced amino acid sequence (SEQ ID NO:2).

Thus, present invention provides an isolated or purified 27875 metalloproteinase polypeptide and variants and fragments thereof. "27875 metalloproteinase polypeptide" or "27875 metalloproteinase protein" refers to the polypeptide in SEQ ID NO:2 or encoded by the deposited cDNA. The term "27875 metalloproteinase protein" or "27875 metalloproteinase polypeptide", however, further includes the numerous variants described herein, as well as fragments derived from the full-length 27875 metalloproteinase and variants.

27875 metalloproteinase polypeptides can be purified to homogeneity. It is understood, however, that preparations in which the polypeptide is not purified to homogeneity are useful and considered to contain an isolated form of the polypeptide. The critical feature is that the preparation allows for the desired function of the polypeptide, even in the presence of considerable amounts of other components. Thus, the invention encompasses various degrees of purity.

As used herein, a polypeptide is said to be "isolated" or "purified" when it is substantially free of cellular material when it is isolated from recombinant and non-recombinant cells, or free of chemical precursors or other chemicals when it is chemically synthesized. A polypeptide, however, can be joined to another polypeptide with which it is not normally associated in a cell and still be considered "isolated" or "purified."

In one embodiment, the language "substantially free of cellular material" includes preparations of 27875 metalloproteinase having less than about 30% (by dry weight) other proteins (i.e., contaminating protein), less than about 20% other proteins, less than about 10% other proteins, or less than about 5% other proteins. When the polypeptide is recombinantly produced, it can also be substantially free of culture medium, i.e., culture medium represents less than about 20%, less than about 10%, or less than about 5% of the volume of the protein preparation.

The 27875 metalloproteinase polypeptide is also considered to be isolated when it is part of a membrane preparation or is purified and then reconstituted with membrane vesicles or liposomes.

The language "substantially free of chemical precursors or other chemicals" includes preparations of the 27875 metalloproteinase polypeptide in which it is separated from chemical precursors or other chemicals that are involved in its synthesis. The language "substantially free of chemical precursors or other chemicals" includes, but is not limited to, preparations of the polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

In one embodiment, the 27875 metalloproteinase polypeptide comprises the amino acid sequence shown in SEQ ID NO:2. However, the invention also encompasses sequence variants. Variants include a substantially homologous protein encoded by the same genetic locus in an organism, i.e., an allelic variant. Variants also encompass proteins derived from other genetic loci in an organism, but having substantial homology to 27875 metalloproteinase of SEQ ID NO:1. Variants also include proteins substantially homologous to 27875 metalloproteinase but derived from another organism, i.e., an ortholog. Variants also include proteins that are substantially homologous to 27875 metalloproteinase that are produced by chemical synthesis. Variants also include proteins that are substantially homologous to 27875 metalloproteinase that are produced by recombinant methods. It is understood, however, that variants exclude any amino acid sequences disclosed prior to the invention.

Preferred 27875 metalloproteinase polypeptides of the present invention have an amino acid sequence sufficiently identical to the amino acid sequence of SEQ ID NO:2. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences that contain a common structural domain having at least about 45%, 55%, or 65% identity, preferably 75% identity, more preferably 85%, 90%. 91%, 92%, 93%, 94%, 95%, 96%, 97%, 98% or 99% identity are defined herein as sufficiently identical.

The determination of percent identity between two sequences using the algorithms of Karlin and Altschul (1990) Proc. Natl. Acad. Sci. USA 87:2264, modified as in Karlin and Altschul (1993) Proc. Natl. Acad. Sci. USA 90:5873–5877. Such an algorithm is incorporated into the NBLAST and XBLAST programs of Altschul et al. (1990) J. Mol. Biol. 215:403. BLAST nucleotide searches can be performed with the NBLAST program, score=100, wordlength=12, to obtain nucleotide sequences homologous to 27875 metalloproteinase nucleic acid molecules of the invention. BLAST protein searches can be performed with the XBLAST program, score=50, wordlength=3, to obtain amino acid sequences homologous to 27875 metalloproteinase protein molecules of the invention. When utilizing BLAST programs, the default parameters of the respective programs (e.g., XBLAST and NBLAST) can be used.

As used herein, two proteins (or a region of the proteins) are substantially homologous when the amino acid sequences are at least about 60–65%, 65–70%, 70–75%, typically at least about 80–85%, and most typically at least about 90–95% or more homologous. A substantially homologous amino acid sequence, according to the present invention, will be encoded by a nucleic acid sequence hybridizing to the nucleic acid sequence, or portion thereof, of the sequence shown in SEQ ID NO:1 under stringent conditions as more fully described below.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the amino acid sequences herein having 502 amino acid residues, at least 165, preferably at least 200, more preferably at least 250, even more preferably at least 300, and even more preferably at least 350, 400, 450, and 500 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The invention also encompasses polypeptides having a lower degree of identity but having sufficient similarity so as to perform one or more of the same functions performed by 27875 metalloproteinase. Similarity is determined by conservative amino acid substitution, as shown in Table 1. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent are found in Bowie et al., *Science* 247:1306–1310 (1990).

TABLE 1

Conservative Amino Acid Substitutions.

| | |
|---|---|
| Aromatic | Phenylalanine |
| | Tryprophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

A variant polypeptide can differ in amino acid sequence by one or more substitutions, deletions, insertions, inversions, fusions, and truncations or a combination of any of these. Variant polypeptides can be fully functional or can lack function in one or more activities. Thus, in the present case, variations can affect the function, for example, of one or more of regions including any of the five thrombospondin domains, the disintegrin domain, zinc-binding domain, metalloproteinase domain, the region containing the propeptide, regulatory regions, other substrate binding regions, regions involved in membrane association, regions involved in post-translational modification, for example, by phosphorylation, and regions that are important for effector function (i.e., agents that act upon the protein, such as pro-peptide cleavage).

Fully functional variants typically contain only conservative variation or variation in non-critical residues or in non-critical regions. Functional variants can also contain substitution of similar amino acids, which results in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

As indicated, variants can be naturally-occurring or can be made by recombinant means or chemical synthesis to provide useful and novel characteristics for 27875 metalloproteinase polypeptide. This includes preventing immunogenicity from pharmaceutical formulations by preventing protein aggregation.

Useful variations further include alteration of functional activity. For example, one embodiment involves a variation at the substrate peptide binding site that results in binding but not hydrolysis or slower hydrolysis of the peptide substrate. A further useful variation at the same site can result in altered affinity for the peptide substrate. Useful variations also include changes that provide for affinity for another peptide substrate. Useful variations further include the ability to bind integrin with greater or lesser affinity, such as not to bind integrin or to bind integrin but not release it. Further useful variations include alteration in the ability of the propeptide to be cleaved by a cleavage protein, for example, by furin, including alteration in the binding or recognition site. Further, the cleavage site can also be modified so that recognition and cleavage are by a different protease. A useful variation includes binding, but not cleavage, by such a protease. Further useful variations involve variations in the TSP domain, such as in the ability to bind heparin or other sulfated glycosaminoglycan, such as greater or lesser affinity, or a change in specificity. A further useful variation involves a variation in the ability to be bound by zinc, including a greater or lesser affinity for the metal. Further variation could include a variation in the specificity of metal binding, in other words, the ability to be bound by a different metal ion.

Another useful variation provides a fusion protein in which one or more domains or subregions are operationally fused to one or more domains, subregions, or motifs from another ADAMs-TS or ADAM. For example, the transmembrane domain from an ADAM protein can be introduced into the 27875 ADAM-TS such that the protein is anchored in the cell surface. Other permutations include the number of thrombospondin domains, mixing of thrombospondin domains from different ADAM-TS families, spacer regions (between thrombospondin domains), from different ADAM-TS families, the metalloproteinase domain, the propeptide domain, and the disintegrin domain. Mixing these various domains can allow the formation of novel ADAM-TS molecules with different host cell, substrate, and effector molecule (one that acts on the ADAM-TS) specificity.

The term "substrate" is intended to refer not only to the peptide substrate that is cleaved by the metalloproteinase domain, but to refer to any component with which the 27875 polypeptide interacts in order to produce an effect on that component or a subsequent biological effect that is a result of interacting with that component. This includes, but is not limited to, for example, interaction with extracellular matrix components and integrin. However, it is understood that a substrate also includes peptides that are cleaved as a result of catalysis in the metalloproteinase domain.

Amino acids that are essential for function can be identified by methods known in the art, such as site-directed mutagenesis or alanine-scanning mutagenesis (Cunningham et al. (1985) *Science* 244:1081–1085). The latter procedure introduces single alanine mutations at every residue in the molecule. The resulting mutant molecules are then tested for biological activity, such as peptide bond hydrolysis in vitro or related biological activity, such as proliferative activity. Sites that are critical for binding can also be determined by structural analysis such as crystallization, nuclear magnetic resonance or photoaffinity labeling (Smith et al. (1992) *J. Mol. Biol.* 224:899–904; de Vos et al. (1992) *Science* 255: 306–312).

The invention thus also includes polypeptide fragments of 27875 metalloproteinase. Fragments can be derived from the amino acid sequence shown in SEQ ID NO:1. However, the invention also encompasses fragments of the variants of the 27875 metalloproteinase polypeptide as described herein. The fragments to which the invention pertains, however, are not to be construed as encompassing fragments that may be disclosed prior to the present invention.

The longest contiguous stretch of amino acid homology between the 27875 metalloproteinase and ADAM-TS-1 is 9 contiguous amino acids. Accordingly, a fragment can comprise at least about 10, 11, 12, 13, 14, 15, 16, 17, 18, 19, 20, 21, 22, 23, 24, 25, 30, 35, 40, 45, 50 or more contiguous amino acids. Fragments can retain one or more of the biological activities of the protein, for example as discussed above, as well as fragments that can be used as an immunogen to generate 27875 metalloproteinase antibodies.

Biologically active fragments (peptides which are, for example, 5, 7, 10, 12, 15, 20, 30, 35, 36, 37, 38, 39, 40, 50, 100 or more amino acids in length) can comprise a functional site. Such sites include but are not limited to those discussed above, such as a catalytic site, regulatory site, site important for substrate recognition or binding, zinc binding region, regions containing a metalloproteinase, disintegrin or TSP motif, phosphorylation sites, glycosylation sites, and other functional sites disclosed herein. Such sites or motifs can be identified by means of routine computerized homology searching procedures, such as those disclosed herein.

Fragments, for example, can extend in one or both directions from the functional site to encompass 5, 10, 15, 20, 30, 40, 50, or up to 100 amino acids. Further, fragments can include sub-fragments of the specific sites or regions disclosed herein, which sub-fragments retain the function of the site or region from which they are derived.

The invention also provides fragments with immunogenic properties. These contain an epitope-bearing portion of the 27875 metalloproteinase polypeptide and variants. These epitope-bearing peptides are useful to raise antibodies that bind specifically to an 27875 metalloproteinase polypeptide or region or fragment. These peptides can contain at least 10, 12, at least 14, or between at least about 15 to about 30 amino acids. The epitope-bearing 27875 metalloproteinase polypeptides may be produced by any conventional means (Houghten, R. A. (1985) *Proc. Natl. Acad. Sci. USA* 82:5131–5135). Simultaneous multiple peptide synthesis is described in U.S. Pat. No. 4,631,211.

Non-limiting examples of antigenic polypeptides that can be used to generate antibodies include but are not limited to peptides derived from extracellular regions. However, intracellularly-made antibodies ("intrabodies") are also encompassed, which would recognize intracellular peptide regions.

Fragments can be discrete (not fused to other amino acids or polypeptides) or can be within a larger polypeptide. Further, several fragments can be comprised within a single larger polypeptide. In one embodiment a fragment designed for expression in a host can have heterologous pre- and pro-polypeptide regions fused to the amino terminus of the 27875 metalloproteinase polypeptide fragment and an additional region fused to the carboxyl terminus of the fragment.

The invention thus provides chimeric or fusion proteins. These comprise an 27875 metalloproteinase peptide sequence operatively linked to a heterologous peptide having an amino acid sequence not substantially homologous to the 27875 metalloproteinase polypeptide. "Operatively linked" indicates that the 27875 metalloproteinase polypeptide and the heterologous peptide are fused in-frame. The heterologous peptide can be fused to the N-terminus or C-terminus of the 27875 metalloproteinase polypeptide or can be internally located.

In one embodiment the fusion protein does not affect 27875 metalloproteinase function per se. For example, the fusion protein can be a GST-fusion protein in which 27875 metalloproteinase sequences are fused to the N- or C-terminus of the GST sequences. Other types of fusion proteins include, but are not limited to, enzymatic fusion proteins, for example beta-galactosidase fusions, yeast two-hybrid GAL4 fusions, poly-His fusions and Ig fusions. Such fusion proteins, particularly poly-His fusions, can facilitate the purification of recombinant 27875 metalloproteinase polypeptide. In certain host cells (e.g., mammalian host cells), expression and/or secretion of a protein can be increased by using a heterologous signal sequence. Therefore, in another embodiment, the fusion protein contains a heterologous signal sequence at its C- or N-terminus.

EP-A-O 464 533 discloses fusion proteins comprising various portions of immunoglobulin constant regions. The Fe is useful in therapy and diagnosis and thus results, for example, in improved pharmacokinetic properties (EP-A 0232 262). In drug discovery, for example, human proteins have been fused with Fe portions for the purpose of high-throughput screening assays to identify antagonists (Bennett et al. (1995) *J. Mol. Recog.* 8:52–58 (1995) and Johanson et al. *J. Biol. Chem.* 270:9459–9471). Thus, this invention also encompasses soluble fusion proteins containing an 27875 metalloproteinase polypeptide and various portions of the constant regions of heavy or light chains of immunoglobulins of various subclass (IgG, IgM, IgA, IgE). Preferred as immunoglobulin is the constant part of the heavy chain of human IgG, particularly IgG1, where fusion takes place at the hinge region. For some uses it is desirable to remove the Fc after the fusion protein has been used for its intended purpose, for example when the fusion protein is to be used as antigen for immunizations. In a particular embodiment, the Fc part can be removed in a simple way by a cleavage sequence, which is also incorporated and can be cleaved with factor Xa.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al. (1992) *Current Protocols in*

*Molecular Biology*). Moreover, many expression vectors are commercially available that already encode a fusion moiety (e.g., a GST protein). An 27875 metalloproteinase-encoding nucleic acid can be cloned into such an expression vector such that the fusion moiety is linked in-frame to 27875 metalloproteinase.

Another form of fusion protein is one that directly affects 27875 metalloproteinase functions. Accordingly, an 27875 metalloproteinase polypeptide is encompassed by the present invention in which one or more of the 27875 metalloproteinase regions (or parts thereof) has been replaced by heterologous or homologous regions (or parts thereof) from another ADAM-TS or an ADAM. Accordingly, various permutations are possible, for example, as discussed above. Thus, chimeric 27875 metalloproteinases can be formed in which one or more of the native domains or subregions has been replaced by another. This includes metalloproteinase, disintegrin or thrombospondin domains.

It is understood however that such regions could be derived from an ADAM-TS, ADAM, metalloprotein, disintegrin or thrombospondin that has not yet been characterized. Moreover, disintegrin, metalloprotein, and thrombospondin function can be derived from peptides that contain these functions but are not found in either an ADAM or ADAM-TS family. Accordingly, these domains could be provided from other metalloproteins, disintegrins or thrombospondins.

The isolated 27875 metalloproteinase protein can be purified from cells that naturally express it, such as cells of osteoblast, lung, heart or kidney lineage, especially purified from cells that have been altered to express it (recombinant), or synthesized using known protein synthesis methods.

In one embodiment, the protein is produced by recombinant DNA techniques. For example, a nucleic acid molecule encoding the 27875 metalloproteinase polypeptide is cloned into an expression vector, the expression vector introduced into a host cell and the protein expressed in the host cell. The protein can then be isolated from the cells by an appropriate purification scheme using standard protein purification techniques. Polypeptides often contain amino acids other than the 20 amino acids commonly referred to as the 20 naturally-occurring amino acids. Further, many amino acids, including the terminal amino acids, may be modified by natural processes, such as processing and other post-translational modifications, or by chemical modification techniques well known in the art. Common modifications that occur naturally in polypeptides are described in basic texts, detailed monographs, and the research literature, and they are well known to those of skill in the art.

Accordingly, the polypeptides also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a pro-protein sequence.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well-known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (1990) *Meth. Enzymol.* 182: 626–646) and Rattan et al. (1992) *Ann. N.Y. Acad. Sci.* 663:48–62).

As is also well known, polypeptides are not always entirely linear. For instance, polypeptides may be branched as a result of ubiquitination, and they may be circular, with or without branching, generally as a result of post-translation events, including natural processing events and events brought about by human manipulation which do not occur naturally. Circular, branched and branched circular polypeptides may be synthesized by non-translational natural processes and by synthetic methods.

Modifications can occur anywhere in a polypeptide, including the peptide backbone, the amino acid side-chains and the amino or carboxyl termini. Blockage of the amino or carboxyl group in a polypeptide, or both, by a covalent modification, is common in naturally-occurring and synthetic polypeptides. For instance, the aminoterminal residue of polypeptides made in *E. coli*, prior to proteolytic processing, almost invariably will be N-formylmethionine.

The modifications can be a function of how the protein is made. For recombinant polypeptides, for example, the modifications will be determined by the host cell posttranslational modification capacity and the modification signals in the polypeptide amino acid sequence. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to efficiently express mammalian proteins having native patterns of glycosylation. Similar considerations apply to other modifications.

The same type of modification may be present in the same or varying degree at several sites in a given polypeptide. Also, a given polypeptide may contain more than one type of modification.

Polypeptide Uses

The protein sequences of the present invention can be used as a "query sequence" to perform a search against public databases to, for example, identify other family members or related sequences. Such searches can be performed using the NBLAST and XBLAST programs (version 2.0) of Altschul et al. (1990) *J. Mol. Biol.* 215:403–10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score 50, wordlength=3 to obtain amino acid sequences homologous to the proteins of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used.

27875 metalloproteinase polypeptides are useful for producing antibodies specific for 27875 metalloproteinase, regions, or fragments.

27875 metalloproteinase polypeptides are useful for biological assays related to metalloproteinases, disintegrins or thrombospondins, particularly those functions found in ADAMs and ADAM-TSs. Such assays involve any of the known ADAM, ADAM-TS, metalloproteinase, disintegrin or thrombospondin functions or activities or properties useful for diagnosis and treatment of 27875 metalloproteinase-related conditions.

These assays include, but are not limited to, binding extracellular matrix, binding integrin, binding zinc or other metals, binding $\alpha_2$-macroglobulin, cleaving specific peptide substrates to produce fragments, affecting cell adhesion, binding heparin or other sulfated glycosaminoglycan, such as heparan sulfate, suppressing vascularization, suppressing vascular endothelial growth, breaking down cartilage, inducing apoptosis of endothelial cells, supressing tumor growth, inhibiting angiogenesis, affecting cellular chemotaxis, affecting cell-cell interaction or cell-matrix interaction, binding integrin, and any of the other biological or functional properties of these proteins, including, but not limited to, those disclosed herein, and in the references cited herein which are incorporated herein by reference for the disclosure of these properties and for the assays based on these properties. Further, assays may relate to changes in the protein, per se, and on the effects of these changes, for example, cleavage of the propeptide by furin or other specific proteinase, activation of the protein following cleavage, induction of expression of the protein in vivo by LPS, inhibition of function by such agents as SF775, as well as any other effects on the protein mentioned herein or cited in the references herein, which are incorporated herein by reference for these effects and for the subsequent biological consequences of these effects.

Such assays include, but are not limited to, those disclosed in Tang et al. (*FEBS Letters* 445:223–225 (1999)) (for example, induction by interleukin I in vitro and by intravenous administration of lipopolysaccharide in vivo, as well as effects on cell adhesion, motility, and growth); Abbaszade et al., above (for example, products resulting from cleavage at the Glu-Ala site in cartilage explants and chondrocyte cultures treated with interleukin I and retinoic acid, determination of aggrecan cleaving activity with and without hydroxamate inhibitors); Kuno et al. (1998), above (binding to the extracellular matrix, binding to sulfated glycosaminoglycans, binding to heparan sulfate); Kuno et al. (1999) proteinase trapping of $\alpha_2$-macroglobulin, furin processing); Tortorella et al (1999), above (detection of aggrecan fragments, especially by neoepitope antibodies, inhibition of cleavage by ADAM-TS inhibitors, inhibition of pro-MMP activation); Vasquez et al., above (suppression of fibroblast growth factor-2-induced vascularization in the cornea pocket assay and inhibition of vascular endothelial growth factor-induced angiogenesis in the chorioallantoic membrane assay, inhibition of endothelial cell proliferation, competitive inhibition with endostatin, proliferation of human dermal endothelial cells, use of the antiangiogenic region of the TSP-1 motif as bait); Kuno et al. (1997), above (heparin binding, induction of expression in vitro by interleukin I, induction of expression in vivo by LPS); Wolfsberg et al., above (degradation of basement membrane, binding of integrin, and fusogenic activity); Guilpin et al. (1988) *J. Biol. Chem.* 273:157–166 ($\alpha_2$-macroglobulin trapping, cleavage of prodomain at the furin site to generate active metalloproteinase); Rosendahl et al., above (*J. Biol. Chem.* 272:24588–24593 (1997)) (TNF $\alpha$ processing); Wolfsberg et al., *Developmental Biology* 169:378–383 (1995) (adhesion by integrin binding in the disintegrin domain, antiadhesive function by zinc-dependent metalloproteinase domain). These references are incorporated herein by reference for these specific assays.

Recombinant assay systems include, but are not limited to, those shown in Abbaszade et al., above; Kuno et al. (1998), above; Kuno et al. (1999), above; Tortorella et al., above; Vasquez et al., above, Kuno et al. (1997), above; Wolfsberg et al. (*Developmental Biology*), above. These references are also incorporated herein by reference for the cloning and expression systems disclosed therein.

27875 metalloproteinase polypeptides are also useful in drug screening assays, in cell-based or cell-free systems. Cell-based systems can be native, i.e., cells that normally express 27875 metalloproteinase, such as lung, fetal kidney, fetal heart, adult lung and osteoblasts, as a biopsy, or expanded in cell culture. In one embodiment, however, cell-based assays involve recombinant host cells expressing 27875 metalloproteinase. Accordingly, these drug-screening assays can be based on effects on protein function as described above for biological assays useful for diagnosis and treatment.

Determining the ability of the test compound to interact with 27875 metalloproteinase can also comprise determining the ability of the test compound to preferentially bind to the polypeptide as compared to the ability of a known binding molecule to bind to the polypeptide.

The polypeptides can be used to identify compounds that modulate 27875 metalloproteinase activity. Such compounds, for example, can increase or decrease affinity or rate of binding to substrate, compete with substrate for binding to 27875 metalloproteinase, or displace substrate bound to 27875 metalloproteinase. Both 27875 metalloproteinase and appropriate variants and fragments can be used in high-throughput screens to assay candidate compounds for the ability to bind to 27875 metalloproteinase. These compounds can be further screened against a functional 27875 metalloproteinase to determine the effect of the compound on 27875 metalloproteinase activity. Compounds can be identified that activate (agonist) or inactivate (antagonist) 27875 metalloproteinase to a desired degree. Modulatory methods can be performed in vitro (e.g., by culturing the cell with the agent) or, alternatively, in vivo (e.g., by administering the agent to a subject).

27875 metalloproteinase polypeptides can be used to screen a compound for the ability to stimulate or inhibit interaction between 27875 metalloproteinase protein and a target molecule that normally interacts with 27875 metalloproteinase, for example, furin, zinc or other metal, substrate peptide of the metalloproteinase module, substrate of the disintegrin module, for example, integrin, or substrate of the thrombospondin module, i.e., sulfated glycosaminoglycan, such as heparin and heparan sulfate, and accordingly, extracellular matrix. The assay includes the steps of combining 27875 metalloproteinase protein with a candidate compound under conditions that allow the 27875 metalloproteinase protein or fragment to interact with the target molecule, and to detect the formation of a complex between the 27875 metalloproteinase protein and the target or to detect the biochemical consequence of the interaction with 27875 metalloproteinase and the target.

Determining the ability of 27875 metalloproteinase to bind to a target molecule can also be accomplished using a technology such as real-time Bimolecular Interaction Analysis (BIA). Sjolander et al. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIAcore™). Changes in the optical phenomenon surface plasmon resonance (SPR) can be used as an indication of real-time reactions between biological molecules.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer or small molecule libraries of compounds (Lam, K. S. (1997) *Anticancer Drug Des.* 12:145).

Examples of methods for the synthesis of molecular libraries can be found in the art, for example in DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233. Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc. Natl. Acad. Sci. USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 97:6378–6382); (Felici (1991) *J. Mol. Biol.* 222:301–310); (Ladner supra).

Candidate compounds include, for example, 1) peptides such as soluble peptides, including Ig-tailed fusion peptides and members of random peptide libraries (see, e.g., Lam et al. (1991) *Nature* 354:82–84; Houghten et al. (1991) *Nature* 354:84–86) and combinatorial chemistry-derived molecular libraries made of D- and/or L-configuration amino acids; 2) phosphopeptides (e.g., members of random and partially degenerate, directed phosphopeptide libraries, see, e.g., Songyang et al. (1993) *Cell* 72:767–778); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries).

One candidate compound is a soluble full-length 27875 metalloproteinase or fragment that competes for peptide, integrin, metal, or glycan binding. Other candidate compounds include mutant 27875 metalloproteinases or appropriate fragments containing mutations that affect 27875 metalloproteinase function and compete for peptide, integrin, metal, or glycan substrate. Accordingly, a fragment that competes for substrate, for example with a higher affinity, or a fragment that binds substrate but does not process or otherwise affect it, is encompassed by the invention.

The invention provides other end points to identify compounds that modulate (stimulate or inhibit) 27875 metalloproteinase activity. The assays typically involve an assay of cellular events that indicate 27875 metalloproteinase activity. Thus, the expression of genes that are up- or down-regulated in response to 27875 metalloproteinase activity can be assayed. In one embodiment, the regulatory region of such genes can be operably linked to a marker that is easily detectable, such as luciferase. Alternatively, modification of 27875 metalloproteinase could also be measured.

Any of the biological or biochemical functions mediated by the 27875 metalloproteinase can be used as an endpoint assay. These include all of the biochemical or biochemical/biological events described herein, in the references cited herein, incorporated by reference for these endpoint assay targets, and other functions known to those of ordinary skill in the art. In the case of the 27875 metalloproteinase, specific end points can include, but are not limited to, the events resulting from expression (or lack thereof) of metalloproteinase, disintegrin or thrombospondin activity. With respect to disorders, this would include, but not be limited to, cartilage breakdown, effects on angiogenesis, such as inhibition, induction of apoptosis of endothelial cells, cell-cell adhesion, as well as cell-matrix interaction stimulation of cell surface receptors by cleavage of extracellular ligand, and resulting clinical effects, such as arthritis and tumor growth. In addition, osteoblast function, differentiation, and proliferation can be assayed as well as the biological effects of osteoblast function such as osteoporosis and osteopetrosis and other disorders and pathology, such as that disclosed above, for bone-forming cells.

Binding and/or activating compounds can also be screened by using chimeric 27875 metal loproteinase proteins in which one or more regions, segments, sites, and the like, as disclosed herein, or parts thereof, can be replaced by heterologous and homologous counterparts derived from other ADAM-TSs, ADAMs, metalloproteinases, disintegrins or thrombospondins. For example, a catalytic region can be used that interacts with a different peptide or glycan specificity and/or affinity than the native 27875 metalloproteinase. Accordingly, a different set of components is available as an end-point assay for activation. As a further alternative, the site of modification by an effector protein, for example phosphorylation, can be replaced with the site for a different effector protein. Activation can also be detected by a reporter gene containing an easily detectable coding region operably linked to a transcriptional regulatory sequence that is part of the native pathway in which 27875 metalloproteinase is involved.

27875 metalloproteinase polypeptides are also useful in competition binding assays in methods designed to discover compounds that interact with 27875 metalloproteinase. Thus, a compound is exposed to an 27875 metalloproteinase polypeptide under conditions that allow the compound to bind or to otherwise interact with the polypeptide. Soluble 27875 metalloproteinase polypeptide is also added to the mixture. If the test compound interacts with the soluble 27875 metalloproteinase polypeptide, it decreases the amount of complex formed or activity from 27875 metalloproteinase target. This type of assay is particularly useful in cases in which compounds are sought that interact with specific regions of 27875 metalloproteinase. Thus, the soluble polypeptide that competes with the target 27875 metalloproteinase region is designed to contain peptide sequences corresponding to the region of interest.

Another type of competition-binding assay can be used to discover compounds that interact with specific functional sites. As an example, bindable zinc and a candidate compound can be added to a sample of 27875 metalloproteinase. Compounds that interact with 27875 metalloproteinase at the same site as the zinc will reduce the amount of complex formed between 27875 metalloproteinase and the zinc. Accordingly, it is possible to discover a compound that specifically prevents interaction between 27875 metalloproteinase and the zinc component. Another example involves adding a candidate compound to a sample of 27875 metalloproteinase and substrate peptide. A compound that competes with the peptide will reduce the amount of hydrolysis or binding of the peptide to 27875 metalloproteinase. Accordingly, compounds can be discovered that directly interact with 27875 metalloproteinase and compete with the peptide. Such assays can involve any other component that interacts with 27875 metalloproteinase, such as integrin or sulfated glycosaminoglycan.

To perform cell free drug screening assays, it is desirable to immobilize either 27875 metalloproteinase, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase/27875 metalloproteinase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes is dissociated. Alternatively, the complexes can be dissociated from the matrix, separated by SDS-PAGE, and the level of 27875 metalloproteinase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of an 27875 metalloproteinase-binding target component, such as a peptide or zinc component, and a candidate compound are incubated in 27875 metalloproteinase-presenting wells and the amount of complex trapped in the well can be quantitated. Methods for detecting such complexes, in addition to those described above for the GST-immobilized complexes, include immunodetection of complexes using antibodies reactive with 27875 metalloproteinase target molecule, or which are reactive with 27875 metalloproteinase and compete with the target molecule; as well as enzyme-linked assays which rely on detecting an enzymatic activity associated with the target molecule.

Modulators of 27875 metalloproteinase activity identified according to these drug screening assays can be used to treat a subject with a disorder related to 27875 metalloproteinase, by treating cells that express the 27875 metalloproteinase. These methods of treatment include the steps of administering the modulators of 27875 metalloproteinase activity in a pharmaceutical composition as described herein, to a subject in need of such treatment.

27875 metalloproteinase is highly expressed in fetal kidney, fetal heart, and undifferentiated osteoblasts. As such it is specifically involved in disorders relating to these tissues. Examples include, but are not limited to, osteoporosis and osteopetrosis, as well as other disorders involving osteoblast differentiation, function, and growth. Furthermore, expression is also relevant to disorders of several other tissues have been described. Disorders of these tissues are disclosed hereinabove. 27875 metalloproteinase polypeptides are thus useful for treating an 27875 metalloproteinase-associated disorder characterized by aberrant expression or activity of an 27875 metalloproteinase. In one embodiment, the method involves administering an agent (e.g., an agent identified by a screening assay described herein), or combination of agents that modulates (e.g., upregulates or downregulates) expression or activity of the protein. In another embodiment, the method involves administering 27875 metalloproteinase as therapy to compensate for reduced or aberrant expression or activity of the protein.

Methods for treatment include but are not limited to the use of soluble 27875 metalloproteinase or fragments of 27875 metalloproteinase protein that compete for substrate or any other component that directly interacts with 27875 metalloproteinase, such as integrin, glycan, zinc, or any of the enzymes that modify 27875 metalloproteinase. These 27875 metalloproteinases or fragments can have a higher affinity for the target so as to provide effective competition.

Stimulation of activity is desirable in situations in which the protein is abnormally downregulated and/or in which increased activity is likely to have a beneficial effect. Likewise, inhibition of activity is desirable in situations in which the protein is abnormally upregulated and/or in which decreased activity is likely to have a beneficial effect. In one example of such a situation, a subject has a disorder characterized by aberrant development or cellular differentiation. In another example, the subject has a disorder characterized by an aberrant hematopoietic response. In another example, it is desirable to achieve tissue regeneration in a subject (e.g., where a subject has undergone bone trauma or osteoporosis).

In yet another aspect of the invention, the proteins of the invention can be used as "bait proteins" in a two-hybrid assay or three-hybrid assay (see, e.g., U.S. Pat. No. 5,283, 317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO 94/10300), to identify other proteins (captured proteins) which bind to or interact with the proteins of the invention and modulate their activity.

27875 metalloproteinase polypeptides also are useful to provide a target for diagnosing a disease or predisposition to disease mediated by 27875 metal loproteinase, including, but not limited to, those diseases discussed herein, and particularly bone-related disorders, as disclosed above. Targets are useful for diagnosing a disease or predisposition to disease mediated by 27875 metalloproteinase. Accordingly, methods are provided for detecting the presence, or levels of, 27875 metalloproteinase in a cell, tissue, or organism. The method involves contacting a biological sample with a compound capable of interacting with 27875 metalloproteinase such that the interaction can be detected. One agent for detecting 27875 metalloproteinase is an antibody capable of selectively binding to 27875 metalloproteinase. A biological sample includes tissues, cells and biological fluids isolated from a subject, as well as tissues, cells and fluids present within a subject.

The 27875 metalloproteinase also provides a target for diagnosing active disease, or predisposition to disease, in a patient having a variant 27875 metalloproteinase. Thus, 27875 metalloproteinase can be isolated from a biological sample and assayed for the presence of a genetic mutation that results in an aberrant protein. This includes amino acid substitution, deletion, insertion, rearrangement, (as the result of aberrant splicing events), and inappropriate post-translational modification. Analytic methods include altered electrophoretic mobility, altered tryptic peptide digest, altered 27875 metalloproteinase activity in cell-based or cell-free assay, alteration in peptide binding or degradation, integrin binding, glycan binding, zinc binding or antibody-binding pattern, altered isoelectric point, direct amino acid sequencing, and any other of the known assay techniques useful for detecting mutations in a protein in general or in an 27875 metalloproteinase specifically, such as are disclosed herein.

In vitro techniques for detection of 27875 metalloproteinase include enzyme linked immunosorbent assays (ELISAs), Western blots, immunoprecipitations and immunofluorescence. Alternatively, the protein can be detected in vivo in a subject by introducing into the subject a labeled anti-27875 metalloproteinase antibody. For example, the antibody can be labeled with a radioactive marker whose presence and location in a subject can be detected by standard imaging techniques. Particularly useful are methods, which detect the allelic variant of 27875 metalloproteinase expressed in a subject, and methods, which detect fragments of 27875 metalloproteinase in a sample.

27875 metalloproteinase polypeptides are also useful in pharmacogenomic analysis. Pharmacogenomics deal with clinically significant hereditary variations in the response to drugs due to altered drug disposition and abnormal action in affected persons. See, e.g., Eichelbaum, M. (1996) *Clin. Exp. Pharmacol. Physiol.* 23(10–11):983–985, and Linder, M. W. (1997) *Clin. Chem.* 43(2):254–266. The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes affects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of 27875 metalloproteinase in which one or more of 27875 metalloproteinase functions in one population is different from those in another population. The polypeptides thus allow a target to ascertain a genetic predisposition that can affect treatment modality. Thus, in a peptide-based treatment, polymorphism may give rise to catalytic regions that are more or less active. Accordingly, dosage would necessarily be modified to maximize the therapeutic effect within a given population containing the polymorphism. As an alternative to genotyping, specific polymorphic polypeptides could be identified.

27875 metalloproteinase polypeptides are also useful for monitoring therapeutic effects during clinical trials and other treatment. Thus, the therapeutic effectiveness of an agent that is designed to increase or decrease gene expression, protein levels or 27875 metalloproteinase activity can be monitored over the course of treatment using 27875 metalloproteinase polypeptides as an end-point target. The monitoring can be, for example, as follows: (i) obtaining a pre-administration sample from a subject prior to administration of the agent; (ii) detecting the level of expression or activity of the protein in the pre-administration sample; (iii) obtaining one or more post-administration samples from the subject; (iv) detecting the level of expression or activity of the protein in the post-administration samples; (v) comparing the level of expression or activity of the protein in the pre-administration sample with the protein in the post-administration sample or samples; and (vi) increasing or decreasing the administration of the agent to the subject accordingly.

Antibodies

The invention also provides antibodies that selectively bind to 27875 metalloproteinase and its variants and fragments. An antibody is considered to selectively bind, even if it also binds to other proteins that are not substantially homologous with 27875 metalloproteinase. These other proteins share homology with a fragment or domain of 27875 metalloproteinase. This conservation in specific regions gives rise to antibodies that bind to both proteins by virtue of the homologous sequence. In this case, it would be understood that antibody binding to 27875 metalloproteinase is still selective.

Antibodies can be polyclonal or monoclonal. An intact antibody, or a fragment thereof (e.g. Fab or F(ab')$_2$) can be used. An appropriate immunogenic preparation can be derived from native, recombinantly expressed, or chemically synthesized peptides.

To generate antibodies, an isolated 27875 metalloproteinase polypeptide is used as an immunogen to generate antibodies using standard techniques for polyclonal and monoclonal antibody preparation. Either the full-length protein or antigenic peptide fragment can be used. Regions having a high antigenicity index are described.

Antibodies are preferably prepared from these regions or from discrete fragments in these regions. However, antibodies can be prepared from any region of the peptide as described herein. A preferred fragment produces an antibody that diminishes or completely prevents peptide hydrolysis or binding. Antibodies can be developed against the entire 27875 metalloproteinase or domains of 27875 metalloproteinase as described herein, for example, the zinc binding region, metalloproteinase motif, the disintegrin domain, the TSP motif, or subregions thereof. Antibodies can also be developed against specific functional sites as disclosed herein.

The antigenic peptide can comprise a contiguous sequence of at least 12, 14, 15, or 30 amino acid residues. In one embodiment, fragments correspond to regions that are located on the surface of the protein, e.g., hydrophilic regions. These fragments are not to be construed, however, as encompassing any fragments, which may be disclosed prior to the invention.

Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibody Uses

The antibodies can be used to isolate a 27875 metalloproteinase by standard techniques, such as affinity chromatography or immunoprecipitation. The antibodies can facilitate the purification of the natural 27875 metalloproteinase from cells and recombinantly produced 27875 metalloproteinase expressed in host cells.

The antibodies are useful to detect the presence of 27875 metalloproteinase in cells or tissues to determine the pattern of expression of 27875 metalloproteinase among various tissues in an organism and over the course of normal development. The antibodies can be used to detect 27875 metalloproteinase in situ, in vitro, or in a cell lysate or supernatant in order to evaluate the abundance and pattern of expression. Antibody detection of circulating fragments of the full length 27875 metalloproteinase can be used to identify 27875 metalloproteinase turnover. In addition, the antibodies can be used to assess abnormal tissue distribution or abnormal expression during development.

Further, the antibodies can be used to assess 27875 metalloproteinase expression in disease states such as in active stages of the disease or in an individual with a predisposition toward disease related to 27875 metalloproteinase function. When a disorder is caused by an inappropriate tissue distribution, developmental expression, or level of expression of 27875 metalloproteinase protein, the antibody can be prepared against the normal 27875 metalloproteinase protein. If a disorder is characterized by a specific mutation in 27875 metalloproteinase, antibodies specific for this mutant protein can be used to assay for the presence of the specific mutant 27875 metalloproteinase. However, intracellularly-made antibodies ("intrabodies") are also encompassed, which would recognize intracellular 27875 metalloproteinase peptide regions.

The antibodies can also be used to assess normal and aberrant subcellular localization of cells in the various tissues in an organism. Antibodies can be developed against the whole 27875 metalloproteinase or portions of 27875 metalloproteinase.

The diagnostic uses can be applied, not only in genetic testing, but also in monitoring a treatment modality. Accordingly, where treatment is ultimately aimed at correcting 27875 metalloproteinase expression level or the presence of aberrant 27875 metalloproteinases and aberrant tissue distribution or developmental expression, antibodies directed against 27875 metalloproteinase or relevant fragments can be used to monitor therapeutic efficacy.

Additionally, antibodies are useful in pharmacogenomic analysis. Thus, antibodies prepared against polymorphic 27875 metalloproteinase can be used to identify individuals that require modified treatment modalities.

The antibodies are also useful as diagnostic tools as an immunological marker for aberrant 27875 metalloproteinase analyzed by electrophoretic mobility, isoelectric point, tryptic peptide digest, and other physical assays known to those in the art.

The antibodies are also useful for tissue typing. Thus, where a specific 27875 metalloproteinase has been correlated with expression in a specific tissue, antibodies that are specific for this 27875 metalloproteinase can be used to identify a tissue type.

The antibodies are also useful in forensic identification. Accordingly, where an individual has been correlated with a specific genetic polymorphism resulting in a specific polymorphic protein, an antibody specific for the polymorphic protein can be used as an aid in identification.

The antibodies are also useful for inhibiting 27875 metalloproteinase function, for example, zinc binding, metalloproteinase activity, disintegrin activity or TSP activity. For example, metalloproteinase activity may be measured by the ability to form a covalent binding complex with $\alpha_2$-macroglobulin (Kuno et al. (1999) *J Biol Chem* 274:18821–18826).

These uses can also be applied in a therapeutic context in which treatment involves inhibiting 27875 metalloproteinase function. An antibody can be used, for example, to block peptide binding. Antibodies can be prepared against specific fragments containing sites required for function or against intact 27875 metalloproteinase associated with a cell.

Completely human antibodies are particularly desirable for therapeutic treatment of human patients. For an overview of this technology for producing human antibodies, see Lonberg et al. (1995) *Int. Rev. Immunol.* 13:65–93. For a detailed discussion of this technology for producing human antibodies and human monoclonal antibodies and protocols for producing such antibodies, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806.

The invention also encompasses kits for using antibodies to detect the presence of an 27875 metalloproteinase protein in a biological sample. The kit can comprise antibodies such as a labeled or labelable antibody and a compound or agent for detecting 27875 metalloproteinase in a biological sample; means for determining the amount of 27875 metalloproteinase in the sample; and means for comparing the amount of 27875 metalloproteinase in the sample with a standard. The compound or agent can be packaged in a suitable container. The kit can further comprise instructions for using the kit to detect 27875 metalloproteinase.

Polynucleotides

The nucleotide sequence in SEQ ID NO:1 was obtained by sequencing the deposited human cDNA. Accordingly, the sequence of the deposited clone is controlling as to any discrepancies between the two and any reference to the sequence of SEQ ID NO:1 includes reference to the sequence of the deposited cDNA.

The specifically disclosed cDNA comprises the coding region and 5' and 3' untranslated sequences in SEQ ID NO:1.

The invention provides isolated polynucleotides encoding the novel 27875 metalloproteinase. The term "27875 metalloproteinase polynucleotide" or "27875 metalloproteinase nucleic acid" refers to the sequence shown in SEQ ID NO:1 or in the deposited cDNA. The term "27875 metalloproteinase polynucleotide" or "27875 metalloproteinase nucleic acid" further includes variants and fragments of 27875 metalloproteinase polynucleotides.

An "isolated" 27875 metalloproteinase nucleic acid is one that is separated from other nucleic acid present in the natural source of 27875 metalloproteinase nucleic acid. Preferably, an "isolated" nucleic acid is free of sequences which naturally flank 27875 metalloproteinase nucleic acid (i.e., sequences located at the 5' and 3' ends of the nucleic acid) in the genomic DNA of the organism from which the nucleic acid is derived. However, there can be some flanking nucleotide sequences, for example up to about 5 KB. The important point is that the 27875 metalloproteinase nucleic acid is isolated from flanking sequences such that it can be subjected to the specific manipulations described herein, such as recombinant expression, preparation of probes and primers, and other uses specific to the 27875 metalloproteinase nucleic acid sequences. In one embodiment, the 27875 metalloproteinase nucleic acid comprises only the coding region.

Moreover, an "isolated" nucleic acid molecule, such as a cDNA or RNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

In some instances, the isolated material will form part of a composition (for example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

In some instances, the isolated material will form part of a composition (or example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

27875 metalloproteinase polynucleotides can encode the mature protein plus additional amino or carboxyterminal amino acids, or amino acids interior to the mature polypeptide (when the mature form has more than one polypeptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

27875 metalloproteinase polynucleotides include, but are not limited to, the sequence encoding the mature polypeptide alone, the sequence encoding the mature polypeptide and additional coding sequences, such as a leader or secretory sequence (e.g., a pre-pro or pro-protein sequence), the sequence encoding the mature polypeptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the polynucleotide may be fused to a marker sequence encoding, for example, a peptide that facilitates purification.

27875 metalloproteinase polynucleotides can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides variant 27875 metalloproteinase polynucleotides, and fragments thereof, that differ from the nucleotide sequence shown in SEQ ID NO:1 due to degeneracy of the genetic code and thus encode the same protein as that encoded by the nucleotide sequence shown in SEQ ID NO:1.

The invention also provides 27875 metalloproteinase nucleic acid molecules encoding the variant polypeptides described herein. Such polynucleotides may be naturally occurring, such as allelic variants (same locus), homologs (different locus), and orthologs (different organism), or may be constructed by recombinant DNA methods or by chemical synthesis. Such non-naturally occurring variants may be made by mutagenesis techniques, including those applied to polynucleotides, cells, or organisms. Accordingly, as discussed above, the variants can contain nucleotide substitutions, deletions, inversions and insertions.

Typically, variants have a substantial identity with a nucleic acid molecules of SEQ ID NO:1 and the complements thereof. Variation can occur in either or both the coding and non-coding regions. The variations can produce both conservative and non-conservative amino acid substitutions.

Orthologs, homologs, and allelic variants can be identified using methods well known in the art. These variants comprise a nucleotide sequence encoding a 27875 metalloproteinase that is typically at least about 60–65%, 65–70%, 70–75%, more typically at least about 80–85%, and most typically at least about 90–95% or more homologous to the nucleotide sequence shown in SEQ ID NO:1 or a fragment of this sequence. Such nucleic acid molecules can readily be identified as being able to hybridize under stringent conditions, to the nucleotide sequence shown in SEQ ID NO:1 or a fragment of the sequence. It is understood that stringent hybridization does not indicate substantial homology where it is due to general homology, such as polyA$^+$ or sequences common to all or most proteins, metalloproteinases, zinc binding proteins, thrombospondins, disintegrins, ADAMs, proteins in the ADAM-TS family, or even all proteins in specific ADAM-TS subfamilies, such as ADAM-TS-1, 3, etc. Moreover, it is understood that variants do not include any of the nucleic acid sequences that may have been disclosed prior to the invention.

As used herein, the term "stringent conditions" is intended to describe conditions comprising hybridization in 6× sodium chloride/sodium citrate (SSC) at about 45° C., followed by one or more washes in 0.2×SSC/0.1% SDS at 65° C. Methods of hybridization are known to those skilled in the art and can be found in *Current Protocols in Molecular Biology*, John Wiley & Sons, N.Y. (1998), incorporated by reference. In one embodiment, an isolated nucleic acid molecule that hybridizes under stringent conditions to the sequence of SEQ ID NO:1 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

The present invention also provides isolated nucleic acids that contain a single or double stranded fragment or portion that hybridizes under stringent conditions to the nucleotide sequence of SEQ ID NO:1 or the complement of SEQ ID NO:1. In one embodiment, the nucleic acid consists of a portion of the nucleotide sequence of SEQ ID NO:1 and the complement of SEQ ID NO:1. The nucleic acid fragments of the invention are at least about 15, preferably at least about 16, 17, 18, 19, 20, 23 or 25 contiguous nucleotides, and can be 30, 33, 35, 40, 50, 60, 70, 75, 80, 90, 100, 200, 500 or more nucleotides in length. Longer fragments, for example, 600 or more nucleotides in length, which encode antigenic proteins or polypeptides described herein are also useful.

Furthermore, the invention provides polynucleotides that comprise a fragment of the full-length 27875 metalloproteinase polynucleotides. The fragment can be single or double-stranded and can comprise DNA or RNA. The fragment can be derived from either the coding or the non-coding sequence.

In one embodiment, the nucleic acid sequence is selected from the group consisting of:
  (a) a nucleotide sequence encoding a fragment of the amino acid sequence shown in SEQ ID NO:2, wherein the fragment comprises at least 26 contiguous amino acids;
  (b) a nucleotide sequence comprising at least 75 consecutive nucleotides of the sequence shown in SEQ ID NO:1;
  (c) a nucleotide sequence comprising at least 33 consecutive nucleotides of residues 1–4800 of SEQ ID NO:1;
  (d) a nucleotide sequence encoding residues 31–1687 of the amino acid shown in SEQ ID NO:2;
  (e) a nucleotide sequence encoding residues 244–259 of SEQ ID NO:2;
  (f) a nucleotide sequence encoding residues 385–394 of SEQ ID NO:2;
  (g) a nucleotide sequence encoding residues 541–592 of SEQ ID NO:2;
  (h) a nucleotide sequence encoding residues 542–592 of SEQ ID NO:2;
  (i) a nucleotide sequence encoding residues 825–868 of SEQ ID NO:2;
  (j) a nucleotide sequence encoding residues 949–988 of SEQ ID NO:2;
  (k) a nucleotide sequence encoding residues 1415–1463 of SEQ ID NO:2; and
  (l) a nucleotide sequence complementary to a nucleotide sequences of (a)–(l).

In another embodiment an isolated 27875 metalloproteinase nucleic acid encodes the entire coding region. In another embodiment the isolated 27875 metalloproteinase nucleic acid encodes a sequence corresponding to the mature protein that may be from about amino acid 6 to the last amino acid. Other fragments include nucleotide sequences encoding the amino acid fragments described herein.

Thus, 27875 metalloproteinase nucleic acid fragments further include sequences corresponding to the regions described herein, subregions also described, and specific functional sites. 27875 metalloproteinase nucleic acid fragments also include combinations of the regions, segments, motifs, and other functional sites described above. It is understood that a 27875 metalloproteinase fragment includes any nucleic acid sequence that does not include the entire gene. A person of ordinary skill in the art would be aware of the many permutations that are possible. Nucleic acid fragments, according to the present invention, are not to be construed as encompassing those fragments that may have been disclosed prior to the invention.

Where the location of the regions or sites have been predicted by computer analysis, one of ordinary sill would appreciate that the amino acid residues constituting these regions can vary depending on the criteria used to define the regions.

Polynucleotide Uses

The nucleotide sequences of the present invention can be used as a "query sequence" to perform a search against public databases, for example, to identify other family members or related sequences. Such searches can be performed using the NBLAST and XBLAST programs (version 2.0) of Altschul et al. (1990) *J. Mol. Biol.* 215:403–10. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (1997) *Nucleic Acids Res.* 25(17):3389–3402. When utilizing BLAST and Gapped BLAST programs, the default parameters of the respective programs (e.g., XBLAST and NBLAST) can be used.

The nucleic acid fragments of the invention provide probes or primers in assays such as those described below. "Probes" are oligonucleotides that hybridize in a base-specific manner to a complementary strand of nucleic acid. Such probes include polypeptide nucleic acids, as described in Nielsen et al. (1991) *Science* 254:1497–1500. Typically, a probe comprises a region of nucleotide sequence that hybridizes under highly stringent conditions to at least about 15, typically about 20–25, and more typically about 40, 50 or 75 consecutive nucleotides of the nucleic acid sequence shown in SEQ ID NO:1 and the complements thereof. More typically, the probe further comprises a label, e.g., radioisotope, fluorescent compound, enzyme, or enzyme co-factor.

As used herein, the term "primer" refers to a single-stranded oligonucleotide which acts as a point of initiation of template-directed DNA synthesis using well-known methods (e.g., PCR, LCR) including, but not limited to those described herein. The appropriate length of the primer depends on the particular use, but typically ranges from about 15 to 30 nucleotides. The term "primer site" refers to the area of the target DNA to which a primer hybridizes. The term "primer pair" refers to a set of primers including a 5' (upstream) primer that hybridizes with the 5' end of the nucleic acid sequence to be amplified and a 3' (downstream) primer that hybridizes with the complement of the sequence to be amplified.

27875 metalloproteinase polynucleotides are thus useful for probes, primers, and in biological assays. Where the polynucleotides are used to assess 27875 metalloproteinase properties or functions, such as in the assays described herein, all or less than all of the entire cDNA can be useful. Assays specifically directed to 27875 metalloproteinase functions, such as assessing agonist or antagonist activity, encompass the use of known fragments. Further, diagnostic methods for assessing 27875 metalloproteinase function can also be practiced with any fragment, including those fragments that may have been known prior to the invention. Similarly, in methods involving treatment of 27875 metalloproteinase dysfunction, all fragments are encompassed including those, which may have been known in the art.

27875 metalloproteinase polynucleotides are useful as a hybridization probe for cDNA and genomic DNA to isolate a full-length cDNA and genomic clones encoding the polypeptides described in SEQ ID NO:1 and to isolate cDNA and genomic clones that correspond to variants producing the same polypeptides shown in SEQ ID NO:2 or the other variants described herein. Variants can be isolated from the same tissue and organism from which the polypeptides shown in SEQ ID NO:2 were isolated, different tissues from the same organism, or from different organisms. This method is useful for isolating genes and cDNA that are developmentally-controlled and therefore may be expressed in the same tissue or different tissues at different points in the development of an organism.

The probe can correspond to any sequence along the entire length of the gene encoding the 27875 metalloproteinase polypeptide. Accordingly, it could be derived from 5' noncoding regions, the coding region, and 3' noncoding regions.

The nucleic acid probe can be, for example, the full-length cDNA of SEQ ID NO:1, or a fragment thereof, such as an oligonucleotide of at least 12, 15, 30, 50, 100, 250 or 500 nucleotides in length and sufficient to specifically hybridize under stringent conditions to mRNA or DNA.

Fragments of the polynucleotides described herein are also useful to synthesize larger fragments or full-length polynucleotides described herein, ribozymes or antisense molecules. For example, a fragment can be hybridized to any portion of an mRNA and a larger or full-length cDNA can be produced.

Antisense nucleic acids of the invention can be designed using the nucleotide sequences of SEQ ID NO:1, and constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyl adenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

Additionally, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670. PNAs can be further modified, e.g., to enhance their stability, specificity or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra, Finn et al. (1996) *Nucleic Acids Res*. 24(17):3357–63, Mag et al. (1989) *Nucleic Acids Res*. 17:5973, and Peterser et al. (1975) *Bioorganic Med. Chem. Lett*. 5:1119.

The nucleic acid molecules and fragments of the invention can also include other appended groups such as peptides (e.g., for targeting host cell 27875 metalloproteinases in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO 88/0918) or the blood brain barrier (see, e.g., PCT Publication No. WO 89/10134). In addition, oligonucleotides can be modified with hybridization-triggered cleavage agents (see, e.g., Krol et al. (1988) *Bio-Techniques* 6:958–976) or intercalating agents (see, e.g., Zon (1988) *Pharm Res*. 5:539–549).

27875 metalloproteinase polynucleotides are also useful as primers for PCR to amplify any given region of an 27875 metalloproteinase polynucleotide.

27875 metalloproteinase polynucleotides are also useful for constructing recombinant vectors. Such vectors include expression vectors that express a portion of, or all of, the 27875 metalloproteinase polypeptides. Vectors also include insertion vectors, used to integrate into another polynucleotide sequence, such as into the cellular genome, to alter in situ expression of 27875 metalloproteinase genes and gene products. For example, an endogenous 27875 metalloproteinase coding sequence can be replaced via homologous recombination with all or part of the coding region containing one or more specifically introduced mutations.

27875 metalloproteinase polynucleotides are also useful for expressing antigenic portions of 27875 metalloproteinase proteins.

27875 metalloproteinase polynucleotides are also useful as probes for determining the chromosomal positions of 27875 metalloproteinase polynucleotides by means of in situ hybridization methods, such as FISH. (For a review of this technique, see Verma et al. (1988) *Human Chromosomes: A Manual of Basic Techniques* (Pergamon Press, New York), and PCR mapping of somatic cell hybrids. The mapping of the sequences to chromosomes is an important first step in correlating these sequences with genes associated with disease.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, *Mendelian Inheritance in Man*, available on-line through Johns Hopkins University Welch Medical Library). The relationship between a gene and a disease mapped to the same chromosomal region, can then be identified through linkage analysis (co-inheritance of physically adjacent genes), described in, for example, Egeland et al. ((1987) *Nature* 325:783–787).

Moreover, differences in the DNA sequences between individuals affected and unaffected with a disease associated with a specified gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations, that are visible from chromosome spreads, or detectable using PCR based on that DNA sequence. Ultimately, complete sequencing of genes from several individuals can be performed to confirm the presence of a mutation and to distinguish mutations from polymorphisms.

27875 metalloproteinase polynucleotide probes are also useful to determine patterns of the presence of the gene encoding 27875 metalloproteinases and their variants with respect to tissue distribution, for example, whether gene duplication has occurred and whether the duplication occurs in all or only a subset of tissues. The genes can be naturally occurring or can have been introduced into a cell, tissue, or organism exogenously.

27875 metalloproteinase polynucleotides are also useful for designing ribozymes corresponding to all, or a part, of the mRNA produced from genes encoding the polynucleotides described herein.

27875 metalloproteinase polynucleotides are also useful for constructing host cells expressing a part, or all, of 27875 metalloproteinase polynucleotides and polypeptides.

27875 metalloproteinase polynucleotides are also useful for constructing transgenic animals expressing all, or a part, of 27875 metalloproteinase polynucleotides and polypeptides.

27875 metalloproteinase polynucleotides are also useful for making vectors that express part, or all, of 27875 metalloproteinase polypeptides.

27875 metalloproteinase polynucleotides are also useful as hybridization probes for determining the level of 27875 metalloproteinase nucleic acid expression. Accordingly, the probes can be used to detect the presence of, or to determine levels of, 27875 metalloproteinase nucleic acid in cells, tissues, and in organisms. The nucleic acid whose level is determined can be DNA or RNA. Accordingly, probes corresponding to the polypeptides described herein can be used to assess gene copy number in a given cell, tissue, or organism. This is particularly relevant in cases in which there has been an amplification of 27875 metalloproteinase genes.

Alternatively, the probe can be used in an in situ hybridization context to assess the position of extra copies of 27875 metalloproteinase genes, as on extrachromosomal elements or as integrated into chromosomes in which the 27875 metalloproteinase gene is not normally found, for example as a homogeneously staining region.

These uses are relevant for diagnosis of disorders involving an increase or decrease in 27875 metalloproteinase expression relative to normal, such as a proliferative disorder, a differentiative or developmental disorder, or a hematopoietic disorder. Disorders in which 27875 metalloproteinase expression is relevant include, but are not limited to, those of bone, such as osteoporosis and osteopetrosis.

Thus, the present invention provides a method for identifying a disease or disorder associated with aberrant expression or activity of 27875 metalloproteinase nucleic acid, in which a test sample is obtained from a subject and nucleic acid (e.g., mRNA, genomic DNA) is detected, wherein the presence of the nucleic acid is diagnostic for a subject having or at risk of developing a disease or disorder associated with aberrant expression or activity of the nucleic acid.

One aspect of the invention relates to diagnostic assays for determining nucleic acid expression as well as activity in the context of a biological sample (e.g., blood, serum, cells, tissue) to determine whether an individual has a disease or disorder, or is at risk of developing a disease or disorder, associated with aberrant nucleic acid expression or activity. Such assays can be used for prognostic or predictive purpose to thereby prophylactically treat an individual prior to the onset of a disorder characterized by or associated with expression or activity of the nucleic acid molecules.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express 27875 metalloproteinase, such as by measuring the level of an 27875 metalloproteinase-encoding nucleic acid in a sample of cells from a subject e.g., mRNA or genomic DNA, or determining if the 27875 metalloproteinase gene has been mutated.

Nucleic acid expression assays are useful for drug screening to identify compounds that modulate 27875 metalloproteinase nucleic acid expression (e.g., antisense, polypeptides, peptidomimetics, small molecules or other drugs). A cell is contacted with a candidate compound and the expression of mRNA determined. The level of expression of the mRNA in the presence of the candidate compound is compared to the level of expression of the mRNA in the absence of the candidate compound. The candidate compound can then be identified as a modulator of nucleic acid expression based on this comparison and be used, for example to treat a disorder characterized by aberrant nucleic acid expression. The modulator can bind to the nucleic acid or indirectly modulate expression, such as by interacting with other cellular components that affect nucleic acid expression.

Modulatory methods can be performed in vitro (e.g., by culturing the cell with the agent) or, alternatively, in vivo (e.g., by administering the gent to a subject) in patients or in transgenic animals. The invention thus provides a method for identifying a compound that can be used to treat a disorder associated with nucleic acid expression of the 27875 metalloproteinase gene. The method typically includes assaying the ability of the compound to modulate the expression of the 27875 metalloproteinase nucleic acid and thus identifying a compound that can be used to treat a disorder characterized by undesired 27875 metalloproteinase nucleic acid expression.

The assays can be performed in cell-based and cell-free systems. Cell-based assays include cells naturally expressing the 27875 metalloproteinase nucleic acid or recombinant cells genetically engineered to express specific nucleic acid sequences. Alternatively, candidate compounds can be assayed in vivo in patients or in transgenic animals.

The assay for 27875 metalloproteinase nucleic acid expression can involve direct assay of nucleic acid levels, such as mRNA levels, or on collateral compounds (such as peptide hydrolysis). Further, the expression of genes that are up- or down-regulated in response to 27875 metalloproteinase activity can also be assayed. In this embodiment the regulatory regions of these genes can be operably linked to a reporter gene such as luciferase.

Thus, modulators of 27875 metalloproteinase gene expression can be identified in a method wherein a cell is contacted with a candidate compound and the expression of mRNA determined. The level of expression of 27875 metalloproteinase mRNA in the presence of the candidate compound is compared to the level of expression of 27875 metalloproteinase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

Accordingly, the invention provides methods of treatment, with the nucleic acid as a target, using a compound identified through drug screening as a gene modulator to modulate 27875 metalloproteinase nucleic acid expression. Modulation includes both up-regulation (i.e. activation or agonization) or down-regulation (suppression or antagonization) or effects on nucleic acid activity (e.g. when nucleic acid is mutated or improperly modified). Treatment is of disorders characterized by aberrant expression or activity of the nucleic acid.

Alternatively, a modulator for 27875 metalloproteinase nucleic acid expression can be a small molecule or drug identified using the screening assays described herein as long as the drug or small molecule inhibits 27875 metalloproteinase nucleic acid expression.

27875 metalloproteinase polynucleotides are also useful for monitoring the effectiveness of modulating compounds on the expression or activity of the 27875 metalloproteinase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

Monitoring can be, for example, as follows: (i) obtaining a pre-administration sample from a subject prior to administration of the agent; (ii) detecting the level of expression of a specified mRNA or genomic DNA of the invention in the pre-administration sample; (iii) obtaining one or more post-administration samples from the subject; (iv) detecting the level of expression or activity of the mRNA or genomic DNA in the post-administration samples; (v) comparing the level of expression or activity of the mRNA or genomic DNA in the pre-administration sample with the mRNA or genomic DNA in the post-administration sample or samples; and (vi) increasing or decreasing the administration of the agent to the subject accordingly.

27875 metalloproteinase polynucleotides are also useful in diagnostic assays for qualitative changes in 27875 metalloproteinase nucleic acid, and particularly in qualitative changes that lead to pathology. The polynucleotides can be used to detect mutations in 27875 metalloproteinase genes and gene expression products such as mRNA. The polynucleotides can be used as hybridization probes to detect naturally-occurring genetic mutations in the 27875 metalloproteinase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the 27875 metalloproteinase gene associated with a dysfunction provides a diagnostic tool for an active disease or susceptibility to disease when the disease results from overexpression, underexpression, or altered expression of an 27875 metalloproteinase.

Mutations in the 27875 metalloproteinase gene can be detected at the nucleic acid level by a variety of techniques. Genomic DNA can be analyzed directly or can be amplified by using PCR prior to analysis. RNA or cDNA can be used in the same way.

In certain embodiments, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364), the latter of which can be particularly useful for detecting point mutations in the gene (see Abravaya et al. (1995) *Nucleic Acids Res*. 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) *Proc. Natl. Acad. Sci. USA* 87:1874–1878), transcriptional amplification system (Kwoh et al. (1989) *Proc. Natl. Acad. Sci. USA* 86:1173–1177), Q-Beta Replicase (Lizardi et al. (1988) *Bio/Technology* 6:1197), or any other nucleic acid amplification method, followed by the detection of the amplified molecules using techniques well-known to those of skill in the art. These detection schemes are especially useful for the detection of nucleic acid molecules if such molecules are present in very low numbers.

Alternatively, mutations in an 27875 metalloproteinase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site.

Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method.

Furthermore, sequence differences between a mutant 27875 metalloproteinase gene and a wild-type gene can be determined by direct DNA sequencing. A variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the gene include methods in which protection from cleavage agents is used to detect mismatched bases in RNA/RNA or RNA/DNA duplexes (Myers et al. (1985) *Science* 230:1242); Cotton et al. (1988) *PNAS* 85:4397; Saleeba et al. (1992) *Meth. Enzymol.* 217:286–295), electrophoretic mobility of mutant and wild type nucleic acid is compared (Orita et al. (1989) *PNAS* 86:2766; Cotton et al. (1993) *Mutat. Res.* 285:125–144; and Hayashi et al. (1992) *Genet. Anal. Tech. Appl.* 9:73–79), and movement of mutant or wild-type fragments in polyacrylamide gels containing a gradient of denaturant is assayed using denaturing gradient gel electrophoresis (Myers et al. (1985) *Nature* 313:495). The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility (Keen et al. (1991) *Trends Genet.* 7:5). Examples of other techniques for detecting point mutations include, selective oligonucleotide hybridization, selective amplification, and selective primer extension.

In other embodiments, genetic mutations can be identified by hybridizing a sample and control nucleic acids, e.g., DNA or RNA, to high density arrays containing hundreds or thousands of oligonucleotide probes (Cronin et al. (1996) *Human Mutation* 7:244–255; Kozal et al. (1996) *Nature Medicine* 2:753–759). For example, genetic mutations can be identified in two dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

27875 metalloproteinase polynucleotides are also useful for testing an individual for a genotype that while not necessarily causing the disease, nevertheless affects the treatment modality. Thus, the polynucleotides can be used to study the relationship between an individual's genotype and the individual's response to a compound used for treatment (pharmacogenomic relationship). In the present case, for example, a mutation in the 27875 metalloproteinase gene that results in altered affinity for zinc could result in an excessive or decreased drug effect with standard concentrations of zinc. Accordingly, the 27875 metalloproteinase polynucleotides described herein can be used to assess the mutation content of the gene in an individual in order to select an appropriate compound or dosage regimen for treatment.

Thus polynucleotides displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The methods can involve obtaining a control biological sample from a control subject, contacting the control sample with a compound or agent capable of detecting mRNA, or genomic DNA, such that the presence of mRNA or genomic DNA is detected in the biological sample, and comparing the presence of mRNA or genomic DNA in the control sample with the presence of mRNA or genomic DNA in the test sample.

27875 metalloproteinase polynucleotides are also useful for chromosome identification when the sequence is identified with an individual chromosome and to a particular location on the chromosome. First, the DNA sequence is matched to the chromosome by in situ or other chromosome-specific hybridization. Sequences can also be correlated to specific chromosomes by preparing PCR primers that can be used for PCR screening of somatic cell hybrids containing individual chromosomes from the desired species. Only hybrids containing the chromosome containing the gene homologous to the primer will yield an amplified fragment. Sublocalization can be achieved using chromosomal fragments. Other strategies include prescreening with labeled flow-sorted chromosomes and preselection by hybridization to chromosome-specific libraries. Further mapping strategies include fluorescence in situ hybridization, which allows hybridization with probes shorter than those traditionally used. Reagents for chromosome mapping can be used individually to mark a single chromosome or a single site on the chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

27875 metalloproteinase polynucleotides can also be used to identify individuals from small biological samples. This can be done for example using restriction fragment-length polymorphism (RFLP) to identify an individual. Thus, the polynucleotides described herein are useful as DNA markers for RFLP (See U.S. Pat. No. 5,272,057).

Furthermore, the 27875 metalloproteinase sequence can be used to provide an alternative technique, which determines the actual DNA sequence of selected fragments in the genome of an individual. Thus, the 27875 metalloproteinase sequences described herein can be used to prepare two PCR primers from the 5' and 3' ends of the sequences. These primers can then be used to amplify DNA from an individual for subsequent sequencing.

Panels of corresponding DNA sequences from individuals prepared in this manner can provide unique individual identifications, as each individual will have a unique set of such DNA sequences. It is estimated that allelic variation in humans occurs with a frequency of about once per each 500 bases. Allelic variation occurs to some degree in the coding regions of these sequences, and to a greater degree in the noncoding regions. 27875 metalloproteinase sequences can be used to obtain such identification sequences from individuals and from tissue. The sequences represent unique fragments of the human genome. Each of the sequences described herein can, to some degree, be used as a standard against which DNA from an individual can be compared for identification purposes.

If a panel of reagents from the sequences is used to generate a unique identification database for an individual, those same reagents can later be used to identify tissue from that individual. Using the unique identification database, positive identification of the individual, living or dead, can be made from extremely small tissue samples.

27875 metalloproteinase polynucleotides can also be used in forensic identification procedures. PCR technology can be used to amplify DNA sequences taken from very small biological samples, such as a single hair follicle, body fluids (e.g. blood, saliva, or semen). The amplified sequence can then be compared to a standard allowing identification of the origin of the sample.

27875 metalloproteinase polynucleotides can thus be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As described above, actual base sequence information can be used for identification as an accurate alternative to patterns formed by restriction enzyme generated fragments. Sequences targeted to the noncoding region are particularly useful since greater polymorphism occurs in the noncoding regions, making it easier to differentiate individuals using this technique.

27875 metalloproteinase polynucleotides can further be used to provide polynucleotide reagents, e.g., labeled or labelable probes which can be used in, for example, an in situ hybridization technique, to identify a specific tissue. This is useful in cases in which a forensic pathologist is presented with a tissue of unknown origin. Panels of 27875 metalloproteinase probes can be used to identify tissue by species and/or by organ type.

In a similar fashion, these primers and probes can be used to screen tissue culture for contamination (i.e. screen for the presence of a mixture of different types of cells in a culture).

Alternatively, 27875 metalloproteinase polynucleotides can be used directly to block transcription or translation of 27875 metalloproteinase gene sequences by means of antisense or ribozyme constructs. Thus, in a disorder characterized by abnormally high or undesirable 27875 metalloproteinase gene expression, nucleic acids can be directly used for treatment.

27875 metalloproteinase polynucleotides are thus useful as antisense constructs to control 27875 metalloproteinase gene expression in cells, tissues, and organisms. A DNA antisense polynucleotide is designed to be complementary to a region of the gene involved in transcription, preventing transcription and hence production of 27875 metalloproteinase protein. An antisense RNA or DNA polynucleotide would hybridize to the mRNA and thus block translation of mRNA into 27875 metalloproteinase protein.

Examples of antisense molecules useful to inhibit nucleic acid expression include antisense molecules complementary to a fragment of the 5' untranslated region of SEQ ID NO:2 which also includes the start codon and antisense molecules which are complementary to a fragment of the 3' untranslated region of SEQ ID NO:1.

Alternatively, a class of antisense molecules can be used to inactivate mRNA in order to decrease expression of 27875 metalloproteinase nucleic acid. Accordingly, these molecules can treat a disorder characterized by abnormal or undesired 27875 metalloproteinase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the 27875 metalloproteinase protein.

27875 metalloproteinase polynucleotides also provide vectors for gene therapy in patients containing cells that are aberrant in 27875 metalloproteinase gene expression. Thus, recombinant cells, which include the patient's cells that have been engineered ex vivo and returned to the patient, are introduced into an individual where the cells produce the desired 27875 metalloproteinase protein to treat the individual.

The invention also encompasses kits for detecting the presence of an 27875 metalloproteinase nucleic acid in a biological sample. For example, the kit can comprise reagents such as a labeled or labelable nucleic acid or agent capable of detecting 27875 metalloproteinase nucleic acid in a biological sample; means for determining the amount of 27875 metalloproteinase nucleic acid in the sample; and means for comparing the amount of 27875 metalloproteinase nucleic acid in the sample with a standard. The compound or agent can be packaged in a suitable container. The kit can further comprise instructions for using the kit to detect 27875 metalloproteinase mRNA or DNA.

Computer Readable Means

The nucleotide or amino acid sequences of the invention are also provided in a variety of mediums to facilitate use thereof. As used herein, "provided" refers to a manufacture, other than an isolated nucleic acid or amino acid molecule, which contains a nucleotide or amino acid sequence of the present invention. Such a manufacture provides the nucleotide or amino acid sequences, or a subset thereof (e.g., a subset of open reading frames (ORFs)) in a form which allows a skilled artisan to examine the manufacture using means not directly applicable to examining the nucleotide or amino acid sequences, or a subset thereof, as they exists in nature or in purified form.

In one application of this embodiment, a nucleotide or amino acid sequence of the present invention can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. The skilled artisan will readily appreciate how any of the presently known computer readable mediums can be used to create a manufacture comprising computer readable medium having recorded thereon a nucleotide or amino acid sequence of the present invention.

As used herein, "recorded" refers to a process for storing information on computer readable medium. The skilled artisan can readily adopt any of the presently known methods for recording information on computer readable medium to generate manufactures comprising the nucleotide or amino acid sequence information of the present invention.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of dataprocessor structuring formats (e.g., text file or database) in order to obtain computer readable medium having recorded thereon the nucleotide sequence information of the present invention.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. Search means are used to identify fragments or regions of the sequences of the invention which match a particular target sequence or target motif.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software includes, but is not limited to, MacPattern (EMBL), BLASTN and BLASTX (NCBIA).

For example, software which implements the BLAST (Altschul et al. (1990) *J. Mol. Biol.* 215:403–410) and BLAZE (Brutlag et al. (1993) *Comp. Chem.* 17:203–207) search algorithms on a Sybase system can be used to identify open reading frames (ORFs) of the sequences of the invention which contain homology to ORFs or proteins from other libraries. Such ORFs are protein encoding fragments and are useful in producing commercially important proteins such as enzymes used in various reactions and in the production of commercially useful metabolites.

Vectors/Host Cells

The invention also provides vectors containing 27875 metalloproteinase polynucleotides. The term "vector" refers to a vehicle, preferably a nucleic acid molecule that can transport 27875 metalloproteinase polynucleotides. When the vector is a nucleic acid molecule, the 27875 metalloproteinase polynucleotides are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of 27875 metalloproteinase polynucleotides. Alternatively, the vector may integrate into the host cell genome and produce additional copies of 27875 metalloproteinase polynucleotides when the host cell replicates.

The invention provides vectors for the maintenance (cloning vectors) or vectors for expression (expression vectors) of 27875 metalloproteinase polynucleotides. The vectors can function in procaryotic or eukaryotic cells or in both (shuttle vectors).

Expression vectors contain cis-acting regulatory regions that are operably linked in the vector to 27875 metalloproteinase polynucleotides such that transcription of the polynucleotides is allowed in a host cell. The polynucleotides can be introduced into the host cell with a separate polynucleotide capable of affecting transcription. Thus, the second polynucleotide may provide a trans-acting factor interacting with the cis-regulatory control region to allow transcription of 27875 metalloproteinase polynucleotides from the vector. Alternatively, a trans-acting factor may be supplied by the host cell. Finally, a trans-acting factor can be produced from the vector itself.

It is understood, however, that in some embodiments, transcription and/or translation of 27875 metalloproteinase polynucleotides can occur in a cell-free system.

The regulatory sequence to which the polynucleotides described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al. (1989) *Molecular Cloning: A Laboratory Manual 2nd. ed.*, Cold Spring Harbor Laboratory Press, Cold Spring Harbor, N.Y.).

A variety of expression vectors can be used to express an 27875 metalloproteinase polynucleotide. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al. (1989) *Molecular Cloning: A Laboratory Manual 2nd. ed.*, Cold Spring Harbor Laboratory Press, Cold Spring Harbor, N.Y.

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

27875 metalloproteinase polynucleotides can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate polynucleotide can be introduced into an appropriate host cell for propagation or expression using well-known techniques. Bacterial cells include, but are not limited to, *E. coli, Streptomyces*, and *Salmonella typhimurium*. Eukaryotic cells include, but are not limited to, yeast, insect cells such as *Drosophila*, animal cells such as COS and CHO cells, and plant cells.

As described herein, it may be desirable to express the polypeptide as a fusion protein. Accordingly, the invention provides fusion vectors that allow for the production of 27875 metalloproteinase polypeptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired polypeptide can ultimately be separated from the fusion moiety. Proteolytic enzymes include, but are not limited to, factor Xa, thrombin, and enterokinase. Typical fusion expression vectors include pGEX (Smith et al. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al. (1988) *Gene* 69:301–315) and pET 11d (Studier et al. (1990) *Gene Expression Technology: Methods in Enzymology* 185:60–89).

Recombinant protein expression can be maximized in a host bacteria by providing a genetic background wherein the host cell has an impaired capacity to proteolytically cleave the recombinant protein. (Gottesman, S. (1990) *Gene Expression Technology: Methods in Enzymology* 185, Academic Press, San Diego, Calif. 119–128). Alternatively, the sequence of the polynucleotide of interest can be altered to provide preferential codon usage for a specific host cell, for example *E. coli.* (Wada et al. (1992) *Nucleic Acids Res.* 20:2111–2118).

27875 metalloproteinase polynucleotides can also be expressed by expression vectors that are operative in yeast. Examples of vectors for expression in yeast e.g., *S. cerevisiae* include pYepSecl (Baldari et al. (1987) *EMBO J.* 6:229–234), pMFa (Kurjan et al. (1982) *Cell* 30:933–943), pJRY88 (Schultz et al. (1987) *Gene* 54:113–123), and pYES2 (Invitrogen Corporation, San Diego, Calif.).

27875 metalloproteinase polynucleotides can also be expressed in insect cells using, for example, baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow et al. (1989) *Virology* 170:31–39).

In certain embodiments of the invention, the polynucleotides described herein are expressed in mammalian cells using mammalian expression vectors. Examples of mammalian expression vectors include pCDM8 (Seed, B. (1987) *Nature* 329:840) and pMT2PC (Kaufman et al. (1987) *EMBO J.* 6:187–195).

The expression vectors listed herein are provided by way of example only of the well-known vectors available to those of ordinary skill in the art that would be useful to express 27875 metalloproteinase polynucleotides. The person of ordinary skill in the art would be aware of other vectors suitable for maintenance propagation or expression of the polynucleotides described herein. These are found for example in Sambrook et al. (1989) *Molecular Cloning: A Laboratory Manual 2nd, ed.*, Cold Spring Harbor Laboratory, Cold Spring Harbor Laboratory Press, Cold Spring Harbor, N.Y.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the polynucleotide sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook et al. (*Molecular Cloning: A Laboratory Manual*, 2d ed., Cold Spring Harbor Laboratory, Cold Spring Harbor Laboratory Press, Cold Spring Harbor, N.Y.).

Host cells can contain more than one vector. Thus, different nucleotide sequences can be introduced on different vectors of the same cell. Similarly, 27875 metalloproteinase polynucleotides can be introduced either alone or with other polynucleotides that are not related to 27875 metalloproteinase polynucleotides such as those providing transacting factors for expression vectors. When more than one vector is introduced into a cell, the vectors can be introduced independently, co-introduced or joined to the 27875 metalloproteinase polynucleotide vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the polynucleotides described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the polypeptide is desired, appropriate secretion signals are incorporated into the vector. The signal sequence can be endogenous to the 27875 metalloproteinase polypeptides or heterologous to these polypeptides.

Where the polypeptide is not secreted into the medium, the protein can be isolated from the host cell by standard disruption procedures, including freeze thaw, sonication, mechanical disruption, use of lysing agents and the like. The polypeptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the polypeptides described herein, the polypeptides can have various glycosylation patterns, depending upon the cell, or maybe non-glycosylated as when produced in bacteria. In addition, the polypeptides may include an initial modified methionine in some cases as a result of a host-mediated process.

Uses of Vectors and Host Cells

It is understood that "host cells" and "recombinant host cells" refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

The host cells expressing the polypeptides described herein, and particularly recombinant host cells, have a variety of uses. First, the cells are useful for producing 27875 metalloproteinase proteins or polypeptides that can be further purified to produce desired amounts of 27875 metalloproteinase protein or fragments. Thus, host cells containing expression vectors are useful for polypeptide production.

Host cells are also useful for conducting cell-based assays involving 27875 metalloproteinase or 27875 metalloproteinase fragments. Thus, a recombinant host cell expressing a native 27875 metalloproteinase is useful to assay for compounds that stimulate or inhibit 27875 metalloproteinase function. This includes zinc or peptide binding, gene expression at the level of transcription or translation, and interaction with other cellular components.

Host cells are also useful for identifying 27875 metalloproteinase mutants in which these functions are affected. If the mutants naturally occur and give rise to a pathology, host cells containing the mutations are useful to assay compounds that have a desired effect on the mutant 27875 metalloproteinase (for example, stimulating or inhibiting function) which may not be indicated by their effect on the native 27875 metalloproteinase.

Recombinant host cells are also useful for expressing the chimeric polypeptides described herein to assess compounds that activate or suppress activation by means of a heterologous domain, segment, site, and the like, as disclosed herein.

Further, mutant 27875 metalloproteinases can be designed in which one or more of the various functions is engineered to be increased or decreased and used to augment or replace 27875 metalloproteinase proteins in an individual. Thus, host cells can provide a therapeutic benefit by replacing an aberrant 27875 metalloproteinase or providing an aberrant 27875 metalloproteinase that provides a therapeutic result. In one embodiment, the cells provide 27875 metalloproteinases that are abnormally active.

In another embodiment, the cells provide 27875 metalloproteinases that are abnormally inactive. These 27875 metalloproteinases can compete with endogenous 27875 metalloproteinases in the individual.

In another embodiment, cells expressing 27875 metalloproteinases that cannot be activated, are introduced into an individual in order to compete with endogenous 27875 metalloproteinases for zinc, glycan, or peptide. For example, in the case in which excessive zinc is part of a treatment modality, it may be necessary to effectively inactivate zinc at a specific point in treatment. Providing cells that compete for the molecule, but which cannot be affected by 27875 metalloproteinase activation would be beneficial.

Homologously recombinant host cells can also be produced that allow the in situ alteration of endogenous metalloproteinase polynucleotide sequences in a host cell genome. The host cell includes, but is not limited to, a stable cell line, cell in vivo, or cloned microorganism. This technology is more fully described in WO 93/09222, WO 91/12650, WO 91/06667, U.S. Pat. Nos. 5,272,071, and 5,641,670. Briefly, specific polynucleotide sequences corresponding to the metalloproteinase polynucleotides or sequences proximal or distal to a metalloproteinase gene are allowed to integrate into a host cell genome by homologous recombination where expression of the gene can be affected. In one embodiment, regulatory sequences are introduced that either increase or decrease expression of an endogenous sequence. Accordingly, a metalloproteinase protein can be produced in a cell not normally producing it. Alternatively, increased expression of metalloproteinase protein can be effected in a cell normally producing the protein at a specific level. Further, expression can be decreased or eliminated by introducing a specific regulatory sequence. The regulatory sequence can be heterologous to the metalloproteinase protein sequence or can be a homologous sequence with a desired mutation that affects expression. Alternatively, the entire gene can be deleted. The regulatory sequence can be specific to the host cell or capable of functioning in more than one cell type. Still further, specific mutations can be introduced into any desired region of the gene to produce mutant metalloproteinase proteins. Such mutations could be introduced, for example, into the specific functional regions such as the peptide substrate-binding site.

In one embodiment, the host cell can be a fertilized oocyte or embryonic stem cell that can be used to produce a transgenic animal containing the altered 27875 metalloproteinase gene. Alternatively, the host cell can be a stem cell or other early tissue precursor that gives rise to a specific subset of cells and can be used to produce transgenic tissues in an animal. See also Thomas et al., *Cell* 51:503 (1987) for a description of homologous recombination vectors. The vector is introduced into an embryonic stem cell line (e.g., by electroporation) and cells in which the introduced gene has homologously recombined with the endogenous 27875 metalloproteinase gene is selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos. WO 90/11354; WO 91/01140; and WO 93/04169.

The genetically engineered host cells can be used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of an 27875 metalloproteinase protein and identifying and evaluating modulators of 27875 metalloproteinase protein activity.

Other examples of transgenic animals include non-human primates, sheep, dogs, cows, goats, chickens, and amphibians.

In one embodiment, a host cell is a fertilized oocyte or an embryonic stem cell into which 27875 metalloproteinase polynucleotide sequences have been introduced.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the 27875 metalloproteinase nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the 27875 metalloproteinase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems, which allow for regulated expression of the transgene. One example of such a system is the cre/loxP recombinase system of bacteriophage P1. For a description of the cre/loxP recombinase system, see, e.g., Lakso et al. (1992) *PNAS* 89:6232–6236. Another example of a recombinase system is the FLP recombinase system of *S. cerevisiae* (O'Gorman et al. (1991) *Science* 251:1351–1355. If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to a pseudopregnant female foster animal. The offspring born of this female foster animal will be a clone of the animal from which the cell, e.g., the somatic cell, is isolated.

Transgenic animals containing recombinant cells that express the polypeptides described herein are useful to conduct the assays described herein in an in vivo context. Accordingly, the various physiological factors that are present in vivo and that could affect binding or activation, may not be evident from in vitro cell-free or cell-based assays. Accordingly, it is useful to provide non-human transgenic animals to assay in vivo 27875 metalloproteinase function, including peptide interaction, the effect of specific mutant 27875 metalloproteinases on 27875 metalloproteinase function and peptide interaction, and the effect of chimeric 27875 metalloproteinases. It is also possible to assess the effect of null mutations, that is mutations that substantially or completely eliminate one or more 27875 metalloproteinase functions.

In general, methods for producing transgenic animals include introducing a nucleic acid sequence according to the present invention, the nucleic acid sequence capable of expressing the protein in a transgenic animal, into a cell in culture or in vivo. When introduced in vivo, the nucleic acid is introduced into an intact organism such that one or more cell types and, accordingly, one or more tissue types, express the nucleic acid encoding the protein. Alternatively, the nucleic acid can be introduced into virtually all cells in an organism by transfecting a cell in culture, such as an embryonic stem cell, as described herein for the production of transgenic animals, and this cell can be used to produce an entire transgenic organism. As described, in a further embodiment, the host cell can be a fertilized oocyte. Such cells are then allowed to develop in a female foster animal to produce the transgenic organism.

Pharmaceutical Compositions 27875 metalloproteinase nucleic acid molecules, proteins, modulators of the protein, and antibodies (also referred to herein as "active compounds") can be incorporated into pharmaceutical compositions suitable for administration to a subject, e.g., a human. Such compositions typically comprise the nucleic acid molecule, protein, modulator, or antibody and a pharmaceutically acceptable carrier.

The term "administer" is used in its broadest sense and includes any method of introducing the compositions of the present invention into a subject. This includes producing polypeptides or polynucleotides in vivo by in vivo transcription or translation of polynucleotides that have been exogenously introduced into a subject. Thus, polypeptides or nucleic acids produced in the subject from the exogenous compositions are encompassed in the term "administer."

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions. A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an 27875 metalloproteinase protein or anti-27875 metalloproteinase antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For oral administration, the agent can be contained in enteric forms to survive the stomach or further coated or mixed to be released in a particular region of the GI tract by known methods. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see e.g., Chen et al. (1994) *PNAS* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The pharmaceutical compositions can be included in a container, pack, or dispenser together with instructions for administration.

This invention may be embodied in many different forms and should not be construed as limited to the embodiments set forth herein; rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

Those skilled in the art will recognize, or be able to ascertain using no more than routine experimentation, many equivalents to the specific embodiments of the invention described herein.

II. 22025, A NOVEL HUMAN CYCLIC NUCLEOTIDE PHOSPHODIESTERASE

BACKGROUND OF THE INVENTION

Cyclic nucleotide phosphodiesterases show specificity for purine cyclic nucleotide substrates and catalyze cyclic AMP (cAMP) and cyclic GMP (cGMP) hydrolysis (Thompson W. J. (1991) *Pharma. Ther.* 51:13–33). Cyclic nucleotide phosphodiesterases regulate the steady-state levels of cAMP and cGMP and modulate both the amplitude and duration of cyclic nucleotide signal. At least eight different but homologous gene families are currently known to exist in mammalian tissues. Most families contain distinct genes, many of which are expressed in different tissues as functionally unique alternative splice variants. (Beavo (1995) *Physiological Reviews* 75:725–748 and U.S. Pat. No. 5,798,246).

All cyclic nucleotide phosphodiesterases contain a core of about 270 conserved amino acids in the COOH-terminal half of the protein thought to be the catalytic domain of the enzyme. The cyclic nucleotide phosphodiesterases within each family display about 65% amino acid homology and the similarity drops to less than 40% when compared between different families with most of the similarity occurring in the catalytic domains.

Most cyclic nucleotide phosphodiesterase genes have more than one alternatively spliced mRNA transcribed from them and in many cases the alternative splicing appears to be highly tissue specific, providing a mechanism for selective expression of different cyclic nucleotide phosphodiesterases (Beavo supra). Cell-type-specific expression suggests that the different isozymes are likely to have different cell-type-specific properties.

Type 1 cyclic nucleotide phosphodiesterases are $Ca^{2+}$/calmodulin dependent, are reported to contain three different genes, each of which appears to have at least two different splice variants, and have been found in the lung, heart and brain. Some of the calmodulin-dependent phosphodiesterases are regulated in vitro by phosphorylation/dephosphorylation events. The effect of phosphorylation is to decrease the affinity of the enzyme for calmodulin, which decreases phosphodiesterase activity, thereby increasing the steady state level of cAMP. Type 2 cyclic nucleotide phosphodiesterases are cGMP stimulated, are localized in the brain and are thought to mediate the effects of cAMP on catecholamine secretion. Type 3 cyclic nucleotide phosphodiesterases are cGMP-inhibited, have a high specificity for cAMP as a substrate, and are one of the major phosphodiesterase isozymes present in vascular smooth muscle and play a role in cardiac function. One isozyme of type 3 is regulated by one or more insulin-dependent kinases. Type 4 cyclic nucleotide phosphodiesterases are the predominant isoenzyme in most inflammatory cells, with some of the members being activated by cAMP-dependent phosphorylation. Type 5 cyclic nucleotide phosphodiesterases have traditionally been thought of as regulators of cGMP function but may also affect cAMP function. High levels of type 5 cyclic nucleotide phosphodiesterases are found in most smooth muscle preparations, platelets and kidney. Type 6 cyclic nucleotide phosphodiesterase family members play a role in vision and are regulated by light and cGMP. A Type 7 cyclic nucleotide phosphodiesterase family member is found in high concentrations in skeletal muscle. A listing of cyclic nucleotide phosphodiesterase families 1–7, their localization and physiological role is given in Beavo supra. A Type 8 family is reported in U.S. Pat. No. 5,798,246.

Many functions of the immune and inflammatory responses are inhibited by agents that increase intracellular levels of cAMP (Verghese (1995) *Mol. Pharmacol.* 47:1164–117 1) while the metabolism of cGMP is involved in smooth muscle, lung and brain cell function (Thompson W. (1991) *Pharma. Ther.* 51:13–33). A variety of diseases have been attributed to increased cyclic nucleotide phosphodiesterase activity which results in decreased levels of cyclic nucleotides. For example, one form of diabetes insipidus in the mouse has been associated with increased phosphodiesterase Family 4 activity and an increase in low-$K_m$ cAMP phosphodiesterase activity has been reported in leukocytes of atopic patients. Defects in cyclic nucleotide phosphodiesterases have also been associated with retinal disease. Retinal degeneration in the rd mouse, human autosomal recessive retinitis pigmentosa, and rod/cone dysplasia 1 in Irish setter dogs has been attributed to mutations in the Family 6 phosphodiesterase, gene B. Family 3 phosphodiesterase has been associated with cardiac disease.

Many inhibitors of different cyclic nucleotide phosphodiesterases have been identified and some have undergone clinical evaluation. For example, Family 3 phosphodiesterase inhibitors are being developed as antithrombotic agents, as antihypertensive agents and as cardiotonic agents useful in the treatment of congestive heart failure. Rolipram, a Family 4 phosphodiesterase inhibitor, has been used in the treatment of depression and other inhibitors of Family 4 phosphodiesterase are undergoing evaluation as anti-inflammatory agents. Rolipram has also been shown to inhibit lipopolysaccharide (LPS) induced TNF-alpha which has been shown to enhance HIV-1 replication in vitro. Therefore, rolipram may inhibit HIV-1 replication (Angel et al. (1995) *AIDS* 9:1137–44). Additionally, based on its ability to suppress the production of TNF alpha and beta and interferon gamma, rolipram has been shown to be effective in the treatment of encephalomyelitis, the experimental animal model for multiple sclerosis (Sommer et al. (1995) *Nat. Med.* 1:244–248) and may be effective in the treatment of tardive dyskinesia (Sasaki et al. (1995) *Eur. J. Pharmacol.* 282:72–76).

There are also nonspecific phosphodiesterase inhibitors such as theophylline, used in the treatment of bronchial asthma and other respiratory diseases, and pentoxifylline, used in the treatment of intermittent claudication and diabetes-induced peripheral vascular disease. Theophylline is thought to act on airway smooth muscle function as well as in an anti-inflammatory or immunomodulatory capacity in the treatment of respiratory diseases (Banner et al. (1995) *Eur. Respir. J* 8:996–1000) where it is thought to act by inhibiting both cyclic nucleotide phosphodiesterase cAMP and cGMP hydrolysis (Banner et al. (1995) *Monaldi Arch. Chest Dis*. 50:286–292). Pentoxifylline, also known to block TNF-alpha production, may inhibit HIV-1 replication (Angel et al. supra). A list of cyclic nucleotide phosphodiesterase inhibitors is given in Beavo supra.

Cyclic nucleotide phosphodiesterases have also been reported to affect cellular proliferation of a variety of cell types and have been implicated in the treatment of various cancers. (Bang et al. (1994) *Proc. Natl. Acad. Sci. USA* 91:5330–5334) reported that the prostate carcinoma cell lines DU 145 and LNCaP were growth-inhibited by delivery of cAMP derivatives and phosphodiesterase inhibitors and observed a permanent conversion in phenotype from epithelial to neuronal morphology; Matousovic et al. ((1995) *J. Clin. Invest*. 96:401–410) suggest that cyclic nucleotide phosphodiesterase isozyme inhibitors have the potential to regulate mesangial cell proliferation; Joulain et al. ((1995) *J. Mediat. Cell Signal* 11:63–79) reports that cyclic nucleotide phosphodiesterase has been shown to be an important target involved in the control of lymphocyte proliferation; and Deonarain et al. ((1994) *Brit. J. Cancer* 70:786–94) suggest a tumor targeting approach to cancer treatment that involves intracellular delivery of phosphodiesterases to particular cellular compartments, resulting in cell death.

Accordingly, cyclic nucleotide phosphodiesterases are a major target for drug action and development. Accordingly, it is valuable to the field of pharmaceutical development to identify and characterize previously unknown phosphodiesterases. The present invention advances the state of the art by providing a previously unidentified human cyclic nucleotide phosphodiesterase.

SUMMARY OF THE INVENTION

It is an object of the invention to identify novel cyclic nucleotide phosphodiesterases. It is a further object of the invention to provide novel cyclic nucleotide phosphodiesterase polypeptides that are useful as reagents or targets in phosphodiesterase assays applicable to treatment and diagnosis of cyclic nucleotide phosphodiesterase-mediated or -related disorders.

It is a further object of the invention to provide polynucleotides corresponding to the novel phosphodiesterase polypeptides that are useful as targets and reagents in phosphodiesterase assays applicable to treatment and diagnosis of phosphodiesterase-mediated or -related disorders and useful for producing novel phosphodiesterase polypeptides by recombinant methods.

A specific object of the invention is to identify compounds that act as agonists and antagonists and modulate the expression of the novel phosphodiesterase.

A further specific object of the invention is to provide compounds that modulate expression of the phosphodiesterase for treatment and diagnosis of phosphodiesterase-related disorders.

The invention is thus based on the identification of a novel human cyclic nucleotide phosphodiesterase. The invention encompasses a long and short form of the phosphodiesterase. The amino acid sequence of the longer form is shown in SEQ ID NO:4 and the amino acid sequence of the shorter form is shown as SEQ ID NO:6. The nucleotide sequence of the longer form is shown as SEQ ID NO:3 and the nucleotide sequence of the shorter form is shown as SEQ ID NO:5.

The invention also provides variant polypeptides having an amino acid sequence that is substantially homologous to the amino acid sequence shown in SEQ ID NO:4 or SEQ ID NO:6 or encoded by the deposited cDNA.

The invention also provides variant nucleic acid sequences that are substantially homologous to the nucleotide sequence shown in SEQ ID NO:3 or SEQ ID NO:5 or in the deposited cDNA.

The invention also provides fragments of the polypeptide shown in SEQ ID NO:4 or SEQ ID NO:6 and nucleotide sequence shown in SEQ ID NO:3 or SEQ ID NO:5, as well as substantially homologous fragments of the polypeptide or nucleic acid.

The invention further provides nucleic acid constructs comprising the nucleic acid molecules described herein. In a preferred embodiment, the nucleic acid molecules of the invention are operatively linked to a regulatory sequence.

The invention also provides vectors and host cells for expressing the phosphodiesterase nucleic acid molecules and polypeptides, and particularly recombinant vectors and host cells.

The invention also provides methods of making the vectors and host cells and methods for using them to produce the phosphodiesterase nucleic acid molecules and polypeptides.

The invention also provides antibodies or antigen-binding fragments thereof that selectively bind the phosphodiesterase polypeptides and fragments.

The invention also provides methods of screening for compounds that modulate expression or activity of the phosphodiesterase polypeptides or nucleic acid (RNA or DNA).

The invention also provides a process for modulating phosphodiesterase polypeptide or nucleic acid expression or activity, especially using the screened compounds. Modulation may be used to treat conditions related to aberrant activity or expression of the phosphodiesterase polypeptides or nucleic acids.

The invention also provides assays for determining the activity of or the presence or absence of the phosphodiesterase polypeptides or nucleic acid molecules in a biological sample, including for disease diagnosis.

The invention also provides assays for determining the presence of a mutation in the polypeptides or nucleic acid molecules, including for disease diagnosis.

In still a further embodiment, the invention provides a computer readable means containing the nucleotide and/or amino acid sequences of the nucleic acids and polypeptides of the invention, respectively.

DETAILED DESCRIPTION OF THE INVENTION

As used herein, a "signaling pathway" refers to the modulation (e.g., stimulation or inhibition) of a cellular function/activity upon the binding of a ligand to a receptor. Examples of such functions include mobilization of intracellular molecules that participate in a signal transduction pathway, e.g., phosphatidylinositol 4,5-bisphosphate (PIP$_2$), inositol 1,4,5-triphosphate (IP$_3$) and adenylate cyclase; polarization of the plasma membrane; production or secretion of molecules; alteration in the structure of a cellular component; cell proliferation, e.g., synthesis of DNA; cell migration; cell differentiation; and cell survival.

The response depends on the type of cell. In some cells, binding of a ligand to the receptor may stimulate an activity such as release of compounds, gating of a channel, cellular adhesion, migration, differentiation, etc., through phosphatidylinositol or cyclic AMP metabolism and turnover while in other cells, binding will produce a different result.

A signaling pathway is the cAMP turnover pathway. As used herein, "cyclic AMP turnover and metabolism" refers to the molecules involved in the turnover and metabolism of cAMP as well as to the activities of these molecules. Cyclic AMP is a second messenger produced in response to ligand-induced stimulation of certain receptors. In the cAMP signaling pathway, binding of a ligand can lead to the activation of the enzyme adenyl cyclase, which catalyzes the synthesis of cAMP. The newly synthesized cAMP can in turn activate a cAMP-dependent protein kinase. This activated kinase can phosphorylate a voltage-gated potassium channel protein, or an associated protein, and lead to the inability of the potassium channel to open during an action potential. The inability of the potassium channel to open results in a decrease in the outward flow of potassium, which normally repolarizes the membrane of a neuron, leading to prolonged membrane depolarization.

Polypeptides

The invention is based on the discovery of a novel human cyclic nucleotide phosphodiesterase. Specifically, an expressed sequence tag (EST) was selected based on homology to phosphodiesterase sequences. This EST was used to design primers based on sequences that it contains and used to identify a cDNA from a kidney and adrenal gland cDNA library. Positive clones were sequenced and the overlapping fragments were assembled. Analysis of the assembled sequence revealed that the cloned cDNA molecule encodes a cyclic nucleotide phosphodiesterase. Nucleic acid encoding a truncated form of the enzyme was also isolated from an osteoblast cDNA library.

Novel phosphodiesterase nucleotides and the deduced polypeptides are described herein. The human 22025 (long) sequence (SEQ ID NO:3), is approximately 2662 nucleotides long including untranslated regions, which encodes a 508 amino acid protein (SEQ ID NO:4). The human 22025 (short) sequence (SEQ ID NO:5), is approximately 3336 nucleotides long including untranslated regions which encodes a 320 amino acid protein (SEQ ID NO:6)

"Phosphodiesterase polypeptide" or "phosphodiesterase protein" refers to the polypeptides in SEQ ID NO:4 or SEQ ID NO:6 or encoded by the deposited cDNAs. The term "phosphodiesterase protein" or "phosphodiesterase polypeptide", however, further includes the numerous variants described herein, as well as fragments derived from the full-length phosphodiesterases and variants.

Tissues and/or cells in which the phosphodiesterases are found include, but are not limited to heart (including fetal), ovary, brain, pancreas, kidneys, breast, liver, testis, prostate, skeletal muscle, and osteoblasts. In addition, the phosphodiesterases are expressed in diseased tissues, including but limited to, those involved in congestive heart failure and breast cancer. Expression has been confirmed by Northern blot analysis and addition, in osteoblasts, by in situ hybridization.

The present invention thus provides an isolated or purified phosphodiesterase polypeptide and variants and fragments thereof.

The phosphodiesterases include a catalytic signature, HDVDHPG (SEQ ID NO:28), at residues 265–271.

Based on a BLAST search, highest homology was shown to Family 7. The long form is designated B2 and the short form B1.

As used herein, a polypeptide is said to be "isolated" or "purified" when it is substantially free of cellular material when it is isolated from recombinant and non-recombinant cells, or free of chemical precursors or other chemicals when it is chemically synthesized. A polypeptide, however, can be joined to another polypeptide with which it is not normally associated in a cell and still be considered "isolated" or "purified."

The phosphodiesterase polypeptides can be purified to homogeneity. It is understood, however, that preparations in which the polypeptide is not purified to homogeneity are useful and considered to contain an isolated form of the polypeptide. The critical feature is that the preparation allows for the desired function of the polypeptide, even in the presence of considerable amounts of other components. Thus, the invention encompasses various degrees of purity.

In one embodiment, the language "substantially free of cellular material" includes preparations of the phosphodiesterase having less than about 30% (by dry weight) other proteins (i.e., contaminating protein), less than about 20% other proteins, less than about 10% other proteins, or less than about 5% other proteins. When the polypeptide is recombinantly produced, it can also be substantially free of culture medium, i.e., culture medium represents less than about 20%, less than about 10%, or less than about 5% of the volume of the protein preparation.

A phosphodiesterase polypeptide is also considered to be isolated when it is part of a membrane preparation or is purified and then reconstituted with membrane vesicles or liposomes.

The language "substantially free of chemical precursors or other chemicals" includes preparations of the phosphodiesterase polypeptide in which it is separated from chemical precursors or other chemicals that are involved in its synthesis. In one embodiment, the language "substantially free of chemical precursors or other chemicals" includes preparations of the polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

In one embodiment, the phosphodiesterase polypeptide comprises the amino acid sequence shown in SEQ ID NO:4 or SEQ ID NO:6. However, the invention also encompasses sequence variants. Variants include a substantially homologous protein encoded by the same genetic locus in an organism, i.e., an allelic variant. The phosphodiesterase has been mapped to human chromosome 6 (6q21-q23.2), with flanking markers AFMA074ZG9 (2.6 cR) and AFM214ZF6 (7.9 cR). Mutations near this locus include, but are not limited to, the following: PPAC, arthropathy, progressive pseudorheumatoid, of childhood; ODDD, oculodentodigital dysplasia; heterocellular hereditary persistence of fetal hemoglobin; DFNA10, deafness, autosomal dominant non-syndromic sensorineural 10; CMD1F, cardiomyopathy, dilated, 1F; and diabetes mellitus, transient neonatal. In the mouse this locus is associated with the following: gl, grey-lethal; dl, downless; Cat5, dominant cataract 5; Lwq3, liver weight QTL 3; mshi, male sterility and histoincompatibility; Mop2, morphine preference 2; H60, histocompatibility 60; Daq4, directional asymmetry QTL 4; Daq5, directional asymmetry QTL 5; and kd/kidney disease. Genes near this locus include PDNP1 (phosphodiesterase 1/nucleotide pyrophosphatase 1 (homologous to mouseLy-41 antigen)), MACS, PTPRK, ARG1, PCMT1, DFNA10, MEKK5, CTGF, SGK, HIVEP2, CMD1F, EPB41L2, HPFH, UTRN, IFNGR1, and ESR1.

Variants also encompass proteins derived from other genetic loci in an organism, but having substantial homology to the phosphodiesterase of SEQ ID NO:4 or SEQ ID NO:6. Variants also include proteins substantially homologous to the phosphodiesterase but derived from another organism, i.e., an ortholog. Variants also include proteins that are substantially homologous to the phosphodiesterase that are produced by chemical synthesis. Variants also include proteins that are substantially homologous to the phosphodiesterase that are produced by recombinant methods. It is understood, however, that variants exclude any amino acid sequences disclosed prior to the invention.

As used herein, two proteins (or a region of the proteins) are substantially homologous when the amino acid sequences are at least about 70–75%, typically at least about 80–85%, and most typically at least about 90–95% or more homologous. A substantially homologous amino acid sequence, according to the present invention, will be encoded by a nucleic acid sequence hybridizing to the nucleic acid sequence, or portion thereof, of the sequence shown in SEQ ID NO:3 or SEQ ID NO:5 under stringent conditions as more fully described below.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the amino acid sequences herein having 502 amino acid residues, at least 165, preferably at least 200, more preferably at least 250, even more preferably at least 300, and even more preferably at least 350, 400, 450, and 500 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The invention also encompasses polypeptides having a lower degree of identity but having sufficient similarity so as to perform one or more of the same functions performed by the phosphodiesterase. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent are found in Bowie et al., Science 247:1306–1310 (1990).

TABLE 2

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part 1*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991).

A preferred, non-limiting example of such a mathematical algorithm is described in Karlin et al. (1993) *Proc. Natl. Acad. Sci.* USA 90:5873–5877. Such an algorithm is incorporated into the NBLAST and XBLAST programs (version 2.0) as described in Altschul et al. (1997) *Nucleic Acids Res.* 25:3389–3402. When utilizing BLAST and Gapped BLAST programs, the default parameters of the respective programs (e.g., NBLAST) can be used. In one embodiment, parameters for sequence comparison can be set at score=100, wordlength=12, or can be varied (e.g., W=5 or W=20).

In a preferred embodiment, the percent identity between two amino acid sequences is determined using the Needleman et al. (1970) (*J. Mol. Biol.* 48:444–453) algorithm which has been incorporated into the GAP program in the GCG software package, using either a BLOSUM 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux et al. (1984) *Nucleic Acids Res.* 12(1):387), using a NWSgapdna.CMP matrix and a gap weight of 40, 50, 60, 70, or 80 and a length weight of 1, 2, 3, 4, 5, or 6.

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the CGC sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis et al. (1994) *Comput. Appl. Biosci.* 10:3–5; and FASTA described in Pearson et al. (1988) *PNAS* 85:2444–8.

A variant polypeptide can differ in amino acid sequence by one or more substitutions, deletions, insertions, inversions, fusions, and truncations or a combination of any of these.

Variant polypeptides can be fully functional or can lack function in one or more activities. Thus, in the present case, variations can affect the function, for example, of one or more of the regions corresponding to the conserved catalytic region, carboxyterminal regulatory regions, aminoterminal regulatory regions, aminoterminal targeting regions, regions involved in membrane association, regions involved in enzyme activation, for example, by phosphorylation, and regions involved in interaction with components of other cyclic nucleotide (e.g., AMP, GMP)-dependent signal transduction pathways.

Fully functional variants typically contain only conservative variation or variation in non-critical residues or in non-critical regions. Functional variants can also contain substitution of similar amino acids, which results in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

As indicated, variants can be naturally-occurring or can be made by recombinant means or chemical synthesis to provide useful and novel characteristics for the phosphodiesterase polypeptide. This includes preventing immunogenicity from pharmaceutical formulations by preventing protein aggregation.

Useful variations further include alteration of catalytic activity. For example, one embodiment involves a variation at the binding site that results in binding but not hydrolysis, or slower hydrolysis, of cAMP. A further useful variation at the same site can result in altered affinity for cAMP. Useful variations also include changes that provide for affinity for another cyclic nucleotide. Another useful variation includes one that prevents activation by protein kinase A. Another useful variation provides a fusion protein in which one or more domains or subregions are operationally fused to one or more domains or subregions from another phosphodiesterase isoform or family.

Amino acids that are essential for function can be identified by methods known in the art, such as site-directed mutagenesis or alanine-scanning mutagenesis (Cunningham et al. (1985) *Science* 244:1081–1085). The latter procedure introduces single alanine mutations at every residue in the molecule. The resulting mutant molecules are then tested for biological activity, such as cAMP hydrolysis in vitro or cAMP-dependent in vitro activity, such as proliferative activity. Sites that are critical for cAMP or protein kinase A binding can also be determined by structural analysis such as crystallization, nuclear magnetic resonance or photoaffinity labeling (Smith et al. (1992) *J. Mol. Biol.* 224:899–904; de Vos et al. (1992) *Science* 255:306–312).

Substantial homology can be to the entire nucleic acid or amino acid sequence or to fragments of these sequences.

The invention thus also includes polypeptide fragments of the phosphodiesterase. Fragments can be derived from the amino acid sequence shown in SEQ ID NO:4 or SEQ ID NO:6. However, the invention also encompasses fragments of the variants of the phosphodiesterases as described herein.

The fragments to which the invention pertains, however, are not to be construed as encompassing fragments that may be disclosed prior to the present invention.

Accordingly, a fragment can comprise at least about 10, 15, 20, 25, 30, 35, 40, 45, 50 or more contiguous amino acids. Fragments can retain one or more of the biological activities of the protein, for example the ability to bind to or hydrolyze cAMP, as well as fragments that can be used as an immunogen to generate phosphodiesterase antibodies.

Biologically active fragments (peptides which are, for example, 5, 7, 10, 12, 15, 20, 30, 35, 36, 37, 38, 39, 40, 50, 100 or more amino acids in length) can comprise a domain or motif, e.g., catalytic site, phosphodiesterase signature, and sites for glycosylation, cAMP and cGMP-dependent protein kinase phosphorylation, protein kinase C phosphorylation, casein kinase II phosphorylation, tyrosine kinase phosphorylation, N-myristoylation, amidation, and glycosaminoglycan attachment. Further possible fragments include the catalytic site, an allosteric binding site, sites important for cellular and subcellular targeting, sites functional for interacting with components of other cAMP-dependent signal transduction pathways, and aminoterminal and carboxyterminal regulatory sites.

Such domains or motifs can be identified by means of routine computerized homology searching procedures.

Fragments, for example, can extend in one or both directions from the functional site to encompass 5, 10, 15, 20, 30, 40, 50, or up to 100 amino acids. Further, fragments can include sub-fragments of the specific domains mentioned above, which sub-fragments retain the function of the domain from which they are derived.

These regions can be identified by well-known methods involving computerized homology analysis.

The invention also provides fragments with immunogenic properties. These contain an epitope-bearing portion of the phosphodiesterase and variants. These epitope-bearing peptides are useful to raise antibodies that bind specifically to a phosphodiesterase polypeptide or region or fragment. These peptides can contain at least 10, 12, at least 14, or between at least about 15 to about 30 amino acids.

Non-limiting examples of antigenic polypeptides that can be used to generate antibodies include but are not limited to peptides derived from an extracellular site. However, intracellularly-made antibodies ("intrabodies") are also encompassed, which would recognize intracellular peptide regions.

The epitope-bearing phosphodiesterase polypeptides may be produced by any conventional means (Houghten, R. A. (1985) *Proc. Natl. Acad. Sci. USA* 82:5131–5135). Simultaneous multiple peptide synthesis is described in U.S. Pat. No. 4,631,211.

Fragments can be discrete (not fused to other amino acids or polypeptides) or can be within a larger polypeptide. Further, several fragments can be comprised within a single larger polypeptide. In one embodiment a fragment designed for expression in a host can have heterologous pre- and pro-polypeptide regions fused to the amino terminus of the phosphodiesterase fragment and an additional region fused to the carboxyl terminus of the fragment.

The invention thus provides chimeric or fusion proteins. These comprise a phosphodiesterase peptide sequence operatively linked to a heterologous peptide having an amino acid sequence not substantially homologous to the phosphodiesterase. "Operatively linked" indicates that the phosphodiesterase peptide and the heterologous peptide are fused in-frame. The heterologous peptide can be fused to the N-terminus or C-terminus of the phosphodiesterase or can be internally located.

In one embodiment the fusion protein does not affect phosphodiesterase function per se. For example, the fusion protein can be a GST-fusion protein in which the phosphodiesterase sequences are fused to the C-terminus of the GST sequences. Other types of fusion proteins include, but are not limited to, enzymatic fusion proteins, for example beta-galactosidase fusions, yeast two-hybrid GAL-4 fusions, poly-His fusions and Ig fusions. Such fusion proteins, particularly poly-His fusions, can facilitate the purification of recombinant phosphodiesterase. In certain host cells (e.g., mammalian host cells), expression and/or secretion of a protein can be increased by using a heterologous signal sequence. Therefore, in another embodiment, the fusion protein contains a heterologous signal sequence at its N-terminus.

EP-A-O 464 533 discloses fusion proteins comprising various portions of immunoglobulin constant regions. The Fc is useful in therapy and diagnosis and thus results, for example, in improved pharmacokinetic properties (EP-A 0232 262). In drug discovery, for example, human proteins have been fused with Fc portions for the purpose of high-throughput screening assays to identify antagonists (Bennett et al. (1995) J. Mol. Recog. 8:52–58 (1995) and Johanson et al. J. Biol. Chem. 270:9459–9471). Thus, this invention also encompasses soluble fusion proteins containing a phosphodiesterase polypeptide and various portions of the constant regions of heavy or light chains of immunoglobulins of various subclass (IgG, IgM, IgA, IgE). Preferred as immunoglobulin is the constant part of the heavy chain of human IgG, particularly IgG1, where fusion takes place at the hinge region. For some uses it is desirable to remove the Fc after the fusion protein has been used for its intended purpose, for example when the fusion protein is to be used as antigen for immunizations. In a particular embodiment, the Fc part can be removed in a simple way by a cleavage sequence, which is also incorporated and can be cleaved with factor Xa.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al. (1992) Current Protocols in Molecular Biology). Moreover, many expression vectors are commercially available that already encode a fusion moiety (e.g., a GST protein). A phosphodiesterase-encoding nucleic acid can be cloned into such an expression vector such that the fusion moiety is linked in-frame to the phosphodiesterase.

Another form of fusion protein is one that directly affects phosphodiesterase functions. Accordingly, a phosphodiesterase polypeptide is encompassed by the present invention in which one or more of the phosphodiesterase domains (or parts thereof) has been replaced by homologous domains (or parts thereof) from another Family 7 phosphodiesterase or other phosphodiesterase family. Accordingly, various permutations are possible. For example, the aminoterminal regulatory domain, or subregion thereof, can be replaced with the domain or subregion from another Family 7 isoform or phosphodiesterase family. As a further example, the catalytic domain or parts thereof, can be replaced; the carboxyterminal domain or subregion can be replaced. Thus, chimeric phosphodiesterases can be formed in which one or more of the native domains or subregions has been replaced by another.

Additionally, chimeric phosphodiesterase proteins can be produced in which one or more functional sites is derived from a different Family 7 isoform, or from another phosphodiesterase family, such as 1–6 and 8. It is understood however that sites could be derived from phosphodiesterase families that occur in the mammalian genome but which have not yet been discovered or characterized. Such sites include but are not limited to the catalytic site, aminoterminal regulatory site, carboxyterminal regulatory site, sites important for targeting to subcellular and cellular locations, sites functional for interaction with components of other cyclic AMP dependent signal transduction pathways, protein kinase A phosphorylation sites, glycosylation sites, and other functional sites disclosed herein.

The isolated phosphodiesterases can be purified from cells that naturally express it, such as from heart (including fetal), ovary, brain, pancreas, kidneys, breast, liver, testis, prostate, skeletal muscle, and osteoblasts, among others, especially purified from cells that have been altered to express it (recombinant), or synthesized using known protein synthesis methods.

In one embodiment, the protein is produced by recombinant DNA techniques. For example, a nucleic acid molecule encoding the phosphodiesterase polypeptide is cloned into an expression vector, the expression vector introduced into a host cell and the protein expressed in the host cell. The protein can then be isolated from the cells by an appropriate purification scheme using standard protein purification techniques. Polypeptides often contain amino acids other than the 20 amino acids commonly referred to as the 20 naturally-occurring amino acids. Further, many amino acids, including the terminal amino acids, may be modified by natural processes, such as processing and other post-translational modifications, or by chemical modification techniques well known in the art. Common modifications that occur naturally in polypeptides are described in basic texts, detailed monographs, and the research literature, and they are well known to those of skill in the art.

Accordingly, the polypeptides also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a pro-protein sequence.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well-known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (1990) *Meth. Enzymol.* 182: 626–646) and Rattan et al. (1992) *Ann. N.Y Acad. Sci.* 663:48–62).

As is also well known, polypeptides are not always entirely linear. For instance, polypeptides may be branched as a result of ubiquitination, and they may be circular, with or without branching, generally as a result of post-translation events, including natural processing events and events brought about by human manipulation which do not occur naturally. Circular, branched and branched circular polypeptides may be synthesized by non-translational natural processes and by synthetic methods.

Modifications can occur anywhere in a polypeptide, including the peptide backbone, the amino acid side-chains and the amino or carboxyl termini. Blockage of the amino or carboxyl group in a polypeptide, or both, by a covalent modification, is common in naturally-occurring and synthetic polypeptides. For instance, the aminoterminal residue of polypeptides made in *E. coli*, prior to proteolytic processing, almost invariably will be N-formylmethionine.

The modifications can be a function of how the protein is made. For recombinant polypeptides, for example, the modifications will be determined by the host cell posttranslational modification capacity and the modification signals in the polypeptide amino acid sequence. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to efficiently express mammalian proteins having native patterns of glycosylation. Similar considerations apply to other modifications.

The same type of modification may be present in the same or varying degree at several sites in a given polypeptide. Also, a given polypeptide may contain more than one type of modification.

Polypeptide Uses

The protein sequences of the present invention can be used as a "query sequence" to perform a search against public databases to, for example, identify other family members or related sequences. Such searches can be performed using the NBLAST and XBLAST programs (version 2.0) of Altschul et al. (1990) *J. Mol. Biol.* 215:403–10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used.

The phosphodiesterase polypeptides are useful for producing antibodies specific for the phosphodiesterase, regions, or fragments. Regions having a high antigenicity index score are described herein.

The phosphodiesterase polypeptides are useful for biological assays related to phosphodiesterases, especially from Family 7. Such assays involve any of the known phosphodiesterase functions or activities or properties useful for diagnosis and treatment of phosphodiesterase-related conditions.

The phosphodiesterase polypeptides are also useful in drug screening assays, in cell-based or cell-free systems. Cell-based systems can be native, i.e., cells that normally express the phosphodiesterase, as a biopsy or expanded in cell culture. In one embodiment, however, cell-based assays involve recombinant host cells expressing the phosphodiesterase.

Determining the ability of the test compound to interact with the phosphodiesterase can also comprise determining the ability of the test compound to preferentially bind to the polypeptide as compared to the ability of a known binding molecule (e.g. cAMP) to bind to the polypeptide.

The polypeptides can be used to identify compounds that modulate phosphodiesterase activity. Such compounds, for example, can increase or decrease affinity or rate of binding to cAMP, compete with cAMP for binding to the phosphodiesterase, or displace cAMP bound to the phosphodiesterase. Both phosphodiesterase and appropriate variants and fragments can be used in high-throughput screens to assay candidate compounds for the ability to bind to the phosphodiesterase. These compounds can be further screened against a functional phosphodiesterase to determine the effect of the compound on the phosphodiesterase activity. Compounds can be identified that activate (agonist) or inactivate (antagonist) the phosphodiesterase to a desired degree. Modulatory methods can be performed in vitro (e.g., by culturing the cell with the agent) or, alternatively, in vivo (e.g., by administering the agent to a subject).

The phosphodiesterase polypeptides can be used to screen a compound for the ability to stimulate or inhibit interaction between the phosphodiesterase protein and a target molecule that normally interacts with the phosphodiesterase protein. The target can be a cyclic nucleotide or another component of the signal pathway with which the phosphodiesterase protein normally interacts (for example, protein kinase A or other interactor involved in cAMP turnover). The assay includes the steps of combining the phosphodiesterase protein with a candidate compound under conditions that allow the phosphodiesterase protein or fragment to interact with the target molecule, and to detect the formation of a complex between the phosphodiesterase protein and the target or to detect the biochemical consequence of the interaction with the phosphodiesterase and the target, such as any of the associated effects of signal transduction such as protein kinase A phosphorylation, cAMP turnover, and biological endpoints of the pathway.

Determining the ability of the phosphodiesterase to bind to a target molecule can also be accomplished using a technology such as real-time Bimolecular Interaction Analysis (BIA). Sjolander et al. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIAcore™). Changes in the optical phenomenon surface plasmon resonance (SPR) can be used as an indication of real-time reactions between biological molecules.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer or small molecule libraries of compounds (Lam, K. S. (1997) *Anticancer Drug Des.* 12:145).

Examples of methods for the synthesis of molecular libraries can be found in the art, for example in DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233. Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc. Natl. Acad. Sci. USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 97:6378–6382); (Felici (1991) *J. Mol. Biol.* 222:301–310); (Ladner supra).

Candidate compounds include, for example, 1) peptides such as soluble peptides, including Ig-tailed fusion peptides and members of random peptide libraries (see, e.g., Lam et al. (1991) *Nature* 354:82–84; Houghten et al. (1991) *Nature* 354:84–86) and combinatorial chemistry-derived molecular libraries made of D- and/or L-configuration amino acids; 2) phosphopeptides (e.g., members of random and partially degenerate, directed phosphopeptide libraries, see, e.g., Songyang et al. (1993) *Cell* 72:767–778); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble full-length phosphodiesterase or fragment that competes for cAMP binding. Other candidate compounds include mutant phosphodiesterases or appropriate fragments containing mutations that affect phosphodiesterase function and thus compete for cAMP. Accordingly, a fragment that competes for cAMP, for example with a higher affinity, or a fragment that binds cAMP but does not degrade it, is encompassed by the invention.

The invention provides other end points to identify compounds that modulate (stimulate or inhibit) phosphodiesterase activity. The assays typically involve an assay of events in the signal transduction pathway that indicate phosphodiesterase activity. Thus, the expression of genes that are up- or down-regulated in response to the phosphodiesterase dependent signal cascade can be assayed. In one embodiment, the regulatory region of such genes can be operably linked to a marker that is easily detectable, such as luciferase. Alternatively, phosphorylation of the phosphodiesterase, or a phosphodiesterase target, could also be measured.

Any of the biological or biochemical functions mediated by the phosphodiesterase can be used as an endpoint assay. These include all of the biochemical or biochemical/biological events described herein, in the references cited herein, incorporated by reference for these endpoint assay targets, and other functions known to those of ordinary skill in the art.

In the case of the phosphodiesterase, specific end points can include cAMP hydrolysis and a decrease in protein kinase A activation.

Binding and/or activating compounds can also be screened by using chimeric phosphodiesterase proteins in which one or more domains, sites, and the like, as disclosed herein, or parts thereof, can be replaced by their heterologous counterparts derived from other Family 7 phosphodiesterases or from phosphodiesterase isoforms of any other phosphodiesterase family. For example, a catalytic region can be used that interacts with a different cyclic nucleotide specificity and/or affinity than the native phosphodiesterase. Accordingly, a different set of signal transduction components is available as an end-point assay for activation. Alternatively, a heterologous targeting sequence can replace the native targeting sequence. This will result in different subcellular or cellular localization and accordingly can result in having an effect on a different signal transduction pathway. Accordingly, a different set of signal transduction components is available as an endpoint assay for activation. As a further alternative, the site of modification by an effector protein, for example phosphorylation by protein kinase A, can be replaced with the site from a different effector protein. This could also provide the use of a different signal transduction pathway for endpoint determination. Activation can also be detected by a reporter gene containing an easily detectable coding region operably linked to a transcriptional regulatory sequence that is part of the native signal transduction pathway.

The phosphodiesterase polypeptides are also useful in competition binding assays in methods designed to discover compounds that interact with the phosphodiesterase. Thus, a compound is exposed to a phosphodiesterase polypeptide under conditions that allow the compound to bind or to otherwise interact with the polypeptide. Soluble phosphodiesterase polypeptide is also added to the mixture. If the test compound interacts with the soluble phosphodiesterase polypeptide, it decreases the amount of complex formed or activity from the phosphodiesterase target. This type of assay is particularly useful in cases in which compounds are sought that interact with specific regions of the phosphodiesterase. Thus, the soluble polypeptide that competes with the target phosphodiesterase region is designed to contain peptide sequences corresponding to the region of interest.

Another type of competition-binding assay can be used to discover compounds that interact with specific functional sites. As an example, protein kinase A and a candidate compound can be added to a sample of the phosphodiesterase. Compounds that interact with the phosphodiesterase at the same site as the protein kinase A will reduce the amount of complex formed between the phosphodiesterase and protein kinase A. Accordingly, it is possible to discover a compound that specifically prevents interaction between the phosphodiesterase and protein kinase A. Another example involves adding a candidate compound to a sample of phosphodiesterase and cAMP. A compound that competes with cAMP will reduce the amount of hydrolysis or binding of the cAMP to the phosphodiesterase. Accordingly, compounds can be discovered that directly interact with the phosphodiesterase and compete with cAMP. Such assays can involve any other component that interacts with the phosphodiesterase.

To perform cell free drug screening assays, it is desirable to immobilize either the phosphodiesterase, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase/phosphodiesterase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes is dissociated. Alternatively, the complexes can be dissociated from the matrix, separated by SDS-PAGE, and the level of phosphodiesterase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a phosphodiesterase-binding target component, such as cAMP or protein kinase A, and a candidate compound are incubated in the phosphodiesterase-presenting wells and the amount of complex trapped in the well can be quantitated. Methods for detecting such complexes, in addition to those described above for the GST-immobilized complexes, include immunodetection of complexes using antibodies reactive with the phosphodiesterase target molecule, or which are reactive with phosphodiesterase and compete with the target molecule; as well as enzyme-linked assays which rely on detecting an enzymatic activity associated with the target molecule.

Modulators of phosphodiesterase activity identified according to these drug screening assays can be used to treat a subject with a disorder mediated by the phosphodiesterase pathway, by treating cells that express the phosphodiesterase, such as heart, ovary, brain, pancreas, kidneys, breast, liver, testis, prostate, skeletal muscle, and osteoblast-containing tissue, such as bone. These methods of treatment include the steps of administering the modulators of phosphodiesterase activity in a pharmaceutical composition as described herein, to a subject in need of such treatment.

The phosphodiesterase is expressed in osteoblasts and is involved in osteoblast differentiation. Accordingly, it is involved in bone matrix deposition and thus, bone formation. As such, the gene is particularly relevant for the treatment of disorders involving bone tissue and particularly in osteoporosis.

Disorders in which the phosphodiesterase expression is relevant include, but are not limited to, dementia, memory loss, congestive heart failure, thrombosis, pulmonary hypertension, glomerulonephritis, bipolar depression, bronchial asthma, atopic diseases, autoimmune encephalomyelitis, organ transplantation, salt retention in nephrotic syndrome, and erectile dysfunction.

The phosphodiesterases are also specifically involved in heart disease, such as in congestive heart failure and breast cancer.

The phosphodiesterase polypeptides are thus useful for treating a phosphodiesterase-associated disorder characterized by aberrant expression or activity of a phosphodiesterase. In one embodiment, the method involves administering an agent (e.g., an agent identified by a screening assay described herein), or combination of agents that modulates (e.g., upregulates or downregulates) expression or activity of the protein. In another embodiment, the method involves administering the phosphodiesterase as therapy to compensate for reduced or aberrant expression or activity of the protein.

Methods for treatment include but are not limited to the use of soluble phosphodiesterase or fragments of the phosphodiesterase protein that compete for cAMP or protein kinase A. These phosphodiesterases or fragments can have a higher affinity for the target so as to provide effective competition.

Stimulation of activity is desirable in situations in which the protein is abnormally downregulated and/or in which increased activity is likely to have a beneficial effect. Likewise, inhibition of activity is desirable in situations in which the protein is abnormally upregulated and/or in which decreased activity is likely to have a beneficial effect. In one example of such a situation, a subject has a disorder characterized by aberrant development or cellular differentiation. In another example, the subject has a proliferative disease (e.g., cancer) or a disorder characterized by an aberrant hematopoietic response. In another example, it is desirable to achieve tissue regeneration in a subject (e.g., where a subject has undergone brain or spinal cord injury and it is desirable to regenerate neuronal tissue in a regulated manner).

In yet another aspect of the invention, the proteins of the invention can be used as "bait proteins" in a two-hybrid assay or three-hybrid assay (see, e.g., U.S. Pat. No. 5,283, 317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO 94/10300), to identify other proteins (captured proteins) which bind to or interact with the proteins of the invention and modulate their activity.

The phosphodiesterase polypeptides also are useful to provide a target for diagnosing a disease or predisposition to disease mediated by the phosphodiesterase, including, but not limited to, diseases involving tissues in which the phosphodiesterases are expressed as disclosed herein, and particularly in osteoporosis, breast cancer, and congestive heart failure. Accordingly, methods are provided for detecting the presence, or levels of, the phosphodiesterase in a cell, tissue, or organism. The method involves contacting a biological sample with a compound capable of interacting with the phosphodiesterase such that the interaction can be detected.

One agent for detecting phosphodiesterase is an antibody capable of selectively binding to phosphodiesterase. A biological sample includes tissues, cells and biological fluids isolated from a subject, as well as tissues, cells and fluids present within a subject.

The phosphodiesterase also provides a target for diagnosing active disease, or predisposition to disease, in a patient having a variant phosphodiesterase. Thus, phosphodiesterase can be isolated from a biological sample and assayed for the presence of a genetic mutation that results in an aberrant protein. This includes amino acid substitution, deletion, insertion, rearrangement, (as the result of aberrant splicing events), and inappropriate post-translational modification. Analytic methods include altered electrophoretic mobility, altered tryptic peptide digest, altered phosphodiesterase activity in cell-based or cell-free assay, alteration in cAMP binding or degradation, protein kinase A binding or phosphorylation, or antibody-binding pattern, altered isoelectric point, direct amino acid sequencing, and any other of the known assay techniques useful for detecting mutations in a protein in general or in a phosphodiesterase specifically.

In vitro techniques for detection of phosphodiesterase include enzyme linked immunosorbent assays (ELISAs), Western blots, immunoprecipitations and immunofluorescence. Alternatively, the protein can be detected in vivo in a subject by introducing into the subject a labeled anti-phosphodiesterase antibody. For example, the antibody can be labeled with a radioactive marker whose presence and location in a subject can be detected by standard imaging techniques. Particularly useful are methods, which detect the allelic variant of the phosphodiesterase expressed in a subject, and methods, which detect fragments of the phosphodiesterase in a sample.

The phosphodiesterase polypeptides are also useful in pharmacogenomic analysis. Pharmacogenomics deal with clinically significant hereditary variations in the response to drugs due to altered drug disposition and abnormal action in affected persons. See, e.g., Eichelbaum, M. (1996) *Clin. Exp. Pharmacol. Physiol.* 23(10–11):983–985, and Linder, M. W. (1997) *Clin. Chem.* 43(2):254–266. The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes affects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the phosphodiesterase in which one or more of the phosphodiesterase functions in one population is different from those in another population. The polypeptides thus allow a target to ascertain a genetic predisposition that can affect treatment modality. Thus, in a cAMP-based treatment, polymorphism may give rise to catalytic regions that are more or less active. Accordingly, dosage would necessarily be modified to maximize the therapeutic effect within a given population containing the polymorphism. As an alternative to genotyping, specific polymorphic polypeptides could be identified.

The phosphodiesterase polypeptides are also useful for monitoring therapeutic effects during clinical trials and other treatment. Thus, the therapeutic effectiveness of an agent that is designed to increase or decrease gene expression, protein levels or phosphodiesterase activity can be monitored over the course of treatment using the phosphodiesterase polypeptides as an end-point target. The monitoring can be, for example, as follows: (i) obtaining a pre-administration sample from a subject prior to administration of the agent; (ii) detecting the level of expression or activity of the protein in the pre-administration sample; (iii) obtaining one or more post-administration samples from the subject; (iv) detecting the level of expression or activity of the protein in the post-administration samples; (v) comparing the level of expression or activity of the protein in the pre-administration sample with the protein in the post-administration sample or samples; and (vi) increasing or decreasing the administration of the agent to the subject accordingly.

Antibodies

The invention also provides antibodies that selectively bind to the phosphodiesterase and its variants and fragments. An antibody is considered to selectively bind, even if it also binds to other proteins that are not substantially homologous with the phosphodiesterase. These other proteins share homology with a fragment or domain of the phosphodiesterase. This conservation in specific regions gives rise to antibodies that bind to both proteins by virtue of the homologous sequence. In this case, it would be understood that antibody binding to the phosphodiesterase is still selective.

To generate antibodies, an isolated phosphodiesterase polypeptide is used as an immunogen to generate antibodies using standard techniques for polyclonal and monoclonal antibody preparation. Either the full-length protein or antigenic peptide fragment can be used.

Antibodies are preferably prepared from these regions or from discrete fragments in these regions. However, antibodies can be prepared from any region of the peptide as described herein. A preferred fragment produces an antibody that diminishes or completely prevents cAMP hydrolysis or binding. Antibodies can be developed against the entire phosphodiesterase or domains of the phosphodiesterase as described herein. Antibodies can also be developed against specific functional sites as disclosed herein.

The antigenic peptide can comprise a contiguous sequence of at least 12, 14, 15, or 30 amino acid residues. In one embodiment, fragments correspond to regions that are located on the surface of the protein, e.g., hydrophilic regions. These fragments are not to be construed, however, as encompassing any fragments, which may be disclosed prior to the invention.

Antibodies can be polyclonal or monoclonal. An intact antibody, or a fragment thereof (e.g. Fab or F(ab')$_2$) can be used.

Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

An appropriate immunogenic preparation can be derived from native, recombinantly expressed, or chemically synthesized peptides.

Antibody Uses

The antibodies can be used to isolate a phosphodiesterase by standard techniques, such as affinity chromatography or immunoprecipitation. The antibodies can facilitate the purification of the natural phosphodiesterase from cells and recombinantly produced phosphodiesterase expressed in host cells.

The antibodies are useful to detect the presence of phosphodiesterase in cells or tissues to determine the pattern of expression of the phosphodiesterase among various tissues in an organism and over the course of normal development.

The antibodies can be used to detect phosphodiesterase in situ, in vitro, or in a cell lysate or supernatant in order to evaluate the abundance and pattern of expression.

The antibodies can be used to assess abnormal tissue distribution or abnormal expression during development.

Antibody detection of circulating fragments of the full length phosphodiesterase can be used to identify phosphodiesterase turnover.

Further, the antibodies can be used to assess phosphodiesterase expression in disease states such as in active stages of the disease or in an individual with a predisposition toward disease related to phosphodiesterase function. When a disorder is caused by an inappropriate tissue distribution, developmental expression, or level of expression of the phosphodiesterase protein, the antibody can be prepared against the normal phosphodiesterase protein. If a disorder is characterized by a specific mutation in the phosphodiesterase, antibodies specific for this mutant protein can be used to assay for the presence of the specific mutant phosphodiesterase. However, intracellularly-made antibodies ("intrabodies") are also encompassed, which would recognize intracellular phosphodiesterase peptide regions.

The antibodies can also be used to assess normal and aberrant subcellular localization of cells in the various tissues in an organism. Antibodies can be developed against the whole phosphodiesterase or portions of the phosphodiesterase.

The diagnostic uses can be applied, not only in genetic testing, but also in monitoring a treatment modality. Accordingly, where treatment is ultimately aimed at correcting phosphodiesterase expression level or the presence of aberrant phosphodiesterases and aberrant tissue distribution or developmental expression, antibodies directed against the phosphodiesterase or relevant fragments can be used to monitor therapeutic efficacy.

Antibodies accordingly can be used diagnostically to monitor protein levels in tissue as part of a clinical testing procedure, e.g., to, for example, determine the efficacy of a given treatment regimen.

Additionally, antibodies are useful in pharmacogenomic analysis. Thus, antibodies prepared against polymorphic phosphodiesterase can be used to identify individuals that require modified treatment modalities.

The antibodies are also useful as diagnostic tools as an immunological marker for aberrant phosphodiesterase analyzed by electrophoretic mobility, isoelectric point, tryptic peptide digest, and other physical assays known to those in the art.

The antibodies are also useful for tissue typing. Thus, where a specific phosphodiesterase has been correlated with expression in a specific tissue, antibodies that are specific for this phosphodiesterase can be used to identify a tissue type.

The antibodies are also useful in forensic identification. Accordingly, where an individual has been correlated with a specific genetic polymorphism resulting in a specific polymorphic protein, an antibody specific for the polymorphic protein can be used as an aid in identification.

The antibodies are also useful for inhibiting phosphodiesterase function, for example, blocking cAMP, protein kinase A, or the catalytic site.

These uses can also be applied in a therapeutic context in which treatment involves inhibiting phosphodiesterase function. An antibody can be used, for example, to block cAMP binding. Antibodies can be prepared against specific fragments containing sites required for function or against intact phosphodiesterase associated with a cell.

Completely human antibodies are particularly desirable for therapeutic treatment of human patients. For an overview of this technology for producing human antibodies, see Lonberg et al. (1995) *Int. Rev. Immunol.* 13:65–93. For a detailed discussion of this technology for producing human antibodies and human monoclonal antibodies and protocols for producing such antibodies, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806.

The invention also encompasses kits for using antibodies to detect the presence of a phosphodiesterase protein in a biological sample. The kit can comprise antibodies such as a labeled or labelable antibody and a compound or agent for detecting phosphodiesterase in a biological sample; means for determining the amount of phosphodiesterase in the sample; and means for comparing the amount of phosphodiesterase in the sample with a standard. The compound or agent can be packaged in a suitable container. The kit can further comprise instructions for using the kit to detect phosphodiesterase.

Polynucleotides

The nucleotide sequences in SEQ ID NO:3 or SEQ ID NO:5 were obtained by sequencing the deposited human cDNA. Accordingly, the sequence of the deposited clone is controlling as to any discrepancies between the two and any reference to the sequences of SEQ ID NO:3 or SEQ ID NO:5 includes reference to the sequences of the deposited cDNA.

The specifically disclosed cDNAs comprise the coding region and 5' and 3' untranslated sequences in SEQ ID NO:3 or SEQ ID NO:5.

The invention provides isolated polynucleotides encoding the novel phosphodiesterases. The term "phosphodiesterase polynucleotide" or "phosphodiesterase nucleic acid" refers to the sequences shown in SEQ ID NO:3 or SEQ ID NO:5 or in the deposited cDNAs. The term "phosphodiesterase polynucleotide" or "phosphodiesterase nucleic acid" further includes variants and fragments of the phosphodiesterase polynucleotides.

An "isolated" phosphodiesterase nucleic acid is one that is separated from other nucleic acid present in the natural source of the phosphodiesterase nucleic acid. Preferably, an "isolated" nucleic acid is free of sequences which naturally flank the phosphodiesterase nucleic acid (i.e., sequences located at the 5' and 3' ends of the nucleic acid) in the genomic DNA of the organism from which the nucleic acid is derived. However, there can be some flanking nucleotide sequences, for example up to about 5 KB. The important point is that the phosphodiesterase nucleic acid is isolated from flanking sequences such that it can be subjected to the specific manipulations described herein, such as recombinant expression, preparation of probes and primers, and other uses specific to the phosphodiesterase nucleic acid sequences.

Moreover, an "isolated" nucleic acid molecule, such as a cDNA or RNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

In some instances, the isolated material will form part of a composition (for example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

In some instances, the isolated material will form part of a composition (or example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

The phosphodiesterase polynucleotides can encode the mature protein plus additional amino or carboxyterminal amino acids, or amino acids interior to the mature polypeptide (when the mature form has more than one polypeptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

The phosphodiesterase polynucleotides include, but are not limited to, the sequence encoding the mature polypeptide alone, the sequence encoding the mature polypeptide and additional coding sequences, such as a leader or secretory sequence (e.g., a pre-pro or pro-protein sequence), the sequence encoding the mature polypeptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the polynucleotide may be fused to a marker sequence encoding, for example, a peptide that facilitates purification.

Phosphodiesterase polynucleotides can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

Phosphodiesterase nucleic acid can comprise the nucleotide sequences shown in SEQ ID NO:3 or SEQ ID NO:5, corresponding to human osteoblast (short form) and kidney and adrenal gland (long form) cDNA.

In one embodiment, the phosphodiesterase nucleic acid comprises only the coding region.

The invention further provides variant phosphodiesterase polynucleotides, and fragments thereof, that differ from the nucleotide sequences shown in SEQ ID NO:3 or SEQ ID NO:5 due to degeneracy of the genetic code and thus encode the same protein as that encoded by the nucleotide sequences shown in SEQ ID NO:3 or SEQ ID NO:5.

The invention also provides phosphodiesterase nucleic acid molecules encoding the variant polypeptides described herein. Such polynucleotides may be naturally occurring, such as allelic variants (same locus), homologs (different locus), and orthologs (different organism), or may be constructed by recombinant DNA methods or by chemical synthesis. Such non-naturally occurring variants may be made by mutagenesis techniques, including those applied to polynucleotides, cells, or organisms. Accordingly, as discussed above, the variants can contain nucleotide substitutions, deletions, inversions and insertions.

Typically, variants have a substantial identity with a nucleic acid molecules of SEQ ID NO:3 or SEQ ID NO:5 and the complements thereof. Variation can occur in either or both the coding and non-coding regions. The variations can produce both conservative and non-conservative amino acid substitutions.

Orthologs, homologs, and allelic variants can be identified using methods well known in the art. These variants comprise a nucleotide sequence encoding a phosphodiesterase that is at least about 60–65%, 65–70%, typically at least about 70–75%, more typically at least about 80–85%, and most typically at least about 90–95% or more homologous to the nucleotide sequence shown in SEQ ID NO:3 or SEQ ID NO:5 or a fragment of this sequence. Such nucleic acid molecules can readily be identified as being able to hybridize under stringent conditions, to the nucleotide sequence shown in SEQ ID NO:3 or SEQ ID NO:5 or a fragment of the sequence. It is understood that stringent hybridization does not indicate substantial homology where it is due to general homology, such as poly A sequences, or sequences common to all or most proteins, all cyclic nucleotide phosphodiesterases, or all Family 7 phosphodiesterases. Moreover, it is understood that variants do not include any of the nucleic acid sequences that may have been disclosed prior to the invention.

As used herein, the term "hybridizes under stringent conditions" is intended to describe conditions for hybridization and washing under which nucleotide sequences encoding a polypeptide at least about 60–65% homologous to each other typically remain hybridized to each other. The conditions can be such that sequences at least about 65%, at least about 70%, at least about 75%, at least about 80%, at least about 90%, at least about 95% or more identical to each other remain hybridized to one another. Such stringent conditions are known to those skilled in the art and can be found in *Current Protocols in Molecular Biology*, John Wiley & Sons, N.Y. (1989), 6.3.1–6.3.6, incorporated by reference. One example of stringent hybridization conditions are hybridization in 6× sodium chloride/sodium citrate (SSC) at about 45° C., followed by one or more washes in 0.2×SSC, 0.1% SDS at 50–65° C. In another non-limiting example, nucleic acid molecules are allowed to hybridize in 6× sodium chloride/sodium citrate (SSC) at about 45° C., followed by one or more low stringency washes in 0.2× SSC/0.1% SDS at room temperature, or by one or more moderate stringency washes in 0.2×SSC/0.1% SDS at 42° C., or washed in 0.2×SSC/0.1% SDS at 65° C. for high stringency. In one embodiment, an isolated nucleic acid molecule that hybridizes under stringent conditions to the sequence of SEQ ID NO:3 or SEQ ID NO:5 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

As understood by those of ordinary skill, the exact conditions can be determined empirically and depend on ionic strength, temperature and the concentration of destabilizing agents such as formamide or denaturing agents such as SDS. Other factors considered in determining the desired hybridization conditions include the length of the nucleic acid sequences, base composition, percent mismatch between the hybridizing sequences and the frequency of occurrence of subsets of the sequences within other non-identical sequences. Thus, equivalent conditions can be determined by varying one or more of these parameters while maintaining a similar degree of identity or similarity between the two nucleic acid molecules.

The present invention also provides isolated nucleic acids that contain a single or double stranded fragment or portion that hybridizes under stringent conditions to the nucleotide sequence of SEQ ID NO:3 or SEQ ID NO:5 or the complement of SEQ ID NO:3 or SEQ ID NO:5. In one embodiment, the nucleic acid consists of a portion of the nucleotide sequence of SEQ ID NO:3 or SEQ ID NO:5 and the complement of SEQ ID NO:3 or SEQ ID NO:5. The nucleic acid fragments of the invention are at least about 15, preferably at least about 18, 20, 23 or 25 nucleotides, and can be 30, 40, 50, 100, 200, 500 or more nucleotides in length. Longer fragments, for example, 30 or more nucleotides in length, which encode antigenic proteins or polypeptides described herein are useful.

Furthermore, the invention provides polynucleotides that comprise a fragment of the full-length phosphodiesterase polynucleotides. The fragment can be single or double-stranded and can comprise DNA or RNA. The fragment can be derived from either the coding or the non-coding sequence.

In another embodiment an isolated phosphodiesterase nucleic acid encodes the entire coding region. In another embodiment the isolated phosphodiesterase nucleic acid encodes a sequence corresponding to the mature protein that may be from about amino acid 6 to the last amino acid. Other fragments include nucleotide sequences encoding the amino acid fragments described herein.

Thus, phosphodiesterase nucleic acid fragments further include sequences corresponding to the domains described herein, subregions also described, and specific functional sites. Phosphodiesterase nucleic acid fragments also include combinations of the domains, segments, and other functional sites described above. A person of ordinary skill in the art would be aware of the many permutations that are possible.

Where the location of the domains or sites have been predicted by computer analysis, one of ordinary sill would appreciate that the amino acid residues constituting these domains can vary depending on the criteria used to define the domains.

However, it is understood that a phosphodiesterase fragment includes any nucleic acid sequence that does not include the entire gene.

The invention also provides phosphodiesterase nucleic acid fragments that encode epitope bearing regions of the phosphodiesterase proteins described herein.

Nucleic acid fragments, according to the present invention, are not to be construed as encompassing those fragments that may have been disclosed prior to the invention.

Polynucleotide Uses

The nucleotide sequences of the present invention can be used as a "query sequence" to perform a search against public databases, for example, to identify other family members or related sequences. Such searches can be performed using the NBLAST and XBLAST programs (version 2.0) of Altschul et al. (1990) *J. Mol. Biol.* 215:403–10. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (1997) *Nucleic Acids Res.* 25(17):3389–3402. When utilizing BLAST and Gapped BLAST programs, the default parameters of the respective programs (e.g., XBLAST and NBLAST) can be used.

The nucleic acid fragments of the invention provide probes or primers in assays such as those described below. "Probes" are oligonucleotides that hybridize in a base-specific manner to a complementary strand of nucleic acid. Such probes include polypeptide nucleic acids, as described in Nielsen et al. (1991) *Science* 254:1497–1500. Typically, a probe comprises a region of nucleotide sequence that hybridizes under highly stringent conditions to at least about 15, typically about 20–25, and more typically about 40, 50 or 75 consecutive nucleotides of the nucleic acid sequence shown in SEQ ID NO:3 or SEQ ID NO:5 and the complements thereof. More typically, the probe further comprises a label, e.g., radioisotope, fluorescent compound, enzyme, or enzyme co-factor.

As used herein, the term "primer" refers to a single-stranded oligonucleotide which acts as a point of initiation of template-directed DNA synthesis using well-known methods (e.g., PCR, LCR) including, but not limited to those described herein. The appropriate length of the primer depends on the particular use, but typically ranges from about 15 to 30 nucleotides. The term "primer site" refers to the area of the target DNA to which a primer hybridizes. The term "primer pair" refers to a set of primers including a 5' (upstream) primer that hybridizes with the 5' end of the nucleic acid sequence to be amplified and a 3' (downstream) primer that hybridizes with the complement of the sequence to be amplified.

The phosphodiesterase polynucleotides are thus useful for probes, primers, and in biological assays.

Where the polynucleotides are used to assess phosphodiesterase properties or functions, such as in the assays described herein, all or less than all of the entire cDNA can be useful. Assays specifically directed to phosphodiesterase functions, such as assessing agonist or antagonist activity, encompass the use of known fragments. Further, diagnostic methods for assessing phosphodiesterase function can also be practiced with any fragment, including those fragments that may have been known prior to the invention. Similarly, in methods involving treatment of phosphodiesterase dysfunction, all fragments are encompassed including those, which may have been known in the art.

The phosphodiesterase polynucleotides are useful as a hybridization probe for cDNA and genomic DNA to isolate a full-length cDNA and genomic clones encoding the polypeptides described in SEQ ID NO:4 or SEQ ID NO:6 and to isolate cDNA and genomic clones that correspond to variants producing the same polypeptides shown in SEQ ID NO:3 or SEQ ID NO:5 or the other variants described herein. Variants can be isolated from the same tissue and organism from which the polypeptides shown in SEQ ID NO:4 or SEQ ID NO:6 were isolated, different tissues from the same organism, or from different organisms. This method is useful for isolating genes and cDNA that are developmentally-controlled and therefore,may be expressed in the same tissue or different tissues at different points in the development of an organism.

The probe can correspond to any sequence along the entire length of the gene encoding the phosphodiesterase. Accordingly, it could be derived from 5' noncoding regions, the coding region, and 3' noncoding regions.

The nucleic acid probe can be, for example, the full-length cDNA of SEQ ID NO:3 or SEQ ID NO:5, or a fragment thereof, such as an oligonucleotide of at least 12, 15, 30, 50, 100, 250 or 500 nucleotides in length and sufficient to specifically hybridize under stringent conditions to mRNA or DNA.

Fragments of the polynucleotides described herein are also useful to synthesize larger fragments or full-length polynucleotides described herein. For example, a fragment can be hybridized to any portion of an mRNA and a larger or full-length cDNA can be produced.

The fragments are also useful to synthesize antisense molecules of desired length and sequence.

Antisense nucleic acids of the invention can be designed using the nucleotide sequences of SEQ ID NO:3 or SEQ ID NO:5, and constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the anti sense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

Additionally, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670. PNAs can be further modified, e.g., to enhance their stability, specificity or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra, Finn et al. (1996) *Nucleic Acids Res*. 24(17):3357–63, Mag et al. (1989) *Nucleic Acids Res*. 17:5973, and Peterser et al. (1975) *Bioorganic Med. Chem. Lett*. 5:1119.

The nucleic acid molecules and fragments of the invention can also include other appended groups such as peptides (e.g., for targeting host cell phosphodiesterases in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO 88/0918) or the blood brain barrier (see, e.g., PCT Publication No. WO 89/10134). In addition, oligonucleotides can be modified with hybridization-triggered cleavage agents (see, e.g., Krol et al. (1988) *Bio-Techniques* 6:958–976) or intercalating agents (see, e.g., Zon (1988) *Pharm Res*. 5:539–549).

The phosphodiesterase polynucleotides are also useful as primers for PCR to amplify any given region of a phosphodiesterase polynucleotide.

The phosphodiesterase polynucleotides are also useful for constructing recombinant vectors. Such vectors include expression vectors that express a portion of, or all of, the phosphodiesterase polypeptides. Vectors also include insertion vectors, used to integrate into another polynucleotide sequence, such as into the cellular genome, to alter in situ expression of phosphodiesterase genes and gene products. For example, an endogenous phosphodiesterase coding sequence can be replaced via homologous recombination with all or part of the coding region containing one or more specifically introduced mutations.

The phosphodiesterase polynucleotides are also useful for expressing antigenic portions of the phosphodiesterase proteins.

The phosphodiesterase polynucleotides are also useful as probes for determining the chromosomal positions of the phosphodiesterase polynucleotides by means of in situ hybridization methods, such as FISH. (For a review of this technique, see Verma et al. (1988) *Human Chromosomes: A Manual of Basic Techniques* (Pergamon Press, New York), and PCR mapping of somatic cell hybrids. The mapping of the sequences to chromosomes is an important first step in correlating these sequences with genes associated with disease.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, *Mendelian Inheritance in Man*, available on-line through Johns Hopkins University Welch Medical Library). The relationship between a gene and a disease mapped to the same chromosomal region, can then be identified through linkage analysis (co-inheritance of physically adjacent genes), described in, for example, Egeland et al. ((1987) *Nature* 325:783–787).

Moreover, differences in the DNA sequences between individuals affected and unaffected with a disease associated with a specified gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations, that are visible from chromosome spreads, or detectable using PCR based on that DNA sequence. Ultimately, complete sequencing of genes from several individuals can be performed to confirm the presence of a mutation and to distinguish mutations from polymorphisms.

The phosphodiesterase polynucleotide probes are also useful to determine patterns of the presence of the gene encoding the phosphodiesterases and their variants with respect to tissue distribution, for example, whether gene duplication has occurred and whether the duplication occurs in all or only a subset of tissues. The genes can be naturally occurring or can have been introduced into a cell, tissue, or organism exogenously.

The phosphodiesterase polynucleotides are also useful for designing ribozymes corresponding to all, or a part, of the mRNA produced from genes encoding the polynucleotides described herein.

The phosphodiesterase polynucleotides are also useful for constructing host cells expressing a part, or all, of the phosphodiesterase polynucleotides and polypeptides.

The phosphodiesterase polynucleotides are also useful for constructing transgenic animals expressing all, or a part, of the phosphodiesterase polynucleotides and polypeptides.

The phosphodiesterase polynucleotides are also useful for making vectors that express part, or all, of the phosphodiesterase polypeptides.

The phosphodiesterase polynucleotides are also useful as hybridization probes for determining the level of phosphodiesterase nucleic acid expression. Accordingly, the probes can be used to detect the presence of, or to determine levels of, phosphodiesterase nucleic acid in cells, tissues, and in organisms. The nucleic acid whose level is determined can be DNA or RNA. Accordingly, probes corresponding to the polypeptides described herein can be used to assess gene copy number in a given cell, tissue, or organism. This is particularly relevant in cases in which there has been an amplification of the phosphodiesterase genes.

Alternatively, the probe can be used in an in situ hybridization context to assess the position of extra copies of the phosphodiesterase genes, as on extrachromosomal elements or as integrated into chromosomes in which the phosphodiesterase gene is not normally found, for example as a homogeneously staining region.

These uses are relevant for diagnosis of disorders involving an increase or decrease in phosphodiesterase expression relative to normal, such as a proliferative disorder, a differentiative or developmental disorder, or a hematopoietic disorder.

The phosphodiesterases are expressed in osteoblasts and are involved in osteoblast differentiation. Accordingly, they are involved in bone matrix deposition and thus, bone formation. As such, the gene is particularly relevant for the treatment of disorders involving bone tissue and particularly in osteoporosis.

The phosphodiesterases are also specifically involved in heart disease, such as congestive heart failure, and in breast cancer.

Disorders in which phosphodiesterase expression is relevant also include, but are not limited to, dementia, memory loss, congestive heart failure, thrombosis, pulmonary hypertesion, glomerutonephritis, bipolar depression, bronchial asthma, atopic diseases, autoimmune encepthelomyelitis, organ transplantation, salt retention in nephrotic syndrome, and erectile dysfunction.

Thus, the present invention provides a method for identifying a disease or disorder associated with aberrant expression or activity of phosphodiesterase nucleic acid, in which a test sample is obtained from a subject and nucleic acid (e.g., mRNA, genomic DNA) is detected, wherein the presence of the nucleic acid is diagnostic for a subject having or at risk of developing a disease or disorder associated with aberrant expression or activity of the nucleic acid.

One aspect of the invention relates to diagnostic assays for determining nucleic acid expression as well as activity in the context of a biological sample (e.g., blood, serum, cells, tissue) to determine whether an individual has a disease or disorder, or is at risk of developing a disease or disorder, associated with aberrant nucleic acid expression or activity. Such assays can be used for prognostic or predictive purpose to thereby prophylactically treat an individual prior to the onset of a disorder characterized by or associated with expression or activity of the nucleic acid molecules.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express the phosphodiesterase, such as by measuring the level of a phosphodiesterase-encoding nucleic acid in a sample of cells from a subject e.g., mRNA or genomic DNA, or determining if the phosphodiesterase gene has been mutated.

Nucleic acid expression assays are useful for drug screening to identify compounds that modulate phosphodiesterase nucleic acid expression (e.g., antisense, polypeptides, peptidomimetics, small molecules or other drugs). A cell is contacted with a candidate compound and the expression of mRNA determined. The level of expression of the mRNA in the presence of the candidate compound is compared to the level of expression of the mRNA in the absence of the candidate compound. The candidate compound can then be identified as a modulator of nucleic acid expression based on this comparison and be used, for example to treat a disorder characterized by aberrant nucleic acid expression. The modulator can bind to the nucleic acid or indirectly modulate expression, such as by interacting with other cellular components that affect nucleic acid expression.

Modulatory methods can be performed in vitro (e.g., by culturing the cell with the agent) or, alternatively, in vivo (e.g., by administering the gent to a subject) in patients or in transgenic animals.

The invention thus provides a method for identifying a compound that can be used to treat a disorder associated with nucleic acid expression of the phosphodiesterase gene. The method typically includes assaying the ability of the compound to modulate the expression of the phosphodiesterase nucleic acid and thus identifying a compound that can be used to treat a disorder characterized by undesired phosphodiesterase nucleic acid expression.

The assays can be performed in cell-based and cell-free systems. Cell-based assays include cells naturally expressing the phosphodiesterase nucleic acid or recombinant cells genetically engineered to express specific nucleic acid sequences.

Alternatively, candidate compounds can be assayed in vivo in patients or in transgenic animals.

The assay for phosphodiesterase nucleic acid expression can involve direct assay of nucleic acid levels, such as mRNA levels, or on collateral compounds involved in the signal pathway (such as cyclic AMP turnover). Further, the expression of genes that are up- or down-regulated in response to the phosphodiesterase signal pathway can also be assayed. In this embodiment the regulatory regions of these genes can be operably linked to a reporter gene such as luciferase.

Thus, modulators of phosphodiesterase gene expression can be identified in a method wherein a cell is contacted with a candidate compound and the expression of mRNA determined. The level of expression of phosphodiesterase mRNA in the presence of the candidate compound is compared to the level of expression of phosphodiesterase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

Accordingly, the invention provides methods of treatment, with the nucleic acid as a target, using a compound identified through drug screening as a gene modulator to modulate phosphodiesterase nucleic acid expression. Modulation includes both up-regulation (i.e. activation or agonization) or down-regulation (suppression or antagonization) or effects on nucleic acid activity (e.g. when nucleic acid is mutated or improperly modified). Treatment is of disorders characterized by aberrant expression or activity of the nucleic acid.

The gene is particularly relevant for the treatment of disorders involving bone tissue and particularly in osteoporosis. The gene is also involved in heart disease, such as congestive heart failure, and in breast cancer. Further disorders in which expression is relevant include, but are not limited to, dementia, memory loss, congestive heart failure, thrombosis, pulmonary hypertesion, glomerulonephritis, bipolar depression, bronchial asthma, atopic diseases, autoimmune encephalomyelitis, organ transplantation, salt retention in nephrotic syndrome, and erectile dysfunction.

Alternatively, a modulator for phosphodiesterase nucleic acid expression can be a small molecule or drug identified using the screening assays described herein as long as the drug or small molecule inhibits the phosphodiesterase nucleic acid expression.

The phosphodiesterase polynucleotides are also useful for monitoring the effectiveness of modulating compounds on the expression or activity of the phosphodiesterase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

Monitoring can be, for example, as follows: (i) obtaining a pre-administration sample from a subject prior to administration of the agent; (ii) detecting the level of expression of a specified mRNA or genomic DNA of the invention in the pre-administration sample; (iii) obtaining one or more post-administration samples from the subject; (iv) detecting the level of expression or activity of the mRNA or genomic DNA in the post-administration samples; (v) comparing the level of expression or activity of the mRNA or genomic DNA in the pre-administration sample with the mRNA or genomic DNA in the post-administration sample or samples; and (vi) increasing or decreasing the administration of the agent to the subject accordingly.

The phosphodiesterase polynucleotides are also useful in diagnostic assays for qualitative changes in phosphodiesterase nucleic acid, and particularly in qualitative changes that lead to pathology. The polynucleotides can be used to detect mutations in phosphodiesterase genes and gene expression products such as mRNA. The polynucleotides can be used as hybridization probes to detect naturally-occurring genetic mutations in the phosphodiesterase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the phosphodiesterase gene associated with a dysfunction provides a diagnostic tool for an active disease or susceptibility to disease when the disease results from overexpression, underexpression, or altered expression of a phosphodiesterase.

Mutations in the phosphodiesterase gene can be detected at the nucleic acid level by a variety of techniques. Genomic DNA can be analyzed directly or can be amplified by using PCR prior to analysis. RNA or cDNA can be used in the same way.

In certain embodiments, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364), the latter of which can be particularly useful for detecting point mutations in the gene (see Abravaya et al. (1995) *Nucleic Acids Res.*

23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) *Proc. Natl. Acad. Sci. USA* 87:1874–1878), transcriptional amplification system (Kwoh et al. (1989) *Proc. Natl. Acad. Sci. USA* 86:1173–1177), Q-Beta Replicase (Lizardi et al. (1988) *Bio/Technology* 6:1197), or any other nucleic acid amplification method, followed by the detection of the amplified molecules using techniques well-known to those of skill in the art. These detection schemes are especially useful for the detection of nucleic acid molecules if such molecules are present in very low numbers.

Alternatively, mutations in a phosphodiesterase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site.

Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method.

Furthermore, sequence differences between a mutant phosphodiesterase gene and a wild-type gene can be determined by direct DNA sequencing. A variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the gene include methods in which protection from cleavage agents is used to detect mismatched bases in RNA/RNA or RNA/DNA duplexes (Myers et al. (1985) *Science* 230:1242); Cotton et al. (1988) *PNAS* 85:4397; Saleeba et al. (1992) *Meth. Enzymol.* 217:286–295), electrophoretic mobility of mutant and wild type nucleic acid is compared (Orita et al. (1989) *PNAS* 86:2766; Cotton et al. (1993) *Mutat. Res.* 285:125–144; and Hayashi et al. (1992) *Genet. Anal. Tech. Appl.* 9:73–79), and movement of mutant or wild-type fragments in polyacrylamide gels containing a gradient of denaturant is assayed using denaturing gradient gel electrophoresis (Myers et al. (1985) *Nature* 313:495). The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility (Keen et al. (1991) *Trends Genet.* 7:5). Examples of other techniques for detecting point mutations include, selective oligonucleotide hybridization, selective amplification, and selective primer extension.

In other embodiments, genetic mutations can be identified by hybridizing a sample and control nucleic acids, e.g., DNA or RNA, to high density arrays containing hundreds or thousands of oligonucleotide probes (Cronin et al. (1996) *Human Mutation* 7:244–255; Kozal et al. (1996) *Nature Medicine* 2:753–759). For example, genetic mutations can be identified in two dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

The phosphodiesterase polynucleotides are also useful for testing an individual for a genotype that while not necessarily causing the disease, nevertheless affects the treatment modality. Thus, the polynucleotides can be used to study the relationship between an individual's genotype and the individual's response to a compound used for treatment (pharmacogenomic relationship). In the present case, for example, a mutation in the phosphodiesterase gene that results in altered affinity for cAMP could result in an excessive or decreased drug effect with standard concentrations of cAMP that activates the phosphodiesterase. Accordingly, the phosphodiesterase polynucleotides described herein can be used to assess the mutation content of the gene in an individual in order to select an appropriate compound or dosage regimen for treatment.

Thus polynucleotides displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The methods can involve obtaining a control biological sample from a control subject, contacting the control sample with a compound or agent capable of detecting mRNA, or genomic DNA, such that the presence of mRNA or genomic DNA is detected in the biological sample, and comparing the presence of mRNA or genomic DNA in the control sample with the presence of mRNA or genomic DNA in the test sample.

The phosphodiesterase polynucleotides are also useful for chromosome identification when the sequence is identified with an individual chromosome and to a particular location on the chromosome. First, the DNA sequence is matched to the chromosome by in situ or other chromosome-specific hybridization. Sequences can also be correlated to specific chromosomes by preparing PCR primers that can be used for PCR screening of somatic cell hybrids containing individual chromosomes from the desired species. Only hybrids containing the chromosome containing the gene homologous to the primer will yield an amplified fragment. Sublocalization can be achieved using chromosomal fragments. Other strategies include prescreening with labeled flow-sorted chromosomes and preselection by hybridization to chromosome-specific libraries. Further mapping strategies include fluorescence in situ hybridization, which allows hybridization with probes shorter than those traditionally used. Reagents for chromosome mapping can be used individually to mark a single chromosome or a single site on the chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

The phosphodiesterase polynucleotides can also be used to identify individuals from small biological samples. This can be done for example using restriction fragment-length polymorphism (RFLP) to identify an individual. Thus, the polynucleotides described herein are useful as DNA markers for RFLP (See U.S. Pat. No. 5,272,057).

Furthermore, the phosphodiesterase sequence can be used to provide an alternative technique, which determines the actual DNA sequence of selected fragments in the genome of an individual. Thus, the phosphodiesterase sequences described herein can be used to prepare two PCR primers from the 5' and 3' ends of the sequences. These primers can then be used to amplify DNA from an individual for subsequent sequencing.

Panels of corresponding DNA sequences from individuals prepared in this manner can provide unique individual identifications, as each individual will have a unique set of such DNA sequences. It is estimated that allelic variation in humans occurs with a frequency of about one per each 500 bases. Allelic variation occurs to some degree in the coding regions of these sequences, and to a greater degree in the noncoding regions. The phosphodiesterase sequences can be used to obtain such identification sequences from individuals and from tissue. The sequences represent unique fragments of the human genome. Each of the sequences described herein can, to some degree, be used as a standard against which DNA from an individual can be compared for identification purposes.

If a panel of reagents from the sequences is used to generate a unique identification database for an individual, those same reagents can later be used to identify tissue from that individual. Using the unique identification database, positive identification of the individual, living or dead, can be made from extremely small tissue samples.

The phosphodiesterase polynucleotides can also be used in forensic identification procedures. PCR technology can be used to amplify DNA sequences taken from very small biological samples, such as a single hair follicle, body fluids (e.g. blood, saliva, or semen). The amplified sequence can then be compared to a standard allowing identification of the origin of the sample.

The phosphodiesterase polynucleotides can thus be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As described above, actual base sequence information can be used for identification as an accurate alternative to patterns formed by restriction enzyme generated fragments. Sequences targeted to the noncoding region are particularly useful since greater polymorphism occurs in the noncoding regions, making it easier to differentiate individuals using this technique.

The phosphodiesterase polynucleotides can further be used to provide polynucleotide reagents, e.g., labeled or labelable probes which can be used in, for example, an in situ hybridization technique, to identify a specific tissue. This is useful in cases in which a forensic pathologist is presented with a tissue of unknown origin. Panels of phosphodiesterase probes can be used to identify tissue by species and/or by organ type.

In a similar fashion, these primers and probes can be used to screen tissue culture for contamination (i.e. screen for the presence of a mixture of different types of cells in a culture).

Alternatively, the phosphodiesterase polynucleotides can be used directly to block transcription or translation of phosphodiesterase gene sequences by means of antisense or ribozyme constructs. Thus, in a disorder characterized by abnormally high or undesirable phosphodiesterase gene expression, nucleic acids can be directly used for treatment.

The phosphodiesterase polynucleotides are thus useful as antisense constructs to control phosphodiesterase gene expression in cells, tissues, and organisms. A DNA antisense polynucleotide is designed to be complementary to a region of the gene involved in transcription, preventing transcription and hence production of phosphodiesterase protein. An antisense RNA or DNA polynucleotide would hybridize to the mRNA and thus block translation of mRNA into phosphodiesterase protein.

Examples of antisense molecules useful to inhibit nucleic acid expression include antisense molecules complementary to a fragment of the 5' untranslated region of SEQ ID NO:3 or SEQ ID NO:5 which also includes the start codon and antisense molecules which are complementary to a fragment of the 3' untranslated region of SEQ ID NO:3 or SEQ ID NO:5.

Alternatively, a class of antisense molecules can be used to inactivate mRNA in order to decrease expression of phosphodiesterase nucleic acid. Accordingly, these molecules can treat a disorder characterized by abnormal or undesired phosphodiesterase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the phosphodiesterase protein.

The phosphodiesterase polynucleotides also provide vectors for gene therapy in patients containing cells that are aberrant in phosphodiesterase gene expression. Thus, recombinant cells, which include the patient's cells that have been engineered ex vivo and returned to the patient, are introduced into an individual where the cells produce the desired phosphodiesterase protein to treat the individual.

The invention also encompasses kits for detecting the presence of a phosphodiesterase nucleic acid in a biological sample. For example, the kit can comprise reagents such as a labeled or labelable nucleic acid or agent capable of detecting phosphodiesterase nucleic acid in a biological sample; means for determining the amount of phosphodiesterase nucleic acid in the sample; and means for comparing the amount of phosphodiesterase nucleic acid in the sample with a standard. The compound or agent can be packaged in a suitable container. The kit can further comprise instructions for using the kit to detect phosphodiesterase mRNA or DNA.

Computer Readable Means

The nucleotide or amino acid sequences of the invention are also provided in a variety of mediums to facilitate use thereof. As used herein, "provided" refers to a manufacture, other than an isolated nucleic acid or amino acid molecule, which contains a nucleotide or amino acid sequence of the present invention. Such a manufacture provides the nucleotide or amino acid sequences, or a subset thereof (e.g., a subset of open reading frames (ORFs)) in a form which allows a skilled artisan to examine the manufacture using means not directly applicable to examining the nucleotide or amino acid sequences, or a subset thereof, as they exists in nature or in purified form.

In one application of this embodiment, a nucleotide or amino acid sequence of the present invention can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. The skilled artisan will readily appreciate how any of the presently known computer readable mediums can be used to create a manufacture comprising computer readable medium having recorded thereon a nucleotide or amino acid sequence of the present invention.

As used herein, "recorded" refers to a process for storing information on computer readable medium. The skilled artisan can readily adopt any of the presently known methods for recording information on computer readable medium to generate manufactures comprising the nucleotide or amino acid sequence information of the present invention.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of dataprocessor structuring formats (e.g., text file or database) in order to obtain computer readable medium having recorded thereon the nucleotide sequence information of the present invention.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. Search means are used to identify fragments or regions of the sequences of the invention which match a particular target sequence or target motif.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software includes, but is not limited to, MacPattern (EMBL), BLASTN and BLASTX (NCBIA).

For example, software which implements the BLAST (Altschul et al. (1990) *J. Mol. Biol.* 215:403–410) and BLAZE (Brutlag et al. (1993) *Comp. Chem.* 17:203–207) search algorithms on a Sybase system can be used to identify open reading frames (ORFs) of the sequences of the invention which contain homology to ORFs or proteins from other libraries. Such ORFs are protein encoding fragments and are useful in producing commercially important proteins such as enzymes used in various reactions and in the production of commercially useful metabolites.

Vectors/Host Cells

The invention also provides vectors containing the phosphodiesterase polynucleotides. The term "vector" refers to a vehicle, preferably a nucleic acid molecule that can transport the phosphodiesterase polynucleotides. When the vector is a nucleic acid molecule, the phosphodiesterase polynucleotides are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the phosphodiesterase polynucleotides. Alternatively, the vector may integrate into the host cell genome and produce additional copies of the phosphodiesterase polynucleotides when the host cell replicates.

The invention provides vectors for the maintenance (cloning vectors) or vectors for expression (expression vectors) of the phosphodiesterase polynucleotides. The vectors can function in procaryotic or eukaryotic cells or in both (shuttle vectors).

Expression vectors contain cis-acting regulatory regions that are operably linked in the vector to the phosphodiesterase polynucleotides such that transcription of the polynucleotides is allowed in a host cell. The polynucleotides can be introduced into the host cell with a separate polynucleotide capable of affecting transcription. Thus, the second polynucleotide may provide a trans-acting factor interacting with the cis-regulatory control region to allow transcription of the phosphodiesterase polynucleotides from the vector. Alternatively, a trans-acting factor may be supplied by the host cell. Finally, a trans-acting factor can be produced from the vector itself.

It is understood, however, that in some embodiments, transcription and/or translation of the phosphodiesterase polynucleotides can occur in a cell-free system.

The regulatory sequence to which the polynucleotides described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al. (1989) *Molecular Cloning: A Laboratory Manual* 2nd. ed., Cold Spring Harbor Laboratory Press, Cold Spring Harbor, N.Y.).

A variety of expression vectors can be used to express a phosphodiesterase polynucleotide. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al. (1989) *Molecular Cloning: A Laboratory Manual* 2nd. ed., Cold Spring Harbor Laboratory Press, Cold Spring Harbor, N.Y.

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The phosphodiesterase polynucleotides can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate polynucleotide can be introduced into an appropriate host cell for propagation or expression using well-known techniques. Bacterial cells include, but are not limited to, *E. coli, Streptomyces*, and *Salmonella typhimurium*. Eukaryotic cells include, but are not limited to, yeast, insect cells such as *Drosophila*, animal cells such as COS and CHO cells, and plant cells.

As described herein, it may be desirable to express the polypeptide as a fusion protein. Accordingly, the invention provides fusion vectors that allow for the production of the phosphodiesterase polypeptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired polypeptide can ultimately be separated from the fusion moiety. Proteolytic enzymes include, but are not limited to, factor Xa, thrombin, and enterokinase. Typical fusion expression vectors include pGEX (Smith et al. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al. (1988) *Gene* 69:301–315) and pET 11d (Studier et al. (1990) *Gene Expression Technology: Methods in Enzymology* 185:60–89).

Recombinant protein expression can be maximized in a host bacteria by providing a genetic background wherein the host cell has an impaired capacity to proteolytically cleave the recombinant protein. (Gottesman, S. (1990) *Gene Expression Technology: Methods in Enzymology* 185, Academic Press, San Diego, Calif. 119–128). Alternatively, the sequence of the polynucleotide of interest can be altered to provide preferential codon usage for a specific host cell, for example *E. coli*. (Wada et al. (1992) *Nucleic Acids Res.* 20:2111–2118).

The phosphodiesterase polynucleotides can also be expressed by expression vectors that are operative in yeast. Examples of vectors for expression in yeast e.g., *S. cerevisiae* include pYepSec1 (Baldari et al. (1987) *EMBO J.* 6:229–234), pMFa (Kurjan et al. (1982) *Cell* 30:933–943), pJRY88 (Schultz et al. (1987) *Gene* 54:113–123), and pYES2 (Invitrogen Corporation, San Diego, Calif.).

The phosphodiesterase polynucleotides can also be expressed in insect cells using, for example, baculovirus expression vectors. Baculovirus vectors available for expression of proteins in cultured insect cells (e.g., Sf9 cells) include the pAc series (Smith et. al. (1983) *Mol. Cell Biol.* 3:2156–2165) and the pVL series (Lucklow et al. (1989) *Virology* 170:31–39).

In certain embodiments of the invention, the polynucleotides described herein are expressed in mammalian cells using mammalian expression vectors. Examples of mammalian expression vectors include pCDM8 (Seed, B. (1987) *Nature* 329:840) and pMT2PC (Kaufman et al. (1987) *EMBO J.* 6:187–195).

The expression vectors listed herein are provided by way of example only of the well-known vectors available to those of ordinary skill in the art that would be useful to express the phosphodiesterase polynucleotides. The person of ordinary skill in the art would be aware of other vectors suitable for maintenance propagation or expression of the polynucleotides described herein. These are found for example in Sambrook et al. (1989) *Molecular Cloning: A Laboratory Manual 2nd, ed., Cold Spring Harbor Laboratory*, Cold Spring Harbor Laboratory Press, Cold Spring Harbor, N.Y.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the polynucleotide sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAF-dextran-mediated transfection, cationic lipid-mediated transfection, electroporation, transduction, infection, lipofection, and other techniques such as those found in Sambrook et al. (*Molecular Cloning: A Laboratory Manual*, 2d ed., Cold Spring Harbor Laboratory, Cold Spring Harbor Laboratory Press, Cold Spring Harbor, N.Y.).

Host cells can contain more than one vector. Thus, different nucleotide sequences can be introduced on different vectors of the same cell. Similarly, the phosphodiesterase polynucleotides can be introduced either alone or with other polynucleotides that are not related to the phosphodiesterase polynucleotides such as those providing trans-acting factors for expression vectors. When more than one vector is introduced into a cell, the vectors can be introduced independently, co-introduced or joined to the phosphodiesterase polynucleotide vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the polynucleotides described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the polypeptide is desired, appropriate secretion signals are incorporated into the vector. The signal sequence can be endogenous to the phosphodiesterase polypeptides or heterologous to these polypeptides.

Where the polypeptide is not secreted into the medium, the protein can be isolated from the host cell by standard disruption procedures, including freeze thaw, sonication, mechanical disruption, use of lysing agents and the like. The polypeptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the polypeptides described herein, the polypeptides can have various glycosylation patterns, depending upon the cell, or maybe non-glycosylated as when produced in bacteria. In addition, the polypeptides may include an initial modified methionine in some cases as a result of a host-mediated process.

Uses of Vectors and Host Cells

It is understood that "host cells" and "recombinant host cells" refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

The host cells expressing the polypeptides described herein, and particularly recombinant host cells, have a variety of uses. First, the cells are useful for producing phosphodiesterase proteins or polypeptides that can be further purified to produce desired amounts of phosphodiesterase protein or fragments. Thus, host cells containing expression vectors are useful for polypeptide production.

Host cells are also useful for conducting cell-based assays involving the phosphodiesterase or phosphodiesterase fragments. Thus, a recombinant host cell expressing a native phosphodiesterase is useful to assay for compounds that stimulate or inhibit phosphodiesterase function. This includes cAMP binding, gene expression at the level of transcription or translation, protein kinase A interaction, and components of the signal transduction pathway.

Host cells are also useful for identifying phosphodiesterase mutants in which these functions are affected. If the mutants naturally occur and give rise to a pathology, host cells containing the mutations are useful to assay compounds that have a desired effect on the mutant phosphodiesterase (for example, stimulating or inhibiting function) which may not be indicated by their effect on the native phosphodiesterase.

Recombinant host cells are also useful for expressing the chimeric polypeptides described herein to assess compounds that activate or suppress activation by means of a heterologous domain, segment, site, and the like, as disclosed herein.

Further, mutant phosphodiesterases can be designed in which one or more of the various functions is engineered to be increased or decreased (e.g., cAMP binding or kinase A binding) and used to augment or replace phosphodiesterase proteins in an individual. Thus, host cells can provide a therapeutic benefit by replacing an aberrant phosphodiesterase or providing an aberrant phosphodiesterase that provides a therapeutic result. In one embodiment, the cells provide phosphodiesterases that are abnormally active.

In another embodiment, the cells provide phosphodiesterases that are abnormally inactive. These phosphodiesterases can compete with endogenous phosphodiesterases in the individual.

In another embodiment, cells expressing phosphodiesterases that cannot be activated, are introduced into an individual in order to compete with endogenous phosphodiesterases for cAMP. For example, in the case in which excessive cAMP is part of a treatment modality, it may be necessary to inactivate this molecule at a specific point in treatment. Providing cells that compete for the molecule, but which cannot be affected by phosphodiesterase activation would be beneficial.

Homologously recombinant host cells can also be produced that allow the in situ alteration of endogenous phosphodiesterase polynucleotide sequences in a host cell genome. This technology is more fully described in WO 93/09222, WO 91/12650 and U.S. Pat. No. 5,641,670. Briefly, specific polynucleotide sequences corresponding to the phosphodiesterase polynucleotides or sequences proximal or distal to a phosphodiesterase gene are allowed to integrate into a host cell genome by homologous recombination where expression of the gene can be affected. In one embodiment, regulatory sequences are introduced that either increase or decrease expression of an endogenous sequence. Accordingly, a phosphodiesterase protein can be produced in a cell not normally producing it, or increased expression of phosphodiesterase protein can result in a cell normally producing the protein at a specific level. Alternatively, the entire gene can be deleted. Still further, specific mutations can be introduced into any desired region of the gene to produce mutant phosphodiesterase proteins. Such mutations could be introduced, for example, into the specific regions disclosed herein.

In one embodiment, the host cell can be a fertilized oocyte or embryonic stem cell that can be used to produce a transgenic animal containing the altered phosphodiesterase gene. Alternatively, the host cell can be a stem cell or other early tissue precursor that gives rise to a specific subset of cells and can be used to produce transgenic tissues in an animal. See also Thomas et al., *Cell* 51:503 (1987) for a description of homologous recombination vectors. The vector is introduced into an embryonic stem cell line (e.g., by electroporation) and cells in which the introduced gene has homologously recombined with the endogenous phosphodiesterase gene is selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos. WO 90/11354; WO 91/01140; and WO 93/04169.

The genetically engineered host cells can be used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a phosphodiesterase protein and identifying and evaluating modulators of phosphodiesterase protein activity.

Other examples of transgenic animals include non-human primates, sheep, dogs, cows, goats, chickens, and amphibians.

In one embodiment, a host cell is a fertilized oocyte or an embryonic stem cell into which phosphodiesterase polynucleotide sequences have been introduced.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the phosphodiesterase nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the phosphodiesterase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems, which allow for regulated expression of the transgene. One example of such a system is the cre/loxP recombinase system of bacteriophage P1. For a description of the cre/loxP recombinase system, see, e.g., Lakso et al. (1992) *PNAS* 89:6232–6236. Another example of a recombinase system is the FLP recombinase system of *S. cerevisiae* (O'Gorman et al. (1991) *Science* 251:1351–1355. If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to a pseudopregnant female foster animal. The offspring born of this female foster animal will be a clone of the animal from which the cell, e.g., the somatic cell, is isolated.

Transgenic animals containing recombinant cells that express the polypeptides described herein are useful to conduct the assays described herein in an in vivo context. Accordingly, the various physiological factors that are present in vivo and that could affect cAMP binding, phosphodiesterase activation, and signal transduction, may not be evident from in vitro cell-free or cell-based assays. Accordingly, it is useful to provide non-human transgenic animals to assay in vivo phosphodiesterase function, including cAMP interaction, the effect of specific mutant phosphodiesterases on phosphodiesterase function and cAMP interaction, and the effect of chimeric phosphodiesterases. It is also possible to assess the effect of null mutations, that is mutations that substantially or completely eliminate one or more phosphodiesterase functions.

Pharmaceutical Compositions

The phosphodiesterase nucleic acid molecules, protein (such as an extracellular loop), modulators of the protein, and antibodies (also referred to herein as "active compounds") can be incorporated into pharmaceutical compositions suitable for administration to a subject, e.g., a human. Such compositions typically comprise the nucleic acid molecule, protein, modulator, or antibody and a pharmaceutically acceptable carrier.

The term "administer" is used in its broadest sense and includes any method of introducing the compositions of the present invention into a subject. This includes producing polypeptides or polynucleotides in vivo as by transcription or translation, in vivo, of polynucleotides that have been exogenously introduced into a subject. Thus, polypeptides or nucleic acids produced in the subject from the exogenous compositions are encompassed in the term "administer."

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions. A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a phosphodiesterase protein or anti-phosphodiesterase antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For oral administration, the agent can be contained in enteric forms to survive the stomach or further coated or mixed to be released in a particular region of the GI tract by known methods. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see e.g., Chen et al. (1994) *PNAS* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

This invention may be embodied in many different forms and should not be construed as limited to the embodiments set forth herein; rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

III. METHODS AND COMPOSITIONS FOR DIAGNOSIS AND TREATMENT OF CANCER USING 27420

BACKGROUND OF THE INVENTION

The methyltransferase family is a large superfamily of enzymes that regulate biological processes by catalyzing the transfer of methyl groups to a wide variety of endogenous and exogenous compounds, including DNA, RNA, proteins, hormones, neurotransmitters, drugs, and xenobiotics (Weinshilboum, R. M. et al. (1999) *Annu. Rev. Pharmacol. Toxicol.* 39:19–52)

Methylation of DNA can play an important role in the control of gene expression in mammalian cells. The enzyme involved in DNA methylation is DNA methyltransferase, which catalyzes the transfer of a methyl group from S-adenosylmethionine to cytosine residues to form 5-methylcytosine, a modified base that is found mostly at CpG sites in the genome. The presence of methylated CpG islands in the promoter region of genes can suppress their expression. This process may be due to the presence of 5-methylcytosine, which apparently interferes with the binding of transcription factors or other DNA-binding proteins, and thus, blocks transcription. In different types of tumors, aberrant or accidental methylation of CpG islands in the promoter region has been observed for many tumor suppressor genes, genes that suppress metastasis, and genes that repair DNA, silencing their expression (Momparler, R. L. and Bovenzi, V. (2000) *J. Cell Physiol.* 183:145–54).

Methylation of proteins is a post-translational modification which can regulate the activity and subcellular localization of numerous proteins. Methylation of proteins can play an important role in protein repair and reversal of protein aging. Proteins undergo a variety of spontaneous degradation processes, including oxidation, glycation, deamidation, isomerization, and racemization (Finch, C. E. (1990) *Longevity, Senescence, and the Genome* (Univ. of Chicago Press, Chicago); Harding, J. J. et al. (1989) *Mech. Aging Dev.* 50:7–16; Stadtman, E. R. (1990) *Biochemistry* 29:6323–6331; Stadtman, E. R. (1992) *Science* 257:1220–1224; Geiger, T. and Clarke, S. (1987) *J. Biol. Chem.* 262:785–794; Yuan, P. M. et al. (1981) *Mech. Agin. Dev.* 17:151–172; Wright, H. T. (1991) *Crit. Rev. Biochem. Mol. Biol.* 26:1–52; Visick, J. E. and Clarke, S. (1995) *Mol. Microbiol.* 16:835–845). These non-enzymatic modifications can produce functionally damaged species that reflect the action of aging at the molecular level (Stadtman (1992) supra; Martin, G. M. et al. (1996) *Nat. Genet.* 13:25–34), and methylation of these damaged proteins can play a part in the repair pathway.

Protein methylation, which uses S-adenosylmethionine as the methyl donor (Kim and Paik (1965) *J. Biol. Chem.* 240:4629–4634; Paik and Kim (1980) in *Biochemistry: A Series of Monographs* (Meister, A. ed.), vol 1, pp. 112–141, John Wiley & Sons, New York), can be classified into three major categories (Paik and Kim (1980) in *Biochemistry: A Series of Monographs* (Meister, A. ed.), vol 1, pp. 112–141, John Wiley & Sons, New York; Paik and Kim (1985) in *Enzymology of Post-translational Modification of Proteins* (Freedman, R. B. and Hawkins, H. C., eds.), vol. 2, pp. 187–228, Academic Press, London; Clarke (1985) *Annu. Rev. Biochem.* 54:479–506; Clarke et al. (1987) *Proc. Nalt. Acad. Sci. USA* 85:4643–4647; Kim et al. (1990) in *Protein Methylation* (Paik, W. K. and Kim, S. eds.), pp. 97–123, CRC Press, Boca Raton, Fla.); N-methylation involving methylation of arginine, lysine, and histidine side chains; O-methylation of either the internal carboxy group of glutamate and isoaspartate residues or the C-terminal cysteine residue; and S-methylation of either cysteine or methionine residues.

Protein methylation is also known to be important in cellular stress responses (Desrosiers, R. and Tanguay, R. (1988) *J. Biol. Chem.* 263:4686–4692). Moreover, protein methyltransferases have recently been demonstrated to be important in cellular signaling events, for example, in receptor-mediated and/or differentiation-dependent signaling (Lin, W. et al. (1996) *J. Biol. Chem.* 271:15034–15044; Abramovich, C. et al. (1997) *EMBO J.* 16:260–266).

One type of protein methylation is mediated by arginine methyltransferases. A subtype of arginine methyltransferase, the type I arginine methyltransferases, catalyze the formation of monomethylarginine and asymmetric NG,NG-dimethylarginine in a variety of substrates (Tang, J. et al. (2000) *J. Biol. Chem.* 275:19866–19876), including many RNA-binding proteins (Najbauer, J. et al. (1993) *J. Biol. Chem.* 268:10501–10509), RNA-transporting proteins (Najbauer et al. (1993) supra), transcription factors (Gary, J. D. and Clarke, S. (1998) *Prog. Nucleic Acids Res. Mol. Biol.* 61:65–131; Chen, D. et al. (1999) *Science* 284:2174–2177), nuclear matrix proteins (Gary and Clarke (1998) supra), and cytokines (Sommer, A. et al. (1989) *Biochem. Biophys. Res. Commun.* 160:1267–1274). Methylation by type I arginine methyltransferases modifies the activities of transcription factors (Gary and Clarke (1998) supra), modulates the affinity of nucleic acid binding proteins for nucleic acids (Gary and Clarke (1998) supra), regulates interferon signaling pathways (Abramovich, C. et al. (1997) *EMBO J.* 16:260–266), and alters targeting of nuclear proteins (Pintucci, G. et al. (1996) *Mol. Biol. Cell* 7:1249–1258).

Given the important role of methyltransferases in a variety of distinct cellular functions, there exists a need to identify novel methyltransferases, as well as modulators of such methyltransferases, for use in regulating diverse biological processes, including biological processes which have a role in human diseases or disorders, such as cancer.

Cancer is the second leading cause of death in the United States, after heart disease (Boring, et al., (1993) *CA Cancer J. Clin.* 43:7). Cancer is characterized primarily by an increase in the number of abnormal, or neoplastic, cells derived from a normal tissue which proliferate to form a tumor mass, the invasion of adjacent tissues by these neoplastic tumor cells, and the generation of malignant cells which spread via the blood or lymphatic system to regional lymph nodes and to distant sites. The latter progression to malignancy is referred to as metastasis.

Colorectal cancer is among the most common cancers affecting the western world. An estimated 129,400 new cases of colorectal cancer occurred in the United States in 1999 (Rudy, et al. (2000) *Am Fam Physician* 61(6): 1759–70, 1773–4). By the age of 70 years, at least 50% of the Western population will develop some form of colorectal tumor, including early benign polyps and invasive adenocarcinomas. It is estimated that approximately 10% of the benign polypoid lesions will progress to invasive carcinoma (Fahy et al. (1998) *Surg Oncol* 7(3–4):115–23). Colorectal cancer arises from a precursor lesion, the adenomatous polyp, which forms in a field of epithelial cell hyperproliferation and crypt dysplasia. Progression from this precursor lesion to colorectal cancer is a multistep process (Winawer (1999) *Am J Med* 106(1A):3S–6S).

SUMMARY OF THE INVENTION

The present invention provides methods and compositions for the diagnosis and treatment of cellular growth or proliferation disorders, e.g., cancer, including, but not limited to colon cancer. The present invention is based, at least in part, on the discovery of novel human arginine methyltransferase family members, referred to herein as "arginine methyltransferase-3" or "MTR-3" nucleic acid and protein molecules. The present invention is also based, at least in part, on the discovery that the novel MTR-3 molecules of the present invention are differentially expressed in tumor cells, e.g., colon tumor cells, as compared to normal cells, e.g., normal colon cells, and are useful in the diagnosis and treatment of cellular growth and proliferation disorders, e.g., cancer, including, but not limited to, colon cancer.

The novel MTR-3 nucleic acid and protein molecules of the present invention are useful as modulating agents in regulating a variety of cellular processes, e.g., transcriptional activation and cellular growth and proliferation. Accordingly, in one aspect, this invention provides isolated nucleic acid molecules encoding MTR-3 proteins or biologically active portions thereof, as well as nucleic acid fragments suitable as primers or hybridization probes for the detection of MTR-3-encoding nucleic acids.

In one embodiment, the invention features an isolated nucleic acid molecule that includes the nucleotide sequence set forth in SEQ ID NO:7 or SEQ ID NO:9. In another embodiment, the invention features an isolated nucleic acid molecule that encodes a polypeptide including the amino acid sequence set forth in SEQ ID NO:8.

In still other embodiments, the invention features isolated nucleic acid molecules including nucleotide sequences that are substantially identical (e.g., 77% identical) to the entire length of the nucleotide sequence set forth as SEQ ID NO:7 or SEQ ID NO:9. The invention further features isolated nucleic acid molecules including at least 1123 contiguous nucleotides of the nucleotide sequence set forth as SEQ ID NO:7 or SEQ ID NO:9. In another embodiment, the invention features isolated nucleic acid molecules which encode a polypeptide including an amino acid sequence that is substantially identical (e.g., 98% identical) to the entire length of the amino acid sequence set forth as SEQ ID NO:8. The present invention also features nucleic acid molecules which encode allelic variants of the polypeptide having the amino acid sequence set forth as SEQ ID NO:8. In addition to isolated nucleic acid molecules encoding full-length polypeptides, the present invention also features nucleic acid molecules which encode fragments, for example, biologically active or antigenic fragments, of the full-length polypeptides of the present invention (e.g., fragments including at least 433 or 448 contiguous amino acid residues of the amino acid sequence of SEQ ID NO:8). In still other embodiments, the invention features nucleic acid molecules that are complementary to, antisense to, or hybridize under stringent conditions to the isolated nucleic acid molecules described herein.

In another aspect, the invention provides vectors including the isolated nucleic acid molecules described herein (e.g., MTR-3-encoding nucleic acid molecules). Such vectors can optionally include nucleotide sequences encoding heterologous polypeptides. Also featured are host cells including such vectors (e.g., host cells including vectors suitable for producing MTR-3 nucleic acid molecules and polypeptides).

In another aspect, the invention features isolated MTR-3 polypeptides and/or biologically active or antigenic fragments thereof. Exemplary embodiments feature a polypeptide including the amino acid sequence set forth as SEQ ID NO:8, a polypeptide including an amino acid sequence at least 98% identical to the entire length of the amino acid sequence set forth as SEQ ID NO:8, a polypeptide encoded by a nucleic acid molecule including a nucleotide sequence at least 77% identical to the entire length of the nucleotide sequence set forth as SEQ ID NO:7 or SEQ ID NO:9. Also featured are fragments of the full-length polypeptides described herein (e.g., fragments including at least 443 or 448 contiguous amino acid residues of the sequence set forth as SEQ ID NO:8) as well as allelic variants of the polypeptide having the amino acid sequence set forth as SEQ ID NO:8.

The MTR-3 polypeptides and/or biologically active or antigenic fragments thereof, are useful, for example, as reagents or targets in assays applicable to treatment and/or diagnosis of cellular growth or proliferation disorders, such as cancer, e.g., colon cancer. In one embodiment, an MTR-3 polypeptide or fragment thereof, has an MTR-3 activity. In another embodiment, an MTR-3 polypeptide or fragment thereof, includes at least one of the following domains: a VLD binding domain, a transmembrane domain, and optionally, has an MTR-3 activity. In a related aspect, the invention features antibodies (e.g., antibodies which specifically bind to any one of the polypeptides described herein) as well as fusion polypeptides including all or a fragment of a polypeptide described herein.

The present invention further features methods for detecting MTR-3 polypeptides and/or MTR-3 nucleic acid molecules, such methods featuring, for example, a probe, primer or antibody described herein. Also featured are kits, e.g., kits for the detection of MTR-3 polypeptides and/or MTR-3 nucleic acid molecules.

The present invention also provides diagnostic assays for identifying the presence or absence of a genetic alteration characterized by at least one of (i) aberrant modification or mutation of a gene encoding an MTR-3 protein; (ii) misregulation of the gene; and (iii) aberrant post-translational modification of an MTR-3 protein, wherein a wild-type form of the gene encodes a protein with an MTR-3 activity.

In another aspect, the invention provides a method for identifying a compound which binds to an MTR-3 polypeptide by contacting the polypeptide, or a cell expressing the polypeptide with a test compound, and determining whether the polypeptide binds to the test compound. In yet another aspect, the invention provides a method for identifying a compound which modulates the activity of an MTR-3 polypeptide comprising contacting an MTR-3 polypeptide with a test compound and determining the effect of the test compound on the activity of the polypeptide.

In another aspect, the invention provides a method for identifying the presence of a nucleic acid molecule associated with a cellular growth or proliferation disorder, in a sample, by contacting a sample comprising nucleic acid molecules with a hybridization probe comprising at least 25 contiguous nucleotides of SEQ ID NO:7 or 9, and detecting the presence of a nucleic acid molecule associated with a cellular growth or proliferation disorder, when the sample contains a nucleic acid molecule that hybridizes to the nucleic acid probe. In one embodiment, the hybridization probe is detectably labeled. In another embodiment the sample comprising nucleic acid molecules is subjected to agarose gel electrophoresis and southern blotting prior to contacting with the hybridization probe. In a further embodiment, the sample comprising nucleic acid molecules is subjected to agarose gel electrophoresis and northern blotting prior to contacting with the hybridization probe. In yet another embodiment, the detecting is by in situ hybridization. In other embodiments, the method is used to detect mRNA or genomic DNA in the sample.

The invention also provides a method for identifying a nucleic acid molecule associated with a cellular growth or proliferation disorder, in a sample, e.g., a colon tissue sample, by contacting a sample comprising nucleic acid molecules with a first and a second amplification primer, the first primer comprising at least 25 contiguous nucleotides of SEQ ID NO:7 or 9 and the second primer comprising at least 25 contiguous nucleotides from the complement of SEQ ID NO:7 or 9, incubating the sample under conditions that allow for nucleic acid amplification, and detecting the presence of a nucleic acid molecule associated with a cellular growth or proliferation disorder, when the sample contains a nucleic acid molecule that is amplified. In one embodiment, the sample comprising nucleic acid molecules is subjected to agarose gel electrophoresis after the incubation step.

In addition, the invention provides a method for identifying a polypeptide associated with a cellular growth or proliferation disorder, in a sample, by contacting a sample comprising polypeptide molecules with a binding substance specific for an MTR-3 polypeptide, and detecting the presence of a polypeptide associated with a cellular growth or proliferation disorder, when the sample contains a polypeptide molecule that binds to the binding substance. The binding substance may be an antibody or an MTR-3 ligand, and may be detectably labeled.

In another aspect, the invention provides a method of identifying a subject at risk for a cellular growth or proliferation disorder. The method includes contacting a sample obtained from the subject comprising nucleic acid molecules with a hybridization probe comprising at least 25 contiguous nucleotides of SEQ ID NO:7 or 9, and detecting the presence of a nucleic acid molecule which identifies a subject a risk for a cellular growth or proliferation disorder, when the sample contains a nucleic acid molecule that hybridizes to the nucleic acid probe.

In a further aspect, the invention provides a method for identifying a subject at risk for a cellular growth or proliferation disorder, by contacting a sample obtained from a subject comprising nucleic acid molecules with a first and a second amplification primer, the first primer comprising at least 25 contiguous nucleotides of SEQ ID NO:7 or 9 and the second primer comprising at least 25 contiguous nucleotides from the complement of SEQ ID NO:7 or 9, incubating the sample under conditions that allow for nucleic acid amplification, and detecting a nucleic acid molecule which identifies a subject at risk for a cellular growth or proliferation disorder, when the sample contains a nucleic acid molecule that is amplified.

In yet another aspect, the invention provides a method of identifying a subject at risk for a cellular growth or proliferation disorder by contacting a sample obtained from the subject comprising polypeptide molecules with a binding substance specific for an MTR-3 polypeptide, and detecting the presence of a polypeptide molecule in the sample that binds to the binding substance.

In another aspect, the invention provides a method for identifying a compound capable of treating a cellular growth or proliferation disorder such as cancer, e.g., colon cancer, characterized by aberrant MTR-3 nucleic acid expression or MTR-3 protein activity. The method includes assaying the ability of the compound to modulate the expression of an MTR-3 nucleic acid or the activity of an MTR-3 protein.

In addition, the invention provides a method for treating a subject having a cellular growth or proliferation disorder, such as cancer e.g., colon cancer, that is characterized by aberrant MTR-3 protein activity or aberrant MTR-3 nucleic acid expression by administering to the subject an MTR-3 modulator. The MTR-3 modulator may be administered in a pharmaceutically acceptable formulation or may be administered using a gene therapy vector.

In one embodiment, an MTR-3 modulator is capable of modulating MTR-3 polypeptide activity. For example, the MTR-3 modulator may be a small molecule, an anti-MTR-3 antibody, an MTR-3 polypeptide comprising the amino acid sequence of SEQ ID NO:8, or a fragment thereof, an MTR-3 polypeptide comprising an amino acid sequence which is at least 96 percent identical to the entire length of the amino acid sequence of SEQ ID NO:8, or an isolated naturally occurring allelic variant of a polypeptide consisting of the amino acid sequence of SEQ ID NO:8.

In another embodiment, the MTR-3 modulator is capable of modulating MTR-3 nucleic acid expression. For example, the MTR-3 modulator may be a small molecule, an antisense MTR-3 nucleic acid molecule, a ribozyme, a nucleic acid molecule comprising the nucleotide sequence of SEQ ID NO:7 or 9, or a fragment thereof, a nucleic acid molecule that is 77% identical to the entire length of the nucleotide sequence of SEQ ID NO:7 or 9, or a nucleic acid molecule encoding a naturally occurring allelic variant of a polypeptide comprising the amino acid sequence of SEQ ID NO:8.

Also featured are methods of regulating metastasis in an individual or inhibiting tumor progression in an individual which include administering to the individual an MTR-3 modulator (e.g., an MTR-3 inhibitor).

Furthermore, the invention provides a method for modulating cellular growth or proliferation comprising contacting a cell with an MTR-3 modulator.

In another embodiment, the invention provides a method for modulating transcriptional activation comprising contacting a cell with an MTR-3 modulator.

Other features and advantages of the invention will be apparent from the following detailed description and claims.

DETAILED DESCRIPTION OF THE INVENTION

The present invention is based, at least in part, on the discovery of novel human arginine methyltransferase family members, referred to herein as "arginine methyltransferase-3" or "MTR-3" nucleic acid and protein molecules. These novel molecules are capable of catalyzing the transfer of a methyl group to or from biological molecules (e.g., polypeptides or amino acids such as arginine residues and/or S-adenosylmethionine) and, thus, play a role in or function in a variety of cellular processes, e.g., protein methylation, arginine methylation, indirect or direct modulation (e.g., activation or inactivation) of gene transcription, and/or cellular proliferation, growth, and/or differentiation.

The present invention further provides methods and compositions for the diagnosis and treatment of a cellular growth or proliferation disorder, e.g., cancer, including, but not limited to, colon cancer. The novel MTR-3 molecules of the present invention may be involved in the modulation (e.g., activation or inactivation) of transcription, e.g., nuclear hormone receptor (e.g., androgen receptor, progesterone receptor, or estrogen receptor) mediated transcription. "Treatment", as used herein, is defined as the application or administration of a therapeutic agent to a patient, or application or administration of a therapeutic agent to an isolated tissue or cell line from a patient, who has a disease or disorder, a symptom of a disease or disorder, or a predisposition toward a disease or disorder, with the purpose to cure, heal, alleviate, relieve, alter, remedy, ameliorate, improve or affect the disease or disorder, the symptoms of the disease or disorder, or the predisposition toward a disease or disorder. A therapeutic agent includes, but is not limited to, small molecules, peptides, antibodies, ribozymes and antisense oligonucleotides.

The novel MTR-3 molecules of the present invention are differentially expressed in tumor cells, e.g., colon tumor cells and colon cells which have metastasized to the liver, as compared to normal cells, e.g., normal colon cells and normal liver cells. Increased expression of MTR-3 in tumor cells results in an increase in transcriptional activation by nuclear hormone receptors (e.g., nuclear hormone receptors present in tumors, such as, for example, estrogen and/or progesterone receptors). Increased transcriptional activation by nuclear receptors, e.g., hormone receptors, contributes to cellular growth and proliferation, thereby increasing tumorigenesis and metastasis of tumor cells, e.g., colon tumor cells or colon cells which have metastasized to the liver (colon metastases to the liver). In addition, methylation, e.g., arginine methylation, has been associated with cellular proliferation in cancer cells (Kim, et al. (1999) *Life Sci.* 65(8):737–45). Therefore, methylation by the MTR-3 molecules of the present invention may be involved in cellular growth, proliferation, and tumorigenesis. Accordingly, the MTR-3 molecules of the present invention provide novel diagnostic targets and therapeutic agents to control cellular growth or proliferation disorders.

As used herein, a "cellular growth or proliferation disorder" includes a disease or disorder that affects a cell growth or proliferation process. As used herein, a "cellular growth or proliferation process" is a process by which a cell increases in number, size or content, by which a cell develops a specialized set of characteristics which differ from that of other cells, or by which a cell moves closer to or further from a particular location or stimulus. A cellular growth or proliferation process includes the metabolic processes of the cell and cellular transcriptional activation mechanisms. A cellular growth or proliferation disorder may be characterized by aberrantly regulated cell growth, proliferation, differentiation, or migration. Cellular growth or proliferation disorders include tumorigenic disease or disorders. As used herein, a "tumorigenic disease or disorder" includes a disease or disorder characterized by aberrantly regulated cell growth, proliferation, differentiation, adhesion, or migration, resulting in the production of or tendency to produce tumors. As used herein, a "tumor" includes a normal benign or malignant mass of tissue. Examples of cellular growth or proliferation disorders include, but are not limited to, cancer, e.g., carcinoma, sarcoma, or leukemia, examples of which include, but are not limited to, colon, ovarian, lung, breast, endometrial, uterine, hepatic, gastrointestinal, prostate, and brain cancer; tumorigenesis and metastasis; skeletal dysplasia; and hematopoietic and/or myeloproliferative disorders.

"Differential expression", as used herein, includes both quantitative as well as qualitative differences in the temporal and/or tissue expression pattern of a gene. Thus, a differentially expressed gene may have its expression activated or inactivated in normal versus cellular growth or proliferation disease states. The degree to which expression differs in normal versus cellular growth or proliferation disease states or control versus experimental states need only be large enough to be visualized via standard characterization techniques, e.g., quantitative PCR, Northern analysis, or subtractive hybridization. The expression pattern of a differentially expressed gene may be used as part of a prognostic or diagnostic cellular growth or proliferation disorder evaluation, or may be used in methods for identifying compounds useful for the treatment of cellular growth or proliferation disorder. In addition, a differentially expressed gene involved in tumorigenic disorders may represent a target gene such that modulation of the expression level of this gene or the activity of the gene product may act to ameliorate a cellular growth or proliferation disorder. Compounds that modulate target gene expression or activity of the target gene product can be used in the treatment of cellular growth or proliferation disorders. Although the MTR-3 genes described herein may be differentially expressed with respect to cellular growth or proliferation disorders, and/or their products may interact with gene products important to cellular growth or proliferation disorders, the genes may also be involved in mechanisms important to additional tumor cell processes.

The MTR-3 molecules of the present invention are involved in the modulation of transcriptional activation and function to modulate cell proliferation, differentiation, and motility. Thus, the MTR-3 molecules of the present invention may play a role in the modulation of cellular transcriptional activation mechanisms, such as the regulation of the activation of transcription (e.g., by nuclear receptors, such as nuclear hormone receptors), the recruitment of a transcription initiation complex to the promoter of genes, and/or cell transversal through the cell cycle.

The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin or alternatively, can contain homologues of non-human origin, e.g., rat proteins. Members of a family can also have common functional characteristics.

For example, the family of MTR-3 polypeptides comprise at least one "transmembrane domain" and preferably four transmembrane domains. As used herein, the term "transmembrane domain" includes an amino acid sequence of about 15–25 amino acid residues in length which spans the plasma membrane. More preferably, a transmembrane domain includes about at least 15, 16, 17, 18, 19, 20, 21, 22, 23, 24, or 25 amino acid residues and spans the plasma membrane. Transmembrane domains are rich in hydrophobic residues, and typically have an alpha-helical structure. In a preferred embodiment, at least 50%, 60%, 70%, 80%, 90%, 95% or more of the amino acids of a transmembrane domain are hydrophobic, e.g., leucines, isoleucines, alanines, valines, phenylalanines, prolines or methionines. Transmembrane domains are described in, for example, Zagotta W. N. et al, (1996) *Annual Rev. Neurosci.* 19: 235–263, the contents of which are incorporated herein by reference. A MEMSAT analysis and a structural, hydrophobicity, and antigenicity analysis resulted in the identification of four transmembrane domains in the amino acid sequence of human MTR-3 (SEQ ID NO:8) at about residues 18–41, 97–113, 187–203, and 382–404. Accordingly, MTR-3 polypeptides having at least 50–60% homology, preferably about 60–70%, more preferably about 70–80%, or about 80–90% homology with a transmembrane domain of human MTR-3 are within the scope of the invention.

In another embodiment, members of the MTR-3 family of proteins include at least one "VLD binding domain" in the protein or corresponding nucleic acid molecule. As used herein, the term "VLD binding domain" includes a protein domain having at least about 3 amino acid residues with the amino acid consensus sequence Valine-Leucine-Aspartic Acid (V-L-D). The amino acid residues of the VLD binding domain have been shown to be important for methyltransferase activity and for transcriptional activation (Chen, et al. (1999) *Science* 284:2174–2177). A VLD binding domain in the proteins of the present invention has at least 3 amino acid residues matching the VLD binding domain consensus sequence, and may also have additional anino acid residues. A VLD binding domain motif was identified in the amino acid sequence of human MTR-3 at about residues 188–190 of SEQ ID NO:8.

Preferably a VLD binding domain comprises at least about 3–10 amino acid residues and has a "VLD binding activity," for example, the ability to interact with an MTR-3 substrate or target molecule (e.g., a non-MTR-3 protein); to convert an MTR-3 substrate or target molecule to a product (e.g., transfer a methyl group to or from the substrate or target molecule); to interact with and/or transfer a methyl group to a second non-MTR-3 protein; to transfer a methyl group to an arginine residue; to modulate intra- or intercellular signaling; to modulate transcriptional activation (e.g., either directly or indirectly); to modulate cellular targeting and/or transport of proteins; and/or to modulate cellular proliferation, growth, or differentiation. Accordingly, identifying the presence of a VLD binding domain can include isolating a fragment of an MTR-3 molecule (e.g., an MTR-3 polypeptide) and assaying for the ability of the fragment to exhibit one of the aforementioned VLD binding domain activities.

Isolated MTR-3 proteins of the present invention, have an amino acid sequence sufficiently homologous to the amino acid sequence of SEQ ID NO:8, or are encoded by a nucleotide sequence sufficiently identical to SEQ ID NO:7 or 9. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains having at least 50%, 55%, 60%, 65%, 70%, 75%, 80%, 85%, 85%, 90%, 91%, 92%, 93%, 94%, 95%, 96%, 97%, 98%, 99% or more homology or identity across the amino acid sequences of the domains and contain at least one structural domains or motifs, are defined herein as sufficiently homologous. Furthermore, amino acid or nucleotide sequences which share at least 50%, 55%, 60%, 65%, 70%, 75%, 80%, 85%, 85%, 90%, 91%, 92%, 93%, 94%, 95%, 96%, 97%, 98%, 99% or more homology or identity and share a common functional activity are defined herein as sufficiently homologous or identical.

In a preferred embodiment, an MTR-3 protein, preferably a human MTR-3 protein, includes a VLD binding domain, a transmembrane domain, and has an amino acid sequence at least about 90%, 91%, 92%, 93%, 94%, 95%, 96%, 97%, 98%, 99% or more identical to the amino acid sequence of SEQ ID NO:8. In yet another preferred embodiment, an MTR-3 protein, preferably a human MTR-3 protein, includes a VLD binding domain, a transmembrane domain, and is encoded by a nucleic acid molecule having a nucleotide sequence which hybridizes under stringent hybridization conditions to a complement of a nucleic acid molecule comprising the nucleotide sequence of SEQ ID NO:7 or 9. In another preferred embodiment, an MTR-3 protein, preferably a human MTR-3 protein, includes a VLD binding domain, a transmembrane domain, and has an MTR-3 activity.

As used interchangeably herein, an "MTR-3 activity", "biological activity of MTR-3" or "functional activity of MTR-3", includes an activity exerted or mediated by an MTR-3 protein, polypeptide or nucleic acid molecule on an MTR-3 responsive cell or on an MTR-3 substrate, as determined in vivo or in vitro, according to standard techniques. In one embodiment, an MTR-3 activity is a direct activity, such as an association with an MTR-3 target molecule. As used herein, a "target molecule" or "binding partner" is a molecule which an MTR-3 protein binds or interacts with in nature, such that MTR-3-mediated function is achieved. An MTR-3 target molecule can be a non-MTR-3 molecule or an MTR-3 protein or polypeptide of the present invention. In an exemplary embodiment, an MTR-3 target molecule is an MTR-3 substrate (e.g., a polypeptide substrate, an arginine residue, or S-adenosylmethionine). An MTR-3 activity can also be an indirect activity, such as a cellular transcription modulating activity mediated by interaction of the MTR-3 protein with an MTR-3 substrate.

In a preferred embodiment, an MTR-3 activity is at least one of the following activities: (i) modulation of transcriptional activation (e.g., either directly or indirectly); (ii) modulation of (directly or indirectly) chromatin structure to, for example, regulate the recruitment of an RNA polymerase II transcription initiation complex to a gene promoter; (iii) modulation of the methylation state of proteins in the transcription machinery; (iv) interaction with an MTR-3 substrate or target molecule (e.g., a non-MTR-3 protein); (v) conversion of an MTR-3 substrate or target molecule to a product (e.g., transfer of a methyl group to or from the substrate or target molecule); (vi) interaction with and/or methyl transfer to a second non-MTR-3 protein; (vii) transfer of a methyl group to an arginine residue; (viii) modulation of protein-protein interaction (e.g., MTR-3-MTR-3 and/or MTR-3-non-MTR-3 interaction); (ix) modulation and/or coordination of protein complex formation (e.g., MTR-3-containing complex formation); (x) regulation of substrate or target molecule activity; (xi) modulation of intra- or inter-cellular signaling, (xii) modulation of cellular targeting and/or transport of proteins; and/or (xiii) modulation of cellular proliferation, growth, or differentiation.

The nucleotide sequence of the isolated human MTR-3 cDNA and the predicted amino acid sequence encoded by the MTR-3 cDNA in SEQ ID NO:7 and 8, respectively.

The human MTR-3 gene, which is approximately 2898 nucleotides in length, encodes a polypeptide which is approximately 608 amino acid residues in length.

Screening Assays

The invention provides a method (also referred to herein as a "screening assay") for identifying modulators, i.e., candidate or test compounds or agents (e.g., peptides, peptidomimetics, small molecules (organic or inorganic) or other drugs) which bind to MTR-3 proteins, have a stimulatory or inhibitory effect on, for example, MTR-3 expression or MTR-3 activity, or have a stimulatory or inhibitory effect on, for example, the expression or activity of an MTR-3 substrate.

These assays are designed to identify compounds that bind to an MTR-3 protein, bind to other inter- or extra-cellular proteins that interact with an MTR-3 protein, and interfere with the interaction of the MTR-3 protein with other inter- or extra-cellular proteins. For example, in the case of the MTR-3 protein, which is a protein that is capable of binding to a substrate and thereby modulating transcriptional activation, methyl transfer to a second non-MTR-3 protein, transfer of a methyl group to an arginine residue, and modulation and/or coordination of protein complex formation, such techniques can be used to identify compounds that stimulate or inhibit any or all of these activities. Such compounds may include, but are not limited to MTR-3 peptides, anti-MTR-3 antibodies, or small organic or inorganic compounds. Such compounds may also include other cellular proteins or peptides.

Compounds identified via assays such as those described herein may be useful, for example, for ameliorating cellular growth and proliferation disorders, e.g., cancer. In instances whereby a cellular growth or proliferation disorder results from an overall lower level of MTR-3 gene expression and/or MTR-3 protein activity in a cell or tissue, MTR-3 modulators may include compounds which accentuate or amplify the activity of the MTR-3 protein such as MTR-3 agonists. Such compounds would bring about an effective increase in MTR-3 protein activity, thus ameliorating symptoms.

In other instances, mutations within the MTR-3 gene may cause aberrant types or excessive amounts of MTR-3 proteins to be made which have a deleterious effect that leads to a cellular growth or proliferation disorder. Similarly, physiological conditions may cause an excessive increase in MTR-3 gene expression leading to a cellular growth or proliferation disease or disorder. In such cases, compounds, e.g., compounds that bind to an MTR-3 protein, may be identified that inhibit the activity of the MTR-3 protein. Assays for testing the effectiveness of compounds identified by techniques such as those described in this section are discussed herein.

In one embodiment, the invention provides assays for screening candidate or test compounds which are substrates of an MTR-3 protein or polypeptide or biologically active portion thereof. In another embodiment, the invention provides assays for screening candidate or test compounds which bind to or modulate the activity of an MTR-3 protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) Anti-cancer Drug Des. 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223, 409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra.).

In one embodiment, an assay is a cell-based assay in which a cell which expresses an MTR-3 protein or biologically active portion thereof is contacted with a test compound and the ability of the test compound to modulate MTR-3 activity is determined. Determining the ability of the test compound to modulate MTR-3 activity can be accomplished by monitoring, for example: (i) modulate transcriptional activation (e.g., either directly or indirectly); (ii) modulate (directly or indirectly) chromatin structure to, for example, regulate the recruitment of an RNA polymerase II transcription initiation complex to a gene promoter; (iii) modulate the methylation state of proteins in the transcription machinery; (iv) interaction with an MTR-3 substrate or target molecule (e.g., a non-MTR-3 protein); (v) conversion of an MTR-3 substrate or target molecule to a product (e.g., transfer of a methyl group to or from the substrate or target molecule); (vi) interaction with and/or methyl transfer to a second non-MTR-3 protein; (vii) transfer of a methyl group to an arginine residue; (viii) modulation of protein-protein interaction (e.g., MTR-3-MTR-3 and/or MTR-3-non-MTR-3 interaction); (ix) modulation and/or coordination of protein complex formation (e.g., MTR-3-containing complex formation); (x) regulation of substrate or target molecule activity; (xi) modulation of intra- or intercellular signaling, (xii) modulation of cellular targeting and/or transport of proteins; and/or (xiii) modulation of cellular proliferation, growth, or differentiation. The cell, for example, can be of mammalian origin, e.g., an epithelial cell, for example a colon epithelial cell, or a tumor cell. The ability of the test compound to modulate MTR-3 binding to a substrate or to bind to MTR-3 can also be determined.

Determining the ability of the test compound to modulate MTR-3 binding to a substrate can be accomplished, for example, by coupling the MTR-3 substrate with a radioisotope or enzymatic label such that binding of the MTR-3 substrate to MTR-3 can be determined by detecting the labeled MTR-3 substrate in a complex. Alternatively, MTR-3 could be coupled with a radioisotope or enzymatic label to monitor the ability of a test compound to modulate MTR-3 binding to an MTR-3 substrate in a complex. Determining the ability of the test compound to bind MTR-3 can be accomplished, for example, by coupling the compound with a radioisotope or enzymatic label such that binding of the compound to MTR-3 can be determined by detecting the labeled MTR-3 compound in a complex. For example, compounds (e.g., MTR-3 substrates) can be labeled with $^{125}I$, $^{35}S$, $^{14}C$, or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., an MTR-3 substrate) to interact with MTR-3 without the labeling of any of the interactants. For example, a microphysiometer can be used to detect the interaction of a compound with MTR-3 without the labeling of either the compound or the MTR-3. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and MTR-3.

In another embodiment, an assay is a cell-based assay comprising contacting a cell expressing an MTR-3 target molecule (e.g., an MTR-3 substrate) with a test compound and determining the ability of the test compound to modulate (e.g., stimulate or inhibit) the activity of the MTR-3 target molecule. Determining the ability of the test compound to modulate the activity of an MTR-3 target molecule can be accomplished, for example, by determining the ability of the MTR-3 protein to bind to or interact with the MTR-3 target molecule.

Determining the ability of the MTR-3 protein, or a biologically active fragment thereof, to bind to or interact with an MTR-3 target molecule can be accomplished by one of the methods described above for determining direct binding. In a preferred embodiment, determining the ability of the MTR-3 protein to bind to or interact with an MTR-3 target molecule can be accomplished by determining the activity of the target molecule. For example, the activity of the target molecule can be determined by detecting induction of a cellular response, detecting catalytic/enzymatic activity of the target on an appropriate substrate, detecting the induction of a reporter gene (comprising a target-responsive regulatory element operatively linked to a nucleic acid encoding a detectable marker, e.g., luciferase), or detecting a target-regulated cellular response (e.g., cell growth or proliferation).

In yet another embodiment, an assay of the present invention is a cell-free assay in which an MTR-3 protein or biologically active portion thereof is contacted with a test compound and the ability of the test compound to bind to the MTR-3 protein or biologically active portion thereof is determined. Preferred biologically active portions of the MTR-3 proteins to be used in assays of the present invention include fragments which participate in interactions with non-MTR-3 molecules, e.g., fragments with high surface probability scores. Binding of the test compound to the MTR-3 protein can be determined either directly or indirectly as described above. In a preferred embodiment, the assay includes contacting the MTR-3 protein or biologically active portion thereof with a known compound which binds MTR-3 to form an assay mixture, contacting the assay mixture with a test compound, and determining the ability of the test compound to interact with an MTR-3 protein, wherein determining the ability of the test compound to interact with an MTR-3 protein comprises determining the ability of the test compound to preferentially bind to MTR-3 or biologically active portion thereof as compared to the known compound.

In another embodiment, the assay is a cell-free assay in which an MTR-3 protein or biologically active portion thereof is contacted with a test compound and the ability of the test compound to modulate (e.g., stimulate or inhibit) the activity of the MTR-3 protein or biologically active portion thereof is determined. Determining the ability of the test compound to modulate the activity of an MTR-3 protein can be accomplished, for example, by determining the ability of the MTR-3 protein to bind to an MTR-3 target molecule by one of the methods described above for determining direct binding. Determining the ability of the MTR-3 protein to bind to an MTR-3 target molecule can also be accomplished using a technology such as real-time Biomolecular Interaction Analysis (BIA). Sjolander, S. and Urbaniczky, C. (1991) Anal. Chem. 63:2338–2345 and Szabo et al. (1995) Curr. Opin. Struct. Biol. 5:699–705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of an MTR-3 protein can be accomplished by determining the ability of the MTR-3 protein to interact with and/or convert an MTR-3 substrate (e.g., to methylate arginine residues of specific proteins, e.g., histones, hnRNPA1, fibrillarin, or nucleolin) or to regulate transcription (e.g., transcriptional activation by nuclear receptors). For example, to determine the ability of an MTR-3 protein to methylate a substrate, assays for methylation such as those described in Chen, et al. (1999) Science 284:2174) and Gu, et al. (1999) Life Sciences 65:737–745 may be carried out. In another embodiment, determining the ability of the test compound to modulate the activity of an MTR-3 protein can be accomplished by determining the ability of the MTR-3 protein to further modulate the activity of a downstream effector of an MTR-3 target molecule. For example, the activity of the effector molecule on an appropriate target can be determined or the binding of the effector to an appropriate target can be determined as previously described.

In yet another embodiment, the cell-free assay involves contacting an MTR-3 protein or biologically active portion thereof with a known compound which binds the MTR-3 protein to form an assay mixture, contacting the assay mixture with a test compound, and determining the ability of the test compound to interact with the MTR-3 protein, wherein determining the ability of the test compound to interact with the MTR-3 protein comprises determining the ability of the MTR-3 protein to preferentially bind to or methylate the target substrate.

In more than one embodiment of the above assay methods of the present invention, it may be desirable to immobilize either MTR-3 or its target molecule to facilitate separation of complexed from uncomplexed forms of one or both of the proteins, as well as to accommodate automation of the assay. Binding of a test compound to an MTR-3 protein, or interaction of an MTR-3 protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/MTR-3 fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or MTR-3 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of MTR-3 binding or activity determined using standard techniques.

Other techniques for immobilizing proteins on matrices can also be used in the screening assays of the invention. For example, either an MTR-3 protein or an MTR-3 target molecule can be immobilized utilizing conjugation of biotin and streptavidin. Biotinylated MTR-3 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with MTR-3 protein or target molecules but which do not interfere with binding of the MTR-3 protein to its target molecule can be derivatized to the wells of the plate, and unbound target or MTR-3 protein trapped in the wells by antibody conjugation. Methods for detecting such complexes, in addition to those described above for the GST-immobilized complexes, include immunodetection of complexes using antibodies reactive with the MTR-3 protein or target molecule, as well as enzyme-linked assays which rely on detecting an enzymatic activity associated with the MTR-3 protein or target molecule.

In another embodiment, modulators of MTR-3 expression are identified in a method wherein a cell is contacted with a candidate compound and the expression of MTR-3 mRNA or protein in the cell is determined. The level of expression of MTR-3 mRNA or protein in the presence of the candidate compound is compared to the level of expression of MTR-3 mRNA or protein in the absence of the candidate compound. The candidate compound can then be identified as a modulator of MTR-3 expression based on this comparison. For example, when expression of MTR-3 mRNA or protein is greater (statistically significantly greater) in the presence of the candidate compound than in its absence, the candidate compound is identified as a stimulator of MTR-3 mRNA or protein expression. Alternatively, when expression of MTR-3 mRNA or protein is less (statistically significantly less) in the presence of the candidate compound than in its absence, the candidate compound is identified as an inhibitor of MTR-3 mRNA or protein expression. The level of MTR-3 mRNA or protein expression in the cells can be determined by methods described herein for detecting MTR-3 mRNA or protein.

In yet another aspect of the invention, the MTR-3 proteins can be used as "bait proteins" in a two-hybrid assay or three-hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Biotechniques 14:920–924; Iwabuchi et al. (1993) Oncogene 8:1693–1696; and Brent WO94/10300), to identify other proteins, which bind to or interact with MTR-3 ("MTR-3-binding proteins" or "MTR-3-6-bp") and are involved in MTR-3 activity. Such MTR-3-binding proteins are also likely to be involved in the propagation of signals by the MTR-3 proteins or MTR-3 targets as, for example, downstream elements of an MTR-3-mediated signaling pathway. Alternatively, such MTR-3-binding proteins are likely to be MTR-3 inhibitors.

The two-hybrid system is based on the modular nature of most transcription factors, which consist of separable DNA-binding and activation domains. Briefly, the assay utilizes two different DNA constructs. In one construct, the gene that codes for an MTR-3 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an MTR-3-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the MTR-3 protein.

In another aspect, the invention pertains to a combination of two or more of the assays described herein. For example, a modulating compound can be identified using a cell-based or a cell free assay, and the ability of the compound to modulate the activity of an MTR-3 protein can be confirmed in vivo, e.g., in an animal such as an animal model for cellular tumorigenesis or a cellular growth or proliferation disorder.

For example, a modulating compound identified as described herein (e.g., an antisense MTR-3 nucleic acid molecule, a ribozyme, an MTR-3-specific antibody, or an MTR-3-binding compound) can be used in an animal model to determine the efficacy, toxicity, or side effects of treatment with such a compound. Alternatively, a modulating compound identified as described herein can be used in an animal model to determine the mechanism of action of such an agent. Examples of animal models of cancer include transplantable models (e.g., xenografts of colon tumors such as Co-3, AC3603 or WiDr or into immunocompromised mice such as SCID or nude mice); transgenic models (e.g., B66-Min/+mouse); chemical induction models, e.g., carcinogen (e.g., azoxymethane, 2-dimethylhydrazine, or N-nitrosodimethylamine) treated rats or mice; models of liver metastasis from colon cancer such as that described by Rashidi et al. (2000) *Anticancer Res* 20(2A):715; and cancer cell implantation or inoculation models as described in, for example, Fingert, et al. (1987) *Cancer Res* 46(14):3824–9 and Teraoka, et al. (1995) *Jpn J Cancer Res* 86(5):419–23.

Furthermore, this invention pertains to uses of novel compounds identified by the above-described screening assays for treatments as described herein. In one embodiment, the invention features a method of treating a subject having a cellular growth or proliferation disorder that involves administering to the subject an MTR-3 modulator such that treatment occurs. In another embodiment, the invention features a method of treating a subject having cancer, e.g., colon cancer, that involves treating a subject with an MTR-3 modulator, such that treatment occurs. Preferred MTR-3 modulators include, but are not limited to, MTR-3 proteins or biologically active fragments, MTR-3 nucleic acid molecules, MTR-3 antibodies, ribozymes, and MTR-3 antisense oligonucleotides designed based on the MTR-3 nucleotide sequences disclosed herein, as well as peptides, organic and non-organic small molecules identified as being capable of modulating MTR-3 expression and/or activity, for example, according to at least one of the screening assays described herein.

Any of the compounds, including but not limited to compounds such as those identified in the foregoing assay systems, may be tested for the ability to ameliorate cellular growth or proliferation disorder symptoms. Cell-based and animal model-based assays for the identification of compounds exhibiting such an ability to ameliorate cellular growth or proliferation disorder systems are described herein.

In one aspect, cell-based systems, as described herein, may be used to identify compounds which may act to ameliorate cellular growth or proliferation disorder symptoms, for example, reduction in tumor burden, tumor size, tumor cell growth, differentiation, and/or proliferation, and invasive and/or metastatic potential before and after treatment. For example, such cell systems may be exposed to a compound, suspected of exhibiting an ability to ameliorate cellular growth or proliferation disorder symptoms, at a sufficient concentration and for a time sufficient to elicit such an amelioration of cellular growth or proliferation disorder symptoms in the exposed cells. After exposure, the cells are examined to determine whether one or more of the cellular growth or proliferation disorder cellular phenotypes has been altered to resemble a more normal or more wild type, non-cellular growth or proliferation disorder phenotype. Cellular phenotypes that are associated with cellular growth and/or proliferation disorders include aberrant proliferation, growth, and migration, anchorage independent growth, and loss of contact inhibition.

In addition, animal-based cellular growth or proliferation disorder systems, such as those described herein, may be used to identify compounds capable of ameliorating cellular growth or proliferation disorder symptoms. Such animal models may be used as test substrates for the identification of drugs, pharmaceuticals, therapies, and interventions which may be effective in treating cellular growth or proliferation disorders. For example, animal models may be exposed to a compound, suspected of exhibiting an ability to ameliorate cellular growth or proliferation disorder symptoms, at a sufficient concentration and for a time sufficient to elicit such an amelioration of cellular growth or proliferation disorder symptoms in the exposed animals. The response of the animals to the exposure may be monitored by assessing the reversal of cellular growth or proliferation disorders, or symptoms associated therewith, for example, reduction in tumor burden, tumor size, and invasive and/or metastatic potential before and after treatment.

With regard to intervention, any treatments which reverse any aspect of cellular growth or proliferation disorder symptoms should be considered as candidates for human cellular growth or proliferation disorder therapeutic intervention. Dosages of test compounds may be determined by deriving dose-response curves. Additionally, gene expression patterns may be utilized to assess the ability of a compound to ameliorate cellular growth and/or proliferation disorder symptoms. For example, the expression pattern of one or more genes may form part of a "gene expression profile" or "transcriptional profile" which may be then be used in such an assessment. "Gene expression profile" or "transcriptional profile", as used herein, includes the pattern of mRNA expression obtained for a given tissue or cell type under a given set of conditions. Such conditions may include, but are not limited to, cell growth, proliferation, differentiation, transformation, tumorigenesis, metastasis, and carcinogen exposure. Gene expression profiles may be generated, for example, by utilizing a differential display procedure, Northern analysis and/or RT-PCR. In one embodiment, MTR-3 gene sequences may be used as probes and/or PCR primers for the generation and corroboration of such gene expression profiles. Gene expression profiles may be characterized for known states within the cell- and/or animal-based model systems. Subsequently, these known gene expression profiles may be compared to ascertain the effect a test compound has to modify such gene expression profiles, and to cause the profile to more closely resemble that of a more desirable profile. For example, administration of a compound may cause the gene expression profile of a cellular growth or proliferation disorder model system to more closely resemble the control system. Administration of a compound may, alternatively, cause the gene expression profile of a control system to begin to mimic a cellular growth and/or proliferation disorder state. Such a compound may, for example, be used in further characterizing the compound of interest, or may be used in the generation of additional animal models.

Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining MTR-3 protein and/or nucleic acid expression as well as MTR-3 activity, in the context of a biological sample (e.g., blood, serum, cells, tissue, e.g., tumor cells or colon tissue) to thereby determine whether an individual is afflicted with a disorder, or is at risk of developing a cellular growth or proliferation disorder, associated with aberrant or unwanted MTR-3 expression or activity. The invention also provides for prognostic (or predictive) assays for determining whether an individual is at risk of developing a disorder associated with MTR-3 protein, nucleic acid expression or activity. For example, mutations in an MTR-3 gene can be assayed in a biological sample. Such assays can be used for prognostic or predictive purpose to thereby prophylactically treat an individual prior to the onset of a disorder characterized by or associated with MTR-3 protein, nucleic acid expression or activity.

Another aspect of the invention pertains to monitoring the influence of agents (e.g., drugs, compounds) on the expression or activity of MTR-3 in clinical trials.

These and other agents are described in further detail in the following sections.

Diagnostic Assays

The present invention encompasses methods for diagnostic and prognostic evaluation of cellular growth or proliferation disorder conditions, and for the identification of subjects exhibiting a predisposition to such conditions.

An exemplary method for detecting the presence or absence of MTR-3 protein or nucleic acid in a biological sample involves obtaining a biological sample from a test subject and contacting the biological sample with a compound or an agent capable of detecting MTR-3 protein or nucleic acid (e.g., mRNA, or genomic DNA) that encodes MTR-3 protein such that the presence of MTR-3 protein or nucleic acid is detected in the biological sample. A preferred agent for detecting MTR-3 mRNA or genomic DNA is a labeled nucleic acid probe capable of hybridizing to MTR-3 mRNA or genomic DNA. The nucleic acid probe can be, for example, the MTR-3 nucleic acid set forth in SEQ ID NO:7 or 9, or a portion thereof, such as an oligonucleotide of at least 15, 20, 25, 30, 35, 40, 45, 50, 100, 250 or 500 nucleotides in length and sufficient to specifically hybridize under stringent conditions to MTR-3 mRNA or genomic DNA. Other suitable probes for use in the diagnostic assays of the invention are described herein.

A preferred agent for detecting MTR-3 protein is an antibody capable of binding to MTR-3 protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect MTR-3 mRNA, protein, or genomic DNA in a biological sample in vitro as well as in vivo. For example, in vitro techniques for detection of MTR-3 mRNA include Northern hybridizations and in situ hybridizations. In vitro techniques for detection of MTR-3 protein include enzyme linked immunosorbent assays (ELISAs), Western blots, immunoprecipitations and immunofluorescence. In vitro techniques for detection of MTR-3 genomic DNA include Southern hybridizations. Furthermore, in vivo techniques for detection of MTR-3 protein include introducing into a subject a labeled anti-MTR-3 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject. Also preferred are biological samples from tumors (e.g., tumor biopsies). Additional preferred biological samples include lung sample, prostate tissue, liver tissue, breast tissue, skeletal muscle tissue, brain tissue, breast tissue, heart tissue, ovarian tissue, kidney tissue, lung tissue, vascular tissue, aortic tissue, thyroid tissue, placental tissue, intestinal tissue, cervical tissue, splenic tissue, esophageal tissue, thymic tissue, tonsillar tissue, lymph nodes and osteogenic cells. Particularly preferred samples are from colon tissue.

In another embodiment, the methods further involve obtaining a control biological sample from a control subject, contacting the control sample with a compound or agent capable of detecting MTR-3 protein, mRNA, or genomic DNA, such that the presence of MTR-3 protein, mRNA or genomic DNA is detected in the biological sample, and comparing the presence of MTR-3 protein, mRNA or genomic DNA in the control sample with the presence of MTR-3 protein, mRNA or genomic DNA in the test sample.

The invention also encompasses kits for detecting the presence of MTR-3 in a biological sample. For example, the kit can comprise a labeled compound or agent capable of detecting MTR-3 protein or mRNA in a biological sample; means for determining the amount of MTR-3 in the sample; and means for comparing the amount of MTR-3 in the sample with a standard. The compound or agent can be packaged in a suitable container. The kit can further comprise instructions for using the kit to detect MTR-3 protein or nucleic acid.

Prognostic Assays

The diagnostic methods described herein can furthermore be utilized to identify subjects having or at risk of developing a cellular growth or proliferation disorder associated with aberrant or unwanted MTR-3 expression or activity. As used herein, the term "aberrant" includes an MTR-3 expression or activity which deviates from the wild type MTR-3 expression or activity. Aberrant expression or activity includes increased or decreased expression or activity, as well as expression or activity which does not follow the wild type developmental pattern of expression or the subcellular pattern of expression. For example, aberrant MTR-3 expression or activity is intended to include the cases in which a mutation in the MTR-3 gene causes the MTR-3 gene to be under-expressed or over-expressed and situations in which such mutations result in a non-functional MTR-3 protein or a protein which does not function in a wild-type fashion, e.g., a protein which does not interact with an MTR-3 ligand or substrate, or one which interacts with a non-MTR-3 ligand or substrate. As used herein, the term "unwanted" includes an unwanted phenomenon involved in a biological response such as cellular proliferation. For example, the term unwanted includes an MTR-3 expression pattern or an MTR-3 protein activity which is undesirable in a subject, e.g., differential (e.g., increased) expression of MTR-3 in tumors, e.g., colon tumors or liver tumors.

The assays described herein, such as the preceding diagnostic assays or the following assays, can be utilized to identify a subject having or at risk of developing a disorder associated with a misregulation in MTR-3 protein activity or nucleic acid expression, such as a cellular growth or proliferation disorder. Alternatively, the prognostic assays can be utilized to identify a subject having or at risk for developing a cellular growth or proliferation disorder, associated with a misregulation in MTR-3 protein activity or nucleic acid expression. Thus, the present invention provides a method for identifying a disorder associated with aberrant or unwanted MTR-3 expression or activity in which a test sample is obtained from a subject and MTR-3 protein or nucleic acid (e.g., mRNA or genomic DNA) is detected, wherein the presence of MTR-3 protein or nucleic acid is diagnostic for a subject having or at risk of developing a disorder associated with aberrant or unwanted MTR-3 expression or activity. As used herein, a "test sample" refers to a biological sample obtained from a subject of interest. For example, a test sample can be a biological fluid (e.g., serum), cell sample, or tissue, e.g., tumor sample or colon cell or tissue sample.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disorder associated with aberrant or unwanted MTR-3 expression or activity. For example, such methods can be used to determine whether a subject can be effectively treated with an agent for a cellular growth or proliferation disorder. Thus, the present invention provides methods for determining whether a subject can be effectively treated with an agent for a cellular growth or proliferation disorder, associated with aberrant or unwanted MTR-3 expression or activity in which a test sample is obtained and MTR-3 protein or nucleic acid expression or activity is detected (e.g., wherein the abundance of MTR-3 protein or nucleic acid expression or activity is diagnostic for a subject that can be administered the agent to treat a disorder associated with aberrant or unwanted MTR-3 expression or activity).

The methods of the invention can also be used to detect genetic alterations in an MTR-3 gene, thereby determining if a subject with the altered gene is at risk for a disorder characterized by misregulation in MTR-3 protein activity or nucleic acid expression, such as a cellular growth or proliferation disorder. In preferred embodiments, the methods include detecting, in a sample of cells from the subject, the presence or absence of a genetic alteration characterized by at least one of an alteration affecting the integrity of a gene encoding an MTR-3-protein, or the mis-expression of the MTR-3 gene. For example, such genetic alterations can be detected by ascertaining the existence of at least one of 1) a deletion of one or more nucleotides from an MTR-3 gene; 2) an addition of one or more nucleotides to an MTR-3 gene; 3) a substitution of one or more nucleotides of an MTR-3 gene, 4) a chromosomal rearrangement of an MTR-3 gene; 5) an alteration in the level of a messenger RNA transcript of an MTR-3 gene, 6) aberrant modification of an MTR-3 gene, such as of the methylation pattern of the genomic DNA, 7) the presence of a non-wild type splicing pattern of a messenger RNA transcript of an MTR-3 gene, 8) a non-wild type level of an MTR-3-protein, 9) allelic loss of an MTR-3 gene, and 10) inappropriate post-translational modification of an MTR-3-protein. As described herein, there are a large number of assays known in the art which can be used for detecting alterations in an MTR-3 gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the MTR-3-gene (see Abravaya et al. (1995) *Nucleic Acids Res*. 23:675–682). This method can include the steps of collecting a sample of cells from a subject, isolating nucleic acid (e.g., genomic, mRNA or both) from the cells of the sample, contacting the nucleic acid sample with one or more primers which specifically hybridize to an MTR-3 gene under conditions such that hybridization and amplification of the MTR-3-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Other amplification methods include: self sustained sequence replication (Guatelli, J. C. et al., (1990) *Proc. Natl. Acad. Sci. USA* 87:1874–1878), transcriptional amplification system (Kwoh, D. Y. et al., (1989) *Proc. Natl. Acad. Sci. USA* 86:1173–1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in an MTR-3 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in MTR-3 can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in MTR-3 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the MTR-3 gene and detect mutations by comparing the sequence of the sample MTR-3 with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the MTR-3 gene include methods in which protection from cleavage agents is used to detect mismatched bases in RNA/RNA or RNA/DNA heteroduplexes (Myers et al. (1985) *Science* 230: 1242). In general, the art technique of "mismatch cleavage" starts by providing heteroduplexes of formed by hybridizing (labeled) RNA or DNA containing the wild-type MTR-3 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad Sci USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in MTR-3 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on an MTR-3 sequence, e.g., a wild-type MTR-3 sequence, is hybridized to a cDNA or other DNA product from a test cell(s). The duplex is treated with a DNA mismatch repair enzyme, and the cleavage products, if any, can be detected from electrophoresis protocols or the like (described in, for example, U.S. Pat. No. 5,459,039).

In other embodiments, alterations in electrophoretic mobility will be used to identify mutations in MTR-3 genes. For example, single strand conformation polymorphism (SSCP) may be used to detect differences in electrophoretic mobility between mutant and wild type nucleic acids (Orita et al. (1989) *Proc Natl. Acad. Sci USA*: 86:2766, see also Cotton (1993) *Mutat. Res.* 285:125–144; and Hayashi (1992) *Genet. Anal. Tech. Appl.* 9:73–79). Single-stranded DNA fragments of sample and control MTR-3 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving an MTR-3 gene.

Furthermore, any cell type or tissue in which MTR-3 is expressed may be utilized in the prognostic assays described herein.

Monitoring of Effects During Clinical Trials

The present invention provides methods for evaluating the efficacy of drugs and monitoring the progress of patients involved in clinical trials for the treatment of cellular growth or proliferation disorders.

Monitoring the influence of compounds (e.g., drugs) on the expression or activity of an MTR-3 protein (e.g., the modulation of cell growth, proliferation and/or migration) can be applied not only in basic drug screening, but also in clinical trials. For example, the effectiveness of a compound determined by a screening assay as described herein to increase MTR-3 gene expression, protein levels, or upregulate MTR-3 activity, can be monitored in clinical trials of subjects exhibiting decreased MTR-3 gene expression, protein levels, or downregulated MTR-3 activity. Alternatively, the effectiveness of an agent determined by a screening assay to decrease MTR-3 gene expression, protein levels, or downregulate MTR-3 activity, can be monitored in clinical trials of subjects exhibiting increased MTR-3 gene expression, protein levels, or upregulated MTR-3 activity. In such clinical trials, the expression or activity of an MTR-3 gene, and preferably, other genes that have been implicated in, for example, an MTR-3-associated disorder can be used as a "read out" or markers of the phenotype a particular cell, e.g., an endothelial cell or a tumor cell. In addition, the expression of an MTR-3 gene, or the level of MTR-3 protein activity may be used as a read out of a particular drug or agent's effect on a cellular growth or proliferation disorder.

For example, and not by way of limitation, genes, including MTR-3, that are modulated in cells by treatment with an agent (e.g., compound, drug or small molecule) which modulates MTR-3 activity (e.g., identified in a screening assay as described herein) can be identified. Thus, to study the effect of agents on MTR-3-associated disorders (e.g., cellular growth or proliferation disorders), for example, in a clinical trial, cells can be isolated and RNA prepared and analyzed for the levels of expression of MTR-3 and other genes implicated in the MTR-3-associated disorder, respectively. The levels of gene expression (e.g., a gene expression pattern) can be quantified by northern blot analysis or RT-PCR, as described herein, or alternatively by measuring the amount of protein produced, by one of the methods as described herein, or by measuring the levels of activity of MTR-3 or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of an MTR-3 protein, mRNA, or genomic DNA in the preadministration sample; (iii) obtaining one or more post-administration samples from the subject; (iv) detecting the level of expression or activity of the MTR-3 protein, mRNA, or genomic DNA in the post-administration samples; (v) comparing the level of expression or activity of the MTR-3 protein, mRNA, or genomic DNA in the pre-administration sample with the MTR-3 protein, mRNA, or genomic DNA in the post administration sample or samples; and (vi) altering the administration of the agent to the subject accordingly. For example, increased administration of the agent may be desirable to increase the expression or activity of MTR-3 to higher levels than detected, i.e., to increase the effectiveness of the agent. Alternatively, decreased administration of the agent may be desirable to decrease expression or activity of MTR-3 to lower levels than detected, i.e. to decrease the effectiveness of the agent. According to such an embodiment, MTR-3 expression or activity may be used as an indicator of the effectiveness of an agent, even in the absence of an observable phenotypic response.

Methods of Treatment

The present invention provides for both prophylactic and therapeutic methods of treating a subject at risk of (or susceptible to) a disorder or having a disorder associated with aberrant or unwanted MTR-3 expression or activity, e.g. a cellular growth or proliferation disorder. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the MTR-3 molecules of the present invention or MTR-3 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

Prophylactic Methods

In one aspect, the invention provides a method for preventing in a subject, a cellular growth or proliferation disorder associated with an aberrant or unwanted MTR-3 expression or activity, by administering to the subject an MTR-3 or an agent which modulates MTR-3 expression or at least one MTR-3 activity. Subjects at risk for a cellular growth or proliferation disorder which is caused or contributed to by aberrant or unwanted MTR-3 expression or activity can be identified by, for example, any or a combination of diagnostic or prognostic assays as described herein. Administration of a prophylactic agent can occur prior to the manifestation of symptoms characteristic of the MTR-3 aberrancy, such that a disorder is prevented or, alternatively, delayed in its progression. Depending on the type of MTR-3 aberrancy, for example, an MTR-3, MTR-3 agonist or MTR-3 antagonist agent can be used for treating the subject. The appropriate agent can be determined based on screening assays described herein.

Therapeutic Methods

Described herein are methods and compositions whereby cellular growth or proliferation disorder symptoms may be ameliorated. Certain cellular growth or proliferation disorders are brought about, at least in part, by an excessive level of a gene product, or by the presence of a gene product exhibiting an abnormal or excessive activity. As such, the reduction in the level and/or activity of such gene products would bring about the amelioration of cellular growth or proliferation disorder symptoms. Techniques for the reduction of gene expression levels or the activity of a protein are discussed below.

Alternatively, certain other cellular growth or proliferation disorders are brought about, at least in part, by the absence or reduction of the level of gene expression, or a reduction in the level of a protein's activity. As such, an increase in the level of gene expression and/or the activity of such proteins would bring about the amelioration of cellular growth or proliferation disorder symptoms.

In some cases, the up-regulation of a gene in a disease state reflects a protective role for that gene product in responding to the disease condition. Enhancement of such a gene's expression, or the activity of the gene product, will reinforce the protective effect it exerts. Some cellular growth or proliferation disorder states may result from an abnormally low level of activity of such a protective gene. In these cases also, an increase in the level of gene expression and/or the activity of such gene products would bring about the amelioration of cellular growth or proliferation disorder symptoms. Techniques for increasing target gene expression levels or target gene product activity levels are discussed herein.

Accordingly, another aspect of the invention pertains to methods of modulating MTR-3 expression or activity for therapeutic purposes. Accordingly, in an exemplary embodiment, the modulatory method of the invention involves contacting a cell with an MTR-3 or agent that modulates one or more of the activities of MTR-3-protein activity associated with the cell (e.g., an endothelial cell, such as a colon cell, or a tumor cell). An agent that modulates MTR-3 protein activity can be an agent as described herein, such as a nucleic acid or a protein, a naturally-occurring target molecule of an MTR-3 protein (e.g., an MTR-3 ligand or substrate), an MTR-3 antibody, a MTR-3 agonist or antagonist, a peptidomimetic of a MTR-3 agonist or antagonist, or other small molecule. In one embodiment, the agent stimulates one or more MTR-3 activities. Examples of such stimulatory agents include active MTR-3 protein and a nucleic acid molecule encoding MTR-3 that has been introduced into the cell. In another embodiment, the agent inhibits one or more MTR-3 activities. Examples of such inhibitory agents include antisense MTR-3 nucleic acid molecules, ribozymes, anti-MTR-3 antibodies, and MTR-3 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a MTR-3 protein or nucleic acid molecule. In one embodiment, the method involves administering an agent (e.g., an agent identified by a screening assay described herein), or combination of agents that modulates (e.g., upregulates or downregulates) MTR-3 expression or activity. In another embodiment, the method involves administering a MTR-3 protein or nucleic acid molecule as therapy to compensate for reduced, aberrant, or unwanted MTR-3 expression or activity, e.g., increased expression in tumors, e.g., colon tumors.

Stimulation of MTR-3 activity is desirable in situations in which MTR-3 is abnormally downregulated and/or in which increased MTR-3 activity is likely to have a beneficial effect. Likewise, inhibition of MTR-3 activity is desirable in situations in which MTR-3 is abnormally upregulated and/or in which decreased MTR-3 activity is likely to have a beneficial effect.

Methods for Inhibiting Target Gene Expression, Synthesis, or Activity

As discussed above, genes involved cellular growth or proliferation disorders, including tumorigenic disorders, may cause such disorders via an increased level of gene activity. In some cases, such up-regulation may have a causative or exacerbating effect on the disease state. A variety of techniques may be used to inhibit the expression, synthesis, or activity of such genes and/or proteins.

For example, compounds such as those identified through assays described above, which exhibit inhibitory activity, may be used in accordance with the invention to ameliorate cellular growth or proliferation disease symptoms. Such molecules may include, but are not limited to, small organic molecules, peptides, antibodies, and the like.

For example, compounds can be administered that compete with endogenous ligand for the MTR-3 protein. The resulting reduction in the amount of ligand-bound MTR-3 protein will modulate endothelial cell physiology. Compounds that can be particularly useful for this purpose include, for example, soluble proteins or peptides or portions and/or analogs thereof, of the MTR-3 protein, including, for example, soluble fusion proteins such as Ig-tailed fusion proteins. (For a discussion of the production of Ig-tailed fusion proteins, see, for example, U.S. Pat. No. 5,116,964). Alternatively, compounds, such as ligand analogs or antibodies, that bind to MTR-3, but do not activate the protein can be effective in inhibiting MTR-3 protein activity.

Further, antisense and ribozyme molecules which inhibit expression of the MTR-3 genes of the present invention may also be used in accordance with the invention to inhibit aberrant MTR-3 gene activity. Still further, triple helix molecules may be utilized in inhibiting aberrant MTR-3 gene activity.

The antisense nucleic acid molecules of the invention are typically administered to a subject or generated in situ such that they hybridize with or bind to cellular mRNA and/or genomic DNA encoding a MTR-3 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215: 327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591) or hairpin ribozymes (described in Fedor (2000) *J Mol Biol* 297 (2):269)) can be used to catalytically cleave MTR-3 mRNA transcripts to thereby inhibit translation of MTR-3 mRNA. A ribozyme having specificity for a MTR-3-encoding nucleic acid can be designed based upon the nucleotide sequence of a MTR-3 cDNA disclosed herein (i.e., SEQ ID NO:7 or 9). For example, a derivative of a Tetrahymena L-19 IVS RNA can be constructed in which the nucleotide sequence of the active site is complementary to the nucleotide sequence to be cleaved in a MTR-3-encoding mRNA (see, for example, Cech et al. U.S. Pat. No. 4,987,071; and Cech et al. U.S. Pat. No. 5,116,742). Alternatively, MTR-3 mRNA can be used to select a catalytic RNA having a specific ribonuclease activity from a pool of RNA molecules (see, for example, Bartel, D. and Szostak, J. W. (1993) *Science* 261:1411–1418).

MTR-3 gene expression can also be inhibited by targeting nucleotide sequences complementary to the regulatory region of the MTR-3 (e.g., the MTR-3 promoter and/or enhancers) to form triple helical structures that prevent transcription of the MTR-3 gene in target cells (see, for example, Helene, C. (1991) *Anticancer Drug Des.* 6(6): 569–84; Helene, C. et al. (1992) *Ann. N.Y. Acad. Sci.* 660:27–36; and Maher, L. J. (1992) *Bioassays* 14(12): 807–15).

Antibodies that are both specific for the MTR-3 protein and interfere with its activity may also be used to modulate or inhibit MTR-3 protein function. Such antibodies may be generated using standard techniques described herein, against the MTR-3 protein itself or against peptides corresponding to portions of the protein. Such antibodies include but are not limited to polyclonal, monoclonal, Fab fragments, single chain antibodies, or chimeric antibodies.

In instances where the target gene protein is intracellular and whole antibodies are used, internalizing antibodies may be preferred. Lipofectin liposomes may be used to deliver the antibody or a fragment of the Fab region which binds to the target epitope into cells. Where fragments of the antibody are used, the smallest inhibitory fragment which binds to the target protein's binding domain is preferred. For example, peptides having an amino acid sequence corresponding to the domain of the variable region of the antibody that binds to the target gene protein may be used. Such peptides may be synthesized chemically or produced via recombinant DNA technology using methods well known in the art (described in, for example, Creighton (1983), supra; and Sambrook et al. (1989) supra). Single chain neutralizing antibodies which bind to intracellular target gene epitopes may also be administered. Such single chain antibodies may be administered, for example, by expressing nucleotide sequences encoding single-chain antibodies within the target cell population by utilizing, for example, techniques such as those described in Marasco et al. (1993) *Proc. Natl. Acad. Sci. USA* 90:7889–7893).

In some instances, the target gene protein is extracellular, or is a transmembrane protein. Antibodies that are specific for one or more extracellular domains of the MTR-3 protein, for example, and that interfere with its activity, are particularly useful in treating cellular growth or proliferation disorders. Such antibodies are especially efficient because they can access the target domains directly from the bloodstream. Any of the administration techniques described below which are appropriate for peptide administration may be utilized to effectively administer inhibitory target gene antibodies to their site of action.

Methods for Restoring or Enhancing Target Gene Activity

Genes that cause cellular growth or proliferation disorders may be underexpressed within cellular growth or proliferation disorder situations. Alternatively, the activity of the protein products of such genes may be decreased, leading to the development of cellular growth or proliferation disorder symptoms. Such down-regulation of gene expression or decrease of protein activity might have a causative or exacerbating effect on the disease state.

In some cases, genes that are up-regulated in the disease state might be exerting a protective effect. A variety of techniques may be used to increase the expression, synthesis, or activity of genes and/or proteins that exert a protective effect in response to cellular growth or proliferation disorder conditions.

Described in this section are methods whereby the level MTR-3 activity may be increased to levels wherein cellular growth or proliferation disorder symptoms are ameliorated. The level of MTR-3 activity may be increased, for example, by either increasing the level of MTR-3 gene expression or by increasing the level of active MTR-3 protein which is present.

For example, a MTR-3 protein, at a level sufficient to ameliorate cellular growth or proliferation disorder symptoms may be administered to a patient exhibiting such symptoms. Any of the techniques discussed below may be used for such administration. One of skill in the art will readily know how to determine the concentration of effective, non-toxic doses of the MTR-3 protein, utilizing techniques such as those described below.

Additionally, RNA sequences encoding a MTR-3 protein may be directly administered to a patient exhibiting cellular growth or proliferation disorder symptoms, at a concentration sufficient to produce a level of MTR-3 protein such that cellular growth or proliferation disorder symptoms are ameliorated. Any of the techniques discussed below, which achieve intracellular administration of compounds, such as, for example, liposome administration, may be used for the administration of such RNA molecules. The RNA molecules may be produced, for example, by recombinant techniques such as those described herein.

Further, subjects may be treated by gene replacement therapy. One or more copies of a MTR-3 gene, or a portion thereof, that directs the production of a normal MTR-3 protein with MTR-3 function, may be inserted into cells using vectors which include, but are not limited to adenovirus, adeno-associated virus, and retrovirus vectors, in addition to other particles that introduce DNA into cells, such as liposomes. Additionally, techniques such as those described above may be used for the introduction of MTR-3 gene sequences into human cells.

Cells, preferably, autologous cells, containing MTR-3 expressing gene sequences may then be introduced or reintroduced into the subject at positions which allow for the amelioration of cellular growth or proliferation disorder symptoms. Such cell replacement techniques may be preferred, for example, when the gene product is a secreted, extracellular gene product.

Pharmacogenomics

The MTR-3 molecules of the present invention, as well as agents, or modulators which have a stimulatory or inhibitory effect on MTR-3 activity (e.g., MTR-3 gene expression) as identified by a screening assay described herein can be administered to individuals to treat (prophylactically or therapeutically) MTR-3-associated disorders (e.g., cellular growth and proliferation disorders) associated with aberrant or unwanted MTR-3 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a MTR-3 molecule or a MTR-3 modulator as well as tailoring the dosage and/or therapeutic regimen of treatment with a MTR-3 molecule or MTR-3 modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol*. 23(10–11): 983–985 and Linder, M. W. et al. (1997) *Clin. Chem*. 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a MTR-3 protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses.

Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a MTR-3 molecule or MTR-3 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a MTR-3 molecule or MTR-3 modulator, such as a modulator identified by one of the exemplary screening assays described herein.

Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

Chromosome Mapping

Once the sequence (or a portion of the sequence) of a gene has been isolated, this sequence can be used to map the location of the gene on a chromosome. This process is called chromosome mapping. Accordingly, portions or fragments of the MTR-3 nucleotide sequences, described herein, can be used to map the location of the MTR-3 genes on a chromosome. The mapping of the MTR-3 sequences to chromosomes is an important first step in correlating these sequences with genes associated with disease.

Briefly, MTR-3 genes can be mapped to chromosomes by preparing PCR primers (preferably 15–25 bp in length) from the MTR-3 nucleotide sequences. Computer analysis of the MTR-3 sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the MTR-3 sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220: 919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the MTR-3 nucleotide sequences to design oligonucleotide primers, sublocalization can be achieved with panels of fragments from specific chromosomes. Other mapping strategies which can similarly be used to map a MTR-3 sequence to its chromosome include in situ hybridization (described in Fan, Y. et al. (1990) *Proc. Natl. Acad. Sci. USA*, 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783–787.

Moreover, differences in the DNA sequences between individuals affected and unaffected with a disease associated with the MTR-3 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing

The MTR-3 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the MTR-3 nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The MTR-3 nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of MTR-3 gene sequences can comfortably provide positive individual identification with a panel of perhaps 10 to 1,000 primers which each yield a noncoding amplified sequence of 100 bases. If predicted coding sequences, such as those in SEQ ID NO:7 are used, a more appropriate number of primers for positive individual identification would be 500–2,000.

If a panel of reagents from MTR-3 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial MTR-3 Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of MTR-3 gene sequences are particularly appropriate for this use as greater numbers of polymorphisms occur in the noncoding regions, making it easier to differentiate individuals using this technique. Examples of polynucleotide reagents include the MTR-3 nucleotide sequences or portions thereof, e.g., fragments derived from the noncoding regions having a length of at least 20 bases, preferably at least 30 bases.

The MTR-3 nucleotide sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such MTR-3 probes can be used to identify tissue by species and/or by organ type.

In a similar fashion, these reagents, e.g., MTR-3 primers or probes can be used to screen tissue culture for contamination (i.e. screen for the presence of a mixture of different types of cells in a culture).

Recombinant Expression Vectors and Host Cells

Another aspect of the invention pertains to vectors, for example recombinant expression vectors, containing a nucleic acid containing an MTR-3 nucleic acid molecule or vectors containing a nucleic acid molecule which encodes an MTR-3 polypeptide (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the methods of the invention may include other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., MTR-3 proteins, mutant forms of MTR-3 proteins, fusion proteins, and the like).

Accordingly, an exemplary embodiment provides a method for producing a polypeptide, preferably an MTR-3 polypeptide, by culturing in a suitable medium a host cell of the invention (e.g., a mammalian host cell such as a non-human mammalian cell) containing a recombinant expression vector, such that the polypeptide is produced.

The recombinant expression vectors of the invention can be designed for expression of MTR-3 proteins in prokaryotic or eukaryotic cells, e.g., for use in the cell-based assays of the invention. For example, MTR-3 proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in MTR-3 activity assays, (e.g., direct assays or competitive assays described in detail below), or to generate antibodies specific for MTR-3 proteins, for example. In a preferred embodiment, a MTR-3 fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a 7 gn10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res*. 20:2111–2118). Such alteration of nucleic acid sequences of the invention can be carried out by standard DNA synthesis techniques.

In another embodiment, the MTR-3 expression vector is a yeast expression vector. Examples of vectors for expression in yeast *S. cerevisiae* include pYepSec1 (Baldari, et al., (1987) *EMBO J*. 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp, San Diego, Calif.).

Alternatively, MTR-3 proteins can be expressed in insect cells using baculovirus expression vectors. Baculovirus vectors available for expression of proteins in cultured insect cells (e.g., Sf 9 cells) include the pAc series (Smith et al. (1983) *Mol. Cell Biol*. 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J*. 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), endothelial cell-specific promoters (e.g., KDR/flk promoter; U.S. Pat. No. 5,888,765), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The expression characteristics of an endogenous MTR-3 gene within a cell line or microorganism may be modified by inserting a heterologous DNA regulatory element into the genome of a stable cell line or cloned microorganism such that the inserted regulatory element is operatively linked with the endogenous MTR-3 gene. For example, an endogenous MTR-3 gene which is normally "transcriptionally silent", i.e., a MTR-3 gene which is normally not expressed, or is expressed only at very low levels in a cell line or microorganism, may be activated by inserting a regulatory element which is capable of promoting the expression of a normally expressed gene product in that cell line or microorganism. Alternatively, a transcriptionally silent, endogenous MTR-3 gene may be activated by insertion of a promiscuous regulatory element that works across cell types.

A heterologous regulatory element may be inserted into a stable cell line or cloned microorganism, such that it is operatively linked with an endogenous MTR-3 gene, using techniques, such as targeted homologous recombination, which are well known to those of skill in the art, and described, e.g., in Chappel, U.S. Pat. No. 5,272,071; PCT publication No. WO 91/06667, published May 16, 1991.

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to MTR-3 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to the use of host cells into which a MTR-3 nucleic acid molecule of the invention is introduced, e.g., a MTR-3 nucleic acid molecule within a recombinant expression vector or a MTR-3 nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a MTR-3 protein can be expressed in bacterial cells such as *E. coli*, insect cells, yeast or mammalian cells (such as human umbilical vein endothelial cells (HUVEC), human microvascular endothelial cells (HMVEC), Chinese hamster ovary cells (CHO), human ovarian surface epithelial (HOSE) cells, or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin, puromycin, zeomycin and methotrexate. Nucleic acid encoding a selectable marker can be introduced into a host cell on the same vector as that encoding a MTR-3 protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a MTR-3 protein. Accordingly, the invention further provides methods for producing a MTR-3 protein using the host cells of the invention. In one embodiment, the method comprises culturing the host cell of the invention (into which a recombinant expression vector encoding a MTR-3 protein has been introduced) in a suitable medium such that a MTR-3 protein is produced. In another embodiment, the method further comprises isolating a MTR-3 protein from the medium or the host cell.

Cell- and Animal-Based Model Systems

Described herein are cell- and animal-based systems which act as models for cellular growth or proliferation disorders. These systems may be used in a variety of applications. For example, the cell- and animal-based model systems may be used to further characterize differentially expressed genes associated with cellular growth or proliferation disorder, e.g., MTR-3. In addition, animal- and cell-based assays may be used as part of screening strategies designed to identify compounds which are capable of ameliorating cellular growth or proliferation disorder symptoms, as described, below. Thus, the animal-and cell-based models may be used to identify drugs, pharmaceuticals, therapies and interventions which may be effective in treating cellular grwoth or proliferation disorders.

Animal-Based Systems

Animal-based model systems of cellular growth or proliferation disorders may include, but are not limited to, non-recombinant and engineered transgenic animals.

Animal based models for studying tumorigenesis in vivo are well known in te art (reviewed in Animal Models of Cancer Predisposition Syndromes, Hiai, H and Hino, O (eds.) 1999, *Progress in Experimental Tumor Research*, Vol. 35; Clarke A R *Carcinogenesis* (2000) 21:435–41) and include, for example, carcinogen-induced tumors (Rithidech, K et al. *Mutat Res* (1999) 428:33–39; Miller, M L et al. *Environ Mol Mutagen* (2000) 35:319–327), injection and/or transplantation of tumor cells into an animal, as well as animals bearing mutations in growth regulatory genes, for example, oncogenes (e.g., ras) (Arbeit, J M et al. *Am J Pathol* (1993) 142:1187–1197; Sinn, E et al. *Cell* (1987) 49:465–475; Thorgeirsson, S S et al. *Toxicol Lett* (2000) 112–113:553–555) and tumor suppressor genes (e.g., p53) (Vooijs, M et al. *Oncogene (*1999) 18:5293–5303; Clark A R *Cancer Metast Rev* (1995) 14:125–148; Kumar, T R et al. *J Intern Med* (1995) 238:233–238; Donehower, L A et al. (1992) Nature 356215–221). Furthermore, experimental model systems are available for the study of, for example, colon cancer (Heyer J, et al. (1999) Oncogene 18(38): 5325–33), ovarian cancer (Hamilton, T C et al. *Semin Oncol* (1984) 11:285–298; Rahman, N A et al. *Mol Cell Endocrinol* (1998) 145:167–174; Beamer, W G et al. *Toxicol Pathol* (1998) 26:704–710), gastric cancer (Thompson, J et al. *Int J Cancer* (2000) 86:863–869; Fodde, R et al. *Cytogenet Cell Genet* (1999) 86:105–111), breast cancer (Li, M et al. *Oncogene* (2000) 19:1010–1019; Green, J E et al. *Oncogene* (2000) 19:1020–1027), melanoma (Satyamoorthy, K et al. *Cancer Metast Rev* (1999) 18:401–405), and prostate cancer (Shirai, T et al. *Mutat Res* (2000) 462:219–226; Bostwick, D G et al. *Prostate* (2000) 43:286–294).

Additionally, animal models exhibiting cellular growth or proliferation disorder symptoms may be engineered by using, for example, MTR-3 gene sequences described above, in conjunction with techniques for producing transgenic animals that are well known to those of skill in the art. For example, MTR-3 gene sequences may be introduced into, and overexpressed in, the genome of the animal of interest, or, if endogenous MTR-3 gene sequences are present, they may either be overexpressed or, alternatively, be disrupted in order to underexpress or inactivate MTR-3 gene expression, such as described for the disruption of apoE in mice (Plump et al., 1992, *Cell* 71: 343–353).

The host cells of the invention can also be used to produce non-human transgenic animals. For example, in one embodiment, a host cell of the invention is a fertilized oocyte or an embryonic stem cell into which MTR-3-coding sequences have been introduced. Such host cells can then be used to create non-human transgenic animals in which exogenous MTR-3 sequences have been introduced into their genome or homologous recombinant animals in which endogenous MTR-3 sequences have been altered. Such animals are useful for studying the function and/or activity of a MTR-3 and for identifying and/or evaluating modulators of MTR-3 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous MTR-3 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a MTR-3-encoding nucleic acid into the male pronuclei of a fertilized oocyte, e.g., by microinjection, retroviral infection, and allowing the oocyte to develop in a pseudopregnant female foster animal. The MTR-3 cDNA sequence of SEQ ID NO:7 or 9 can be introduced as a transgene into the genome of a non-human animal. Alternatively, a nonhuman homologue of a human MTR-3 gene, such as a mouse or rat MTR-3 gene, can be used as a transgene. Alternatively, a MTR-3 gene homologue, such as another MTR-3 family member, can be isolated based on hybridization to the MTR-3 cDNA sequences of SEQ ID NO:7 or 9 and used as a transgene. Intronic sequences and polyadenylation signals can also be included in the transgene to increase the efficiency of expression of the transgene. A tissue-specific regulatory sequence(s) can be operably linked to a MTR-3 transgene to direct expression of a MTR-3 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of a MTR-3 transgene in its genome and/or expression of MTR-3 mRNA in tissues or cells of the animals. A transgenic founder animal can then be used to breed additional animals carrying the transgene. Moreover, transgenic animals carrying a transgene encoding a MTR-3 protein can further be bred to other transgenic animals carrying other transgenes.

To create a homologous recombinant animal, a vector is prepared which contains at least a portion of a MTR-3 gene into which a deletion, addition or substitution has been introduced to thereby alter, e.g., functionally disrupt, the MTR-3 gene. The MTR-3 gene can be a human gene (e.g., the cDNA of SEQ ID NO:7 or 9), but more preferably, is a non-human homologue of a human MTR-3 gene (e.g., a cDNA isolated by stringent hybridization with the nucleotide sequence of SEQ ID NO:7 or 9). For example, a mouse MTR-3 gene can be used to construct a homologous recombination nucleic acid molecule, e.g., a vector, suitable for altering an endogenous MTR-3 gene in the mouse genome. In a preferred embodiment, the homologous recombination nucleic acid molecule is designed such that, upon homologous recombination, the endogenous MTR-3 gene is functionally disrupted (i.e., no longer encodes a functional protein; also referred to as a "knock out" vector). Alternatively, the homologous recombination nucleic acid molecule can be designed such that, upon homologous recombination, the endogenous MTR-3 gene is mutated or otherwise altered but still encodes functional protein (e.g., the upstream regulatory region can be altered to thereby alter the expression of the endogenous MTR-3 protein). In the homologous recombination nucleic acid molecule, the altered portion of the MTR-3 gene is flanked at its 5' and 3' ends by additional nucleic acid sequence of the MTR-3 gene to allow for homologous recombination to occur between the exogenous MTR-3 gene carried by the homologous recombination nucleic acid molecule and an endogenous MTR-3 gene in a cell, e.g., an embryonic stem cell. The additional flanking MTR-3 nucleic acid sequence is of sufficient length for successful homologous recombination with the endogenous gene. Typically, several kilobases of flanking DNA (both at the 5' and 3 ' ends) are included in the homologous recombination nucleic acid molecule (see, e.g., Thomas, K. R. and Capecchi, M. R. (1987) Cell 51:503 for a description of homologous recombination vectors). The homologous recombination nucleic acid molecule is introduced into a cell, e.g., an embryonic stem cell line (e.g., by electroporation) and cells in which the introduced MTR-3 gene has homologously recombined with the endogenous MTR-3 gene are selected (see e.g., Li, E. et al. (1992) Cell 69:915). The selected cells can then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijistra et al.; and WO 93/04169 by Berns et al.

In another embodiment, transgenic non-human animals of the invention can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

The MTR-3 transgenic animals that express MTR-3 mRNA or a MTR-3 peptide (detected immunocytochemically, using antibodies directed against MTR-3 epitopes) at easily detectable levels should then be further evaluated to identify those animals which display characteristic cellular growth or proliferation disorder symptoms. Tumorigenic disease symptoms include, for example, tumor burden, invasion and/or metastasis.

Additionally, specific cell types (e.g., tumor cells, colon cells) within the transgenic animals may be analyzed and assayed for cellular phenotypes characteristic of cellular growth or proliferation disorders. In the case of endothelial cells, such phenotypes include, but are not limited to cell proliferation, growth and migration. Cellular phenotypes associated with a tumorigenic disorder include, for example, dysregulated proliferation and migration, anchorage independent growth, and loss of contact inhibition. Cellular phenotypes may include a particular cell type's pattern of expression of genes associated with cellular growth or proliferation disorders as compared to known expression profiles of the particular cell type in animals exhibiting cellular growth or proliferation disorder symptoms.

Cell-Based Systems

Cells that contain and express MTR-3 gene sequences which encode a MTR-3 protein, and, further, exhibit cellular phenotypes associated with cellular growth or proliferation disorders, may be used to identify compounds that exhibit anti-tumorigenic disease activity. Such cells may include endothelial cells such as human umbilical vein endothelial cells (HUVECs), human microvascular endothelial cells (HMVEC); tumor cell lines such as HT-1080 (ATCC# CCL-121), HCT-15 (ATCC# CCL-225), HCC70 (ATCC# CRL-2315), M059J (ATCC# CRL-2366), and NCI-N417 (ATCC# CRL-5809); as well as generic mammalian cell lines such as HeLa cells and COS cells, e.g., COS-7 (ATCC# CRL-1651). Further, such cells may include recombinant, transgenic cell lines. For example, the cellular growth or proliferation disorder animal models of the invention, discussed above, may be used to generate cell lines, containing one or more cell types involved in cellular growth or proliferation disorders, that can be used as cell culture models for this disorder. While primary cultures derived from the cellular growth or proliferation disorder transgenic animals of the invention may be utilized, the generation of continuous cell lines is preferred. For examples of techniques which may be used to derive a continuous cell line from the transgenic animals, see Small et al., (1985) *Mol. Cell Biol.* 5:642–648.

Alternatively, cells of a cell type known to be involved in cellular growth or proliferation disorders may be transfected with sequences capable of increasing or decreasing the amount of MTR-3 gene expression within the cell. For example, MTR-3 gene sequences may be introduced into, and overexpressed in, the genome of the cell of interest, or, if endogenous MTR-3 gene sequences are present, they may be either overexpressed or, alternatively disrupted in order to underexpress or inactivate MTR-3 gene expression.

In order to overexpress an MTR-3 gene, the coding portion of the MTR-3 gene may be ligated to a regulatory sequence which is capable of driving gene expression in the cell type of interest, e.g., a tumor cell or a colon cell. Such regulatory regions will be well known to those of skill in the art, and may be utilized in the absence of undue experimentation. Recombinant methods for expressing target genes are described above.

For underexpression of an endogenous MTR-3 gene sequence, such a sequence may be isolated and engineered such that when reintroduced into the genome of the cell type of interest, the endogenous MTR-3 alleles will be inactivated. Preferably, the engineered MTR-3 sequence is introduced via gene targeting such that the endogenous MTR-3 sequence is disrupted upon integration of the engineered MTR-3 sequence into the cell's genome. Transfection of host cells with MTR-3 genes is discussed, above.

Cells treated with compounds or transfected with MTR-3 genes can be examined for phenotypes associated with cellular growth or proliferation disorders. Cells (e.g., tumor cells) can be treated with test compounds or transfected with genetically engineered MTR-3 genes and examined for phenotypes associated with tumorigenic disease, including, but not limited to changes in cellular morphology, cell proliferation, cell migration, cell transformation, anchorage independent growth, and loss of contact inhibition.

Transfection of MTR-3 nucleic acid may be accomplished by using standard techniques (described in, for example, Ausubel (1989) supra). Transfected cells should be evaluated for the presence of the recombinant MTR-3 gene sequences, for expression and accumulation of MTR-3 mRNA, and for the presence of recombinant MTR-3 protein production. In instances wherein a decrease in MTR-3 gene expression is desired, standard techniques may be used to demonstrate whether a decrease in endogenous MTR-3 gene expression and/or in MTR-3 protein production is achieved.

Cellular models for the study of tumorigenesis are known in the art, and include cell lines derived from clinical tumors, cells exposed to chemotherapeutic agents, cells exposed to carcinogenic agents, and cell lines with genetic alterations in growth regulatory genes, for example, oncogenes (e.g., ras) and tumor suppressor genes (e.g., p 53).

Pharmaceutical Compositions

Active compounds of the invention can be incorporated into pharmaceutical compositions suitable for administration. As used herein, the language "active compounds" includes MTR-3 nucleic acid molecules, fragments of MTR-3 proteins, and anti-MTR-3 antibodies, as well as identified compounds that modulate MTR-3 gene expression, synthesis, and/or activity. Such compositions typically comprise the compound, nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of a MTR-3 protein or a MTR-3 substrate) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals. In one embodiment, a therapeutically effective dose refers to that amount of an active compound sufficient to result in amelioration of symptoms of cellular growth or proliferation disorders.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

In certain embodiments of the invention, a modulator of MTR-3 activity is administered in combination with other agents (e.g., a small molecule), or in conjunction with another, complementary treatment regime. For example, in one embodiment, a modulator of MTR-3 activity is used to treat a tumorigenic disorder, e.g., colon cancer. Accordingly, modulation of MTR-3 activity may be used in conjunction with, for example, chemotherapeutic agents and/or radiation treatment.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (CDDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, $\alpha$-interferon, $\beta$-interferon, nerve growth factor, platelet derived growth factor, tissue plasminogen activator; or, biological response modifiers such as, for example, lymphokines, interleukin-1 ("L-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery ($2^{nd}$ Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982). Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Isolated Nucleic Acid Molecules

One aspect of the invention pertains to isolated nucleic acid molecules that encode MTR-3 proteins or biologically active portions thereof, as well as nucleic acid fragments sufficient for use as hybridization probes to identify MTR- 3-encoding nucleic acid molecules (e.g., MTR-3 mRNA) and fragments for use as PCR primers for the amplification or mutation of MTR-3 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated MTR-3 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:7 or 9, or a portion thereof, can be isolated using standard molecular biology techniques and the sequence information provided herein. Using all or a portion of the nucleic acid sequence of SEQ ID NO:7 or 9 as hybridization probes, MTR-3 nucleic acid molecules can be isolated using standard hybridization and cloning techniques (e.g., as described in Sambrook, J. et al. *Molecular Cloning: A Laboratory Manual. 2nd, ed., Cold Spring Harbor Laboratory*, Cold Spring Harbor Laboratory Press, Cold Spring Harbor, N.Y., 1989).

Moreover, a nucleic acid molecule encompassing all or a portion of SEQ ID NO:7 or 9, can be isolated by the polymerase chain reaction (PCR) using synthetic oligonucleotide primers designed based upon the sequence of SEQ ID NO:7 or 9.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to MTR-3 nucleotide sequences can be prepared by standard synthetic techniques, e.g., using an automated DNA synthesizer.

In one embodiment, an isolated nucleic acid molecule of the invention comprises the nucleotide sequence shown in SEQ ID NO:7 or 9. This cDNA may comprise sequences encoding the human MTR-3 protein (e.g., the "coding region", from nucleotides), as well as 5' untranslated sequence (nucleotides 1–39) and 3' untranslated sequences (nucleotides 1864–2898) of SEQ ID NO:7. Alternatively, the nucleic acid molecule can comprise only the coding region of SEQ ID NO:7 (e.g., nucleotides 40–1863, corresponding to SEQ ID NO:9). Accordingly, in another embodiment, an isolated nucleic acid molecule of the invention comprises SEQ ID NO:9 and nucleotides 1–39 of SEQ ID NO:9. In yet another embodiment, the isolated nucleic acid molecule comprises SEQ ID NO:9 and nucleotides 1864–2898 of SEQ ID NO:7. In yet another embodiment, the nucleic acid molecule consists of the nucleotide sequence set forth as SEQ ID NO:7 or SEQ ID NO:9.

In still another embodiment, an isolated nucleic acid molecule of the invention comprises a nucleic acid molecule which is a complement of the nucleotide sequence shown in SEQ ID NO:7 or 9, or a portion of any of these nucleotide sequences. A nucleic acid molecule which is complementary to the nucleotide sequence shown in SEQ ID NO:7 or 9, is one which is sufficiently complementary to the nucleotide sequence shown in SEQ ID NO:7 or 9, such that it can hybridize to the nucleotide sequence shown in SEQ ID NO:7 or 9, thereby forming a stable duplex.

In still another embodiment, an isolated nucleic acid molecule of the present invention comprises a nucleotide sequence which is at least about 50%, 55%, 60%, 65%, 70%, 75%, 80%, 85%, 90%, 91%, 92%, 93%, 94%, 95%, 96%, 97%, 98%, 99% or more identical to the nucleotide sequence shown in SEQ ID NO:7 or 9 (e.g., to the entire length of the nucleotide sequence), or a portion or complement of any of these nucleotide sequences. In one embodiment, a nucleic acid molecule of the present invention comprises a nucleotide sequence which is at least (or no greater than) 50–100, 100–250, 250–500, 500–750, 750–1000, 1000–1250, 1250–1500, 1500–1750, 1750–2000, 2000–2250, 2250–2500, 2500–2750, 2750–3000, 3000–3210 or more nucleotides in length and hybridizes under stringent hybridization conditions to a complement of a nucleic acid molecule of SEQ ID NO:7 or 9.

Moreover, the nucleic acid molecule of the invention can comprise only a portion of the nucleic acid sequence of SEQ ID NO:7 or 9, for example, a fragment which can be used as a probe or primer or a fragment encoding a portion of an MTR-3 protein, e.g., a biologically active portion of an MTR-3 protein. The nucleotide sequence determined from the cloning of the MTR-3 gene allows for the generation of probes and primers designed for use in identifying and/or cloning other MTR-3 family members, as well as MTR-3 homologues from other species. The probe/primer (e.g., oligonucleotide) typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:7 or 9, of an anti-sense sequence of SEQ ID NO:7 or 9, or of a naturally occurring allelic variant or mutant of SEQ ID NO:7 or 9.

Exemplary probes or primers are at least (or no greater than) 12 or 15, 20 or 25, 30, 35, 40, 45, 50, 55, 60, 65, 70, 75 or more nucleotides in length and/or comprise consecutive nucleotides of an isolated nucleic acid molecule described herein. Also included within the scope of the present invention are probes or primers comprising contiguous or consecutive nucleotides of an isolated nucleic acid molecule described herein, but for the difference of 1, 2, 3, 4, 5, 6, 7, 8, 9 or 10 bases within the probe or primer sequence. Probes based on the MTR-3 nucleotide sequences can be used to detect (e.g., specifically detect) transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. In another embodiment a set of primers is provided, e.g., primers suitable for use in a PCR, which can be used to amplify a selected region of an MTR-3 sequence, e.g., a domain, region, site or other sequence described herein. The primers should be at least 5, 10, or 50 base pairs in length and less than 100, or less than 200, base pairs in length. The primers should be identical, or differ by no greater than 1, 2, 3, 4, 5, 6, 7, 8, 9 or 10 bases when compared to a sequence disclosed herein or to the sequence of a naturally occurring variant. Such probes can be used as a part of a diagnostic test kit for identifying cells or tissue which misexpress an MTR-3 protein, such as by measuring a level of an MTR-3-encoding nucleic acid in a sample of cells from a subject, e.g., detecting MTR-3 mRNA levels or determining whether a genomic MTR-3 gene has been mutated or deleted.

A nucleic acid fragment encoding a "biologically active portion of an MTR-3 protein" can be prepared by isolating a portion of the nucleotide sequence of SEQ ID NO:7 or 9, which encodes a polypeptide having an MTR-3 biological activity (the biological activities of the MTR-3 proteins are described herein), expressing the encoded portion of the MTR-3 protein (e.g., by recombinant expression in vitro) and assessing the activity of the encoded portion of the MTR-3 protein. In an exemplary embodiment, the nucleic acid molecule is at least 50–100, 100–250, 250–500, 500–700, 750–1000, 1000–1250, 1250–1500, 1500–1750, 1750–2000, 2000–2250, 2250–2500, 2500–2750, 2750–3000, 3000–3210 or more nucleotides in length and encodes a protein having an MTR-3 activity (as described herein).

The invention further encompasses nucleic acid molecules that differ from the nucleotide sequence shown in SEQ ID NO:7 or 9, due to degeneracy of the genetic code and thus encode the same MTR-3 proteins as those encoded by the nucleotide sequence shown in SEQ ID NO:7 or 9. In another embodiment, an isolated nucleic acid molecule of the invention has a nucleotide sequence encoding a protein having an amino acid sequence which differs by at least 1, but no greater than 5, 10, 20, 50 or 100 amino acid residues from the amino acid sequence shown in SEQ ID NO:8. In yet another embodiment, the nucleic acid molecule encodes the amino acid sequence of human MTR-3. If an alignment is needed for this comparison, the sequences should be aligned for maximum homology.

Nucleic acid variants can be naturally occurring, such as allelic variants (same locus), homologues (different locus), and orthologues (different organism) or can be non-naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

Allelic variants result, for example, from DNA sequence polymorphisms within a population (e.g., the human population) that lead to changes in the amino acid sequences of the MTR-3 proteins. Such genetic polymorphism in the MTR-3 genes may exist among individuals within a population due to natural allelic variation. As used herein, the terms "gene" and "recombinant gene" refer to nucleic acid molecules which include an open reading frame encoding an MTR-3 protein, preferably a mammalian MTR-3 protein, and can further include non-coding regulatory sequences, and introns.

Accordingly, in one embodiment, the invention features isolated nucleic acid molecules which encode a naturally occurring allelic variant of a polypeptide comprising the amino acid sequence of SEQ ID NO:8, wherein the nucleic acid molecule hybridizes to a complement of a nucleic acid molecule comprising SEQ ID NO:7 or 9, for example, under stringent hybridization conditions.

Allelic variants of MTR-3, e.g., human MTR-3, include both functional and non-functional MTR-3 proteins. Functional allelic variants are naturally occurring amino acid sequence variants of the MTR-3 protein that maintain the ability to, e.g., bind or interact with an MTR-3 substrate or target molecule, transfer a methyl group to or from an MTR-3 substrate or target molecule, and/or modulate transcriptional activation. Functional allelic variants will typically contain only conservative substitution of one or more amino acids of SEQ ID NO:8, or substitution, deletion or insertion of non-critical residues in non-critical regions of the protein.

Non-functional allelic variants are naturally occurring amino acid sequence variants of the MTR-3 protein, e.g., human MTR-3, that do not have the ability to, e.g., bind or interact with an MTR-3 substrate or target molecule, transfer a methyl group to or from an MTR-3 substrate or target molecule, and/or modulate transcriptional activation. Non-functional allelic variants will typically contain a non-conservative substitution, a deletion, or insertion, or premature truncation of the amino acid sequence of SEQ ID NO:8, or a substitution, insertion, or deletion in critical residues or critical regions of the protein.

The present invention further provides non-human orthologues (e.g., non-human orthologues of the human MTR-3 protein). Orthologues of the human MTR-3 protein are proteins that are isolated from non-human organisms and possess the same MTR-3 substrate or target molecule binding mechanisms, methyltransferase activity, and/or modulation of transcriptional activation mechanisms of the human MTR-3 protein. Orthologues of the human MTR-3 protein can readily be identified as comprising an amino acid sequence that is substantially homologous to SEQ ID NO:8. The mouse orthologue of human MTR-3 has been identified by Chen, et al. (1999) *Science* 284:2174–2177.

Moreover, nucleic acid molecules encoding other MTR-3 family members and, thus, which have a nucleotide sequence which differs from the MTR-3 sequences of SEQ ID NO:7 or 9, are intended to be within the scope of the invention. For example, another MTR-3 cDNA can be identified based on the nucleotide sequence of human MTR-3. Moreover, nucleic acid molecules encoding MTR-3 proteins from different species, and which, thus, have a nucleotide sequence which differs from the MTR-3 sequences of SEQ ID NO:7 or 9, are intended to be within the scope of the invention. For example, a monkey MTR-3 cDNA can be identified based on the nucleotide sequence of a human MTR-3.

Nucleic acid molecules corresponding to natural allelic variants and homologues of the MTR-3 cDNAs of the invention can be isolated based on their homology to the MTR-3 nucleic acids disclosed herein using the cDNAs disclosed herein, or a portion thereof, as a hybridization probe according to standard hybridization techniques under stringent hybridization conditions. Nucleic acid molecules corresponding to natural allelic variants and homologues of the MTR-3 cDNAs of the invention can further be isolated by mapping to the same chromosome or locus as the MTR-3 gene.

Orthologues, homologues and allelic variants can be identified using methods known in the art (e.g., by hybridization to an isolated nucleic acid molecule of the present invention, for example, under stringent hybridization conditions). In one embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:7 or 9. In other embodiment, the nucleic acid is at least 50–100, 100–250, 250–500, 500–700, 750–1000, 1000–1250, 1250–1500, 1500–1750, 1750–2000, 2000–2250, 2250–2500, 2500–2750, 2750–3000, 3000–3210 or more nucleotides in length.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in *Current Protocols in Molecular Biology*, Ausubel et al., eds., John Wiley & Sons, Inc. (1995), sections 2, 4, and 6. Additional stringent conditions can be found in *Molecular Cloning: A Laboratory Manual*, Sambrook et al., Cold Spring Harbor Press, Cold Spring Harbor, N.Y. (1989), chapters 7, 9, and 11. A preferred, non-limiting example of stringent hybridization conditions includes hybridization in 4× sodium chloride/sodium citrate (SSC), at about 65–70° C. (or alternatively hybridization in 4×SSC plus 50% formamide at about 42–50° C.) followed by one or more washes in 1×SSC, at about 65–70° C. A preferred, non-limiting example of highly stringent hybridization conditions includes hybridization in 1×SSC, at about 65–70° C. (or alternatively hybridization in 1×SSC plus 50% formamide at about 42–50° C.) followed by one or more washes in 0.3×SSC, at about 65–70° C. A preferred, non-limiting example of reduced stringency hybridization conditions includes hybridization in 4×SSC, at about 50–60° C. (or alternatively hybridization in 6×SSC plus 50% formamide at about 40–45° C.) followed by one or more washes in 2×SSC, at about 50–60° C. Ranges intermediate to the above-recited values, e.g., at 65–70° C. or at 42–50° C. are also intended to be encompassed by the present invention. SSPE (1×SSPE is 0.15M NaCl, 10 mM NaH$_2$PO$_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m(° C.)=2(\# \text{ of A+T bases})+4(\# \text{ of G+C bases})$. For hybrids between 18 and 49 base pairs in length, $T_m(° C.)=81.5+16.6(\log_{10}[\text{Na}^+])+0.41(\% \text{ G+C})-(600/N)$, where N is the number of bases in the hybrid, and [Na$^+$] is the concentration of sodium ions in the hybridization buffer ([Na$^+$] for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25–0.5M NaH$_2$PO$_4$, 7% SDS at about 65° C., followed by one or more washes at 0.02M NaH$_2$PO$_4$, 1% SDS at 65° C. (see e.g., Church and Gilbert (1984) *Proc. Natl. Acacl. Sci. USA* 81:1991–1995), or alternatively 0.2×SSC, 1% SDS.

Preferably, an isolated nucleic acid molecule of the invention that hybridizes under stringent conditions to the sequence of SEQ ID NO:7 or 9 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the MTR-3 sequences that may exist in the population, the skilled artisan will further appreciate that changes can be introduced by mutation into the nucleotide sequences of SEQ ID NO:7 or 9, thereby leading to changes in the amino acid sequence of the encoded MTR-3 proteins, without altering the functional ability of the MTR-3 proteins. For example, nucleotide substitutions leading to amino acid substitutions at "non-essential" amino acid residues can be made in the sequence of SEQ ID NO:7 or 9. A "non-essential" amino acid residue is a residue that can be altered from the wild-type sequence of MTR-3 (e.g., the sequence of SEQ ID NO:8) without altering the biological activity, whereas an "essential" amino acid residue is required for biological activity. For example, amino acid residues that are conserved among the MTR-3 proteins of the present invention, e.g., those present in a VLD binding domain or a methyltransferase domain, are predicted to be particularly unamenable to alteration. Furthermore, additional amino acid residues that are conserved between the MTR-3 proteins of the present invention and other members of the methyltransferase family are not likely to be amenable to alteration.

Accordingly, another aspect of the invention pertains to nucleic acid molecules encoding MTR-3 proteins that contain changes in amino acid residues that are not essential for activity. Such MTR-3 proteins differ in amino acid sequence from SEQ ID NO:8, yet retain biological activity. In one embodiment, the isolated nucleic acid molecule comprises a nucleotide sequence encoding a protein, wherein the protein comprises an amino acid sequence at least about 50%, 55%, 60%, 65%, 70%, 75%, 80%, 85%, 90%, 91%, 92%, 93%, 94%, 95%, 96%, 97%, 98% 99% or more identical to SEQ ID NO:8, e.g., to the entire length of SEQ ID NO:8.

An isolated nucleic acid molecule encoding an MTR-3 protein homologous to the protein of SEQ ID NO:8 can be created by introducing one or more nucleotide substitutions, additions or deletions into the nucleotide sequence of SEQ ID NO:7 or 9, such that one or more amino acid substitutions, additions or deletions are introduced into the encoded protein. Mutations can be introduced into SEQ ID NO:7 or 9, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in an MTR-3 protein is preferably replaced with another amino acid residue from the same side chain family. Alternatively, in another embodiment, mutations can be introduced randomly along all or part of an MTR-3 coding sequence, such as by saturation mutagenesis, and the resultant mutants can be screened for MTR-3 biological activity to identify mutants that retain activity. Following mutagenesis of SEQ ID NO:7 or 9, the encoded protein can be expressed recombinantly and the activity of the protein can be determined.

In a preferred embodiment, a mutant MTR-3 protein can be assayed for the ability to (i) modulate transcriptional activation (e.g., either directly or indirectly); (ii) modulate (directly or indirectly) chromatin structure to, for example, regulate the recruitment of an RNA polymerase II transcription initiation complex to a gene promoter; (iii) modulate the methylation state of proteins in the transcription machinery; (iv) interact with an MTR-3 substrate or target molecule (e.g., a non-MTR-3 protein); (v) convert an MTR-3 substrate or target molecule to a product (e.g., transfer of a methyl group to or from the substrate or target molecule); (vi) interact with and/or methyl transfer to a second non-MTR-3 protein; (vii) transfer a methyl group to an arginine residue; (viii) modulate protein-protein interaction (e.g., MTR-3-MTR-3 and/or MTR-3-non-MTR-3 interaction); (ix) modulate and/or coordination of protein complex formation (e.g., MTR-3-containing complex formation); (x) regulate substrate or target molecule activity; (xi) modulate intra- or inter-cellular signaling, (xii) modulate cellular targeting and/or transport of proteins; and/or (xiii) modulate cellular proliferation, growth, or differentiation.

In addition to the nucleic acid molecules encoding MTR-3 proteins described above, another aspect of the invention pertains to isolated nucleic acid molecules which are antisense thereto. In an exemplary embodiment, the invention provides an isolated nucleic acid molecule which is antisense to an MTR-3 nucleic acid molecule (e.g., is antisense to the coding strand of an MTR-3 nucleic acid molecule). An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire MTR-3 coding strand, or to only a portion thereof. In one embodiment, an antisense nucleic acid molecule is antisense to "coding region sequences" of the coding strand of a nucleotide sequence encoding MTR-3. The term "coding region sequences" refers to the region of the nucleotide sequence comprising codons which are translated into amino acid residues (e.g., the coding region sequences of human MTR-3 corresponding to SEQ ID NO:9). In another embodiment, the antisense nucleic acid molecule is antisense to a "noncoding region" of the coding strand of a nucleotide sequence encoding MTR-3. The term "noncoding region" refers to 5' and/or 3' sequences which flank the coding region sequences that are not translated into amino acids (also referred to as 5' and 3' untranslated regions).

Given the coding strand sequences encoding MTR-3 disclosed herein (e.g., SEQ ID NO:9), antisense nucleic acids of the invention can be designed according to the rules of Watson and Crick base pairing. The antisense nucleic acid molecule can be complementary to coding region sequences of MTR-3 mRNA, but more preferably is an oligonucleotide which is antisense to only a portion of the MTR-3 mRNA. An antisense oligonucleotide can be, for example, about 5, 10, 15, 20, 25, 30, 35, 40, 45, 50, 55, 60, 65, 70, 75, 80, or more nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In yet another embodiment, the antisense nucleic acid molecule of the invention is an $\alpha$-anomeric nucleic acid molecule or a ribozyme as described above in section 3.

Alternatively, MTR-3 gene expression can be inhibited by targeting nucleotide sequences complementary to the regulatory region of the MTR-3 (e.g., the MTR-3 promoter and/or enhancers; e.g., nucleotides 1–347 of SEQ ID NO:7) to form triple helical structures that prevent transcription of the MTR-3 gene in target cells. See generally, Helene, C. (1991) *Anticancer Drug Des*. 6(6):569–84; Helene, C. et al. (1992) *Ann. N.Y. Acad. Sci*. 660:27–36; and Maher, L. J. (1992) *Bioassays* 14(12):807–15.

In yet another embodiment, the MTR-3 nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup, B. and Nielsen, P. E. (1996) *Bioorg. Med. Chem*. 4(1):5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup and Nielsen (1996) supra and Perry-O'Keefe et al. (1996) *Proc. Natl. Acad. Sci. USA* 93:14670–675.

PNAs of MTR-3 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of MTR-3 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup and Nielsen (1996) supra)); or as probes or primers for DNA sequencing or hybridization (Hyrup and Nielsen (1996) supra; Perry-O'Keefe et al. (1996) supra).

In another embodiment, PNAs of MTR-3 can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of MTR-3 nucleic acid molecules can be generated which may combine the advantageous properties of PNA and DNA. Such chimeras allow DNA recognition enzymes (e.g., RNase H and DNA polymerases) to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup and Nielsen (1996) supra). The synthesis of PNA-DNA chimeras can be performed as described in Hyrup and Nielsen (1996) supra and Finn, P. J. et al. (1996) *Nucleic Acids Res.* 24(17):3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res.* 17:5973–88). PNA monomers are then coupled in a stepwise manner to produce a chimeric molecule with a 5' PNA segment and a 3' DNA segment (Finn, P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5:1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958–976) or intercalating agents (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

Isolated MTR-3 Proteins and Anti-MTR-3 Antibodies

One aspect of the invention pertains to isolated or recombinant MTR-3 proteins and polypeptides, and biologically active portions thereof, as well as polypeptide fragments suitable for use as immunogens to raise anti-MTR-3 antibodies. In one embodiment, native MTR-3 proteins can be isolated from cells or tissue sources by an appropriate purification scheme using standard protein purification techniques. In another embodiment, MTR-3 proteins are produced by recombinant DNA techniques. Alternative to recombinant expression, an MTR-3 protein or polypeptide can be synthesized chemically using standard peptide synthesis techniques.

An "isolated" or "purified" protein or biologically active portion thereof is substantially free of cellular material or other contaminating proteins from the cell or tissue source from which the MTR-3 protein is derived, or substantially free from chemical precursors or other chemicals when chemically synthesized. The language "substantially free of cellular material" includes preparations of MTR-3 protein in which the protein is separated from cellular components of the cells from which it is isolated or recombinantly produced. In one embodiment, the language "substantially free of cellular material" includes preparations of MTR-3 protein having less than about 30% (by dry weight) of non-MTR-3 protein (also referred to herein as a "contaminating protein"), more preferably less than about 20% of non-MTR-3 protein, still more preferably less than about 10% of non-MTR-3 protein, and most preferably less than about 5% non-MTR-3 protein. When the MTR-3 protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of MTR-3 protein in which the protein is separated from chemical precursors or other chemicals which are involved in the synthesis of the protein. In one embodiment, the language "substantially free of chemical precursors or other chemicals" includes preparations of MTR-3 protein having less than about 30% (by dry weight) of chemical precursors or non-MTR-3 chemicals, more preferably less than about 20% chemical precursors or non-MTR-3 chemicals, still more preferably less than about 10% chemical precursors or non-MTR-3 chemicals, and most preferably less than about 5% chemical precursors or non-MTR-3 chemicals.

As used herein, a "biologically active portion" of an MTR-3 protein includes a fragment of an MTR-3 protein which participates in an interaction between an MTR-3 molecule and a non-MTR-3 molecule (e.g., an MTR-3 substrate). Biologically active portions of an MTR-3 protein include peptides comprising amino acid sequences sufficiently identical to or derived from the MTR-3 amino acid sequences, e.g., the amino acid sequences shown in SEQ ID NO:8, which include sufficient amino acid residues to exhibit at least one activity of an MTR-3 protein. Typically, biologically active portions comprise a domain or motif with at least one activity of the MTR-3 protein, e.g., MTR-3 activity, methyltransferase activity, modulation of protein transport, modulation of intra- or inter-cellular signaling, modulation of transcriptional activation, and/or modulation of cell growth, proliferation, and/or differentiation mechanisms. A biologically active portion of an MTR-3 protein can be a polypeptide which is, for example, 10, 25, 50, 75, 100, 125, 150, 175, 200, 250, 300, 350, 400, 450, 500, 550, 600 or more amino acids in length. Biologically active portions of an MTR-3 protein can be used as targets for developing agents which modulate an MTR-3 mediated activity, e.g., methyltransferase activity, modulation of protein transport, modulation of intra- or inter-cellular signaling, modulation of transcriptional activation, and/or modulation of cell growth, proliferation, and/or differentiation mechanisms.

In one embodiment, a biologically active portion of an MTR-3 protein comprises at least one MTR-3 domain, one VLD binding domain, and/or one transmembrane domain. Moreover, other biologically active portions, in which other regions of the protein are deleted, can be prepared by recombinant techniques and evaluated for one or more of the functional activities of a native MTR-3 protein.

Another aspect of the invention features fragments of the protein having the amino acid sequence of SEQ ID NO:8, for example, for use as immunogens. In one embodiment, a fragment comprises at least 5 amino acids (e.g., contiguous or consecutive amino acids) of the amino acid sequence of SEQ ID NO:8. In another embodiment, a fragment comprises at least 8, 10, 15, 20, 25, 30, 35, 40, 45, 50 or more amino acids (e.g., contiguous or consecutive amino acids) of the amino acid sequence of SEQ ID NO:8.

In a preferred embodiment, an MTR-3 protein has an amino acid sequence shown in SEQ ID NO:8. In other embodiments, the MTR-3 protein is substantially identical to SEQ ID NO:8, and retains the functional activity of the protein of SEQ ID NO:8, yet differs in amino acid sequence due to natural allelic variation or mutagenesis, as described in detail in subsection I above. In another embodiment, the MTR-3 protein is a protein which comprises an amino acid sequence at least about 50%, 55%, 60%, 65%, 70%, 75%, 80%, 85%, 90%, 91%, 92%, 93%, 94%, 95%, 96%, 97%, 98%, 99% or more identical to SEQ ID NO:8.

In another embodiment, the invention features an MTR-3 protein which is encoded by a nucleic acid molecule consisting of a nucleotide sequence at least about 50%, 55%, 60%, 65%, 70%, 75%, 80%, 85%, 90%, 91%, 92%, 93%, 94%, 95%, 96%, 97%, 98%, 99% or more identical to a nucleotide sequence of SEQ ID NO:7 or 9, or a complement thereof. This invention further features an MTR-3 protein which is encoded by a nucleic acid molecule consisting of a nucleotide sequence which hybridizes under stringent hybridization conditions to a complement of a nucleic acid molecule comprising the nucleotide sequence of SEQ ID NO:7 or 9, or a complement thereof.

To determine the percent identity of two amino acid sequences or of two nucleic acid sequences, the sequences are aligned for optimal comparison purposes (e.g., gaps can he introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the MTR-3 amino acid sequence of SEQ ID NO:8 having 608 amino acid residues, at least 182, preferably at least 243, more preferably at least 304, even more preferably at least 364, and even more preferably at least 425, 486, or 547 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444–453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A preferred, non-limiting example of parameters to be used in conjunction with the GAP program include a Blosum 62 scoring matrix with a gap penalty of 12, a gap extend penalty of 4, and a frameshift gap penalty of 5.

In another embodiment, the percent identity between two amino acid or nucleotide sequences is determined using the algorithm of Meyers and Miller (*Comput. Appl. Biosci.*, 4:11–17 (1988)) which has been incorporated into the ALIGN program (version 2.0 or version 2.0U), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul et al. (1990) *J. Mol. Biol.* 215:403–10. BLAST nucleotide searches can be performed with the NBLAST program, score=100, wordlength=12 to obtain nucleotide sequences homologous to MTR-3 nucleic acid molecules of the invention. BLAST protein searches can be performed with the XBLAST program, score=50, wordlength=3 to obtain amino acid sequences homologous to MTR-3 protein molecules of the invention. To obtain gapped alignments for comparison purposes, Gapped BLAST can be utilized as described in Altschul et al. (1997) *Nucleic Acids Res.* 25(17):3389–3402. When utilizing BLAST and Gapped BLAST programs, the default parameters of the respective programs (e.g., XBLAST and NBLAST) can be used.

The invention also provides MTR-3 chimeric or fusion proteins. As used herein, an MTR-3 "chimeric protein" or "fusion protein" comprises an MTR-3 polypeptide operatively linked to a non-MTR-3 polypeptide. A "MTR-3 polypeptide" refers to a polypeptide having an amino acid sequence corresponding to MTR-3, whereas a "non-MTR-3 polypeptide" refers to a polypeptide having an amino acid sequence corresponding to a protein which is not substantially homologous to the MTR-3 protein, e.g., a protein which is different from the MTR-3 protein and which is derived from the same or a different organism. Within an MTR-3 fusion protein the MTR-3 polypeptide can correspond to all or a portion of an MTR-3 protein. In a preferred embodiment, an MTR-3 fusion protein comprises at least one biologically active portion of an MTR-3 protein. In another preferred embodiment, an MTR-3 fusion protein comprises at least two biologically active portions of an MTR-3 protein. Within the fusion protein, the term "operatively linked" is intended to indicate that the MTR-3 polypeptide and the non-MTR-3 polypeptide are fused in-frame to each other. The non-MTR-3 polypeptide can be fused to the N-terminus or C-terminus of the MTR-3 polypeptide.

For example, in one embodiment, the fusion protein is a GST-MTR-3 fusion protein in which the MTR-3 sequences are fused to the C-terminus of the GST sequences. Such fusion proteins can facilitate the purification of recombinant MTR-3. In another embodiment, the fusion protein is an MTR-3 protein containing a heterologous signal sequence at its N-terminus. In certain host cells (e.g., mammalian host cells), expression and/or secretion of MTR-3 can be increased through use of a heterologous signal sequence.

The MTR-3 fusion proteins of the invention can be incorporated into pharmaceutical compositions and administered to a subject in viva. The MTR-3 fusion proteins can be used to affect the bioavailability of an MTR-3 substrate. Use of MTR-3 fusion proteins may be useful therapeutically for the treatment of disorders caused by, for example, (i) aberrant modification or mutation of a gene encoding an MTR-3 protein; (ii) mis-regulation of the MTR-3 gene; and (iii) aberrant post-translational modification of an MTR-3 protein.

Moreover, the MTR-3-fusion proteins of the invention can be used as immunogens to produce anti-MTR-3 antibodies in a subject, to purify MTR-3 substrates, and in screening assays to identify molecules which inhibit or enhance the interaction of MTR-3 with an MTR-3 substrate.

Preferably, an MTR-3 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). An MTR-3-encoding nucleic acid can be cloned into such an expression vector such that the fusion moiety is linked in-frame to the MTR-3 protein.

The present invention also pertains to variants of the MTR-3 proteins which function as either MTR-3 agonists (mimetics) or as MTR-3 antagonists. Variants of the MTR-3 proteins can be generated by mutagenesis, e.g., discrete point mutation or truncation of an MTR-3 protein. An agonist of the MTR-3 proteins can retain substantially the same, or a subset, of the biological activities of the naturally occurring form of an MTR-3 protein. An antagonist of an MTR-3 protein can inhibit one or more of the activities of the naturally occurring form of the MTR-3 protein by, for example, competitively modulating an MTR-3-mediated activity of an MTR-3 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the MTR-3 protein.

In one embodiment, variants of an MTR-3 protein which function as either MTR-3 agonists (mimetics) or as MTR-3 antagonists can be identified by screening combinatorial libraries of mutants, e.g., truncation mutants, of an MTR-3 protein for MTR-3 protein agonist or antagonist activity. In one embodiment, a variegated library of MTR-3 variants is generated by combinatorial mutagenesis at the nucleic acid level and is encoded by a variegated gene library. A variegated library of MTR-3 variants can be produced by, for example, enzymatically ligating a mixture of synthetic oligonucleotides into gene sequences such that a degenerate set of potential MTR-3 sequences is expressible as individual polypeptides, or alternatively, as a set of larger fusion proteins (e.g., for phage display) containing the set of MTR-3 sequences therein. There are a variety of methods which can be used to produce libraries of potential MTR-3 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential MTR-3 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of an MTR-3 protein coding sequence can be used to generate a variegated population of MTR-3 fragments for screening and subsequent selection of variants of an MTR-3 protein. In one embodiment, a library of coding sequence fragments can be generated by treating a double stranded PCR fragment of an MTR-3 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the MTR-3 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of MTR-3 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify MTR-3 variants (Arkin and Youvan (1992) *Proc. Natl. Acad. Sci. USA* 89:7811–7815; Delagrave et al. (1993) *Protein Engineering* 6(3):327–331).

In one embodiment, cell based assays can be exploited to analyze a variegated MTR-3 library. For example, a library of expression vectors can be transfected into a cell line which ordinarily responds to MTR-3 in a particular MTR-3 substrate-dependent manner. The transfected cells are then contacted with MTR-3 and the effect of the expression of the mutant on signaling by the MTR-3 substrate can be detected, e.g., by measuring levels methylated amino acid residues in the substrate, gene transcription, and/or cell proliferation, growth or differentiation. Plasmid DNA can then be recovered from the cells which score for inhibition, or alternatively, potentiation of signaling by the MTR-3 substrate, or which score for increased or decreased levels of methylation of the substrate, and the individual clones further characterized.

An isolated MTR-3 protein, or a portion or fragment thereof, can be used as an immunogen to generate antibodies that bind MTR-3 using standard techniques for polyclonal and monoclonal antibody preparation. A full-length MTR-3 protein can be used or, alternatively, the invention provides antigenic peptide fragments of MTR-3 for use as immunogens. The antigenic peptide of MTR-3 comprises at least 8 amino acid residues of the amino acid sequence shown in SEQ ID NO:8 and encompasses an epitope of MTR-3 such that an antibody raised against the peptide forms a specific immune complex with MTR-3. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of MTR-3 that are located on the surface of the protein, e.g., hydrophilic regions, as well as regions with high antigenicity.

An MTR-3 immunogen typically is used to prepare antibodies by immunizing a suitable subject (e.g., rabbit, goat, mouse, or other mammal) with the immunogen. An appropriate immunogenic preparation can contain, for example, recombinantly expressed MTR-3 protein or a chemically-synthesized MTR-3 polypeptide. The preparation can further include an adjuvant, such as Freund's complete or incomplete adjuvant, or similar immunostimulatory agent. Immunization of a suitable subject with an immunogenic MTR-3 preparation induces a polyclonal anti-MTR-3 antibody response.

Accordingly, another aspect of the invention pertains to anti-MTR-3 antibodies. The term "antibody" as used herein refers to immunoglobulin molecules and immunologically active portions of immunoglobulin molecules, i.e., molecules that contain an antigen binding site which specifically binds (immunoreacts with) an antigen, such as MTR-3. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind MTR-3. The term "monoclonal antibody" or "monoclonal antibody composition", as used herein, refers to a population of antibody molecules that contain only one species of an antigen binding site capable of immunoreacting with a particular epitope of MTR-3. A monoclonal antibody composition thus typically displays a single binding affinity for a particular MTR-3 protein with which it immunoreacts.

Polyclonal anti-MTR-3 antibodies can be prepared as described above by immunizing a suitable subject with an MTR-3 immunogen. The anti-MTR-3 antibody titer in the immunized subject can be monitored over time by standard techniques, such as with an enzyme linked immunosorbent assay (ELISA) using immobilized MTR-3. If desired, the antibody molecules directed against MTR-3 can be isolated from the mammal (e.g., from the blood) and further purified by well known techniques, such as protein A chromatography to obtain the IgG fraction. At an appropriate time after immunization, e.g., when the anti-MTR-3 antibody titers are highest, antibody-producing cells can be obtained from the subject and used to prepare monoclonal antibodies by standard techniques, such as the hybridoma technique originally described by Kohler and Milstein (1975) *Nature* 256:495–497 (see also Brown et al. (1981) *J. Immunol.* 127:539–46; Brown et al. (1980) *J. Biol. Chem.* 255:4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol. Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally Kenneth, R. H. in *Monoclonal Antibodies: A New Dimension In Biological Analyses*, Plenum Publishing Corp., New York, N.Y. (1980); Lerner, E. A. (1981) *Yale J. Biol. Med.*, 54:387–402; Gefter, M. L. et al. (1977) *Somatic Cell Genet.* 3:231–36). Briefly, an immortal cell line (typically a myeloma) is fused to lymphocytes (typically splenocytes) from a mammal immunized with an MTR-3 immunogen as described above, and the culture supernatants of the resulting hybridoma cells are screened to identify a hybridoma producing a monoclonal antibody that binds MTR-3.

Any of the many well known protocols used for fusing lymphocytes and immortalized cell lines can be applied for the purpose of generating an anti-MTR-3 monoclonal antibody (see, e.g., Galfre, G. et al. (1977) *Nature* 266:55052; Gefter et al. *Somatic Cell Genet.*, supra; Lerner (1981) supra; Kenneth, *Monoclonal Antibodies*, supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind MTR-3, e.g., using a standard ELISA assay.

Alternative to preparing monoclonal antibody-secreting hybridomas, a monoclonal anti-MTR-3 antibody can be identified and isolated by screening a recombinant combinatorial immunoglobulin library (e.g., an antibody phage display library) with MTR-3 to thereby isolate immunoglobulin library members that bind MTR-3. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrad et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths etal. (1993) *EMBO J.* 12:725–734; Hawkins etal. (1992) *J. Mol. Biol.* 226:889–896; Clarkson et al. (1991) *Nature* 352:624–628; Gram et al. (1992) *Proc. Natl. Acad. Sci. USA* 89:3576–3580; Garrad et al. (1991) *Bio/Technology* 9:1373–1377; Hoogenboom et al. (1991) *Nuc. Acid Res*. 19:4133–4137; Barbas et al. (1991) *Proc. Natl. Acad. Sci. USA* 88:7978–7982; and McCafferty et al. (1990) *Nature* 348:552–554.

Additionally, recombinant anti-MTR-3 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol*. 139:3521–3526; Sun et al. (1987) *Proc. Natl. Acad. Sci. USA* 84:214–218; Nishimura et al. (1987) *Canc. Res*. 47:999–1005; Wood et al. (1985) *Nature* 314:446–449; and Shaw et al. (1988) *J. Natl. Cancer Inst*. 80:1553–1559); Morrison, S. L. (1985) *Science* 229:1202–1207; Oi et al. (1986) *BioTechniques* 4:214; Winter U.S. Pat. No. 5,225,539; Jones et al. (1986) *Nature* 321:552–525; Verhoeyan et al. (1988) *Science* 239:1534; and Beidler et al. (1988) *J. Immunol*. 141:4053–4060.

An anti-MTR-3 antibody (e.g., monoclonal antibody) can be used to isolate MTR-3 by standard techniques, such as affinity chromatography or immunoprecipitation. An anti-MTR-3 antibody can facilitate the purification of natural MTR-3 from cells and of recombinantly produced MTR-3 expressed in host cells. Moreover, an anti-MTR-3 antibody can be used to detect MTR-3 protein (e.g., in a cellular lysate or cell supernatant) in order to evaluate the abundance and pattern of expression of the MTR-3 protein. Anti-MTR-3 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

This invention is further illustrated by the following examples which should not be construed as limiting. The contents of all references, patents and published patent applications cited throughout this application, as well as the Sequence Listing, are incorporated herein by reference.

EXAMPLES

Example 1

Identification and Characterization of Human MTR-3 cDNA

In this example, the identification and characterization of the gene encoding human MTR-3 (clone Fbh27420) also referred to herein as "27420" is described.

Isolation of the MTR-3 cDNA

The invention is based, at least in part, on the discovery of a human gene encoding a novel protein, referred to herein as MTR-3. The entire sequence of human clone Fbh27420 was determined and found to contain an open reading frame termed human "MTR-3". The amino acid sequence of the human MTR-3 expression product is described herein. The MTR-3 protein sequence set forth in SEQ ID NO:8 comprises about 608 amino acids. The coding region (open reading frame) of SEQ ID NO:7 is set forth as SEQ ID NO:9.

Analysis of the Human MTR-3 Molecule

A BLASTN 2.0 search against the PATENT_2 nucleotide database, using a score of 100 and a word length of 12 (Altschul et al. (1990) *J. Mol. Biol*. 215:403) and of the nucleotide sequence of human MTR-3 as a query sequence revealed a number of nucleotides with some similarity to that of the invention, including a human transferase (PCT Publication No. 00/00594) with 99% identity over nucleotides 1399–2520 of SEQ ID NO:7, 99% identity over nucleotides 396–1401 of SEQ ID NO:7, and 100% identity over nucleotides 302–388 of SEQ ID NO:7.

A BLASTX 2.0 search against the PATENT_2/gsprot protein database, using a wordlength of 3, a score of 100, and a BLOSUM62 matrix, and using the amino acid sequence of human MTR-3 as a query sequence, identified a number of proteins with some similarity to human MTR-3 protein. For example, a human transferase (PCT Publication No. 00/00594) is 99% identical to human MTR-3 over amino acid residues 162–608 of SEQ ID NO:8.

The amino acid sequence of human MTR-3 was analyzed using the program PSORT to predict the localization of the protein within the cell. This program assesses the presence of different targeting and localization amino acid sequences within the query sequence. The results of the analysis predict that human MTR-3 (SEQ ID NO:8) is localized to the cytoplasm, mitochondria, and nucleus).

A search of the amino acid sequence of MTR-3 was performed against the HMM database. This search resulted in the identification of a potential "cellulose binding domain" in the amino acid sequence of MTR-3 (SEQ ID NO:8) at about residues 563–585 (score=5.0).

A MEMSAT analysis of the polypeptide sequence of SEQ ID NO:8 was also performed predicting four potential transmembrane domains in the amino acid sequence of human MTR-3 (SEQ ID NO:8) at about residues 18–41 (score=0.4), 97–113 (score=1.1), 187–203 (score=2.0), and 382–404 (score=2.7).

A search of the amino acid sequence of MTR-3 was also performed against the ProSite database. This search resulted in the identification in the amino acid sequence of human MTR-3 of a number of potential N-glycosylation sites at about residues 179–182, 230–233, 504–507, and 545–548, a potential glycosaminoglycan attachment site at about residues 569–572, a potential cAMP- and cGMP-dependent protein kinase phosphorylation site at about residues 444–447, a number of potential protein kinase C phosphorylation sites at about residues 126–128, 138–140, 232–234, and 352–254, a number of potential casein kinase II phosphorylation sites at about residues 39–42, 73–76, 113–116, 246–249, 288–291, 491–494, and 516–519 and a number of potential N-myristoylation sites at about residues 11–16, 22–27, 192–197, 320–325, 382–387, 397–402, 460–465, 486–491, 500–505, 508–513, 527–532, 552–557, 558–563, 565–570, and 571–576.

A search of the amino acid sequence of human MTR-3 was also performed against the ProDom database. The search resulted in the identification of a potential "arginine N-methyltransferase domain" in the amino acid sequence of MTR-3 at about residues 292–460.

Tissue Distribution of Human MTR-3 mRNA by RT-PCR

RT-PCR was used to detect the presence of MTR-3 mRNA in various tumor and metastatic tissue samples as compared to normal tissue samples. RT-PCR was also used to detect the presence of MTR-3 mRNA in various xenograft cell lines. In breast tissue, MTR-3 mRNA was detected in 1/1 normal tissue samples as compared to 4/4 tumor clinical samples after 30 cycles of PCR. In xenograft cell lines isolated from breast tissue, MTR-3 mRNA was detected in 1/1 normal and 5/5 xenograft cell lines. Positive breast cell lines were: ZR-75, T47D, MCF-7, MDA-MB-435, and MDA-MB-231.

In colon tissue, MTR-3 mRNA was detected in 2/2 normal tissue samples as compared to 5/5 tumor tissue samples after 30 cycles of PCR. Positive colon cell lines were: HCT116, HCT15, HT29, SW620, DLD1, KM12, and SW 480. In liver tissue, MTR-3 mRNA was detected in 2/2 normal samples and in 5/5 colon metastases to the liver after 30 cycles of PCR.

Tissue Distribution of Human MTR-3 mRNA by Northern Analysis

This example describes the tissue distribution of MTR-3 mRNA, as determined by Northern analysis.

Northern blot hybridizations with the various RNA samples are performed under standard conditions and washed under stringent conditions, i.e., 0.2×SSC at 65° C. The DNA probe is radioactively labeled with $^{32}$P-dCTP using the Prime-It kit (Stratagene, La Jolla, Calif.) according to the instructions of the supplier. Filters containing human mRNA (MultiTissue Northern I and MultiTissue Northern II from Clontech, Palo Alto, Calif.) are probed in ExpressHyb hybridization solution (Clontech) and washed at high stringency according to manufacturer's recommendations.

Electronic Northern analysis was carried out by identification of the MTR-3 sequence in various libraries using BLAST. Electronic Northern analysis indicated expression in many tissues, including lung, heart, kidney, t-cells, and placenta.

Tissue Distribution of MTR-3 by In situ Analysis

For in situ analysis, various tissues, e.g., tissues obtained from normal colon, colon tumors, and colon metastases to the liver were first frozen on dry ice. Ten-micrometer-thick sections of the tissues were post-fixed with 4% formaldehyde in DEPC treated 1× phosphate-buffered saline at room temperature for 10 minutes before being rinsed twice in DEPC 1× phosphate-buffered saline and once in 0.1 M triethanolamine-HCl (pH 8.0). Following incubation in 0.25% acetic anhydride-0.1 M triethanolamine-HCl for 10 minutes, sections were rinsed in DEPC 2×SSC (1×SSC is 0.15M NaCl plus 0.015M sodium citrate). Tissue was then dehydrated through a series of ethanol washes, incubated in 100% chloroform for 5 minutes, and then rinsed in 100% ethanol for 1 minute and 95% ethanol for 1 minute and allowed to air dry.

Hybridizations were performed with $^{35}$S-radiolabeled ($5\times10^7$ cpm/ml) cRNA probes. Probes were incubated in the presence of a solution containing 600 mM NaCl, 10 mM Tris (pH 7.5), 1 mM EDTA, 0.01% sheared salmon sperm DNA, 0.01% yeast tRNA, 0.05% yeast total RNA type X1, 1× Denhardt's solution, 50% formamide, 10% dextran sulfate, 100 mM dithiothreitol, 0.1% sodium dodecyl sulfate (SDS), and 0.1% sodium thiosulfate for 18 hours at 55° C.

After hybridization, slides were washed with 2×SSC. Sections were then sequentially incubated at 37° C. in TNE (a solution containing 10 mM Tris-HCl (pH 7.6), 500 mM NaCl, and 1 mM EDTA), for 10 minutes, in TNE with 10 μg of RNase A per ml for 30 minutes, and finally in TNE for 10 minutes. Slides were then rinsed with 2×SSC at room temperature, washed with 2×SSC at 50° C. for 1 hour, washed with 0.2×SSC at 55° C. for 1 hour, and 0.2×SSC at 60° C. for 1 hour. Sections were then dehydrated rapidly through serial ethanol-0.3 M sodium acetate concentrations before being air dried and exposed to Kodak Biomax MR scientific imaging film for 24 hours and subsequently dipped in NB-2 photoemulsion and exposed at 4° C. for 7 days before being developed and counter stained.

In situ hybridization results indicated expression in 0/2 normal colon cells, in 3/3 colon tumor cells, and in 2/2 colon metastases to the liver. Results further indicated negative expression in normal or tumor cells from breast tissue and normal or tumor cells from liver tissue.

Tissue Expression Analysis of MTR-3 mRNA Using Taqman Analysis

This example describes the tissue distribution of human MTR-3 mRNA in a variety of cells and tissues, as determined using the TaqMan™ procedure. The Taqman™ procedure is a quantitative, reverse transcription PCR-based approach for detecting mRNA. The RT-PCR reaction exploits the 5' nuclease activity of AmpliTaq Gold™ DNA Polymerase to cleave a TaqMan™ probe during PCR. Briefly, cDNA was generated from the samples of interest, e.g., lung tumor samples, normal lung samples, colon tumor samples, and normal colon samples, and used as the starting material for PCR amplification. In addition to the 5' and 3' gene-specific primers, a gene-specific oligonucleotide probe (complementary to the region being amplified) was included in the reaction (i.e., the Taqman™ probe). The TaqMan™ probe includes the oligonucleotide with a fluorescent reporter dye covalently linked to the 5' end of the probe (such as FAM (6-carboxyfluorescein), TET (6-carboxy-4,7, 2',7'-tetrachlorofluorescein), JOE (6-carboxy-4,5-dichloro-2,7-dimethoxyfluorescein), or VIC) and a quencher dye (TAMRA (6-carboxy-N,N,N',N'-tetramethylrhodamine) at the 3' end of the probe.

During the PCR reaction, cleavage of the probe separates the reporter dye and the quencher dye, resulting in increased fluorescence of the reporter. Accumulation of PCR products is detected directly by monitoring the increase in fluorescence of the reporter dye. When the probe is intact, the proximity of the reporter dye to the quencher dye results in suppression of the reporter fluorescence. During PCR, if the target of interest is present, the probe specifically anneals between the forward and reverse primer sites. The 5'-3' nucleolytic activity of the AmpliTaq™ Gold DNA Polymerase cleaves the probe between the reporter and the quencher only if the probe hybridizes to the target. The probe fragments are then displaced from the target, and polymerization of the strand continues. The 3' end of the probe is blocked to prevent extension of the probe during PCR. This process occurs in every cycle and does not interfere with the exponential accumulation of product. RNA was prepared using the trizol method and treated with DNase to remove contaminating genomic DNA. cDNA was synthesized using standard techniques. Mock cDNA synthesis in the absence of reverse transcriptase resulted in samples with no detectable PCR amplification of the control gene confirms efficient removal of genomic DNA contamination.

A human normal tissue panel indicated broad distribution of human MTR-3 expression, with highest expression in testis. Increased expression of human MTR-3 was detected in colon tumor samples (T) versus normal colon tissue samples (N). Increased expression of human MTR-3 was detected in colon metastases to the liver (Liver Met) versus normal liver tissue samples (N). Overexpression in breast and lung tumors versus respective normal tissue samples was also detected.

These data reveal a significant up-regulation of MTR-3 mRNA in carcinomas, colon carcinomas in particular. Given that the mRNA for MTR-3 is expressed in a variety of tumors, with significant up-regulation in carcinoma samples in comparison to normal samples, it is believed that inhibition of MTR-3 activity may inhibit tumor progression by, for example, inhibiting transcriptional activation and cellular growth and proliferation.

Example 2

Expression of Recombinant MTR-3 Protein in Bacterial Cells

In this example, human MTR-3 is expressed as a recombinant glutathione-S-transferase (GST) fusion polypeptide in E. coli and the fusion polypeptide is isolated and characterized. Specifically, MTR-3 is fused to GST and this fusion polypeptide is expressed in E. coli, e.g., strain PEB199. Expression of the GST-MTR-3 fusion protein in PEB199 is induced with IPTG. The recombinant fusion polypeptide is purified from crude bacterial lysates of the induced PEB 199 strain by affinity chromatography on glutathione beads. Using polyacrylamide gel electrophoretic analysis of the polypeptide purified from the bacterial lysates, the molecular weight of the resultant fusion polypeptide is determined.

Example 3

Expression of Recombinant MTR-3 Protein in COS Cells

To express the human MTR-3 gene in COS cells, the pcDNA/Amp vector by Invitrogen Corporation (San Diego, Calif.) is used. This vector contains an SV40 origin of replication, an ampicillin resistance gene, an E. coli replication origin, a CMV promoter followed by a polylinker region, and an SV40 intron and polyadenylation site. A DNA fragment encoding the entire MTR-3 protein and an HA tag (Wilson et al. (1984) Cell 37:767) or a FLAG tag fused in-frame to its 3' end of the fragment is cloned into the polylinker region of the vector, thereby placing the expression of the recombinant protein under the control of the CMV promoter.

To construct the plasmid, the MTR-3 DNA sequence is amplified by PCR using two primers. The 5' primer contains the restriction site of interest followed by approximately twenty nucleotides of the MTR-3 coding sequence starting from the initiation codon; the 3' end sequence contains complementary sequences to the other restriction site of interest, a translation stop codon, the HA tag or FLAG tag and the last 20 nucleotides of the MTR-3 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the MTR-3 gene is inserted in the correct orientation. The ligation mixture is transformed into E. coli cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the MTR-3-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989. The expression of the MTR-3 polypeptide is detected by radiolabelling ($^{35}$S-methionine or $^{35}$S-cysteine available from NEN, Boston, Mass., can be used) and immunoprecipitation (Harlow, E. and Lane, D. Antibodies: A Laboratory Manual, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA-specific monoclonal antibody. Precipitated polypeptides are then analyzed by SDS-PAGE.

Alternatively, DNA containing the MTR-3 coding sequence is cloned directly into the polylinker of the pCDNA/Amp vector using the appropriate restriction sites. The resulting plasmid is transfected into COS cells in the manner described above, and the expression of the MTR-3 polypeptide is detected by radiolabelling and immunoprecipitation using an MTR-3 specific monoclonal antibody.

IV. METHOD OF TREATING BONE DISEASE USING 17906

BACKGROUND OF THE INVENTION

Carboxypeptidases

Proteolytic enzymes are involved in many cellular processes. The carboxypeptidase family of enzymes catalyzes the cleavage of C-tenninal amino acids of peptides and proteins, altering their biological activity. Lysosomal carboxypeptidase enzymes are highly concentrated in lysosomes, but may also be active extracellularly after their release from lysosomes in soluble form or bound to transmembrane or other membrane-associated proteins. Carboxypeptidases may cleave peptides in a sequence-specific manner. For example, prolylcarboxypeptidases cleave only peptides linked to proline residues (for example, des-Arg9-bradykinin, angiotensin II). There is also evidence that these enzymes are involved in terminating signal transduction by inactivating peptide ligands after receptor endocytosis.

In contrast to endoproteases which cleave internal peptide bonds of proteins and polypeptides, carboxypeptidases (CPs) catalyze the cleavage of only the C-terminal peptide bond, releasing one amino acid at a time. The two main groups of CPs include serine CPs and metallo-CPs, the serine CPs containing a signature trio of Ser, Asp, His in the active site. This trio is also contained in prolylendopeptidase serine proteases. Serine CPs include polycarboxypeptidase (PRCP) also referred to as angiotensinase C; and deamidase, also referred to as cathepsin A and lysosomal protective protein. See Skidgel et al. (1998) *Immunological Reviews* 161:129–141.

Metallo-CPs contain a signature glutamic acid as the primary catalytic residue and require zinc-binding for activity. Metallo-CPs can be grouped by substrate specificity into CPA and CPB types; the CPA type preferentially cleaving C-terminal hydrophobic residues, and the CPB type cleaving only peptides with C-terminal basic Arg or Lys residues. See R. A. Skidgel (1993) In: *Hooper N M, ed. Zinc Metalloproteases in Health and Disease*, London: Taylor & Francis, Ltd., p. 241–283.

CPM is a B type carboxypeptidase which is anchored on cell membranes via gylcosylphosphatidylinositol (GPI) association with its mildly hydrophobic stretch of 15 C-terminal amino acids. As in many other proteins sharing this anchoring mechanism, CPM is released from the membrane by bacterial phosphatidylinositol-specific phospholipase C. Human CPM is a glycoprotein of 426 amino acid residues with 43% identity to human intracellular secretory granular CP (CPE), 41% with the active 50 kDa subunit of human plasma CPN, and 15% with bovine pancreatic CPA or CPB. The active sites of these CPs contain conserved amino acid residues corresponding to the zinc binding residues $His^{66}Glu^{69}$ and $His^{173}$, substrate binding residues $Arg^{137}$ and $Tyr^{242}$, and the catalytic $Glu^{264}$, as designated for CPM. Sequence homologies around these conserved residues is high, with an identity between CPs M, E and N of approximately 70–90%. See Tan et al. (1989) *J. Biol. Chem.* 264:13165–13170; Deddish et al. (1990) *J. Biol. Chem.* 265:15083–15089; R. A. Skidgel (1993) In: *Hooper N M, ed. Zinc Metalloproteases in Health and Disease*, London: Taylor & Francis, Ltd., p. 241–283. CPM has been mapped to the chromosomal location of chromosome 12q13-q15 which is associated with a variety of solid tumors.

The optimal pH range of CPM is in the neutral range of 6.5–7.5. As no endogenous inhibitors are known for CPM, the enzyme is considered to be constitutively active. Synthetic inhibitors including Arg analogs DL-2 mercaptomethyl-3-guanidinoethylthiopropanoic acid (MGTA) and guanidinoethylmercaptosuccinic acid (GEMSA) inhibit CPM. See R. A. Skidgel (1991) In: *Conn P M, ed. Methods in Neurosciences: Peptide Technology Vol.* 6, Orlando: Academic Press, p. 373–385; Plummer et al. (1981) *Biochem. Biophys. Res. Comm.* 98: 448–254.

As with other B type regulatory CPs, CPM cleaves only C-terminal Arg or Lys residues; however, CPM has a preference for the C-terminal Arg. The penultimate amino acid also affects the rate of hydrolysis. Naturally occurring peptide substrates of CPM include bradykinin, $Arg^6$- and $Lys^6$ enkephalins, dynorphin $A^{1-13}$ and epidermal growth factor (EGF). See Sidgel et al. (1989) *J. Biol. Chem.* 264:2236–2241; McGwire et al. (1995) *J. Biol. Chem.* 270:17154–17158.

CPM is primarily found on the plasma membrane, with highest levels found in lung and placenta. It is also present in kidney, blood vessels, intestine, brain and peripheral nerves. See R. A. Skidgel (1988) *Trends Pharm. Sci.* 9:299–304; Skidgel et al. (1984) *Biochem. Pharmacol.* 33: 3471–3478; Skidgel et al. (1991) *FASEB J.* 5: 1578; Nagae et al. (1992) *J. Neurochem.* 59:2201–2212; Nagae et al. (1993) *Am. J. Respir. Cell Mol. Biol.* 9:221–229. Expression of CPM is responsive to differentiation of monocytes and lymphocytes. See de Saint-Vis et al. (1995) *Blood* 86:1098–1105; Rehli et al. (1995) *J. Biol. Chem.* 270: 15644–15649.

CPM participates in the control of peptide hormone activity at the cell surface and degradation of extracellular proteins and peptides. It catalyzes the second step in prohormone processing and removes C-terminal Arg or Lys residues from peptides released from prohormones. CPM functions as a soluble enzyme after its release from the plasma membrane and may function in the plasma membrane form to control peptide receptor activities. CPM can regulate receptor specificity of kinins by cleaving the C-terminal $ARG^9$, for example, from bradykinin. The intact bradykinin binds the B2 receptor. The cleaved bradykinin (des-$ARG^9$-bradykinin). Des-$ARG^9$-bradykinin also binds the B1 receptors: stimulates IL-1 and tumor necrosis factor release from macrophages. Regulation of the B1 receptor is associated with injury or inflammation. CPM may also be involved with other inflammatory mediators, such as anaphylatoxin C5a which mediates histamine release. In addition, CPM may metabolize growth factors containing terminal Arg or Lys, such as EGF, EGF-like peptides, nerve growth factor (NGF) amphiregulin, hepatocyte growth factor, erythropoietin, and macrophage-stimulating protein. In the lung, varying levels of CPM are associated with pneumocystic or bacterial pneumonia or lung cancer, and in the placenta, CPM may protect the fetus from maternally derived peptides. See R. A. Skidgel (1992) *J. Cardiovasc. Pharmacol.* 20 (Suppl. 9):S4–S9; Bhoola et al. (1992) *Pharmacol. Rev.* 44:1–80; R. A. Skidgel (1993) In: *Hooper N M, ed. Zinc Metalloproteases in Health and Disease*, London: Taylor & Francis, Ltd., p. 241–283; Dragovic et al. (1995) *Am. J. Respir. Crit. Care Med.* 152:760–764; Nagae et al. (1992) *J. Neurochem.* 59:2201–2212; MacFadden et al. (1988) *FASEB J.* 2:1179 (Abstract).

Another B-type regulatory CP metalloprotein is CPD, a membrane-bound glycoprotein. Human CPD is a protein of 1,377 amino acids with 75% identity with duck GP180 and 90% identity with rat CPD. Human CPD contains two hydrophobic regions located at the C- and N-termini. A 55–60 residue cytoplasmic domain is highly conserved among duck, human and rat sequences and may be significant in intracellular sorting, protein—protein interactions or endocytosis. CPD contains three tandem CP homology domains numbered sequentially from the N- to the C-terminus, and thereby may contain more than one active site. See Tan et al. (1997) *Biochem. J.* 327:81–87; Skidgel et al. (1993) In: Robertson J L S, Nicholls M G, eds. *The Renin Angiotensin System*, Vol. 1, London: Gower Medical Publishing, p. 10.1–10.10. CPD is located on human chromosome 17, 17P, 11.1–17q, 11.2.

CPD is primarily found on intracellular membranes, mainly in the Golgi, with some CPD found on the plasma membrane. The tissue distribution of CPD is wide and includes most duck tissues and mammalian tissues as well, including brain, pituitary, placenta, pancreas, adrenal, kidney, lung, heart, spleen, intestine, ovary, and testes. See McGwire et al. (1997) *Life Sci.* 60:715–724; Song et al. (1995) *J. Biol. Chem.* 270:25007–25013; Xin et al. (1997) *DNA Cell Biol.* 16:897–909; Tan et al. (1997) *Biochem. J.* 327:81–87; Song et al. (1996) *J. Biol. Chem.* 271:28884–28889.

The function of CPD is speculated to include peptide and protein processing in the constitutive secretory pathway after endoprotease cleavage of precursor proteins. The enzyme has an acidic pH optimum. Mammalian CPD may act as a hepatitis B virus binding protein, similar to the duck CPD. See R. A. Skidgel (1998) *Immunological Reviews* 161:129–141.

Serine CPs include PRCP and deamidase. PRCP cloned from a human kidney library indicates a glycoprotein of 51 kDa[3]; and containing 496 amino acids, including a 30 residue signal peptide and a 15 residue propeptide. See Tan et al. (1993) *J. Biol. Chem.* 268:16631–16638. A serine repeat is found in the C-terminal half, similar to the serine repeat of a yeast CP encoded by the KEX1 gene.

PRCP has an acidic pH optimum for synthetic peptide substrates, but retains activity at neutral ranges with longer naturally occurring peptides. PRCP cleaves peptides only if the penultimate residue is proline. The enzyme does not cleave Pro-Pro-COOH or (OH)-Pro-Pro-COOH bond. See Odya et al. (1978) *J. Biol. Chem.* 253:5927–5931. Substrates of PRCP include des-Arg$^9$-bradykinin and angiotensin II.

PRCP may be involved in terminating signal transduction by inactivating peptide ligands after receptor endocytosis. PRCP is contained in lysosomes and released in response to stimulation. The enzyme is widely distributed and found in human placenta, lung, liver, and kidney.

Another serine CP, deamidase, is likely a 94 kDa homodimer of 52 kDa subunits. Human platelet deamidase is activated by cleavage of a 14 amino acid fragment from the C-terminus. The enzyme binds and maintains activity and stability of β-galactocidase and neuraminidase in lysosomes, a defect of which is associated with severe galactosialidosis. See Bonten et al. (1995) *J. Biol. Chem.* 270: 26441–26445; Galjart et al. (1988) *Cell* 54:755–764; D'Azzo et al. (1982) *Proc. Natl. Acad. Sci.* 79:4535–4539. The gene for the human deamidase is mapped to chromosome 20 at q13.1.

Deamidase cleaves various peptides containing C-terminal or penultimate hydrophobic residues including substance P, angiotensin I, bradykinin, endothelin, and fMet-Leu-Phe. Like PRCP, deamidase is also found in lysosomes, and distributed in human placenta, lung, liver, and kidney. Like PRCP, deamidase is implicated in blocking part of the signal transduction pathway stimulated by peptides. Bradykinin, containing a C-terminal Arg$^9$ and a penultimate hydrophobic amino acid Phe$^8$, is cleaved by deamidase. Similarly, angiotensin, containing a C-terminal His and a penultimate Phe, is cleaved by deamidase. Accordingly, deamidase is implicated in termination of bradykinin activity on the B2 receptor to generate a B1 receptor agonist. Deamidase may also have a role in chemotaxis and in metabolism of the anticancer growth factor antagonist. See Skidgel et al. (1998) *Immunological Reviews* 161:129–141; Jackman etal. (1990) *J. Biol. Chem.* 265:11265–11272; Jackman et al. (1995) *Am. J. Respir. Cell Mol. Biol.* 13:196–204; Hinek et al. (1996) *Biol. Chem.* 377:471–480; Jones et al. (1995) *Peptides* 16:777–783; Cummings et al. (1995) *Biochem Pharmacol.* 49:1709–1712.

Given the wide distribution and various physiological and pathological roles of carboxypeptidases, methods and compositions directed at regulating levels of these enzymes are useful for regulating peptide hormone activity, modulating metabolism of substance P, angiotensin I, angiotensin II, bradykinin, and endothelin, and regulation of signal transduction by inactivation of peptide ligands subsequent to receptor endocytosis.

Accordingly, carboxypeptidases are a major target for drug action and development.

The carboxypeptidase gene used in the methods of the invention (GenBank Accession AF095719) was purported to be involved in the histone hyperacetylation signaling pathway relating to prostate cancer differentiation. (Huang H. et al. Cancer Res. (1999). "Carboxypeptidase A3 (CPA3): a novel gene highly induced by histone deacetylase inhibitors during differentiation of prostate epithelial cancer cells" 15;59(12):2981–8). It was suggested that the CPA3 gene is involved in the histone hyperacetylation signaling pathway activated during NaBu-mediated differentiation of the androgen-independent prostate cancer cell line, PC-3 cells.

Bone Disorders

Human bone is subject to constant breakdown and re-synthesis in a complex process mediated by two cell types: osteoblasts, which produce new bone, and osteoclasts, which destroy bone. The activities of these two cell types are kept under control and in proper balance by a complex network of cytokines, growth factors and other cellular signals. It is understood that a number of known bone disorders may have their genesis in aberrant control of these cells. Likewise, a considerable amount of medical research has focussed on identifying the aspects of this control network which can be exploited to re-generate bone in patients with bone diseases.

Osteoporosis is one of several known degenerative bone disorders which can cause significant risk and hardship to those affected. It is generally defined as the gradual decrease in bone strength and density that occurs with advancing age, particularly among post-menopausal women. The clinical manifestations of osteoporosis include fractures of the vertebral bodies, the neck, and intertrochanteric regions of the femur, and the distal radius. Osteoporotic individuals may fracture any bone more easily than their non-osteoporotic counterparts. As many as many as 15–20 million individuals in the United States are afflicted with osteoporosis. About 1.3 million fractures attributable to osteoporosis occur annually in people age 45 and older. Among those who live to be age 90, 32 percent of women and 17 percent of men will suffer a hip fracture, mostly due to osteoporosis.

In addition to osteoporosis, there is a plethora of other conditions which are characterized by the need to enhance bone formation. Perhaps the most obvious is in the case of bone fractures, where it would be desirable to stimulate bone growth and to hasten and complete bone repair. Agents that enhance bone formation would also be useful in certain surgical procedures (e.g., facial reconstruction). Other conditions which result in a deficit or abnormal formation of bone include osteogenesis imperfecta (brittle bone disease), hypophosphatasia, Paget's disease, fibrous dysplasia, osteopetrosis, myeloma bone disease, and the depletion of calcium in bone which is related to primary hyperparathyroidism.

There are currently no pharmaceutical approaches to managing any of these conditions that is completely satisfactory. Bone deterioration associated with osteoporosis and other bone conditions may be treated with estrogens or bisphosphonates, which have known side effects, or with further invasive surgical procedures. Bone fractures are still treated exclusively using casts, braces, anchoring devices and other strictly mechanical means. More recently, surgical approaches to these types of injury utilize bovine or human cadaver bone which is chemically treated (to remove proteins) in order to prevent rejection. However, such bone implants, while mechanically important, are biologically dead (they do not contain bone-forming cells, growth factors, or other regulatory proteins). Thus, they do not greatly modulate the repair process. All of these concerns demonstrate a great need for new or novel forms of bone therapy.

SUMMARY OF THE INVENTION

The present invention provides methods for the diagnosis and treatment of bone associated disease, including but not limited to, osteogenesis imperfecta (brittle bone disease), osteoporosis, Paget's disease (enlarged bones), fibrous dysplasia (uneven bone growth), hypophosphatasia, osteopetrosis, primary hyperthyroidism, or myeloma bone disease. The present invention is based, at least in part, on the discovery that the 17906 gene is down-regulated during osteoblast differentiation, and, thus, may be associated with a bone disorder.

In one aspect, the invention provides a method for identifying the presence of a nucleic acid molecule associated with a bone associated disorder in a sample by contacting a sample comprising nucleic acid molecules with a hybridization probe comprising at least 25 contiguous nucleotides of SEQ ID NO:10, and detecting the presence of a nucleic acid molecule associated with a bone associated disorder when the sample contains a nucleic acid molecule that hybridizes to the nucleic acid probe. In one embodiment, the hybridization probe is detectably labeled. In another embodiment the sample comprising nucleic acid molecules is subjected to agarose gel electrophoresis and southern blotting prior to contacting with the hybridization probe. In a further embodiment, the sample comprising nucleic acid molecules is subjected to agarose gel electrophoresis and northern blotting prior to contacting with the hybridization probe. In yet another embodiment, the detecting is by in situ hybridization. In other embodiments, the method is used to detect mRNA or genomic DNA in the sample.

The invention also provides a method for identifying a nucleic acid associated with a bone associated disorder in a sample, by contacting a sample comprising nucleic acid molecules with a first and a second amplification primer, the first primer comprising at least 25 contiguous nucleotides of SEQ ID NO:10 and the second primer comprising at least 25 contiguous nucleotides from the complement of SEQ ID NO:10, incubating the sample under conditions that allow for nucleic acid amplification, and detecting the presence of a nucleic acid molecule associated with a bone associated disorder when the sample contains a nucleic acid molecule that is amplified. In one embodiment, the sample comprising nucleic acid molecules is subjected to agarose gel electrophoresis after the incubation step.

In addition, the invention provides a method for identifying a polypeptide associated with a bone associated disorder in a sample by contacting a sample comprising polypeptide molecules with a binding substance specific for a 17906 polypeptide, and detecting the presence of a polypeptide associated with a bone associated disorder when the sample contains a polypeptide molecule that binds to the binding substance. In one embodiment the binding substance is an antibody. In another embodiment, the binding substance is a 17906 ligand. In a further embodiment, the binding substance is detectably labeled.

In another aspect, the invention provides a method of identifying a subject at risk for a bone associated disorder by contacting a sample obtained from the subject comprising nucleic acid molecules with a hybridization probe comprising at least 25 contiguous nucleotides of SEQ ID NO:10, and detecting the presence of a nucleic acid molecule which identifies a subject a risk for a bone associated disorder when the sample contains a nucleic acid molecule that hybridizes to the nucleic acid probe.

In a further aspect, the invention provides a method for identifying a subject at risk for a bone associated disorder by contacting a sample obtained from a subject comprising nucleic acid molecules with a first and a second amplification primer, the first primer comprising at least 25 contiguous nucleotides of SEQ ID NO:10 and the second primer comprising at least 25 contiguous nucleotides from the complement of SEQ ID NO:10, incubating the sample under conditions that allow for nucleic acid amplification, and detecting a nucleic acid molecule which identifies a subject at risk for a bone associated disorder when the sample contains a nucleic acid molecule that is amplified.

In yet another aspect, the invention provides a method of identifying a subject at risk for a bone associated disorder by contacting a sample obtained from the subject comprising polypeptide molecules with a binding substance specific for a 17906 polypeptide, and identifying a subject at risk for a bone associated disorder by detecting the presence of a polypeptide molecule in the sample that binds to the binding substance.

In another aspect, the invention provides a method for identifying a compound capable of treating a bone associated disorder characterized by aberrant 17906 nucleic acid expression or 17906 protein activity by assaying the ability of the compound to modulate the expression of a 17906 nucleic acid or the activity of a 17906 protein. In one embodiment, the disorder is osteoporosis. In a further embodiment, the ability of the compound to modulate the activity of the 17906 protein is determined by detecting the induction of an intracellular second messenger.

In addition, the invention provides a method for treating a subject having a bone associated disorder characterized by aberrant 17906 protein activity or aberrant 17906 nucleic acid expression by administering to the subject a 17906 modulator. In one embodiment, the 17906 modulator is administered in a pharmaceutically acceptable formulation. In another embodiment the 17906 modulator is administered using a gene therapy vector. In a further embodiment, the 17906 modulator is a small molecule.

In one embodiment, a modulator is capable of modulating 17906 polypeptide activity. In another embodiment, the 17906 modulator is an anti-17906 antibody. In a further embodiment, the 17906 modulator is a 17906 polypeptide comprising the amino acid sequence of SEQ ID NO:11, or a fragment thereof. In yet another embodiment, the 17906 modulator is a 17906 polypeptide comprising an amino acid sequence which is at least 90 percent identical to the amino acid sequence of SEQ ID NO:11, wherein the percent identity is calculated using the ALIGN program for comparing amino acid sequences, a PAM120 weight residue table, a gap length penalty of 12, and a gap penalty of 4. In a further embodiment, the 17906 modulator is an isolated naturally occurring allelic variant of a polypeptide consisting of the amino acid sequence of SEQ ID NO:11, wherein the polypeptide is encoded by a nucleic acid molecule which hybridizes to a complement of a nucleic acid molecule consisting of SEQ ID NO:10 at 6×SSC at 45° C., followed by one or more washes in 0.2×SSC, 0.1% SDS at 50–65° C.

In one embodiment, the 17906 modulator is capable of modulating 17906 nucleic acid expression. In another embodiment, the 17906 modulator is an antisense 17906 nucleic acid molecule. In yet another embodiment, the 17906 modulator is a ribozyme. In a further embodiment, the 17906 modulator comprises the nucleotide sequence of SEQ ID NO:10, or a fragment thereof. In another embodiment, the 17906 modulator comprises a nucleic acid molecule encoding a polypeptide comprising an amino acid sequence which is at least 90 percent identical to the amino acid sequence of SEQ ID NO:11, wherein the percent identity is calculated using the ALIGN program for comparing amino acid sequences, a PAM120 weight residue table, a gap length penalty of 12, and a gap penalty of 4. In yet another embodiment, the 17906 modulator comprises a nucleic acid molecule encoding a naturally occurring allelic variant of a polypeptide comprising the amino acid sequence of SEQ ID NO:11, wherein the nucleic acid molecule which hybridizes to a complement of a nucleic acid molecule consisting of SEQ ID NO:10 at 6×SSC at 45° C., followed by one or more washes in 0.2×SSC, 0.1% SDS at 50–65° C.

In another aspect, the invention provides a method for identifying a compound capable of modulating a osteocyte activity by contacting a osteocyte with a test compound and assaying the ability of the test compound to modulate the expression of a 17906 nucleic acid or the activity of a 17906 protein. In certain embodiments, a compound that modulates the expression of a 17906 nucleic acid or the activity of a 17906 protein modulates osteocyte proliferation, migration, or the expression of cell surface adhesion molecules.

Furthermore, the invention provides a method for modulating a osteocyte activity comprising contacting a osteocyte with a 17906 modulator.

Other features and advantages of the invention will be apparent from the following detailed description and claims.

DETAILED DESCRIPTION OF THE INVENTION

The present invention provides methods and compositions for the diagnosis and treatment of bone associated disease, including but not limited to, osteogenesis imperfecta (brittle bone disease), osteoporosis, Paget's disease (enlarged bones), fibrous dysplasia (uneven bone growth), hypophosphatasia, osteopetrosis, primary hyperthyroidism, or myeloma bone disease. The present invention is based, at least in part, on the discovery that carboxypepsidase genes, referred to herein as "carboxypepsidase 17906" or "17906" nucleic acid and protein molecules, are down-regulated during osteoblast differentiation, and, thus, may be associated with a bone disorder.

As used herein, "differential expression" includes both quantitative as well as qualitative differences in the temporal and/or tissue expression pattern of a gene. Thus, a differentially expressed gene may have its expression activated or inactivated in normal versus bone associated disease conditions. The degree to which expression differs in normal versus bone associated disease or control versus experimental states need only be large enough to be visualized via standard characterization techniques, e.g., quantitative PCR, Northern analysis, or subtractive hybridization. The expression pattern of a differentially expressed gene may be used as part of a prognostic or diagnostic bone associated disease evaluation, or may be used in methods for identifying compounds useful for the treatment of bone associated disease. In addition, a differentially expressed gene involved in bone associated disease may represent a target gene such that modulation of the level of target gene expression or of target gene product activity may act to ameliorate a bone associated disease condition. Compounds that modulate target gene expression or activity of the target gene product can be used in the treatment of bone associated disease. Although the 17906 genes described herein may be differentially expressed with respect to bone associated disease, and/or their products may interact with gene products important to bone associated disease, the genes may also be involved in mechanisms important to additional bone associated processes.

The 17906 molecules of the present invention may be involved in signal transduction and, thus, may that function to modulate cell proliferation, differentiation, and motility. Thus, the 17906 molecules of the present invention may play a role in cellular growth signaling mechanisms. As used herein, the term "cellular growth signaling mechanisms" includes signal transmission from cell receptors, e.g., G protein coupled receptors, which regulates 1) cell transversal through the cell cycle, 2) cell differentiation, 3) cell survival, and/or 4) cell migration and patterning.

Accordingly, the 17906 molecules of the present invention may be involved in cellular signal transduction pathways that modulate bone cell activity. As used herein, a "bone cell activity", "osteocyte activity", or "bone cell function" includes cell proliferation differentiation, migration, and expression of cell surface adhesion molecules, as well as cellular process that contribute to the physiological role of bone cells (e.g., the regulation of calcium secretion).

Thus, the 17906 molecules, by participating in cellular growth signaling mechanisms, may modulate cell behavior and act as targets and therapeutic agents for controlling cellular proliferation and differentiation of bone cells.

The 17906 molecules of the present invention may also act as novel diagnostic targets and therapeutic agents for bone associated diseases or disorders. As used herein, a "bone associated disease or disorder" includes a disease or disorder which affects bones. The term bone associated disorder includes a disorder affecting the normal function of the bones. For example, a bone associated disorder includes osteogenesis imperfecta (brittle bone disease), osteoporosis, Paget's disease (enlarged bones), fibrous dysplasia (uneven bone growth), hypophosphatasia, osteopetrosis, primary hyperthyroidism, or myeloma bone disease. bone associated disorders are described in, for example, Lamber et al. (2000) *Pharmacotherapy* 20:34–51; Eisman et al. (1999) *Endocrine Reviews* 20:788–804; Byers et al. (1992) *Annual Rev. Med.*, 43:269–282.

A bone associated disorder also includes a bone cell disorder. As used herein a "bone cell disorder" includes a disorder characterized by aberrant or unwanted bone cell activity, e.g., proliferation, migration, angiogenesis, or aberrant expression of cell surface adhesion molecules.

The present invention provides methods for identifying the presence of a 17906 nucleic acid or polypeptide molecule associated with a bone associated disorder. In addition, the invention provides methods for identifying a subject at risk for a bone associated disorder by detecting the presence of a 17906 nucleic acid or polypeptide molecule.

The invention also provides a method for identifying a compound capable of treating a bone associated disorder characterized by aberrant 17906 nucleic acid expression or 17906 protein activity by assaying the ability of the compound to modulate the expression of a 17906 nucleic acid or the activity of a 17906 protein. Furthermore, the invention provides a method for treating a subject having a bone associated disorder characterized by aberrant 17906 protein activity or aberrant 17906 nucleic acid expression by administering to the subject a 17906 modulator which is capable of modulating 17906 protein activity or 17906 nucleic acid expression.

Moreover, the invention provides a method for identifying a compound capable of modulating an bone cell activity by modulating the expression of a 17906 nucleic acid or the activity of a 17906 protein. The invention provides a method for modulating an bone cell activity comprising contacting an bone cell with a 17906 modulator.

Various aspects of the invention are described in further detail in the following subsections.

Screening Assays

The invention provides a method (also referred to herein as a "screening assay") for identifying modulators, i.e., candidate or test compounds or agents (e.g., peptides, peptidomimetics, small molecules (organic or inorganic) or other drugs) which bind to 17906 proteins, have a stimulatory or inhibitory effect on, for example, 17906 expression or 17906 activity, or have a stimulatory or inhibitory effect on, for example, the expression or activity of a 17906 substrate.

These assays are designed to identify compounds that bind to a 17906 protein, bind to other cellular or extracellular proteins that interact with a 17906 protein, and interfere with the interaction of the 17906 protein with other cellular or extracellular proteins. For example, in the case of the 17906 protein, which is a transmembrane receptor-type protein, such techniques can identify ligands for such a receptor. A 17906 protein ligand can, for example, act as the basis for amelioration of bone associated diseases, such as, for example, osteoporosis. Such compounds may include, but are not limited to peptides, antibodies, or small organic or inorganic compounds. Such compounds may also include other cellular proteins.

Compounds identified via assays such as those described herein may be useful, for example, for ameliorating bone associated disease. In instances whereby a bone associated disease condition results from an overall lower level of 17906 gene expression and/or 17906 protein in a cell or tissue, compounds that interact with the 17906 protein may include compounds which accentuate or amplify the activity of the bound 17906 protein. Such compounds would bring about an effective increase in the level of 17906 protein activity, thus ameliorating symptoms.

In other instances mutations within the 17906 gene may cause aberrant types or excessive amounts of 17906 proteins to be made which have a deleterious effect that leads to bone associated disease. Similarly, physiological conditions may cause an excessive increase in 17906 gene expression leading to bone associated disease. In such cases, compounds that bind to a 17906 protein may be identified that inhibit the activity of the 17906 protein. Assays for testing the effectiveness of compounds identified by techniques such as those described in this section are discussed herein.

In one embodiment, the invention provides assays for screening candidate or test compounds which are substrates of a 17906 protein or polypeptide or biologically active portion thereof. In another embodiment, the invention provides assays for screening candidate or test compounds which bind to or modulate the activity of a 17906 protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) Anticancer Drug Des. 12:145).

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233.

Libraries of compounds may be presented in solution (e.g., Houghten (1992) Biotechniques 13:412–421), or on beads (Lam (1991) Nature 354:82–84), chips (Fodor (1993) Nature 364:555–556), bacteria (Ladner U.S. Pat. No. 5,223,409), spores (Ladner U.S. Pat. No. '409), plasmids (Cull et al. (1992) Proc Natl Acad Sci USA 89:1865–1869) or on phage (Scott and Smith (1990) Science 249:386–390); (Devlin (1990) Science 249:404–406); (Cwirla et al. (1990) Proc. Natl. Acad. Sci. 87:6378–6382); (Felici (1991) J. Mol. Biol. 222:301–310); (Ladner supra.).

In one embodiment, an assay is a cell-based assay in which a cell which expresses a 17906 protein or biologically active portion thereof is contacted with a test compound and the ability of the test compound to modulate 17906 activity is determined. Determining the ability of the test compound to modulate 17906 activity can be accomplished by monitoring, for example, intracellular calcium, $IP_3$, cAMP, or diacylglycerol concentration, the phosphorylation profile of intracellular proteins, cell proliferation and/or migration, the expression of cell surface adhesion molecules, or the activity of a 17906-regulated transcription factor. The cell can be of mammalian origin, e.g., a bone cell. In one embodiment, compounds that interact with a 17906 receptor domain can be screened for their ability to function as ligands, i.e., to bind to the 17906 receptor and modulate a signal transduction pathway. Identification of 17906 ligands, and measuring the activity of the ligand-receptor complex, leads to the identification of modulators (e.g., antagonists) of this interaction. Such modulators may be useful in the treatment of bone associated disease.

The ability of the test compound to modulate 17906 binding to a substrate or to bind to 17906 can also be determined. Determining the ability of the test compound to modulate 17906 binding to a substrate can be accomplished, for example, by coupling the 17906 substrate with a radioisotope or enzymatic label such that binding of the 17906 substrate to 17906 can be determined by detecting the labeled 17906 substrate in a complex. 17906 could also be coupled with a radioisotope or enzymatic label to monitor the ability of a test compound to modulate 17906 binding to a 17906 substrate in a complex. Determining the ability of the test compound to bind 17906 can be accomplished, for example, by coupling the compound with a radioisotope or enzymatic label such that binding of the compound to 17906 can be determined by detecting the labeled 17906 compound in a complex. For example, compounds (e.g., 17906 ligands or substrates) can be labeled with $^{125}$I, $^{35}$S, $^{14}$C, or $^{3}$H, either directly or indirectly, and the radioisotope detected by direct counting of radioemission or by scintillation counting. Compounds can further be enzymatically labeled with, for example, horseradish peroxidase, alkaline phosphatase, or luciferase, and the enzymatic label detected by determination of conversion of an appropriate substrate to product.

The presence of 17906 in the serum of the transgenic and wild type animals can be determined by, for example, a carboxipeptidase assay. Briefly, 5 µl of serum of mice, for example, can be combined with 45 µl of 55 µM of an appropriate 17906 substrate including but not limited to e.g., angiotensin I, a kinin, or kinetensin, in 17906 buffer. Then, the rate of proteolytic degradation of the substrate can be measured by measuring the production of fluorescence (in flurorescence units) per second for 30 minutes at room temperature at a gain setting of 10. The average rate of fluoresence units per second (FU/sec) correlates directly with the amount of 17906 in the serum. As a control for the specificity of 17906, a standard carboxypeptidase assay can be performed (Holmquist and Riordan, Carboxypeptidase A, pp 44–60, Peptidase and their Inhibitors in Method of Enzymatic Analysis (1984)). Further, an additional carboxypeptidase assay can be performed in accordance with that described in Ostrowska, H. et al. (1998) *Rocz Akad. Med. Bialymst.*, 43:39–55, which is incorporated herein by reference.

It is also within the scope of this invention to determine the ability of a compound (e.g., a 17906 ligand or substrate) to interact with 17906 without the labeling of any of the interactants. For example, a microphysiometer can be used to detect the interaction of a compound with 17906 without the labeling of either the compound or the 17906 (McConnell, H. M. et al. (1992) *Science* 257:1906–1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 17906.

In another embodiment, an assay is a cell-based assay comprising contacting a cell expressing a 17906 target molecule (e.g., a 17906 substrate) with a test compound and determining the ability of the test compound to modulate (e.g., stimulate or inhibit) the activity of the 17906 target molecule. Determining the ability of the test compound to modulate the activity of a 17906 target molecule can be accomplished, for example, by determining the ability of the 17906 protein to bind to or interact with the 17906 target molecule.

Determining the ability of the 17906 protein or a biologically active fragment thereof, to bind to or interact with a 17906 target molecule can be accomplished by one of the methods described above for determining direct binding. In a preferred embodiment, determining the ability of the 17906 protein to bind to or interact with a 17906 target molecule can be accomplished by determining the activity of the target molecule. For example, the activity of the target molecule can be determined by detecting induction of a cellular second messenger of the target (i.e., intracellular $Ca^{2+}$, diacylglycerol, $IP_3$, cAMP), detecting catalytic/enzymatic activity of the target an appropriate substrate, detecting the induction of a reporter gene (comprising a target-responsive regulatory element operatively linked to a nucleic acid encoding a detectable marker, e.g., luciferase), or detecting a target-regulated cellular response (e.g., cell proliferation or migration).

In yet another embodiment, an assay of the present invention is a cell-free assay in which a 17906 protein or biologically active portion thereof, is contacted with a test compound and the ability of the test compound to bind to the 17906 protein or biologically active portion thereof is determined. Preferred biologically active portions of the 17906 proteins to be used in assays of the present invention include fragments which participate in interactions with non-17906 molecules, e.g., fragments with high surface probability scores. Binding of the test compound to the 17906 protein can be determined either directly or indirectly as described above. In a preferred embodiment, the assay includes contacting the 17906 protein or biologically active portion thereof with a known compound which binds 17906 to form an assay mixture, contacting the assay mixture with a test compound, and determining the ability of the test compound to interact with a 17906 protein, wherein determining the ability of the test compound to interact with a 17906 protein comprises determining the ability of the test compound to preferentially bind to 17906 or biologically active portion thereof as compared to the known compound. Compounds that modulate the interaction of 17906 with a known target protein may be useful in regulating the activity of a 17906 protein, especially a mutant 17906 protein.

In another embodiment, the assay is a cell-free assay in which a 17906 protein or biologically active portion thereof is contacted with a test compound and the ability of the test compound to modulate (e.g., stimulate or inhibit) the activity of the 17906 protein or biologically active portion thereof is determined. Determining the ability of the test compound to modulate the activity of a 17906 protein can be accomplished, for example, by determining the ability of the 17906 protein to bind to a 17906 target molecule by one of the methods described above for determining direct binding. Determining the ability of the 17906 protein to bind to a 17906 target molecule can also be accomplished using a technology such as real-time Biomolecular Interaction Analysis (BIA) (Sjolander, S. and Urbaniczky, C. (1991) *Anal. Chem.* 63:2338–2345 and Szabo et al. (1995) *Curr. Opin. Struct. Biol.* 5:699–705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In another embodiment, determining the ability of the test compound to modulate the activity of a 17906 protein can be accomplished by determining the ability of the 17906 protein to further modulate the activity of a downstream effector of a 17906 target molecule. For example, the activity of the effector molecule on an appropriate target can be determined or the binding of the effector to an appropriate target can be determined as previously described.

In yet another embodiment, the cell-free assay involves contacting a 17906 protein or biologically active portion thereof with a known compound which binds the 17906 protein to form an assay mixture, contacting the assay mixture with a test compound, and determining the ability of the test compound to interact with the 17906 protein, wherein determining the ability of the test compound to interact with the 17906 protein comprises determining the ability of the 17906 protein to preferentially bind to or modulate the activity of a 17906 target molecule.

In more than one embodiment of the above assay methods of the present invention, it may be desirable to immobilize either 17906 or its target molecule to facilitate separation of complexed from uncomplexed forms of one or both of the proteins, as well as to accommodate automation of the assay. Binding of a test compound to a 17906 protein, or interaction of a 17906 protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/17906 fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or 17906 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of 17906 binding or activity determined using standard techniques.

Other techniques for immobilizing proteins on matrices can also be used in the screening assays of the invention. For example, either a 17906 protein or a 17906 target molecule can be immobilized utilizing conjugation of biotin and streptavidin. Biotinylated 17906 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with 17906 protein or target molecules but which do not interfere with binding of the 17906 protein to its target molecule can be derivatized to the wells of the plate, and unbound target or 17906 protein trapped in the wells by antibody conjugation. Methods for detecting such complexes, in addition to those described above for the GST-immobilized complexes, include immunodetection of complexes using antibodies reactive with the 17906 protein or target molecule, as well as enzyme-linked assays which rely on detecting an enzymatic activity associated with the 17906 protein or target molecule.

In another embodiment, modulators of 17906 expression are identified in a method wherein a cell is contacted with a candidate compound and the expression of 17906 mRNA or protein in the cell is determined. The level of expression of 17906 mRNA or protein in the presence of the candidate compound is compared to the level of expression of 17906 mRNA or protein in the absence of the candidate compound. The candidate compound can then be identified as a modulator of 17906 expression based on this comparison. For example, when expression of 17906 mRNA or protein is greater (statistically significantly greater) in the presence of the candidate compound than in its absence, the candidate compound is identified as a stimulator of 17906 mRNA or protein expression. Alternatively, when expression of 17906 mRNA or protein is less (statistically significantly less) in the presence of the candidate compound than in its absence, the candidate compound is identified as an inhibitor of 17906 mRNA or protein expression. The level of 17906 mRNA or protein expression in the cells can be determined by methods described herein for detecting 17906 mRNA or protein.

In yet another aspect of the invention, the 17906 proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with 17906 ("17906-binding proteins" or "17906-bp") and are involved in 17906 activity. Such 17906-binding proteins are also likely to be involved in the propagation of signals by the 17906 proteins or 17906 targets as, for example, downstream elements of a 17906-mediated signaling pathway. Alternatively, such 17906-binding proteins are likely to be 17906 inhibitors.

The two-hybrid system is based on the modular nature of most transcription factors, which consist of separable DNA-binding and activation domains. Briefly, the assay utilizes two different DNA constructs. In one construct, the gene that codes for a 17906 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a 17906-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 17906 protein.

In another aspect, the invention pertains to a combination of two or more of the assays described herein. For example, a modulating agent can be identified using a cell-based or a cell free assay, and the ability of the agent to modulate the activity of a 17906 protein can be confirmed in vivo, e.g., in an animal such as an animal model for bone associated disease, as described herein.

This invention further pertains to novel agents identified by the above-described screening assays. Accordingly, it is within the scope of this invention to further use an agent identified as described herein in an appropriate animal model. For example, an agent identified as described herein (e.g., a 17906 modulating agent, an antisense 17906 nucleic acid molecule, a 17906-specific antibody, or a 17906-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

Any of the compounds, including but not limited to compounds such as those identified in the foregoing assay systems, may be tested for the ability to ameliorate bone associated disease symptoms. Cell-based and animal model-based assays for the identification of compounds exhibiting such an ability to ameliorate bone associated disease systems are described herein.

In one aspect, cell-based systems, as described herein, may be used to identify compounds which may act to ameliorate bone associated disease symptoms. For example, such cell systems may be exposed to a compound, suspected of exhibiting an ability to ameliorate bone associated disease symptoms, at a sufficient concentration and for a time sufficient to elicit such an amelioration of bone associated disease symptoms in the exposed cells. After exposure, the cells are examined to determine whether one or more of the bone associated disease cellular phenotypes has been altered to resemble a more normal or more wild type phenotype. Cellular phenotypes that are associated with bone associated disease states include aberrant proliferation and migration, deposition of extracellular matrix components, and expression of growth factors, cytokines, and other inflammatory mediators.

In addition, animal-based bone associated disease systems, such as those described herein, may be used to identify compounds capable of ameliorating bone associated disease symptoms. Such animal models may be used as test substrates for the identification of drugs, pharmaceuticals, therapies, and interventions which may be effective in treating bone associated disease. For example, animal models may be exposed to a compound, suspected of exhibiting an ability to ameliorate bone associated disease symptoms, at a sufficient concentration and for a time sufficient to elicit such an amelioration of bone associated disease symptoms in the exposed animals. The response of the animals to the exposure may be monitored by assessing the reversal of disorders associated with bone associated disease, for example, by measuring bone loss and/or measuring bone loss before and after treatment.

With regard to intervention, any treatments which reverse any aspect of bone associated disease symptoms should be considered as candidates for human bone associated disease therapeutic intervention. Dosages of test agents may be determined by deriving dose-response curves.

Additionally, gene expression patterns may be utilized to assess the ability of a compound to ameliorate bone associated disease symptoms. For example, the expression pattern of one or more genes may form part of a "gene expression profile" or "transcriptional profile" which may be then be used in such an assessment. "Gene expression profile" or "transcriptional profile", as used herein, includes the pattern of mRNA expression obtained for a given tissue or cell type under a given set of conditions. Such conditions may include, but are not limited to, atherosclerosis, ischemia/reperfusion, hypertension, restenosis, and arterial inflammation, including any of the control or experimental conditions described herein. Gene expression profiles may be generated, for example, by utilizing a differential display procedure, Northern analysis and/or real-time quantitative RT-PCR. In one embodiment, 17906 gene sequences may be used as probes and/or PCR primers for the generation and corroboration of such gene expression profiles.

Gene expression profiles may be characterized for known states, either bone associated disease or normal, within the cell- and/or animal-based model systems. Subsequently, these known gene expression profiles may be compared to ascertain the effect a test compound has to modify such gene expression profiles, and to cause the profile to more closely resemble that of a more desirable profile.

For example, administration of a compound may cause the gene expression profile of a bone associated disease model system to more closely resemble the control system. Administration of a compound may, alternatively, cause the gene expression profile of a control system to begin to mimic a bone associated disease state. Such a compound may, for example, be used in further characterizing the compound of interest, or may be used in the generation of additional animal models.

Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining 17906 protein and/or nucleic acid expression as well as 17906 activity, in the context of a biological sample (e.g., blood, serum, cells, tissue) to thereby determine whether an individual is afflicted with a disease or disorder, or is at risk of developing a bone associated disorder, associated with aberrant or unwanted 17906 expression or activity. The invention also provides for prognostic (or predictive) assays for determining whether an individual is at risk of developing a disorder associated with 17906 protein, nucleic acid expression or activity. For example, mutations in a 17906 gene can be assayed in a biological sample. Such assays can be used for prognostic or predictive purpose to thereby prophylactically treat an individual prior to the onset of a disorder characterized by or associated with 17906 protein, nucleic acid expression or activity.

Another aspect of the invention pertains to monitoring the influence of agents (e.g., drugs, compounds) on the expression or activity of 17906 in clinical trials.

These and other agents are described in further detail in the following sections.

Diagnostic Assays

The present invention encompasses methods for diagnostic and prognostic evaluation of bone associated disease conditions, and for the identification of subjects exhibiting a predisposition to such conditions.

An exemplary method for detecting the presence or absence of 17906 protein or nucleic acid in a biological sample involves obtaining a biological sample from a test subject and contacting the biological sample with a compound or an agent capable of detecting 17906 protein or nucleic acid (e.g., mRNA, or genomic DNA) that encodes 17906 protein such that the presence of 17906 protein or nucleic acid is detected in the biological sample. A preferred agent for detecting 17906 mRNA or genomic DNA is a labeled nucleic acid probe capable of hybridizing to 17906 mRNA or genomic DNA. The nucleic acid probe can be, for example, the 17906 nucleic acid set forth in SEQ ID NO:10, or a portion thereof, such as an oligonucleotide of at least 15, 20, 25, 30, 35, 40, 45, 50, 100, 250 or 500 nucleotides in length and sufficient to specifically hybridize under stringent conditions to 17906 mRNA or genomic DNA. Other suitable probes for use in the diagnostic assays of the invention are described herein.

A preferred agent for detecting 17906 protein is an antibody capable of binding to 17906 protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect 17906 mRNA, protein, or genomic DNA in a biological sample in vitro as well as in vivo. For example, in vitro techniques for detection of 17906 mRNA include Northern hybridizations and in situ hybridizations. In vitro techniques for detection of 17906 protein include enzyme linked immunosorbent assays (ELISAs), Western blots, immunoprecipitations and immunofluorescence. In vitro techniques for detection of 17906 genomic DNA include Southern hybridizations. Furthermore, in vivo techniques for detection of 17906 protein include introducing into a subject a labeled anti-17906 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting 17906 protein, mRNA, or genomic DNA, such that the presence of 17906 protein, mRNA or genomic DNA is detected in the biological sample, and comparing the presence of 17906 protein, mRNA or genomic DNA in the control sample with the presence of 17906 protein, mRNA or genomic DNA in the test sample.

The invention also encompasses kits for detecting the presence of 17906 in a biological sample. For example, the kit can comprise a labeled compound or agent capable of detecting 17906 protein or mRNA in a biological sample; means for determining the amount of 17906 in the sample; and means for comparing the amount of 17906 in the sample with a standard. The compound or agent can be packaged in a suitable container. The kit can further comprise instructions for using the kit to detect 17906 protein or nucleic acid.

Prognostic Assays

The diagnostic methods described herein can furthermore be utilized to identify subjects having or at risk of developing a bone associated disease or disorder associated with aberrant or unwanted 17906 expression or activity. As used herein, the term "aberrant" includes a 17906 expression or activity which deviates from the wild type 17906 expression or activity. Aberrant expression or activity includes increased or decreased expression or activity, as well as expression or activity which does not follow the wild type developmental pattern of expression or the subcellular pattern of expression. For example, aberrant 17906 expression or activity is intended to include the cases in which a mutation in the 17906 gene causes the 17906 gene to be under-expressed or over-expressed and situations in which such mutations result in a non-functional 17906 protein or a protein which does not function in a wild-type fashion, e.g., a protein which does not interact with a 17906 ligand or substrate, or one which interacts with a non-17906 ligand or substrate. As used herein, the term "unwanted" includes an unwanted phenomenon involved in a biological response such as cellular proliferation. For example, the term unwanted includes a 17906 expression pattern or a 17906 protein activity which is undesirable in a subject.

The assays described herein, such as the preceding diagnostic assays or the following assays, can be utilized to identify a subject having or at risk of developing a disorder associated with a misregulation in 17906 protein activity or nucleic acid expression, such as a bone associated disorder. Alternatively, the prognostic assays can be utilized to identify a subject having or at risk for developing a bone associated disorder associated with a misregulation in 17906 protein activity or nucleic acid expression. Thus, the present invention provides a method for identifying a disease or disorder associated with aberrant or unwanted 17906 expression or activity in which a test sample is obtained from a subject and 17906 protein or nucleic acid (e.g., mRNA or genomic DNA) is detected, wherein the presence of 17906 protein or nucleic acid is diagnostic for a subject having or at risk of developing a disease or disorder associated with aberrant or unwanted 17906 expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 17906 expression or activity. For example, such methods can be used to determine whether a subject can be effectively treated with an agent for a bone associated disorder. Thus, the present invention provides methods for determining whether a subject can be effectively treated with an agent for a bone associated disorder associated with aberrant or unwanted 17906 expression or activity in which a test sample is obtained and 17906 protein or nucleic acid expression or activity is detected (e.g., wherein the abundance of 17906 protein or nucleic acid expression or activity is diagnostic for a subject that can be administered the agent to treat a disorder associated with aberrant or unwanted 17906 expression or activity).

The methods of the invention can also be used to detect genetic alterations in a 17906 gene, thereby determining if a subject with the altered gene is at risk for a disorder characterized by misregulation in 17906 protein activity or nucleic acid expression, such as a proliferative disorder. In preferred embodiments, the methods include detecting, in a sample of cells from the subject, the presence or absence of a genetic alteration characterized by at least one of an alteration affecting the integrity of a gene encoding a 17906-protein, or the mis-expression of the 17906 gene. For example, such genetic alterations can be detected by ascertaining the existence of at least one of 1) a deletion of one or more nucleotides from a 17906 gene; 2) an addition of one or more nucleotides to a 17906 gene; 3) a substitution of one or more nucleotides of a 17906 gene, 4) a chromosomal rearrangement of a 17906 gene; 5) an alteration in the level of a messenger RNA transcript of a 17906 gene, 6) aberrant modification of a 17906 gene, such as of the methylation pattern of the genomic DNA, 7) the presence of a non-wild type splicing pattern of a messenger RNA transcript of a 17906 gene, 8) a non-wild type level of a 17906-protein, 9) allelic loss of a 17906 gene, and 10)

inappropriate post-translational modification of a 17906-protein. As described herein, there are a large number of assays known in the art which can be used for detecting alterations in a 17906 gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the 17906-gene (see Abravaya et al. (1995) *Nucleic Acids Res*. 23:675–682). This method can include the steps of collecting a sample of cells from a subject, isolating nucleic acid (e.g., genomic, mRNA or both) from the cells of the sample, contacting the nucleic acid sample with one or more primers which specifically hybridize to a 17906 gene under conditions such that hybridization and amplification of the 17906-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Other amplification methods include: self sustained sequence replication (Guatelli, J. C. et al., (1990) *Proc. Natl. Acad. Sci. USA* 87:1874–1878), transcriptional amplification system (Kwoh, D. Y. et al., (1989) *Proc. Natl. Acad. Sci. USA* 86:1173–1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a 17906 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 17906 can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in 17906 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 17906 gene and detect mutations by comparing the sequence of the sample 17906 with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr*. 36:127–162; and Griffin et al. (1993) *Appl. Biochem. Biotechnol*. 38:147–159).

Other methods for detecting mutations in the 17906 gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type 17906 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad Sci USA* 85:4397; Saleeba et al. (1992) *Methods Enzymol*. 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in 17906 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a 17906 sequence, e.g., a wild-type 17906 sequence, is hybridized to a cDNA or other DNA product from a test cell(s). The duplex is treated with a DNA mismatch repair enzyme, and the cleavage products, if any, can be detected from electrophoresis protocols or the like (described in, for example, U.S. Pat. No. 5,459,039).

In other embodiments, alterations in electrophoretic mobility will be used to identify mutations in 17906 genes. For example, single strand conformation polymorphism (SSCP) may be used to detect differences in electrophoretic mobility between mutant and wild type nucleic acids (Orita et al. (1989) *Proc Natl. Acad. Sci USA*: 86:2766, see also Cotton (1993) *Mutat. Res.* 285:125–144; and Hayashi (1992) *Genet. Anal. Tech. Appl.* 9:73–79). Single-stranded DNA fragments of sample and control 17906 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen etal. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a 17906 gene.

Furthermore, any cell type or tissue in which 17906 is expressed may be utilized in the prognostic assays described herein.

Monitoring of Effects During Clinical Trials

The present invention provides methods for evaluating the efficacy of drugs and monitoring the progress of patients involved in clinical trials for the treatment of bone associated disease.

Monitoring the influence of agents (e.g., drugs) on the expression or activity of a 17906 protein (e.g., the modulation of cell proliferation and/or migration) can be applied not only in basic drug screening, but also in clinical trials. For example, the effectiveness of an agent determined by a screening assay as described herein to increase 17906 gene expression, protein levels, or upregulate 17906 activity, can be monitored in clinical trials of subjects exhibiting decreased 17906 gene expression, protein levels, or downregulated 17906 activity. Alternatively, the effectiveness of an agent determined by a screening assay to decrease 17906 gene expression, protein levels, or downregulate 17906 activity, can be monitored in clinical trials of subjects exhibiting increased 17906 gene expression, protein levels, or upregulated 17906 activity. In such clinical trials, the expression or activity of a 17906 gene, and preferably, other genes that have been implicated in, for example, a 17906-associated disorder can be used as a "read out" or markers of the phenotype a particular cell, e.g., a bone cell. In addition, the expression of a 17906 gene, or the level of 17906 protein activity may be used as a read out of a particular drug or agent's effect on a bone associated disease state.

For example, and not by way of limitation, genes, including 17906, that are modulated in cells by treatment with an agent (e.g., compound, drug or small molecule) which modulates 17906 activity (e.g., identified in a screening assay as described herein) can be identified. Thus, to study the effect of agents on 17906-associated disorders (e.g., bone associated disorders characterized by deregulated bone cell activity), for example, in a clinical trial, cells can be isolated and RNA prepared and analyzed for the levels of expression of 17906 and other genes implicated in the 17906-associated disorder, respectively. The levels of gene expression (e.g., a gene expression pattern) can be quantified by northern blot analysis or real-time quantitative RT-PCR, as described herein, or alternatively by measuring the amount of protein produced, by one of the methods as described herein, or by measuring the levels of activity of 17906 or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of a 17906 protein, mRNA, or genomic DNA in the preadministration sample; (iii) obtaining one or more post-administration samples from the subject; (iv) detecting the level of expression or activity of the 17906 protein, mRNA, or genomic DNA in the post-administration samples; (v) comparing the level of expression or activity of the 17906 protein, mRNA, or genomic DNA in the pre-administration sample with the 17906 protein, mRNA, or genomic DNA in the post administration sample or samples; and (vi) altering the administration of the agent to the subject accordingly. For example, increased administration of the agent may be desirable to increase the expression or activity of 17906 to higher levels than detected, i.e., to increase the effectiveness of the agent. Alternatively, decreased administration of the agent may be desirable to decrease expression or activity of 17906 to lower levels than detected, i.e. to decrease the effectiveness of the agent. According to such an embodiment, 17906 expression or activity may be used as an indicator of the effectiveness of an agent, even in the absence of an observable phenotypic response.

Methods of Treatment

The present invention provides for both prophylactic and therapeutic methods of treating a subject at risk of (or susceptible to) a disorder or having a disorder associated with aberrant or unwanted 17906 expression or activity, e.g. a bone associated disorder. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the 17906 molecules of the present invention or 17906 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

Prophylactic Methods

In one aspect, the invention provides a method for preventing in a subject, a bone associated disease or condition associated with an aberrant or unwanted 17906 expression or activity, by administering to the subject a 17906 or an agent which modulates 17906 expression or at least one 17906 activity. Subjects at risk for a bone associated disease which is caused or contributed to by aberrant or unwanted 17906 expression or activity can be identified by, for example, any or a combination of diagnostic or prognostic assays as described herein. Administration of a prophylactic agent can occur prior to the manifestation of symptoms characteristic of the 17906 aberrancy, such that a disease or disorder is prevented or, alternatively, delayed in its progression. Depending on the type of 17906 aberrancy, for example, a 17906, 17906 agonist or 17906 antagonist agent can be used for treating the subject. The appropriate agent can be determined based on screening assays described herein.

Therapeutic Methods

Described herein are methods and compositions whereby bone associated disease symptoms may be ameliorated. Certain bone associated diseases are brought about, at least in part, by an excessive level of a gene product, or by the presence of a gene product exhibiting an abnormal or excessive activity. As such, the reduction in the level and/or activity of such gene products would bring about the amelioration of bone associated disease symptoms. Techniques for the reduction of gene expression levels or the activity of a protein are discussed below.

Alternatively, certain other bone associated diseases are brought about, at least in part, by the absence or reduction of the level of gene expression, or a reduction in the level of a protein's activity. As such, an increase in the level of gene expression and/or the activity of such proteins would bring about the amelioration of bone associated disease symptoms.

In some cases, the up-regulation of a gene in a disease state reflects a protective role for that gene product in responding to the disease condition. Enhancement of such a gene's expression, or the activity of the gene product, will reinforce the protective effect it exerts. Some bone associated disease states may result from an abnormally low level of activity of such a protective gene. In these cases also, an increase in the level of gene expression and/or the activity of such gene products would bring about the amelioration of bone associated disease symptoms. Techniques for increasing target gene expression levels or target gene product activity levels are discussed herein.

Accordingly, another aspect of the invention pertains to methods of modulating 17906 expression or activity for therapeutic purposes. Accordingly, in an exemplary embodiment, the modulatory method of the invention involves contacting a cell with a 17906 or agent that modulates one or more of the activities of 17906 protein activity associated with the cell (e.g., a bone cell). An agent that modulates 17906 protein activity can be an agent as described herein, such as a nucleic acid or a protein, a naturally-occurring target molecule of a 17906 protein (e.g., a 17906 ligand or substrate), a 17906 antibody, a 17906 agonist or antagonist, a peptidomimetic of a 17906 agonist or antagonist, or other small molecule. In one embodiment, the agent stimulates one or more 17906 activities. Examples of such stimulatory agents include active 17906 protein and a nucleic acid molecule encoding 17906 that has been introduced into the cell. In another embodiment, the agent inhibits one or more 17906 activities. Examples of such inhibitory agents include antisense 17906 nucleic acid molecules, anti-17906 antibodies, and 17906 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 17906 protein or nucleic acid molecule. In one embodiment, the method involves administering an agent (e.g., an agent identified by a screening assay described herein), or combination of agents that modulates (e.g., upregulates or downregulates) 17906 expression or activity. In another embodiment, the method involves administering a 17906 protein or nucleic acid molecule as therapy to compensate for reduced, aberrant, or unwanted 17906 expression or activity.

Stimulation of 17906 activity is desirable in situations in which 17906 is abnormally downregulated and/or in which increased 17906 activity is likely to have a beneficial effect. Likewise, inhibition of 17906 activity is desirable in situations in which 17906 is abnonnally upregulated and/or in which decreased 17906 activity is likely to have a beneficial effect.

Methods for Inhibiting Target Gene Expression, Synthesis, or Activity

As discussed above, genes involved in bone associated disorders may cause such disorders via an increased level of gene activity. In some cases, such up-regulation may have a causative or exacerbating effect on the disease state. A variety of techniques may be used to inhibit the expression, synthesis, or activity of such genes and/or proteins.

For example, compounds such as those identified through assays described above, which exhibit inhibitory activity, may be used in accordance with the invention to ameliorate bone associated disease symptoms. Such molecules may include, but are not limited to, small organic molecules, peptides, antibodies, and the like.

For example, compounds can be administered that compete with endogenous ligand for the 17906 protein. The resulting reduction in the amount of ligand-bound 17906 protein will modulate bone cell physiology. Compounds that can be particularly useful for this purpose include, for example, soluble proteins or peptides, such as peptides comprising one or more of the extracellular domains, or portions and/or analogs thereof, of the 17906 protein, including, for example, soluble fusion proteins such as Ig-tailed fusion proteins. (For a discussion of the production of Ig-tailed fusion proteins, see, for example, U.S. Pat. No. 5,116,964). Alternatively, compounds, such as ligand analogs or antibodies, that bind to the 17906 receptor site, but do not activate the protein, (e.g., receptor-ligand antagonists) can be effective in inhibiting 17906 protein activity.

Further, antisense and ribozyme molecules which inhibit expression of the 17906 gene may also be used in accordance with the invention to inhibit aberrant 17906 gene activity. Still further, triple helix molecules may be utilized in inhibiting aberrant 17906 gene activity.

The antisense nucleic acid molecules of the invention are typically administered to a subject or generated in situ such that they hybridize with or bind to cellular mRNA and/or genomic DNA encoding a 17906 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215: 327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave 17906 mRNA transcripts to thereby inhibit translation of 17906 mRNA. A ribozyme having specificity for a 17906-encoding nucleic acid can be designed based upon the nucleotide sequence of a 17906 cDNA disclosed herein (i.e., SEQ ID NO:10). For example, a derivative of a Tetrahymena L-19 IVS RNA can be constructed in which the nucleotide sequence of the active site is complementary to the nucleotide sequence to be cleaved in a 17906-encoding mRNA (see, for example, Cech et al. U.S. Pat. No. 4,987,071; and Cech et al. U.S. Pat. No. 5,116,742). Alternatively, 17906 mRNA can be used to select a catalytic RNA having a specific ribonuclease activity from a pool of RNA molecules (see, for example, Bartel, D. and Szostak, J. W. (1993) *Science* 261:1411–1418).

17906 gene expression can also be inhibited by targeting nucleotide sequences complementary to the regulatory region of the 17906 (e.g., the 17906 promoter and/or enhancers) to form triple helical structures that prevent transcription of the 17906 gene in target cells (see, for example, Helene, C. (1991) *Anticancer Drug Des.* 6(6): 569–84; Helene, C. et al. (1992) *Ann. N.Y Acad. Sci.* 660:27–36; and Maher, L J. (1992) *Bioassays* 14(12):807–15).

Antibodies that are both specific for the 17906 protein and interfere with its activity may also be used to modulate or inhibit 17906 protein function. Such antibodies may be generated using standard techniques described herein, against the 17906 protein itself or against peptides corresponding to portions of the protein. Such antibodies include but are not limited to polyclonal, monoclonal, Fab fragments, single chain antibodies, or chimeric antibodies.

In instances where the target gene protein is intracellular and whole antibodies are used, internalizing antibodies may be preferred. Lipofectin liposomes may be used to deliver the antibody or a fragment of the Fab region which binds to the target epitope into cells. Where fragments of the antibody are used, the smallest inhibitory fragment which binds to the target protein's binding domain is preferred. For example, peptides having an amino acid sequence corresponding to the domain of the variable region of the antibody that binds to the target gene protein may be used. Such peptides may be synthesized chemically or produced via recombinant DNA technology using methods well known in the art (described in, for example, Creighton (1983), supra; and Sambrook et al. (1989) supra). Single chain neutralizing antibodies which bind to intracellular target gene epitopes may also be administered. Such single chain antibodies may be administered, for example, by expressing nucleotide sequences encoding single-chain antibodies within the target cell population by utilizing, for example, techniques such as those described in Marasco et al. (1993) *Proc. Natl. Acacl. Sci. USA* 90:7889–7893).

In some instances, the target gene protein is extracellular, or is a transmembrane protein, such as the 17906 protein. Antibodies that are specific for one or more extracellular domains of the 17906 protein, for example, and that interfere with its activity, are particularly useful in treating bone associated disease. Such antibodies are especially efficient because they can access the target domains directly from the bloodstream. Any of the administration techniques described below which are appropriate for peptide administration may be utilized to effectively administer inhibitory target gene antibodies to their site of action.

Methods for Restoring, Enhancing or Inhibiting Target Gene Activity

Described in this section are methods whereby the level 17906 activity may be modulated to levels wherein bone associated disease symptoms are ameliorated. The level of 17906 activity may be modulated, for example, by either modulating the level of 17906 gene expression or by modulating the level of active 17906 protein which is present.

Specifically, 17906 is down-regulated in osteoblast differentiation, thus 17906 may be used to modulate osteoblast activity, either by increasing 17906 activity and promoting bone cell proliferation or inhibiting 17906 activity and promoting bone cell differentiation, for example. Modulation to further decrease differentiation and to allow bone cells to proliferate is useful for bone regeneration and thus useful for treating diseases such as osteoporosis. Modulation to increase differentiation and reduce proliferation is useful for reducing bone cell growth and thus is useful for treating diseases such as myeloma bone disease.

Genes that cause bone associated disease may be underexpressed within bone associated disease situations. Bone associated disease symptoms may also develop due to the decrease of activity of the protein products of such genes. Such down-regulation of gene expression or decrease of protein activity might have a causative or exacerbating effect on the disease state.

In some cases, genes that are down-regulated in the disease state might be exerting a protective effect. A variety of techniques may be used to decrease the expression, synthesis, or activity of 17906 genes and/or proteins that exert a causatory effect on bone associated disease conditions.

In contrast, an inhibitor of a 17906 protein, at a level sufficient to ameliorate bone associated disease symptoms may be administered to a patient exhibiting such symptoms. Any of the techniques discussed below may be used for such administration. One of skill in the art will readily know how to determine the concentration of effective, non-toxic doses of an inhibitor of the 17906 protein, utilizing techniques such as those described below.

Additionally, antisense 17906 DNA sequences may be directly administered to a patient exhibiting bone associated disease symptoms, at a concentration sufficient to reduce the level of 17906 protein such that bone associated disease symptoms are ameliorated. Any of the techniques discussed below, which achieve intracellular administration of compounds, such as, for example, liposome administration, may be used for the administration of such antisense DNA molecules. The DNA molecules may be produced, for example, by recombinant techniques such as those described herein.

Further, subjects may be treated by gene replacement therapy. One or more copies of an antagonist of the 17906 molecule, e.g., a portion of the 17906 gene, may be inserted into cells using vectors which include, but are not limited to adenovirus, adeno-associated virus, and retrovirus vectors, in addition to other particles that introduce DNA into cells, such as liposomes. Additionally, techniques such as those described above may be used for the introduction of 17906 gene sequences into human cells.

Cells, preferably, autologous cells, containing 17906 antagonist expressing gene sequences may then be introduced or reintroduced into the subject at positions which allow for the amelioration of bone associated disease symptoms. Such cell replacement techniques may be preferred, for example, when the gene product is a secreted, extracellular gene product.

Pharmacogenomics

The 17906 molecules of the present invention, as well as agents, or modulators which have a stimulatory or inhibitory effect on 17906 activity (e.g., 17906 gene expression) as identified by a screening assay described herein can be administered to individuals to treat (prophylactically or therapeutically) 17906-associated disorders (e.g., bone associated disorders) associated with aberrant or unwanted 17906 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a 17906 molecule or a 17906 modulator as well as tailoring the dosage and/or therapeutic regimen of treatment with a 17906 molecule or 17906 modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10–11): 983–985 and Linder, M. W. et al. (1997) *Clin. Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occuffing polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a 17906 protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a 17906 molecule or 17906 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a 17906 molecule or 17906 modulator, such as a modulator identified by one of the exemplary screening assays described herein.

Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

Chromosome Mapping

Once the sequence (or a portion of the sequence) of a gene has been isolated, this sequence can be used to map the location of the gene on a chromosome. This process is called chromosome mapping. Accordingly, portions or fragments of the 17906 nucleotide sequences, described herein, can be used to map the location of the 17906 genes on a chromosome. The mapping of the 17906 sequences to chromosomes is an important first step in correlating these sequences with genes associated with disease. The 17906 gene has been mapped to human chromosome position 15q14–15.

Briefly, 17906 genes can be mapped to chromosomes by preparing PCR primers (preferably 15–25 bp in length) from the 17906 nucleotide sequences. Computer analysis of the 17906 sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the 17906 sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220: 919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the 17906 nucleotide sequences to design oligonucleotide primers, sublocalization can be achieved with panels of fragments from specific chromosomes. Other mapping strategies which can similarly be used to map a 17906 sequence to its chromosome include in situ hybridization (described in Fan, Y. et al. (1990) *Proc. Natl. Acad. Sci. USA*, 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) Nature, 325:783–787.

Moreover, differences in the DNA sequences between individuals affected and unaffected with a disease associated with the 17906 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing

The 17906 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the 17906 nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The 17906 nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of 17906 gene sequences can comfortably provide positive individual identification with a panel of perhaps 10 to 1,000 primers which each yield a noncoding amplified sequence of 100 bases. If predicted coding sequences, such as those in SEQ ID NO:10 are used, a more appropriate number of primers for positive individual identification would be 500–2,000.

If a panel of reagents from 17906 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 17906 Sequences in Forensic Biology

DNA-based identification techniques can also be used in forensic biology. Forensic biology is a scientific field employing genetic-typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of 17906 gene sequences are particularly appropriate for this use as greater numbers of polymorphisms occur in the noncoding regions, making it easier to differentiate individuals using this technique. Examples of polynucleotide reagents include the 17906 nucleotide sequences or portions thereof, e.g., fragments derived from the noncoding regions having a length of at least 20 bases, preferably at least 30 bases.

The 17906 nucleotide sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such 17906 probes can be used to identify tissue by species and/or by organ type.

In a similar fashion, these reagents, e.g., 17906 primers or probes can be used to screen tissue culture for contamination (i.e. screen for the presence of a mixture of different types of cells in a culture).

Recombinant Expression Vectors and Host Cells

The methods of the invention include the use of vectors, preferably expression vectors, containing a nucleic acid encoding a 17906 protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the methods of the invention may include other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., 17906 proteins, mutant forms of 17906 proteins, fusion proteins, and the like).

The recombinant expression vectors of the invention can be designed for expression of 17906 proteins in prokaryotic or eukaryotic cells, e.g., for use in the cell-based assays of the invention. For example, 17906 proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in 17906 activity assays, (e.g., direct assays or competitive assays described in detail below), or to generate antibodies specific for 17906 proteins, for example. In a preferred embodiment, a 17906 fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res*. 20:2111–2118). Such alteration of nucleic acid sequences of the invention can be carried out by standard DNA synthesis techniques.

In another embodiment, the 17906 expression vector is a yeast expression vector. Examples of vectors for expression in yeast *S. cerevisiae* include pYepSec1 (Baldari, et al., (1987) *EMBO J.* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp, San Diego, Calif.).

Alternatively, 17906 proteins can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The expression characteristics of an endogenous 17906 gene within a cell line or microorganism may be modified by inserting a heterologous DNA regulatory element into the genome of a stable cell line or cloned microorganism such that the inserted regulatory element is operatively linked with the endogenous 17906 gene. For example, an endogenous 17906 gene which is normally "transcriptionally silent", i.e., a 17906 gene which is normally not expressed, or is expressed only at very low levels in a cell line or microorganism, may be activated by inserting a regulatory element which is capable of promoting the expression of a normally expressed gene product in that cell line or microorganism. Alternatively, a transcriptionally silent, endogenous 17906 gene may be activated by insertion of a promiscuous regulatory element that works across cell types.

A heterologous regulatory element may be inserted into a stable cell line or cloned microorganism, such that it is operatively linked with an endogenous 17906 gene, using techniques, such as targeted homologous recombination, which are well known to those of skill in the art, and described, e.g., in Chappel, U.S. Pat. No. 5,272,071; PCT publication No. WO 91/06667, published May 16, 1991.

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to 17906 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a 17906 nucleic acid molecule of the invention is introduced, e.g., a 17906 nucleic acid molecule within a recombinant expression vector or a 17906 nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 17906 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a 17906 protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a 17906 protein. Accordingly, the invention further provides methods for producing a 17906 protein using the host cells of the invention. In one embodiment, the method comprises culturing the host cell of the invention (into which a recombinant expression vector encoding a 17906 protein has been introduced) in a suitable medium such that a 17906 protein is produced. In another embodiment, the method further comprises isolating a 17906 protein from the medium or the host cell.

Cell- and Animal-Based Model Systems

Described herein are cell- and animal-based systems which act as models for bone associated disease. These systems may be used in a variety of applications. For example, the cell- and animal-based model systems may be used to further characterize differentially expressed genes associated with bone associated disease, e.g., 17906. In addition, animal- and cell-based assays may be used as part of screening strategies designed to identify compounds which are capable of ameliorating bone associated disease symptoms, as described, below. Thus, the animal- and cell-based models may be used to identify drugs, pharmaceuticals, therapies and interventions which may be effective in treating bone associated disease. Furthermore, such animal models may be used to determine the LD50 and the ED50 in animal subjects, and such data can be used to determine the in vivo efficacy of potential bone associated disease treatments.

Animal-Based Systems

Animal-based model systems of bone associated disease may include, but are not limited to, non-recombinant and engineered transgenic animals.

Non-recombinant animal models for bone associated disease may include, for example, genetic models.

Additionally, animal models exhibiting bone associated disease symptoms may be engineered by using, for example, 17906 gene sequences described above, in conjunction with techniques for producing transgenic animals that are well known to those of skill in the art. For example, 17906 gene sequences may be introduced into, and overexpressed in, the genome of the animal of interest, or, if endogenous 17906 gene sequences are present, they may either be overexpressed or, alternatively, be disrupted in order to underexpress or inactivate 17906 gene expression.

The host cells of the invention can also be used to produce non-human transgenic animals. For example, in one embodiment, a host cell of the invention is a fertilized oocyte or an embryonic stem cell into which 17906-coding sequences have been introduced. Such host cells can then be used to create non-human transgenic animals in which exogenous 17906 sequences have been introduced into their genome or homologous recombinant animals in which endogenous 17906 sequences have been altered. Such animals are useful for studying the function and/or activity of a 17906 and for identifying and/or evaluating modulators of 17906 activity.

As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous 17906 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a 17906-encoding nucleic acid into the male pronuclei of a fertilized oocyte, e.g., by microinjection, retroviral infection, and allowing the oocyte to develop in a pseudopregnant female foster animal. The 17906 cDNA sequence of SEQ ID NO:10 can be introduced as a transgene into the genome of a non-human animal. Alternatively, a nonhuman homologue of a human 17906 gene, such as a mouse or rat 17906 gene, can be used as a transgene. Alternatively, a 17906 gene homologue, such as another 17906 family member, can be isolated based on hybridization to the 17906 cDNA sequences of SEQ ID NO:10 and used as a transgene. Intronic sequences and polyadenylation signals can also be included in the transgene to increase the efficiency of expression of the transgene. A tissue-specific regulatory sequence(s) can be operably linked to a 17906 transgene to direct expression of a 17906 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of a 17906 transgene in its genome and/or expression of 17906 mRNA in tissues or cells of the animals. A transgenic founder animal can then be used to breed additional animals carrying the transgene. Moreover, transgenic animals carrying a transgene encoding a 17906 protein can further be bred to other transgenic animals carrying other transgenes.

To create a homologous recombinant animal, a vector is prepared which contains at least a portion of a 17906 gene into which a deletion, addition or substitution has been introduced to thereby alter, e.g., functionally disrupt, the 17906 gene. The 17906 gene can be a human gene (e.g., the cDNA of SEQ ID NO:10), but more preferably, is a non-human homologue of a human 17906 gene (e.g., a cDNA isolated by stringent hybridization with the nucleotide sequence of SEQ ID NO:10). For example, a mouse 17906 gene can be used to construct a homologous recombination nucleic acid molecule, e.g., a vector, suitable for altering an endogenous 17906 gene in the mouse genome. In a preferred embodiment, the homologous recombination nucleic acid molecule is designed such that, upon homologous recombination, the endogenous 17906 gene is functionally disrupted (i.e., no longer encodes a functional protein; also referred to as a "knock out" vector). Alternatively, the homologous recombination nucleic acid molecule can be designed such that, upon homologous recombination, the endogenous 17906 gene is mutated or otherwise altered but still encodes functional protein (e.g., the upstream regulatory region can be altered to thereby alter the expression of the endogenous 17906 protein). In the homologous recombination nucleic acid molecule, the altered portion of the 17906 gene is flanked at its 5' and 3' ends by additional nucleic acid sequence of the 17906 gene to allow for homologous recombination to occur between the exogenous 17906 gene carried by the homologous recombination nucleic acid molecule and an endogenous 17906 gene in a cell, e.g., an embryonic stem cell. The additional flanking 17906 nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecchi, M. R. (1987) *Cell* 51:503 for a description of homologous recombination vectors). The homologous recombination nucleic acid molecule is introduced into a cell, e.g., an embryonic stem cell line (e.g., by electroporation) and cells in which the introduced 17906 gene has homologously recombined with the endogenous 17906 gene are selected (see e.g., Li, E. et al. (1992) *Cell* 69:915). The selected cells can then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci.* USA 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_O$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

The 17906 transgenic animals that express 17906 mRNA or a 17906 peptide (detected immunocytochemically, using antibodies directed against 17906 epitopes) at easily detectable levels should then be further evaluated to identify those animals which display characteristic bone associated disease symptoms. Such symptoms may include, for example, increased prevalence and size of fatty streaks and/or bone associated disease plaques.

Additionally, specific cell types within the transgenic animals may be analyzed and assayed for cellular phenotypes characteristic of bone associated disease. In the case of monocytes, such phenotypes may include but are not limited to increases in rates of LDL uptake, adhesion to bone cells, transmigration, foam cell formation, fatty streak formation, and production of foam cell specific products. Cellular phenotypes may include a particular cell type's pattern of expression of genes associated with bone associated disease as compared to known expression profiles of the particular cell type in animals exhibiting bone associated disease symptoms.

An alternative animal-based model system of bone associated disease useful in the present invention is found in ovariectomized rats as described by Dunstan et al. (Dunstan, C. R. et al. *J. Bone Miner Res.* Vol. 14(6):953–9, 1999). After ovariectomy (OVX), adult female rats begin losing bone density, which can lead to conditions similar to severe osteoporosis. As such the ovariectomized rats may be examined for the prevention of bone density decreases or for new bone formation after various treatments, including those of the present invention.

Ovariectomized rats may also be used as a model for orally administered agents to assay for effects on bone loss, as shown by Mundy et al. (Mundy, G. et al. Science, Vol. 386:1946–1949, 1999). Mundy et al. also describe another animal-based model system of detecting bone growth by injection into the subcutaneous tissue overlying the murine calvaria in mice (Mundy, G. et al. Science, Vol. 386:1946, 1999). Lastly, Mundy et al. describe a model system based on neonatal murine calvarial (skullcap) bones in organ culture as well as an in vitro model for bone formation based on a murine osteoblast cell line. Both of these may be used as described below for cell-based model systems.

Cell-Based Systems

Cells that contain and express 17906 gene sequences which encode a 17906 protein, and/or exhibit cellular phenotypes associated with bone associated disease, may be used to identify compounds that exhibit anti-bone associated disease activity. Such cells may include non-recombinant monocyte cell lines, such as U937 (ATCC# CRL-1593), THP-1 (ATCC#TIB-202), and P388D1 (ATCC# TIB-63); hepatic cells such as human Hepa; as well as generic mammalian cell lines such as HeLa cells and COS cells, e.g., COS-7 (ATCC# CRL-1651). Further, such cells may include recombinant, transgenic cell lines. For example, the bone associated disease animal models of the invention, discussed above, may be used to generate cell lines, containing one or more cell types involved in bone associated disease, that can be used as cell culture models for this disorder. While primary cultures derived from the bone associated disease transgenic animals of the invention may be utilized, the generation of continuous cell lines is preferred. For examples of techniques which may be used to derive a continuous cell line from the transgenic animals, see Small et al., (1985) *Mol. Cell Biol.* 5:642–648.

Alternatively, cells of a cell type known to be involved in bone associated disease may be transfected with sequences capable of increasing or decreasing the amount of 17906 gene expression within the cell. For example, 17906 gene sequences may be introduced into, and overexpressed in, the genome of the cell of interest, or, if endogenous 17906 gene sequences are present, they may be either overexpressed or, alternatively disrupted in order to underexpress or inactivate 17906 gene expression.

In order to overexpress a 17906 gene, the coding portion of the 17906 gene may be ligated to a regulatory sequence which is capable of driving gene expression in the cell type of interest, e.g., a bone cell. Such regulatory regions will be well known to those of skill in the art, and may be utilized in the absence of undue experimentation. Recombinant methods for expressing target genes are described above.

For underexpression of an endogenous 17906 gene sequence, such a sequence may be isolated and engineered such that when reintroduced into the genome of the cell type of interest, the endogenous 17906 alleles will be inactivated. Preferably, the engineered 17906 sequence is introduced via gene targeting such that the endogenous 17906 sequence is disrupted upon integration of the engineered 17906 sequence into the cell's genome. Transfection of host cells with 17906 genes is discussed, above.

Cells treated with compounds or transfected with 17906 genes can be examined for phenotypes associated with bone associated disease. In the case of osteocytes, such phenotypes include but are not limited to expression of cytokines or growth factors. Expression of cytokines or growth factors may be measured using any of the assays described herein.

Similarly, bone cells can be treated with test compounds or transfected with genetically engineered 17906 genes. The bone cells can then be examined for phenotypes associated with bone associated disease, including, but not limited to changes in cellular morphology, cell proliferation, and cell migration; or for the effects on production of other proteins involved in bone associated disease such as adhesion molecules (e.g., ICAM, VCAM), PDGF, and E-selectin.

Transfection of 17906 nucleic acid may be accomplished by using standard techniques (described in, for example, Ausubel (1989) supra). Transfected cells should be evaluated for the presence of the recombinant 17906 gene sequences, for expression and accumulation of 17906 mRNA, and for the presence of recombinant 17906 protein production. In instances wherein a decrease in 17906 gene expression is desired, standard techniques may be used to demonstrate whether a decrease in endogenous 17906 gene expression and/or in 17906 protein production is achieved.

Pharmaceutical Compositions

Active compounds for use in the methods of the invention can be incorporated into pharmaceutical compositions suitable for administration. As used herein, the language "active compounds" includes 17906 nucleic acid molecules, fragments of 17906 proteins, and anti-17906 antibodies, as well as identified compounds that modulate 17906 gene expression, synthesis, and/or activity. Such compositions typically comprise the compound, nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of a 17906 protein or a 17906 ligand) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches.and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals. In one embodiment, a therapeutically effective dose refers to that amount of an active compound sufficient to result in amelioration of symptoms of bone associated disease.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery ($2^{nd}$ Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982). Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Isolated Nucleic Acid Molecules

The nucleotide sequence of the isolated human 17906 cDNA and the predicted amino acid sequence of the human 17906 polypeptide are shown in SEQ ID NOs:10 and 11, respectively. The nucleotide sequence encoding human 17906 is identical to the nucleic acid molecule with Gen-Bank Accession Number AF095719 (Huang, H. et al. Cancer Res. (1999) 59(12):2981–2988).

The human 17906 gene, which is approximately 2795 nucleotides in length, encodes a protein having a molecular weight of approximately 46.4 kD and which is approximately 422 amino acid residues in length.

The methods of the invention include the use of isolated nucleic acid molecules that encode 17906 proteins or biologically active portions thereof, as well as nucleic acid fragments sufficient for use as hybridization probes to identify 17906-encoding nucleic acid molecules (e.g., 17906 mRNA) and fragments for use as PCR primers for the amplification or mutation of 17906 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated 17906 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:10, or a portion thereof, can be isolated using standard molecular biology techniques and the sequence information provided herein. Using all or portion of the nucleic acid sequence of SEQ ID NO:10, as a hybridization probe, 17906 nucleic acid molecules can be isolated using standard hybridization and cloning techniques (e.g., as described in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989).

Moreover, a nucleic acid molecule encompassing all or a portion of SEQ ID NO:10 can be isolated by the polymerase chain reaction (PCR) using synthetic oligonucleotide primers designed based upon the sequence of SEQ ID NO:10.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to 17906 nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:10. The sequence of SEQ ID NO:10 corresponds to the human 17906 cDNA. This cDNA comprises sequences encoding the human 17906 protein (i.e., "the coding region of SEQ ID NO:10").

In another preferred embodiment, an isolated nucleic acid molecule of the invention comprises a nucleic acid molecule which is a complement of the nucleotide sequence shown in SEQ ID NO:10, or a portion of any of this nucleotide sequence. A nucleic acid molecule which is complementary to the nucleotide sequence shown in SEQ ID NO:10 is one which is sufficiently complementary to the nucleotide sequence shown in SEQ ID NO:10 such that it can hybridize to the nucleotide sequence shown in SEQ ID NO:10, thereby forming a stable duplex.

In still another preferred embodiment, an isolated nucleic acid molecule of the present invention comprises a nucleotide sequence which is at least about 30%, 35%, 40%, 45%, 50%, 55%, 60%, 65%, 70%, 75%, 80%, 85%, 90%, 95%, 98% or more identical to the entire length of the nucleotide sequence shown in SEQ ID NO:10, or a portion of any of this nucleotide sequence.

Moreover, the nucleic acid molecule of the invention can comprise only a portion of the nucleic acid sequence of SEQ ID NO:10, for example, a fragment which can be used as a probe or primer or a fragment encoding a portion of a 17906 protein, e.g., a biologically active portion of a 17906 protein. The nucleotide sequence determined from the cloning of the 17906 gene allows for the generation of probes and primers designed for use in identifying and/or cloning other 17906 family members, as well as 17906 homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:10, of an anti-sense sequence of SEQ ID NO:10, or of a naturally occurring allelic variant or mutant of SEQ ID NO:10. In one embodiment, a nucleic acid molecule of the present invention comprises a nucleotide sequence which is greater than 100, 100–200, 200–300, 300–400, 400–500, 500–600, 600–700, 700–800, or more nucleotides in length and hybridizes under stringent hybridization conditions to a nucleic acid molecule of SEQ ID NO:10.

Probes based on the 17906 nucleotide sequence can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a 17906 protein, such as by measuring a level of a 17906-encoding nucleic acid in a sample of cells from a subject e.g., detecting 17906 mRNA levels or determining whether a genomic 17906 gene has been mutated or deleted.

A nucleic acid fragment encoding a "biologically active portion of a 17906 protein" can be prepared by isolating a portion of the nucleotide sequence of SEQ ID NO:10 which encodes a polypeptide having a 17906 biological activity (the biological activities of the 17906 protein is described herein), expressing the encoded portion of the 17906 protein (e.g., by recombinant expression in vitro) and assessing the activity of the encoded portion of the 17906 protein.

The methods of the invention further encompass nucleic acid molecules that differ from the nucleotide sequence shown in SEQ ID NO:10, due to degeneracy of the genetic code and thus encode the same 17906 protein as those encoded by the nucleotide sequence shown in SEQ ID NO:10. In another embodiment, an isolated nucleic acid molecule of the invention has a nucleotide sequence encoding a protein having an amino acid sequence shown in SEQ ID NO:11.

In addition to the 17906 nucleotide sequence shown in SEQ ID NO:10, it will be appreciated by those skilled in the art that DNA sequence polymorphisms that lead to changes in the amino acid sequences of the 17906 protein may exist within a population (e.g., the human population). Such genetic polymorphism in the 17906 gene may exist among individuals within a population due to natural allelic variation. As used herein, the terms "gene" and "recombinant gene" refer to nucleic acid molecules which include an open reading frame encoding a 17906 protein, preferably a mammalian 17906 protein, and can further include non-coding regulatory sequences, and introns.

Allelic variants of human 17906 include both functional and non-functional 17906 proteins. Functional allelic variants are naturally occurring amino acid sequence variants of the human 17906 protein that maintain the ability to bind a 17906 ligand or substrate and/or modulate cell proliferation and/or migration mechanisms. Functional allelic variants will typically contain only conservative substitution of one or more amino acids of SEQ ID NO:11, or substitution, deletion or insertion of non-critical residues in non-critical regions of the protein.

Non-functional allelic variants are naturally occurring amino acid sequence variants of the human 17906 protein that do not have the ability to either bind a 17906 ligand or substrate and/or modulate cell proliferation and/or migration mechanisms. Non-functional allelic variants will typically contain a non-conservative substitution, a deletion, or insertion or premature truncation of the amino acid sequence of SEQ ID NO:10, or a substitution, insertion or deletion in critical residues or critical regions.

The methods of the present invention may further use non-human orthologues of the human 17906 protein. Orthologues of the human 17906 protein are proteins that are isolated from non-human organisms and possess the same 17906 ligand binding and/or modulation of cell proliferation and/or migration mechanisms of the human 17906 protein. Orthologues of the human 17906 protein can readily be identified as comprising an amino acid sequence that is substantially identical to SEQ ID NO:11.

Moreover, nucleic acid molecules encoding other 17906 family members and, thus, which have a nucleotide sequence which differs from the 17906 sequence of SEQ ID NO:10 are intended to be within the scope of the invention. For example, another 17906 cDNA can be identified based on the nucleotide sequence of human 17906. Moreover, nucleic acid molecules encoding 17906 proteins from different species, and which, thus, have a nucleotide sequence which differs from the 17906 sequence of SEQ ID NO:10 are intended to be within the scope of the invention. For example, a mouse 17906 cDNA can be identified based on the nucleotide sequence of human 17906.

Nucleic acid molecules corresponding to natural allelic variants and homologues of the 17906 cDNA of the invention can be isolated based on their homology to the 17906 nucleic acid disclosed herein using the cDNAs disclosed herein, or a portion thereof, as a hybridization probe according to standard hybridization techniques under stringent hybridization conditions. Nucleic acid molecules corresponding to natural allelic variants and homologues of the 17906 cDNA of the invention can further be isolated by mapping to the same chromosome or locus as the 17906 gene.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:10. In other embodiment, the nucleic acid is at least 30, 50, 100, 150, 200, 250, 300, 350, 400, 450, 500, 550, 600, 650, 700, 750, 800, 1000, 1200, or more nucleotides in length. As used herein, the term "hybridizes under stringent conditions" is intended to describe conditions for hybridization and washing under which nucleotide sequences at least 60% identical to each other typically remain hybridized to each other. Preferably, the conditions are such that sequences at least about 70%, more preferably at least about 80%, even more preferably at least about 85% or 90% identical to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50° C., preferably at 55° C., more preferably at 60° C., and even more preferably at 65° C. Ranges intermediate to the above-recited values, e.g., at 60–65° C. or at 55–60° C. are also intended to be encompassed by the present invention. Preferably, an isolated nucleic acid molecule of the invention that hybridizes under stringent conditions to the sequence of SEQ ID NO:10 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the 17906 sequences that may exist in the population, the skilled artisan will further appreciate that changes can be introduced by mutation into the nucleotide sequence of SEQ ID NO:10, thereby leading to changes in the amino acid sequence of the encoded 17906 protein, without altering the functional ability of the 17906 protein. For example, nucleotide substitutions leading to amino acid substitutions at "non-essential" amino acid residues can be made in the sequence of SEQ ID NO:10. A "non-essential" amino acid residue is a residue that can be altered from the wild-type sequence of 17906 (e.g., the sequence of SEQ ID NO:11) without altering the biological activity, whereas an "essential" amino acid residue is required for biological activity. For example, amino acid residues that are conserved among the 17906 proteins of the present invention are predicted to be particularly unamenable to alteration. Furthermore, additional amino acid residues that are conserved between the 17906 proteins of the present invention and other members of the G protein-coupled receptor family are not likely to be amenable to alteration.

Accordingly, the methods of the invention may include the use of nucleic acid molecules encoding 17906 proteins that contain changes in amino acid residues that are not essential for activity. Such 17906 proteins differ in amino acid sequence from SEQ ID NO:11, yet retain biological activity. In one embodiment, the isolated nucleic acid molecule comprises a nucleotide sequence encoding a protein, wherein the protein comprises an amino acid sequence at least about 30%, 35%, 40%, 45%, 50%, 55%, 60%, 65%, 70%, 75%, 80%, 85%, 90%, 95%, 98% or more identical to SEQ ID NO:11.

An isolated nucleic acid molecule encoding a 17906 protein identical to the protein of SEQ ID NO:11 can be created by introducing one or more nucleotide substitutions, additions or deletions into the nucleotide sequence of SEQ ID NO:10 such that one or more amino acid substitutions, additions or deletions are introduced into the encoded protein. Mutations can be introduced into SEQ ID NO:10 by standard techniques, such as site-directed mutagenesis and PCR-mediated mutagenesis. Preferably, conservative amino acid substitutions are made at one or more predicted nonessential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a 17906 protein is preferably replaced with another amino acid residue from the same side chain family. Alternatively, in another embodiment, mutations can be introduced randomly along all or part of a 17906 coding sequence, such as by saturation mutagenesis, and the resultant mutants can be screened for 17906 biological activity to identify mutants that retain activity. Following mutagenesis of SEQ ID NO:10, the encoded protein can be expressed recombinantly and the activity of the protein can be determined.

In a preferred embodiment, a mutant 17906 protein can be assayed for the ability to (1) interact with a non-17906 protein molecule, e.g., a 17906 ligand or substrate; (2) activate a 17906-dependent signal transduction pathway; or (3) modulate cell proliferation and/or migration mechanisms, or modulate the expression of cell surface adhesion molecules.

In addition to the nucleic acid molecules encoding 17906 proteins described herein, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire 17906 coding strand, or to only a portion thereof. In one embodiment, an antisense nucleic acid molecule is antisense to a "coding region" of the coding strand of a nucleotide sequence encoding 17906. The term "coding region" refers to the region of the nucleotide sequence comprising codons which are translated into amino acid residues (e.g., the coding region of human 17906 corresponds to nucleotides 8-1273 of SEQ ID NO:10). In another embodiment, the antisense nucleic acid molecule is antisense to a "noncoding region" of the coding strand of a nucleotide sequence encoding 17906. The term "noncoding region" refers to 5' and 3' sequences which flank the coding region that are not translated into amino acids (i.e., also referred to as 5' and 3' untranslated regions).

Given the coding strand sequences encoding 17906 disclosed herein (e.g., nucleotides 8-1273 of SEQ ID NO:10), antisense nucleic acids of the invention can be designed according to the rules of Watson and Crick base pairing. The antisense nucleic acid molecule can be complementary to the entire coding region of 17906 mRNA, but more preferably is an oligonucleotide which is antisense to only a portion of the coding or noncoding region of 17906 mRNA. For example, the antisense oligonucleotide can be complementary to the region surrounding the translation start site of 17906 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

In yet another embodiment, the 17906 nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. Proc. Natl. Acad. Sci. 93: 14670–675.

PNAs of 17906 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 17906 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of 17906 can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of 17906 nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res*. 24 (17): 3357–63. For example, a DNA chain can be synthesized on a solid support using standard phosphoramidite coupling chemistry and modified nucleoside analogs, e.g., 5'-(4-methoxytrityl) amino-5'-deoxy-thymidine phosphoramidite, can be used as a between the PNA and the 5' end of DNA (Mag, M. et al. (1989) *Nucleic Acid Res*. 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett*. 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. W088/09810) or the blood-brain barrier (see, e.g., PCT Publication No. W089/10134). In addition, oligonucleotides can be modified with hybridization-triggered cleavage agents (See, e.g., Krol et al. (1988) *Bio-Techniques* 6:958–976) or intercalating agents. (See, e.g., Zon (1988) *Pharm. Res*. 5:539–549). To this end, the oligonucleotide may be conjugated to another molecule, (e.g., a peptide, hybridization triggered cross-linking agent, transport agent, or hybridization-triggered cleavage agent).

Isolated 17906 Proteins and Anti-17906 Antibodies

The methods of the invention include the use of isolated 17906 proteins, and biologically active portions thereof, as well as polypeptide fragments suitable for use as immunogens to raise anti-17906 antibodies.

Isolated proteins of the present invention, preferably 17906 proteins, have an amino acid sequence sufficiently identical to the amino acid sequence of SEQ ID NO:11, or are encoded by a nucleotide sequence sufficiently identical to SEQ ID NO:10. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50% homology, preferably 60% homology, more preferably 70%–80%, and even more preferably 90–95% homology across the amino acid sequences of the domains and contain at least one and preferably two structural domains or motifs, are defined herein as sufficiently identical. Furthermore, amino acid or nucleotide sequences which share at least 30%, 40%, or 50%, preferably 60%, more preferably 70–80%, or 90–95% homology and share a common functional activity are defined herein as sufficiently identical.

As used interchangeably herein, a "17906 activity", "biological activity of 17906" or "functional activity of 17906", refers to an activity exerted by a 17906 protein, polypeptide or nucleic acid molecule on a 17906 responsive cell (e.g., a bone cell) or tissue, or on a 17906 protein substrate, as determined in vivo, or in vitro, according to standard techniques. In one embodiment, a 17906 activity is a direct activity, such as an association with a 17906 target molecule. As used herein, a "target molecule" or "binding partner" is a molecule with which a 17906 protein binds or interacts in nature, such that 17906-mediated function is achieved. A 17906 target molecule can be a non-17906 molecule or a 17906 protein or polypeptide of the present invention. In an exemplary embodiment, a 17906 target molecule is a 17906 ligand. Alternatively, a 17906 activity is an indirect activity, such as a cellular signaling activity mediated by interaction of the 17906 protein with a 17906 ligand. Preferably, a 17906 activity is the ability to act as a signal transduction molecule and to modulate bone cell proliferation, differentiation, and/or migration. Accordingly, another embodiment of the invention features isolated 17906 proteins and polypeptides having a 17906 activity.

In one embodiment, native 17906 proteins can be isolated from cells or tissue sources by an appropriate purification scheme using standard protein purification techniques. In another embodiment, 17906 proteins are produced by recombinant DNA techniques. Alternative to recombinant expression, a 17906 protein or polypeptide can be synthesized chemically using standard peptide synthesis techniques.

An "isolated" or "purified" protein or biologically active portion thereof is substantially free of cellular material or other contaminating proteins from the cell or tissue source from which the 17906 protein is derived, or substantially free from chemical precursors or other chemicals when chemically synthesized. The language "substantially free of cellular material" includes preparations of 17906 protein in which the protein is separated from cellular components of the cells from which it is isolated or recombinantly produced. In one embodiment, the language "substantially free of cellular material" includes preparations of 17906 protein having less than about 30% (by dry weight) of non-17906 protein (also referred to herein as a "contaminating protein"), more preferably less than about 20% of non-17906 protein, still more preferably less than about 10% of non-17906 protein, and most preferably less than about 5% non-17906 protein. When the 17906 protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of 17906 protein in which the protein is separated from chemical precursors or other chemicals which are involved in the synthesis of the protein. In one embodiment, the language "substantially free of chemical precursors or other chemicals" includes preparations of 17906 protein having less than about 30% (by dry weight) of chemical precursors or non-17906 chemicals, more preferably less than about 20% chemical precursors or non-17906 chemicals, still more preferably less than about 10% chemical precursors or non-17906 chemicals, and most preferably less than about 5% chemical precursors or non-17906 chemicals.

As used herein, a "biologically active portion" of a 17906 protein includes a fragment of a 17906 protein which participates in an interaction between a 17906 molecule and a non-17906 molecule. Biologically active portions of a 17906 protein include peptides comprising amino acid sequences sufficiently identical to or derived from the amino acid sequence of the 17906 protein, e.g., the amino acid sequence shown in SEQ ID NO:11, which include less amino acids than the full length 17906 protein, and exhibit at least one activity of a 17906 protein. Typically, biologically active portions comprise a domain or motif with at least one activity of the 17906 protein, e.g., modulating cell proliferation mechanisms. A biologically active portion of a 17906 protein can be a polypeptide which is, for example, 10, 25, 50, 100, 200, or more amino acids in length. Biologically active portions of a 17906 protein can be used as targets for developing agents which modulate a 17906 mediated activity, e.g., a cell proliferation mechanism. A biologically active portion of a 17906 protein comprises a protein in which regions of the protein are deleted, can be prepared by recombinant techniques and evaluated for one or more of the functional activities of a native 17906 protein.

In a preferred embodiment, the 17906 protein has an amino acid sequence shown in SEQ ID NO:11. In other embodiments, the 17906 protein is substantially identical to SEQ ID NO:11, and retains the functional activity of the protein of SEQ ID NO:11, yet differs in amino acid sequence due to natural allelic variation or mutagenesis, as described in detail in subsection I above. Accordingly, in another embodiment, the 17906 protein is a protein which comprises an amino acid sequence at least about 30%, 35%, 40%, 45%, 50%, 55%, 60%, 65%, 70%, 75%, 80%, 85%, 90%, 95%, 98% or more identical to SEQ ID NO:11.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the 17906 amino acid sequence of SEQ ID NO:11 having 516 amino acid residues, at least 136, preferably at least 181, more preferably at least 227, even more preferably at least 272, and even more preferably at least 317, 362 or 408 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444–453 (1970)) algorithm which has been incorporated into the GAP program in the GCG software package, using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (Myers and Miller, *Comput. Appl. Biosci.* 4:11–17 (1988)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to 17906 nucleic acid molecules of the invention. BLAST protein searches can be performed with the XBLAST program, score=100, wordlength=3 to obtain amino acid sequences homologous to 17906 protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used.

The methods of the invention may also use 17906 chimeric or fusion proteins. As used herein, a 17906 "chimeric protein" or "fusion protein" comprises a 17906 polypeptide operatively linked to a non-17906 polypeptide. A "17906 polypeptide" refers to a polypeptide having an amino acid sequence corresponding to 17906, whereas a "non-17906 polypeptide" refers to a polypeptide having an amino acid sequence corresponding to a protein which is not substantially homologous to the 17906 protein, e.g., a protein which is different from the 17906 protein and which is derived from the same or a different organism. Within a 17906 fusion protein the 17906 polypeptide can correspond to all or a portion of a 17906 protein. In a preferred embodiment, a 17906 fusion protein comprises at least one biologically active portion of a 17906 protein. In another preferred embodiment, a 17906 fusion protein comprises at least two biologically active portions of a 17906 protein. Within the fusion protein, the term "operatively linked" is intended to indicate that the 17906 polypeptide and the non-17906 polypeptide are fused in-frame to each other. The non-17906 polypeptide can be fused to the N-terminus or C-terminus of the 17906 polypeptide.

For example, in one embodiment, the fusion protein is a GST-17906 fusion protein in which the 17906 sequences are fused to the C-terminus of the GST sequences. Such fusion proteins can facilitate the purification of recombinant 17906. In another embodiment, the fusion protein is a 17906 protein containing a heterologous signal sequence at its N-terminus. In certain host cells (e.g., mammalian host cells), expression and/or secretion of 17906 can be increased through use of a heterologous signal sequence.

The 17906 fusion proteins of the invention can be incorporated into pharmaceutical compositions and administered to a subject in vivo. The 17906 fusion proteins can be used to affect the bioavailability of a 17906 ligand. Use of 17906 fusion proteins may be useful therapeutically for the treatment of disorders caused by, for example, (i) aberrant modification or mutation of a gene encoding a 17906 protein; (ii) mis-regulation of the 17906 gene; and (iii) aberrant post-translational modification of a 17906 protein. In one embodiment, a 17906 fusion protein may be used to treat a bone associated disorder. In another embodiment, a 17906 fusion protein may be used to treat a bone cell disorder.

Moreover, the 17906-fusion proteins of the invention can be used as immunogens to produce anti-17906 antibodies in a subject, to purify 17906 ligands and in screening assays to identify molecules which inhibit the interaction of 17906 with a 17906 substrate.

Preferably, a 17906 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A 17906-encoding nucleic acid can be cloned into such an expression vector such that the fusion moiety is linked in-frame to the 17906 protein.

The methods of the present invention may also include the use of variants of the 17906 protein which function as either 17906 agonists (mimetics) or as 17906 antagonists. Variants of the 17906 protein can be generated by mutagenesis, e.g., discrete point mutation or truncation of a 17906 protein. An agonist of the 17906 protein can retain substantially the same, or a subset, of the biological activities of the naturally occurring form of a 17906 protein. An antagonist of a 17906 protein can inhibit one or more of the activities of the naturally occurring form of the 17906 protein by, for example, competitively modulating a 17906-mediated activity of a 17906 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the 17906 protein.

In one embodiment, variants of a 17906 protein which function as either 17906 agonists (mimetics) or as 17906 antagonists can be identified by screening combinatorial libraries of mutants, e.g., truncation mutants, of a 17906 protein for 17906 protein agonist or antagonist activity. In one embodiment, a variegated library of 17906 variants is generated by combinatorial mutagenesis at the nucleic acid level and is encoded by a variegated gene library. A variegated library of 17906 variants can be produced by, for example, enzymatically ligating a mixture of synthetic oligonucleotides into gene sequences such that a degenerate set of potential 17906 sequences is expressible as individual polypeptides, or alternatively, as a set of larger fusion proteins (e.g., for phage display) containing the set of 17906 sequences therein. There are a variety of methods which can be used to produce libraries of potential 17906 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential 17906 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a 17906 protein coding sequence can be used to generate a variegated population of 17906 fragments for screening and subsequent selection of variants of a 17906 protein. In one embodiment, a library of coding sequence fragments can be generated by treating a double stranded PCR fragment of a 17906 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the 17906 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of 17906 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify 17906 variants (Arkin and Yourvan (1992) *Proc. Natl. Acad. Sci. USA* 89:7811–7815; Delgrave et al. (1993) *Protein Engineering* 6(3):327–331).

In one embodiment, cell based assays can be exploited to analyze a variegated 17906 library. For example, a library of expression vectors can be transfected into a cell line, e.g., a bone cell line, which ordinarily responds to a 17906 ligand in a particular 17906-dependent manner. The transfected cells are then contacted with a 17906 ligand and the effect of expression of the mutant on signaling by the 17906 receptor can be detected, e.g., by monitoring the generation of an intracellular second messenger (e.g., calcium, cAMP, $IP_3$, or diacylglycerol), the phosphorylation profile of intracellular proteins, cell proliferation and/or migration, the expression profile of cell surface adhesion molecules, or the activity of a 17906-regulated transcription factor. Plasmid DNA can then be recovered from the cells which score for inhibition, or alternatively, potentiation of signaling by the 17906 receptor, and the individual clones further characterized.

An isolated 17906 protein, or a portion or fragment thereof, can be used as an immunogen to generate antibodies that bind 17906 using standard techniques for polyclonal and monoclonal antibody preparation. A full-length 17906 protein can be used or, alternatively, the invention provides antigenic peptide fragments of 17906 for use as immunogens. The antigenic peptide of 17906 comprises at least 8 amino acid residues of the amino acid sequence shown in SEQ ID NO:11 and encompasses an epitope of 17906 such that an antibody raised against the peptide forms a specific immune complex with 17906. Preferably, the antigenic peptide comprises at least 10 amino acid residues, more preferably at least 15 amino acid residues, even more preferably at least 20 amino acid residues, and most preferably at least 30 amino acid residues. Preferred epitopes encompassed by the antigenic peptide are regions of 17906 that are located on the surface of the protein, e.g., hydrophilic regions, as well as regions with high antigenicity.

A 17906 immunogen typically is used to prepare antibodies by immunizing a suitable subject, (e.g., rabbit, goat, mouse or other mammal) with the immunogen. An appropriate immunogenic preparation can contain, for example, recombinantly expressed 17906 protein or a chemically synthesized 17906 polypeptide. The preparation can further include an adjuvant, such as Freund's complete or incomplete adjuvant, or similar immunostimulatory agent. Immunization of a suitable subject with an immunogenic 17906 preparation induces a polyclonal anti-17906 antibody response.

Accordingly, another aspect of the invention pertains to anti-17906 antibodies. The term "antibody" as used herein refers to immunoglobulin molecules and immunologically active portions of immunoglobulin molecules, i.e., molecules that contain an antigen binding site which specifically binds (immunoreacts with) an antigen, such as 17906. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind 17906. The term "monoclonal antibody" or "monoclonal antibody composition", as used herein, refers to a population of antibody molecules that contain only one species of an antigen binding site capable of immunoreacting with a particular epitope of 17906. A monoclonal antibody composition thus typically displays a single binding affinity for a particular 17906 protein with which it immunoreacts.

Polyclonal anti-17906 antibodies can be prepared as described above by immunizing a suitable subject with a 17906 immunogen. The anti-17906 antibody titer in the immunized subject can be monitored over time by standard techniques, such as with an enzyme linked immunosorbent assay (ELISA) using immobilized 17906. If desired, the antibody molecules directed against 17906 can be isolated from the mammal (e.g., from the blood) and further purified by well known techniques, such as protein A chromatography to obtain the IgG fraction. At an appropriate time after immunization, e.g., when the anti-17906 antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.* 255:4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with a 17906 immunogen as described above, and the culture supernatants of the resulting hybridoma cells are screened to identify a hybridoma producing a monoclonal antibody that binds 17906.

Any of the many well known protocols used for fusing lymphocytes and immortalized cell lines can be applied for the purpose of generating an anti-17906 monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind 17906, e.g., using a standard ELISA assay.

Alternative to preparing monoclonal antibody-secreting hybridomas, a monoclonal anti-17906 antibody can be identified and isolated by screening a recombinant combinatorial immunoglobulin library (e.g., an antibody phage display library) with 17906 to thereby isolate immunoglobulin library members that bind 17906. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J* 12:725–734; Hawkins et al. (1992) *J. Mol. Biol.* 226: 889–896; Clarkson et al. (1991) *Nature* 352:624–628; Gram et al. (1992) *Proc. Natl. Acad. Sci. USA* 89:3576–3580; Garrad et al. (1991) *Bio/Technology* 9:1373–1377; Hoogenboom et al. (1991) *Nuc. Acid Res.* 19:4133–4137; Barbas et al. (1991) *Proc. Natl. Acad. Sci. USA* 88:7978–7982; and McCafferty et al. *Nature* (1990) 348:552–554.

Additionally, recombinant anti-17906 antibodies, such as chimeric and humanized monoclonal antibodies, comprising both human and non-human portions, which can be made using standard recombinant DNA techniques, can also be used in the methods of the present invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125, 023; Better et al. (1988) *Science* 240:1041–1043; Liu et al. (1987) *Proc. Natl. Acad. Sci. USA* 84:3439–3443; Liu et al. (1987)*J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314: 446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

An anti-17906 antibody (e.g., monoclonal antibody) can be used to isolate 17906 by standard techniques, such as affinity chromatography or immunoprecipitation. An anti-17906 antibody can facilitate the purification of natural 17906 from cells and of recombinantly produced 17906 expressed in host cells. Moreover, an anti-17906 antibody can be used to detect 17906 protein (e.g., in a cellular lysate or cell supernatant) in order to evaluate the abundance and pattern of expression of the 17906 protein. Anti-17906 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

This invention is further illustrated by the following examples which should not be construed as limiting. The contents of all references, patents and published patent applications cited throughout this application, as well as the Sequence Listing, are incorporated herein by reference.

EXAMPLES

Example 1

Regulation of 17906 Expression in Cells Involved in Osteogenesis

TaqMan real-time quantitative RT-PCR was used to detect the presence of RNA transcript corresponding to human 17906 in several tissues. It was found that the corresponding orthologs of 17906 are expressed in a variety of tissues such as epithelial, fibroblast, osteoblast and glial cells, as well as, breast tumor, brain cortex and brain hypothalamus tissues.

Reverse Transcriptase PCR (RT-PCR) was used to detect the presence of RNA transcript corresponding to human 17906 in RNA prepared from cells and tissues related to osteoblasts. Expression of 17906 was assessed in several tissues. A relatively low expression of the transcript was found in differentiated osteoblasts, and relatively high expression of the transcript was found in primary cultured osteoblasts.

Relative expression levels of the 17906 was assessed in osteogenic cells and adipogenic cells using TaqMan PCR.

TaqMan PCR was also used to assess the expression of 17906 in several cellular models of osteoporosis.

Relative mRNA expression levels of the 17906 gene was also assessed in osteoblasts stimulated with parathyroid hormone (PTH), interleukin-1α (IL-1α), and dexamethasone (DEX).

Example 2

Expression of Recombinant 17906 Protein in Bacterial Cells

In this example, 17906 is expressed as a recombinant glutathione-S-transferase (GST) fusion polypeptide in *E. coli* and the fusion polypeptide is isolated and characterized. Specifically, 17906 is fused to GST and this fusion polypeptide is expressed in *E. coli*, e.g., strain PEB199. Expression of the GST-17906 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide

Example 3

Expression of Recombinant 17906 Protein in Cos Cells

To express the 17906 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 17906 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the 17906 DNA sequence is amplified by PCR using two primers. The 5' primer contains the restriction site of interest followed by approximately twenty nucleotides of the 17906 coding sequence starting from the initiation codon; the 3' end sequence contains complementary sequences to the other restriction site of interest, a translation stop codon, the HA tag or FLAG tag and the last 20 nucleotides of the 17906 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the 17906 gene is inserted in the correct orientation. The ligation mixture is transformed into *E. coli* cells (strains HB101, DH5□, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 17906-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989. The expression of the VR-3 or VR-5 polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labelled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 17906 coding sequence is cloned directly into the polylinker of the pCDNA/Amp vector using the appropriate restriction sites. The resulting plasmid is transfected into COS cells in the manner described above, and the expression of the 17906 polypeptide is detected by radiolabelling and immunoprecipitation using a 17906 specific monoclonal antibody.

V. METHODS AND COMPOSITIONS FOR THE DIAGNOSIS AND TREATMENT OF HEMATOLOGICAL DISORDERS USING 16319

BACKGROUND OF THE INVENTION

Hematological disorders are blood associated disorders. Blood is a highly specialized tissue which carries oxygen and nutrients to all parts of the body and waste products back to the lungs, kidneys and liver for disposal. Thus, blood maintains communication between different parts of the body. Blood is also an essential part of the immune system, crucial to fluid and temperature balance, a hydraulic fluid for certain functions and a highway for hormonal messages.

All blood cells in adults are produced in the bone marrow. Red cells, white cells and platelets are produced in the marrow of bones, especially the vertebrae, ribs, hips, skull and sternum. These essential blood cells fight infection, carry oxygen and help control bleeding. Specifically, red blood cells are disc-shaped cells containing hemoglobin, which enables these cells to pick up and deliver oxygen to all parts of the body. White blood cells are the body's primary defense against infection. They can move out of the blood stream and reach tissues being invaded. Platelets are small blood cells that control bleeding by forming clusters to plug small holes in blood vessels and assist in the clotting process.

Each day the bone marrow generates and releases into the circulation several billion fully-differentiated, functional blood cells. Hematopoiesis is the process by which blood cells develop and differentiate from pluripotent stem cells in the bone marrow. Production of these cells derives from a small stock of quiescent progenitor cells (including the most primitive stem cells and other less primitive but still immature progenitors). The most primitive stem cells have the capacity to generate several billion cells containing all blood lineages. The production of such a large number of cells is achieved by extensive proliferation coupled with successive differentiation steps leading to a balanced production of mature cells.

The production of mature blood cells by the hematopoietic system involves complex interactions between soluble factors, the marrow microenvironment, and hematopoietic progenitors. In particular, hematopoiesis involves a complex interplay of polypeptide growth factors acting via membrane-bound receptors on their target cells. Signaling by growth factors results in cellular proliferation and differentiation, with a response to a particular growth factor often being lineage-specific and/or stage-specific. Development of a single cell type, such as a red blood cell, from a stem cell may require the coordinated action of a plurality of growth factors acting in the proper sequence.

Impaired blood cell production occurs when the proliferation and differentiation of the stem cells or committed cells is disturbed. Impaired blood cell production is the root of hematological disorders. Some of the more common diseases caused by impaired blood cell production, i.e., hematological disorders, include aplastic anemia, hypoplastic anemia, pure red cell aplasia and anemia associated with renal failure or endocrine disorders. Disturbances in the proliferation and differentiation of erythroblasts include defects in DNA synthesis such as impaired utilization of vitamin B12 or folic acid and the megaloblastic anemias, defects in heme or globin synthesis, and anemias of unknown origins such as sideroblastic anemia, anemia associated with chronic infections such as malaria, trypanosomiasis, HIV, hepatitis virus or other viruses, and myelophthisic anemias caused by marrow deficiencies. Impaired blood cell production also affects cancer patients and other autoimmune disease patients who receive bone marrow irradiation or chemotherapy treatment.

Hematological disorders are, thus, a diverse family of disorders embracing clinical and laboratory aspects of a large number of diseases, both malignant and non-malignant. Although some progress has been made in diagnostic and therapeutic strategies to combat hematological disorders, molecular advances are continuing at a rate exceeding the rate of progress in therapeutics. Thus, novel methods for diagnosis and treatment of hematological disorders based on known molecular advances are urgently needed in the field.

SUMMARY OF THE INVENTION

The present invention provides methods and compositions for the diagnosis and treatment of hematological disorders. The present invention is based, at least in part, on the discovery that the 16319 gene, is expressed at high levels in hematopoietic cells of various lineages and stages of differentiation. Specifically, 16319 is expressed in high levels in CD34+ progenitor cells (including stem cells from bone marrow, cord blood and peripheral blood) and this high level of expression is maintained in erythroid cells in vitro and Glycophorin A positive cells in vivo. Thus, the 16319 molecules, by participating in the TGF-β downstream signaling pathway, modulate hematopoietic cell behavior and are useful as targets and therapeutic agents for the modulation of hematopoietic cell activity, e.g., cell proliferation or apoptosis, and the treatment of hematological disorders.

Accordingly, the present invention provides methods for the diagnosis and treatment of hematological diseases including but not limited to apalstic anemia, hemophilia, sickle cell anemia, thalassemia, blood loss and other blood disorders, e.g., blood disorders related to bone marrow irradiation treatments, chemotherapy treatments or compromised kidney function.

In one aspect, the invention provides methods for identifying a compound capable of treating a hematological disorder, e.g., anemia or thalassemia. The method includes assaying the ability of the compound to modulate 16319 nucleic acid expression or 16319 polypeptide activity. In one embodiment, the ability of the compound to modulate nucleic acid expression or 16319 polypeptide activity is determined by detecting modulation of proliferation of a hematopoietic cell. In another embodiment, the ability of the compound to modulate nucleic acid expression or 16319 polypeptide activity is determined by detecting modulation of apoptosis of a hematopoietic cell.

In another aspect, the invention provides methods for identifying a compound capable of modulating a hematological activity, e.g., hematopoietic cell proliferation, differentiation, or cell death. The method includes contacting a cell expressing a 16319 nucleic acid or polypeptide (e.g., a hematopoietic cell) with a test compound and assaying the ability of the test compound to modulate the expression of a 16319 nucleic acid or the activity of a 16319 polypeptide.

Another aspect of the invention provides a method for modulating a hematological activity, e.g., hematopoietic cell proliferation, cell differentiation, or cell death. The method includes contacting a hematopoietic cell with an effective amount of a 16319 modulator, for example, an anti-16319 antibody, a 16319 polypeptide comprising the amino acid sequence of SEQ ID NO:13 or a fragment thereof, a 16319 polypeptide comprising an amino acid sequence which is at least 90 percent identical to the amino acid sequence of SEQ ID NO:13, an isolated naturally occurring allelic variant of a polypeptide consisting of the amino acid sequence of SEQ ID NO:13, a small molecule, an antisense 16319 nucleic acid molecule, a nucleic acid molecule of SEQ ID NO:12 or a fragment thereof, or a ribozyme.

In yet another aspect, the invention features a method for treating a subject having a hematological disorder, e.g., a hematological disorder characterized by aberrant 16319 polypeptide activity or aberrant 16319 nucleic acid expression, e.g., anemia or thalessemia. The method includes administering to the subject a therapeutically effective amount of a 16319 modulator, e.g., in a pharmaceutically acceptable formulation or by using a gene therapy vector. Embodiments of this aspect of the invention include the 16319 modulator being a small molecule, an anti-16319 antibody, a 16319 polypeptide comprising the amino acid sequence of SEQ ID NO:13 or a fragment thereof, a 16319 polypeptide comprising an amino acid sequence which is at least 90 percent identical to the amino acid sequence of SEQ ID NO:13, an isolated naturally occurring allelic variant of a polypeptide consisting of the amino acid sequence of SEQ ID NO:13, an antisense 16319 nucleic acid molecule, a nucleic acid molecule of SEQ ID NO:12 or a fragment thereof, or a ribozyme.

In another aspect, the invention provides a method for modulating, e.g., increasing or decreasing, hematopoietic cell apoptosis in a subject by administering to the subject a 16319 modulator in an amount effective for modulating hematopoietic cell apoptosis.

In another aspect, the invention provides a method for modulating, e.g., increasing or decreasing, hematopoietic cell proliferation in a subject by administering to the subject a 16319 modulator in an amount effective for modulating hematopoietic cell proliferation.

Other features and advantages of the invention will be apparent from the following detailed description and claims.

DETAILED DESCRIPTION OF THE INVENTION

In recent years, studies of growth factors have considerably changed our understanding of hematopoietic regulation and clinical therapeutic strategies. These growth factors often act in cascade, directing cells toward either the cell cycle, cell differentiation or cell death. Transforming growth factor-β (TGF-β) is one of the key regulatory elements of the hematopoietic system. (Jacobsen et al., (1991) *Blood* 78:2239; Snoeck H W et al., (1996) *J. Exp. Med.* 183:705; Van Ranst P C et al., (1996) *Exp. Hematol.* 24:1509) TGF-βs are generally potent growth inhibitors, although they can act in a stimulatory manner on some cell types. Hematopoietic cells, in particular, are potently growth inhibited by TGF-β. (Martin et al., *Ann. N. Y. Acad. Sci.* (1995) 752:300–8.)

TGF-β's anti-proliferative effect on cells is mediated in part by inhibition of phosphorylation of the retinoblastoma protein (RB) and blockage of the cell cycle at the G1/S phase. (Terada et al. (1999) *Kidney International* 56:1378–1390.) The G1 phase of the cell cycle represents the interval in which cells respond maximally to extracellular signals, including mitogens, anti-proliferative factors, matrix adhesive substances, and intercellular contacts. The R point is when cells become committed to duplicating their DNA and undergoing mitosis. Phosphorylation of RB temporally coincides with passage through the R point of the cell cycle. TGF-β's inhibition of RB phosphorylation prevents the cell from exiting the G1 phase and proceeding to the R point for initiation of the determinative stages of replication. (Sundershan, C., et al. (1998) *J. Cell. Physiol.* 176:67–75.) Studies have shown that phosphorylation of RB is initially triggered by holoenzymes composed of cyclin-D subunits. The cyclin-D subunits are induced and assembled into holoenzymes as cells enter the replicative cycle in response to mitogenic stimulation. (Terada et al. (1999) *Kidney International* 56:1378–1390.)

The TGF-β-associated-kinase-1 ("16319") has been shown to be intimately involved in the TGF-β signaling pathway. (Yamaguchi et al., *Science* (1995) 270: 2008–11.) 16319 is a member of the mitogen-activated protein kinase kinase kinase (MAPKKK) family. MAPKs play an important role in transducing extracellular signals into a cellular response and are classically activated by growth factors. (Terada et al., (1999) *Neph. Dial. Transplant.* 14 (supl 1):45–47. As described in Yamaguchi et al. and Terada et al., 16319 is known to participate in the signal transduction pathway of TGF-β. In particular, it has been shown that the TGF-β-16319 pathway significantly reduces the levels of cyclin-D1 in cells by inhibiting cyclin-D1 promoter activity. (Terada et al. (1999) *Nephrol Dial Transplantation* 14 [Suppl 1]:45–47). By reducing the levels of cyclin-D1 in cells, 16319 facilitates the anti-proliferative effects of TGF-β by preventing the phosphorylation of RB which prevents the cell from exiting the G1 phase and proceeding with replication.

The present invention demonstrates that 16319 is expressed at high levels in CD34+ progenitor cells from bone marrow, cord blood and peripheral blood, and that these high levels of expression are maintained in erythroid cells in vitro and in Glycophorin A positive (GPA+) cells in vivo. CD34 is known to be expressed on early lymphohematopoietic stem and progenitor cells and on hematopoietic progenitors derived from fetal yolk sac, embryonic liver, and extra-hepatic embryonic tissues including aorta-associated hematopoietic progenitors in the 5 week human embryo (Nishio et al., (2001) *Exp. Hematol.* 29(1):19–29). Glycophorin A protein is known as a late erythroid lineage specific protein. Thus, the present invention demonstrates a novel association of the 16319 protein with hematopoietic cells of various lineages and at various stages of differentiation. Since 16319 is a known modulator of cell cycle progression, modulation of 16319 allows for the modulation of hematopoietic cell cycle progression. Accordingly, the present invention provides methods and compositions for the diagnosis and treatment of hematological disorders.

As used herein, a "hematological disorder" includes a disease, disorder, or condition which affects a hematopoietic cell or tissue. Hematological disorders include diseases, disorders, or conditions associated with aberrant hematological content or function. Hematological disorders can be characterized by a misregulation (e.g., downregulation or upregulation) of 16319 activity. Examples of hematological disorders include disorders resulting from bone marrow irradiation or chemotherapy treatments for cancer, disorders such as Pernicious Anemia, Hemorrhagic Anemia, Hemolytic Anemia, Aplastic Anemia, Sickle Cell Anemia, Sideroblastic Anemia, Anemia associated with chronic infections such as Malaria, Trypanosomiasis, HIV, Hepatitis virus or other viruses, Myelophthisic Anemias caused by marrow deficiencies, renal failure resulting from Anemia, Anemia, Polycethemia, Infectious Mononucleosis (IM), Acute Non-Lymphocytic Leukemia (ANLL), Acute Myeloid Leukemia (AML), Acute Promyelocytic Leukemia (APL), Acute Myclomonocytic Leukemia (AMMoL), Polycethemia Vera, Lymphoma, Acute Lymphocytic Leukemia (ALL), Chronic Lymphocytic Leukemia, Wilm's Tumor, Ewing's Sarcoma, Retinoblastoma, Hemophilia, disorders associated with an increased risk of Thrombosis, Herpes, Thalessemia, antibody-mediated disorders such as transfusion reactions and Erythroblastosis, mechanical trauma to red blood cells such as micro-angiopathic hemolytic anemias, Thrombotic Thrombocytopenic Purpura and disseminated intravascular coagulation, infections by parasites such as Plasmodium, chemical injuries from, e.g., lead poisoning, and Hypersplenism.

As used herein, "16319" encompasses proteins characterized by their ability to modulate signal transduction to thereby modulate hematopoietic cell proliferation or apoptosis in vitro or in vivo. A representative human 16319 cDNA sequence is shown herein in SEQ ID NO:12, and the corresponding amino acid sequence is shown in SEQ ID NO:13. Those skilled in the art will recognize that the illustrated sequences correspond to a single allele of the human 16319 gene, and that allelic variation is expected to exist. Allelic variants include those containing silent mutations and those in which mutations result in amino acid sequence changes. It will also be evident that one skilled in the art could create additional variants, such as by engineering sites that would facilitate manipulation of the nucleotide sequence using alternative codons, by substitution of codons to produce conservative changes in amino acid sequence, etc. The use of allelic and engineered variant 16319s is contemplated by the present invention. The use of 16319 molecules from non-human species are also contemplated by the present invention.

The present invention provides methods and compositions for the diagnosis and treatment of hematological disorders. The 16319 modulators identified according to the methods of the invention can be used to modulate hematopoietic cell proliferation and are, therefore, useful in treating or diagnosing hematological disorders. For example, inhibition of the activity of a 16319 molecule can cause increased hematopoietic cell proliferation and, therefore, increased blood cell production in a subject, thereby preventing hematological disorders, e.g., aplastic anemia or sickle cell anemia in the subject. Thus, the 16319 modulators used in the methods of the of the invention can be used to treat hematological disorders. The 16319 modulators identified according to the methods of the invention can also be used to inhibit apoptosis of hematopoietic cells, e.g., by inhibiting 16319, thus increasing blood cell production in a subject, thereby preventing hematological disorders, e.g., aplastic anemia or sickle cell anemia in the subject.

Alternatively, stimulation of the activity of a 16319 molecule can cause decreased hematopoietic cell proliferation and, therefore, decreased blood cell production in a subject, thereby preventing hematological disorders, e.g., hemorrhagic anemia, polycethemia, infectious mononucleosis or leukemia in the subject. Thus, the 16319 modulators used in the methods of the of the invention can be used to treat hematological disorders. 16319 modulators can also increase apoptosis of hematopoietic cells, thus decreasing blood cell production in a subject, thereby inhibiting hematological disorders, e.g., hemorrhagic anemia, polycethimia, infectious mononucleosis or leukemia in the subject.

As used interchangeably herein, "16319 activity," "biological activity of 16319" or "functional activity of 16319," includes an activity exerted by a 16319 protein, polypeptide or nucleic acid molecule on a 16319 responsive cell or tissue, e.g., a hematopoietic cell, or on a 16319 protein substrate, as determined in vivo, or in vitro, according to standard techniques. 16319 activity can be a direct activity, such as an association with a 16319-target molecule e.g., RB. As used herein, a "substrate" or "target molecule" or "binding partner" is a molecule with which a 16319 protein binds or interacts in nature, such that 16319-mediated function, e.g., modulation of apoptosis or modulation of cell proliferation, is achieved. A 16319 target molecule can be a non-16319 molecule or a 16319 protein or polypeptide. Examples of such target molecules include proteins in the same signaling path as the 16319 protein, e.g., proteins which may function upstream (including both stimulators and inhibitors of activity) or downstream of the 16319 protein in a pathway involving regulation of hematopoietic cell proliferation or apoptosis. Alternatively, a 16319 activity is an indirect activity, such as a cellular signaling activity mediated by interaction of the 16319 protein with a 16319 target molecule. The biological activities of 16319 are described herein. For example, the 16319 proteins can have one or more of the following activities: (1) they modulate hematopoietic cell proliferation; (2) they modulate apoptosis of hematopoietic cells; (3) they modulate cyclin D levels in a cell; (4) they modulate the phosphorylation state of RB; and (5) they modulate the anti-proliferative effects of TGF-β.

As used herein, the term "hematopoietic cell" includes yolk sac stem cells, primitive erythroid cells, fetal liver cells, fetal spleen cells, fetal bone marrow cells, non-fetal bone marrow cells, megakaryocytes, stem cells, lymphoid stem cells, myeloid stem cells, progenitor cells, progenitor lymphocytes, progenitor T lymphocytes, progenitor B lymphocytes, progenitor erythrocytes, progenitor neutrophils, progenitor eosinophils, progenitor basophils, progenitor monocytes, progenitor mast cells, progenitor platelets, committed lymphocytes, committed T lymphocytes, committed B lymphocytes, committed erythrocytes, committed neutrophils, committed eosinophils, committed basophils, committed monocytes, committed mast cells, committed platelets, differentiated lymphocytes, differentiated T lymphocytes, differentiated B lymphocytes, differentiated erythrocytes, differentiated neutrophils, differentiated eosinophils, differentiated basophils, differentiated monocytes, differentiated mast cells, differentiated platelets, mature lymphocytes, mature T lymphocytes, mature B lymphocytes, mature erythrocytes, mature neutrophils, mature eosinophils, mature basophils, mature monocytes, mature mast cells, and mature platelets.

As used herein, the term "progenitor cell" includes any somatic cell which has the capacity to generate fully differentiated, functional progeny by differentiation and proliferation. Progenitor cells include progenitors from any tissue or organ system, including, but not limited to, blood, nerve, muscle, skin, gut, bone, kidney, liver, pancreas, thymus, and the like. Progenitor cells are distinguished from "committed cells" and "differentiated cells," which are defined as those cells which may or may not have the capacity to proliferate, i.e., self-replicate, but which are unable to undergo further differentiation to a different cell type under normal physiological conditions. Moreover, progenitor cells are further distinguished from abnormal cells such as cancer cells, especially leukemia cells, which proliferate (self-replicate) but which generally do not further differentiate, despite appearing to be immature or undifferentiated.

Progenitor cells include all the cells in a lineage of differentiation and proliferation prior to the most differentiated or the fully mature cell. Thus, for example, progenitors include the skin progenitor in the mature individual, which is capable of differentiation to only one type of cell, but which is itself not fully mature or fully differentiated. Production of mature, functional blood cells results from proliferation and differentiation of "unipotential progenitors," i.e., those progenitors which have the capacity to make only one type of one type of blood cell. For red blood cell production, a progenitor called a "CFU-E" (colony forming unit-erythroid) has the capacity to generate two to 32 progeny cells.

Various other hematopoietic progenitors have been characterized. For example, hematopoietic progenitor cells include those cells which are capable of successive cycles of differentiating and proliferating to yield up to eight different mature hematopoietic cell lineages. At the most primitive or undifferentiated end of the hematopoietic spectrum, hematopoietic progenitor cells include the hematopoietic "stem cells." These rare cells, which represent 1 in 10,000 to 1 in 100,000 of cells in the bone marrow, each have the capacity to generate a billion mature blood cells of all lineages and are responsible for sustaining blood cell production over the life of an animal. They reside in the marrow primarily in a quiescent state and may form identical daughter cells through a process called self-renewal. Accordingly, such an uncommitted progenitor can be described as being "totipotent," i.e., both necessary and sufficient for generating all types of mature blood cells. Progenitor cells which retain a capacity to generate all blood cell lineages but which can not self-renew are termed "pluripotent." Cells which can produce some but not all blood lineages and can not self-renew are termed "multipotent."

As used herein, "hematopoietic cell activity" includes an activity exerted by a hematopoietic cell, or an activity that takes place in a hematopoietic cell. For example, such activities include cellular processes that contribute to the physiological role of hematopoietic cells, such as hematopoiesis, but are not limited to, cell proliferation, differentiation, growth, migration and programmed cell death.

As used herein, the term "modulate" includes alteration of, e.g., by increasing or decreasing the particular parameter being described, e.g., 16319 activity.

As used herein the term "apoptosis" includes programmed cell death which can be characterized using techniques which are known in the art. Apoptotic cell death can be characterized, e.g., by cell shrinkage, membrane blebbing and chromatin condensation culminating in cell fragmentation. Cells undergoing apoptosis also display a characteristic pattern of internucleosomal DNA cleavage.

1. Screening Assays:

The invention provides methods (also referred to herein as "screening assays") for identifying modulators, i.e., candidate or test compounds or agents (e.g., peptides, peptidomimetics, small molecules, ribozymes, or 16319 antisense molecules) which bind to 16319 proteins, have a stimulatory or inhibitory effect on 16319 expression or 16319 activity, or have a stimulatory or inhibitory effect on the expression or activity of a 16319 target molecule. Compounds identified using the assays described herein may be useful for treating hematological disorders.

Candidate/test compounds include, for example, 1) peptides such as soluble peptides, including Ig-tailed fusion peptides and members of random peptide libraries (see, e.g., Lam, K. S. et al. (1991) *Nature* 354:82–84; Houghten, R. et al. (1991) *Nature* 354:84–86) and combinatorial chemistry-derived molecular libraries made of D- and/or L-configuration amino acids; 2) phosphopeptides (e.g., members of random and partially degenerate, directed phosphopeptide libraries, see, e.g., Songyang, Z. et al. (1993) *Cell* 72:767–778); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc Natl Acad Sci USA* 89:1865–1869) or phage (Scott and Smith (1990) *Science* 249:386–390; Devlin (1990) *Science* 249:404–406; Cwirla et al. (1990) *Proc. Natl. Acad. Sci.* 87:6378–6382; Felici (1991) *J. Mol. Biol.* 222:301–310; Ladner supra.).

Assays that may be used to identify compounds that modulate 16319 activity include assays for cytochrome C release from mitochondria during cell apoptosis, e.g., hematopoietic cell apoptosis (as described in, for example, Bossy-Wetzel E. et al. (2000) *Methods in Enzymol.* 322: 235–42); cytofluorometric quantitation of nuclear apoptosis induced in a cell-free system (as described in, for example, Lorenzo H. K. et al. (2000) *Methods in Enzymol.* 322: 198–201); apoptotic nuclease assays (as described in, for example, Hughes F. M. (2000) *Methods in Enzymol.* 322: 47–62); analysis of apoptotic cells, e.g., apoptotic hematopoietic cells, by flow and laser scanning cytometry (as described in, for example, Darzynkiewicz Z. et al. (2000) Methods in Enzymol. 322:18–39); detection of apoptosis by annexin V labeling (as described in, for example, Bossy-Wetzel E. et al. (2000) *Methods in Enzymol.* 322:15–18); transient transfection assays for cell death genes (as described in, for example, Miura M. et al. (2000) *Methods in Enzymol.* 322:480–92); and assays that detect DNA cleavage in apoptotic cells, e.g., apoptotic hematopoietic cells (as described in, for example, Kauffman S. H. et al. (2000) *Methods in Enzymol.* 322:3–15).

Proliferation assays that may be used to identify compounds that modulate 16319 activity include assays using 32D cells (a multi-lineage murine hematopoietic cell line) as described in U.S. Pat. No. 6,231,880, the contents of which are incorporated herein by reference. Cell proliferation assays which measure the growth phenotype of cells with an ablated growth regulatory gene of interest, e.g., 16319 are described in Sudershan, C., et al. (1998) *J. Cell. Physiol.* 176:67–75. The ability of a test compound to modulate 16319 activity may also be determined by monitoring cellular processes such as cell division, protein synthesis, nucleic acid (DNA or RNA) synthesis, nucleic acid (principally DNA) fragmentation and apoptosis.

In one aspect, an assay is a cell-based assay in which a cell which expresses a 16319 protein or biologically active portion thereof (e.g., the 16319 gene lacking the twenty-two amino terminal amino acid residues) of the 16319 protein that is believed to be involved in the modulation of hematopoietic cell proliferation, or modulation of apoptosis of hematopoietic cells, is contacted with a test compound and the ability of the test compound to modulate 16319 activity is determined. In a preferred embodiment, the biologically active portion of the 16319 protein includes a domain or motif that can modulate apoptosis of hematopoietic cells and/or which can modulate hematopoietic cell proliferation. Determining the ability of the test compound to modulate 16319 activity can be accomplished by monitoring, for example, the production of one or more specific metabolites in a cell which expresses 16319 (see, e.g., Saada et al. (2000) *Biochem Biophys. Res. Commun.* 269: 382–386) or by monitoring cell death, cell proliferation, or cell differentiation in the cell. The cell, for example, can be of mammalian origin, e.g., a hematopoietic cell such as a committed erythrocyte or a progenitor cell.

The ability of the test compound to modulate 16319 binding to a substrate or to bind to 16319 can also be determined. Determining the ability of the test compound to modulate 16319 binding to a substrate can be accomplished, for example, by coupling the 16319 substrate with a radioisotope or enzymatic label such that binding of the 16319 substrate to 16319 can be determined by detecting the labeled 16319 substrate in a complex. Alternatively, 16319 could be coupled with a radioisotope or enzymatic label to monitor the ability of a test compound to modulate 16319 binding to a 16319 substrate in a complex. Determining the ability of the test compound to bind 16319 can be accomplished, for example, by coupling the compound with a radioisotope or enzymatic label such that binding of the compound to 16319 can be determined by detecting the labeled 16319 compound in a complex. For example, 16319 substrates can be labeled with $^{125}$I, $^{35}$S, $^{14}$C, or $^{3}$H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound to interact with 16319 without the labeling of any of the interactants. For example, a microphysiometer can be used to detect the interaction of a compound with 16319 without the labeling of either the compound or the 16319 (McConnell, H. M. et al. (1992) *Science* 257:1906–1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 16319.

The ability of a 16319 modulator to modulate, e.g., inhibit or increase, 16319 activity can also be determined through screening assays which identify modulators which either increase or decrease apoptosis and cell proliferation. In one embodiment, the invention provides for a screening assay involving contacting cells which express a 16319 protein or polypeptide with a test compound, and examining the cells for the morphological features of apoptosis. For example, cells expressing a 16319 protein or polypeptide can be contacted with a test compound and nuclearly stained with acridine orange. Subsequently, nuclear DNA can be extracted and analyzed for DNA fragmentation as described in Inohora et al., (1997) *EMBO J.* 16:1686–1694.

To determine whether a test compound modulates 16319 expression, in vitro transcriptional assays can be performed. To perform such an assay, the full length promoter and enhancer of 16319 can be linked to a reporter gene such as chloramphenicol acetyltransferase (CAT) and introduced into host cells. The same host cells can then be transfected with the test compound. The effect of the test compound can be measured by testing CAT activity and comparing it to CAT activity in cells which do not contain the test compound. An increase or decrease in CAT activity indicates a modulation of 16319 expression and is, therefore, an indicator of the ability of the test compound to modulate hematopoietic cell proliferation or apoptosis.

In yet another embodiment, an assay of the present invention is a cell-free assay in which a 16319 protein or biologically active portion thereof (e.g., (e.g., the 16319 gene without the twenty-two amino terminus amino acids) is contacted with a test compound and the ability of the test compound to bind to or to modulate (e.g., stimulate or inhibit) the activity of the 16319 protein or biologically active portion thereof is determined. Preferred biologically active portions of the 16319 proteins to be used in assays of the present invention include fragments which participate in interactions with non-16319 molecules, e.g., fragments with high surface probability scores. Binding of the test compound to the 16319 protein can be determined either directly or indirectly as described above. Determining the ability of the 16319 protein to bind to a test compound can also be accomplished using a technology such as real-time Biomolecular Interaction Analysis (BIA) (Sjolander, S. and Urbaniczky, C. (1991) *Anal. Chem.* 63:2338–2345; Szabo et al. (1995) *Curr. Opin. Struct. Biol.* 5:699–705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In more than one embodiment of the above assay methods of the present invention, it may be desirable to immobilize either 16319 or a 16319 target molecule to facilitate separation of complexed from uncomplexed forms of one or both of the proteins, as well as to accommodate automation of the assay. Binding of a test compound to a 16319 protein, or interaction of a 16319 protein with a 16319 target molecule in the presence and absence of a test compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/16319 fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or 16319 protein, and the mixture incubated under conditions conducive to complex formation (e.g., at physiological conditions for salt and pH). Following incubation, the beads or microtitre plate wells are washed to remove any unbound components, the matrix is immobilized in the case of beads, and complex formation is determined either directly or indirectly, for example, as described above. Alternatively, the complexes can be dissociated from the matrix, and the level of 16319 binding or activity determined using standard techniques.

Other techniques for immobilizing proteins on matrices can also be used in the screening assays of the invention. For example, either a 16319 protein or a 16319 target molecule can be immobilized utilizing conjugation of biotin and streptavidin. Biotinylated 16319 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies which are reactive with 16319 protein or target molecules but which do not interfere with binding of the 16319 protein to its target molecule can be derivatized to the wells of the plate, and unbound target or 16319 protein is trapped in the wells by antibody conjugation. Methods for detecting such complexes, in addition to those described above for the GST-immobilized complexes, include immunodetection of complexes using antibodies reactive with the 16319 protein or target molecule, as well as enzyme-linked assays which rely on detecting an enzymatic activity associated with the 16319 protein or target molecule.

In yet another aspect of the invention, the 16319 protein or fragments thereof (e.g., the N-terminal region of the 16319 protein that is believed to be involved in the regulation of apoptotic activity) can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with 16319 ("16319-binding proteins" or "16319-bp") and are involved in 16319 activity. Such 16319-binding proteins are also likely to be involved in the propagation of signals by the 16319 proteins or 16319 targets as, for example, downstream elements of a 16319-mediated signaling pathway. Alternatively, such 16319-binding proteins are likely to be 16319 inhibitors.

The two-hybrid system is based on the modular nature of most transcription factors, which consist of separable DNA-binding and activation domains. Briefly, the assay utilizes two different DNA constructs. In one construct, the gene that codes for a 16319 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a 16319-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 16319 protein.

In another aspect, the invention pertains to a combination of two or more of the assays described herein. For example, a modulating agent can be identified using a cell-based or a cell-free assay, and the ability of the agent to modulate the activity of a 16319 protein can be confirmed in vivo, e.g., in an animal such as an animal model for aplastic anemia, sickle cell anemia, thalessemia or sideroblastic anemia. Examples of animals that can be used include, for example, the 16319-DN transgenic mouse model described in EP 1127944; the C57 mouse model for testing whether a compound has in vivo activity in stimulating erythropoiesis as described in U.S. Pat. No. 6,231,880 (also describes cell proliferation stimulation induced by hematopoietic growth factors in baboons); the transgenic mouse model for bone marrow transplantation for sickle cell anemia described in lannone, R. et al., (2001) *Blood* 97(12):3960–3965; a rat model for Aplastic Anemia described in Santiago, S. et al. (2001) *Transplant Proc.* 33(4):2600–2602; transgenic animal models to screen for fetal hemoglobin-stimulating compounds as described in Fibach, E. (2001) *Semin Hematol* 38(4):374–381; mouse models for the treatment of autoimmune diseases by hematopoietic stem cell transplantation is described in Ikehara, S. (2001) *Experimental Hematology* 29:661–669 (specifically, mice with thrombocytic purpura, thrombocytopenia, renal failure, hemolytic anemia, systemic lupus erythematosus, hemolytic anemia, sjogren syndrome, rheumatoid arthritis, pancreatitis, sialoadentis, autoimmune hepatitis, myocardial infarcton, insulin-dependent diabetes mellitus, non-insulin-dependent diabetes mellitus and fogal segmental glomerular sclerosis are described); the three mouse models with globin gene mutations resulting in human thalessemia as described in Martinell, J., et al. (1981) *Proc. Natl. Acad. Sci.* 78(8):5056–5060; animal models for X-linked Sideroblastic Anemia are described in Yamamoto, M. et al., (2000) *Intl. J. Hematology Review* 72:157–164; the mouse model for anemic yolk sacs as described in Martin, J. S., et al. (1995) *Ann. N. Y. Acad. Sci.* 752:300–8; various animal models for sickle cell anemia are described in Nagel. R. L. (2001) *Brit J. Hematol.* 112:19–25 (specifically, models with a combination of murine globins and human globin chains, the NYC1 model, the S+S Antilles model, and transgenic models with exclusively human globin chains are described); and animal models of cyclic hematopoiesis as described in Jones, J. B. & Lange, R. D. (1983) *Exp. Hematol.* 11(7):571–580. Additionally, transgenic animals for the Human Beta Globin Gene Locus as described in U.S. Pat. No. 6,231,880 may be used.

Moreover, a 16319 modulator identified as described herein (e.g., an antisense 16319 nucleic acid molecule, a 16319-specific antibody, or a small molecule) can be used in an animal model to determine the efficacy, toxicity, or side effects of treatment with such a modulator. Alternatively, a 16319 modulator identified as described herein can be used in an animal model to determine the mechanism of action of such a modulator.

Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining 16319 protein and/or nucleic acid expression as well as 16319 activity, in the context of a biological sample (e.g., blood) to thereby determine whether an individual is afflicted with a hematological disorder. The invention also provides for prognostic (or predictive) assays for determining whether an individual is at risk of developing a hematological disorder. For example, mutations in a 16319 gene can be assayed for in a biological sample. Such assays can be used for prognostic or predictive purpose to thereby phophylactically treat an individual prior to the onset of a hematological disorder.

Another aspect of the invention pertains to monitoring the influence of 16319 modulators (e.g., anti-16319 antibodies or 16319 ribozymes) on the expression or activity of 16319 in clinical trials.

These and other agents are described in further detail in the following sections.

Diagnostic Assays for Rematological Disorders

To determine whether a subject is afflicted with a hematological disorder, a biological sample may be obtained from a subject and the biological sample may be contacted with a compound or an agent capable of detecting a 16319 protein or nucleic acid (e.g., mRNA or genomic DNA) that encodes a 16319 protein, in the biological sample. A preferred agent for detecting 16319 mRNA or genomic DNA is a labeled nucleic acid probe capable of hybridizing to 16319 mRNA or genomic DNA. The nucleic acid probe can be, for example, the 16319 nucleic acid set forth in SEQ ID NO:12, or a portion thereof, such as an oligonucleotide of at least 15, 20, 25, 30, 25, 40, 45, 50, 100, 250 or 500 nucleotides in length and sufficient to specifically hybridize under stringent conditions to 16319 mRNA or genomic DNA. Other suitable probes for use in the diagnostic assays of the invention are described herein.

A preferred agent for detecting 16319 protein in a sample is an antibody capable of binding to 16319 protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

The term "biological sample" is intended to include tissues (e.g., blood), cells, and biological fluids isolated from a subject, as well as tissues, cells, and fluids present within a subject. That is, the detection method of the invention can be used to detect 16319 mRNA, protein, or genomic DNA in a biological sample in vitro as well as in vivo. For example, in vitro techniques for detection of 16319 mRNA include Northern hybridizations and in situ hybridizations. In vitro techniques for detection of 16319 protein include enzyme linked immunosorbent assays (ELISAs), Western blots, immunoprecipitations and immunofluorescence. In vitro techniques for detection of 16319 genomic DNA include Southern hybridizations. Furthermore, in vivo techniques for detection of 16319 protein include introducing into a subject a labeled anti-16319 antibody. For example, the antibody can be labeled with a radioactive marker whose presence and location in a subject can be detected by standard imaging techniques.

In another embodiment, the methods further involve obtaining a control biological sample from a control subject, contacting the control sample with a compound or agent capable of detecting 16319 protein, mRNA, or genomic DNA, such that the presence of 16319 protein, mRNA or genomic DNA is detected in the biological sample, and comparing the presence of 16319 protein, mRNA or genomic DNA in the control sample with the presence of 16319 protein, mRNA or genomic DNA in the test sample.

Prognostic Assays for Hematological Disorders

The present invention further pertains to methods for identifying subjects having or at risk of developing a hematological disorder associated with aberrant 16319 expression or activity.

As used herein, the term "aberrant" includes a 16319 expression or activity which deviates from the wild type 16319 expression or activity. Aberrant expression or activity includes increased or decreased expression or activity, as well as expression or activity which does not follow the wild type developmental pattern of expression or the subcellular pattern of expression. For example, aberrant 16319 expression or activity is intended to include the cases in which a mutation in the 16319 gene causes the 16319 gene to be under-expressed or over-expressed and situations in which such mutations result in a non-functional 16319 protein or a protein which does not function in a wild-type fashion, e.g., a protein which does not interact with a 16319 substrate, or one which interacts with a non-16319 substrate.

The assays described herein, such as the preceding diagnostic assays or the following assays, can be used to identify a subject having or at risk of developing a hematological disorder, e.g., aplastic anemia, Sickle Cell Anemia, polycythemia or leukemia. A biological sample may be obtained from a subject and tested for the presence or absence of a genetic alteration. For example, such genetic alterations can be detected by ascertaining the existence of at least one of 1) a deletion of one or more nucleotides from a 16319 gene, 2) an addition of one or more nucleotides to a 16319 gene, 3) a substitution of one or more nucleotides of a 16319 gene, 4) a chromosomal rearrangement of a 16319 gene, 5) an alteration in the level of a messenger RNA transcript of a 16319 gene, 6) aberrant modification of a 16319 gene, such as of the methylation pattern of the genomic DNA, 7) the presence of a non-wild type splicing pattern of a messenger RNA transcript of a 16319 gene, 8) a non-wild type level of a 16319-protein, 9) allelic loss of a 16319 gene, and 10) inappropriate post-translational modification of a 16319-protein.

As described herein, there are a large number of assays known in the art which can be used for detecting genetic alterations in a 16319 gene. For example, a genetic alteration in a 16319 gene may be detected using a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in a 16319 gene (see Abravaya et al. (1995) *Nucleic Acids Res.* 23:675–682). This method includes collecting a biological sample from a subject, isolating nucleic acid (e.g., genomic DNA, mRNA or both) from the sample, contacting the nucleic acid sample with one or more primers which specifically hybridize to a 16319 gene under conditions such that hybridization and amplification of the 16319 gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) *Proc. Natl. Acad. Sci. USA* 87:1874–1878), transcriptional amplification system (Kwoh, D. Y. et al. (1989) *Proc. Natl. Acad. Sci. USA* 86:1173–1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a 16319 gene from a biological sample can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 16319 can be identified by hybridizing biological sample derived and control nucleic acids, e.g., DNA or RNA, to high density arrays containing hundreds or thousands of oligonucleotide probes (Cronin, M. T. et al. (1996) *Human Mutation* 7:244–255; Kozal, M. J. et al. (1996) *Nature Medicine* 2:753–759). For example, genetic mutations in 16319 can be identified in two dimensional arrays containing light-generated DNA probes as described in Cronin, M. T. et al. (1996) supra. Briefly, a first hybridization array of probes can be used to scan through long stretches of DNA in a sample and control to identify base changes between the sequences by making linear arrays of sequential, overlapping probes. This step allows for the identification of point mutations. This step is followed by a second hybridization array that allows for the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 16319 gene in a biological sample and detect mutations by comparing the sequence of the 16319 in the biological sample with the corresponding wild-type (control) sequence. Examples of sequencing reactions include those based on techniques developed by Maxam and Gilbert (1977) *Proc. Natl. Acad. Sci. USA* 74:560) or Sanger (1977) *Proc. Natl. Acad. Sci. USA* 74:5463). It is also contemplated that any of a variety of automated sequencing procedures can be utilized when performing the diagnostic assays (Naeve, C. W. (1995) *Biotechniques* 19:448–53), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the 16319 gene include methods in which protection from cleavage agents is used to detect mismatched bases in RNA/RNA or RNA/DNA heteroduplexes (Myers et al. (1985) *Science* 230:1242). In general, the art technique of "mismatch cleavage"

starts by providing heteroduplexes formed by hybridizing (labeled) RNA or DNA containing the wild-type 16319 sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad Sci USA* 85:4397 and Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in 16319 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a 16319 sequence, e.g., a wild-type 16319 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in 16319 genes. For example, single strand conformation polymorphism (SSCP) may be used to detect differences in electrophoretic mobility between mutant and wild type nucleic acids (Orita et al. (1989) *Proc Natl. Acad. Sci USA*: 86:2766; see also Cotton (1993) *Mutat. Res.* 285:125–144 and Hayashi (1992) *Genet. Anal. Tech. Appl.* 9:73–79). Single-stranded DNA fragments of sample and control 16319 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res*. 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

Furthermore, the prognostic assays described herein can be used to determine whether a subject can be administered a 16319 modulator (e.g., an agonist, antagonist, peptidomimetic, protein, peptide, nucleic acid, or small molecule) to effectively treat a hematological disorder.

Monitoring of Effects During Clinical Trials

The present invention further provides methods for determining the effectiveness of a 16319 modulator (e.g., a 16319 modulator identified herein) in treating a hematological disorder in a subject. For example, the effectiveness of a 16319 modulator in increasing 16319 gene expression, protein levels, or in upregulating 16319 activity, can be monitored in clinical trials of subjects exhibiting decreased 16319 gene expression, protein levels, or downregulated 16319 activity. Alternatively, the effectiveness of a 16319 modulator in decreasing 16319 gene expression, protein levels, or in downregulating 16319 activity, can be monitored in clinical trials of subjects exhibiting increased 16319 gene expression, protein levels, or 16319 activity. In such clinical trials, the expression or activity of a 16319 gene, and preferably, other genes that have been implicated in, for example, a hematological disorder can be used as a "read out" or marker of the phenotype of a particular cell.

For example, and not by way of limitation, genes, including 16319, that are modulated in cells by treatment with an agent which modulates 16319 activity (e.g., identified in a screening assay as described herein) can be identified. Thus, to study the effect of agents which modulate 16319 activity on subjects suffering from a hematological disorder in, for example, a clinical trial, cells can be isolated and RNA prepared and analyzed for the levels of expression of 16319 and other genes implicated in the hematological disorder. The levels of gene expression (e.g., a gene expression pattern) can be quantified by Northern blot analysis or RT-PCR, as described herein, or alternatively by measuring the amount of protein produced, by one of the methods described herein, or by measuring the levels of activity of 16319 or other genes. In this way, the gene expression pattern can serve as a marker, indicative of the physiological response of the cells to the agent which modulates 16319 activity. This response state may be determined before, and at various points during treatment of the individual with the agent which modulates 16319 activity.

In a preferred embodiment, the present invention provides a method for monitoring the effectiveness of treatment of a subject with an agent which modulates 16319 activity (e.g., an agonist, antagonist, peptidomimetic, protein, peptide, nucleic acid, or small molecule identified by the screening assays described herein) including the steps of (i) obtaining a pre-administration sample from a subject prior to administration of the agent; (ii) detecting the level of expression of a 16319 protein, mRNA, or genomic DNA in the pre-administration sample; (iii) obtaining one or more post-administration samples from the subject; (iv) detecting the level of expression or activity of the 16319 protein, mRNA, or genomic DNA in the post-administration samples; (v) comparing the level of expression or activity of the 16319 protein, mRNA, or genomic DNA in the pre-administration sample with the 16319 protein, mRNA, or genomic DNA in the post administration sample or samples; and (vi) altering the administration of the agent to the subject accordingly. For example, increased administration of the agent may be desirable to increase the expression or activity of 16319 to higher levels than detected, i.e., to increase the effectiveness of the agent. Alternatively, decreased administration of the agent may be desirable to decrease expression or activity of 16319 to lower levels than detected, i.e. to decrease the effectiveness of the agent. According to such an embodiment, 16319 expression or activity may be used as an indicator of the effectiveness of an agent, even in the absence of an observable phenotypic response.

Methods of Treatment of Subjects Suffering from Hematological Disorders

The present invention provides for both prophylactic and therapeutic methods of treating a subject, e.g., a human, at risk of (or susceptible to) a hematological disorder such as aplastic anemia, Sickle Cell Anemia, polycythemia or leukemia. With regard to both prophylactic and therapeutic methods of treatment, such treatments may be specifically tailored or modified, based on knowledge obtained from the field of pharmacogenomics. "Pharmacogenomics," as used herein, refers to the application of genomics technologies such as gene sequencing, statistical genetics, and gene expression analysis to drugs in clinical development and on the market. More specifically, the term refers to the study of how a patient's genes determine his or her response to a drug (e.g., a patient's "drug response phenotype", or "drug response genotype").

Thus, another aspect of the invention provides methods for tailoring an subject's prophylactic or therapeutic treatment with either the 16319 molecules of the present invention or 16319 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

Prophylactic Methods

In one aspect, the invention provides a method for preventing in a subject, a hematological disorder by administering to the subject an agent which modulates 16319 expression or 16319 activity, e.g., modulation of hematopoietic cell proliferation or modulation of apoptosis of hematopoietic cells. Subjects at risk for a hematological disorder can be identified by, for example, any or a combination of the diagnostic or prognostic assays described herein. Administration of a prophylactic agent can occur prior to the manifestation of symptoms characteristic of aberrant 16319 expression or activity, such that a hematological disorder is prevented or, alternatively, delayed in its progression. Depending on the type of 16319 aberrancy, for example, a 16319, 16319 agonist or 16319 antagonist agent can be used for treating the subject. The appropriate agent can be determined based on screening assays described herein.

Therapeutic Methods

Another aspect of the invention pertains to methods for treating a subject suffering from a hematological disorder. These methods involve administering to a subject an agent which modulates 16319 expression or activity (e.g., an agent identified by a screening assay described herein), or a combination of such agents. In another embodiment, the method involves administering to a subject a 16319 protein or nucleic acid molecule as therapy to compensate for reduced, aberrant, or unwanted 16319 expression or activity.

Stimulation of 16319 activity is desirable in situations in which 16319 is abnormally downregulated and/or in which increased 16319 activity is likely to have a beneficial effect, i.e., an increase in induction of apoptosis or a decrease in the proliferation of hematopoietic cells, thereby ameliorating hematological disorders such as polycythemia or infectious mononucleosis in a subject. Likewise, inhibition of 16319 activity is desirable in situations in which 16319 is abnormally upregulated and/or in which decreased 16319 activity is likely to have a beneficial effect, e.g., inhibition of apoptosis in hematopoietic cells and an increase in hematopoietic cell proliferation, thereby ameliorating a hematological disorder such as aplastic anemia or hemorrhagic anemia in a subject.

Pharmaceutical Compositions

The agents which modulate 16319 activity can be administered to a subject using pharmaceutical compositions suitable for such administration. Such compositions typically comprise the agent (e.g., nucleic acid molecule, protein, or antibody) and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition used in the therapeutic methods of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the agent that modulates 16319 activity (e.g., a fragment of a 16319 protein or an anti-16319 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The agents that modulate 16319 activity can also be prepared in the form of suppositories (e.g., with conventional suppository bases such as cocoa butter and other glycerides) or retention enemas for rectal delivery.

In one embodiment, the agents that modulate 16319 activity are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the agent that modulates 16319 activity and the particular therapeutic effect to be achieved, and the limitations inherent in the art of compounding such an agent for the treatment of subjects.

Toxicity and therapeutic efficacy of such agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and can be expressed as the ratio LD50/ED50. Agents which exhibit large therapeutic indices are preferred. While agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage for use in humans. The dosage of such 16319 modulating agents lies preferably within a range of circulating concentrations that include the ED50 with little or no toxicity. The dosage may vary within this range depending upon the dosage form employed and the route of administration utilized. For any agent used in the therapeutic methods of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982). Alternatively, an antibody can be conjugated to a second antibody to form an antibody heteroconjugate as described by Segal in U.S. Pat. No. 4,676,980.

The nucleic acid molecules used in the methods of the invention can be inserted into vectors and used as gene therapy vectors. Gene therapy vectors can be delivered to a subject by, for example, intravenous injection, local administration (see U.S. Pat. No. 5,328,470) or by stereotactic injection (see, e.g., Chen et al. (1994) Proc. Natl. Acad. Sci. USA 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

Transplantation and Transfusions

The present invention provides methods for increasing hematopoietic cells in patients, particularly patients undergoing radiation therapy and/or chemotherapy, e.g., in the treatment of cancer. Such therapies kill dividing progenitor cells in the marrow and peripheral blood, limiting therapy and often requiring transfusions to restore circulating levels of platelets and other blood cells. Of particular interest are those patients receiving bone marrow and/or peripheral blood stem cell transplants following radiation therapy and patients suffering from congenital metabolic defects necessitating bone marrow transplant. Among these indications are bone marrow transplants associated with the treatment of breast cancer, leukemia, lymphoma, multiple myeloma, and congenital defects such as severe combined immune deficiency, thallasemia, and sickle cell anemia. Peripheral blood stem cell transplantation may be preferred in conditions where a risk of tumor cells in the blood is not present.

As used herein, the term "transplantation" includes the process of removing cells from a donor subject and subsequently administering the cells to a recipient subject. The term encompasses both allogeneic transplantation, wherein the donor and recipient are different subjects of the same species; and autologous transplantation, wherein the donor and recipient are the same subject.

Methods for carrying out bone marrow and peripheral blood stem cell transplants are known in the art. (Snyder et al., "Transfusion Medicine" in Benz and McArthur, eds., Hematology 1994, American Society of Hematology, 96–106, 1994.) For example, peripheral blood stem cells are collected by leukapheresis according to accepted clinical procedures. Hematopoietic progenitor cells can be selected on the basis of cell surface markers (e.g. CD34), allowing for enrichment of the desired cells and depletion of contaminating tumor cells. The collected cells are stored frozen in a suitable cryoprotectant (e.g. dimethyl sulfoxide, hydroxyethyl starch) until needed. Marrow cells are collected from donors by bone puncture under anesthesia. To reduce the volume, the collected marrow is usually processed to separate plasma from the cellular components. Removal of plasma can also eliminate red cell incompatibilities in allogeneic transplantation. The cell fraction can be enriched for mononuclear cells using density gradient techniques or automated separation methods and depleted of T cells using various cytotoxic agents. Collected marrow cells are cryopreserved according to established procedures that include controlled-rate freezing and the use of cryoprotectants. Stem cells are thawed in a warm water bath immediately prior to use to minimize loss associated with thawing. In the case of allogeneic transplants, donors and recipients are tissue matched to minimize the risk of graft-versus-host disease.

An increase in hematopoietic cells results from transplantation into a recipient patient of stem cells, particularly cells of the myeloid lineage, including CD34+ stem cells and cells derived from CD34+ stem cells. Of particular interest are cells in the megakaryocyte and erythrocyte lineages, which reconstitute the recipient's platelet and erythrocyte populations, respectively.

In one aspect of the invention, a donor is treated, prior to donation of marrow or peripheral blood cells, with a compound that inhibits 16319, in an amount sufficient to stimulate proliferation of hematopoietic cells and/or in an amount sufficient to inhibit apoptosis of hematopoietic cells. Treatment of the donor will be carried out for a period of from one to several days, preferably about 2–5 days, during a period of from 3 days to 2 weeks prior to harvesting of bone marrow or peripheral blood stem cells. It is preferred to treat the donor during a period of five to ten days prior to harvesting of cells. The increase in CD34+ stem cells and other cells of the myeloid lineage in the donor will be manifested by improved recovery of hematopoietic cells in the transplant recipient. In another aspect of the invention, the recipient is treated with a compound that inhibits 16319 after transplantation to further enhance hematopoietic cell recovery.

Another aspect of the invention features a method for increasing the number of hematopoietic cells in a subject, for example, a subject undergoing radiation therapy and/or chemotherapy, e.g., for the treatment of cancer. The method includes the process of removing cells from a donor and subsequently administering the cells to a recipient. In one aspect of the invention, a donor is treated, prior to donation of marrow or peripheral blood cells, with a compound that inhibits 16319, in an amount sufficient to stimulate proliferation of hematopoietic cells and/or in an amount sufficient to inhibit apoptosis of hematopoietic cells. In another aspect of the invention, the recipient is treated with a compound that inhibits 16319 after transplantation to further enhance hematopoietic cell recovery.

In another aspect, the invention provides methods for increasing hematopoietic progenitor and committed erythroid cells in a recipient subject in need of such an increase. The methods include administering to a donor subject an amount of 16319 sufficient to inhibit induction of apoptosis and prevent inhibition of cell proliferation of hematopoietic cells in the donor; collecting cells from the donor, wherein the cells are bone marrow cells or peripheral blood stem cells; and administering the bone marrow cells or peripheral blood stem cells to a recipient subject. The donor and recipient may be different or the same subject. In one embodiment of the invention, the recipient subject has been treated with chemotherapy or radiation therapy.

In another aspect, the invention provides methods of preparing cells for transplantation comprising administering to a donor subject an amount of 16319 or a 16319 modulator sufficient to inhibit induction of apoptosis and prevent inhibition of cell proliferation of hematopoietic cells in the donor subject, and collecting cells from the donor subject, e.g., bone marrow cells or peripheral blood stem cells.

In another aspect, the invention provides a method of stimulating platelet recovery or erythrocyte recovery in a subject receiving chemotherapy or radiation therapy. The method includes administering to the subject an amount of 16319 or a 16319 modulator sufficient to stimulate proliferation of cells of the myeloid lineage in the subject; collecting bone marrow cells or peripheral blood stem cells from the subject prior to chemotherapy or radiation therapy; and returning the collected cells to the subject subsequent to chemotherapy or radiation therapy. Within one embodiment this method further includes administering to the subject, after or concurrently with returning the collected cells, an amount of 16319 or a 16319 modulator sufficient to enhance platelet recovery or erythrocyte recovery.

Pharmacogenomics

In conjunction with the therapeutic methods of the invention, pharmacogenomics (i.e., the study of the relationship between a subject's genotype and that subject's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer an agent which modulates 16319 activity, as well as tailoring the dosage and/or therapeutic regimen of treatment with an agent which modulates 16319 activity.

Pharmacogenomics deals with clinically significant hereditary variations in the response to drugs due to altered drug disposition and abnormal action in affected persons. See, for example, Eichelbaum, M. et al. (1996) Clin. Exp. Pharmacol. Physiol. 23(10–11): 983–985 and Linder, M. W. et al. (1997) Clin. Chem. 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate aminopeptidase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants). Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach" can be utilized to identify genes that predict drug response. According to this method, if a gene that encodes a drug target is known (e.g., a 16319 protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and the cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling" can be utilized to identify genes that predict drug response. For example, the gene expression of an animal dosed with a drug (e.g., a 16319 molecule or 16319 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of a subject. This knowledge, when applied to dosing or drug selection, can avoid adverse reactions or therapeutic failure and, thus, enhance therapeutic or prophylactic efficiency when treating a subject suffering from a hematological disorder with an agent which modulates 16319 activity.

Recombinant Expression Vectors and Host Cells Used in the Methods of the Invention The methods of the invention (e.g., the screening assays described herein) include the use of vectors, preferably expression vectors, containing a nucleic acid encoding a 16319 protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors to be used in the methods of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel (1990) *Methods Enzymol.* 185:3–7. Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., 16319 proteins, mutant forms of 16319 proteins, fusion proteins, and the like).

The recombinant expression vectors to be used in the methods of the invention can be designed for expression of 16319 proteins in prokaryotic or eukaryotic cells. For example, 16319 proteins can be expressed in bacterial cells such as *E. coli*, insect cells (using baculovirus expression vectors), yeast cells, or mammalian cells. Suitable host cells are discussed further in Goeddel (1990) supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in 16319 activity assays, (e.g., direct assays or competitive assays described in detail below), or to generate antibodies specific for 16319 proteins. In a preferred embodiment, a 16319 fusion protein expressed in a retroviral expression vector of the present invention can be utilized to infect bone marrow cells which are subsequently transplanted into irradiated recipients. The pathology of the subject recipient is then examined after sufficient time has passed (e.g., six weeks).

In another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J. et al., *Molecular Cloning: A Laboratory Manual.* 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid).

The methods of the invention may further use a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to 16319 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific, or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes, see Weintraub, H. et al., Antisense RNA as a molecular tool for genetic analysis, *Reviews—Trends in Genetics*, Vol. 1(1) 1986.

Another aspect of the invention pertains to the use of host cells into which a 16319 nucleic acid molecule of the invention is introduced, e.g., a 16319 nucleic acid molecule within a recombinant expression vector or a 16319 nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 16319 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (*Molecular Cloning: A Laboratory Manual.* 2nd, ed., *Cold Spring Harbor Laboratory*, Cold Spring Harbor Laboratory Press, Cold Spring Harbor, N.Y., 1989), and other laboratory manuals.

A host cell used in the methods of the invention, such as a prokaryotic or eukaryotic host cell in culture, can be used to produce (i.e., express) a 16319 protein. Accordingly, the invention further provides methods for producing a 16319 protein using the host cells of the invention. In one embodiment, the method comprises culturing the host cell of the invention (into which a recombinant expression vector encoding a 16319 protein has been introduced) in a suitable medium such that a 16319 protein is produced. In another embodiment, the method further comprises isolating a 16319 protein from the medium or the host cell.

Isolated Nucleic Acid Molecules Used in the Methods of the Invention

The coding sequence of the isolated human 16319 cDNA and the predicted amino acid sequence of the human 16319 polypeptide are shown SEQ ID NOs:12 and 13, respectively. The 16319 sequence is also described in Yamaguchi, et al. (1995), supra, the contents of which are incorporated herein by reference.

The methods of the invention include the use of isolated nucleic acid molecules that encode 16319 proteins or biologically active portions thereof, as well as nucleic acid fragments sufficient for use as hybridization probes to identify 16319-encoding nucleic acid molecules (e.g., 16319 mRNA) and fragments for use as PCR primers for the amplification or mutation of 16319 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

A nucleic acid molecule used in the methods of the present invention, e.g., a nucleic acid molecule having the nucleotide sequence of SEQ ID NO:12, or a portion thereof, can be isolated using standard molecular biology techniques and the sequence information provided herein. Using all or portion of the nucleic acid sequence of SEQ ID NO:12 as a hybridization probe, 16319 nucleic acid molecules can be isolated using standard hybridization and cloning techniques (e.g., as described in Sambrook, J., Fritsh, E. F., and Maniatis, T. *Molecular Cloning: A Laboratory Manual.* 2nd, ed., *Cold Spring Harbor Laboratory*, Cold Spring Harbor Laboratory Press, Cold Spring Harbor, N.Y., 1989).

Moreover, a nucleic acid molecule encompassing all or a portion of SEQ ID NO:12 can be isolated by the polymerase chain reaction (PCR) using synthetic oligonucleotide primers designed based upon the sequence of SEQ ID NO:12.

A nucleic acid used in the methods of the invention can be amplified using cDNA, mRNA or, alternatively, genomic DNA as a template and appropriate oligonucleotide primers according to standard PCR amplification techniques. Furthermore, oligonucleotides corresponding to 16319 nucleotide sequences can be prepared by standard synthetic techniques, e.g., using an automated DNA synthesizer.

In a preferred embodiment, the isolated nucleic acid molecules used in the methods of the invention comprise the nucleotide sequence shown in SEQ ID NO:12, a complement of the nucleotide sequence shown in SEQ ID NO:12, or a portion of any of these nucleotide sequences. A nucleic acid molecule which is complementary to the nucleotide sequence shown in SEQ ID NO:12, is one which is sufficiently complementary to the nucleotide sequence shown in SEQ ID NO:12 such that it can hybridize to the nucleotide sequence shown in SEQ ID NO:12 thereby forming a stable duplex.

In still another preferred embodiment, an isolated nucleic acid molecule used in the methods of the present invention comprises a nucleotide sequence which is at least about 55%, 60%, 65%, 70%, 75%, 80%, 85%, 90%, 95%, 96%, 97%, 98%, 99% or more identical to the entire length of the nucleotide sequence shown in SEQ ID NO:12 or a portion of any of this nucleotide sequence.

Moreover, the nucleic acid molecules used in the methods of the invention can comprise only a portion of the nucleic acid sequence of SEQ ID NO:12, for example, a fragment which can be used as a probe or primer or a fragment encoding a portion of a 16319 protein, e.g., a biologically active portion of a 16319 protein. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:12 of an anti-sense sequence of SEQ ID NO:12 or of a naturally occurring allelic variant or mutant of SEQ ID NO:12. In one embodiment, a nucleic acid molecule used in the methods of the present invention comprises a nucleotide sequence which is greater than 100, 100–200, 200–300, 300–400, 400–500, 500–600, or more nucleotides in length and hybridizes under stringent hybridization conditions to a nucleic acid molecule of SEQ ID NO:12.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in *Current Protocols in Molecular Biology*, Ausubel et al., eds., John Wiley & Sons, Inc. (1995), sections 2, 4 and 6. Additional stringent conditions can be found in *Molecular Cloning. A Laboratory Manual*, Sambrook et al., Cold Spring Harbor Press, Cold Spring Harbor, N.Y. (1989), chapters 7, 9 and 11. A preferred, non-limiting example of stringent hybridization conditions includes hybridization in 4× sodium chloride/sodium citrate (SSC), at about 65–70° C. (or hybridization in 4×SSC plus 50% formamide at about 42–50° C.) followed by one or more washes in 1×SSC, at about 65–70° C. A preferred, non-limiting example of highly stringent hybridization conditions includes hybridization in 1×SSC, at about 65–70° C. (or hybridization in 1×SSC plus 50% formamide at about 42–50° C.) followed by one or more washes in 0.3×SSC, at about 65–70° C. A preferred, non-limiting example of reduced stringency hybridization conditions includes hybridization in 4×SSC, at about 50–60° C. (or alternatively hybridization in 6×SSC plus 50% formarnmide at about 40–45° C.) followed by one or more washes in 2×SSC, at about 50–60° C. Ranges intermediate to the above-recited values, e.g., at 65–70° C. or at 42–50° C. are also intended to be encompassed by the present invention. SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m(°C.)=2(\# \text{ of A+T bases})+4(\# \text{ of G+C bases})$. For hybrids between 18 and 49 base pairs in length, $T_m(°C.)=81.5+16.6(\log_{10}[Na^+])+0.41(\%G+C)-(600/N)$, where N is the number of bases in the hybrid, and $[Na^+]$ is the concentration of sodium ions in the hybridization buffer ($[Na^+]$ for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25–0.5M $NaH_2PO_4$, 7% SDS at about 65° C., followed by one or more washes at 0.02M $NaH_2PO_4$, 1% SDS at 65° C., see e.g., Church and Gilbert (1984) *Proc. Natl. Acad. Sci. USA* 81:1991–1995, (or alternatively 0.2×SSC, 1% SDS).

In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a 16319 protein, such as by measuring a level of a 16319-encoding nucleic acid in a sample of cells from a subject e.g., detecting 16319 mRNA levels or determining whether a genomic 16319 gene has been mutated or deleted.

The methods of the invention further encompass the use of nucleic acid molecules that differ from the nucleotide sequence shown in SEQ ID NO:12 due to degeneracy of the genetic code and thus encode the same 16319 proteins as those encoded by the nucleotide sequence shown in SEQ ID NO:12. In another embodiment, an isolated nucleic acid molecule included in the methods of the invention has a nucleotide sequence encoding a protein having an amino acid sequence shown in SEQ ID NO:13.

The methods of the invention further include the use of allelic variants of human 16319, e.g., fuctional and non-functional allelic variants. Functional allelic variants are naturally occurring amino acid sequence variants of the human 16319 protein that maintain a 16319 activity. Functional allelic variants will typically contain only conservative substitution of one or more amino acids of SEQ ID NO:13, or substitution, deletion or insertion of non-critical residues in non-critical regions of the protein.

Non-functional allelic variants are naturally occurring amino acid sequence variants of the human 16319 protein that do not have a 16319 activity. Non-functional allelic variants will typically contain a non-conservative substitution, deletion, or insertion or premature truncation of the amino acid sequence of SEQ ID NO:13, or a substitution, insertion or deletion in critical residues or critical regions of the protein.

The methods of the present invention may further use non-human orthologues of the human 16319 protein. Orthologues of the human 16319 protein are proteins that are isolated from non-human organisms and possess the same 16319 activity.

The methods of the present invention further include the use of nucleic acid molecules comprising the nucleotide sequence of SEQ:12 or a portion thereof, in which a mutation has been introduced. The mutation may lead to amino acid substitutions at "non-essential" amino acid residues or at "essential" amino acid residues. A "non-essential" amino acid residue is a residue that can be altered from the wild-type sequence of 16319 (e.g., the sequence of SEQ ID NO:13) without altering the biological activity, whereas an "essential" amino acid residue is required for biological activity. For example, amino acid residues that are conserved among the 16319 proteins of the present invention and other members of the CIDE family (e.g., CiDE-B, FSP-27, and DFF45) are not likely to be amenable to alteration.

Mutations can be introduced into SEQ ID NO:12 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a 16319 protein is preferably replaced with another amino acid residue from the same side chain family. Alternatively, in another embodiment, mutations can be introduced randomly along all or part of a 16319 coding sequence, such as by saturation mutagenesis, and the resultant mutants can be screened for 16319 biological activity to identify mutants that retain activity. Following mutagenesis of SEQ ID NO:12 the encoded protein can be expressed recombinantly and the activity of the protein can be determined using the assay described herein.

Another aspect of the invention pertains to the use of isolated nucleic acid molecules which are antisense to the nucleotide sequence of SEQ ID NO:12. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire 16319 coding strand, or to only a portion thereof. In one embodiment, an antisense nucleic acid molecule is antisense to a "coding region" of the coding strand of a nucleotide sequence encoding a 16319. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding 16319. The term "noncoding region" refers to 5' and 3' sequences which flank the coding region that are not translated into amino acids (also referred to as 5' and 3' untranslated regions).

Given the coding strand sequences encoding 16319 disclosed herein, antisense nucleic acids of the invention can be designed according to the rules of Watson and Crick base pairing. The antisense nucleic acid molecule can be complementary to the entire coding region of 16319 mRNA, but more preferably is an oligonucleotide which is antisense to only a portion of the coding or noncoding region of 16319 mRNA. For example, the antisense oligonucleotide can be complementary to the region surrounding the translation start site of 16319 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyl uracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethy luracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5- oxyacetic acid methylester, uracil-5-oxyacetic acid (v), 5-methyl -2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules used in the methods of the invention are typically administered to a subject or generated in situ such that they hybridize with or bind to cellular mRNA and/or genomic DNA encoding a 16319 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule used in the methods of the invention is an cx-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid used in the methods of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave 16319 mRNA transcripts to thereby inhibit translation of 16319 mRNA. A ribozyme having specificity for a 16319-encoding nucleic acid can be designed based upon the nucleotide sequence of a 16319 cDNA disclosed herein (i.e., SEQ ID NO:12). For example, a derivative of a Tetrahymena L-19 IVS RNA can be constructed in which the nucleotide sequence of the active site is complementary to the nucleotide sequence to be cleaved in a 16319-encoding mRNA. See, e.g., Cech et al. U.S. Pat. No. 4,987,071; and Cech et al. U.S. Pat. No. 5,116,742. Alternatively, 16319 mRNA can be used to select a catalytic RNA having a specific ribonuclease activity from a pool of RNA molecules. See, e.g., Bartel, D. and Szostak, J. W. (1993) Science 261:1411–1418.

Alternatively, 16319 gene expression can be inhibited by targeting nucleotide sequences complementary to the regulatory region of the 16319 (e.g., the 16319 promoter and/or enhancers) to form triple helical structures that prevent transcription of the 16319 gene in target cells. See generally, Helene, C. (1991) Anticancer Drug Des. 6(6): 569–84; Helene, C. et al. (1992) Ann. N.Y. Acad. Sci. 660:27–36; and Maher, L.J. (1992) Bioassays 14(12):807–15.

In yet another embodiment, the 16319 nucleic acid molecules used in the methods of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) Bioorganic & Medicinal Chemistry 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. (1996) Proc. Natl. Acad. Sci. 93:14670–675.

PNAs of 16319 nucleic acid molecules can be used in the therapeutic and diagnostic applications described herein. For example, PNAs can be used as antisense or antigene agents for sequence-specific modulation of gene expression by, for example, inducing transcription or translation arrest or inhibiting replication. PNAs of 16319 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. et al. (1996) supra)); or as probes or primers for DNA sequencing or hybridization (Hyrup B. et al. (1996) supra; Perry-O'Keefe et al. (1996) supra).

In another embodiment, PNAs of 16319 can be modified, (e.g., to enhance their stability or cellular uptake), by attaching lipophilic or other helper groups to PNA, by the formation of PNA-DNA-chimeras, or by the use of liposomes or other techniques of drug delivery known in the art. For example, PNA-DNA chimeras of 16319 nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. et al. (1996) supra). The synthesis of PNA-DNA chimeras can be performed as described in Hyrup B. et al. (1996) supra and Finn P. J. et al. (1996) Nucleic Acids Res. 24 (17): 3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) Nucleic Acid Res. 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) Bioorganic Med. Chem. Lett. 5: 1119–11124).

In other embodiments, the oligonucleotide used in the methods of the invention may include other appended groups such as peptides (e.g., for targeting host cell receptors in vivo), or agents facilitating transport across the cell membrane (see, e.g., Letsinger et al. (1989) Proc. Natl. Acad. Sci. USA 86:6553–6556; Lemaitre et al. (1987) Proc. Natl. Acad. Sci. USA 84:648–652; PCT Publication No. W088/09810) or the blood-brain barrier (see, e.g., PCT Publication No. W089/10134). In addition, oligonucleotides can be modified with hybridization-triggered cleavage agents (See, e.g., Krol et al. (1988) Bio-Techniques 6:958–976) or intercalating agents. (See, e.g., Zon (1988) Pharm. Res. 5:539–549). To this end, the oligonucleotide may be conjugated to another molecule, (e.g., a peptide, hybridization triggered cross-linking agent, transport agent, or hybridization-triggered cleavage agent).

Isolated 16319 Proteins and Anti-16319 Antibodies Used in the Methods of the Invention The methods of the invention include the use of isolated 16319 proteins, and biologically active portions thereof, as well as polypeptide fragments suitable for use as immunogens to raise anti-16319 antibodies. In one embodiment, native 16319 proteins can be isolated from cells or tissue sources by an appropriate purification scheme using standard protein purification techniques. In another embodiment, 16319 proteins are produced by recombinant DNA techniques. Alternative to recombinant expression, a 16319 protein or polypeptide can be synthesized chemically using standard peptide synthesis techniques.

As used herein, a "biologically active portion" of a 16319 protein includes a fragment of a 16319 protein having a 16319 activity. Biologically active portions of a 16319 protein include peptides comprising amino acid sequences sufficiently identical to or derived from the amino acid sequence of the 16319 protein, e.g., the amino acid sequence shown in SEQ ID NO:13, which include fewer amino acids than the full length 16319 proteins, and exhibit at least one activity of a 16319 protein. Typically, biologically active portions comprise a domain or motif with at least one activity of the 16319 protein (e.g., the N-terminal region of the 16319 protein that is believed to be involved in the regulation of apoptotic activity). A biologically active portion of a 16319 protein can be a polypeptide which is, for example, 25, 50, 75, 100, 125, 150, 175, 200, 250, 300 or more amino acids in length. Biologically active portions of a 16319 protein can be used as targets for developing agents which modulate a 16319 activity.

In a preferred embodiment, the 16319 protein used in the methods of the invention has an amino acid sequence shown in SEQ ID NO:13. In other embodiments, the 16319 protein is substantially identical to SEQ ID NO:13, and retains the functional activity of the protein of SEQ ID NO:13, yet differs in amino acid sequence due to natural allelic variation or mutagenesis, as described in detail in subsection V above. Accordingly, in another embodiment, the 16319 protein used in the methods of the invention is a protein which comprises an amino acid sequence at least about 50%, 55%, 60%, 65%, 70%, 75%, 80%, 85%, 90%, 95%, 96%, 97%, 98%, 99% or more identical to SEQ ID NO:13.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the 16319 amino acid sequence of SEQ ID NO:13 having 500 amino acid residues, at least 75, preferably at least 150, more preferably at least 225, even more preferably at least 300, and even more preferably at least 400 or more amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* 48:444–453 (1970)) algorithm which has been incorporated into the GAP program in the GCG software package, using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (*Comput. Appl. Biosci.* 4:11–17 (1988)) which has been incorporated into the ALIGN program (version 2.0 or 2.0U), using a PAM120 weight residue table, a gap length penalty of 12 and a gap penalty of 4.

The methods of the invention may also use 16319 chimeric or fusion proteins. As used herein, a 16319 "chimeric protein" or "fusion protein" comprises a 16319 polypeptide operatively linked to a non-16319 polypeptide. An "16319 polypeptide" refers to a polypeptide having an amino acid sequence corresponding to a 16319 molecule, whereas a "non-16319 polypeptide" refers to a polypeptide having an amino acid sequence corresponding to a protein which is not substantially homologous to the 16319 protein, e.g., a protein which is different from the 16319 protein and which is derived from the same or a different organism. Within a 16319 fusion protein the 16319 polypeptide can correspond to all or a portion of a 16319 protein. In a preferred embodiment, a 16319 fusion protein comprises at least one biologically active portion of a 16319 protein. In another preferred embodiment, a 16319 fusion protein comprises at least two biologically active portions of a 16319 protein. Within the fusion protein, the term "operatively linked" is intended to indicate that the 16319 polypeptide and the non-16319 polypeptide are fused in-frame to each other. The non-16319 polypeptide can be fused to the N-terminus or C-terminus of the 16319 polypeptide.

For example, in one embodiment, the fusion protein is a GST-16319 fusion protein in which the 16319 sequences are fused to the C-terminus of the GST sequences. Such fusion proteins can facilitate the purification of recombinant 16319.

In another embodiment, this fusion protein is a 16319 protein containing a heterologous signal sequence at its N-terminus. In certain host cells (e.g., mammalian host cells), expression and/or secretion of 16319 can be increased through use of a heterologous signal sequence.

The 16319 fusion proteins used in the methods of the invention can be incorporated into pharmaceutical compositions and administered to a subject in vivo. The 16319 fusion proteins can be used to affect the bioavailability of a 16319 substrate. Use of 16319 fusion proteins may be useful therapeutically for the treatment of disorders caused by, for example, (i) aberrant modification or mutation of a gene encoding a 16319protein; (ii) mis-regulation of the 16319 gene; and (iii) aberrant post-translational modification of a 16319 protein.

Moreover, the 16319-fusion proteins used in the methods of the invention can be used as immunogens to produce anti-16319 antibodies in a subject, to purify 16319 ligands and in screening assays to identify molecules which inhibit the interaction of 16319 with a 16319 substrate.

Preferably, a 16319 chimeric or fusion protein used in the methods of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A 16319-encoding nucleic acid can be cloned into such an expression vector such that the fusion moiety is linked in-frame to the 16319 protein.

The present invention also pertains to the use of variants of the 16319 proteins which function as either 16319 agonists (mimetics) or as 16319 antagonists. Variants of the 16319 proteins can be generated by mutagenesis, e.g., discrete point mutation or truncation of a 16319 protein. An agonist of the 16319 proteins can retain substantially the same, or a subset, of the biological activities of the naturally occurring form of a 16319 protein. An antagonist of a 16319 protein can inhibit one or more of the activities of the naturally occurring form of the 16319 protein by, for example, competitively modulating a 16319-mediated activity of a 16319 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the 16319 protein.

In one embodiment, variants of a 16319 protein which function as either 16319 agonists (mimetics) or as 16319 antagonists can be identified by screening combinatorial libraries of mutants, e.g., truncation mutants, of a 16319 protein for 16319 protein agonist or antagonist activity. In one embodiment, a variegated library of 16319 variants is generated by combinatorial mutagenesis at the nucleic acid level and is encoded by a variegated gene library. A variegated library of 16319 variants can be produced by, for example, enzymatically ligating a mixture of synthetic oligonucleotides into gene sequences such that a degenerate set of potential 16319 sequences is expressible as individual polypeptides, or alternatively, as a set of larger fusion proteins (e.g., for phage display) containing the set of 16319 sequences therein. There are a variety of methods which can be used to produce libraries of potential 16319 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential 16319 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of a 16319 protein coding sequence can be used to generate a variegated population of 16319 fragments for screening and subsequent selection of variants of a 16319 protein. In one embodiment, a library of coding sequence fragments can be generated by treating a double stranded PCR fragment of a 16319 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the 16319 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of 16319 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify 16319 variants (Arkin and Yourvan (1992) *Proc. Natl. Acad. Sci. USA* 89:7811–7815; Delgrave et al. (1993) *Protein Engineering* 6(3):327–331).

The methods of the present invention further include the use of anti-16319 antibodies. An isolated 16319 protein, or a portion or fragment thereof, can be used as an immunogen to generate antibodies that bind 16319 using standard techniques for polyclonal and monoclonal antibody preparation. A full-length 16319 protein can be used or, alternatively, antigenic peptide fragments of 16319 can be used as immunogens. The antigenic peptide of 16319 comprises at least 8 amino acid residues of the amino acid sequence shown in SEQ ID NO:13 and encompasses an epitope of 16319 such that an antibody raised against the peptide forms a specific immune complex with the 16319 protein. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of 16319 that are located on the surface of the protein, e.g., hydrophilic regions, as well as regions with high antigenicity.

A 16319 immunogen is typically used to prepare antibodies by immunizing a suitable subject, (e.g., rabbit, goat, mouse, or other mammal) with the immunogen. An appropriate immunogenic preparation can contain, for example, recombinantly expressed 16319 protein or a chemically synthesized 16319 polypeptide. The preparation can further include an adjuvant, such as Freund's complete or incomplete adjuvant, or similar immunostimulatory agent. Immunization of a suitable subject with an immunogenic 16319 preparation induces a polyclonal anti-16319 antibody response.

The term "antibody" as used herein refers to immunoglobulin molecules and immunologically active portions of immunoglobulin molecules, i.e., molecules that contain an antigen binding site which specifically binds (immunoreacts with) an antigen, such as a 16319. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind 16319 molecules. The term "monoclonal antibody" or "monoclonal antibody composition", as used herein, refers to a population of antibody molecules that contain only one species of an antigen binding site capable of immunoreacting with a particular epitope of 16319. A monoclonal antibody composition thus typically displays a single binding affinity for a particular 16319 protein with which it immunoreacts.

Polyclonal anti-16319 antibodies can be prepared as described above by immunizing a suitable subject with a 16319 immunogen. The anti-16319 antibody titer in the immunized subject can be monitored over time by standard techniques, such as with an enzyme linked immunosorbent assay (ELISA) using immobilized 16319. If desired, the antibody molecules directed against 16319 can be isolated from the mammal (e.g., from the blood) and further purified by well known techniques, such as protein A chromatography to obtain the IgG fraction. At an appropriate time after immunization, e.g., when the anti-16319 antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.*

127:539–46; Brown et al. (1980) *J. Biol. Chem.* 255:4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985) *Monoclonal Antibodies and Cancer Therapy*, Alan R. Liss, Inc., pp. 77–96) or trioma techniques. The technology for producing monoclonal antibody hybridomas is well known (see generally Kenneth, R. H. in *Monoclonal Antibodies: A New Dimension In Biological Analyses*, Plenum Publishing Corp., New York, N.Y. (1980); Lerner, E. A. (1981) *Yale J. Biol. Med.* 54:387–402; Gefter, M. L. et al. (1977) *Somatic Cell Genet.* 3:231–36). Briefly, an immortal cell line (typically a myeloma) is fused to lymphocytes (typically splenocytes) from a mammal immunized with a 16319 immunogen as described above, and the culture supernatants of the resulting hybridoma cells are screened to identify a hybridoma producing a monoclonal antibody that binds 16319.

Any of the many well known protocols used for fusing lymphocytes and immortalized cell lines can be applied for the purpose of generating an anti-16319 monoclonal antibody (see, e.g., G. Galfre et al. (1977) *Nature* 266:55052; Gefter et al. (1977) supra; Lerner (1981) supra; and Kenneth (1980) supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind 16319, e.g., using a standard ELISA assay.

Alternative to preparing monoclonal antibody-secreting hybridomas, a monoclonal anti-16319 antibody can be identified and isolated by screening a recombinant combinatorial immunoglobulin library (e.g., an antibody phage display library) with 16319 to thereby isolate immunoglobulin library members that bind 16319. Kits for generating and screening phage display libraries are commercially available (e.g., the Pharmacia *Recombinant Phage Antibody System*, Catalog No. 27-9400-01; and the Stratagene *SurfP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication No. WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J* 12:725–734; Hawkins et al. (1992) *J. Mol. Biol.* 226:889–896; Clarkson et al. (1991) *Nature* 352:624–628; Gram et al. (1992) *Proc. Natl. Acad. Sci. USA* 89:3576–3580; Garrad et al. (1991) *Bio/Technology* 9:1373–1377; Hoogenboom et al. (1991) *Nuc. Acid Res.* 19:4133–4137; Barbas et al. (1991) *Proc. Natl. Acad. Sci. USA* 88:7978–7982; and McCafferty et al. (1990) *Nature* 348:552–554.

Additionally, recombinant anti-16319 antibodies, such as chimeric and humanized monoclonal antibodies, comprising both human and non-human portions, which can be made using standard recombinant DNA techniques, are within the scope of the methods of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987)*J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; Shaw et al. (1988) *J. Natl. Cancer Inst.* 80:1553–1559; Morrison, S. L. (1985) *Science* 229:1202–1207; Oi et al. (1986) *BioTechniques* 4:214; Winter U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

An anti-16319 antibody can be used to detect 16319 protein (e.g., in a cellular lysate or cell supernatant) in order to evaluate the abundance and pattern of expression of the 16319 protein. Anti-16319 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, □-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include 125I, $^{131}$I, $^{35}$S or $^{3}$H.

Electronic Apparatus Readable Media and Arrays

Electronic apparatus readable media comprising a 16319 modulator of the present invention is also provided. As used herein, "electronic apparatus readable media" refers to any suitable medium for storing, holding or containing data or information that can be read and accessed directly by an electronic apparatus. Such media can include, but are not limited to: magnetic storage media, such as floppy discs, hard disc storage medium, and magnetic tape; optical storage media such as compact disc; electronic storage media such as RAM, ROM, EPROM, EEPROM and the like; general hard disks and hybrids of these categories such as magnetic/optical storage media. The medium is adapted or configured for having recorded thereon a marker of the present invention.

As used herein, the term "electronic apparatus" is intended to include any suitable computing or processing apparatus or other device configured or adapted for storing data or information. Examples of electronic apparatus suitable for use with the present invention include stand-alone computing apparatus; networks, including a local area network (LAN), a wide area network (WAN) Internet, Intranet, and Extranet; electronic appliances such as a personal digital assistants (PDAs), cellular phone, pager and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the 16319 modulators of the present invention.

A variety of software programs and formats can be used to store the marker information of the present invention on the electronic apparatus readable medium. For example, the nucleic acid sequence corresponding to the 16319 modulators can be represented in a word processing text file, formatted in commercially-available software such as WordPerfect and MicroSoft Word, or represented in the form of an ASCII file, stored in a database application, such as DB2, Sybase, Oracle, or the like, as well as in other forms. Any number of dataprocessor structuring formats (e.g., text file or database) may be employed in order to obtain or create a medium having recorded thereon the 16319 modulators of the present invention.

By providing the 16319 modulators of the invention in readable form, one can routinely access the marker sequence information for a variety of purposes. For example, one skilled in the art can use the nucleotide or amino acid sequences of the present invention in readable form to compare a target sequence or target structural motif with the sequence information stored within the data storage means. Search means are used to identify fragments or regions of the sequences of the invention which match a particular target sequence or target motif.

The present invention therefore provides a medium for holding instructions for performing a method for determining whether a subject has a hematological disorder or a pre-disposition to a hematological disroder, wherein the method comprises the steps of determining the presence or absence of a 16319 modulator and based on the presence or absence of the 16319 modulator, determining whether the subject has a hematological disorder or a pre-disposition to a hematological disorder and/or recommending a particular treatment for the hematological disorder or pre-hematological disorder condition.

The present invention further provides in an electronic system and/or in a network, a method for determining whether a subject has a hematological disorder or a predisposition to a hematological disorder associated with a 16319 modulator wherein the method comprises the steps of determining the presence or absence of the 16319 modulator, and based on the presence or absence of the 16319 modulator, determining whether the subject has a hematological disorder or a pre-disposition to a hematological disorder, and/or recommending a particular treatment for the hematological disorder or pre-hematological disorder condition. The method may further comprise the step of receiving phenotypic information associated with the subject and/or acquiring from a network phenotypic information associated with the subject.

The present invention also provides in a network, a method for determining whether a subject has a hematological disorder or a pre-disposition to a hematological disorder associated with a 16319 modulator, said method comprising the steps of receiving information associated with the 16319 modulator receiving phenotypic information associated with the subject, acquiring information from the network corresponding to the 16319 modulator and/or hematological disorder, and based on one or more of the phenotypic information, the 16319 modulator, and the acquired information, determining whether the subject has a hematological disorder or a pre-disposition to a hematological disorder. The method may further comprise the step of recommending a particular treatment for the hematological disorder or pre-hematological disorder condition.

The present invention also provides a business method for determining whether a subject has a hematological disorder or a pre-disposition to a hematological disorder, said method comprising the steps of receiving information associated with the 16319 modulator, receiving phenotypic information associated with the subject, acquiring information from the network corresponding to the 16319 modulator and/or hematological disorder, and based on one or more of the phenotypic information, the 16319 modulator, and the acquired information, determining whether the subject has a hematological disorder or a pre-disposition to a hematological disorder. The method may further comprise the step of recommending a particular treatment for the hematological disorder or pre-hematological disorder condition.

The invention also includes an array comprising a 16319 modulator of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression. This allows a profile to be developed showing a battery of genes specifically expressed in one or more tissues.

In addition to such qualitative determination, the invention allows the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of hematological disorder, progression of hematological disorder, and processes, such a cellular transformation associated with hematological disorder.

The array is also useful for ascertaining the effect of the expression of a gene on the expression of other genes in the same cell or in different cells. This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes that could serve as a molecular target for diagnosis or therapeutic intervention.

This invention is further illustrated by the following examples which should not be construed as limiting. The contents of all references, patents and published patent applications cited throughout this application, as well as the Sequence Listing is incorporated herein by reference.

EXAMPLES

Example 1

Identification of 16319 as a Modulator of Hematological Disorders

In order to determine whether the 16319 molecules of the present invention are involved in hematological disorders, 16319 gene expression during various points of hematopoietic cell differentiation of different hematopietic cell lineages (e.g., erythroid, myeloid and megakaryocyte lineages) was measured.

Materials and Methods

For analysis of human and murine 16319 expression in hematopoietic cells and tissue, the following methods were used:

Tissues were collected from 7 week old female C57/Bl6J mice. Total RNA was prepared using the trizol method and treated with DNAse to remove contaminating genomic DNA. cDNA was synthesized using standard techniques. Mock cDNA synthesis in the absence of reverse transcriptase resulted in samples with no detectable PCR amplification of the control RNA gene confirming efficient removal of genomic DNA contamination. 16319 expression was measured by TaqMan® quantitative PCR analysis, performed according to the manufacturer's directions (Perkin Elmer Applied Biosystems, Foster City, Calif.).

The samples included the following normal cells and tissues: lung, heart, spleen, kidney, liver, fetal liver, brain, colon, muscle, bone marrow, cord blood, GPA hi, GPA lo, stromal, CD14 (B cells), CD11b+, erythrocytes, BFU, mast cells, megakaryocytes, neutrophils, CD3 (T cells), peripheral blood, K562 (leukemia cells), HL60 (human peripheral blood leukemia promyelocytic cells), MF11, MF12, HUVEC (human endothelial cells), HCEAC, platelets pool, erythrleukemia, premyelocytic leukemia, thrombosis and virology samples.

PCR probes were designed by PrimerExpress software (PE Biosystems) based on the sequence of human 16319 (SEQ ID NO:12).

To standardize the results between different tissues, two probes, distinguished by different fluorescent labels, were added to each sample. The differential labeling of the probe for the 16319 gene and the probe for control RNA as an internal control thus enabled their simultaneous measurement in the same well. Forward and reverse primers and the probes for both control RNA and human 16319 were added to the TaqMan Universal PCR Master Mix (PE Applied Biosystems). Although the final concentration of primer and probe could vary, each was internally consistent within a given experiment. A typical experiment contained 200 nM of forward and reverse primers, plus 100 nM of the probe for the control RNA, and 4500 nM of each of the forward and reverse primers, plus 150 nM of the probe for 16319. TaqMan matrix experiments were carried out using an ABI PRISM 770 Sequence Detection System (PE Applied Biosystems). The thermal cycler conditions were as follows: hold for 2 minutes at 50° C. and 10 minutes at 95° C., followed by two-step PCR for 40 cycles of 95° C. for 15 seconds, followed by 60° C. for 1 minute.

The following method was used to quantitatively calculate 16319 gene expression in the tissue samples, relative to the control RNA expression in the same tissue. The threshold values at which the PCR amplification started were determined using the manufacturer's software. PCR cycle number at threshold value was designated as CT. Relative expression was calculated as:

$$2^{-((CTtest-CT18S)\text{tissue of interest}-(CTtest-CT18S)\text{lowest expressing tissue in panel})}$$

Samples were run in duplicate and the averages of 2 relative expression determinations are shown. All probes were tested on serial dilutions of RNA from a tissue with high expression levels and only probes which gave relative expression levels that were linear to the amount of template cDNA with a slope similar to the slope for the internal control 18S were used.

For Northern Blotting, human mRNA blots (Clontech) were probed with a 520 nucleotide SacI fragment containing 420 nucleotides of the 5' coding sequence and 100 nucleotides of the 5' UTR of human 16319. Probes were labeled with $^{32}P$ and hybridized using the Rapid-Hyb buffer (Amersham).

Results

The expression of 16319 was examined during various points of hematopoietic cell differentiation of different hematopietic cell lineages (e.g., erythroid, myeloid and megakaryocyte lineages) using Taqman analysis. The results indicate that 16319 was most highly expressed in CD34+ progenitor cells, and this high level of expression was maintained in erythroid and Glycophorin A positive cells. 16319 was also highly expressed in fetal liver cells. To verify expression of 16319, Northern Blotting was performed using commercially available Clontech Blots.

The results described above demonstrate that 16319 is expressed in hematopoietic cells during different stages of differentiation. Thus, 16319 is an important gene which is expressed in early progenitor and committed cells and ultimately plays a determinitive role in hematopoietic cell proliferation.

VI. METHODS AND COMPOSITIONS FOR THE DIAGNOSIS AND TREATMENT OF VIRAL DISEASE USING 55092

BACKGROUND OF THE INVENTION

Phospholipases are involved in the signal transduction pathway in which a cell response such as proliferation or secretion is produced in response to an extracellular stimulus. The interaction of extracellular signals (e.g., hormones, growth factors, cytokines, neurotransmitters, and physical stimuli) with cell surface receptors (e.g., G protein-coupled receptors and receptor tyrosine kinases) often activates a phospholipase D (PLD)-mediated signal transduction pathway that is important in the regulation of cell function and cell fate. Phospholipase D catalyzes the hydrolysis of phosphatidylcholine and other phospholipids yielding phosphatidic acid and is, thus, able to modify various lipid constituents of the plasma membrane and generate intracellular messengers that act to recruit and/or modulate specific target proteins. For example, addition of short chain analogues of phosphatidic acid to intact cells has been shown to regulate membrane transport, e.g., secretion of viral glycoproteins and matrix metalloproteinase proteins (Bi, K et al. (1997) *Curr. Biol.* 7:301–7; Williger, B T et al. (1999) *J. Biol. Chem.* 74:735–8). Moreover, phosphatidic acid is further metabolized to form diacylglycerol, a potent activator of protein kinase C, and lysophosphatidic acid (Exton, J H (2000) *Ann. N Y Acad. Sci.* 905:61–8; Ktistakis N T et al. (1999) *Biochem. Soc. Trans.* 27:634–637). PLD is also able to catalyze a transesterification reaction (transphosphatidylation) utilizing short-chain primary alcohols as phosphatidyl group acceptors and producing phosphatidylalcohols. PLD activity is regulated by factors such as small GTP binding proteins of the ADP-ribosylation factor (ARF) and Rho families, and protein kinase C. PLD activities have been identified in multiple cellular membranes including the nuclear envelope, endoplasmic reticulum, Golgi apparatus, transport/secretory vesicles, and the plasma membrane (Ktistakis N T et al. (1999) *Biochem. Soc. Trans.* 27:634–637). Different PLD isoforms are localized in distinct cellular organelles, and serve diverse functions in signal transduction, membrane homeostasis, membrane vesicle trafficking and cytoskeletal dynamics (Singer W D et al. (1997) *Ann. Rev. Biochem.* 66:475–509; Exton, J H (2000) *Ann. N Y Acad. Sci.*905:61–8).

The phospholipase D gene superfamily, as defined by structural domains and sequence motifs, includes PLDs, phosphatidyltransferases, phospholipid synthases, phosphodiesterases, endonucleases, and viral envelope proteins (Cao, J-X et al. (1997) *Virus Research* 48:11–18; Pedersen K M et al. (1998) *J. Biol. Chem.* 273:31494–31504; Barcena J (2000) *J. Gen. Virol.* 81:1073–1085; Liscovitch, M et al. (2000) *Biochem. J.* 345:401–415). PLD superfamily members share conserved motifs, including the HKD motif (HXKX$_4$D) (SEQ ID NO:19) which has been implicated in catalytic activity (Ponting C P et al. (1996) Protein Science 5:914–922; Koonin, E V (1996) *TIBS* 21:242–243; Sung T-C et al. (1997) *EMBO J.* 16:4519–4530).

Vaccinia virus produces two different infectious forms, intracellular mature virus (IMV) which are infectious when released by cell lysis, and extracellular enveloped virus (EEV) which is important in long-distance spread of infectious virus in vitro and in vivo. Acquisition of the EEV envelope occurs by the wrapping of IMV with vesicles derived from the trans-Golgi network. Two genes encoding proteins with homology to PLD are present in vaccinia virus and other poxviruses. The K4 protein contains two HKD motifs and adjacent conserved sequences, and P37 contains a partially conserved motif (Sung T-C et al. (1997) *EMBO J.* 16:4519–4530). P37, a 37 kDa palmitylated protein encoded by the F13L gene, is the major protein in the external envelope of EEV, and within infected cells is localized in the Golgi region associated with vesicles which form double-walled envelopes around IMV. P37 has been shown to play an important role in the viral envelopment process and subsequent release of enveloped virus (Borrego B et al. (1999) J. Gen. Virol. 80:425–432). Viral mutants lacking P37 are severely compromised, as trans-Golgi envelopment does not occur, thus, blocking viral particle egress and cell-cell virus transmission (Blasco R and Moss B (1991) *J. Virol.* 65:5910–5920; Blasco R and Moss B (1995) *Gene* 158:157–162). Similarly, mutation of the P37 HKD motif results in viruses that are unable to produce EEV and which fail to mediate low-pH-induced fusion of infected cells (Roper R L and Moss B (1999) *J. Virol.* 73:1108–1117).

Viruses are ubiquitous pathogens capable of producing primary, latent, and recurrent infections which contribute to a variety of clinical illnesses. Viruses may cause infected cells to produce specific proteins that interact with each other and with cellular proteins and viral nucleic acids to cause viral progeny to be made, to destroy the infected cell, and to spread infection. Thus, there is a vital need for antiviral drug development and rapid diagnostic methods in order to achieve efficient management strategies for viral infections.

SUMMARY OF THE INVENTION

The present invention provides methods and compositions for the diagnosis and treatment of viral disease, including but not limited to, herpes simplex virus, hepatitis B virus, and hepatitis C virus infection. The present invention is based, at least in part, on the discovery that the PLD 55092 gene is differentially expressed in cells infected with herpes simplex virus, hepatitis B virus, and hepatitis C virus relative to their expression in non-infected cells.

In one aspect, the invention provides a method for identifying the presence of a nucleic acid molecule associated with a viral disease, in a sample by contacting a sample comprising nucleic acid molecules with a hybridization probe comprising at least 25 contiguous nucleotides of SEQ ID NO:14, and detecting the presence of a nucleic acid molecule associated with a viral disease, when the sample contains a nucleic acid molecule that hybridizes to the nucleic acid probe. In one embodiment, the hybridization probe is detectably labeled. In another embodiment the sample comprising nucleic acid molecules is subjected to agarose gel electrophoresis and southern blotting prior to contacting with the hybridization probe. In a further embodiment, the sample comprising nucleic acid molecules is subjected to agarose gel electrophoresis and northern blotting prior to contacting with the hybridization probe. In yet another embodiment, the detecting is by in situ hybridization. In other embodiments, the method is used to detect mRNA or genomic DNA in the sample.

The invention also provides a method for identifying a nucleic acid associated with a viral disease, in a sample, by contacting a sample comprising nucleic acid molecules with a first and a second amplification primer, the first primer comprising at least 25 contiguous nucleotides of SEQ ID NO:14 and the second primer comprising at least 25 contiguous nucleotides from the complement of SEQ ID NO:14, incubating the sample under conditions that allow for nucleic acid amplification, and detecting the presence of a nucleic acid molecule associated with a viral disease, when the sample contains a nucleic acid molecule that is amplified. In one embodiment, the sample comprising nucleic acid molecules is subjected to agarose gel electrophoresis after the incubation step.

In addition, the invention provides a method for identifying a polypeptide associated with a viral disease, in a sample by contacting a sample comprising polypeptide molecules with a binding substance specific for a PLD 55092 polypeptide, and detecting the presence of a polypeptide associated with a viral disease, when the sample contains a polypeptide molecule that binds to the binding substance. In one embodiment the binding substance is an antibody. In another embodiment, the binding substance is detectably labeled.

In another aspect, the invention provides a method of identifying a subject having or at risk for developing a viral disease, by contacting a sample obtained from the subject comprising nucleic acid molecules with a hybridization probe comprising at least 25 contiguous nucleotides of SEQ ID NO:14, and detecting the presence of a nucleic acid molecule when the sample contains a nucleic acid molecule that hybridizes to the nucleic acid probe, thereby identifying a subject having or at risk for developing a viral disease.

In a further aspect, the invention provides a method for identifying a subject having or at risk for developing a viral disease, by contacting a sample obtained from a subject comprising nucleic acid molecules with a first and a second amplification primer, the first primer comprising at least 25 contiguous nucleotides of SEQ ID NO:14 and the second primer comprising at least 25 contiguous nucleotides from the complement of SEQ ID NO:14, incubating the sample under conditions that allow for nucleic acid amplification, and detecting a nucleic acid molecule when the sample contains a nucleic acid molecule that is amplified, thereby identifying a subject having or at risk for developing a viral disease.

In yet another aspect, the invention provides a method of identifying a subject having or at risk for developing a viral disease, by contacting a sample obtained from the subject comprising polypeptide molecules with a binding substance specific for a PLD 55092 polypeptide by detecting the presence of a polypeptide molecule in the sample that binds to the binding substance, thereby identifying a subject having or at risk for developing a viral disease.

In another aspect, the invention provides a method for identifying a compound capable of treating a viral disease, characterized by aberrant PLD 55092 nucleic acid expression or PLD 55092 protein activity, by assaying the ability of the compound to modulate the expression of a PLD 55092 nucleic acid or the activity of a PLD 55092 protein. In one embodiment, the disease is a disease associated with herpes simplex virus infection. In another embodiment, the disease is a disease associated with hepatitis B virus infection. In yet another embodiment, the disease is a disease associated with hepatitis C virus infection. In a further embodiment, the ability of the compound to modulate the activity of the PLD 55092 protein is determined by detecting the induction of an intracellular second messenger, e.g., phosphatidic acid.

In yet another aspect, the invention provides a method for treating a subject having a viral disease characterized by aberrant PLD 55092 protein activity or aberrant PLD 55092 nucleic acid expression by administering to the subject a PLD 55092 modulator. The PLD 55092 modulator may be administered in a pharmaceutically acceptable formulation, or using a gene therapy vector.

In one embodiment, a PLD 55092 modulator is capable of modulating PLD 55092 polypeptide activity. For example, the PLD 55092 modulator may be a small molecule; an anti-PLD 55092 antibody; a PLD 55092 polypeptide comprising the amino acid sequence of SEQ ID NO:15, or a fragment thereof; a PLD 55092 polypeptide comprising an amino acid sequence which is at least 90 percent identical to the amino acid sequence of SEQ ID NO:15, wherein the percent identity is calculated using the ALIGN program for comparing amino acid sequences, a PAM120 weight residue table, a gap length penalty of 12, and a gap penalty of 4; or an isolated naturally occurring allelic variant of a polypeptide consisting of the amino acid sequence of SEQ ID NO:15, wherein the polypeptide is encoded by a nucleic acid molecule which hybridizes to a complement of a nucleic acid molecule consisting of SEQ ID NO:14 at 4×SSC at 65–70° C. followed by one or more washes in 1×SSC, at 65–70° C.

In another embodiment, the PLD 55092 modulator is capable of modulating PLD 55092 nucleic acid expression. For example, the PLD 55092 modulator may be a small molecule; an antisense PLD 55092 nucleic acid molecule; a ribozyme; a nucleic acid molecule comprising the nucleotide sequence of SEQ ID NO:14, or a fragment thereof; a nucleic acid molecule encoding a polypeptide comprising an amino acid sequence which is at least 90 percent identical to the amino acid sequence of SEQ ID NO:15, wherein the percent identity is calculated using the ALIGN program for comparing amino acid sequences, a PAM 120 weight residue table, a gap length penalty of 12, and a gap penalty of 4; or a nucleic acid molecule encoding a naturally occurring allelic variant of a polypeptide comprising the amino acid sequence of SEQ ID NO:15, wherein the nucleic acid molecule which hybridizes to a complement of a nucleic acid molecule consisting of SEQ ID NO:14 at 4×SSC at 65–70° C. followed by one or more washes in 1×SSC, at 65–70° C.

In another aspect, the invention provides a method for identifying a compound capable of modulating a virus activity, e.g., virus replication, virus envelopment, extracellular virion formation and/or cell-cell virus transmission. The method includes contacting a virus or a virus infected cell with a test compound and assaying the ability of the test compound to modulate the expression of a PLD 55092 nucleic acid or the activity of a PLD 55092 protein.

Furthermore, the invention provides a method for modulating a virus activity by contacting a virus or a virus infected cell with a PLD 55092 modulator.

Other features and advantages of the invention will be apparent from the following detailed description and claims.

DETAILED DESCRIPTION OF THE INVENTION

The present invention provides methods and compositions for the diagnosis and treatment of viral disease, including but not limited to herpes simplex virus infection, hepatitis B virus infection and hepatitis C virus infection, and the clinical sequelae associated with viral infection. The present invention is based, at least in part, on the discovery that phospholipase D (PLD) superfamily genes, referred to herein as "phospholipase D 55092" or "PLD 5,5092" nucleic acid and protein molecules, are differentially expressed in viral disease states, e.g., viral infection, relative to their expression in normal, or non-viral disease states.

Without intending to be limited by mechanism, it is believed that the PLD 55092 molecules of the present invention are involved in signal transduction and membrane biogenesis events regulating viral vesicular secretion and viral membrane biogenesis. The PLD 55092 molecules of the present invention may also mediate signal transduction events necessary for viral replication. Moreover, since the PLD 55092 molecules of the present invention are mostly neuron specific (see Examples infra) it is believed that PLD 55092 function may regulate viral transport and/or secretion in neurons and other infected cell types.

"Differential expression", as used herein, includes both quantitative as well as qualitative differences in the temporal and/or tissue expression pattern of a gene. Thus, a differentially expressed gene may have its expression activated or inactivated in normal versus viral disease conditions (for example, in virally infected cells and/or tissues). The degree to which expression differs in normal versus viral disease or control versus experimental states need only be large enough to be visualized via standard characterization techniques, e.g., quantitative PCR, Northern analysis, subtractive hybridization. The expression pattern of a differentially expressed gene may be used as part of a prognostic or diagnostic viral disease evaluation, or may be used in methods for identifying compounds useful for the treatment of viral disease. In addition, a differentially expressed gene involved in viral disease may represent a target gene such that modulation of the level of target gene expression or of target. gene product activity may act to ameliorate a viral disease condition. Compounds that modulate target gene expression or activity of the target gene product can be used in the treatment of viral disease.

Viral diseases include, but are not limited to, infection with herpes simplex virus (type 1 and type 2), varicella zoster virus, poliomyelitis virus, cytomegalovirus, influenza virus (A and B), respiratory syncytial virus, coxsackie virus, ebola virus, hantavirus, human papilloma virus, rotavirus, west nile virus, Epstein-Barr virus, human immunodeficiency virus, and hepatitis virus (A, B and C). The clinical sequelae of viral infection include herpes, AIDS, lassa fever, kaposi's sarcoma, meningitis, mumps, polio, chicken pox, colds and flu, dengue fever, encephalitis, Fifth disease, shingles, genital warts, rubella, yellow fever, hepatitis A, B and C, measles, rabies, and smallpox.

Although the PLD 55092 genes described herein may be differentially expressed with respect to viral disease, and/or their products may interact with gene products important to viral disease, the genes may also be involved in mechanisms important to additional viral and cellular regulatory processes, e.g., lipid metabolism, membrane homeostasis, vesicular trafficking and signal transduction.

Accordingly, the PLD 55092 molecules of the present invention may be involved in processes that modulate virus activity. As used herein, a "virus activity" or "virus function" includes virus replication, assembly, maturation, envelopment, extracellular virus formation, virus egress, and virus transmission.

The PLD 55092 molecules of the present invention may also mediate signal transduction events involved in oncogenesis and/or generation of pain signals. Thus, the PLD molecules of the present invention may also act as novel diagnostic targets and therapeutic agents for proliferative disorders, e.g., cancer, or pain disorders.

The present invention provides methods for identifying the presence of a PLD 55092 nucleic acid or polypeptide molecule associated with viral disease. In addition, the invention provides methods for identifying a subject having or at risk for developing a viral disease, by detecting the presence of a PLD 55092 nucleic acid or polypeptide molecule. within the subject or a sample, e.g., a tissue sample, obtained from the subject.

The invention also provides a method for identifying a compound capable of treating a viral disease, characterized by aberrant PLD 55092 nucleic acid expression or PLD 55092 protein activity by assaying the ability of the compound to modulate the expression of a PLD 55092 nucleic acid or the activity of a PLD 55092 protein. Furthermore, the invention provides a method for treating a subject having a viral disease characterized by aberrant PLD 55092 protein activity or aberrant PLD 55092 nucleic acid expression by administering to the subject a PLD 55092 modulator which is capable of modulating PLD 55092 protein activity or PLD 55092 nucleic acid expression.

Moreover, the invention provides a method for identifying a compound capable of modulating a virus activity by modulating the expression of a PLD 55092 nucleic acid or the activity of a PLD 55092 protein. The invention further provides a method for modulating a virus activity by contacting a virus with a PLD 55092 modulator.

Various aspects of the invention are described in further detail in the following subsections.

Screening Assays

The invention provides a method (also referred to herein as a "screening assay") for identifying modulators, i.e., candidate or test compounds or agents (e.g., peptides, peptidomimetics, small molecules (organic or inorganic) or other drugs) which bind to PLD 55092 proteins, have a stimulatory or inhibitory effect on, for example, PLD 55092 expression or PLD 55092 activity, or have a stimulatory or inhibitory effect on, for example, the expression or activity of a PLD 55092 substrate.

These assays are designed to identify compounds that bind to a PLD 55092 protein, bind to other intracellular or extracellular proteins that interact with a PLD 55092 protein, and interfere with the interaction of the PLD 55092 protein with other cellular or extracellular proteins. For example, in the case of the PLD 55092 protein, which is a phospholipase D type protein, such techniques can identify substrates and/or effectors for such a protein. A PLD 55092 protein substrate and/or effector can, for example, be used to ameliorate viral diseases. Such compounds may include, but are not limited to peptides, antibodies, or small organic or inorganic compounds. Such compounds may also include other cellular proteins.

Compounds identified via assays such as those described herein may be useful, for example, for ameliorating viral disease. In instances whereby a viral disease or condition associated with viral infection results from an overall lower level of PLD 55092 gene expression and/or PLD 55092 protein in a cell or tissue, compounds that interact with the PLD 55092 protein may include compounds which accentuate or amplify the activity of the bound PLD 55092 protein. Such compounds would bring about an effective increase in the level of PLD 55092 protein activity, thus, ameliorating symptoms.

In other instances, mutations within the PLD 55092 gene may cause aberrant types or excessive amounts of PLD 55092 proteins to be made which have a deleterious effect that leads to a viral disease. Similarly, physiological conditions may cause an excessive increase in PLD 55092 gene expression leading to a viral disease. In such cases, compounds that bind to a PLD 55092 protein may be identified that inhibit the activity of the PLD 55092 protein. Assays for testing the effectiveness of compounds identified by techniques such as those described in this section are discussed herein.

In one embodiment, the invention provides assays for screening candidate or test compounds which are substrates of a PLD 55092 protein or polypeptide or biologically active portion thereof. In another embodiment, the invention provides assays for screening candidate or test compounds which bind to or modulate the activity of a PLD 55092 protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra.).

In one embodiment, an assay is a cell-based assay in which a cell which expresses a PLD 55092 protein or biologically active portion thereof is contacted with a test compound and the ability of the test compound to modulate PLD 55092 activity is determined. Determining the ability of the test compound to modulate PLD 55092 activity can be accomplished by monitoring, for example, intracellular phosphatidic acid, $PIP_2$, diacylglycerol, or phosphatidylalcohol concentration, cell proliferation and/or migration, vesicle transport, or the activity of a PLD 55092-regulated transcription factor. The cell can be of mammalian origin, e.g., a neuronal cell. In one embodiment, the cell is a virally infected cell, and the ability of the test compound to modulate PLD 55092 activity can be accomplished by monitoring plaque formation and/or low pH fusion of infected cells. In another embodiment, compounds that interact with a PLD 55092 protein can be screened for their ability to function as substrates and/or effectors, i.e., to bind to the PLD 55092 protein and modulate a PLD 55092-mediated signal transduction pathway. Identification of PLD 55092 substrates and/or effectors, and measuring the activity of the substrate-protein and/or effector-protein complex, leads to the identification of modulators (e.g., antagonists) of this interaction. Such modulators may be useful in the treatment of viral disease.

The ability of the test compound to modulate PLD 55092 binding to a substrate or to bind to PLD 55092 can also be determined. Determining the ability of the test compound to modulate PLD 55092 binding to a substrate can be accomplished, for example, by coupling the PLD 55092 substrate with a radioisotope or enzymatic label such that binding of the PLD 55092 substrate to PLD 55092 can be determined by detecting the labeled PLD 55092 substrate in a complex. PLD 55092 could also be coupled, with a radioisotope or enzymatic label to monitor the ability of a test compound to modulate PLD 55092 binding to a PLD 55092 substrate in a complex. Determining the ability of the test compound to bind PLD 55092 can be accomplished, for example, by coupling the compound with a radioisotope or enzymatic label such that binding of the compound to PLD 55092 can be determined by detecting the labeled PLD 55092 compound in a complex. For example, compounds (e.g., PLD 55092 ligands or substrates) can be labeled with $^{125}I$, $^{35}S$, $^{14}C$, or $^3H$, either directly or indirectly, and the radioisotope detected by direct counting of radioemission or by scintillation counting. Compounds can further be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., a PLD 55092 ligand or substrate) to interact with PLD 55092 without the labeling of any of the interactants. For example, a microphysiometer can be used to detect the interaction of a compound with PLD 55092 without the labeling of either the compound or the PLD 55092 (McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and PLD 55092.

In another embodiment, an assay is a cell-based assay comprising contacting a cell expressing a PLD 55092 target molecule (e.g., a PLD 55092 substrate) with a test compound and determining the ability of the test compound to modulate (e.g., stimulate or inhibit) the activity of the PLD 55092 target molecule. Determining the ability of the test compound to modulate the activity of a PLD 55092 target molecule can be accomplished, for example, by determining the ability of the PLD 55092 protein to bind to or interact with the PLD 55092 target molecule.

Determining the ability of the PLD 55092 protein or a biologically active fragment thereof, to bind to or interact with a PLD 55092 target molecule can be accomplished by one of the methods described above for determining direct binding. In a preferred embodiment, determining the ability of the PLD 55092 protein to bind to or interact with a PLD 55092 target molecule can be accomplished by determining the activity of the target molecule. For example, the activity of the target molecule can be determined by detecting induction of a cellular second messenger of the target (i.e., intracellular phosphatidic acid, diacylglycerol, $PIP_2$), detecting catalytic/enzymatic activity of the target on an appropriate substrate, detecting the induction of a reporter gene (comprising a target-responsive regulatory element operatively linked to a nucleic acid encoding a detectable marker, e.g., luciferase), or detecting a target-regulated cellular response (e.g., gene expression, cell proliferation or migration).

In yet another embodiment, an assay of the present invention is a cell-free assay in which a PLD 55092 protein or biologically active portion thereof, is contacted with a test compound and the ability of the test compound to bind to the PLD 55092 protein or biologically active portion thereof is determined. Preferred biologically active portions of the PLD 55092 proteins to be used in assays of the present invention include fragments which participate in interactions with non-PLD 55092 molecules. Binding of the test compound to the PLD 55092 protein can be determined either directly or indirectly as described above. In a preferred embodiment, the assay includes contacting the PLD 55092 protein or biologically active portion thereof with a known compound which binds PLD 55092 to form an assay mixture, contacting the assay mixture with a test compound, and determining the ability of the test compound to interact with a PLD 55092 protein, wherein determining the ability of the test compound to interact with a PLD 55092 protein comprises determining the ability of the test compound to preferentially bind to PLD 55092 or biologically active portion thereof as compared to the known compound. Compounds that modulate the interaction of PLD 55092 with a known target protein may be useful in regulating the activity of a PLD 55092 protein, especially a mutant PLD 55092 protein.

In another embodiment, the assay is a cell-free assay in which a PLD 55092 protein or biologically active portion thereof is contacted with a test compound and the ability of the test compound to modulate (e.g., stimulate or inhibit) the activity of the PLD 55092 protein or biologically active portion thereof is determined. Determining the ability of the test compound to modulate the activity of a PLD 55092 protein can be accomplished, for example, by determining the ability of the PLD 55092 protein to bind to a PLD 55092 target molecule by one of the methods described above for determining direct binding. Determining the ability of the PLD 55092 protein to bind to a PLD 55092 target molecule can also be accomplished using a technology such as real-time Biomolecular Interaction Analysis (BIA) (Sjolander, S. and Urbaniczky, C. (1991) Anal. Chem. 63:2338–2345 and Szabo et al. (1995) Curr. Opin. Struct. Biol. 5:699–705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules. Determining the ability of the test compound to modulate PLD 55092 activity can also be monitored using an assay for phospholipase D activity, e.g., cleavage of a substrate, transphosphatidylation.

In another embodiment, determining the ability of the test compound to modulate the activity of a PLD 55092 protein can be accomplished by determining the ability of the PLD 55092 protein to further modulate the activity of a downstream effector of a PLD 55092 target molecule. For example, the activity of the effector molecule on an appropriate target can be determined or the binding of the effector to an appropriate target can be determined as previously described.

In yet another embodiment, the cell-free assay involves contacting a PLD 55092 protein or biologically active portion thereof with a known compound which binds the PLD 55092 protein to form an assay mixture, contacting the assay mixture with a test compound, and determining the ability of the test compound to interact with the PLD 55092 protein, wherein determining the ability of the test compound to interact with the PLD 55092 protein comprises determining the ability of the PLD 55092 protein to preferentially bind to or modulate the activity of a PLD 55092 target molecule.

In more than one embodiment of the above assay methods of the present invention, it may be desirable to immobilize either PLD 55092 or its target molecule to facilitate separation of complexed from uncomplexed forms of one or both of the proteins, as well as to accommodate automation of the assay. Binding of a test compound to a PLD 55092 protein, or interaction of a PLD 55092 protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/PLD 55092 fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or PLD 55092 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of PLD 55092 binding or activity determined using standard techniques.

Other techniques for immobilizing proteins on matrices can also be used in the screening assays of the invention. For example, either a PLD 55092 protein or a PLD 55092 target molecule can be immobilized utilizing conjugation of biotin and streptavidin. Biotinylated PLD 55092 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with PLD 55092 protein or target molecules but which do not interfere with binding of the PLD 55092 protein to its target molecule can be derivatized to the wells of the plate, and unbound target or PLD 55092 protein trapped in the wells by antibody conjugation. Methods for detecting such complexes, in addition to those described above for the GST-immobilized complexes, include immunodetection of complexes using antibodies reactive with the PLD 55092 protein or target molecule, as well as enzyme-linked assays which rely on detecting an enzymatic activity associated with the PLD 55092 protein or target molecule.

In another embodiment, modulators of PLD 55092 expression are identified in a method wherein a cell is contacted with a candidate compound and the expression of PLD 55092 mRNA or protein in the cell is determined. The level of expression of PLD 55092 mRNA or protein in the presence of the candidate compound is compared to the level of expression of PLD 55092 mRNA or protein in the absence of the candidate compound. The candidate compound can then be identified as a modulator of PLD 55092 expression based on this comparison. For example, when expression of PLD 55092 mRNA or protein is greater (statistically significantly greater) in the presence of the candidate compound than in its absence, the candidate compound is identified as a stimulator of PLD 55092 mRNA or protein expression. Alternatively, when expression of PLD 55092 mRNA or protein is less (statistically significantly less) in the presence of the candidate compound than in its absence, the candidate compound is identified as an inhibitor of PLD 55092 mRNA or protein expression. The level of PLD 55092 mRNA or protein expression in the cells can be determined by methods described herein for detecting PLD 55092 mRNA or protein.

In yet another aspect of the invention, the PLD 55092 proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with PLD 55092 ("PLD 55092-binding proteins" or "PLD 55092-bp") and are involved in PLD 55092 activity. Such PLD 55092-binding proteins are also likely to be involved in the propagation of signals by the PLD 55092 proteins or PLD 55092 targets as, for example, downstream elements of a PLD 55092-mediated signaling pathway. Alternatively, such PLD 55092-binding proteins are likely to be PLD 55092 inhibitors.

The two-hybrid system is based on the modular nature of most transcription factors, which consist of separable DNA-binding and activation domains. Briefly, the assay utilizes two different DNA constructs. In one construct, the gene that codes for a PLD 55092 protein, or a fragment thereof, is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a PLD 55092-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the PLD 55092 protein.

In another aspect, the invention pertains to a combination of two or more of the assays described herein. For example, a modulating agent can be identified using a cell-based or a cell free assay, and the ability of the agent to modulate the activity of a PLD 55092 protein can be confirmed in vivo, e.g., in an animal such as an animal model for viral disease, as described herein.

This invention further pertains to novel agents identified by the above-described screening assays. Accordingly, it is within the scope of this invention to further use an agent identified as described herein in an appropriate animal model. For example, an agent identified as described herein (e.g., a PLD 55092 modulating agent, an antisense PLD 55092 nucleic acid molecule, a PLD 55092-specific antibody, or a PLD 55092-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

Any of the compounds, including but not limited to compounds such as those identified in the foregoing assay systems, may be tested for the ability to ameliorate viral disease symptoms and/or viral infection. Cell-based and animal model-based assays for the identification of compounds exhibiting such an ability to ameliorate viral disease systems are described herein.

In one aspect, cell-based systems, as described herein, may be used to identify compounds which may act to ameliorate viral disease symptoms, e.g., viral infection. For example, such cell systems (e.g., cells infected with virus) may be exposed to a compound, suspected of exhibiting an ability to ameliorate viral disease symptoms, at a sufficient concentration and for a time sufficient to elicit such an amelioration of viral disease symptoms in the exposed cells. After exposure, the cells are examined to determine whether one or more of the viral disease cellular phenotypes has been altered to resemble a more normal or more wild type, non-viral disease phenotype. Cellular phenotypes that are associated with viral disease include viral infection (e.g., virus burden), cell lysis, plaque formation, and low pH induced fusion of infected cells.

In addition, animal-based viral disease systems, such as those described herein, may be used to identify compounds capable of ameliorating viral disease symptoms. Such animal models may be used as test substrates for the identification of drugs, pharmaceuticals, therapies, and interventions which may be effective in treating viral disease. For example, animal models may be exposed to a compound, suspected of exhibiting an ability to ameliorate viral disease symptoms and/or viral infection, at a sufficient concentration and for a time sufficient to elicit such an amelioration of viral disease symptoms in the exposed animals. The response of the animals to the exposure may be monitored by assessing the reversal of disorders associated with viral disease, for example, by monitoring viral burden before and after treatment.

With regard to intervention, any treatments which reverse any aspect of viral disease symptoms should be considered as candidates for human viral disease therapeutic intervention. Dosages of test agents may be determined by deriving dose-response curves.

Additionally, gene expression patterns may be utilized to assess the ability of a compound to ameliorate viral disease symptoms. For example, the expression pattern of one or more genes may form part of a "gene expression profile" or "transcriptional profile" which may be then be used in such an assessment. "Gene expression profile" or "transcriptional profile", as used herein, includes the pattern of mRNA expression obtained for a given tissue or cell type under a given set of conditions. Such conditions may include, but are not limited to, infection with herpes simplex virus, hepatitis B virus or hepatitis C virus, including any of the control or experimental conditions described herein. Gene expression profiles may be generated, for example, by utilizing a differential display procedure, Northern analysis and/or RT-PCR. In one embodiment, PLD 55092 gene sequences may be used as probes and/or PCR primers for the generation and corroboration of such gene expression profiles.

Gene expression profiles may be characterized for known states, either viral disease or normal, within the cell- and/or animal-based model systems. Subsequently, these known gene expression profiles may be compared to ascertain the effect a test compound has to modify such gene expression profiles, and to cause the profile to more closely resemble that of a more desirable profile.

For example, administration of a compound may cause the gene expression profile of a viral disease model system to more closely resemble the control system. Administration of a compound may, alternatively, cause the gene expression profile of a control system to begin to mimic a viral disease state. Such a compound may, for example, be used in further characterizing the compound of interest, or may be used in the generation of additional animal models.

Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining PLD 55092 protein and/or nucleic acid expression as well as PLD 55092 activity, in the context of a biological sample (e.g., blood, serum, cells, tissue) to thereby determine whether an individual is afflicted with a disease or disorder, or is at risk of developing a viral disease, a pain disorder, or a cellular proliferation, growth, differentiation, or migration disorder, associated with aberrant or unwanted PLD 55092 expression or activity. The invention also provides for prognostic (or predictive) assays for determining whether an individual is at risk of developing a disorder associated with PLD 55092 protein, nucleic acid expression or activity. For example, mutations in a PLD 55092 gene can be assayed in a biological sample. Such assays can be used for prognostic or predictive purpose to thereby prophylactically treat an individual prior to the onset of a disorder characterized by or associated with PLD 55092 protein, nucleic acid expression or activity.

Another aspect of the invention pertains to monitoring the influence of agents (e.g., drugs, compounds) on the expression or activity of PLD 55092 in clinical trials.

These and other agents are described in further detail in the following sections.

Diagnostic Assays

The present invention encompasses methods for diagnostic and prognostic evaluation of viral disease conditions, and for the identification of subjects exhibiting a predisposition to such conditions.

An exemplary method for detecting the presence or absence of PLD 55092 protein or nucleic acid in a biological sample involves obtaining a biological sample from a test subject and contacting the biological sample with a compound or an agent capable of detecting PLD 55092 protein or nucleic acid (e.g., mRNA, or genomic DNA) that encodes PLD 55092 protein such that the presence of PLD 55092 protein or nucleic acid is detected in the biological sample. A preferred agent for detecting PLD 55092 mRNA or genomic DNA is a labeled nucleic acid probe capable of hybridizing to PLD 55092 mRNA or genomic DNA. The nucleic acid probe can be, for example, the PLD 55092 nucleic acid set forth in SEQ ID NO:14, or a portion thereof, such as an oligonucleotide of at least 15, 20, 25, 30, 35, 40, 45, 50, 100, 250 or 500 nucleotides in length and sufficient to specifically hybridize under stringent conditions to PLD 55092 mRNA or genomic DNA. Other suitable probes for use in the diagnostic assays of the invention are described herein.

A preferred agent for detecting PLD 55092 protein is an antibody capable of binding to PLD 55092 protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect PLD 55092 mRNA, protein, or genomic DNA in a biological sample in vitro as well as in vivo. For example, in vitro techniques for detection of PLD 55092 mRNA include Northern hybridizations and in situ hybridizations. In vitro techniques for detection of PLD 55092 protein include enzyme linked immunosorbent assays (ELISAs), Western blots, immunoprecipitations and immunofluorescence. In vitro techniques for detection of PLD 55092 genomic DNA include Southern hybridizations. Furthermore, in vivo techniques for detection of PLD 55092 protein include introducing into a subject a labeled anti-PLD 55092 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting PLD 55092 protein, mRNA, or genomic DNA, such that the presence of PLD 55092 protein, mRNA or genomic DNA is detected in the biological sample, and comparing the presence of PLD 55092 protein, mRNA or genomic DNA in the control sample with the presence of PLD 55092 protein, mRNA or genomic DNA in the test sample.

The invention also encompasses kits for detecting the presence of PLD 55092 in a biological sample. For example, the kit can comprise a labeled compound or agent capable of detecting PLD 55092 protein or mRNA in a biological sample; means for determining the amount of PLD 55092 in the sample; and means for comparing the amount of PLD 55092 in the sample with a standard. The compound or agent can be packaged in a suitable container. The kit can further comprise instructions for using the kit to detect PLD 55092 protein or nucleic acid.

Prognostic Assays

The diagnostic methods described herein can furthermore be utilized to identify subjects having or at risk of developing a viral disease or disorder associated with aberrant or unwanted PLD 55092 expression or activity. As used herein, the term "aberrant" includes a PLD 55092 expression or activity which deviates from the wild type PLD 55092 expression or activity. Aberrant expression or activity includes increased or decreased expression or activity, as well as expression or activity which does not follow the wild type developmental pattern of expression or the subeellular pattern of expression. For example, aberrant PLD 55092 expression or activity is intended to include the cases in which a mutation in the PLD 55092 gene causes the PLD 55092 gene to be under-expressed or over-expressed and situations in which such mutations result in a non-functional PLD 55092 protein or a protein which does not function in a wild-type fashion, e.g., a protein which does not interact with a PLD 55092 ligand or substrate, or one which interacts with a non-PLD 55092 ligand or substrate. As used herein, the term "unwanted" includes an unwanted phenomenon involved in a biological response such as viral replication and dissemination. For example, the term unwanted includes a PLD 55092 expression pattern or a PLD 55092 protein activity which is undesirable in a subject.

The assays described herein, such as the preceding diagnostic assays or the following assays, can be utilized to identify a subject having or at risk of developing a disorder associated with a misregulation in PLD 55092 protein activity or nucleic acid expression, such as a viral disease, a pain disorder, or a cellular proliferation, growth, differentiation, or migration disorder. Alternatively, the prognostic assays can be utilized to identify a subject having or at risk for developing a viral disease, a pain disorder, or a cellular proliferation, growth, differentiation, or migration disorder, associated with a misregulation in PLD 55092 protein activity or nucleic acid expression. Thus, the present invention provides a method for identifying a disease or disorder associated with aberrant or unwanted PLD 55092 expression or activity in which a test sample is obtained from a subject and PLD 55092 protein or nucleic acid (e.g., mRNA or genomic DNA) is detected, wherein the presence of PLD 55092 protein or nucleic acid is diagnostic for a subject having or at risk of developing a disease or disorder associated with aberrant or unwanted PLD 55092 expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted PLD 55092 expression or activity. For example, such methods can be used to determine whether a subject can be effectively treated with an agent for a viral disease, a pain disorder, or a cellular proliferation, growth, differentiation, or migration disorder. Thus, the present invention provides methods for determining whether a subject can be effectively treated with an agent for a viral disease, a pain disorder, or a cellular proliferation, growth, differentiation, or migration disorder associated with aberrant or unwanted PLD 55092 expression or activity in which a test sample is obtained and PLD 55092 protein or nucleic acid expression or activity is detected (e.g., wherein the abundance of PLD 55092 protein or nucleic acid expression or activity is diagnostic for a subject that can be administered the agent to treat a disorder associated with aberrant or unwanted PLD 55092 expression or activity).

The methods of the invention can also be used to detect genetic alterations in a PLD 55092 gene, thereby determining if a subject with the altered gene is at risk for a disorder characterized by misregulation in PLD 55092 protein activity or nucleic acid expression, such as a viral disease, a pain disorder, or a cellular proliferation, growth, differentiation, or migration disorder. In preferred embodiments, the methods include detecting, in a sample of cells from the subject, the presence or absence of a genetic alteration characterized by at least one of an alteration affecting the integrity of a gene encoding a PLD 55092 protein, or the mis-expression of the PLD 55092 gene. For example, such genetic alterations can be detected by ascertaining the existence of at least one of 1) a deletion of one or more nucleotides from a PLD 55092 gene; 2) an addition of one or more nucleotides to a PLD 55092 gene; 3) a substitution of one or more nucleotides of a PLD 55092 gene, 4) a chromosomal rearrangement of a PLD 55092 gene; 5) an alteration in the level of a messenger RNA transcript of a PLD 55092 gene, 6) aberrant modification of a PLD 55092 gene, such as of the methylation pattern of the genomic DNA, 7) the presence of a non-wild type splicing pattern of a messenger RNA transcript of a PLD 55092 gene, 8) a non-wild type level of a PLD 55092 protein, 9) allelic loss of a PLD 55092 gene, and 10) inappropriate post-translational modification of a PLD 55092 protein. As described herein, there are a large number of assays known in the art which can be used for detecting alterations in a PLD 55092 gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the PLD 55092 gene (see Abravaya et al. (1995) *Nucleic Acids Res*. 23:675–682). This method can include the steps of collecting a sample of cells from a subject, isolating nucleic acid (e.g., genomic, mRNA or both) from the cells of the sample, contacting the nucleic acid sample with one or more primers which specifically hybridize to a PLD 55092 gene under conditions such that hybridization and amplification of the PLD 55092 gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Other amplification methods include: self sustained sequence replication (Guatelli, J. C. et al., (1990) *Proc. Natl. Acad. Sci. USA* 87:1874–1878), transcriptional amplification system (Kwoh, D. Y. et al., (1989) *Proc. Natl. Acad. Sci. USA* 86:1173–1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a PLD 55092 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in PLD 55092 can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M.

J. et al. (1996) *Nature Medicine* 2: 753–759). For example, genetic mutations in PLD 55092 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the PLD 55092 gene and detect mutations by comparing the sequence of the sample PLD 55092 with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr*. 36:127–162; and Griffin et al. (1993) *Appl. Biochem. Biotechnol*. 38:147–159).

Other methods for detecting mutations in the PLD 55092 gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type PLD 55092 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad Sci USA* 85:4397; Saleeba et al. (1992) *Methods Enzymol*. 217: 286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in PLD 55092 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a PLD 55092 sequence, e.g., a wild-type PLD 55092 sequence, is hybridized to a cDNA or other DNA product from a test cell(s). The duplex is treated with a DNA mismatch repair enzyme, and the cleavage products, if any, can be detected from electrophoresis protocols or the like (described in, for example, U.S. Pat. No. 5,459,039).

In other embodiments, alterations in electrophoretic mobility will be used to identify mutations in PLD 55092 genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat. Res*. 285:125–144; and Hayashi (1992) *Genet. Anal. Tech. Appl*. 9:73–79). Single-stranded DNA fragments of sample and control PLD 55092 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res*. 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a PLD 55092 gene.

Furthermore, any cell type or tissue in which PLD 55092 is expressed may be utilized in the prognostic assays described herein.

Monitoring of Effects During Clinical Trials

The present invention provides methods for evaluating the efficacy of drugs and monitoring the progress of patients involved in clinical trials for the treatment of viral disease.

Monitoring the influence of agents (e.g., drugs) on the expression or activity of a PLD 55092 protein (e.g., the modulation of viral replication, assembly, maturation, and/or transmission; lipid metabolism; vesicle trafficking; or cell proliferation, differentiation and/or migration) can be applied not only in basic drug screening, but also in clinical trials. For example, the effectiveness of an agent determined by a screening assay as described herein to increase PLD 55092 gene expression, protein levels, or upregulate PLD 55092 activity, can be monitored in clinical trials of subjects exhibiting decreased PLD 55092 gene expression, protein levels, or downregulated PLD 55092 activity. Alternatively, the effectiveness of an agent determined by a screening assay to decrease PLD 55092 gene expression, protein levels, or downregulate PLD 55092 activity, can be monitored in clinical trials of subjects exhibiting increased PLD 55092 gene expression, protein levels, or upregulated PLD 55092 activity. In such clinical trials, the expression or activity of a PLD 55092 gene, and preferably, other genes that have been implicated in, for example, a PLD 55092-associated disorder can be used as a "read out" or markers of the phenotype a particular cell, e.g., a neuronal cell. In addition, the expression of a PLD 55092 gene, or the level of PLD 55092 protein activity may be used as a read out of a particular drug or agent's effect on a viral disease state.

For example, and not by way of limitation, genes, including PLD 55092, that are modulated in cells by treatment with an agent (e.g., compound, drug or small molecule) which modulates PLD 55092 activity (e.g., identified in a screening assay as described herein) can be identified. Thus, to study the effect of agents on PLD 55092-associated disorders (e.g., viral disease, pain disorders, or cellular proliferation, growth, differentiation, or migration disorders), for example, in a clinical trial, cells can be isolated and RNA prepared and analyzed for the levels of expression of PLD 55092 and other genes implicated in the PLD 55092-associated disorder, respectively. The levels of gene expression (e.g., a gene expression pattern) can be quantified by northern blot analysis or RT-PCR, as described herein, or alternatively by measuring the amount of protein produced, by one of the methods as described herein, or by measuring the levels of activity of PLD 55092 or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of a PLD 55092 protein, mRNA, or genomic DNA in the preadministration sample; (iii) obtaining one or more post-administration samples from the subject; (iv) detecting the level of expression or activity of the PLD 55092 protein, mRNA, or genomic DNA in the post-administration samples; (v) comparing the level of expression or activity of the PLD 55092 protein, mRNA, or genomic DNA in the pre-administration sample with the PLD 55092 protein, mRNA, or genomic DNA in the post administration sample or samples; and (vi) altering the administration of the agent to the subject accordingly. For example, increased administration of the agent may be desirable to increase the expression or activity of PLD 55092 to higher levels than detected, i.e., to increase the effectiveness of the agent. Alternatively, decreased administration of the agent may be desirable to decrease expression or activity of PLD 55092 to lower levels than detected, i.e. to decrease the effectiveness of the agent. According to such an embodiment, PLD 55092 expression or activity may be used as an indicator of the effectiveness of an agent, even in the absence of an observable phenotypic response.

Methods of Treatment

The present invention provides for both prophylactic and therapeutic methods of treating a subject at risk of (or susceptible to) a disorder or having a disorder associated with aberrant or unwanted PLD 55092 expression or activity, e.g. a viral disease, a pain disorder, or a cellular proliferation, growth, differentiation, or migration disorder. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the PLD 55092 molecules of the present invention or PLD 55092 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

Treatment is defined as the application or administration of a therapeutic agent to a patient, or the application or administration of a therapeutic agent to an isolated tissue or cell line from a patient, who has a disease, a symptom of disease or a predisposition toward a disease, with the purpose of curing, healing, alleviating, relieving, altering, remedying, ameliorating, improving or affecting the disease, the symptoms of disease or the predisposition toward disease as described herein.

A therapeutic agent includes, but is not limited to, small molecules, peptides, antibodies, ribozymes and antisense oligonucleotides.

Prophylactic Methods

In one aspect, the invention provides a method for preventing in a subject, a viral disease, a pain disorder, or a cellular proliferation, growth, differentiation, or migration disorder associated with an aberrant or unwanted PLD 55092 expression or activity, by administering to the subject a PLD 55092 or an agent which modulates PLD 55092 expression or at least one PLD 55092 activity. Subjects at risk for a viral disease, a pain disorder, or a cellular proliferation, growth, differentiation, or migration disorder which is caused or contributed to by aberrant or unwanted PLD 55092 expression or activity can be identified by, for example, any or a combination of diagnostic or prognostic assays as described herein. Administration of a prophylactic agent can occur prior to the manifestation of symptoms characteristic of the PLD 55092 aberrancy, such that a disease or disorder is prevented or, alternatively, delayed in its progression. Depending on the type of PLD 55092 aberrancy, for example, a PLD 55092, PLD 55092 agonist or PLD 55092 antagonist agent can be used for treating the subject. The appropriate agent can be determined based on screening assays described herein.

Therapeutic Methods

Described herein are methods and compositions whereby viral disease symptoms may be ameliorated. Certain viral diseases are brought about, at least in part, by an excessive level of a gene product, or by the presence of a gene product exhibiting an abnormal or excessive activity. As such, the reduction in the level and/or activity of such gene products would bring about the amelioration of viral disease symptoms. Techniques for the reduction of gene expression levels or the activity of a protein are discussed below.

Alternatively, certain other viral diseases are brought about, at least in part, by the absence or reduction of the level of gene expression, or a reduction in the level of a protein's activity. As such, an increase in the level of gene expression and/or the activity of such proteins would bring about the amelioration of viral disease symptoms.

In some cases, the up-regulation of a gene in a disease state reflects a protective role for that gene product in responding to the disease condition. Enhancement of such a gene's expression, or the activity of the gene product, will reinforce the protective effect it exerts. Some viral disease states may result from an abnormally low level of activity of such a protective gene. In these cases also, an increase in the level of gene expression and/or the activity of such gene products would bring about the amelioration of viral disease symptoms. Techniques for increasing target gene expression levels or target gene product activity levels are discussed herein.

Accordingly, another aspect of the invention pertains to methods of modulating PLD 55092 expression or activity for therapeutic purposes. Accordingly, in an exemplary embodiment, the modulatory method of the invention involves contacting a cell with a PLD 55092 or agent that modulates one or more of the activities of PLD 55092 protein activity associated with the cell. An agent that modulates PLD 55092 protein activity can be an agent as described herein, such as a nucleic acid or a protein, a naturally-occurring target molecule of a PLD 55092 protein (e.g., a PLD 55092 ligand or substrate), a PLD 55092 antibody, a PLD 55092 agonist or antagonist, a peptidomimetic of a PLD 55092 agonist or antagonist, or other small molecule. In one embodiment, the agent stimulates one or more PLD 55092 activities. Examples of such stimulatory agents include active PLD 55092 protein and a nucleic acid molecule encoding PLD 55092 that has been introduced into the cell. In another embodiment, the agent inhibits one or more PLD 55092 activities. Examples of such inhibitory agents include antisense PLD 55092 nucleic acid molecules, anti-PLD 55092 antibodies, and PLD 55092 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a PLD 55092 protein or nucleic acid molecule. In one embodiment, the method involves administering an agent (e.g., an agent identified by a screening assay described herein), or combination of agents that modulates (e.g., upregulates or downregulates) PLD 55092 expression or activity. In another embodiment, the method involves administering a PLD 55092 protein or nucleic acid molecule as therapy to compensate for reduced, aberrant, or unwanted PLD 55092 expression or activity.

Stimulation of PLD 55092 activity is desirable in situations in which PLD 55092 is abnormally downregulated and/or in which increased PLD 55092 activity is likely to have a beneficial effect. Likewise, inhibition of PLD 55092 activity is desirable in situations in which PLD 55092 is abnormally upregulated and/or in which decreased PLD 55092 activity is likely to have a beneficial effect.

Methods for Inhibiting Target Gene Expression, Synthesis, or Activity

As discussed above, genes involved in viral disease, pain disorders, or cellular proliferation, growth, differentiation, or migration disorders may cause such disorders via an increased level of gene activity. In some cases, such up-regulation may have a causative or exacerbating effect on the disease state. A variety of techniques may be used to inhibit the expression, synthesis, or activity of such genes and/or proteins.

For example, compounds such as those identified through assays described above, which exhibit inhibitory activity, may be used in accordance with the invention to ameliorate viral disease symptoms. Such molecules may include, but are not limited to, small organic molecules, peptides, antibodies, and the like.

For example, compounds can be administered that compete with endogenous substrate and/or ligand for the PLD 55092 protein. The resulting reduction in the amount of substrate-bound or ligand-bound PLD 55092 protein will modulate virus and/or cell physiology. Compounds that can be particularly useful for this purpose include, for example, soluble proteins or peptides, such as peptides comprising one or more of the biologically active domains, or portions and/or analogs thereof, of the PLD 55092 protein, including, for example, soluble fusion proteins such as Ig-tailed fusion proteins. (For a discussion of the production of Ig-tailed fusion proteins, see, for example, U.S. Pat. No. 5,116,964). Alternatively, compounds, such as ligand analogs or antibodies, that bind to the PLD 55092 catalytic site, but do not activate the protein, (e.g., antagonists) can be effective in inhibiting PLD 55092 protein activity.

Further, antisense and ribozyme molecules which inhibit expression of the PLD 55092 gene may also be used in accordance with the invention to inhibit aberrant PLD 55092 gene activity. Still further, triple helix molecules may be utilized in inhibiting aberrant PLD 55092 gene activity.

The antisense nucleic acid molecules of the invention are typically administered to a subject or generated in situ such that they hybridize with or bind to cellular mRNA and/or genomic DNA encoding a PLD 55092 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215: 327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave PLD 55092 mRNA transcripts to thereby inhibit translation of PLD 55092 mRNA. A ribozyme having specificity for a PLD 55092-encoding nucleic acid can be designed based upon the nucleotide sequence of a PLD 55092 cDNA disclosed herein (i.e., SEQ ID NO:14). For example, a derivative of a Tetrahymena L-19 IVS RNA can be constructed in which the nucleotide sequence of the active site is complementary to the nucleotide sequence to be cleaved in a PLD 55092-encoding mRNA (see, for example, Cech et al. U.S. Pat. No. 4,987, 071; and Cech et al. U.S. Pat. No. 5,116,742). Alternatively, PLD 55092 mRNA can be used to select a catalytic RNA having a specific ribonuclease activity from a pool of RNA molecules (see, for example, Bartel, D. and Szostak, J. W. (1993) *Science* 261:1411–1418).

PLD 55092 gene expression can also be inhibited by targeting nucleotide sequences complementary to the regulatory region of the PLD 55092 (e.g., the PLD 55092 promoter and/or enhancers) to form triple helical structures that prevent transcription of the PLD 55092 gene in target cells (see, for example, Helene, C. (1991) *Anticancer Drug Des.* 6(6):569–84; Helene, C. et al. (1992) *Ann. N.Y. Acad. Sci.* 660:27–36; and Maher, L. J. (1992) *Bioassays* 14(12): 807–15).

Antibodies that are both specific for the PLD 55092 protein and interfere with its activity may also be used to modulate or inhibit PLD 55092 protein function. Such antibodies may be generated using standard techniques described herein, against the PLD 55092 protein itself or against peptides corresponding to portions of the protein. Such antibodies include but are not limited to polyclonal, monoclonal, Fab fragments, single chain antibodies, or chimeric antibodies.

In instances where the target gene protein is intracellular and whole antibodies are used, internalizing antibodies may be preferred. Lipofectin liposomes may be used to deliver the antibody or a fragment of the Fab region which binds to the target epitope into cells. Where fragments of the antibody are used, the smallest inhibitory fragment which binds to the target protein's binding domain is preferred. For example, peptides having an amino acid sequence corresponding to the domain of the variable region of the antibody that binds to the target gene protein may be used. Such peptides may be synthesized chemically or produced via recombinant DNA technology using methods well known in the art (described in, for example, Creighton (1983), supra; and Sambrook et al. (1989) supra). Single chain neutralizing antibodies which bind to intracellular target gene epitopes may also be administered. Such single chain antibodies may be administered, for example, by expressing nucleotide sequences encoding single-chain antibodies within the target cell population by utilizing, for example, techniques such as those described in Marasco et al. (1993) *Proc. Natl. Acad. Sci. USA* 90:7889–7893).

In some instances, the target gene protein is extracellular, or is a transmembrane protein. Antibodies that are specific for one or more extracellular domains of the protein, for example, and that interfere with its activity, are particularly useful in treating disease. Such antibodies are especially efficient because they can access the target domains directly from the bloodstream. Any of the administration techniques described below which are appropriate for peptide administration may be utilized to effectively administer inhibitory target gene antibodies to their site of action.

Methods for Restoring or Enhancing Target Gene Activity

Genes that cause viral disease, a pain disorder, or a cellular proliferation, growth, differentiation, or migration disorder may be underexpressed within disease situations. Alternatively, the activity of the protein products of such genes may be decreased, leading to the development of symptoms of viral disease, a pain disorder, or a cellular proliferation, growth, differentiation, or migration disorder. Such down-regulation of gene expression or decrease of protein activity might have a causative or exacerbating effect on the disease state.

In some cases, genes that are up-regulated in the disease state might be exerting a protective effect. A variety of techniques may be used to increase the expression, synthesis, or activity of genes and/or proteins that exert a protective effect in response to viral disease conditions.

Described in this section are methods whereby the level PLD 55092 activity may be increased to levels wherein viral disease symptoms are ameliorated. The level of PLD 55092 activity may be increased, for example, by either increasing the level of PLD 55092 gene expression or by increasing the level of active PLD 55092 protein which is present.

For example, a PLD 55092 protein, at a level sufficient to ameliorate viral disease symptoms may be administered to a patient exhibiting such symptoms. Any of the techniques discussed below may be used for such administration. One of skill in the art will readily know how to determine the concentration of effective, non-toxic doses of the PLD 55092 protein, utilizing techniques such as those described below.

Additionally, RNA sequences encoding a PLD 55092 protein may be directly administered to a patient exhibiting viral disease symptoms, at a concentration sufficient to produce a level of PLD 55092 protein such that viral disease symptoms are ameliorated. Any of the techniques discussed below, which achieve intracellular administration of compounds, such as, for example, liposome administration, may be used for the administration of such RNA molecules. The RNA molecules may be produced, for example, by recombinant techniques such as those described herein.

Further, subjects may be treated by gene replacement therapy. One or more copies of a PLD 55092 gene, or a portion thereof, that directs the production of a normal PLD 55092 protein with PLD 55092 function, may be inserted into cells using vectors which include, but are not limited to adenovirus, adeno-associated virus, and retrovirus vectors, in addition to other particles that introduce DNA into cells, such as liposomes. Additionally, techniques such as those described above may be used for the introduction of PLD 55092 gene sequences into human cells.

Cells, preferably, autologous cells, containing PLD 55092 expressing gene sequences may then be introduced or reintroduced into the subject at positions which allow for the amelioration of viral disease symptoms. Such cell replacement techniques may be preferred, for example, when the gene product is a secreted, extracellular gene product.

Pharmacogenomics

The PLD 55092 molecules of the present invention, as well as agents, or modulators which have a stimulatory or inhibitory effect on PLD 55092 activity (e.g., PLD 55092 gene expression) as identified by a screening assay described herein can be administered to individuals to treat (prophylactically or therapeutically) PLD 55092-associated disorders (e.g., a viral disease, a pain disorder, or a cellular proliferation, growth, differentiation, or migration disorder) associated with aberrant or unwanted PLD 55092 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a PLD 55092 molecule or a PLD 55092 modulator as well as tailoring the dosage and/or therapeutic regimen of treatment with a PLD 55092 molecule or PLD 55092 modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10–11): 983–985 and Linder, M. W. et al. (1997) *Clin. Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a PLD 55092 protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses.

Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a PLD 55092 molecule or PLD 55092 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a PLD 55092 molecule or PLD 55092 modulator, such as a modulator identified by one of the exemplary screening assays described herein.

Use of PLD 55092 Molecules as Surrogate Markers

The PLD 55092 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the PLD 55092 molecules of the invention may be detected, and may be correlated with one or more biological states in vivo. For example, the PLD 55092 molecules of the invention may serve as surrogate markers for one or more disorders or disease states or for conditions leading up to disease states.

As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the causation of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35:258–264; and James (1994) *AIDS Treatment News Archive* 209.

The PLD 55092 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a PLD 55092 marker) transcription or expression, the amplified marker may be in a quantity which is more readily detectable than the drug itself. Also, the marker may be more easily detected due to the nature of the marker itself; for example, using the methods described herein, anti-PLD 55092 antibodies may be employed in an immune-based detection system for a PLD 55092 protein marker, or PLD 55092-specific radiolabeled probes may be used to detect a PLD 55092 mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90:229–238; Schentag (1999) *Am. J. Health-Syst. Pharm.* 56 Suppl. 3:S21–S24; and Nicolau (1999) *Am. J. Health-Syst. Pharm.* 56 Suppl. 3:S16–S20.

The PLD 55092 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35(12):1650–1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., PLD 55092 protein or RNA) for specific tumor markers in a subject, a drug or course of treatment may be selected that is optimized for the treatment of the specific tumor likely to be present in the subject. Similarly, the presence or absence of a specific-sequence mutation in PLD 55092 DNA may correlate PLD 55092 drug response. The use of pharmacogenomic markers therefore permits the application of the most appropriate treatment for each subject without having to administer the therapy.

Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

Chromosome Mapping

Once the sequence (or a portion of the sequence) of a gene has been isolated, this sequence can be used to map the location of the gene on a chromosome. This process is called chromosome mapping. Accordingly, portions or fragments of the PLD 55092 nucleotide sequences, described herein, can be used to map the location of the PLD 55092 genes on a chromosome. The mapping of the PLD 55092 sequences to chromosomes is an important first step in correlating these sequences with genes associated with disease.

Briefly, PLD 55092 genes can be mapped to chromosomes by preparing PCR primers (preferably 15–25 bp in length) from the PLD 55092 nucleotide sequences. Computer analysis of the PLD 55092 sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the PLD 55092 sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220: 919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the PLD 55092 nucleotide sequences to design oligonucleotide primers, sublocalization can be achieved with panels of fragments from specific chromosomes. Other mapping strategies which can similarly be used to map a PLD 55092 sequence to its chromosome include in situ hybridization (described in Fan, Y. et al. (1990) *Proc. Natl. Acad. Sci. USA*, 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783–787.

Moreover, differences in the DNA sequences between individuals affected and unaffected with a disease associated with the PLD 55092 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing

The PLD 55092 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the PLD 55092 nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The PLD 55092 nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of PLD 55092 gene sequences can comfortably provide positive individual identification with a panel of perhaps 10 to 1,000 primers which each yield a noncoding amplified sequence of 100 bases. If predicted coding sequences are used, a more appropriate number of primers for positive individual identification would be 500–2,000.

If a panel of reagents from PLD 55092 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial PLD 55092 Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of PLD 55092 gene sequences are particularly appropriate for this use as greater numbers of polymorphisms occur in the noncoding regions, making it easier to differentiate individuals using this technique. Examples of polynucleotide reagents include the PLD 55092 nucleotide sequences or portions thereof, e.g., fragments derived from the noncoding regions having a length of at least 20 bases, preferably at least 30 bases.

The PLD 55092 nucleotide sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such PLD 55092 probes can be used to identify tissue by species and/or by organ type.

In a similar fashion, these reagents, e.g., PLD 55092 primers or probes can be used to screen tissue culture for contamination (i.e. screen for the presence of a mixture of different types of cells in a culture).

Recombinant Expression Vectors and Host Cells

The methods of the invention include the use of vectors, preferably expression vectors, containing a nucleic acid encoding a PLD 55092 protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the methods of the invention may include other forms of expression vectors, such as viral vectors (e.g., replication defective retroviruses, adenoviruses and adeno-associated viruses), which serve equivalent functions.

The recombinant expression vectors used in the methods of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., PLD 55092 proteins, mutant forms of PLD 55092 proteins, fusion proteins, and the like).

The recombinant expression vectors used in the methods of the invention can be designed for expression of PLD 55092 proteins in prokaryotic or eukaryotic cells, e.g., for use in the cell-based assays of the invention. For example, PLD 55092 proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in PLD 55092 activity assays, (e.g., direct assays or competitive assays described in detail below), or to generate antibodies specific for PLD 55092 proteins, for example. In a preferred embodiment, a PLD 55092 fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21 (DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology. Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the PLD 55092 expression vector is a yeast expression vector. Examples of vectors for expression in yeast *S. cerevisiae* include pYepSec1 (Baldari, et al., (1987) *EMBO J.* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp, San Diego, Calif.).

Alternatively, PLD 55092 proteins can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed.,* Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), endothelial cell-specific promoters (e.g., KDR/flk promoter; U.S. Pat. No. 5,888,765), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The expression characteristics of an endogenous PLD 55092 gene within a cell line or microorganism may be modified by inserting a heterologous DNA regulatory element into the genome of a stable cell line or cloned microorganism such that the inserted regulatory element is operatively linked with the endogenous PLD 55092 gene. For example, an endogenous PLD 55092 gene which is normally "transcriptionally silent", i.e., a PLD 55092 gene which is normally not expressed, or is expressed only at very low levels in a cell line or microorganism, may be activated by inserting a regulatory element which is capable of promoting the expression of a normally expressed gene product in that cell line or microorganism. Alternatively, a transcriptionally silent, endogenous PLD 55092 gene may be activated by insertion of a promiscuous regulatory element that works across cell types.

A heterologous regulatory element may be inserted into a stable cell line or cloned microorganism, such that it is operatively linked with an endogenous PLD 55092 gene, using techniques, such as targeted homologous recombination, which are well known to those of skill in the art, and described, e.g., in Chappel, U.S. Pat. No. 5,272,071; PCT publication No. WO 91/06667, published May 16, 1991.

The methods of the invention use a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to PLD 55092 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect the methods of the invention pertains to the use of host cells into which a PLD 55092 nucleic acid molecule of the invention is introduced, e.g., a PLD 55092 nucleic acid molecule within a recombinant expression vector or a PLD 55092 nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the tern as used herein.

A host cell can be any prokaryotic or eukaryotic cell. For example, a PLD 55092 protein can be expressed in bacterial cells such as *E. coli*, insect cells, yeast or mammalian cells (such as Chinese hamster ovary cells (CHO) HEPG2 cells, NT2 cells, MRC5 cells, or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin, puromycin, zeomycin and methotrexate. Nucleic acid encoding a selectable marker can be introduced into a host cell on the same vector as that encoding a PLD 55092 protein or can be introduced on a separate vector. Cells stably transfected with the introduced nucleic acid can be identified by drug selection (e.g., cells that have incorporated the selectable marker gene will survive, while the other cells die).

A host cell used in the methods of the invention, such as a prokaryotic or eukaryotic host cell in culture, can be used to produce (i.e., express) a PLD 55092 protein. Accordingly, the invention further provides methods for producing a PLD 55092 protein using the host cells of the invention. In one embodiment, the method comprises culturing the host cell of the invention (into which a recombinant expression vector encoding a PLD 55092 protein has been introduced) in a suitable medium such that a PLD 55092 protein is produced. In another embodiment, the method further comprises isolating a PLD 55092 protein from the medium or the host cell.

Cell- and Animal-Based Model Systems

Described herein are cell- and animal-based systems which act as models for viral disease. These systems may be used in a variety of applications. For example, the cell- and animal-based model systems may be used to further characterize differentially expressed genes associated with viral disease, e.g., PLD 55092. In addition, animal- and cell-based assays may be used as part of screening strategies designed to identify compounds which are capable of ameliorating viral disease symptoms, as described, below. Thus, the animal- and cell-based models may be used to identify drugs, pharmaceuticals, therapies and interventions which may be effective in treating viral disease. Furthermore, such animal models may be used to determine the LD50 and the ED50 in animal subjects, and such data can be used to determine the in vivo efficacy of potential viral disease treatments.

Animal-Based Systems

Animal-based model systems of viral disease may include, but are not limited to, non-recombinant and engineered transgenic animals.

Non-recombinant animal models for viral disease may include, for example, genetic models. Transgenic mouse models for viral disease are reviewed in Rall G F et al. (*Virol.* (2000) 271:220–226), Eckert R L et al. (*Int. J. Oncol.* (2000) 16:853–70), and Morrey J D et al. (*Antiviral Ther.* (1998) 3:59–68).

Non-recombinant, non-genetic animal models of viral disease may include, for example, animal models in which the animal has been exposed to viral infection, as described in, for example, Mosier, D (2000), Virol. 271:215–219; Lavi, E et al. (1999) J. Neuropathol. Exp. Neurol. 58:1197–1206; Briese, T et al. (1999) J. Neurovirol. 5:604–612; Johannessen, I et al. (1999) Rev. Med. Virol. 9:263–277; Hayashi, K et al. (2000) Pathol. Int. 50:85–97; Michalak, T I (2000) Immunol. Rev. 174:98–111; McSharry, J J (1999) Antiviral Res. 43:1–21; Bernstein, D I et al. (2000) Antiviral Res. 47:159–169; Thackray, A M et al. (2000) J. Gen. Virol. 81:2385–2396; Nakazato, I et al. (2000) Pathol. Res. Pract. 196:635–645; and Takasaki, I et al. (2000) Jpn. J. Pharmacol. 83:319–326.

Additionally, animal models exhibiting viral disease symptoms may be engineered by using, for example, PLD 55092 gene sequences described above, in conjunction with techniques for producing transgenic animals that are well known to those of skill in the art. For example, PLD 55092 gene sequences may be introduced into, and overexpressed in, the genome of the animal of interest, or, if endogenous PLD 55092 gene sequences are present, they may either be overexpressed or, alternatively, be disrupted in order to underexpress or inactivate PLD 55092 gene expression, such as described for the disruption of apoe in mice (Plump et al., 1992, *Cell* 71: 343–353).

The host cells of the invention can also be used to produce non-human transgenic animals. For example, in one embodiment, a host cell of the invention is a fertilized oocyte or an embryonic stem cell into which PLD 55092-coding sequences have been introduced. Such host cells can then be used to create non-human transgenic animals in which exogenous PLD 55092 sequences have been introduced into their genome or homologous recombinant animals in which endogenous PLD 55092 sequences have been altered. Such animals are useful for studying the function and/or activity of a PLD 55092 and for identifying and/or evaluating modulators of PLD 55092 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous PLD 55092 gene has been altered by homologous recombination between the endogenous gene and an exogenous DNA molecule introduced into a cell of the animal, e.g., an embryonic cell of the animal, prior to development of the animal.

A transgenic animal used in the methods of the invention can be created by introducing a PLD 55092-encoding nucleic acid into the male pronuclei of a fertilized oocyte, e.g., by microinjection, retroviral infection, and allowing the oocyte to develop in a pseudopregnant female foster animal. The PLD 55092 cDNA sequence of SEQ ID NO:14 can be introduced as a transgene into the genome of a non-human animal. Alternatively, a nonhuman homologue of a human PLD 55092 gene, such as a mouse or rat PLD 55092 gene, can be used as a transgene. Alternatively, a PLD 55092 gene homologue, such as another PLD 55092 family member, can be isolated based on hybridization to the PLD 55092 cDNA sequences of SEQ ID NO:14 and used as a transgene. Intronic sequences and polyadenylation signals can also be included in the transgene to increase the efficiency of expression of the transgene. A tissue-specific regulatory sequence(s) can be operably linked to a PLD 55092 transgene to direct expression of a PLD 55092 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of a PLD 55092 transgene in its genome and/or expression of PLD 55092 mRNA in tissues or cells of the animals. A transgenic founder animal can then be used to breed additional animals carrying the transgene. Moreover, transgenic animals carrying a transgene encoding a PLD 55092 protein can further be bred to other transgenic animals carrying other transgenes.

To create a homologous recombinant animal, a vector is prepared which contains at least a portion of a PLD 55092 gene into which a deletion, addition or substitution has been introduced to thereby alter, e.g., functionally disrupt, the PLD 55092 gene. The PLD 55092 gene can be a human gene (e.g., the cDNA of SEQ ID NO:14), but more preferably, is a non-human homologue of a human PLD 55092 gene (e.g., a cDNA isolated by stringent hybridization with the nucleotide sequence of SEQ ID NO:14). For example, a mouse PLD 55092 gene can be used to construct a homologous recombination nucleic acid molecule, e.g., a vector, suitable for altering an endogenous PLD 55092 gene in the mouse genome. In a preferred embodiment, the homologous recombination nucleic acid molecule is designed such that, upon homologous recombination, the endogenous PLD 55092 gene is functionally disrupted (i.e., no longer encodes a functional protein; also referred to as a "knock out" vector). Alternatively, the homologous recombination nucleic acid molecule can be designed such that, upon homologous recombination, the endogenous PLD 55092 gene is mutated or otherwise altered but still encodes functional protein (e.g., the upstream regulatory region can be altered to thereby alter the expression of the endogenous PLD 55092 protein). In the homologous recombination nucleic acid molecule, the altered portion of the PLD 55092 gene is flanked at its 5' and 3' ends by additional nucleic acid sequence of the PLD 55092 gene to allow for homologous recombination to occur between the exogenous PLD 55092 gene carried by the homologous recombination nucleic acid molecule and an endogenous PLD 55092 gene in a cell, e.g., an embryonic stem cell. The additional flanking PLD 55092 nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecchi, M. R. (1987) *Cell* 51:503 for a description of homologous recombination vectors). The homologous recombination nucleic acid molecule is introduced into a cell, e.g., an embryonic stem cell line (e.g., by electroporation) and cells in which the introduced PLD 55092 gene has homologously recombined with the endogenous PLD 55092 gene are selected (see e.g., Li, E. et al. (1992) *Cell* 69:915). The selected cells can then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-human animals for use in the methods of the invention can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

The PLD 55092 transgenic animals that express PLD 55092 mRNA or a PLD 55092 peptide (detected immunocytochemically, using antibodies directed against PLD 55092 epitopes) at easily detectable levels should then be further evaluated to identify those animals which display characteristic viral disease symptoms. Such viral disease symptoms may include, for example, viremia.

Additionally, specific cell types (e.g., neuronal cells) within the transgenic animals may be analyzed and assayed for cellular phenotypes characteristic of viral disease. Cellular phenotypes may include a particular cell type's pattern of expression of genes associated with viral disease as compared to known expression profiles of the particular cell type in animals exhibiting viral disease symptoms.

Cell-Based Systems

Cells that contain and express PLD 55092 gene sequences which encode a PLD 55092 protein, and, further, exhibit cellular phenotypes associated with viral disease, may be used to identify compounds that exhibit anti-viral disease activity. Such cells may include generic mammalian cell lines such as HeLa cells and COS cells, e.g., COS-7 (ATCC# CRL-1651). Further, such cells may include recombinant, transgenic cell lines. For example, the viral disease animal models of the invention, discussed above, may be used to generate cell lines, containing one or more cell types involved in viral disease, that can be used as cell culture models for this disorder. While primary cultures derived from the viral disease transgenic animals of the invention may be utilized, the generation of continuous cell lines is preferred. For examples of techniques which may be used to derive a continuous cell line from the transgenic animals, see Small et al., (1985) *Mol. Cell Biol.* 5:642–648.

Alternatively, cells of a cell type known to be involved in viral disease and/or susceptible to viral infection may be transfected with sequences capable of increasing or decreasing the amount of PLD 55092 gene expression within the cell. For example, PLD 55092 gene sequences may be introduced into, and overexpressed in, the genome of the cell of interest, or, if endogenous PLD 55092 gene sequences are present, they may be either overexpressed or, alternatively disrupted in order to underexpress or inactivate PLD 55092 gene expression.

In order to overexpress a PLD 55092 gene, the coding portion of the PLD 55092 gene may be ligated to a regulatory sequence which is capable of driving gene expression in the cell type of interest, e.g., a neuronal cell or a liver cell. Such regulatory regions will be well known to those of skill in the art, and may be utilized in the absence of undue experimentation. Recombinant methods for expressing target genes are described above.

For underexpression of an endogenous PLD 55092 gene sequence, such a sequence may be isolated and engineered such that when reintroduced into the genome of the cell type of interest, the endogenous PLD 55092 alleles will be inactivated. Preferably, the engineered PLD 55092 sequence is introduced via gene targeting such that the endogenous PLD 55092 sequence is disrupted upon integration of the engineered PLD 55092 sequence into the cell's genome. Transfection of host cells with PLD 55092 genes is discussed, above.

Cells (e.g., virally infected cells) treated with compounds or transfected with PLD 55092 genes can be examined for phenotypes associated with viral infection and/or disease, e.g., plaque formation or low pH induced fusion of infected cells (Sung T-C et al. (1997) *EMBO J.* 16:4519–4530; Roper R L and Moss B (1999) *J. Virol.* 73:1108–1117; Blasco R and Moss B (1991) *J. Virol.* 65:5910–5920). Moreover, cells treated with compounds or transfected with PLD 55092 genes can be examined for phenotypes, including, but not limited to changes in cellular morphology, cell proliferation, cell differentiation, cell migration, and vesicular trafficking.

Transfection of PLD 55092 nucleic acid may be accomplished by using standard techniques (described in, for example, Ausubel (1989) supra). Transfected cells should be evaluated for the presence of the recombinant PLD 55092 gene sequences, for expression and accumulation of PLD 55092 mRNA, and for the presence of recombinant PLD 55092 protein production. In instances wherein a decrease in PLD 55092 gene expression is desired, standard techniques may be used to demonstrate whether a decrease in endogenous PLD 55092 gene expression and/or in PLD 55092 protein production is achieved.

Cellular models for the study of viral disease include models of cell infection with virus, e.g., herpes simplex virus, Epstein Barr virus, hepatitis virus, human papilloma virus.

Pharmaceutical Compositions

Active compounds for use in the methods of the invention can be incorporated into pharmaceutical compositions suitable for administration. As used herein, the language "active compounds" includes PLD 55092 nucleic acid molecules, fragments of PLD 55092 proteins, and anti-PLD 55092 antibodies, as well as identified compounds that modulate PLD 55092 gene expression, synthesis, and/or activity. Such compositions typically comprise the compound, nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of a PLD 55092 protein or a PLD 55092 substrate) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals. In one embodiment, a therapeutically effective dose refers to that amount of an active compound sufficient to result in amelioration of symptoms of viral disease or infection. In other embodiments, a therapeutically effective dose refers to that amount of an active compound sufficient to suppress disease recurrence, reduce and/or delay disease onset, reduce viremia, and protect against viral infection.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

In certain embodiments of the invention, a modulator of PLD 55092 activity is administered in combination with other agents (e.g., a small molecule), or in conjunction with another, complementary treatment regime. For example, in one embodiment, a modulator of PLD 55092 activity is used to treat a viral disease, e.g., a disease associated with Herpes simplex virus infection. Accordingly, modulation of PLD 55092 activity may be used in conjunction with, for example, antiviral agents, e.g., acyclovir, valaciclovir, famciclovir.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (CDDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery ($2^{nd}$ Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982). Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Isolated Nucleic Acid Molecules

The nucleotide sequence of the isolated human PLD 55092 cDNA and the predicted amino acid sequence of the human PLD 55092 polypeptide are shown in SEQ ID NOs:14, respectively.

The human PLD 55092 gene, which is approximately 1917 nucleotides in length, encodes a protein having a molecular weight of approximately 55 kD and which is approximately 506 amino acid residues in length.

The methods of the invention include the use of isolated nucleic acid molecules that encode PLD 55092 proteins or biologically active portions thereof, as well as nucleic acid fragments sufficient for use as hybridization probes to identify PLD 55092-encoding nucleic acid molecules (e.g., PLD 55092 mRNA) and fragments for use as PCR primers for the amplification or mutation of PLD 55092 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated PLD 55092 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule used in the methods of the present invention, e.g., a nucleic acid molecule having the nucleotide sequence of SEQ ID NO:14, or a portion thereof, can be isolated using standard molecular biology techniques and the sequence information provided herein. Using all or portion of the nucleic acid sequence of SEQ ID NO:14, as a hybridization probe, PLD 55092 nucleic acid molecules can be isolated using standard hybridization and cloning techniques (e.g., as described in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989).

Moreover, a nucleic acid molecule encompassing all or a portion of SEQ ID NO:14 or 16 can be isolated by the polymerase chain reaction (PCR) using synthetic oligonucleotide primers designed based upon the sequence of SEQ ID NO:14.

A nucleic acid used in the methods of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to PLD 55092 nucleotide sequences can be prepared by standard synthetic techniques, e.g., using an automated DNA synthesizer.

In a preferred embodiment, an isolated nucleic acid molecule used in the methods of the invention comprises the nucleotide sequence shown in SEQ ID NO:14. This cDNA may comprise sequences encoding the human PLD 55092 protein (i.e., "the coding region", from nucleotides 122–1642), as well as 5' untranslated sequences (nucleotides 1–121) and 3' untranslated sequences (nucleotides 1643–1917) of SEQ ID NO:14. Alternatively, the nucleic acid molecule can comprise only the coding region of SEQ ID NO:14 (e.g., nucleotides 122–1642 of SEQ ID NO:14).

In another preferred embodiment, an isolated nucleic acid molecule used in the methods of the invention comprises a nucleic acid molecule which is a complement of the nucleotide sequence shown in SEQ ID NO:14, or a portion of any of this nucleotide sequence. A nucleic acid molecule which is complementary to the nucleotide sequence shown in SEQ ID NO:14 is one which is sufficiently complementary to the nucleotide sequence shown in SEQ ID NO:14 such that it can hybridize to the nucleotide sequence shown in SEQ ID NO:14, thereby forming a stable duplex.

In still another preferred embodiment, an isolated nucleic acid molecule used in the methods of the present invention comprises a nucleotide sequence which is at least about 30%, 35%, 40%, 45%, 50%, 55%, 60%, 65%, 70%, 75%, 80%, 85%, 90%, 91%, 92%, 93%, 94%, 95%, 96%, 97%, 98%, 99% or more identical to the entire length of the nucleotide sequence shown in SEQ ID NO:14, or a portion of any of this nucleotide sequence.

Moreover, a nucleic acid molecule used in the methods of the invention can comprise only a portion of the nucleic acid sequence of SEQ ID NO:14, for example, a fragment which can be used as a probe or primer or a fragment encoding a portion of a PLD 55092 protein, e.g., a biologically active portion of a PLD 55092 protein. The nucleotide sequence determined from the cloning of the PLD 55092 gene allows for the generation of probes and primers designed for use in identifying and/or cloning other PLD 55092 family members, as well as PLD 55092 homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:14, of an anti-sense sequence of SEQ ID NO:14, or of a naturally occurring allelic variant or mutant of SEQ ID NO:14. In one embodiment, a nucleic acid molecule of the present invention comprises a nucleotide sequence which is greater than 100, 100–200, 200–300, 300–400, 400–500, 500–600, 600–700, 700–800, 800–900, 900–1000, 1000–1100, 1100–120, 1200–1300, 1300–1400, 1400–1500, 1500–1600, 1600–1700, 1700–1800, 1800 or more nucleotides in length and hybridizes under stringent hybridization conditions to a nucleic acid molecule of SEQ ID NO:14.

Probes based on the PLD 55092 nucleotide sequence can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a PLD 55092 protein, such as by measuring a level of a PLD 55092-encoding nucleic acid in a sample of cells from a subject e.g., detecting PLD) 55092 mRNA levels or determining whether a genomic PLD 55092 gene has been mutated or deleted.

A nucleic acid fragment encoding a "biologically active portion of a PLD 55092 protein" can be prepared by isolating a portion of the nucleotide sequence of SEQ ID NO:14 which encodes a polypeptide having a PLD 55092 biological activity (the biological activities of the PLD 55092 protein is described herein), expressing the encoded portion of the PLD 55092 protein (e.g., by recombinant expression in vitro) and assessing the activity of the encoded portion of the PLD 55092 protein.

The methods of the invention further encompass the use of nucleic acid molecules that differ from the nucleotide sequence shown in SEQ ID NO:14, due to degeneracy of the genetic code and thus encode the same PLD 55092 protein as those encoded by the nucleotide sequence shown in SEQ ID NO:14. In another embodiment, an isolated nucleic acid molecule of the invention has a nucleotide sequence encoding a protein having an amino acid sequence shown in SEQ ID NO:15.

In addition to the PLD 55092 nucleotide sequence shown in SEQ ID NO:14, it will be appreciated by those skilled in the art that DNA sequence polymorphisms that lead to changes in the amino acid sequences of the PLD 55092 protein may exist within a population (e.g., the human population). Such genetic polymorphism in the PLD 55092 gene may exist among individuals within a population due to natural allelic variation. As used herein, the terms "gene" and "recombinant gene" refer to nucleic acid molecules which include an open reading frame encoding a PLD 55092 protein, preferably a mammalian PLD 55092 protein, and can further include non-coding regulatory sequences, and introns.

Allelic variants of human PLD 55092 include both functional and non-functional PLD 55092 proteins. Functional allelic variants are naturally occurring amino acid sequence variants of the human PLD 55092 protein that maintain the ability to bind a PLD 55092 ligand or substrate and/or modulate signal transduction, lipid metabolism, and/or vesicle trafficking mechanisms. Functional allelic variants will typically contain only conservative substitution of one or more amino acids of SEQ ID NO:15, or substitution, deletion or insertion of non-critical residues in non-critical regions of the protein.

Non-functional allelic variants are naturally occurring amino acid sequence variants of the human PLD 55092 protein that do not have the ability to either bind a PLD 55092 ligand or substrate and/or modulate signal transduction, lipid metabolism, and/or vesicle trafficking mechanisms. Non-functional allelic variants will typically contain a non-conservative substitution, a deletion, or insertion or premature truncation of the amino acid sequence of SEQ ID NO:15, or a substitution, insertion or deletion in critical residues or critical regions.

The methods of the present invention may further use non-human orthologues of the human PLD 55092 protein. Orthologues of the human PLD 55092 protein are proteins that are isolated from non-human organisms and possess the same PLD 55092 ligand binding and/or modulation of signal transduction, lipid metabolism, and/or vesicle trafficking mechanisms of the human PLD 55092 protein. Orthologues of the human PLD 55092 protein can readily be identified as comprising an amino acid sequence that is substantially identical to SEQ ID NO:15.

Moreover, nucleic acid molecules encoding other PLD 55092 family members and, thus, which have a nucleotide sequence which differs from the PLD 55092 sequence of SEQ ID NO:14 are intended to be within the scope of the invention. For example, another PLD 55092 cDNA can be identified based on the nucleotide sequence of human PLD 55092. Moreover, nucleic acid molecules encoding PLD 55092 proteins from different species, and which, thus, have a nucleotide sequence which differs from the PLD 55092 sequence of SEQ ID NO:14 are intended to be within the scope of the invention. For example, a mouse PLD 55092 cDNA can be identified based on the nucleotide sequence of human PLD 55092.

Nucleic acid molecules corresponding to natural allelic variants and homologues of the PLD 55092 cDNA of the invention can be isolated based on their homology to the PLD 55092 nucleic acid disclosed herein using the cDNAs disclosed herein, or a portion thereof, as a hybridization probe according to standard hybridization techniques under stringent hybridization conditions. Nucleic acid molecules corresponding to natural allelic variants and homologues of the PLD 55092 cDNA of the invention can further be isolated by mapping to the same chromosome or locus as the PLD 55092 gene.

Accordingly, in another embodiment, an isolated nucleic acid molecule used in the methods of the invention is at least 15, 20, 25, 30 or more nucleotides in length and hybridizes under stringent conditions to the nucleic acid molecule comprising the nucleotide sequence of SEQ ID NO:14. In other embodiment, the nucleic acid is at least 30, 50, 100, 150, 200, 250, 300, 350, 400, 450, 500, 550, 600, 650, 700, 750, 800, 1000, 1200, 1400, 1600 or more nucleotides in length.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in *Current Protocols in Molecular Biology*, Ausubel et al., eds., John Wiley & Sons, Inc. (1995), sections 2, 4 and 6. Additional stringent conditions can be found in *Molecular Cloning: A Laboratory Manual*, Sambrook et al., Cold Spring Harbor Press, Cold Spring Harbor, N.Y. (1989), chapters 7, 9 and 11. A preferred, non-limiting example of stringent hybridization conditions includes hybridization in 4× sodium chloride/sodium citrate (SSC), at about 65–70° C. (or hybridization in 4×SSC plus 50% formamide at about 42–50° C.) followed by one or more washes in 1×SSC, at about 65–70° C. A preferred, non-limiting example of highly stringent hybridization conditions includes hybridization in 1×SSC, at about 65–70° C. (or hybridization in 1×SSC plus 50% formamide at about 42–50° C.) followed by one or more washes in 0.3×SSC, at about 65–70° C. A preferred, non-limiting example of reduced stringency hybridization conditions includes hybridization in 4×SSC, at about 50–60° C. (or hybridization in 6×SSC plus 50% formamide at about 40–45° C.) followed by one or more washes in 2×SSC, at about 50–60° C. Ranges intermediate to the above-recited values, e.g., at 65–70° C. or at 42–50° C. are also intended to be encompassed by the present invention. SSPE (1×SSPE is 0.15M NaCl, 10 mM NaH$_2$PO$_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5–10° C. less than the melting temperature (T$_m$) of the hybrid, where T$_m$ is determined according to the following equations. For hybrids less than 18 base pairs in length, T$_m$(° C.)=2(# of A+T bases)+4(# of G+C bases). For hybrids between 18 and 49 base pairs in length, T$_m$(° C.)=81.5+16.6 (log$_{10}$[Na$^+$])+0.41(%G+C)−(600/N), where N is the number of bases in the hybrid, and [Na$^+$] is the concentration of sodium ions in the hybridization buffer ([Na$^+$] for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25–0.5M NaH$_2$PO$_4$, 7% SDS at about 65° C., followed by one or more washes at 0.02M NaH$_2$PO$_4$, 1% SDS at 65° C., see, e.g., Church and Gilbert (1984) *Proc. Natl. Acad. Sci. USA* 81:1991–1995, (or alternatively 0.2×SSC, 1% SDS).

Preferably, an isolated nucleic acid molecule of the invention that hybridizes under stringent conditions to the sequence of SEQ ID NO:14 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the PLD 55092 sequences that may exist in the population, the skilled artisan will further appreciate that changes can be introduced by mutation into the nucleotide sequence of SEQ ID NO:14, thereby leading to changes in the amino acid sequence of the encoded PLD 55092 protein, without altering the functional ability of the PLD 55092 protein. For example, nucleotide substitutions leading to amino acid substitutions at "non-essential" amino acid residues can be made in the sequence of SEQ ID NO:14. A "non-essential" amino acid residue is a residue that can be altered from the wild-type sequence of PLD 55092 (e.g., the sequence of SEQ ID NO:15) without altering the biological activity, whereas an "essential" amino acid residue is required for biological activity. For example, amino acid residues that are conserved among the PLD 55092 proteins of the present invention, e.g., those present in a HKD motif, are predicted to be particularly unamenable to alteration. Furthermore, additional amino acid residues that are conserved between the PLD 55092 proteins of the present invention and other members of the PLD gene superfamily (Koonin, EV (1996) *TIBS* 21:242–243; Ponting, C P et al. (1996) *Protein Sci.* 5:914–922; Liscovitch, M et al. (2000) *Biochem. J.* 345: 401–415) are not likely to be amenable to alteration.

Accordingly, the methods of the invention may include the use of nucleic acid molecules encoding PLD 55092 proteins that contain changes in amino acid residues that are not essential for activity. Such PLD 55092 proteins differ in amino acid sequence from SEQ ID NO:15, yet retain biological activity. In one embodiment, the isolated nucleic acid molecule comprises a nucleotide sequence encoding a protein, wherein the protein comprises an amino acid sequence at least about 30%, 35%, 40%, 45%, 50%, 55%, 60%, 65%, 70%, 75%, 80%, 85%, 90%, 91%, 92%, 93%, 94%, 95%, 96%, 97%, 98%, 99% or more identical to SEQ ID NO:15.

An isolated nucleic acid molecule encoding a PLD 55092 protein identical to the protein of SEQ ID NO:15 can be created by introducing one or more nucleotide substitutions, additions or deletions into the nucleotide sequence of SEQ ID NO:14 such that one or more amino acid substitutions, additions or deletions are introduced into the encoded protein. Mutations can be introduced into SEQ ID NO:14 by standard techniques, such as site-directed mutagenesis and PCR-mediated mutagenesis. Preferably, conservative amino acid substitutions are made at one or more predicted nonessential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a PLD 55092 protein is preferably replaced with another amino acid residue from the same side chain family. Alternatively, in another embodiment, mutations can be introduced randomly along all or part of a PLD 55092 coding sequence, such as by saturation mutagenesis, and the resultant mutants can be screened for PLD 55092 biological activity to identify mutants that retain activity. Following mutagenesis of SEQ ID NO:14, the encoded protein can be expressed recombinantly and the activity of the protein can be determined.

In a preferred embodiment, a mutant PLD 55092 protein can be assayed for the ability to (1) interact with a non-PLD 55092 protein molecule, e.g., a PLD 55092 ligand or substrate; (2) activate a PLD 55092-dependent signal transduction pathway; (3) modulate lipid metabolism; (4) modulate membrane vesicular trafficking; (5) modulate membrane homeostasis; or (6) modulate cell proliferation, differentiation and/or migration mechanisms.

In addition to the nucleic acid molecules encoding PLD 55092 proteins described herein, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire PLD 55092 coding strand, or to only a portion thereof. In one embodiment, an antisense nucleic acid molecule is antisense to a "coding region" of the coding strand of a nucleotide sequence encoding PLD 55092. The term "coding region" refers to the region of the nucleotide sequence comprising codons which are translated into amino acid residues (e.g., the coding region of human PLD 55092 corresponds to nucleotides 122–1642 of SEQ ID NO:14). In another embodiment, the antisense nucleic acid molecule is antisense to a "noncoding region" of the coding strand of a nucleotide sequence encoding PLD 55092. The term "noncoding region" refers to 5' and 3' sequences which flank the coding region that are not translated into amino acids (i.e., also referred to as 5' and 3' untranslated regions).

Given the coding strand sequences encoding PLD 55092 disclosed herein (e.g., nucleotides 122–1642 of SEQ ID NO:14), antisense nucleic acids of the invention can be designed according to the rules of Watson and Crick base pairing. The antisense nucleic acid molecule can be complementary to the entire coding region of PLD 55092 mRNA, but more preferably is an oligonucleotide which is antisense to only a portion of the coding or noncoding region of PLD 55092 mRNA. For example, the antisense oligonucleotide can be complementary to the region surrounding the translation start site of PLD 55092 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

In yet another embodiment, the PLD 55092 nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. Proc. Natl. Acad. Sci. 93: 14670–675.

PNAs of PLD 55092 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of PLD 55092 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of PLD 55092 can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of PLD 55092 nucleic acid molecules can be generated which may combine the advantageous properties of PNA and DNA. Such chimeras allow DNA recognition enzymes, (e.g., RNase H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res.* 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. W088/09810) or the blood-brain barrier (see, e.g., PCT Publication No. W089/10134). In addition, oligonucleotides can be modified with hybridization-triggered cleavage agents (See, e.g., Krol et al. (1988) *Bio-Techniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

Isolated PLD 55092 Proteins and Anti-PLD 55092 Antibodies

The methods of the invention include the use of isolated PLD 55092 proteins, and biologically active portions thereof, as well as polypeptide fragments suitable for use as immunogens to raise anti-PLD 55092 antibodies.

Isolated proteins used in the methods of the present invention, preferably PLD 55092 proteins, have an amino acid sequence sufficiently identical to the amino acid sequence of SEQ ID NO:15, or are encoded by a nucleotide sequence sufficiently identical to SEQ ID NO:14. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50% homology, preferably 60% homology, more preferably 70%-80%, and even more preferably 90–95% homology across the amino acid sequences of the domains and contain at least one and preferably two structural domains or motifs, are defined herein as sufficiently identical. Furthermore, amino acid or nucleotide sequences which share at least 30%, 40%, or 50%, preferably 60%, more preferably 70–80%, or 90–95% homology and share a common functional activity are defined herein as sufficiently identical.

As used interchangeably herein, a "PLD 55092 activity", "biological activity of PLD 55092" or "functional activity of PLD 55092", refers to an activity exerted by a PLD 55092 protein, polypeptide or nucleic acid molecule on a PLD 55092 responsive cell (e.g., a neuronal cell) or tissue (e.g., brain), or on a PLD 55092 substrate, as determined in vivo, or in vitro, according to standard techniques. In one embodiment, a PLD 55092 activity is a direct activity, such as an association with a PLD 55092 target molecule. As used herein, a "target molecule" or "binding partner" is a molecule with which a PLD 55092 protein binds or interacts in nature, such that PLD 55092-mediated function is achieved. A PLD 55092 target molecule can be a non-PLD 55092 molecule or a PLD 55092 protein or polypeptide of the present invention. In an exemplary embodiment, a PLD 55092 target molecule is a PLD 55092 substrate (e.g., a phospholipid). Alternatively, a PLD 55092 activity is an indirect activity, such as a cellular signaling activity mediated by interaction of the PLD 55092 protein with a PLD 55092 substrate. Preferably, a PLD 55092 activity is the ability to act as a signal transduction molecule and to modulate cellular proliferation, differentiation and/or migration mechanisms. In another embodiment, a PLD 55092 activity is the ability to modulate lipid metabolism, membrane vesicular trafficking and/or membrane homeostasis. In yet another embodiment, a PLD 55092 activity is the ability to modulate virus replication, assembly, maturation and transmission. Accordingly, another embodiment of the invention features isolated PLD 55092 proteins and polypeptides having a PLD 55092 activity.

In one embodiment, native PLD 55092 proteins can be isolated from cells or tissue sources by an appropriate purification scheme using standard protein purification techniques. In another embodiment, PLD 55092 proteins are produced by recombinant DNA techniques. Alternative to recombinant expression, a PLD 55092 protein or polypeptide can be synthesized chemically using standard peptide synthesis techniques.

An "isolated" or "purified" protein or biologically active portion thereof is substantially free of cellular material or other contaminating proteins from the cell or tissue source from which the PLD 55092 protein is derived, or substantially free from chemical precursors or other chemicals when chemically synthesized. The language "substantially free of cellular material" includes preparations of PLD 55092 protein in which the protein is separated from cellular components of the cells from which it is isolated or recombinantly produced. In one embodiment, the language "substantially free of cellular material" includes preparations of PLD 55092 protein having less than about 30% (by dry weight) of non-PLD 55092 protein (also referred to herein as a "contaminating protein"), more preferably less than about 20% of non-PLD 55092 protein, still more preferably less than about 10% of non-PLD 55092 protein, and most preferably less than about 5% non-PLD 55092 protein. When the PLD 55092 protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of PLD 55092 protein in which the protein is separated from chemical precursors or other chemicals which are involved in the synthesis of the protein. In one embodiment, the language "substantially free of chemical precursors or other chemicals" includes preparations of PLD 55092 protein having less than about 30% (by dry weight) of chemical precursors or non-PLD 55092 chemicals, more preferably less than about 20% chemical precursors or non-PLD 55092 chemicals, still more preferably less than about 10% chemical precursors or non-PLD 55092 chemicals, and most preferably less than about 5% chemical precursors or non-PLD 55092 chemicals.

As used herein, a "biologically active portion" of a PLD 55092 protein includes a fragment of a PLD 55092 protein which participates in an interaction between a PLD 55092 molecule and a non-PLD 55092 molecule. Biologically active portions of a PLD 55092 protein include peptides comprising amino acid sequences sufficiently identical to or derived from the amino acid sequence of the PLD 55092 protein, e.g., the amino acid sequence shown in SEQ ID NO:15, which include less amino acids than the full length PLD 55092 protein, and exhibit at least one activity of a PLD 55092 protein. Typically, biologically active portions comprise a domain or motif with at least one activity of the PLD 55092 protein, e.g., modulating cell signaling mechanisms, lipid homeostasis, vesicle trafficking, and/or cell proliferation, differentiation and migration mechanisms. A biologically active portion of a PLD 55092 protein can be a polypeptide which is, for example, 10, 25, 50, 100, 200, or more amino acids in length. Biologically active portions of a PLD 55092 protein can be used as targets for developing agents which modulate a PLD 55092 mediated activity, e.g., a cell signaling mechanism, lipid homeostasis mechanism, vesicle trafficking mechanism, and/or a cell proliferation, differentiation and migration mechanism. A biologically active portion of a PLD 55092 protein comprises a protein in which regions of the protein are deleted, can be prepared by recombinant techniques and evaluated for one or more of the functional activities of a native PLD 55092 protein.

In a preferred embodiment, the PLD 55092 protein has an amino acid sequence shown in SEQ ID NO:15. In other embodiments, the PLD 55092 protein is substantially identical to SEQ ID NO:15, and retains the functional activity of the protein of SEQ ID NO:15, yet differs in amino acid sequence due to natural allelic variation or mutagenesis, as described in detail in subsection I above. Accordingly, in another embodiment, the PLD 55092 protein is a protein which comprises an amino acid sequence at least about 30%, 35%, 40%, 45%, 50%, 55%, 60%, 65%, 70%, 75%, 80%, 85%, 90%, 91%, 92%, 93%, 94%, 95%, 96%, 97%, 98%, 99% or more identical to SEQ ID NO:15.

To determine the percent identity of two amino acid sequences or of two nucleic-acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the PLD 55092 amino acid sequence of SEQ ID NO:15 having 506 amino acid residues, at least 152, preferably at least 202, more preferably at least 253, even more preferably at least 304, and even more preferably at least 354, 405 or 455 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444–453 (1970)) algorithm which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A preferred, non-limiting example of parameters to be used in conjunction with the GAP program include a Blosum 62 scoring matrix with a gap penalty of 12, a gap extend penalty of 4, and a frameshift gap penalty of 5.

In another embodiment, the percent identity between two amino acid or nucleotide sequences is determined using the algorithm of E. Meyers-and W. Miller (*Comput. Appl. Biosci.*, 4:11–17 (1988)) which has been incorporated into the ALIGN program (version 2.0 or version 2.0U), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to PLD 55092 nucleic acid molecules of the invention. BLAST protein searches can be performed with the XBLAST program, score=100, wordlength=3 to obtain amino acid sequences homologous to PLD 55092 protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used.

The methods of the invention may also use PLD 55092 chimeric or fusion proteins. As used herein, a PLD 55092 "chimeric protein" or "fusion protein" comprises a PLD 55092 polypeptide operatively linked to a non-PLD 55092 polypeptide. A "PLD 55092 polypeptide" refers to a polypeptide having an amino acid sequence corresponding to PLD 55092, whereas a "non-PLD 55092 polypeptide" refers to a polypeptide having an amino acid sequence corresponding to a protein which is not substantially homologous to the PLD 55092 protein, e.g., a protein which is different from the PLD 55092 protein and which is derived from the same or a different organism. Within a PLD 55092 fusion protein the PLD 55092 polypeptide can correspond to all or a portion of a PLD 55092 protein. In a preferred embodiment, a PLD 55092 fusion protein comprises at least one biologically active portion of a PLD 55092 protein. In another preferred embodiment, a PLD 55092 fusion protein comprises at least two biologically active portions of a PLD 55092 protein. Within the fusion protein, the term "operatively linked" is intended to indicate that the PLD 55092 polypeptide and the non-PLD 55092 polypeptide are fused in-frame to each other. The non-PLD 55092 polypeptide can be fused to the N-terminus or C-terminus of the PLD 55092 polypeptide.

For example, in one embodiment, the fusion protein is a GST-PLD 55092 fusion protein in which the PLD 55092 sequences are fused to the C-terminus of the GST sequences. Such fusion proteins can facilitate the purification of recombinant PLD 55092.

In another embodiment, the fusion protein is a PLD 55092 protein containing a heterologous signal sequence at its N-terminus. In certain host cells (e.g., mammalian host cells), expression and/or secretion of PLD 55092 can be increased through use of a heterologous signal sequence.

The PLD 55092 fusion proteins used in the methods of the invention can be incorporated into pharmaceutical compositions and administered to a subject in vivo. The PLD 55092 fusion proteins can be used to affect the bioavailability of a PLD 55092 substrate. Use of PLD 55092 fusion proteins may be useful therapeutically for the treatment of disorders caused by, for example, (i) aberrant modification or mutation of a gene encoding a PLD 55092 protein; (ii) mis-regulation of the PLD 55092 gene; and (iii) aberrant post-translational modification of a PLD 55092 protein. In one embodiment, a PLD 55092 fusion protein may be used to treat a viral disease. In another embodiment, a PLD 55092 fusion protein may be used to treat a pain disorder. In a further embodiment, a PLD 55092 fusion protein may be used to treat a cellular proliferation, growth, differentiation, or migration disorder.

Moreover, the PLD 55092-fusion proteins of the invention can be used as immunogens to produce anti-PLD 55092 antibodies in a subject, to purify PLD 55092 ligands and in screening assays to identify molecules which inhibit the interaction of PLD 55092 with a PLD 55092 substrate.

Preferably, a PLD 55092 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A PLD 55092-encoding nucleic acid can be cloned into such an expression vector such that the fusion moiety is linked in-frame to the PLD 55092 protein.

The methods of the present invention may also include the use of variants of the PLD 55092 protein which function as either PLD 55092 agonists (mimetics) or as PLD 55092 antagonists. Variants of the PLD 55092 protein can be generated by mutagenesis, e.g., discrete point mutation or truncation of a PLD 55092 protein. An agonist of the PLD 55092 protein can retain substantially the same, or a subset, of the biological activities of the naturally occurring form of a PLD 55092 protein. An antagonist of a PLD 55092 protein can inhibit one or more of the activities of the naturally occurring form of the PLD 55092 protein by, for example, competitively modulating a PLD 55092-mediated activity of a PLD 55092 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the PLD 55092 protein.

In one embodiment, variants of a PLD 55092 protein which function as either PLD 55092 agonists (mimetics) or as PLD 55092 antagonists can be identified by screening combinatorial libraries of mutants, e.g., truncation mutants, of a PLD 55092 protein for PLD 55092 protein agonist or antagonist activity. In one embodiment, a variegated library of PLD 55092 variants is generated by combinatorial mutagenesis at the nucleic acid level and is encoded by a variegated gene library. A variegated library of PLD 55092 variants can be produced by, for example, enzymatically ligating a mixture of synthetic oligonucleotides into gene sequences such that a degenerate set of potential PLD 55092 sequences is expressible as individual polypeptides, or alternatively, as a set of larger fusion proteins (e.g., for phage display) containing the set of PLD 55092 sequences therein. There are a variety of methods which can be used to produce libraries of potential PLD 55092 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential PLD 55092 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a PLD 55092 protein coding sequence can be used to generate a variegated population of PLD 55092 fragments for screening and subsequent selection of variants of a PLD 55092 protein. In one embodiment, a library of coding sequence fragments can be generated by treating a double stranded PCR fragment of a PLD 55092 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the PLD 55092 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of PLD 55092 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recrusive ensemble mutagenesis (REM), a new technique which enhances the frequency of functional mutants in the libraries, can be used in combination with the screening assays to identify PLD 55092 variants (Arkin and Yourvan (1992) *Proc. Natl. Acad. Sci. USA* 89:7811–7815; Delgrave et al. (1993) *Protein Engineering* 6(3):327–331).

In one embodiment, cell based assays can be exploited to analyze a variegated PLD 55092 library. For example, a library of expression vectors can be transfected into a cell line, e.g., a neuronal cell line, which ordinarily responds to a ligand in a particular PLD 55092-dependent manner. The transfected cells are then contacted with a ligand and the effect of expression of the mutant on signaling by PLD 55092 can be detected, e.g., by monitoring the generation of an intracellular second messenger (e.g., phosphatidic acid, $PIP_2$, or diacylglycerol), vesicle trafficking, cell proliferation, differentiation and/or migration, or the activity of a PLD 55092-regulated transcription factor. Plasmid DNA can then be recovered from the cells which score for inhibition, or alternatively, potentiation of signaling by PLD 55092, and the individual clones further characterized.

An isolated PLD 55092 protein, or a portion or fragment thereof, can be used as an immunogen to generate antibodies that bind PLD 55092 using standard techniques for polyclonal and monoclonal antibody preparation. A full-length PLD 55092 protein can be used or, alternatively, the invention provides antigenic peptide fragments of PLD 55092 for use as immunogens. The antigenic peptide of PLD 55092 comprises at least 8 amino acid residues of the amino acid sequence shown in SEQ ID NO:15 and encompasses an epitope of PLD 55092 such that an antibody raised against the peptide forms a specific immune complex with PLD 55092. Preferably, the antigenic peptide comprises at least 10 amino acid residues, more preferably at least 15 amino acid residues, even more preferably at least 20 amino acid residues, and most preferably at least 30 amino acid residues. Preferred epitopes encompassed by the antigenic peptide are regions of PLD 55092 that are located on the surface of the protein, e.g., hydrophilic regions, as well as regions with high antigenicity.

A PLD 55092 immunogen typically is used to prepare antibodies by immunizing a suitable subject, (e.g., rabbit, goat, mouse or other mammal) with the immunogen. An appropriate immunogenic preparation can contain, for example, recombinantly expressed PLD 55092 protein or a chemically synthesized PLD 55092 polypeptide. The preparation can further include an adjuvant, such as Freund's complete or incomplete adjuvant, or similar immunostimulatory agent. Immunization of a suitable subject with an immunogenic PLD 55092 preparation induces a polyclonal anti-PLD 55092 antibody response.

Accordingly, another aspect of the invention pertains to the use of anti-PLD 55092 antibodies. The term "antibody" as used herein refers to immunoglobulin molecules and immunologically active portions of immunoglobulin molecules, i.e., molecules that contain an antigen binding site which specifically binds (immunoreacts with) an antigen, such as PLD 55092. Examples of immunologically active portions of immunoglobulin molecules include F(ab) and $F(ab')_2$ fragments which can be generated by treating the antibody with an enzyme such as pepsin. The invention provides polyclonal and monoclonal antibodies that bind PLD 55092. The term "monoclonal antibody" or "monoclonal antibody composition", as used herein, refers to a population of antibody molecules that contain only one species of an antigen binding site capable of immunoreacting with a particular epitope of PLD 55092. A monoclonal antibody composition thus typically displays a single binding affinity for a particular PLD 55092 protein with which it immunoreacts.

Polyclonal anti-PLD 55092 antibodies can be prepared as described above by immunizing a suitable subject with a PLD 55092 immunogen. The anti-PLD 55092 antibody titer in the immunized subject can be monitored over time by standard techniques, such as with an enzyme linked immunosorbent assay (ELISA) using immobilized PLD 55092. If desired, the antibody molecules directed against PLD 55092 can be isolated from the mammal (e.g., from the blood) and further purified by well known techniques, such as protein A chromatography to obtain the IgG fraction. At an appropriate time after immunization, e.g., when the anti-PLD 55092 antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.* 255:4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, New York (1980); E. A. Lerner (1981) *Yale J. Biol. Med.*, 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with a PLD 55092 immunogen as described above, and the culture supernatants of the resulting hybridoma cells are screened to identify a hybridoma producing a monoclonal antibody that binds PLD 55092.

Any of the many well known protocols used for fusing lymphocytes and immortalized cell lines can be applied for the purpose of generating an anti-PLD 55092 monoclonal antibody (see, e.g., G. Galfre et al. (1977) *Nature* 266: 55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind PLD 55092, e.g., using a standard ELISA assay.

Alternative to preparing monoclonal antibody-secreting hybridomas, a monoclonal anti-PLD 55092 antibody can be identified and isolated by screening a recombinant combinatorial immunoglobulin library (e.g., an antibody phage display library) with PLD 55092 to thereby isolate immunoglobulin library members that bind PLD 55092. Kits for generating and screening phage display libraries are commercially available (e.g., the Pharmacia *Recombinant Phage Antibody System*, Catalog No. 27-9400-01; and the Stratagene SurfZAP™ *Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J* 12:725–734; Hawkins et al. (1992) *J. Mol. Biol.* 226:889–896; Clarkson et al. (1991) *Nature* 352:624–628; Gram et al. (1992) *Proc. Natl. Acad. Sci. USA* 89:3576–3580; Garrad et al. (1991) *Bio/Technology* 9:1373–1377; Hoogenboom et al. (1991) *Nuc. Acid Res.* 19:4133–4137; Barbas et al. (1991) *Proc. Natl. Acad. Sci. USA* 88:7978–7982; and McCafferty et al. *Nature* (1990) 348:552–554.

Additionally, recombinant anti-PLD 55092 antibodies, such as chimeric and humanized monoclonal antibodies, comprising both human and non-human portions, which can be made using standard recombinant DNA techniques, can also be used in the methods of the present invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240: 1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225, 539; Jones et al. (1986) *Nature* 321:552–525; Verhoeyan et al. (1988) *Science* 239:1534; and Beidler et al. (1988) *J. Immunol.* 141:4053–4060.

An anti-PLD 55092 antibody (e.g., monoclonal antibody) can be used to isolate PLD 55092 by standard techniques, such as affinity chromatography or immunoprecipitation. An anti-PLD 55092 antibody can facilitate the purification of natural PLD 55092 from cells and of recombinantly produced PLD 55092 expressed in host cells. Moreover, an anti-PLD 55092 antibody can be used to detect PLD 55092 protein (e.g., in a cellular lysate or cell supernatant) in order to evaluate the abundance and pattern of expression of the PLD 55092 protein. Anti-PLD 55092 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

This invention is further illustrated by the following examples which should not be construed as limiting. The contents of all references, patents and published patent applications cited throughout this application, as well as the Sequence Listing, are incorporated herein by reference.

EXAMPLES

Example I regulation of PLD 55092 Expression in Virus Infected Tissues

The expression of PLD 55092 in virus infected human tissues was analyzed by TaqMan® Quantitative Polymerase Chain Reaction.

Probes were designed by PrimerExpress software (PE Biosystems) based on the sequence of the PLD 55092 gene. Each PLD 55092 gene probe was labeled using FAM (6-carboxyfluorescein), and the β2-microglobulin reference probe was labeled with a different fluorescent dye, VIC. The differential labeling of the target gene and internal reference gene, thus, enabled measurement in the same well. Forward and reverse primers and probes for both the β2-microglobulin and the target gene were added to the TaqMan® Universal PCR Master Mix (PE Applied Biosystems). Although the final concentration of primer and probe could vary, each was internally consistent within a given experiment. A typical experiment contained 200 nM of forward and reverse primers plus 100 nM of probe for β-2 microglobulin and 600 nM of forward and reverse primers plus 200 nM of probe for the target gene. TaqMan matrix experiments were carried out using an ABI PRISM 7700 Sequence Detection System (PE Applied Biosystems). The thermal cycler conditions were as follows: hold for 2 minutes at 50° C. and 10 minutes at 95° C., followed by two-step PCR for 40 cycles of 95° C. for 15 seconds followed by 60° C. for 1 minute.

A comparative Ct method was used for the relative quantitation of gene expression. The following method was used to quantitatively calculate PLD 55092 gene expression in the various samples relative to β-2 microglobulin expression in the same sample. The threshold cycle (Ct) value was defined as the cycle at which a statistically significant increase in fluorescence is detected. A lower Ct value was indicative of a higher mRNA concentration. The Ct value of the PLD 55092 gene was normalized by subtracting the Ct value of the β-2 microglobulin gene to obtain a ΔCt value using the following formula:

$$\Delta Ct = Ct_{55092} - Ct_{\beta-2\ microglobulin}$$

Expression was then calibrated against a cDNA control sample containing no template. The ΔCt value for the calibrator sample was then subtracted from ΔCt for each tissue sample according to the following formula:

$$\Delta\Delta Ct = \Delta Ct_{sample} - \Delta Ct_{calibrator}$$

Relative expression was then calculated using the arithmetic formula given by $2^{-\Delta\Delta Ct}$.

As demonstrated using this TaqMan tehnology, PLD 55092 gene expression was up-regulated in hepatitis B and C virus infected human livers as compared to control normal human liver samples, in hepatitis B virus infected tissue culture cells, and in herpes simplex virus infected human ganglia, but not in herpes simplex virus infected human neuroblastoma cells. There was no induction in resting or activated T cells suggesting that induction is not an immune response.

Thus, modulation of PLD 55092 activity and/or PLD 55092 mediated signal transduction may be of therapeutic importance in viral infection.

Example 2

PLD 55092 Expression in Human and Mouse Tissues

The expression of PLD 55092 in normal or uninfected human tissues obtained from pathology phase I of human biopsy and autopsy materials was analyzed by TaqMan® Quantitative Polymerase Chain Reaction, as described above.

PLD 55092 was strongly expressed in the brain cortex and hypothalamus, as well as in glioblastoma cells. PLD 55092 was also expressed in dorsal root ganglia, the spinal cord, and tonsil cells, and expressed at lower levels in prostate, lymph node, and bone marrow mononuclear cells. There was no induction in resting or activated T cells.

VII. METHODS AND COMPOSITIONS FOR TREATING CARDIOVASCULAR DISEASE USING 10218

BACKGROUND OF THE INVENTION

Cardiovascular disease is a major health risk throughout the industrialized world. Atherosclerosis, the most prevalent of cardiovascular diseases, is the principal cause of heart attack, stroke, and peripheral vascular disease resulting in significant disability and limb loss, and thereby the principle cause of death in the United States.

Atherosclerosis is a complex disease involving many cell types and molecular factors (described in, for example, Ross (1993) Nature 362: 801–809). The process, in normal circumstances a protective response to insults to the endothelium and smooth muscle cells (SMCs) of the wall of the artery, consists of the formation of fibrofatty and fibrous lesions or plaques, preceded and accompanied by inflammation. The advanced lesions of atherosclerosis may occlude the artery concerned, and result from an excessive inflammatory-fibroproliferative response to numerous different forms of insult. Injury or dysfunction of the vascular endothelium is a common feature of many conditions that predispose an individual to accelerated development of atherosclerotic cardiovascular disease. For example, shear stresses are thought to be responsible for the frequent occurrence of atherosclerotic plaques in regions of the circulatory system where turbulent blood flow occurs, such as branch points and irregular structures.

The first observable event in the formation of an atherosclerotic plaque occurs when blood-borne monocytes adhere to the vascular endothelial layer and transmigrate through to the sub-endothelial space. Adjacent endothelial cells at the same time produce oxidized low density lipoprotein (LDL). These oxidized LDLs are then taken up in large amounts by the monocytes through scavenger receptors expressed on their surfaces. In contrast to the regulated pathway by which native LDL (nLDL) is taken up by nLDL specific receptors, the scavenger pathway of uptake is not regulated by the monocytes.

These lipid-filled monocytes are called foam cells, and are the major constituent of the fatty streak. Interactions between foam cells and the endothelial and smooth muscle cells which surround them lead to a state of chronic local inflammation which can eventually lead to smooth muscle cell proliferation and migration, and the formation of a fibrous plaque.

Such plaque may totally or partially block blood flow through a blood vessel leading to a heart attack or stroke. Plaque can also weaken the arterial wall, resulting in an aneurysm. Moreover, occlusion of the blood vessels caused by plaques restrict the flow of blood, resulting in ischemia. Ischemia is a condition characterized by a lack of oxygen supply in tissues of organs due to inadequate perfusion. Such inadequate perfusion can have a number of natural causes, including atherosclerotic or restenotic lesions, anemia, or stroke. Many medical interventions, such as the interruption of the flow of blood during bypass surgery, for example, also lead to ischemia. In addition to sometimes being caused by diseased cardiovascular tissue, ischemia may sometimes affect cardiovascular tissue, such as in ischemic heart disease. Ischemia may occur in any organ, however, that is suffering a lack of oxygen supply.

The P2X receptors are a family of ligand-gated membrane ion channels activated by the binding of extracellular adenosine 5'-triphosphate (ATP). Seven different P2X receptor subunit cDNAs have been identified (P2X$_1$, P2X$_2$, P2X$_3$, P2X$_4$, P2X$_5$, P2X$_6$, and P2X$_7$) (MacKenzie, et al. (1999) *Ann. N.Y. Acad. Sci.* 868:716–729). They are characterized by two transmembrane domains with a large extracellular loop where 10 cysteine residues are preserved; and by intracellular N- and C-terminals (Burnstock (2000) *British Journal of Anesthesia* 84:476–880). P2X receptors are widely distributed in various tissues of mammals, including smooth muscle of the urinary bladder and arteries, kidney, pancreas, lung, cardiac myocytes, sensory and sympathetic ganglia, brain and spinal cord, and each subtype seems to be preferentially expressed in different tissue (Yamamoto, et al. (2000) *Am. J. Pilysiol. Heart Circ. Physiol.* 279: H285–H292).

The human P2X$_4$ gene was cloned from the brain and forms functional homomeric ATP-activated channels when expressed in heterologous cellular systems (Garcia-Guzman, et al. (1997) *Molecular Pharmacology* 51:109–118). This receptor has been found to be expressed in human endothelial cells, and is involved in ATP-induced Ca$^{2+}$ influx in endothelial cells (Yamamoto, et al. (2000) *Am. J. Physiol. Heart Circ. Physiol.* 279:H285–H292).

Calcium concentration plays a role in cardiovascular diseases, including atherosclerosis. Calcium channel blockers (CCB) have been used to effectively modulate high blood pressure. It has been postulated that CCB's could also be used to avoid calcium deposits in arterial walls, which is one of the main components of atherosclerotic plaques (Perez (2000) *J. Hum. Hypertens*. 14 Suppl 1:S96–9). Intracelllular calcium levels have also been correlated with late phase platelet aggregation and formation of a hemostaic plug, which has been implicated in the pathogenesis of atherosclerosis (Covic, et al. (2000) *Biochemistry* 39:5458–5467). Recent studies also have focused on the role of free radicals on calcium signaling. Vascular calcium signaling is altered by oxidant stress in ischemia-related disease states (Lounsbury et al. (2000) *Free Radical. Biol. Med.* 28:1362). Extracellular calcium has been shown to function as an ionic chemokinetic agent capable of modulating the innate immune response in vivo and in vitro by direct and indirect actions on monocytic cells. Therefore, calcium deposition may be both a consequence of and/or a cause of chronic inflammatory changes at sites of injury, infection, and atherosclerosis (Olszak, et al. (2000) *J. Clin. Invest.* 105: 1299–305).

SUMMARY OF THE INVENTION

The present invention provides methods and compositions for the diagnosis and treatment of cardiovascular disease, including, but not limited to, atherosclerosis. The present invention is based, at least in part, on the discovery that the P2X4 gene (referred to herein as "10218"), is differentially expressed in macrophages stimulated by highly atherosclerotic agents, e.g., interferon gamma (IFNγ) and CD40L, and in atherosclerotic lesions as compared to non-lesioned vessels in an animal model of atherosclerosis and normal vessels in wild-type animals. Moreover, 10218 is expressed in highly vascularized organs and blood vessels. Accordingly, the present invention provides methods for the diagnosis and treatment of cardiovascular disease including, but not limited to, atherosclerosis.

In one aspect, the present invention provides methods for identifying a compound capable of treating a cardiovascular disease, e.g., atherosclerosis, characterized by aberrant 10218 nucleic acid expression or 10218 polypeptide activity by assaying the ability of the compound or agent to modulate 10218 expression or activity. In one embodiment, the identified compound inhibits 10218 expression or activity.

In another aspect, the present invention provides methods for identifying a subject suffering from a cardiovascular disease, e.g., atherosclerosis, comprising obtaining a biological sample from the subject, and detecting in the sample aberrant or abnormal 10218 expression or activity, thereby identifying a subject suffering from a cardiovascular disease.

In yet another embodiment, the present invention provides methods for identifying a subject having a cardiovascular disease, e.g., atherosclerosis, or at risk for developing a cardiovascular disease comprising contacting a sample obtained from the subject containing nucleic acid molecules with a hybridization probe comprising at least 25 contiguous nucleotides of SEQ ID NO:16 and detecting the presence of a nucleic acid molecule in the sample that hybridizes to the probe. In one embodiment, the hybridization probe is detectably labeled. In another embodiment, the sample is subjected to agarose gel electrophoresis and southern blotting prior to contacting with the hybridization probe. In yet another embodiment, the sample is subjected to agarose gel electrophoresis and northern blotting prior to contacting with the hybridization probe. In a further embodiment, the detecting is by in situ hybridization.

In yet another aspect, the present invention provides methods for treating a subject having a cardiovascular disease, e.g., atherosclerosis, characterized by aberrant 10281 polypeptide activity or aberrant 10281 nucleic acid expression by administering to the subject a 10281 modulator, for example, a small molecule, an antibody specific for 10281, a 10281 polypeptide, a fragment of a 10281 polypeptide, a 10281 nucleic acid molecule, a fragment of a 10281 nucleic acid molecule, an antisense 10281 nucleic acid molecule, and a ribozyme. In one embodiment, the 10281 modulator is administered in a pharmaceutically acceptable formulation. In a further embodiment, the 10281 modulator is administered using a gene therapy vector. In another embodiment, the 10281 polypeptide comprises the amino acid sequence of SEQ ID NO:17, or a fragment thereof or an amino acid sequence which is at least 90 percent identical to the amino acid sequence of SEQ ID NO:17, where the percent identity is calculated using the ALIGN program for comparing amino acid sequences, a PAM120 weight residue table, a gap length penalty of 12, and a gap penalty of 4. In yet another embodiment, the 10281 polypeptide is an isolated naturally occurring allelic variant of a polypeptide consisting of the amino acid sequence of SEQ ID NO:17, wherein the polypeptide is encoded by a nucleic acid molecule which hybridizes to a complement of a nucleic acid molecule consisting of SEQ ID NO:16 at 6×SSC at 45° C., followed by one or more washes in 0.2×SSC, 0.1% SDS at 65° C. In still another embodiment, the 10281 nucleic acid molecule comprises the nucleotide sequence of SEQ ID NO:16, or a fragment thereof.

Other features and advantages of the invention will be apparent from the following detailed description and claims.

DETAILED DESCRIPTION OF THE INVENTION

The present invention provides methods and compositions for the diagnosis and treatment of cardiovascular disease, including but not limited to, atherosclerosis, ischemia/reperfusion injury, hypertension, restenosis, arterial inflammation, and endothelial cell disorders. "Treatment", as used herein, is defined as the application or administration of a therapeutic agent to a patient, or application or administration of a therapeutic agent to an isolated tissue or cell line from a patient, who has a disease or disorder, a symptom of disease or disorder or a predisposition toward a disease or disorder, with the purpose of curing, healing, alleviating, relieving, altering, remedying, ameliorating, improving or affecting the disease or disorder, the symptoms of disease or disorder or the predisposition toward a disease or disorder. A therapeutic agent includes, but is not limited to, the small molecules, peptides, antibodies, ribozymes and antisense oligonucleotides described herein.

The present invention is based, at least in part, on the discovery that the $P2X_4$ nucleic acid and protein molecules (referred to herein as "10218" nucleic acid and protein molecules), are differentially expressed in cardiovascular disease states relative to their expression in normal, or non-cardiovascular disease states, as well as in macrophages stimulated with highly atherogenic cytokines, e.g., interferon gamma (IFNγ) and CD40L. 10218 nucleic acid and protein molecules are also expressed in highly vascularized organs, e.g., heart, kidney, liver, and skeletal muscle, and blood vessels, e.g., arteries and veins. The 10281 modulators identified according to the methods of the invention can be used to modulate (e.g., inhibit, treat, or prevent) or diagnose cardiovascular disease, including, but not limited to, atherosclerosis.

"Differential expression", as used herein, includes both quantitative as well as qualitative differences in the temporal and/or tissue expression pattern of a gene. Thus, a differentially expressed gene may have its expression activated or inactivated in normal versus cardiovascular disease conditions (for example, in an experimental cardiovascular disease system such as in an animal model for atherosclerosis). The degree to which expression differs in normal versus cardiovascular disease or control versus experimental states need only be large enough to be visualized via standard characterization techniques, e.g., quantitative PCR, Northern analysis, subtractive hybridization. The expression pattern of a differentially expressed gene may be used as part of a prognostic or diagnostic cardiovascular disease, e.g., artherosclerosis, evaluation, or may be used in methods for identifying compounds useful for the treatment of cardiovascular disease, e.g., atherosclerosis. In addition, a differentially expressed gene involved in cardiovascular disease may represent a target gene such that modulation of the level of target gene expression or of target gene product activity may act to ameliorate a cardiovascular disease condition, e.g., atherosclerosis. Compounds that modulate target gene expression or activity of the target gene product can be used in the treatment of cardiovascular disease. Although the 10218 genes described herein may be differentially expressed with respect to cardiovascular disease, and/or their products may interact with gene products important to cardiovascular disease, the genes may also be involved in mechanisms important to additional cardiovascular cell processes.

The 10218 molecules used in the methods of the invention are ligand-gated membrane ion channels which are activated by the binding of extracellular adenosine 5'-triphosphate (ATP). They are involved in ATP-induced $Ca^{2+}$ influx in endothelial cells (Yamamoto, et al. (2000) *Am. J. Physiol. Heart Circ. Physiol*. 279:H285–H292). Calcium concentration is postulated to be involved in cardiovascular disease, including, but not limited to atherosclerosis. For example, calcium is a major component of atherosclerotic plaques and is also implicated in high blood pressure (Perez (2000) *J. Hum. Hypertens*. 14 Suppl 1:S96–9). Calcium is also involved in late phase platelet aggregation and formation (Covic, et al. (2000) *Biochemistry* 39:5458–5467) and calcium deposition may be both a consequence and/or a cause of chronic inflammatory changes at atherosclerotic sites (Olszak, et al. (2000) *J. Clin. Invest*. 105:1299–305). Therefore, given the differential expression of the 10218 molecules in cardiovascular disease states and in macrophages stimulated with highly atherogenic cytokines, as well as their expression in vessels and arteries, modulation of the 10218 molecules may modulate, e.g., inhibit, treat, or prevent, cardiovascular disease, and, in particular, atherosclerosis.

As used herein, "cardiovascular disease" or a "cardiovascular disorder" includes a disease or disorder which affects the cardiovascular system, e.g., the heart or the blood vessels. A cardiovascular disease includes disorders such as atherosclerosis, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, atrial fibrillation, long-QT syndrome, congestive heart failure, sinus node dysfunction, angina, heart failure, hypertension, atrial fibrillation, atrial flutter, dilated cardiomyopathy, idiopathic cardiomyopathy, myocardial infarction, coronary artery disease, coronary artery spasm, ischemic disease, arrhythmia, and cardiovascular developmental disorders (e.g., arteriovenous malformations, arteriovenous fistulae, raynaud's syndrome, neurogenic thoracic outlet syndrome, causalgia/reflex sympathetic dystrophy, hemangioma, aneurysm, cavernous angioma, aortic valve stenosis, atrial septal defects, atrioventricular canal, coarctation of the aorta, ebsteins anomaly, hypoplastic left heart syndrome, interruption of the aortic arch, mitral valve prolapse, ductus arteriosus, patent foramen ovale, partial anomalous pulmonary venous return, pulmonary atresia with ventricular septal defect, pulmonary atresia without ventricular septal defect, persistance of the fetal circulation, pulmonary valve stenosis, single ventricle, total anomalous pulmonary venous return, transposition of the great vessels, tricuspid atresia, truncus arteriosus, ventricular septal defects). In a preferred embodiment, a cardiovascular disease is atherosclerosis. A cardiovascular disease or disorder also includes an endothelial cell disorder.

As used herein, an "endothelial cell disorder" includes a disorder characterized by aberrant, unregulated, or unwanted endothelial cell activity, e.g., proliferation, migration, angiogenesis, or vascularization; or aberrant expression of cell surface adhesion molecules or-genes associated with angiogenesis, e.g., TIE-2, FLT and FLK. Endothelial cell disorders include tumorigenesis, tumor metastasis, psoriasis, diabetic retinopathy, endometriosis, Grave's disease, ischemic disease (e.g., atherosclerosis), and chronic inflammatory diseases (e.g., rheumatoid arthritis).

As used interchangeably herein, "10218 activity," "biological activity of 10218" or "functional activity of 10218," includes an activity exerted by a 10218 protein, polypeptide or nucleic acid molecule on a 10218 responsive cell or tissue, e.g., endothelial cells or vascular tissue, or on a 10218 protein substrate, as determined in vivo, or in vitro, according to standard techniques. 10218 activity can be a direct activity, such as an association with a 10218-target molecule. As used herein, a "substrate" or "target molecule" or "binding partner" is a molecule with which a 10218 protein binds or interacts in nature, e.g. ATP, such that 10218-mediated function, e.g., modulation of calcium concentration, is achieved. A 10218 target molecule can be a non-10218 molecule or a 10218 protein or polypeptide. Examples of such target molecules include proteins in the same signaling path as the 10218 protein, e.g., proteins which may function upstream (including both stimulators and inhibitors of activity) or downstream of the 10218 protein in a pathway involving regulation of intercellular or extracellular calcium concentration, e.g., calcium influx modulated by ATP binding. Alternatively, a 10218 activity is an indirect activity, such as a cellular signaling activity mediated by interaction of the 10218 protein with a 10218 target molecule. The biological activities of 10218 are described herein. For example, the 10218 proteins can have one or more of the following activities: 1) they bind ATP; 2) they bind calcium; 3) they modulate intercellular calcium infux in cells, e.g., endothelial cells; 4) they modulate cellular migration, e.g., monocyte or platelet migration; and 5) they modulate atherosclerotic lesion formation.

Various aspects of the invention are described in further detail in the following subsections:

Screening Assays:

The invention provides a method (also referred to herein as a "screening assay") for identifying modulators, i.e., candidate or test compounds or agents (e.g., peptides, peptidomimetics, small molecules (organic or inorganic) or other drugs) which bind to 10218 proteins, have a stimulatory or inhibitory effect on, for example, 10218 expression or 10218 activity, or have a stimulatory or inhibitory effect on, for example, the expression or activity of a 10218 substrate. Compounds identified using the assays described herein may be useful for treating cardiovascular diseases, e.g., atherosclerosis.

These assays are designed to identify compounds that bind to a 10218 protein, bind to other intracellular or extracellular proteins that interact with a 10218 protein, and interfere with the interaction of the 10218 protein with other intercellular or extracellular proteins. For example, in the case of the 10218 protein, which is a transmembrane receptor-type protein, such techniques can identify ligands for such a receptor. A 10218 protein ligand can, for example, be used to ameliorate cardiovascular diseases, e.g., atherosclerosis, ischemia/reperfusion, hypertension, restenosis, arterial inflammation, and endothelial cell disorders. Such compounds may include, but are not limited to peptides, antibodies, or small organic or inorganic compounds. Such compounds may also include other cellular proteins.

Compounds identified via assays such as those described herein may be useful, for example, for ameliorating cardiovascular disease, e.g., athersclerosis. In instances whereby a cardiovascular disease condition results from an overall lower level of 10218 gene expression and/or 10218 protein in a cell or tissue, compounds that interact with the 10218 protein may include compounds which accentuate or amplify the activity of the bound 10218 protein. Such compounds would bring about an effective increase in the level of 10218 protein activity, thus ameliorating symptoms.

In other instances, mutations within the 10218 gene may cause aberrant types or excessive amounts of 10218 proteins to be made which have a deleterious effect that leads to a cardiovascular disease. Similarly, physiological conditions may cause an excessive increase in 10218 gene expression leading to a cardiovascular disease. In such cases, compounds that bind to a 10218 protein may be identified that inhibit the activity of the 10218 protein. Assays for testing the effectiveness of compounds identified by techniques such as those described in this section are discussed herein.

In one embodiment, the invention provides assays for screening candidate or test compounds which are substrates of a 10218 protein or polypeptide or biologically active portion thereof. In another embodiment, the invention provides assays for screening candidate or test compounds which bind to or modulate the activity of a 10218 protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) Anticancer Drug Des. 12:145).

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233.

Libraries of compounds may be presented in solution (e.g., Houghten (1992) Biotechniques 13:412–421), or on beads (Lam (1991) Nature 354:82–84), chips (Fodor (1993) Nature 364:555–556), bacteria (Ladner U.S. Pat. No. 5,223,409), spores (Ladner U.S. Pat. No. '409), plasmids (Cull et al. (1992) Proc Natl Acad Sci USA 89:1865–1869) or on phage (Scott and Smith (1990) Science 249:386–390); (Devlin (1990) Science 249:404–406); (Cwirla et al. (1990) Proc. Natl. Acad. Sci. 87:6378–6382); (Felici (1991) J. Mol. Biol. 222:301–310); (Ladner supra.).

In one embodiment, an assay is a cell-based assay in which a cell which expresses a 10218 protein or biologically active portion thereof is contacted with a test compound and the ability of the test compound to modulate 10218 activity is determined. Determining the ability of the test compound to modulate 10218 activity can be accomplished by monitoring, for example, intracellular calcium, $IP_3$, cAMP, or diacylglycerol concentration, the phosphorylation profile of intracellular proteins, cell proliferation and/or migration, gene expression of, for example, cell surface adhesion molecules or genes associated with angiogenesis, or the activity of a 10218-regulated transcription factor. The cell can be of mammalian origin, e.g., an endothelial cell. In one embodiment, compounds that interact with a 10218 receptor domain can be screened for their ability to function as ligands, i.e., to bind to the 10218 receptor and modulate a signal transduction pathway. Identification of 10218 ligands, and measuring the activity of the ligand-receptor complex, leads to the identification of modulators (e.g., antagonists) of this interaction. Such modulators may be useful in the treatment of cardiovascular disease.

The ability of the test compound to modulate 10218 binding to a substrate or to bind to 10218 can also be determined. Determining the ability of the test compound to modulate 10218 binding to a substrate can be accomplished, for example, by coupling the 10218 substrate with a radioisotope or enzymatic label such that binding of the 10218 substrate to 10218 can be determined by detecting the labeled 10218 substrate in a complex. 10218 could also be coupled with a radioisotope or enzymatic label to monitor the ability of a test compound to modulate 10218 binding to a 10218 substrate in a complex. Determining the ability of the test compound to bind 10218 can be accomplished, for example, by coupling the compound with a radioisotope or enzymatic label such that binding of the compound to 10218 can be determined by detecting the labeled 10218 compound in a complex. For example, compounds (e.g., 10218 ligands or substrates) can be labeled with $^{125}I$, $^{35}S$, $^{14}C$, or $^{3}H$, either directly or indirectly, and the radioisotope detected by direct counting of radioeminission or by scintillation counting. Compounds can further be enzymatically labeled with, for example, horseradish peroxidase, alkaline phosphatase, or luciferase, and the enzymatic label detected by determination of conversion of an appropriate substrate to product.

The ability of a test compound to modulate the 10218 receptor's ability to associate with (e.g., bind) calcium can tested for using the assays described in, for example, Liu L. (1999) *Cell Signal*. 11(5):317–24 and Kawai T. et al. (1999) *Oncogene* 18(23):3471–80, the contents of which are incorporated herein by reference.

It is also within the scope of this invention to determine the ability of a compound (e.g., a 10218 ligand or substrate) to interact with 10218 without the labeling of any of the interactants. For example, a microphysiometer can be used to detect the interaction of a compound with 10218 without the labeling of either the compound or the 10218 (McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 10218.

In another embodiment, an assay is a cell-based assay comprising contacting a cell expressing a 10218 target molecule (e.g., a 10218 substrate) with a test compound and determining the ability of the test compound to modulate (e.g., stimulate or inhibit) the activity of the 10218 target molecule. Determining the ability of the test compound to modulate the activity of a 10218 target molecule can be accomplished, for example, by determining the ability of the 10218 protein to bind to or interact with the 10218 target molecule.

Determining the ability of the 10218 protein or a biologically active fragment thereof, to bind to or interact with a 10218 target molecule can be accomplished by one of the methods described above for determining direct binding. In a preferred embodiment, determining the ability of the 10218 protein to bind to or interact with a 10218 target molecule can be accomplished by determining the activity of the target molecule. For example, the activity of the target molecule can be determined by detecting induction of a cellular second messenger of the target (i.e., intracellular $Ca^{2+}$, diacylglycerol, $IP_3$, cAMP), detecting catalytic/enzymatic activity of the target on an appropriate substrate, detecting the induction of a reporter gene (comprising a target-responsive regulatory element operatively linked to a nucleic acid encoding a detectable marker, e.g., luciferase), or detecting a target-regulated cellular response (e.g., gene expression).

In yet another embodiment, an assay of the present invention is a cell-free assay in which a 10218 protein or biologically active portion thereof, is contacted with a test compound and the ability of the test compound to bind to the 10218 protein or biologically active portion thereof is determined. Preferred biologically active portions of the 10218 proteins to be used in assays of the present invention include fragments which participate in interactions with non-10218 molecules, e.g., fragments with high surface probability scores. Binding of the test compound to the 10218 protein can be determined either directly or indirectly as described above. In a preferred embodiment, the assay includes contacting the 10218 protein or biologically active portion thereof with a known compound which binds 10218 to form an assay mixture, contacting the assay mixture with a test compound, and determining the ability of the test compound to interact with a 10218 protein, wherein determining the ability of the test compound to interact with a 10218 protein comprises determining the ability of the test compound to preferentially bind to 10218 or biologically active portion thereof as compared to the known compound. Compounds that modulate the interaction of 10218 with a known target protein may be useful in regulating the activity of a 10218 protein, especially a mutant 10218 protein.

In another embodiment, the assay is a cell-free assay in which a 10218 protein or biologically active portion thereof is contacted with a test compound and the ability of the test compound to modulate (e.g., stimulate or inhibit) the activity of the 10218 protein or biologically active portion thereof is determined. Determining the ability of the test compound to modulate the activity of a 10218 protein can be accomplished, for example, by determining the ability of the 10218 protein to bind to a 10218 target molecule by one of the methods described above for determining direct binding. Determining the ability of the 10218 protein to bind to a 10218 target molecule can also be accomplished using a technology such as real-time Biomolecular Interaction Analysis (BIA) (Sjolander, S. and Urbaniczky, C. (1991) *Anal. Chem*. 63:2338–2345 and Szabo et al. (1995) *Curr. Opin. Struct. Biol*. 5:699–705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In another embodiment, determining the ability of the test compound to modulate the activity of a 10218 protein can be accomplished by determining the ability of the 10218 protein to further modulate the activity of a downstream effector of a 10218 target molecule. For example, the activity of the effector molecule on an appropriate target can be determined or the binding of the effector to an appropriate target can be determined as previously described.

In yet another embodiment, the cell-free assay involves contacting a 10218 protein or biologically active portion thereof with a known compound which binds the 10218 protein to form an assay mixture, contacting the assay mixture with a test compound, and determining the ability of the test compound to interact with the 10218 protein, wherein determining the ability of the test compound to interact with the 10218 protein comprises determining the ability of the 10218 protein to preferentially bind to or modulate the activity of a 10218 target molecule.

In more than one embodiment of the above assay methods of the present invention, it may be desirable to immobilize either 10218 or its target molecule to facilitate separation of complexed from uncomplexed forms of one or both of the proteins, as well as to accommodate automation of the assay. Binding of a test compound to a 10218 protein, or interaction of a 10218 protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/10218 fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or 10218 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of 10218 binding or activity determined using standard techniques.

Other techniques for immobilizing proteins on matrices can also be used in the screening assays of the invention. For example, either a 10218 protein or a 10218 target molecule can be immobilized utilizing conjugation of biotin and streptavidin. Biotinylated 10218 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with 10218 protein or target molecules but which do not interfere with binding of the 10218 protein to its target molecule can be derivatized to the wells of the plate, and unbound target or 10218 protein trapped in the wells by antibody conjugation. Methods for detecting such complexes, in addition to those described above for the GST-immobilized complexes, include immunodetection of complexes using antibodies reactive with the 10218 protein or target molecule, as well as enzyme-linked assays which rely on detecting an enzymatic activity associated with the 10218 protein or target molecule.

In another embodiment, modulators of 10218 expression are identified in a method wherein a cell is contacted with a candidate compound and the expression of 10218 mRNA or protein in the cell is determined. The level of expression of 10218 mRNA or protein in the presence of the candidate compound is compared to the level of expression of 10218 mRNA or protein in the absence of the candidate compound. The candidate compound can then be identified as a modulator of 10218 expression based on this comparison. For example, when expression of 10218 mRNA or protein is greater (statistically significantly greater) in the presence of the candidate compound than in its absence, the candidate compound is identified as a stimulator of 10218 mRNA or protein expression. Alternatively, when expression of 10218 mRNA or protein is less (statistically significantly less) in the presence of the candidate compound than in its absence, the candidate compound is identified as an inhibitor of 10218 mRNA or protein expression. The level of 10218 mRNA or protein expression in the cells can be determined by methods described herein for detecting 10218 mRNA or protein.

In yet another aspect of the invention, the 10218 proteins can be used as "bait proteins" in a two-hybrid assay or three-hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Biotechniques 14:920–924; Iwabuchi et al. (1993) Oncogene 8:1693–1696; and Brent WO94/10300), to identify other proteins, which bind to or interact with 10218 ("10218-binding proteins" or "10218-bp") and are involved in 10218 activity. Such 10218-binding proteins are also likely to be involved in the propagation of signals by the 10218 proteins or 10218 targets as, for example, downstream elements of a 10218-mediated signaling pathway. Alternatively, such 10218-binding proteins are likely to be 10218 inhibitors.

The two-hybrid system is based on the modular nature of most transcription factors, which consist of separable DNA-binding and activation domains. Briefly, the assay utilizes two different DNA constructs. In one construct, the gene that codes for a 10218 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a 10218-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 10218 protein.

In another aspect, the invention pertains to a combination of two or more of the assays described herein. For example, a modulating agent can be identified using a cell-based or a cell free assay, and the ability of the agent to modulate the activity of a 10218 protein can be confirmed in vivo, e.g., in an animal such as an animal model for cardiovascular disease, e.g., atherosclerosis, as described herein.

This invention further pertains to novel agents identified by the above-described screening assays. Accordingly, it is within the scope of this invention to further use an agent identified as described herein in an appropriate animal model. For example, an agent identified as described herein (e.g., a 10218 modulating agent, an antisense 10218 nucleic acid molecule, a 10218-specific antibody, or a 10218-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

Any of the compounds, including but not limited to compounds such as those identified in the foregoing assay systems, may be tested for the ability to ameliorate cardiovascular disease symptoms. Cell-based and animal model-based assays for the identification of compounds exhibiting such an ability to ameliorate cardiovascular disease systems are described herein.

In one aspect, cell-based systems, as described herein, may be used to identify compounds which may act to ameliorate cardiovascular disease symptoms. For example, such cell systems may be exposed to a compound, suspected of exhibiting an ability to ameliorate cardiovascular disease symptoms, at a sufficient concentration and for a time sufficient to elicit such an amelioration of cardiovascular disease symptoms in the exposed cells. After exposure, the cells are examined to determine whether one or more of the cardiovascular disease cellular phenotypes has been altered to resemble a more normal or more wild type, non-cardiovascular disease phenotype. Cellular phenotypes that are associated with cardiovascular disease states include aberrant proliferation and migration, angiogenesis, deposition of extracellular matrix components, accumulation of intracellular lipids, and expression of growth factors, cytokines, and other inflammatory mediators.

In addition, animal-based cardiovascular disease systems, such as those described herein, may be used to identify compounds capable of ameliorating cardiovascular disease symptoms. Such animal models may be used as test substrates for the identification of drugs, pharmaceuticals, therapies, and interventions which may be effective in treating cardiovascular disease. For example, animal models may be exposed to a compound, suspected of exhibiting an ability to ameliorate cardiovascular disease symptoms, at a sufficient concentration and for a time sufficient to elicit such an amelioration of cardiovascular disease symptoms in the exposed animals. The response of the animals to the exposure may be monitored by assessing the reversal of disorders associated with cardiovascular disease, for example, by counting the number of atherosclerotic plaques and/or measuring their size before and after treatment.

With regard to intervention, any treatments which reverse any aspect of cardiovascular disease symptoms should be considered as candidates for human cardiovascular disease therapeutic intervention. Dosages of test agents may be determined by deriving dose-response curves.

Additionally, gene expression patterns may be utilized to assess the ability of a compound to ameliorate cardiovascular disease symptoms. For example, the expression pattern of one or more genes may form part of a "gene expression profile" or "transcriptional profile" which may be then be used in such an assessment. "Gene expression profile" or "transcriptional profile", as used herein, includes the pattern of mRNA expression obtained for a given tissue or cell type under a given set of conditions. Such conditions may include, but are not limited to, atherosclerosis, ischemia/reperfusion, hypertension, restenosis, and arterial inflammation, including any of the control or experimental conditions described herein, for example, atherogenic cytokine stimulation of macrophages. Gene expression profiles may be generated, for example, by utilizing a differential display procedure, Northern analysis and/or RT-PCR. In one embodiment, 10218 gene sequences may be used as probes and/or PCR primers for the generation and corroboration of such gene expression profiles.

Gene expression profiles may be characterized for known states, either cardiovascular disease or normal, within the cell- and/or animal-based model systems. Subsequently, these known gene expression profiles may be compared to ascertain the effect a test compound has to modify such gene expression profiles, and to cause the profile to more closely resemble that of a more desirable profile.

For example, administration of a compound may cause the gene expression profile of a cardiovascular disease model system to more closely resemble the control system. Administration of a compound may, alternatively, cause the gene expression profile of a control system to begin to mimic a cardiovascular disease state. Such a compound may, for example, be used in further characterizing the compound of interest, or may be used in the generation of additional animal models.

Cell- and Animal-Based Model Systems

Described herein are cell- and animal-based systems which act as models for cardiovascular disease. These systems may be used in a variety of applications. For example, the cell- and animal-based model systems may be used to further characterize differentially expressed genes associated with cardiovascular disease, e.g., 10218. In addition, animal- and cell-based assays may be used as part of screening strategies designed to identify compounds which are capable of ameliorating cardiovascular disease symptoms, as described, below. Thus, the animal- and cell-based models may be used to identify drugs, pharmaceuticals, therapies and interventions which may be effective in treating cardiovascular disease. Furthermore, such animal models may be used to determine the LD50 and the ED50 in animal subjects, and such data can be used to determine the in vivo efficacy of potential cardiovascular disease treatments.

Animal-Based Systems

Animal-based model systems of cardiovascular disease may include, but are not limited to, non-recombinant and engineered transgenic animals.

Non-recombinant animal models for cardiovascular disease may include, for example, genetic models. Such genetic cardiovascular disease models may include, for example, ApoB or ApoR deficient pigs (Rapacz, et al., 1986, *Science* 234:1573–1577) and Watanabe heritable hyperlipidemic (WHHL) rabbits (Kita et al., 1987, *Proc. Natl. Acad. Sci USA* 84: 5928–5931). Transgenic mouse models in cardiovascular disease and angiogenesis are reviewed in Carmeliet, P. and Collen, D. (2000) J. Pathol. 190:387–405.

Non-recombinant, non-genetic animal models of atherosclerosis may include, for example, pig, rabbit, or rat models in which the animal has been exposed to either chemical wounding through dietary supplementation of LDL, or mechanical wounding through balloon catheter angioplasty. Animal models of cardiovascular disease also include rat myocardial infarction models (described in, for example, Schwarz, E R et al. (2000) *J. Am. Coll. Cardiol.* 35:1323–1330) and models of chromic cardiac ischemia in rabbits (described in, for example, Operschall, C et al. (2000) *J. Appl. Physiol.* 88:1438–1445).

Additionally, animal models exhibiting cardiovascular disease symptoms may be engineered by using, for example, 10218 gene sequences described above, in conjunction with techniques for producing transgenic animals that are well known to those of skill in the art. For example, 10218 gene sequences may be introduced into, and overexpressed in, the genome of the animal of interest, or, if endogenous 10218 gene sequences are present, they may either be overexpressed or, alternatively, be disrupted in order to underexpress or inactivate 10218 gene expression, such as described for the disruption of ApoE in mice (Plump et al., 1992, *Cell* 71: 343–353).

The host cells of the invention can also be used to produce non-human transgenic animals. For example, in one embodiment, a host cell of the invention is a fertilized oocyte or an embryonic stem cell into which 10218-coding sequences have been introduced. Such host cells can then be used to create non-human transgenic animals in which exogenous 10218 sequences have been introduced into their genome or homologous recombinant animals in which endogenous 10218 sequences have been altered. Such animals are useful for studying the function and/or activity of a 10218 and for identifying and/or evaluating modulators of 10218 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous 10218 gene has been altered by homologous recombination between the endogenous gene and an exogenous DNA molecule introduced into a cell of the animal, e.g., an embryonic cell of the animal, prior to development of the animal.

A transgenic animal used in the methods of the invention can be created by introducing a 10218-encoding nucleic acid into the male pronuclei of a fertilized oocyte, e.g., by microinjection, retroviral infection, and allowing the oocyte to develop in a pseudopregnant female foster animal. The 10218 cDNA sequence of SEQ ID NO:16 or 18 can be introduced as a transgene into the genome of a non-human animal. Alternatively, a nonhuman homologue of a human 10218 gene, such as a mouse or rat 10218 gene, can be used as a transgene. Alternatively, a 10218 gene homologue, such as another 10218 family member, can be isolated based on hybridization to the 10218 cDNA sequences of SEQ ID NO:16 or 18 and used as a transgene. Intronic sequences and polyadenylation signals can also be included in the transgene to increase the efficiency of expression of the transgene. A tissue-specific regulatory sequence(s) can be operably linked to a 10218 transgene to direct expression of a 10218 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of a 10218 transgene in its genome and/or expression of 10218 mRNA in tissues or cells of the animals. A transgenic founder animal can then be used to breed additional animals carrying the transgene. Moreover, transgenic animals carrying a transgene encoding a 10218 protein can further be bred to other transgenic animals carrying other transgenes.

To create a homologous recombinant animal, a vector is prepared which contains at least a portion of a 10218 gene into which a deletion, addition or substitution has been introduced to thereby alter, e.g., functionally disrupt, the 10218 gene. The 10218 gene can be a human gene (e.g., the cDNA of SEQ ID NO:16 or 18), but more preferably, is a non-human homologue of a human 10218 gene (e.g., a cDNA isolated by stringent hybridization with the nucleotide sequence of SEQ ID NO:16 or 18). For example, a rat 10218 gene can be used to construct a homologous recombination nucleic acid molecule, e.g., a vector, suitable for altering an endogenous 10218 gene in the mouse genome. In a preferred embodiment, the homologous recombination nucleic acid molecule is designed such that, upon homologous recombination, the endogenous 10218 gene is functionally disrupted (i.e., no longer encodes a functional protein; also referred to as a "knock out" vector). Alternatively, the homologous recombination nucleic acid molecule can be designed such that, upon homologous recombination, the endogenous 10218 gene is mutated or otherwise altered but still encodes functional protein (e.g., the upstream regulatory region can be altered to thereby alter the expression of the endogenous 10218 protein). In the homologous recombination nucleic acid molecule, the altered portion of the 10218 gene is flanked at its 5' and 3' ends by additional nucleic acid sequence of the 10218 gene to allow for homologous recombination to occur between the exogenous 10218 gene carried by the homologous recombination nucleic acid molecule and an endogenous 10218 gene in a cell, e.g., an embryonic stem cell. The additional flanking 10218 nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecehi, M. R. (1987) *Cell* 51:503 for a description of homologous recombination vectors). The homologous recombination nucleic acid molecule is introduced into a cell, e.g., an embryonic stem cell line (e.g., by electroporation) and cells in which the introduced 10218 gene has homologously recombined with the endogenous 10218 gene are selected (see e.g., Li, E. et al. (1992) *Cell* 69:915). The selected cells can then injected into a blastocyst of an animal (e.g., a mouse) to form aggregation chimeras (see e.g., Bradley, A. in *Teratocarcinomas and Embryonic Steni Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-human animals for use in the methods of the invention can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

The 10218 transgenic animals that express 10218 mRNA or a 10218 peptide (detected immunocytochemically, using antibodies directed against 10218 epitopes) at easily detectable levels should then be further evaluated to identify those animals which display characteristic cardiovascular disease symptoms. Such cardiovascular disease symptoms may include, for example, increased prevalence and size of fatty streaks and/or cardiovascular disease plaques.

Additionally, specific cell types (e.g., endothelial cells) within the transgenic animals may be analyzed and assayed for cellular phenotypes characteristic of cardiovascular disease. In the case of endothelial cells, such phenotypes include, but are not limited to cell proliferation, migration, angiogenesis, production of proinflammatory growth factors and cytokines, and adhesion to inflammatory cells. In the case of monocytes, such phenotypes may include but are not limited to increases in rates of LDL uptake, adhesion to endothelial cells, transmigration, foam cell formation, fatty streak formation, and production of foam cell specific products. Cellular phenotypes may include a particular cell type's pattern of expression of genes associated with cardiovascular disease as compared to known expression profiles of the particular cell type in animals exhibiting cardiovascular disease symptoms.

Cell-Based Systems

Cells that contain and express 10218 gene sequences which encode a 10218 protein, and, further, exhibit cellular phenotypes associated with cardiovascular disease, may be used to identify compounds that exhibit anti-cardiovascular disease activity. Such cells may include non-recombinant monocyte cell lines, such as U937 (ATCC# CRL-1593), THP-1 (ATCC#TIB-202), and P388D1 (ATCC# TIB-63); endothelial cells such as human umbilical vein endothelial cells (HUVECs), human microvascular endothelial cells (HMVEC), and bovine aortic endothelial cells (BAECs); as well as generic mammalian cell lines such as HeLa cells and COS cells, e.g., COS-7 (ATCC# CRL-1651). Further, such cells may include recombinant, transgenic cell lines. For example, the cardiovascular disease animal models of the invention, discussed above, may be used to generate cell lines, containing one or more cell types involved in cardiovascular disease, that can be used as cell culture models for this disorder. While primary cultures derived from the cardiovascular disease transgenic animals of the invention may be utilized, the generation of continuous cell lines is preferred. For examples of techniques which may be used to derive a continuous cell line from the transgenic animals, see Small et al., (1985) Mol. Cell Biol. 5:642–648.

Alternatively, cells of a cell type known to be involved in cardiovascular disease may be transfected with sequences capable of increasing or decreasing the amount of 10218 gene expression within the cell. For example, 10218 gene sequences may be introduced into, and overexpressed in, the genome of the cell of interest, or, if endogenous 10218 gene sequences are present, they may be either overexpressed or, alternatively disrupted in order to underexpress or inactivate 10218 gene expression.

In order to overexpress a 10218 gene, the coding portion of the 10218 gene may be ligated to a regulatory sequence which is capable of driving gene expression in the cell type of interest, e.g., an endothelial cell. Such regulatory regions will be well known to those of skill in the art, and may be utilized in the absence of undue experimentation. Recombinant methods for expressing target genes are described above.

For underexpression of an endogenous 10218 gene sequence, such a sequence may be isolated and engineered such that when reintroduced into the genome of the cell type of interest, the endogenous 10218 alleles will be inactivated. Preferably, the engineered 10218 sequence is introduced via gene targeting such that the endogenous 10218 sequence is disrupted upon integration of the engineered 10218 sequence into the cell's genome. Transfection of host cells with 10218 genes is discussed, above.

Cells treated with compounds or transfected with 10218 genes can be examined for phenotypes associated with cardiovascular disease. In the case of monocytes, such phenotypes include but are not limited to increases in rates of LDL uptake, adhesion to endothelial cells, transmigration, foam cell formation, fatty streak formation, and production by foam cells of growth factors such as bFGF, IGF-I, VEGF, IL-1, M-CSF, TGFβ, TGFα, TNFα, HB-EGF, PDGF, IFN-γ, and GM-CSF. Transmigration rates, for example, may be measured using the in vitro system of Navab et al. (1988) J. Clin. Invest. 82:1853–1863, by quantifying the number of monocytes that migrate across the endothelial monolayer and into the collagen layer of the subendothelial space.

Similarly, endothelial cells can be treated with test compounds or transfected with genetically engineered 10218 genes. The endothelial cells can then be examined for phenotypes associated with cardiovascular disease, including, but not limited to changes in cellular morphology, cell proliferation, cell migration, and mononuclear cell adhesion; or for the effects on production of other proteins involved in cardiovascular disease such as adhesion molecules (e.g., ICAM, VCAM, E-selectin), growth factors and cytokines (e.g., PDGF, IL-1β, TNFα, MCF), and proteins involved in angiogenesis (e.g., FLK, FLT).

Transfection of 10218 nucleic acid may be accomplished by using standard techniques (described in, for example, Ausubel (1989) supra). Transfected cells should be evaluated for the presence of the recombinant 10218 gene sequences, for expression and accumulation of 10218 mRNA, and for the presence of recombinant 10218 protein production. In instances wherein a decrease in 10218 gene expression is desired, standard techniques may be used to demonstrate whether a decrease in endogenous 10218 gene expression and/or in 10218 protein production is achieved.

Cellular models for the study of cardiovascular disease and angiogenesis include models of endothelial cell differentiation on Matrigel (Baatout, S. et al. (1996) Rom. J. Intern. Med. 34:263–269; Benelli, R et al. (1999) Int. J. Biol. Markers 14:243–246), embryonic stem cell models of vascular morphogenesis (Doetschman, T. et al. (1993) Hypertension 22:618–629), the culture of microvessel fragments in physiological gels (Hoying, J B et al. (1996) In Vitro Cell Dev. Biol. Anim. 32: 409–419; U.S. Pat. No. 5,976,782), and the treatment of endothelial cells and smooth muscle cells with atherogenic and angiogenic factors including growth factors and cytokines (e.g., IL-1β, PDGF, TNFα, VEGF), homocysteine, and LDL. In vitro angiogenesis models are described in, for example, Black, A F et al. (1999) Cell Biol. Toxicol. 15:81–90.

Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining 10218 protein and/or nucleic acid expression as well as 10218 activity, in the context of a biological sample (e.g., blood, serum, cells, e.g., endothelial cells, or tissue, e.g., vascular tissue) to thereby determine whether an individual is afflicted with a cardiovascular disease. The invention also provides for prognostic (or predictive) assays for determining whether an individual is at risk of developing a cardiovascular disorder. For example, mutations in a 10218 gene can be assayed for in a biological sample. Such assays can be used for prognostic or predictive purpose to thereby phophylactically treat an individual prior to the onset of a cardiovascular disorder, e.g., atherosclerosis.

Another aspect of the invention pertains to monitoring the influence of 10218 modulators (e.g., anti-10218 antibodies or 10218 ribozymes) on the expression or activity of 10218 in clinical trials.

These and other agents are described in further detail in the following sections.

Diagnostic Assays for Cardiovascular Disease

To determine whether a subject is afflicted with a cardiovascular disease, a biological sample may be obtained from a subject and the biological sample may be contacted with a compound or an agent capable of detecting a 10218 protein or nucleic acid (e.g., mRNA or genomic DNA) that encodes a 10218 protein, in the biological sample. A preferred agent for detecting 10218 mRNA or genomic DNA is a labeled nucleic acid probe capable of hybridizing to 10218 mRNA or genomic DNA. The nucleic acid probe can be, for example, the 10218 nucleic acid set forth in SEQ ID NO:16, or a portion thereof, such as an oligonucleotide of at least 15, 20, 25, 30, 25, 40, 45, 50, 100, 250 or 500 nucleotides in length and sufficient to specifically hybridize under stringent conditions to 10218 mRNA or genomic DNA. Other suitable probes for use in the diagnostic assays of the invention are described herein.

A preferred agent for detecting 10218 protein in a sample is an antibody capable of binding to 10218 protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

The term "biological sample" is intended to include tissues, cells, and biological fluids isolated from a subject, as well as tissues, cells, and fluids present within a subject. That is, the detection method of the invention can be used to detect 10218 mRNA, protein, or genomic DNA in a biological sample in vitro as well as in vivo. For example, in vitro techniques for detection of 10218 mRNA include Northern hybridizations and in situ hybridizations. In vitro techniques for detection of 10218 protein include enzyme linked immunosorbent assays (ELISAs), Western blots, immunoprecipitations and immunofluorescence. In vitro techniques for detection of 10218 genomic DNA include Southern hybridizations. Furthermore, in vivo techniques for detection of 10218 protein include introducing into a subject a labeled anti-10218 antibody. For example, the antibody can be labeled with a radioactive marker whose presence and location in a subject can be detected by standard imaging techniques.

In another embodiment, the methods further involve obtaining a control biological sample from a control subject, contacting the control sample with a compound or agent capable of detecting 10218 protein, mRNA, or genomic DNA, such that the presence of 10218 protein, mRNA or genomic DNA is detected in the biological sample, and comparing the presence of 10218 protein, mRNA or genomic DNA in the control sample with the presence of 10218 protein, mRNA or genomic DNA in the test sample.

Prognostic Assays for Cardiovascular Disease

The present invention further pertains to methods for identifying subjects having or at risk of developing a cardiovascular disease associated with aberrant 10218 expression or activity.

As used herein, the term "aberrant" includes a 10218 expression or activity which deviates from the wild type 10218 expression or activity. Aberrant expression or activity includes increased or decreased expression or activity, as well as expression or activity which does not follow the wild type developmental pattern of expression or the subcellular pattern of expression. For example, aberrant 10218 expression or activity is intended to include the cases in which a mutation in the 10218 gene causes the 10218 gene to be under-expressed or over-expressed and situations in which such mutations result in a non-functional 10218 protein or a protein which does not function in a wild-type fashion, e.g., a protein which does not interact with a 10218 substrate, or one which interacts with a non-10218 substrate.

The assays described herein, such as the preceding diagnostic assays or the following assays, can be used to identify a subject having or at risk of developing a cardiovascular disease, e.g., including but not limited to, atherosclerosis, ischemia/reperfusion injury, hypertension, restenosis, arterial inflammation, and endothelial cell disorders. A biological sample may be obtained from a subject and tested for the presence or absence of a genetic alteration. For example, such genetic alterations can be detected by ascertaining the existence of at least one of 1) a deletion of one or more nucleotides from a 10218 gene, 2) an addition of one or more nucleotides to a 10218 gene, 3) a substitution of one or more nucleotides of a 10218 gene, 4) a chromosomal rearrangement of a 10218 gene, 5) an alteration in the level of a messenger RNA transcript of a 10218 gene, 6) aberrant modification of a 10218 gene, such as of the methylation pattern of the genomic DNA, 7) the presence of a non-wild type splicing pattern of a messenger RNA transcript of a 10218 gene, 8) a non-wild type level of a 10218-protein, 9) allelic loss of a 10218 gene, and 10) inappropriate post-translational modification of a 10218-protein.

As described herein, there are a large number of assays known in the art which can be used for detecting genetic alterations in a 10218 gene. For example, a genetic alteration in a 10218 gene may be detected using a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080;

and Nakazawa et al. (1994) *Proc. Natl. Acad. Sci. USA* 91:360–364), the latter of which can be particularly useful for detecting point mutations in a 10218 gene (see Abravaya et al. (1995) *Nucleic Acids Res.* 23:675–682). This method includes collecting a biological sample from a subject, isolating nucleic acid (e.g., genomic DNA, mRNA or both) from the sample, contacting the nucleic acid sample with one or more primers which specifically hybridize to a 10218 gene under conditions such that hybridization and amplification of the 10218 gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) *Proc. Natl. Acad. Sci. USA* 87:1874–1878), transcriptional amplification system (Kwoh, D. Y. et al. (1989) *Proc. Natl. Acad. Sci. USA* 86:1173–1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a 10218 gene from a biological sample can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 10218 can be identified by hybridizing biological sample derived and control nucleic acids, e.g., DNA or RNA, to high density arrays containing hundreds or thousands of oligonucleotide probes (Cronin, M. T. et al. (1996) *Human Mutation* 7:244–255; Kozal, M. J. et al. (1996) *Nature Medicine* 2:753–759). For example, genetic mutations in 10218 can be identified in two dimensional arrays containing light-generated DNA probes as described in Cronin, M. T. et al. (1996) supra. Briefly, a first hybridization array of probes can be used to scan through long stretches of DNA in a sample and control to identify base changes between the sequences by making linear arrays of sequential, overlapping probes. This step allows for the identification of point mutations. This step is followed by a second hybridization array that allows for the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 10218 gene in a biological sample and detect mutations by comparing the sequence of the 10218 in the biological sample with the corresponding wild-type (control) sequence. Examples of sequencing reactions include those based on techniques developed by Maxam and Gilbert (1977) *Proc. Natl. Acad. Sci. USA* 74:560) or Sanger (1977) *Proc. Natl. Acad. Sci. USA* 74:5463). It is also contemplated that any of a variety of automated sequencing procedures can be utilized when performing the diagnostic assays (Naeve, C. W. (1995) *Biotechniques* 19:448–53), including sequencing by mass spectrometry (see, e.g., PCT International Publication No. WO 94/16101; Cohen et al. (1996) *Adv. Chromatogr.* No. 36:127–162; and Griffin et al. (1993) *Appl. Biochem. Biotechnol.* 38:147–159).

Other methods for detecting mutations in the 10218 gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes formed by hybridizing (labeled) RNA or DNA containing the wild-type 10218 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad Sci USA* 85:4397 and Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in 10218 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a 10218 sequence, e.g., a wild-type 10218 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in 10218 genes. For example, single strand conformation polymorphism (SSCP) may be used to detect differences in electrophoretic mobility between mutant and wild type nucleic acids (Orita et al. (1989) *Proc Natl. Acad. Sci USA*: 86:2766; see also Cotton (1993) *Mutat. Res.* 285:125–144 and Hayashi (1992) *Genet. Anal. Tech. Appl.* 9:73–79). Single-stranded DNA fragments of sample and control 10218 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

Furthermore, the prognostic assays described herein can be used to determine whether a subject can be administered a 10218 modulator (e.g., an agonist, antagonist, peptidomimetic, protein, peptide, nucleic acid, or small molecule) to effectively treat a cardiovascular disease, e.g., atherosclerosis.

Monitoring of Effects During Clinical Trials

The present invention further provides methods for determining the effectiveness of a 10218 modulator (e.g., a 10218 modulator identified herein) in treating a cardiovascular disease, e.g., atherosclerosis, in a subject. For example, the effectiveness of a 10218 modulator in increasing 10218 gene expression, protein levels, or in upregulating 10218 activity, can be monitored in clinical trials of subjects exhibiting decreased 10218 gene expression, protein levels, or down-regulated 10218 activity. Alternatively, the effectiveness of a 10218 modulator in decreasing 10218 gene expression, protein levels, or in downregulating 10218 activity, can be monitored in clinical trials of subjects exhibiting increased 10218 gene expression, protein levels, or 10218 activity. In such clinical trials, the expression or activity of a 10218 gene, and preferably, other genes that have been implicated in, for example, atherosclerosis can be used as a "read out" or marker of the phenotype of a particular cell, e.g., a vascular endothelial cell.

For example, and not by way of limitation, genes, including 10218, that are modulated in cells by treatment with an agent which modulates 10218 activity (e.g., identified in a screening assay as described herein) can be identified. Thus, to study the effect of agents which modulate 10218 activity on subjects suffering from a cardiovascular disease in, for example, a clinical trial, cells can be isolated and RNA prepared and analyzed for the levels of expression of 10218 and other genes implicated in the cardiovascular disease. The levels of gene expression (e.g., a gene expression pattern) can be quantified by Northern blot analysis or RT-PCR, as described herein, or alternatively by measuring the amount of protein produced, by one of the methods described herein, or by measuring the levels of activity of 10218 or other genes. In this way, the gene expression pattern can serve as a marker, indicative of the physiological response of the cells to the agent which modulates 10218 activity. This response state may be determined before, and at various points during treatment of the individual with the agent which modulates 10218 activity.

In a preferred embodiment, the present invention provides a method for monitoring the effectiveness of treatment of a subject with an agent which modulates 10218 activity (e.g., an agonist, antagonist, peptidomimetic, protein, peptide, nucleic acid, or small molecule identified by the screening assays described herein) including the steps of (i) obtaining a pre-administration sample from a subject prior to administration of the agent; (ii) detecting the level of expression of a 10218 protein, mRNA, or genomic DNA in the pre-administration sample; (iii) obtaining one or more post-administration samples from the subject; (iv) detecting the level of expression or activity of the 10218 protein, mRNA, or genomic DNA in the post-administration samples; (v) comparing the level of expression or activity of the 10218 protein, mRNA, or genomic DNA in the pre-administration sample with the 10218 protein, mRNA, or genomic DNA in the post administration sample or samples; and (vi) altering the administration of the agent to the subject accordingly. For example, increased administration of the agent may be desirable to increase the expression or activity of 10218 to higher levels than detected, i.e., to increase the effectiveness of the agent. Alternatively, decreased administration of the agent may be desirable to decrease expression or activity of 10218 to lower levels than detected, i.e. to decrease the effectiveness of the agent. According to such an embodiment, 10218 expression or activity may be used as an indicator of the effectiveness of an agent, even in the absence of an observable phenotypic response.

Methods of Treatment of Subjects Suffering from Cardiovascular Disease

The present invention provides for both prophylactic and therapeutic methods of treating a subject, e.g., a human, at risk of (or susceptible to) a cardiovascular disease such as atherosclerosis, ischemialreperfusion injury, hypertension, restenosis, arterial inflammation, and endothelial cell disorders. With regard to both prophylactic and therapeutic methods of treatment, such treatments may be specifically tailored or modified, based on knowledge obtained from the field of pharmacogenomics. "Pharmacogenomics," as used herein, refers to the application of genomics technologies such as gene sequencing, statistical genetics, and gene expression analysis to drugs in clinical development and on the market. More specifically, the term refers to the study of how a patient's genes determine his or her response to a drug (e.g., a patient's "drug response phenotype", or "drug response genotype").

Thus, another aspect of the invention provides methods for tailoring an subject's prophylactic or therapeutic treatment with either the 10218 molecules of the present invention or 10218 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

Prophylactic Methods

In one aspect, the invention provides a method for preventing in a subject, a cardiovascular disease by administering to the subject an agent which modulates 10218 expression or 10218 activity, e.g., modulation of calcium influx, cellular migration, or formation of atherosclerotic lesions. Subjects at risk for a cardiovascular disease, e.g., atherosclerosis, can be identified by, for example, any or a combination of the diagnostic or prognostic assays described herein. Administration of a prophylactic agent can occur prior to the manifestation of symptoms characteristic of aberrant 10218 expression or activity, such that a cardiovascular disease is prevented or, alternatively, delayed in its progression. Depending on the type of 10218 aberrancy, for example, a 10218, 10218 agonist or 10218 antagonist agent can be used for treating the subject. The appropriate agent can be determined based on screening assays described herein.

Therapeutic Methods

Described herein are methods and compositions whereby cardiovascular disease symptoms may be ameliorated. Certain cardiovascular diseases are brought about, at least in part, by an excessive level of a gene product, or by the presence of a gene product exhibiting an abnormal or excessive activity. As such, the reduction in the level and/or activity of such gene products would bring about the amelioration of cardiovascular disease symptoms. Techniques for the reduction of gene expression levels or the activity of a protein are discussed below.

Alternatively, certain other cardiovascular diseases are brought about, at least in part, by the absence or reduction of the level of gene expression, or a reduction in the level of a protein's activity. As such, an increase in the level of gene expression and/or the activity of such proteins would bring about the amelioration of cardiovascular disease symptoms.

In some cases, the up-regulation of a gene in a disease state reflects a protective role for that gene product in responding to the disease condition. Enhancement of such a gene's expression, or the activity of the gene product, will reinforce the protective effect it exerts. Some cardiovascular disease states may result from an abnormally low level of activity of such a protective gene. In these cases also, an increase in the level of gene expression and/or the activity of such gene products would bring about the amelioration of cardiovascular disease symptoms. Techniques for increasing target gene expression levels or target gene product activity levels are discussed herein.

Accordingly, another aspect of the invention pertains to methods of modulating 10281 expression or activity for therapeutic purposes. Accordingly, in an exemplary embodiment, the modulatory method of the invention involves contacting a cell with a 10281 or agent that modulates one or more of the activities of 10281 protein activity associated with the cell (e.g., an endothelial cell or an ovarian cell). An agent that modulates 10281 protein activity can be an agent as described herein, such as a nucleic acid or a protein, a naturally-occurring target molecule of a 10281 protein (e.g., a 10281 ligand or substrate), a 10281 antibody, a 10281 agonist or antagonist, a peptidomimetic of a 10281 agonist or antagonist, or other small molecule. In one embodiment, the agent stimulates one or more 10281 activities. Examples of such stimulatory agents include active 10281 protein and a nucleic acid molecule encoding 10281 that has been introduced into the cell. In another embodiment, the agent inhibits one or more 10281 activities. Examples of such inhibitory agents include antisense 10281 nucleic acid molecules, anti-10281 antibodies, and 10281 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 10281 protein or nucleic acid molecule. In one embodiment, the method involves administering an agent (e.g., an agent identified by a screening assay described herein), or combination of agents that modulates (e.g., upregulates or downregulates) 10281 expression or activity. In another embodiment, the method involves administering a 10281 protein or nucleic acid molecule as therapy to compensate for reduced, aberrant, or unwanted 10281 expression or activity.

Stimulation of 10281 activity is desirable in situations in which 10281 is abnormally downregulated and/or in which increased 10281 activity is likely to have a beneficial effect. Likewise, inhibition of 10281 activity is desirable in situations in which 10281 is abnormally upregulated and/or in which decreased 10281 activity is likely to have a beneficial effect.

Methods for Inhibiting Target Gene Expression, Synthesis, or Activity

As discussed above, genes involved in cardiovascular disorders may cause such disorders via an increased level of gene activity. In some cases, such up-regulation may have a causative or exacerbating effect on the disease state. A variety of techniques may be used to inhibit the expression, synthesis, or activity of such genes and/or proteins.

For example, compounds such as those identified through assays described above, which exhibit inhibitory activity, may be used in accordance with the invention to ameliorate cardiovascular disease symptoms. Such molecules may include, but are not limited to, small organic molecules, peptides, antibodies, and the like.

For example, compounds can be administered that compete with endogenous ligand for the 10281 protein. The resulting reduction in the amount of ligand-bound 10281 protein will modulate endothelial cell physiology. Compounds that can be particularly useful for this purpose include, for example, soluble proteins or peptides, such as peptides comprising one or more of the extracellular domains, or portions and/or analogs thereof, of the 10281 protein, including, for example, soluble fusion proteins such as Ig-tailed fusion proteins. (For a discussion of the production of Ig-tailed fusion proteins, see, for example, U.S. Pat. No. 5,116,964). Alternatively, compounds, such as ligand analogs or antibodies, that bind to the 10281 receptor site, but do not activate the protein, (e.g., receptor-ligand antagonists) can be effective in inhibiting 10281 protein activity.

Further, antisense and ribozyme molecules which inhibit expression of the 10281 gene may also be used in accordance with the invention to inhibit aberrant 10281 gene activity. Still further, triple helix molecules may be utilized in inhibiting aberrant 10281 gene activity.

The antisense nucleic acid molecules used in the methods of the invention are typically administered to a subject or generated in situ such that they hybridize with or bind to cellular mRNA and/or genomic DNA encoding a 10281 protein to thereby inhibit expression of the protein, e.g., by inhibiting transcription and/or translation. The hybridization can be by conventional nucleotide complementarity to form a stable duplex, or, for example, in the case of-an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, an antisense nucleic acid molecule used in the methods of the invention is an α-anomeric nucleic acidlecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid used in the methods of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave 10281 mRNA transcripts to thereby inhibit translation of 10281 mRNA. A ribozyme having specificity for a 10281-encoding nucleic acid can be designed based upon the nucleotide sequence of a 10281 cDNA disclosed herein (i.e., SEQ ID NO:16 or 18). For example, a derivative of a *Tetrahymena* L-19 IVS RNA can be constructed in which the nucleotide sequence of the active site is complementary to the nucleotide sequence to be cleaved in a 10281-encoding mRNA (see, for example, Cech et al. U.S. Pat. No. 4,987,071; and Cech et al. U.S. Pat. No. 5,116,742). Alternatively, 10281 mRNA can be used to select a catalytic RNA having a specific ribonuclease activity from a pool of RNA molecules (see, for example, Bartel, D. and Szostak, J. W. (1993) *Science* 261:1411–1418).

10281 gene expression can also be inhibited by targeting nucleotide sequences complementary to the regulatory region of the 10281 (e.g., the 10281 promoter and/or enhancers) to form triple helical structures that prevent transcription of the 10281 gene in target cells (see, for example, Helene, C. (1991) *Anticancer Drug Des*. 6(6): 569–84; Helene, C. et al. (1992) *Ann. N.Y Acad. Sci*. 660:27–36; and Maher, L. J. (1992) *Bioassays* 14(12): 807–15).

Antibodies that are both specific for the 10281 protein and interfere with its activity may also be used to modulate or inhibit 10281 protein function. Such antibodies may be generated using standard techniques described herein, against the 10281 protein itself or against peptides corresponding to portions of the protein. Such antibodies include but are not limited to polyclonal, monoclonal, Fab fragments, single chain antibodies, or chimeric antibodies.

In instances where the target gene protein is intracellular and whole antibodies are used, internalizing antibodies may be preferred. Lipofectin liposomes may be used to deliver the antibody or a fragment of the Fab region which binds to the target epitope into cells. Where fragments of the antibody are used, the smallest inhibitory fragment which binds to the target protein's binding domain is preferred. For example, peptides having an amino acid sequence corresponding to the domain of the variable region of the antibody that binds to the target gene protein may be used. Such peptides may be synthesized chemically or produced via recombinant DNA technology using methods well known in the art (described in, for example, Creighton (1983), supra; and Sambrook et al. (1989) supra). Single chain neutralizing antibodies which bind to intracellular target gene epitopes may also be administered. Such single chain antibodies may be administered, for example, by expressing nucleotide sequences encoding single-chain antibodies within the target cell population by utilizing, for example, techniques such as those described in Marasco et al. (1993) *Proc. Natl. Acad. Sci. USA* 90:7889–7893).

In some instances, the target gene protein is extracellular, or is a transmembrane protein, such as the 10281 protein. Antibodies that are specific for one or more extracellular domains of the 10281 protein, for example, and that interfere with its activity, are particularly useful in treating cardiovascular disease. Such antibodies are especially efficient because they can access the target domains directly from the bloodstream. Any of the administration techniques described below which are appropriate for peptide administration may be utilized to effectively administer inhibitory target gene antibodies to their site of action.

Methods for Restoring or Enhancing Target Gene Activity

Genes that cause cardiovascular disease may be underexpressed within cardiovascular disease situations. Alternatively, the activity of the protein products of such genes may be decreased, leading to the development of cardiovascular disease symptoms. Such down-regulation of gene expression or decrease of protein activity might have a causative or exacerbating effect on the disease state.

In some cases, genes that are up-regulated in the disease state might be exerting a protective effect. A variety of techniques may be used to increase the expression, synthesis, or activity of genes and/or proteins that exert a protective effect in response to cardiovascular disease conditions.

Described in this section are methods whereby the level 10281 activity may be increased to levels wherein cardiovascular disease symptoms are ameliorated. The level of 10281 activity may be increased, for example, by either increasing the level of 10281 gene expression or by increasing the level of active 10281 protein which is present.

For example, a 10281 protein, at a level sufficient to ameliorate cardiovascular disease symptoms may be administered to a patient exhibiting such symptoms. Any of the techniques discussed below may be used for such administration. One of skill in the art will readily know how to determine the concentration of effective, non-toxic doses of the 10281 protein, utilizing techniques such as those described below.

Additionally, RNA sequences encoding a 10281 protein may be directly administered to a patient exhibiting cardiovascular disease symptoms, at a concentration sufficient to produce a level of 10281 protein such that cardiovascular disease symptoms are ameliorated. Any of the techniques discussed below, which achieve intracellular administration of compounds, such as, for example, liposome administration, may be used for the administration of such RNA molecules. The RNA molecules may be produced, for example, by recombinant techniques such as those described herein.

Further, subjects may be treated by gene replacement therapy. One or more copies of a 10281 gene, or a portion thereof, that directs the production of a normal 10281 protein with 10281 function, may be inserted into cells using vectors which include, but are not limited to adenovirus, adeno-associated virus, and retrovirus vectors, in addition to other particles that introduce DNA into cells, such as liposomes. Additionally, techniques such as those described above may be used for the introduction of 10281 gene sequences into human cells.

Cells, preferably, autologous cells, containing 10281 expressing gene sequences may then be introduced or reintroduced into the subject at positions which allow for the amelioration of cardiovascular disease symptoms. Such cell replacement techniques may be preferred, for example, when the gene product is a secreted, extracellular gene product.

Pharmaceutical Compositions

Another aspect of the invention pertains to methods for treating a subject suffering from a cardiovascular disease, e.g., atherosclerosis. These methods involve administering to a subject an agent which modulates 10218 expression or activity (e.g., an agent identified by a screening assay described herein), or a combination of such agents. In another embodiment, the method involves administering to a subject a 10218 protein or nucleic acid molecule as therapy to compensate for reduced, aberrant, or unwanted 10218 expression or activity.

Stimulation of 10218 activity is desirable in situations in which 10218 is abnormally downregulated and/or in which increased 10218 activity is likely to have a beneficial effect. Likewise, inhibition of 10218 activity is desirable in situations in which 10218 is abnormally upregulated and/or in which decreased 10218 activity is likely to have a beneficial effect, e.g., inhibition of atherosclerotic lesion formation.

The agents which modulate 10218 activity can be administered to a subject using pharmaceutical compositions suitable for such administration. Such compositions typically comprise the agent (e.g., nucleic acid molecule, protein, or antibody) and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition used in the therapeutic methods of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the agent that modulates 10218 activity (e.g., a fragment of a 10218 protein or an anti-10218 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The agents that modulate 10218 activity can also be prepared in the form of suppositories (e.g., with conventional suppository bases such as cocoa butter and other glycerides) or retention enemas for rectal delivery.

In one embodiment, the agents that modulate 10218 activity are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the agent that modulates 10218 activity and the particular therapeutic effect to be achieved, and the limitations inherent in the art of compounding such an agent for the treatment of subjects.

Toxicity and therapeutic efficacy of such agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and can be expressed as the ratio LD50/ED50. Agents which exhibit large therapeutic indices are preferred. While agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage for use in humans. The dosage of such 10218 modulating agents lies preferably within a range of circulating concentrations that include the ED50 with little or no toxicity. The dosage may vary within this range depending upon the dosage form employed and the route of administration utilized. For any agent used in the therapeutic methods of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982). Alternatively, an antibody can be conjugated to a second antibody to form an antibody heteroconjugate as described by Segal in U.S. Pat. No. 4,676,980.

The nucleic acid molecules used in the methods of the invention can be inserted into vectors and used as gene therapy vectors. Gene therapy vectors can be delivered to a subject by, for example, intravenous injection, local administration (see U.S. Pat. No. 5,328,470) or by stereotactic injection (see, e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

Pharmacogenomics

In conjunction with the therapeutic methods of the invention, pharmacogenomics (i.e., the study of the relationship between a subject's genotype and that subject's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer an agent which modulates 10218 activity, as well as tailoring the dosage and/or therapeutic regimen of treatment with an agent which modulates 10218 activity.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol*. 23(10–11): 983–985 and Linder, M. W. et al. (1997) *Clin. Chem*. 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate aminopeptidase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants). Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach" can be utilized to identify genes that predict drug response. According to this method, if a gene that encodes a drug target is known (e.g., a 10218 protein used in the methods of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and the cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling" can be utilized to identify genes that predict drug response. For example, the gene expression of an animal dosed with a drug (e.g., a 10218 molecule or 10218 modulator used in the methods of the present invention) can give an indication whether gene pathways related to toxicity have been turned on.

Information generated from more than one of the above pharmacogenomics approaches can be used to determine appropriate dosage and treatment regimens for prophylactic or therapeutic treatment of a subject. This knowledge, when applied to dosing or drug selection, can avoid adverse reactions or therapeutic failure and, thus, enhance therapeutic or prophylactic efficiency when treating a subject suffering from a cardiovascular disease, e.g., atherosclerosis, with an agent which modulates 10218 activity.

Recombinant Expression Vectors and Host Cells Used in the Methods of the Invention The methods of the invention (e.g., the screening assays described herein) include the use of vectors, preferably expression vectors, containing a nucleic acid encoding a 10218 protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors to be used in the methods of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel (1990) *Methods Enzymol.* 185:3–7. Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., 10218 proteins, mutant forms of 10218 proteins, fusion proteins, and the like).

The recombinant expression vectors to be used in the methods of the invention can be designed for expression of 10218 proteins in prokaryotic or eukaryotic cells. For example, 10218 proteins can be expressed in bacterial cells such as *E. coli*, insect cells (using baculovirus expression vectors), yeast cells, or mammalian cells. Suitable host cells are discussed further in Goeddel (1990) supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in 10218 activity assays, (e.g., direct assays or competitive assays described in detail below), or to generate antibodies specific for 10218 proteins. In a preferred embodiment, a 10218 fusion protein expressed in a retroviral expression vector of the present invention can be utilized to infect bone marrow cells which are subsequently transplanted into irradiated recipients. The pathology of the subject recipient is then examined after sufficient time has passed (e.g., six weeks).

In another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J. et al., *Molecular Cloning: A Laboratory Manual.* 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid).

The methods of the invention may further use a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to 10218 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific, or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes, see Weintraub, H. et al., Antisense RNA as a molecular tool for genetic analysis, *Reviews—Trends in Genetics*, Vol. 1(1) 1986.

Another aspect of the invention pertains to the use of host cells into which a 10218 nucleic acid molecule of the invention is introduced, e.g., a 10218 nucleic acid molecule within a recombinant expression vector or a 10218 nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 10218 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (*Molecular Cloning: A Laboratory Manual.* 2nd, ed., Cold Spring Harbor Laboratory, Cold Spring Harbor Laboratory Press, Cold Spring Harbor, N.Y., 1989), and other laboratory manuals.

A host cell used in the methods of the invention, such as a prokaryotic or eukaryotic host cell in culture, can be used to produce (i.e., express) a 10218 protein. Accordingly, the invention further provides methods for producing a 10218 protein using the host cells of the invention. In one embodiment, the method comprises culturing the host cell of the invention (into which a recombinant expression vector encoding a 10218 protein has been introduced) in a suitable medium such that a 10218 protein is produced. In another embodiment, the method further comprises isolating a 10218 protein from the medium or the host cell.

Isolated Nucleic Acid Molecules Used in the Methods of the Invention

The coding sequence of the isolated human 10218 cDNA (also referred to herein as P2X$_4$) and the predicted amino acid sequence of the human 10218 polypeptide are shown in SEQ ID NOs:18 and 17, respectively. The 10218 amino acid sequence is also described in Garcia-Guzman, et al. (1997) *Molecular Pharmacolgy* 51:109 (the contents of which are incorporated herein by reference). The nucleotide sequence of 10218 is also described in GenBank Accession Nos. NM_002560 (SEQ ID NO:16) and Y07684 (the contents of which are included herein by refernce).

The methods of the invention include the use of isolated nucleic acid molecules that encode 10218 proteins or biologically active portions thereof, as well as nucleic acid fragments sufficient for use as hybridization probes to identify 10218-encoding nucleic acid molecules (e.g., 10218 mRNA) and fragments for use as PCR primers for the amplification or mutation of 10218 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

A nucleic acid molecule used in the methods of the present invention, e.g., a nucleic acid molecule having the nucleotide sequence of SEQ ID NO:16, or a portion thereof, can be isolated using standard molecular biology techniques and the sequence information provided herein. Using all or portion of the nucleic acid sequence of SEQ ID NO:16 as a hybridization probe, 10218 nucleic acid molecules can be isolated using standard hybridization and cloning techniques (e.g., as described in Sambrook, J., Fritsh, E. F., and Maniatis, T. *Molecular Cloning: A Laboratory Manual*. 2nd, ed., *Cold Spring Harbor Laboratory*, Cold Spring Harbor Laboratory Press, Cold Spring Harbor, N.Y., 1989).

Moreover, a nucleic acid molecule encompassing all or a portion of SEQ ID NO:16 can be isolated by the polymerase chain reaction (PCR) using synthetic oligonucleotide primers designed based upon the sequence of SEQ ID NO:16.

A nucleic acid used in the methods of the invention can be amplified using cDNA, mRNA or, alternatively, genomic DNA as a template and appropriate oligonucleotide primers according to standard PCR amplification techniques. Furthermore, oligonucleotides corresponding to 10218 nucleotide sequences can be prepared by standard, synthetic techniques, e.g., using an automated DNA synthesizer.

In a preferred embodiment, the isolated nucleic acid molecules used in the methods of the invention comprise the nucleotide sequence shown in SEQ ID NO:16, a complement of the nucleotide sequence shown in SEQ ID NO:16, or a portion of any of these nucleotide sequences. A nucleic acid molecule which is complementary to the nucleotide sequence shown in SEQ ID NO:16, is one which is sufficiently complementary to the nucleotide sequence shown in SEQ ID NO:16 such that it can hybridize to the nucleotide sequence shown in SEQ ID NO:16 thereby forming a stable duplex.

In still another preferred embodiment, an isolated nucleic acid molecule used in the methods of the present invention comprises a nucleotide sequence which is at least about 55%, 60%, 65%, 70%, 75%, 80%, 85%, 90%, 95%, 96%, 97%, 98%, 99% or more identical to the entire length of the nucleotide sequence shown in SEQ ID NO:16 or a portion of any of this nucleotide sequence.

Moreover, the nucleic acid molecules used in the methods of the invention can comprise only a portion of the nucleic acid sequence of SEQ ID NO:16, for example, a fragment which can be used as a probe or primer or a fragment encoding a portion of a 10218 protein, e.g., a biologically active portion of a 10218 protein. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:16 of an anti-sense sequence of SEQ ID NO:16 or of a naturally occurring allelic variant or mutant of SEQ ID NO:16. In one embodiment, a nucleic acid molecule used in the methods of the present invention comprises a nucleotide sequence which is greater than 100, 100–200, 200–300, 300–400, 400–500, 500–600, 600–700, 700–800, 800–900, 900–1000, 1000–1100, 1100–1200, 1200–1300, or more nucleotides in length and hybridizes under stringent hybridization conditions to a nucleic acid molecule of SEQ ID NO:16.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in *Current Protocols in Molecular Biology*, Ausubel et al., eds., John Wiley & Sons, Inc. (1995), sections 2, 4 and 6. Additional stringent conditions can be found in *Molecular Cloning: A Laboratory Manual*, Sambrook et al., Cold Spring Harbor Press, Cold Spring Harbor, N.Y. (1989), chapters 7, 9 and 11. A preferred, non-limiting example of stringent hybridization conditions includes hybridization in 4× sodium chloride/sodium citrate (SSC), at about 65–70° C. (or hybridization in 4×SSC plus 50% formamide at about 42–50° C.) followed by one or more washes in 1×SSC, at about 65–70° C. A preferred, non-limiting example of highly stringent hybridization conditions includes hybridization in 1×SSC, at about 65–70° C. (or hybridization in 1×SSC plus 50% formamide at about 42–50° C.) followed by one or more washes in 0.3×SSC, at about 65–70° C. A preferred, non-limiting example of reduced stringency hybridization conditions includes hybridization in 4×SSC, at about 50–60° C. (or alternatively hybridization in 6×SSC plus 50% formamide at about 40–45° C.) followed by one or more washes in 2×SSC, at about 50–60° C. Ranges intermediate to the above-recited values, e.g., at 65–70° C. or at 42–50° C. are also intended to be encompassed by the present invention. SSPE (1×SSPE is 0.15M NaCl, 10 mM NaH$_2$PO$_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5–10° C. less than the melting temperature (T$_m$) of the hybrid, where T$_m$ is determined according to the following equations. For hybrids less than 18 base pairs in length, T$_m$(° C.)=2(# of A+T bases)+4(# of G+C bases). For hybrids between 18 and 49 base pairs in length, T$_m$(° C.)=81.5+16.6(log$_{10}$[Na$^+$])+0.41(% G+C)−(600/N), where N is the number of bases in the hybrid, and [Na$^+$] is the concentration of sodium ions in the hybridization buffer ([Na$^+$] for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25–0.5M NaH$_2$PO$_4$, 7% SDS at about 65° C., followed by one or more washes at 0.02M NaH$_2$PO$_4$, 1% SDS at 65° C., see e.g., Church and Gilbert (1984) *Proc. Natl. Acad. Sci. USA* 81:1991–1995, (or alternatively 0.2×SSC, 1% SDS).

In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a 10218 protein, such as by measuring a level of a 10218-encoding nucleic acid in a sample of cells from a subject e.g., detecting 10218 mRNA levels or determining whether a genomic 10218 gene has been mutated or deleted.

The methods of the invention further encompass the use of nucleic acid molecules that differ from the nucleotide sequence shown in SEQ ID NO:16 due to degeneracy of the genetic code and thus encode the same 10218 proteins as those encoded by the nucleotide sequence shown in SEQ ID NO:16. In another embodiment, an isolated nucleic acid molecule included in the methods of the invention has a nucleotide sequence encoding a protein having an amino acid sequence shown in SEQ ID NO:17.

The methods of the invention further include the use of allelic variants of human 10218, e.g., functional and non-functional allelic variants. Functional allelic variants are naturally occurring amino acid sequence variants of the human 10218 protein that maintain a 10218 activity. Functional allelic variants will typically contain only conservative substitution of one or more amino acids of SEQ ID NO:17, or substitution, deletion or insertion of non-critical residues in non-critical regions of the protein.

Non-functional allelic variants are naturally occurring amino acid sequence variants of the human 10218 protein that do not have a 10218 activity. Non-functional allelic variants will typically contain a non-conservative substitution, deletion, or insertion or premature truncation of the amino acid sequence of SEQ ID NO:17, or a substitution, insertion or deletion in critical residues or critical regions of the protein.

The methods of the present invention may further use non-human orthologues of the human 10218 protein. Orthologues of the human 10218 protein are proteins that are isolated from non-human organisms and possess the same 10218 activity.

The methods of the present invention further include the use of nucleic acid molecules comprising the nucleotide sequence of SEQ ID NO:16 or a portion thereof, in which a mutation has been introduced. The mutation may lead to amino acid substitutions at "non-essential" amino acid residues or at "essential" amino acid residues. A "non-essential" amino acid residue is a residue that can be altered from the wild-type sequence of 10218 (e.g., the sequence of SEQ ID NO:17) without altering the biological activity, whereas an "essential" amino acid residue is required for biological activity. For example, amino acid residues that are conserved among the 10218 proteins of the present invention and other members of the P2X family (e.g., P2X$_1$, P2X$_2$, P2X$_3$, P2X$_5$, P2X$_6$, and P2X$_7$) are not likely to be amenable to alteration.

Mutations can be introduced into SEQ ID NO:16 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a 10218 protein is preferably replaced with another amino acid residue from the same side chain family. Alternatively, in another embodiment, mutations can be introduced randomly along all or part of a 10218 coding sequence, such as by saturation mutagenesis, and the resultant mutants can be screened for 10218 biological activity to identify mutants that retain activity. Following mutagenesis of SEQ ID NO:16 the encoded protein can be expressed recombinantly and the activity of the protein can be determined using the assay described herein.

Another aspect of the invention pertains to the use of isolated nucleic acid molecules which are antisense to the nucleotide sequence of SEQ ID NO:16. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire 10218 coding strand, or to only a portion thereof In one embodiment, an antisense nucleic acid molecule is antisense to a "coding region" of the coding strand of a nucleotide sequence encoding a 10218. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding 10218. The term "noncoding region" refers to 5' and 3' sequences which flank the coding region that are not translated into amino acids (also referred to as 5' and 3' untranslated regions).

Given the coding strand sequences encoding 10218 disclosed herein, antisense nucleic acids of the invention can be designed according to the rules of Watson and Crick base pairing. The antisense nucleic acid molecule can be complementary to the entire coding region of 10218 mRNA, but more preferably is an oligonucleotide which is antisense to only a portion of the coding or noncoding region of 10218 mRNA. For example, the antisense oligonucleotide can be complementary to the region surrounding the translation start site of 10218 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest). Antisense nucleic acid molecules used in the methods of the invention are further described above, in section IV.

In yet another embodiment, the 10218 nucleic acid molecules used in the methods of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. (1996) *Proc. Natl. Acad. Sci.* 93:14670–675.

PNAs of 10218 nucleic acid molecules can be used in the therapeutic and diagnostic applications described herein. For example, PNAs can be used as antisense or antigene agents for sequence-specific modulation of gene expression by, for example, inducing transcription or translation arrest or inhibiting replication. PNAs of 10218 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. et al. (1996) supra)); or as probes or primers for DNA sequencing or hybridization (Hyrup B. et al. (1996) supra; Perry-O'Keefe et al. (1996) supra).

In another embodiment, PNAs of 10218 can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of 10218 nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. et al. (1996) supra). The synthesis of PNA-DNA chimeras can be performed as described in Hyrup B. et al. (1996) supra and Finn P. J. et al. (1996) *Nucleic Acids Res*. 24 (17): 3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res*. 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett*. 5: 1119–11124).

In other embodiments, the oligonucleotide used in the methods of the invention may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958–976) or intercalating agents. (See, e.g., Zon (1988) *Pharm. Res*. 5:539–549). To this end, the oligonucleotide may be conjugated to another molecule, (e.g., a peptide, hybridization triggered cross-linking agent, transport agent, or hybridization-triggered cleavage agent).

Isolated 10218 Proteins and Anti-10218 Antibodies Used in the Methods of the Invention The methods of the invention include the use of isolated 10218 proteins, and biologically active portions thereof, as well as polypeptide fragments suitable for use as immunogens to raise anti-10218 antibodies. In one embodiment, native 10218 proteins can be isolated from cells or tissue sources by an appropriate purification scheme using standard protein purification techniques. In another embodiment, 10218 proteins are produced by recombinant DNA techniques. Alternative to recombinant expression, a 10218 protein or polypeptide can be synthesized chemically using standard peptide synthesis techniques.

As used herein, a "biologically active portion" of a 10218 protein includes a fragment of a 10218 protein having a 10218 activity. Biologically active portions of a 10218 protein include peptides comprising amino acid sequences sufficiently identical to or derived from the amino acid sequence of the 10218 protein, e.g., the amino acid sequence shown in SEQ ID NO:17, which include fewer amino acids than the full length 10218 proteins, and exhibit at least one activity of a 10218 protein. Typically, biologically active portions comprise a domain or motif with at least one activity of the 10218 protein (e.g., the N-terminal region of the 10218 protein that is believed to be involved in the regulation of apoptotic activity). A biologically active portion of a 10218 protein can be a polypeptide which is, for example, 25, 50, 75, 100, 125, 150, 175, 200, 250, 300 or more amino acids in length. Biologically active portions of a 10218 protein can be used as targets for developing agents which modulate a 10218 activity.

In a preferred embodiment, the 10218 protein used in the methods of the invention has an amino acid sequence shown in SEQ ID NO:17. In other embodiments, the 10218 protein is substantially identical to SEQ ID NO:17, and retains the functional activity of the protein of SEQ ID NO:17, yet differs in amino acid sequence due to natural allelic variation or mutagenesis, as described in detail in subsection V above. Accordingly, in another embodiment, the 10218 protein used in the methods of the invention is a protein which comprises an amino acid sequence at least about 50%, 55%, 60%, 65%, 70%, 75%, 80%, 85%, 90%, 95%, 96%, 97%, 98%, 99% or more identical to SEQ ID NO:17.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the 10218 amino acid sequence of SEQ ID NO:17 having 500 amino acid residues, at least 75, preferably at least 150, more preferably at least 225, even more preferably at least 300, and even more preferably at least 400 or more amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* 48:444–453 (1970)) algorithm which has been incorporated into the GAP program in the GCG software package, using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (*Comput. Appl. Biosci.* 4:11–17 (1988)) which has been incorporated into the ALIGN program (version 2.0 or 2.0U), using a PAM120 weight residue table, a gap length penalty of 12 and a gap penalty of 4.

The methods of the invention may also use 10218 chimeric or fusion proteins. As used herein, a 10218 "chimeric protein" or "fusion protein" comprises a 10218 polypeptide operatively linked to a non-10218 polypeptide. An "10218 polypeptide" refers to a polypeptide having an amino acid sequence corresponding to a 10218 molecule, whereas a "non-10218 polypeptide" refers to a polypeptide having an amino acid sequence corresponding to a protein which is not substantially homologous to the 10218 protein, e.g., a protein which is different from the 10218 protein and which is derived from the same or a different organism. Within a 10218 fusion protein the 10218 polypeptide can correspond to all or a portion of a 10218 protein. In a preferred embodiment, a 10218 fusion protein comprises at least one biologically active portion of a 10218 protein. In another preferred embodiment, a 10218 fusion protein comprises at least two biologically active portions of a 10218 protein. Within the fusion protein, the term "operatively linked" is intended to indicate that the 10218 polypeptide and the non-10218 polypeptide are fused in-frame to each other. The non-10218 polypeptide can be fused to the N-terminus or C-terminus of the 10218 polypeptide.

For example, in one embodiment, the fusion protein is a GST-10218 fusion protein in which the 10218 sequences are fused to the C-terminus of the GST sequences. Such fusion proteins can facilitate the purification of recombinant 10218.

In another embodiment, this fusion protein is a 10218 protein containing a heterologous signal sequence at its N-terminus. In certain host cells (e.g., mammalian host cells), expression and/or secretion of 10218 can be increased through use of a heterologous signal sequence.

The 10218 fusion proteins used in the methods of the invention can be incorporated into pharmaceutical compositions and administered to a subject in vivo. The 10218 fusion proteins can be used to affect the bioavailability of a 10218 substrate. Use of 10218 fusion proteins may be useful therapeutically for the treatment of disorders caused by, for example, (i) aberrant modification or mutation of a gene encoding a 10218 protein; (ii) mis-regulation of the 10218 gene; and (iii) aberrant post-translational modification of a 10218 protein.

Moreover, the 10218-fusion proteins used in the methods of the invention can be used as immunogens to produce anti-10218 antibodies in a subject, to purify 10218 ligands and in screening assays to identify molecules which inhibit the interaction of 10218 with a 10218 substrate.

Preferably, a 10218 chimeric or fusion protein used in the methods of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A 10218-encoding nucleic acid can be cloned into such an expression vector such that the fusion moiety is linked in-frame to the 10218 protein.

The present invention also pertains to the use of variants of the 10218 proteins which function as either 10218 agonists (mimetics) or as 10218 antagonists. Variants of the 10218 proteins can be generated by mutagenesis, e.g., discrete point mutation or truncation of a 10218 protein. An agonist of the 10218 proteins can retain substantially the same, or a subset, of the biological activities of the naturally occurring form of a 10218 protein. An antagonist of a 10218 protein can inhibit one or more of the activities of the naturally occurring form of the 10218 protein by, for example, competitively modulating a 10218-mediated activity of a 10218 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the 10218 protein.

In one embodiment, variants of a 10218 protein which function as either 10218 agonists (mimetics) or as 10218 antagonists can be identified by screening combinatorial libraries of mutants, e.g., truncation mutants, of a 10218 protein for 10218 protein agonist or antagonist activity. In one embodiment, a variegated library of 10218 variants is generated by combinatorial mutagenesis at the nucleic acid level and is encoded by a variegated gene library. A variegated library of 10218 variants can be produced by, for example, enzymatically ligating a mixture of synthetic oligonucleotides into gene sequences such that a degenerate set of potential 10218 sequences is expressible as individual polypeptides, or alternatively, as a set of larger fusion proteins (e.g., for phage display) containing the set of 10218 sequences therein. There are a variety of methods which can be used to produce libraries of potential 10218 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential 10218 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of a 10218 protein coding sequence can be used to generate a variegated population of 10218 fragments for screening and subsequent selection of variants of a 10218 protein. In one embodiment, a library of coding sequence fragments can be generated by treating a double stranded PCR fragment of a 10218 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the 10218 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of 10218 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify 10218 variants (Arkin and Yourvan (1992) *Proc. Natl. Acad. Sci. USA* 89:7811–7815; Delgrave et al. (1993) *Protein Engineering* 6(3):327–331).

The methods of the present invention further include the use of anti-10218 antibodies. An isolated 10218 protein, or a portion or fragment thereof, can be used as an immunogen to generate antibodies that bind 10218 using standard techniques for polyclonal and monoclonal antibody preparation. A full-length 10218 protein can be used or, alternatively, antigenic peptide fragments of 10218 can be used as immunogens. The antigenic peptide of 10218 comprises at least 8 amino acid residues of the amino acid sequence shown in SEQ ID NO:17 and encompasses an epitope of 10218 such that an antibody raised against the peptide forms a specific immune complex with the 10218 protein. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of 10218 that are located on the surface of the protein, e.g., hydrophilic regions, as well as regions with high antigenicity.

A 10218 immunogen is typically used to prepare antibodies by immunizing a suitable subject, (e.g., rabbit, goat, mouse, or other mammal) with the immunogen. An appropriate immunogenic preparation can contain, for example, recombinantly expressed 10218 protein or a chemically synthesized 10218 polypeptide. The preparation can further include an adjuvant, such as Freund's complete or incomplete adjuvant, or similar immunostimulatory agent. Immunization of a suitable subject with an immunogenic 10218 preparation induces a polyclonal anti-10218 antibody response.

The term "antibody" as used herein refers to immunoglobulin molecules and immunologically active portions of immunoglobulin molecules, i.e., molecules that contain an antigen binding site which specifically binds (immunoreacts with) an antigen, such as a 10218. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind 10218 molecules. The term "monoclonal antibody" or "monoclonal antibody composition", as used herein, refers to a population of antibody molecules that contain only one species of an antigen binding site capable of immunoreacting with a particular epitope of 10218. A monoclonal antibody composition thus typically displays a single binding affinity for a particular 10218 protein with which it immunoreacts.

Polyclonal anti-10218 antibodies can be prepared as described above by immunizing a suitable subject with a 10218 immunogen. The anti-10218 antibody titer in the immunized subject can be monitored over time by standard techniques, such as with an enzyme linked immunosorbent assay (ELISA) using immobilized 10218. If desired, the antibody molecules directed against 10218 can be isolated from the mammal (e.g., from the blood) and further purified by well known techniques, such as protein A chromatography to obtain the IgG fraction. At an appropriate time after immunization, e.g., when the anti-10218 antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.* 255:4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985) *Monoclonal Antibodies and Cancer Therapy*, Alan R. Liss, Inc., pp. 77–96) or trioma techniques. The technology for producing monoclonal antibody hybridomas is well known (see generally Kenneth, R. H. in *Monoclonal Antibodies: A New Dimension In Biological Analyses*, Plenum Publishing Corp., New York, N.Y. (1980); Lerner, E. A. (1981) *Yale J. Biol. Med.* 54:387–402; Gefter, M. L. et al. (1977) *Somatic Cell Genet.* 3:231–36). Briefly, an immortal cell line (typically a myeloma) is fused to lymphocytes (typically splenocytes) from a mammal immunized with a 10218 immunogen as described above, and the culture supernatants of the resulting hybridoma cells are screened to identify a hybridoma producing a monoclonal antibody that binds 10218.

Any of the many well known protocols used for fusing lymphocytes and immortalized cell lines can be applied for the purpose of generating an anti-10218 monoclonal antibody (see, e.g., G. Galfre et al. (1977) *Nature* 266:55052; Gefter et al. (1977) supra; Lerner (1981) supra; and Kenneth (1980) supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind 10218, e.g., using a standard ELISA assay.

Alternative to preparing monoclonal antibody-secreting hybridomas, a monoclonal anti-10218 antibody can be identified and isolated by screening a recombinant combinatorial immunoglobulin library (e.g., an antibody phage display library) with 10218 to thereby isolate immunoglobulin library members that bind 10218. Kits for generating and screening phage display libraries are commercially available (e.g., the Pharmacia *Recombinant Phage Antibody System*, Catalog No. 27-9400-01; and the Stratagene *SurfZAP*™ *Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J* 12:725–734; Hawkins et al. (1992) *J. Mol. Biol.* 226: 889–896; Clarkson et al. (1991) *Nature* 352:624–628; Gram et al. (1992) *Proc. Natl. Acad. Sci. USA* 89:3576–3580; Garrad et al. (1991) *Bio/Technology* 9:1373–1377; Hoogenboom et al. (1991) *Nuc. Acid Res.* 19:4133–4137; Barbas et al. (1991) *Proc. Natl. Acad. Sci. USA* 88:7978–7982; and McCafferty et al. (1990) *Nature* 348:552–554.

Additionally, recombinant anti-10218 antibodies, such as chimeric and humanized monoclonal antibodies, comprising both human and non-human portions, which can be made using standard recombinant DNA techniques, are within the scope of the methods of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125, 023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc.*

*Natl. Acad. Sci. USA* 84:214–218; Nishimura et al. (1987) *Canc. Res.* 47:999–1005; Wood et al. (1985) *Nature* 314: 446–449; Shaw et al. (1988) *J. Natl. Cancer Inst.* 80:1553–1559; Morrison, S. L. (1985) *Science* 229:1202–1207; Oi et al. (1986) *BioTechniques* 4:214; Winter U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

An anti-10218 antibody can be used to detect 10218 protein (e.g., in a cellular lysate or cell supernatant) in order to evaluate the abundance and pattern of expression of the 10218 protein. Anti-10218 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

This invention is further illustrated by the following examples which should not be construed as limiting. The contents of all references, patents and published patent applications cited throughout this application, as well as the Sequence Listing is incorporated herein by reference.

EXAMPLES

Example 1

Analysis of Expression of Human P2X$_4$ (10218) in Macrophages

This experiment describes the expression of 10218 in macrophages stimulated with interferon gamma (IFNγ) and CD40L, cytokines which are known to be highly atherogenic, in order to mimic the physiologic conditions involved in the atherosclerotic state.

Macrophages were treated with IFNγ and CD40L and expresion of 10218 mRNA was assessed by Taqman™ analysis.

Macrophages treated with IFNγ and CD40L show increased expression of 10218 at 4 hours and at 18 hours after treatment. This data indicates a role of 10218 in the formation of atherosclerotic lesions.

Example 2

Analysis of Expression of Human P2X$_4$ (10218) mRNA in Atheroscerotic Lesions in Apoe Knockout Mice This experiment describes the use of ApoE knockout mice to study the regulation of 10218 in atherosclerotic lesions at various stages of lesion development and as compared to normal vessels.

The ApoE knockout mouse was created by gene targeting in embryonic stem cells to disrupt the ApoE gene. The homozygous inactivation of the ApoE gene results in animals that are devoid of ApoE in their sera. These mice exhibit five times the normal serum plasma cholesterol and spontaneous atherosclerotic lesions. This is similar to a disease in humans who have a variant form of the ApoE gene that is defective in binding to the LDL receptor and are at risk for early development of atherosclerosis, and increased plasma triglyceride and cholesterol levels. ApoE knockout mice are routinely used to study modulators of atherosclerosis and the pathogenesis of atherosclerosis.

In the ApoE knockout animals, the aortic arch region is prone to formation of atherosclerotic lesions, whereas the abdominal aorta is typically free of such lesions. At 5 weeks of age lesion development is minimal, whereas by 18 weeks of age complex lesion formation is observed, which persists at 33 weeks of age.

In this experiment, the expression of 10218 was assessed in C57 ApoE knockout animals at 8, 12, 17, 20, 22, 25, and 30 weeks of age. Non-lesioned and lesioned tissue sections were dissected from either the abdominal aorta (non-lesioned) or the aortic arch (lesioned) from ApoE knockout animals at each of the above ages. Vessels from wild-type mice were used as a control. 10218 is upregulated in lesioned vessels as compared to non-lesioned vessels and vessels obtained from normal animals at 17, 20, 22, 25, and 30 weeks of age indicating a correlation between 10218 expression and the pathogenesis of atherosclerosis.

Example 3

Tissue Distribution of Human P2X$_4$ (10218) mRNA Using Taqman™ Analysis

This example describes the tissue distribution of human 10218 mRNA in a variety of cells and tissues, as determined using the TaqMan™ procedure. The Taqman™ procedure is a quantitative, reverse transcription PCR-based approach for detecting mRNA. The RT-PCR reaction exploits the 5' nuclease activity of AmpliTaq Gold™ DNA Polymerase to cleave a TaqMan™ probe during PCR. Briefly, cDNA was generated from the samples of interest, e.g., heart, kidney, liver, skeletal muscle, and various vessels, and used as the starting material for PCR amplification. In addition to the 5' and 3' gene-specific primers, a gene-specific oligonucleotide probe (complementary to the region being amplified) was included in the reaction (i.e., the Taqman™ probe). The TaqMan™ probe includes the oligonucleotide with a fluorescent reporter dye covalently linked to the 5' end of the probe (such as FAM (6-carboxyfluorescein), TET (6-carboxy-4,7,2',7'-tetrachlorofluorescein), JOE (6-carboxy-4,5-dichloro-2,7-dimethoxyfluorescein), or VIC) and a quencher dye (TAMRA (6-carboxy-N,N,N',N'-tetramethylrhodamine) at the 3' end of the probe.

During the PCR reaction, cleavage of the probe separates the reporter dye and the quencher dye, resulting in increased fluorescence of the reporter. Accumulation of PCR products is detected directly by monitoring the increase in fluorescence of the reporter dye. When the probe is intact, the proximity of the reporter dye to the quencher dye results in suppression of the reporter fluorescence. During PCR, if the target of interest is present, the probe specifically anneals between the forward and reverse primer sites. The 5'-3' nucleolytic activity of the AmpliTaq™ Gold DNA Polymerase cleaves the probe between the reporter and the quencher only if the probe hybridizes to the target. The probe fragments are then displaced from the target, and polymerization of the strand continues. The 3' end of the probe is blocked to prevent extension of the probe during PCR. This process occurs in every cycle and does not interfere with the exponential accumulation of product. RNA was prepared using the trizol method and treated with DNase to remove contaminating genomic DNA. cDNA was synthesized using standard techniques. Mock cDNA synthesis in the absence of reverse transcriptase resulted in samples with no detectable PCR amplification of the control gene confirms efficient removal of genomic DNA contamination.

A phase 1.3.4 panel including human normal and tumor tissue indicated highest expression of 10218 mRNA in the pancreas, static and shear HUVEC, and the brain. Expression of 10219 was also detected in the kidney, heart, skeletal muscle, and liver, which are all vascular rich organs. A cardiovascular vessel panel indicated expression in various human vessels, including aortic smooth muscle cells (SMC), coronary SMC, carotid artery, muscular artery, diseased aorta, and normal vein. Highest expression was detected in LSS HUVEC and static HUVEC. These expression data indicate expression of 10218 across various vessels and in highly vascularized organs, indicating a role of 10218 in the modulation of cardiovascular disease, e.g., atherosclerosis.

What is claimed is:

1. An isolated polypeptide comprising an amino acid sequence which is at least 95% identical to the amino acid sequence of SEQ ID NO:4, wherein the polypeptide has cyclic AMP phosphodiesterase activity.

2. The isolated polypeptide of claim 1, wherein the polypeptide comprises the amino acid sequence of SEQ ID NO:4.

3. The isolated polypeptide of claim 1, wherein the polypeptide consists of the amino acid sequence of SEQ ID NO:4.

4. The polypeptide of claims 1, further comprising a heterologous amino acid sequence.

5. The polypeptide of claim 2, further comprising a heterologous amino acid sequence.

6. An isolated polypeptide which is encoded by a nucleic acid molecule comprising a nucleotide sequence which is at least 95% identical to the nucleotide sequence of SEQ (ID NO:3, wherein the polypeptide has cyclic AMP phosphodiesterase activity.

7. The isolated polypeptide of claim 6, wherein the polypeptide is encoded by a nucleic acid molecule comprising the nucleotide sequence of SEQ ID NO:3.

8. The polypeptide of claim 6, further comprising a heterologous amino acid sequence.

9. The polypeptide of claim 7, further comprising a heterologous amino acid sequence.

* * * * *

UNITED STATES PATENT AND TRADEMARK OFFICE
CERTIFICATE OF CORRECTION

| | | |
|---|---|---|
| PATENT NO. | : 7,098,015 B2 | Page 1 of 1 |
| APPLICATION NO. | : 10/386414 | |
| DATED | : August 29, 2006 | |
| INVENTOR(S) | : Keith E. Robison et al. | |

It is certified that error appears in the above-identified patent and that said Letters Patent is hereby corrected as shown below:

Title Page item 75 should read

INVENTORS: Keith E. Robison, Wilmington, MA (US), Rosanna Kapeller-Libermann, Chestnut Hill, MA (US), and David White, Braintree, MA (US)

Signed and Sealed this

Twenty-first Day of August, 2007

JON W. DUDAS
*Director of the United States Patent and Trademark Office*